US012054725B2

(12) United States Patent
Li et al.

(10) Patent No.: US 12,054,725 B2
(45) Date of Patent: Aug. 6, 2024

(54) U6 POLYMERASE III PROMOTER AND METHODS OF USE

(71) Applicant: CORTEVA AGRISCIENCE LLC, Indianapolis, IN (US)

(72) Inventors: Zhongsen Li, Hockessin, DE (US); Zhan-Bin Liu, Clive, IA (US)

(73) Assignee: E.I. DU PONT DE NEMOURS AND COMPANY, IN (US)

(*) Notice: Subject to any disclaimer, the term of this patent is extended or adjusted under 35 U.S.C. 154(b) by 0 days.

(21) Appl. No.: 17/814,351

(22) Filed: Jul. 22, 2022

(65) Prior Publication Data

US 2023/0193304 A1 Jun. 22, 2023

Related U.S. Application Data

(63) Continuation of application No. 16/552,632, filed on Aug. 27, 2019, now Pat. No. 11,427,830, which is a continuation of application No. 14/913,630, filed as application No. PCT/US2014/051782 on Aug. 20, 2014, now Pat. No. 10,519,457.

(60) Provisional application No. 62/023,239, filed on Jul. 11, 2014, provisional application No. 61/937,045, filed on Feb. 7, 2014, provisional application No. 61/882,532, filed on Sep. 25, 2013, provisional application No. 61/868,706, filed on Aug. 22, 2013.

(51) Int. Cl.

| | |
|---|---|
| ***A01H 5/10*** | (2018.01) |
| ***A01H 1/00*** | (2006.01) |
| ***A01H 5/00*** | (2018.01) |
| ***C12N 15/00*** | (2006.01) |
| ***C12N 15/63*** | (2006.01) |
| ***C12N 15/82*** | (2006.01) |

(52) U.S. Cl.

CPC ........... *C12N 15/8216* (2013.01); *A01H 1/00* (2013.01); *A01H 5/00* (2013.01); *A01H 5/10* (2013.01); *C12N 15/00* (2013.01); *C12N 15/63* (2013.01)

(58) Field of Classification Search

None

See application file for complete search history.

(56) References Cited

U.S. PATENT DOCUMENTS

2007/0083945 A1* 4/2007 Byrum ................ C07K 14/415 536/23.6

OTHER PUBLICATIONS

Byrum et al. N_Geneseq Database, Accession No. ARD65600, US20070083945, Apr. 12, 2007, Seq ID No. 147296.*

* cited by examiner

*Primary Examiner* — Phuong T Bui

(57) ABSTRACT

The disclosure relates to gene expression regulatory sequences, specifically to the promoter of a U6 polymerase III gene and fragments thereof and their use in promoting the expression of one or more heterologous nucleic acid fragments in plants. The invention further discloses compositions, polynucleotide constructs, transformed host cells, mutated plants, transgenic plants and seeds containing the recombinant construct with the promoter, and methods for preparing and using the same.

18 Claims, 51 Drawing Sheets

Figure 1A:
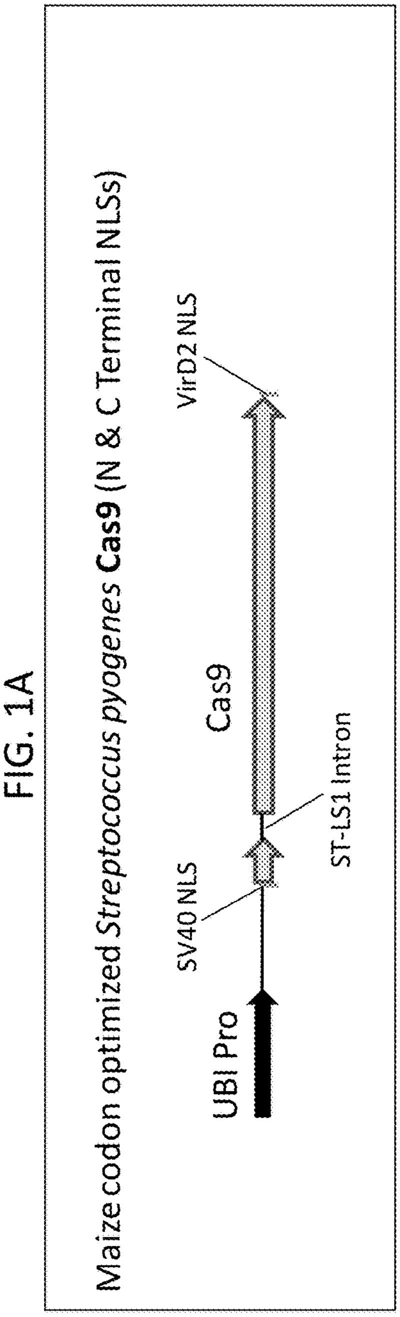

Specification includes a Sequence Listing.

FIG. 3A

Expected Site of Cleavage

PAM

| | LIGCas-1 | | SEQ ID NO: |
|---|---|---|---|
| Reference | CTGTAACGATTTACGCACCTGCTGGGAATTGTACCGTACGTGCCCCGGCGGAGGATATATATACCTCACACGTACGCGTACGCGTATATATAC | Count | 55 |
| Mutation 1 | AGGACTGTAACGATTTACGCACCTGCTGGGAATTGTACCGTACGTGCCCCGGTCGGAGGATATATATACCTCACACGTACGCGTACGCGTATATATAC | 14488 | 56 |
| Mutation 2 | AGGACTGTAACGATTTACGCACCTGCTGGGAATTGTACCGTACGTGCCCCGGACGGAGGATATATATACCTCACACGTACGCGTACGCGTATATATAC | 7746 | 57 |
| Mutation 3 | AGGACTGTAACGATTTACGCACCTGCTGGGAATTGTACCGTACGTGCCCCGGGCGGAGGATATATATACCTCACACGTACGCGTACGCGTATATATAC | 5028 | 58 |
| Mutation 4 | AGGACTGTAACGATTTACGCACCTGCTGGGAATTGTACCGTACGTGC--GGTCGGAGGATATATATACCTCACACGTACGCGTACGCGTATATATAC | 1425 | 59 |
| Mutation 5 | AGGACTGTAACGATTTACGCACCTGCTGGGAATTGTACCGTACGTGCCCCGGCCGGAGGATATATATACCTCACACGTACGCGTACGCGTATATATAC | 1056 | 60 |
| Mutation 6 | AGGACTGTAACGATTTACGCACCTGCTGGGAATTGTACCGTACGTGCCCCG-CGGAGGATATATATACCTCACACGTACGCGTACGCGTATATATAC | 963 | 61 |
| Mutation 7 | AGGACTGTAACGATTTACGCACCTGCTGGGAATTGTACCGTACGTGCCCCGG-GGAGGATATATATACCTCACACGTACGCGTACGCGTATATATAC | 732 | 62 |
| Mutation 8 | AGGACTGTAACGATTTACGCACCTGCTGGGAATTGTACCGTACGTGCCCCGG---AGGATATATATACCTCACACGTACGCGTACGCGTATATATAC | 730 | 63 |
| Mutation 9 | AGGACTGTAACGATTTACGCACCTGCTGGGAATTGTACCGTACGTGC---GTCGGAGGATATATATACCTCACACGTACGCGTACGCGTATATATAC | 492 | 64 |
| Mutation 10 | AGGACTGTAACGATTTACGCACCTGCTGGGAATTGTACCG------------------------------------------------------TAC | 390 | 65 |

Expected Site of Cleavage

PAM

| | LIGCas-2 | | SEQ ID NO: |
|---|---|---|---|
| Reference | CTGTAACGATTTACGCACCTGCTGGGAATTGTACCGTACGTGCCCCGGCGGAGGATATATATACCTCACACGTACGCGTACGCGTATATATAC | Count | 55 |
| Mutation 1 | TCCTCTGTAACGATTTACGCACCTGCTGGGAATTGTACCGTACGTGACCCCGGCGGAGGATATATATACCTCACACGTACGCGTACGCGTATATATAC | 4221 | 66 |
| Mutation 2 | TCCTCTGTAACGATTTACGCACCTGCTGGGAATTGTACCGTACGT-CCCCGGCGGAGGATATATATACCTCACACGTACGCGTACGCGTATATATAC | 3452 | 67 |
| Mutation 3 | TCCTCTGTAACGATTTACGCACCTGCTGGGAATTGTACCGTACGTGTCCCCGGCGGAGGATATATATACCTCACACGTACGCGTACGCGTATATATAC | 3395 | 68 |
| Mutation 4 | TCCTCTGTAACGATTTACGCACCTGCTGGGAATTGTACCGTAC---CCCCGGCGGAGGATATATATACCTCACACGTACGCGTACGCGTATATATAC | 1870 | 69 |
| Mutation 5 | TCCTCTGTAACGATTTACGCACCTGCTGGGAATTGTACCGTA----CCCCGGCGGAGGATATATATACCTCACACGTACGCGTACGCGTATATATAC | 1344 | 70 |
| Mutation 6 | TCCTCTGTAACGATTTACGCACCTGCTGGGAATTGTACCGTACGTGGCCCCGGCGGAGGATATATATACCTCACACGTACGCGTACGCGTATATATAC | 876 | 71 |
| Mutation 7 | TCCTCTGTAACGATTTACGCACCTGCTGGGAATTGTACCGTA-----CCCGGCGGAGGATATATATACCTCACACGTACGCGTACGCGTATATATAC | 507 | 72 |
| Mutation 8 | TCCTCTGTAACGATTTACGCACCTGCTGGGAATTGTACCGTACGTGAACCCCGGCGGAGGATATATATACCTCACACGTACGCGTACGCGTATATATAC | 364 | 73 |
| Mutation 9 | TCCTCTGTAACGATTTACGCACCTGCTGGGAATTGTACCGTACGTG------------------------------------TACGCGTATATATAC | 331 | 74 |
| Mutation 10 | TCCTCTGTAACGATTTACGCACCTGCTGGGAATTGTACCGTACG--CCCCGGCGGAGGATATATATACCTCACACGTACGCGTACGCGTATATATAC | 315 | 75 |

FIG. 3B

Expected Site of Cleavage

PAM

| | LIGCas-3 | | SEQ ID NO: |
|---|---|---|---|
| Reference | CGCAAATGAGTAGCAGCGCACGTATATATACGCGTACGCGTACGTGTGAGGTATATATATCCTCCGCCGGGGCACGTACGGTACAATTCCCAG | Count | 76 |
| Mutation 1 | AAGGCGCAAATGAGTAGCAGCGCACGTATATATACGCGTACGCGTACGT*T*GTGAGGTATATATATCCTCCGCCGGGGCACGTACGGTACAATTCCCAG | 16861 | 77 |
| Mutation 2 | AAGGCGCAAATGAGTAGCAGCGCACGTATATATACGCGTACGCGTACG-GTGAGGTATATATATCCTCCGCCGGGGCACGTACGGTACAATTCCCAG | 3648 | 78 |
| Mutation 3 | AAGGCGCAAATGAGTAGCAGCGCACGTATATATACGCGTACGCGTAC-TGTGAGGTATATATATCCTCCGCCGGGGCACGTACGGTACAATTCCCAG | 2263 | 79 |
| Mutation 4 | AAGGCGCAAATGAGTAGCAGCGCACGTATATATACGCGTACGCGTACG--TGAGGTATATATATCCTCCGCCGGGGCACGTACGGTACAATTCCCAG | 2132 | 80 |
| Mutation 5 | AAGGCGCAAATGAGTAGCAGCGCACGTATATATA-----------------------------TCCTCCGCCGGGGCACGTACGGTACAATTCCCAG | 1181 | 81 |
| Mutation 6 | AAGGCGCAAATGAGTAGCAGCGCACGTATATATACG------------------------------------------CGTACGGTACAATTCCCAG | 848 | 82 |
| Mutation 7 | AAGGCGCAAATGAGTAGCAGCGCACGTATATATACGCGTACGCGT--GTGAGGTATATATATCCTCCGCCGGGGCACGTACGGTACAATTCCCAG | 327 | 83 |
| Mutation 8 | AAGGCGCAAATGAGTAGCAGCGCACGTATATATACGCGTACGC----------------------------CGGGGCACGTACGGTACAATTCCCAG | 263 | 84 |
| Mutation 9 | AAGGCGCAAATGAGTAGCAGCGCACGTATATAT-------------------------------CCTCCGCCGGGGCACGTACGGTACAATTCCCAG | 227 | 85 |
| Mutation 10 | AAGGCGCAAATGAGTAGCAGCGCACGTATATATACGCGTACGCGTA--TGTGAGGTATATATATCCTCCGCCGGGGCACGTACGGTACAATTCCCAG | 209 | 86 |

Expected Site of Cleavage

| | LIG3-4 HOMING ENDONUCLEASE | | SEQ ID NO: |
|---|---|---|---|
| Reference | CGCAAATGAGTAGCAGCGCACGTATATATACGCGTACGCGTACGTGTGAGGTATATATATCCTCCGCCGGGGCACGTACGGTACAATTCCCAG | Count | 76 |
| Mutation 1 | CCTTCGCAAATGAGTAGCAGCGCACGTATATATACGCGTACGCGTACGTG--AGGTATATATATCCTCCGCCGGGGCACGTACGGTACAATTCCCAG | 358 | 87 |
| Mutation 2 | CCTTCGCAAATGAGTAGCAGCGCACGTATATATA-----------------------------TCCTCCGCCGGGGCACGTACGGTACAATTCCCAG | 241 | 88 |
| Mutation 3 | CCTTCGCAAATGAGTAGCAGCGCACGTATATATACGCGTACGCGT--------------------------------ACGTACGGTACAATTCCCAG | 150 | 89 |
| Mutation 4 | CCTTCGCAAATGAGTAGCAGCGCACGTATATATACG------------------------------------------CGTACGGTACAATTCCCAG | 143 | 90 |
| Mutation 5 | CCTTCGCAAATGAGTAGCAGCGCACGTATATATACGCGTA----------------------------CGCCGGGGCACGTACGGTACAATTCCCAG | 97 | 91 |
| Mutation 6 | CCTTCGCAAATGAGTAGCAGCGCACGTATATATACGTGT------------GAGGTATATATATCCTCCGCCGGGGCACGTACGGTACAATTCCCAG | 52 | 92 |
| Mutation 7 | CCTTCGCAAATGAGTAGCAGCGCACGTATATATACGCGTACGCGT----GTGAGGTATATATATCCTCCGCCGGGGCACGTACGGTACAATTCCCAG | 50 | 93 |
| Mutation 8 | CCTTCGCAAATGAGTAGCAGCGCACGTATATAT-------------------------------CCTCCGCCGGGGCACGTACGGTACAATTCCCAG | 46 | 94 |
| Mutation 9 | CCTTCGCAAATGAGTAGCAGCGCACGTATATATACGCGTACGCGTACGTGT--GGTATATATATCCTCCGCCGGGGCACGTACGGTACAATTCCCAG | 42 | 95 |
| Mutation 10 | CCTTCGCAAATGAGTAGCAGCGCACGTATATATACGCGTACG-----*GTATATATAC*GTGTGAGGTATATATATCCTCCGCCGGGGCACGTACGGTACA | 32 | 96 |

Primer 1: CCCGTTATTGTATGAGGTAATGAC (SEQ ID NO: 98)
Primer 2: GCTCGTGTCCAAGCGTCACTTACGATTAGCT (SEQ ID NO: 99)
Primer 3: CCATGTCTAACTGTTCATTTATATGATTCTCT (SEQ ID NO: 100)
Primer 4: GCAGCCGATAGGTTCATCATCTTC (SEQ ID NO: 101)

FIG. 6

Expected Site of Cleavage

PAM

| | 55CasRNA-1 | SEQ ID NO: |
|---|---|---|
| Reference | CCGGTTTCGCGTGCTCTGGCTTTACATTACATGGGCAGGTCTCACGACGGTTGGGCTGGAGAGCCGGCTGGTAGGGGAGGACCTCAACGGC | 104 |
| Mutation 1 | CCGGTTTCGCGTGCTCTGGCTTTACATTACATGGGCAGGTCTCACGA-GGTTGGGCTGGAGAGCCGGCTGGTAGGGGAGGACCTCAACGGC | 105 |
| Mutation 2 | CCGGTTTCGCGTGCTCTGGCTTTACATTACATGGGCAGGTCTCAC-ACGGTTGGGCTGGAGAGCCGGCTGGTAGGGGAGGACCTCAACGGC | 106 |
| Mutation 3 | CGGTTTCGCGTGCTCTGGCTTTACATTACATGGGCAGGTCTCACGACGG*T*TTGGGCTGGAGAGCCGGCTGGTAGGGGAGGACCTCAACGGC | 107 |
| Mutation 4 | CCGGTTTCGCGTGCTCTGGCTTTACATTGCATGAGCAGGTC*GT*--GACGGTTGGGCTGGAGAGCCGGCTGGTAGGGGAGGACCTCAACGGC | 108 |
| Mutation 5 | GGGCAGGTCT--CGACGGTTGGGCTGGAGAGCCGGCTGGTAGGGGAGGACCTCAACGGC | 109 |
| Mutation 6 | CCGGTTTCGCGTGCTC----------------------------------TTGGGCTGGAGAGCCGGCTGGTAGGGGAGGACCTCAACGGC | 110 |

DD43CR1 20 bp    Guide RNA 76 bp    Terminator

GTCCCTTGTACTTGTACGTAGTTTTAGAGCTAGAAATAGCAAGTTAAAATAAGGCTAGTCCGTTATCAACTTGAAAAAGTGGCACCGAGTCGGTGCTTTTTTTT

FIG. 11A

U6-13.1:DD20CR1+EF1A2:CAS9

| SEQ ID NO:142 | GGAATTTACAGCACAAGTAGATCACTTGTACTTATCAAAATTCGGAACTGACACACGACATGATGGAACGTGACTAAGGTGGGTTTTTGACTTTGCATGTCGAAGTGAGAGTGAT | Count |
|---|---|---|
| SEQ ID NO:147 | GGAATTTACAGCACAAGTAGATCACTTGTACTTATCAAAATTCGGAACTGACACACGA--TGATGGAACGTGACTAAGGTGGGTTTTTGACTTTGCATGTCGA | 102 |
| SEQ ID NO:148 | GGAATTTACAGCACAAGTAGATCACTTGTACTTATCAAAATTCGGAACTGACACACGA-----TGGAACGTGACTAAGGTGGGTTTTTGACTTTGCATGTCGAAGT | 101 |
| SEQ ID NO:149 | GGAATTTACAGCACAAGTAGATCACTTGTACTTATCAAAATTCGGAACTGACACACGAC-TGATGGAACGTGACTAAGGTGGGTTTTTGACTTTGCATGTCG | 53 |
| SEQ ID NO:150 | GGAATTTACAGCACAAGTAGATCACTTGTACTTATCAAAATTCGGAACTGACACAC------ATGGAACGTGACTAAGGTGGGTTTTTGACTTTGCATGTCGAAGTG | 27 |
| SEQ ID NO:151 | GGAATTTACAGCACAAGTAGATCACTTGTACTTATCAAAATTCGGAACTGACACA-----TGATGGAACGTGACTAAGGTGGGTTTTTGACTTTGCATGTCGAAGT | 20 |
| SEQ ID NO:152 | GGAATTTACAGCACAAGTAGATCACTTGTACTTATCAAAATTCGGAACTGACACA-GACATGATGGAACGTGACTAAGGTGGGTTTTTGACTTTGCATGTCG | 11 |
| SEQ ID NO:153 | GGAATTTACAGCACAAGTAGATCACTTGTACTTATCAAAATTCGGAACTGACAC--GACATGATGGAACGTGACTAAGGTGGGTTTTTGACTTTGCATGTCGA | 11 |
| SEQ ID NO:154 | GGAATTTACAGCACAAGTAGATCACTTGTACTTATCAAAATTCGGAACTGACACA**AGAA**ATGATGGAACGTGACTAAGGTGGGTTTTTGACTTTGCATGTC | 9 |
| SEQ ID NO:155 | GGAATTTACAGCACAAGTAGATCACTTGTACTTATCAAAATTCGGAACTGACACAC**GATT**-----GAACGTGACTAAGGTGGGTTTTTGACTTTGCATGTCGAAGT | 3 |
| SEQ ID NO:156 | GGAATTTACAGCACAAGTAGATCACTTGTACTTATCAAAATTCGGAACTGACACAC**ATT**------GAACGTGACTAAGGTGGGTTTTTGACTTTGCATGTCGAAGTG | 2 |

FIG. 11B

U6-13.1:DD20CR2+EF1A2:CAS9

| SEQ ID No:143 | TTCCTTTACAGCACAAGTAGATCACTTGTACTTATCAAAATTCGGAACTGACACACGACATGATGGAACGTGACTAAGGTGGGTTTTTGACTTTGCATGTCGAAGTGAGAGTGA | Count |
|---|---|---|
| SEQ ID No:157 | TTCCTTTACAGCACAAGTAGATCACTTGTACTTATCAAAATTCGGAACTGACACACGACATGATGGAACGT--CTAAGGTGGGTTTTTGACTTTGCATGTCGA | 107 |
| SEQ ID No:158 | TTCCTTTACAGCACAAGTAGATCACTTGTACTTATCAAAATTCGGAACTGACACACGACATGATGGAAC----CTAAGGTGGGTTTTTGACTTTGCATGTCGAAG | 72 |
| SEQ ID No:159 | TTCCTTTACAGCACAAGTAGATCACTTGTACTTATCAAAATTCGGAACTGACACACGACATGATGGAACGTGACT-AGGTGGGTTTTTGACTTTGCATGTCG | 69 |
| SEQ ID No:160 | TTCCTTTACAGCACAAGTAGATCACTTGTACTTATCAAAATTCGGAACTGACACACGACATGATGGAAC-----TAAGGTGGGTTTTTGACTTTGCATGTCGAAGT | 68 |
| SEQ ID No:161 | TTCCTTTACAGCACAAGTAGATCACTTGTACTTATCAAAATTCGGAACTGACACACGACATGATGGAACG-----AAGGTGGGTTTTTGACTTTGCATGTCGAAGT | 40 |
| SEQ ID No:162 | TTCCTTTACAGCACAAGTAGATCACTTGTACTTATCAAAATTCGGAACTGACACACGACATGATGGA---------AGGTGGGTTTTTGACTTTGCATGTCGAAGTGAGA | 36 |
| SEQ ID No:163 | TTCCTTTACAGCACAAGTAGATCACTTGTACTTATCAAAATTCGGAACTGACACACGACATGATGGA-CGTGACTAAGGTGGGTTTTTGACTTTGCATGTCG | 10 |
| SEQ ID No:164 | TTCCTTTACAGCACAAGTAGATCACTTGTACTTATCAAAATTCGGAACTGACACACGACATGATGGAAC**TTT**ACTAAGGTGGGTTTTTGACTTTGCATGTC | 8 |
| SEQ ID No:165 | TTCCTTTACAGCACAAGTAGATCACTTGTACTTATCAAAATTCGGAACTGACACACGACATGATGGAACGTGAC-AAGGTGGGTTTTTGACTTTGCATGTCG | 6 |
| SEQ ID No:166 | TTCCTTTACAGCACAAGTAGATCACTTGTACTTATCAAAATTCGGAACTGACACACTACATTATTTAAC**TTT**ACTAAGGTGGGTTTTTGACTTTGCATGTC | 3 |

FIG. 11C

U6-13.1:DD43CR1+EF1A2:CAS9

| | | |
|---|---|---|
| SEQ ID NO:144 | AGCTGTAAATACAGCCTTACAACTCACAAGTCCCTTGTACTTGTACGTACGGAGGGTATTCTAGAAAAGAGGAATTGGAGTCTGCCTCTTCTTTTAGTCCTAAATTAA | Count |
| **SEQ ID NO:167** | AGCTGTAAATACAGCCTTACAACTCACAAGTCCCTTGTACTTGTACGTACGGAGGGTATTCTAGAAAAGAGGAATTGGAGTCTGCCTCTTCTTTTAGTCCTAAATTAA | 136 |
| **SEQ ID NO:168** | AGCTGTAAATACAGCCTTACAACTCACAAGTCCCTTGTA----------CGGAGGGTATTCTAGAAAAGAGGAATTGGAGTCTGCCTCTTCTTTTAGTCCTAAATTAAA | 131 |
| **SEQ ID NO:169** | AGCTGTAAATACAGCCTTACAACTCACAAGTCCCTTGTACTTGTA----CGGAGGGTATTCTAGAAAAGAGGAATTGGAGTCTGCCTCTTCTTTTAGTCCTAAAT | 63 |
| **SEQ ID NO:170** | AGCTGTAAATACAGCCTTACAACTCACAAGTCCCTT------------ACGGAGGGTATTCTAGAAAAGAGGAATTGGAGTCTGCCTCTTCTTTTAGTCCTAAATTAAA | 58 |
| **SEQ ID NO:171** | AGCTGTAAATACAGCCTTACAACTCACAAGTCCCTTGTACTTGTAC**C**GTACGGAGGGTATTCTAGAAAAGAGGAATTGGAGTCTGCCTCTTCTTTTAGTCC | 52 |
| **SEQ ID NO:172** | AGCTGTAAATACAGCCTTACAACTCACAAGTCCCTTGTACT-----GTACGGAGGGTATTCTAGAAAAGAGGAATTGGAGTCTGCCTCTTCTTTTAGTCCTAAATT | 15 |
| **SEQ ID NO:173** | AGCTGTAAATACAGCCTTACAACTCACAAGTCCCTTGTAGT-------ACGGAGGGTATTCTAGAAAAGAGGAATTGGAGTCTGCCTCTTCTTTTAGTCCTAAATTAA | 14 |
| **SEQ ID NO:174** | AGCTGTAAATACAGCCTTACAACTCACAAGTCCCTTGTACTTGTACGT----AGGGTATTCTAGAAAAGAGGAATTGGAGTCTGCCTCTTCTTTTAGTCCTAAAT | 10 |
| **SEQ ID NO:175** | AGCTGTAAATACAGCCTTACAACTCACAAGTCC-**TACACTCTTTCCCTACACGACG**-----------------------------CTCTTCTTTTAGTCCTAAATTAAA | 5 |
| **SEQ ID NO:176** | AGCTGTAAATACAGCCTTACAACTCACAAGTCCCTTGTACTTGTAC**CT**TACGGAGGGTATTCTAGAAAAGAGGAATTGGAGTCTGCCTCTTCTTTTAGTCC | 5 |

FIG. 11D

U6-13.1:DD43CR2+EF1A2:CAS9

| | | |
|---|---|---|
| SEQ ID NO:145 | CTAGGTAAATACAGCCTTACAACTCACAAGTCCCTTGTACTTGTACGTACGGAGGGTATTCTAGAAAAGAGGAATTGGAGTCTGCCTCTTCTTTTAGTCCTAAATTAA | Count |
| SEQ ID NO:177 | CTAGGTAAATACAGCCTTACAACTCACAAGTCCCTTGTACTTGTACGTACGGAGGGTATTCTAGAAAA------TTGGAGTCTGCCTCTTCTTTTAGTCCTAAATTA | 137 |
| SEQ ID NO:178 | CTAGGTAAATACAGCCTTACAACTCACAAGTCCCTTGTACTTGTACGTACGGAGGGTATTCTAGAAAAGA---ATTGGAGTCTGCCTCTTCTTTTAGTCCTAAA | 126 |
| SEQ ID NO:179 | CTAGGTAAATACAGCCTTACAACTCACAAGTCCCTTGTACTTGTACGTACGGAGGGTATTCTAGAA--------TTGGAGTCTGCCTCTTCTTTTAGTCCTAAATTAAA | 118 |
| SEQ ID NO:180 | CTAGGTAAATACAGCCTTACAACTCACAAGTCCCTTGTACTTGTACGTACGGAGGGTATTCTAGAAAAGA--AATTGGAGTCTGCCTCTTCTTTTAGTCCTAA | 115 |
| SEQ ID NO:181 | CTAGGTAAATACAGCCTTACAACTCACAAGTCCCTTGTACTTGTACGTACGGAGGGTATTCTAGAAAA-----ATTGGAGTCTGCCTCTTCTTTTAGTCCTAAATT | 102 |
| SEQ ID NO:182 | CTAGGTAAATACAGCCTTACAACTCACAAGTCCCTTGTACTTGTACGTACGGAGGGTATTCTAGAAAAGAGG-ATTGGAGTCTGCCTCTTCTTTTAGTCCTA | 81 |
| SEQ ID NO:183 | CTAGGTAAATACAGCCTTACAACTCACAAGTCCCTTGTACTTGTACGTACGGAGGGTATTCTAGAAA-------TTGGAGTCTGCCTCTTCTTTTAGTCCTAAATTAA | 75 |
| SEQ ID NO:184 | CTAGGTAAATACAGCCTTACAACTCACAAGTCCCTTGTACTTGTACGTACGGAGGGTATTCTA-----------TTGGAGTCTGCCTCTTCTTTTAGTCCTAAATTAAAGAT | 61 |
| SEQ ID NO:185 | CTAGGTAAATACAGCCTTACAACTCACAAGTCCCTTGTACTTGTACGTACGGAGGGTATTCTAG----------------TCTGCCTCTTCTTTTAGTCCTAAATTAAAGATC | 58 |
| SEQ ID NO:186 | CTAGGTAAATACAGCCTTACAACTCACAAGTCCCTTGTACTTGTACGTACGGAGGGTATTCTAGAAAAG-----------TCTGCCTCTTCTTTTAGTCCTAAATTAAAGAT | 44 |
| SEQ ID NO:187 | CTAGGTAAATACAGCCTTACAACTCACAAGTCCCTTGTACTTGTACGTACGGAGGGTATTCTAGAAAAGA-GAATTGGAGTCTGCCTCTTCTTTTAGTCCTA | 41 |
| SEQ ID NO:188 | CTAGGTAAATACAGCCTTACAACTCACAAGTCCCTTGTACTTGTACGTACGGAGGGTATTCTAGAAAAGAGGA------GTCTGCCTCTTCTTTTAGTCCTAAATTA | 34 |
| SEQ ID NO:189 | CTAGGTAAATACAGCCTTACAACTCACAAGTCCCTTGTACTTGTACGTACGGAGGGTATTCTA----------ATTGGAGTCTGCCTCTTCTTTTAGTCCTAAATTAAAGA | 33 |
| SEQ ID NO:190 | CTAGGTAAATACAGCCTTACAACTCACAAGTCCCTTGTACTTGTACGTACGGAGGGTATTCTAGAAAAGAGGAA**A**TTGGAGTCTGCCTCTTCTTTTAGTCC | 28 |
| SEQ ID NO:191 | CTAGGTAAATACAGCCTTACAACTCACAAGTCCCTTGTACTTGTACGTACGGAGGGTATTCTAGAAA-GAGGAATTGGAGTCTGCCTCTTCTTTTAGTCCTA | 27 |

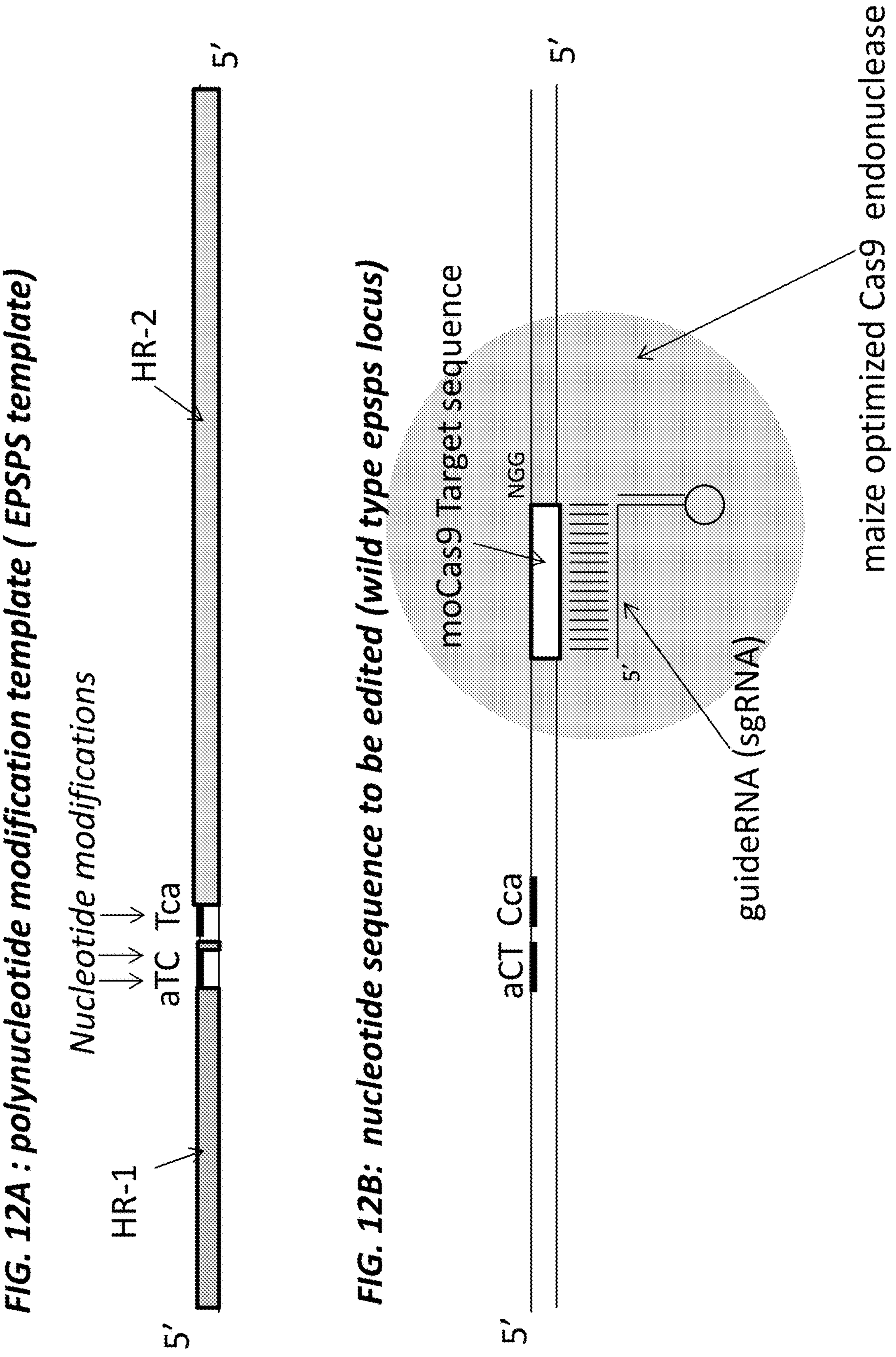
FIG. 12A : polynucleotide modification template ( EPSPS template)
FIG. 12B: nucleotide sequence to be edited (wild type epsps locus)

FIG. 14

*Events with Intact moCas target sequence (underlined)*

SEQ ID NO: 205 GGGGAATGCTGGAACTGCAATGCGGCCATTGACAGCAGCTGTTACTGCTGCTGGTGGAAATGC

*Events with mutagenized moCas target sequences (underlined)*

SEQ ID NO: 206 GGGGAATGCTGGAACTGCAATGCGGCCATTG---GCAGCTGTTACTGCTGCTGGTGGAAATGC

SEQ ID NO: 207 GGGGAATGCTGGAACTGCA-------------CAGCAGCTGTTACTGCTGCTGGTGGAAATGC

SEQ ID NO: 208 GGGGAATGCTG------------------------------TTACTGCTGCTGGTGGAAATGC

FIG. 19A MHP14 locus

MHP14Cas-1

GTTAAATCTGACGTGAATCTGTTTGGAATTGAAAAACAAGTGCTTCCTTTCATACACCACTATGTCGCTTCAATGTTTGT SEQ ID NO:237
CAATTTAGACTGCACTTAGACAAACCTTAACTTTTTGTTCACGAAGGAAAGTATGTGGTGATACAGCGAAGTTACAAACA SEQ ID NO:238

MHP14Cas-3

FIG. 19B TS8 locus

CCAGTACTGCACGTTACGTACGTACGAACTAATATACTCCACCAGCTGATCACTGATGAGCCGAGC SEQ ID NO: 239
GGTCATGACGTGCAATGCATGCATGCTTGATTATATGAGGTGGTCGACTAGTGACTACTCGGCTCG SEQ ID NO: 240

TS8Cas-1 TS8Cas-2

FIG. 19C TS9 locus

CCGACGTGCGTGCAACCTCGAGGCCGCAAACAGCC SEQ ID NO:241
GGCTGCACGCACGTTGGAGCTCCGGCGTTTGTCGG SEQ ID NO:242

TS9Cas-3 TS9Cas-2

FIG. 19D TS10 locus

TS10Cas-3

GCTCGTGTTGGAGATACAGGGACAGCAAGTACTTGGCCCTTAACTAGCGAAGGCGAGGCGGCCATGGA SEQ ID NO:243
CGAGCACAACCTCTATGTCCCTGTCGTTCATGAACCGGGAATTGATCGCTTCCGCTCCGCCGGTACCT SEQ ID NO:244

TS10Cas-1

FIG. 23 A) Linked gRNA and Cas9 gene expression cassettes
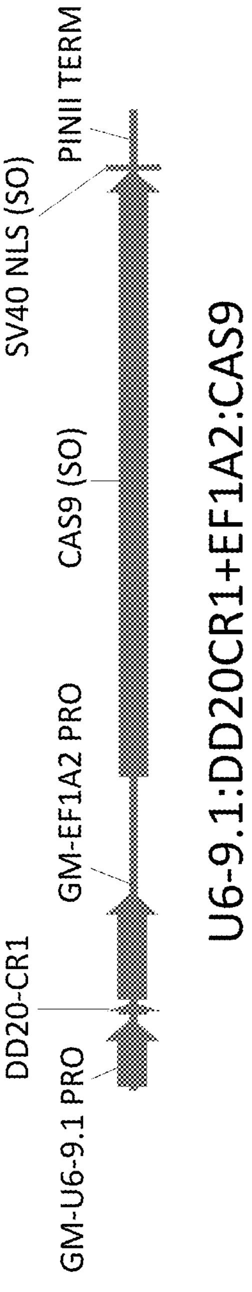
FIG. 23 B) Repair DNA cassette with homologous regions.
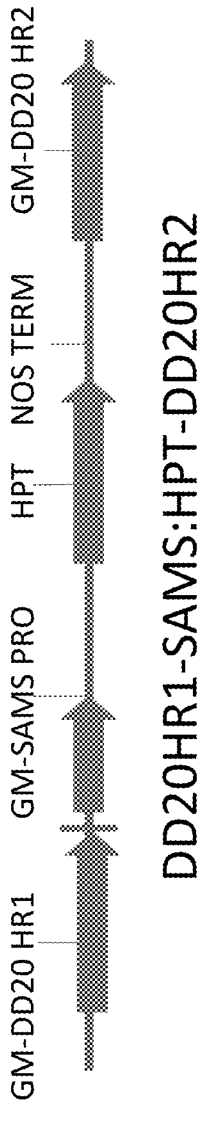

FIG. 24 A) Diagram of Glycine max chromosome 04 indicating relative positions of DD20 and DD43 target sites.
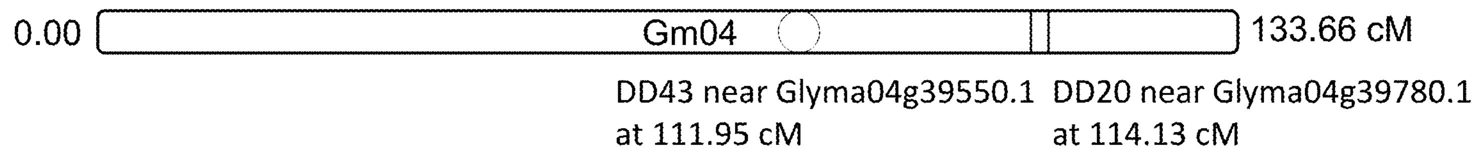
FIG. 24 B) DD20 qPCR amplicon, 45936307-45936370
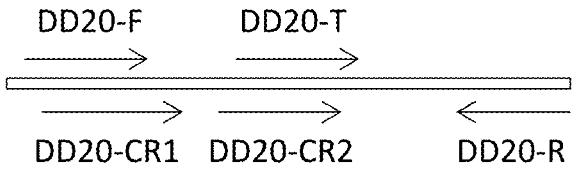
FIG. 24 C) DD43 qPCR amplicon, 45731879-45731993
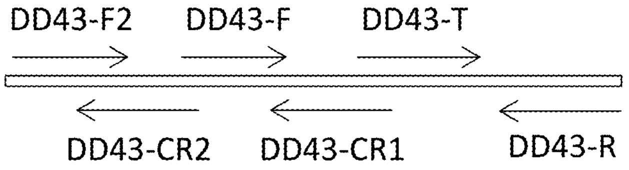

FIG. 25 A) Transiently expressed gRNA and Cas9 assembled in vivo capable to cleave genomic DNA at target DD20.
FIG. 25 B) DNA break repaired by NHEJ.
FIG. 25 C) DNA break repaired by HR.
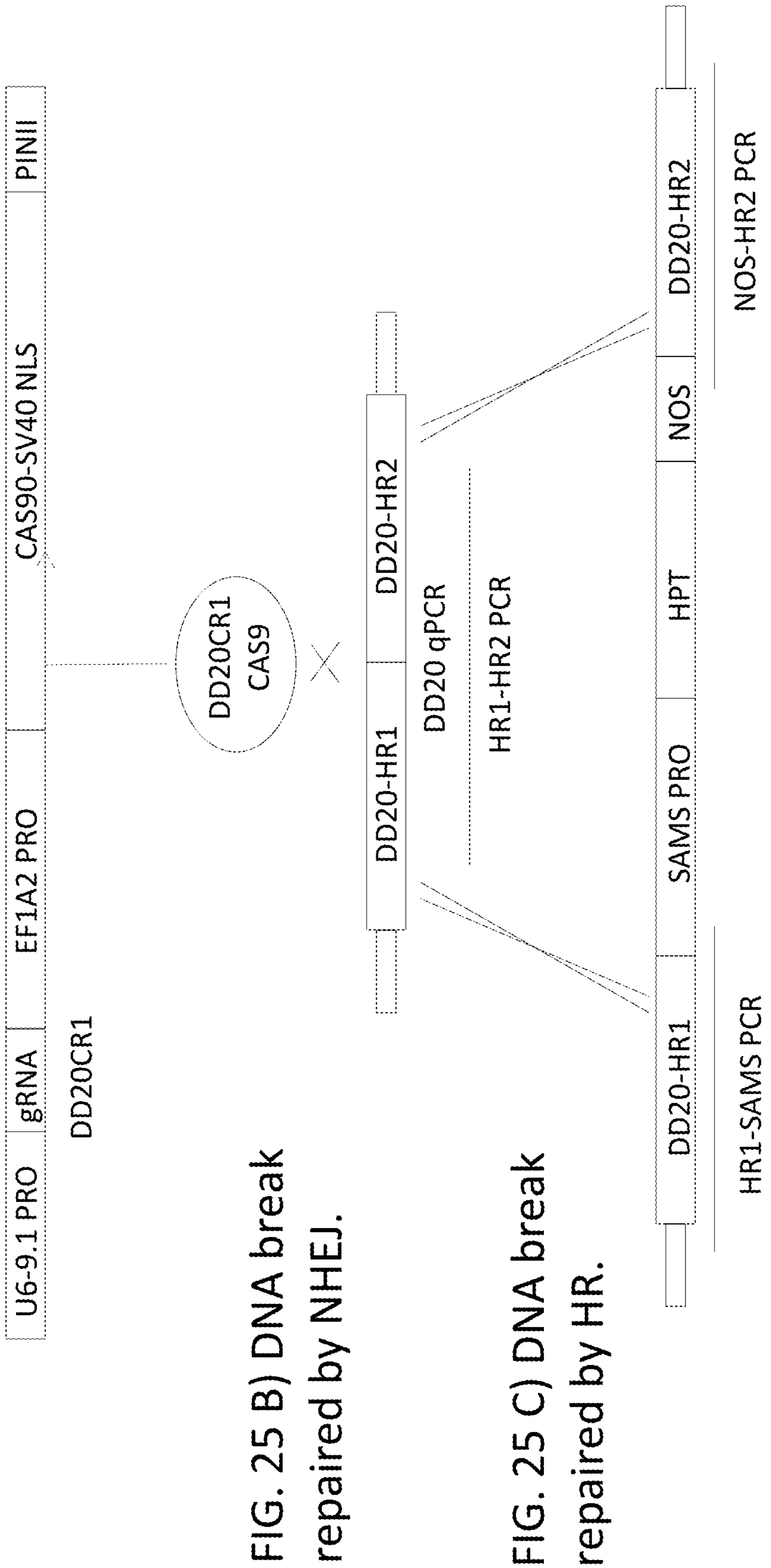

FIG. 26A

DD20CR1 target site

SEQID NO:335 ACTTGTACTTATCAAAATTCGGAACTGACACACGACATGATGGAACGTGACTAAGGTGGG
SEQID NO:336 ACTTGTACTTATCAAAATTCGGAACTGACACACGAC-TGATGGAACGTGACTAAGGTGGG
SEQID NO:337 ACTTGTACTTATCAAAATTCGGAACTGACACACGA-ATGATGGAACGTGACTAAGGTGGG
SEQID NO:338 ACTTGTACTTATCAAAATTCGGAACTGACACACGA--TGATGGAACGTGACTAAGGTGGG
SEQID NO:339 ACTTGTACTTATCAAAATTCGGAACTGACACACGAC--GATGGAACGTGACTAAGGTGGG
SEQID NO:340 ACTTGTACTTATCAAAATTCGGAACTGACACACGG--TGATGGAACGTGACTAAGGTGGG
SEQID NO:341 ACTTGTACTTATCAAAATTCGGAACTGACACAC---ATGATGGAACGTGACTAAGGTGGG
SEQID NO:342 ACTTGTACTTATCAAAATTCGGAACTGACACACG---TGATGGAACGTGACTAAGGTGGG
SEQID NO:343 ACTTGTACTTATCAAAATTCGGAACTGACACAC----TGATGGAACGTGACTAAGGTGGG
SEQID NO:344 ACTTGTACTTATCAAAATTCGGAACTGACACACG----GATGGAACGTGACTAAGGTGGG
SEQID NO:345 ACTTGTACTTATCAAAATTCGGAACTGACACAC-----GATGGAACGTGACTAAGGTGGG
SEQID NO:346 ACTTGTACTTATCAAAATTCGGAACTGACACA-----TGATGGAACGTGACTAAGGTGGG
SEQID NO:347 ACTTGTACTTATCAAAATTCGGAACTGACACAC------ATGGAACGTGACTAAGGTGGG
SEQID NO:348 ACTTGTACTTATCAAAATTCGGAACTGACAC------TGATGGAACGTGACTAAGGTGGG
SEQID NO:349 ACTTGTACTTATCAAAATTCGGAACTGACAC-------GATGGAACGTGACTAAGGTGGG
SEQID NO:350 ACTTGTACTTATCAAAATTCGGAACTGA---------TGATGGAACGTGACTAAGGTGGG
SEQID NO:351 ACTTGTACTTATCAAAATTCGGAACTGACA----------TGGAACGTGACTAAGGTGGG
SEQID NO:352 ACTTGTACTTATCAAAATTCGGAACTG----------TGATGGAACGTGACTAAGGTGGG
SEQID NO:353 ACTTGTACTTATCAAAATTCGGAACTGACACAC---------GAACGTGACTAAGGTGGG
SEQID NO:354 ACTTGTACTTATCAAAATTCGGAACTGACAC----------GGAACGTGACTAAGGTGGG
SEQID NO:355 ACTTGTACCTATCAAAATTCGGAACTGA-----------ATGGAACGTGACTAAGGTGGG
SEQID NO:356 ACTTGTACTTATCAAAATTCGGAACTGA------------TGGAACGTGACTAAGGTGGG
SEQID NO:357 ACTTGTACTTATCAAAATTCGGAACTGA--------------GAACGTGACTAAGGTGGG
SEQID NO:358 ACTTGTACTTATCAAAATTCGGAACTGACACACGACAT^TC-----------------GG
SEQID NO:359 ACTTGTACTTATCAAAATTCGGAACTGACA----------------------AAGGTGGG
SEQID NO:360 ACTTGTACTTATCAAAATTCGGAAC---------------------GTGACTAAGGTGGG
SEQID NO:361 ACT------------------------------------ATGGAACGTGACTAAGGTGGG

Insertion starts at ^ with the insert size indicated.

SEQID NO:362 ACTTGTACTTATCAAAATTCGGAACTGACACACG^155-GATGGAACGTGACTAAGGTGGG
SEQID NO:363 ACTTGTACTTATCAAAA^50-----------------TGATGGAACGTGACTAAGGTGGG

FIG. 26B

DD20CR2 target site

```
SEQID NO:364   GACACACGACATGATGGAACGTGACTAAGGTGGGTTTTTGACTTTGCATGTCGAAGTGAG
SEQID NO:365   GACACACGACATGATGGAACGTGAACTAAGGTGGGTTTTTGACTTTGCATGTCGAAGTGAG
SEQID NO:366   GACACACGACATGATGGAACGTA-CTAAGGTGGGTTTTTGACTTTGCATGTCGAAGTGAG
SEQID NO:367   GACACACGACATGATGGAACGT--CTAAGGTGGGTTTTTGACTTTGCATGTCGAAGTGAG
SEQID NO:368   GACACACGACATGATGGAACGTGA--AAGGTGGGTTTTTGACTTTGCATGTCGAAGTGAG
SEQID NO:369   GACACACGACATGATGGAACG---CTAAGGTGGGTTTTTGACTTTGCATGTCGAAGTGAG
SEQID NO:370   GACACACGACATGATGGAACGTG---AAGGTGGGTTTTTGACTTTGCATGTCGAAGTGAG
SEQID NO:371   GACACACGACATGATGGAACGTG----AGGTGGGTTTTTGACTTTGCATGTCGAAGTGAG
SEQID NO:372   GACACACGACATGATGGAACG----TAAGGTGGGTTTTTGACTTTGCATGTCGAAGTGAG
SEQID NO:373   GACACACGACATGATGGAAC----CTAAGGTGGGTTTTTGACTTTGCATGTCGAAGTGAG
SEQID NO:374   GACACACGACATGATGGAACGTG----AGGTGGGTTTTTGACTTTGCATGTCGAAGTGAG
SEQID NO:375   GACACACGACATGATGGAA-----CTAAGGTGGGTTTTTGACTTTGCATGTCGAAGTGAG
SEQID NO:376   GACACACGACATGATGGAA------TAAGGTGGGTTTTTGACTTTGCATGTCGAAGTGAG
SEQID NO:377   GACACACGACATGATGG-------CTAAGGTGGGTTTTTGACTTTGCATGTCGAAGTGAG
SEQID NO:378   GACACACGACATGATGGA-------TAAGGTGGGTTTTTGACTTTGCATGTCGAAGTGAG
SEQID NO:379   GACACACGACATGATGGA---------AGGTGGGTTTTTGACTTTGCATGTCGAAGTGAG
SEQID NO:380   GACACACGACATGATGG----------AGGTGGGTTTTTGACTTTGCATGTCGAAGTGAG
SEQID NO:381   GACACACGACATGATGG----------------GTTTTTGACTTTGCATGTCGAAGTGAG
SEQID NO:382   GACACACGAC-----------------AGGTGGGTTTTTGACTTTGCATGTCGAAGTGAG
SEQID NO:383   GACAC--------------------TAAGGTGGGTTTTTGACTTTGCATGTCGAAGTGAG
SEQID NO:384   GACACACGACATGATGGAAC-----------------------------------GTGAG
SEQID NO:385   GACACACGACATGATGG--------133bp deletion---------------------
```

FIG. 26C

DD43CR1 target site

```
SEQID NO:386   AGCCTTACAACTCACAAGTCCCTTGTACTTGTACGTACGGAGGGTATTCTAGAAAAGAGG
SEQID NO:387   AGCCTTACAACTCACAAGTCCCTTGTACTTGTAC-TACGGAGGGTATTCTAGAAAAGAGG
SEQID NO:388   AGCCTTACAACTCACAAGTCCCTTGTACTTGTA-GTACGGAGGGTATTCTAGAAAAGAGG
SEQID NO:389   AGCCTTACAACTCACAAGTCCCTTGTACTTGT--GTACGGAGGGTATTCTAGAAAAGAGG
SEQID NO:390   AGCCTTACAACTCACAAGTCCCTTGTACTTG--CGTACGGAGGGTATTCTAGAAAAGAGG
SEQID NO:391   AGCCTTACAACTCACAAGTCCCTTGTACTTG---GTACGGAGGGTATTCTAGAAAAGAGG
SEQID NO:392   AGCCTTACAACTCACAAGTCCCTTGTACTTGT---TACGGAGGGTATTCTAGAAAAGAGG
SEQID NO:393   AGCCTTACAACTCACAAGTCCCTTGTACTT----GTACGGAGGGTATTCTAGAAAAGAGG
SEQID NO:394   AGCCTTACAACTCACAAGTCCCTTGTACTT-----TACGGAGGGTATTCTAGAAAAGAGG
SEQID NO:395   AGCCTTACAACTCACAAGTCCCTTGTACT-----GTACGGAGGGTATTCTAGAAAAGAGG
SEQID NO:396   AGCCTTACAACTCACAAGCCCCTTGTACT------TACGGAGGGTATTCTAGAAAAGAGG
SEQID NO:397   AGCCTTACAACTCACAAGTCCCTTGTA--------TACGGAGGGTATTCTAGAAAAGAGG
SEQID NO:398   AGCCTTACAACTCACAAGTCCCTTGT--------GTACGGAGGGTATTCTAGAAAAGAGG
SEQID NO:399   AGCCTTACAACTCACAAGTCCCTTG----------TACGGAGGGTATTCTAGAAAAGAGG
SEQID NO:400   AGCCTTACAACTCACAAGTCCCTT-----------TACGGAGGGTATTCTAGAAAAGAGG
SEQID NO:401   AGCCTTACAACTCACAAGTCCCT------------TACGGAGGGTATTCTAGAAAAGAGG
SEQID NO:402   AGCCTTACAACTCACAAGTCCC-------------TACGGAGGGTATTCTAGAAAAGAGG
SEQID NO:403   AGCCTTACAACTCACAAGTCCCTTGTACTTGTA-----------------AGAAAAGAGG
SEQID NO:404   AGCCTTACAACTCACAAGTCC----------TAAATTAA^AGGTTATTCTAGAAAAGAGG
Insertion starts at ^ with the insert size indicated.
SEQID NO:405   AGCCTTACAACTCACAAGTCCCTTGTACTTGTAC^167GTACGGAGGGTATTCTAGAAAAGAGG
SEQID NO:406   AGCCTTACAACTCACAAGTCCCTTGTACTTGTA^38--GTACGGAGGGTATTCTAGAAAAGAGG
SEQID NO:407   AGCCTTACAACTCACAAGTCCCTTGTA^130-------GTACGGAGGGTATTCTAGAAAAGAGG
SEQID NO:408   AGCCTTACAACTCACAAGTCCCTTGTACTTGTAC^171GTACGGAGGGTATTCTAGAAAAGAGG
SEQID NO:409   AGCCTTACAACTCACAAGTCCCTTGTACTTGTAC^220GTACGGAGGGTATTCTAGAAAAGAGG
SEQID NO:410   AGCCTTACAACTCACAAGTCCCTTGTACTTGTAC^190GTACGGAGGGTATTCTAGAAAAGAGG
SEQID NO:411   AGCCTTACAACTCACAAGTCCCTT^110----------GTACGGAGGGTATTCTAGAAAAGAGG
SEQID NO:412   AGCCTTACAACTCACAAGTCCCTTGTACTTGTAC^125GTACGGAGGGTATTCTAGAAAAGAGG
SEQID NO:413   AGCCTTACAACTCACAAGTCCCTTGTACTTGTAC^154GTACGGAGGGTATTCTAGAAAAGAGG
SEQID NO:414   AGCCTTACAACTCACAAGTCCCTTGTACTTGTA^177------GAGGGTATTCTAGAAAAGAGG
```

FIG. 27A

Expected Site of Cleavage

PAM

| LIGCas-1 | | SEQ ID NO: |
|---|---|---|
| CTGTAACGATTTACGCACCTGCTGGGAATTGTACCGTACGTGCCCCGGCGGAGGATATATATACCTCACACGTACGCGTACGCGTATATATAC | Count | 55 |
| TCCTCTGTAACGATTTACGCACCTGCTGGGAATTGTACCGTACGTGCCCCGGTCGGAGGATATATATACCTCACACGTACGCGTACGCGTATATATAC | 2116 | 415 |
| TCCTCTGTAACGATTTACGCACCTGCTGGGAATTGTACCGTACGTGCCCCGGACGGAGGATATATATACCTCACACGTACGCGTACGCGTATATATAC | 1156 | 416 |
| TCCTCTGTAACGATTTACGCACCTGCTGGGAATTGTACCGTACGTGCCCCGGGCGGAGGATATATATACCTCACACGTACGCGTACGCGTATATATAC | 473 | 417 |
| TCCTCTGTAACGATTTACGCACCTGCTGGGAATTGTACCGTACGTGCCCCGGCCGGAGGATATATATACCTCACACGTACGCGTACGCGTATATATAC | 161 | 418 |
| TCCTCTGTAACGATTTACGCACCTGCTGGGAATTGTACCGTACGTGCCCCGGATCGGAGGATATATATACCTCACACGTACGCGTACGCGTATATATAC | 133 | 419 |
| TCCTCTGTAACGATTTACGCACCTGCTGGGAATTGTACCGTACGTGCCCCGG---AGGATATATATACCTCACACGTACGCGTACGCGTATATATAC | 82 | 420 |
| TCCTCTGTAACGATTTACGCACCTGCTGGGAATTGTACCGTACGTGCCCCGG----------------TTCACACGTACGCGTACGCGTATATATAC | 77 | 421 |
| TCCTCTGTAACGATTTACGCACCTGCTGGGAATTGTACCGTACGT--------------------------------ACGCGTACGCGTATATATAC | 55 | 422 |
| TCCTCTGTAACGATTTACGCACCTGCTGGGAATTGTACCGTACGTGCCCCGGTTCGGAGGATATATATACCTCACACGTACGCGTACGCGTATATATAC | 39 | 423 |
| TCCTCTGTAACGATTTACGCACCTGCTGGGAATTGTACCGTACGTGCCCC--CGGAGGATATATATACCTCACACGTACGCGTACGCGTATATATAC | 39 | 424 |

FIG. 27B

Expected Site of Cleavage

PAM

| LIGCas-2 | | SEQ ID NO: |
|---|---|---|
| CTGTAACGATTTACGCACCTGCTGGGAATTGTACCGTACGTGCCCCGGCGGAGGATATATATACCTCACACGTACGCGTACGCGTATATATAC | Count | 55 |
| GAAGCTGTAACGATTTACGCACCTGCTGGGAATTGTACCGTACGTGACCCCGGCGGAGGATATATATACCTCACACGTACGCGTACGCGTATATATAC | 1048 | 425 |
| GAAGCTGTAACGATTTACGCACCTGCTGGGAATTGTACCGTACGTGTCCCCGGCGGAGGATATATATACCTCACACGTACGCGTACGCGTATATATAC | 743 | 426 |
| GAAGCTGTAACGATTTACGCACCTGCTGGGAATTGTACCGTACGT-CCCCGGCGGAGGATATATATACCTCACACGTACGCGTACGCGTATATATAC | 543 | 427 |
| GAAGCTGTAACGATTTACGCACCTGCTGGGAATTGTACCGTACGTGGCCCCGGCGGAGGATATATATACCTCACACGTACGCGTACGCGTATATATAC | 220 | 428 |
| GAAGCTGTAACGATTTACGCACCTGCTGGGAATTGTACCGTACGTGCACCCCGGCGGAGGATATATATACCTCACACGTACGCGTACGCGTATATATAC | 193 | 429 |
| GAAGCTGTAACGATTTACGCACCTGCTGGGAATTGTACC-----------CGGCGGAGGATATATATACCTCACACGTACGCGTACGCGTATATATAC | 159 | 430 |
| GAAGCTGTAACGATTTACGCACCTGCTGGGAATTGTACCGT-----CCCCGGCGGAGGATATATATACCTCACACGTACGCGTACGCGTATATATAC | 137 | 431 |
| GAAGCTGTAACGATTTACGCACCTGCTGGGAATTGTACCGTAC---CCCCGGCGGAGGATATATATACCTCACACGTACGCGTACGCGTATATATAC | 94 | 432 |
| GAAGCTGTAACGATTTACGCACCTGCTGGGAATTGTACCGTACG--CCCCGGCGGAGGATATATATACCTCACACGTACGCGTACGCGTATATATAC | 93 | 433 |
| GAAGCTGTAACGATTTACGCACCTGCTGGGAATTGTACC----------CCGGCGGAGGATATATATACCTCACACGTACGCGTACGCGTATATATAC | 60 | 434 |

FIG. 27C

Expected Site of Cleavage

PAM

| LIGCas-3 | | SEQ ID NO: |
|---|---|---|
| CGCAAATGAGTAGCAGCGCACGTATATATACGCGTACGCGTACGTGTGAGGTATATATATCCTCCGCCGGGGCACGTACGGTACAATTCCCAG | Count | 76 |
| AAGGCGCAAATGAGTAGCAGCGCACGTATATATACGCGTACGCGTACGT*T*GTGAGGTATATATATCCTCCGCCGGGGCACGTACGGTACAATTCCCAG | 1208 | 435 |
| AAGGCGCAAATGAGTAGCAGCGCACGTATATATACGCGTACGCGTACG-GTGAGGTATATATATCCTCCGCCGGGGCACGTACGGTACAATTCCCAG | 453 | 436 |
| AAGGCGCAAATGAGTAGCAGCGCACGTATATATACGCGTACGCGTACGT--GAGGTATATATATCCTCCGCCGGGGCACGTACGGTACAATTCCCAG | 338 | 437 |
| AAGGCGCAAATGAGTAGCAGCGCACGTATATATACGCGTACGCGTAC-TGTGAGGTATATATATCCTCCGCCGGGGCACGTACGGTACAATTCCCAG | 145 | 438 |
| AAGGCGCAAATGAGTAGCAGCGCACGTATATATA-----------------------------TCCTCCGCCGGGGCACGTACGGTACAATTCCCAG | 94 | 439 |
| AAGGCGCAAATGAGTAGCAGCGCACGTATATATACGCGTACGCGT----GTGAGGTATATATATCCTCCGCCGGGGCACGTACGGTACAATTCCCAG | 53 | 440 |
| AAGGCGCAAATGAGTAGCAGCGCACGTATATATACGCGTACG--------TGAGGTATATATATCCTCCGCCGGGGCACGTACGGTACAATTCCCAG | 42 | 441 |
| AAGGCGCAAATGAGTAGCAGCGCACGTATATATACGCGTACGCGTAC--------TATATATATCCTCCGCCGGGGCACGTACGGTACAATTCCCAG | 37 | 442 |
| AAGGCGCAAATGAGTAGCAGCGCACGTATATATACGCGTACGCGTACG---GAGGTATATATATCCTCCGCCGGGGCACGTACGGTACAATTCCCAG | 20 | 443 |
| AAGGCGCAAATGAGTAGCAGCGCACGTATATATACGCGTACGCGTACG-ATGAGGTATATATATCCTCCGCCGGGGCACGTACGGTACAATTCCCAG | 19 | 444 |

FIG. 34 A

| | |
|---|---|
| **VEDAKEEV** | **Maize** |
| GKESKEEI | Petunia |
| GKKSEEEI | Tomato |
| EKDAKEEV | Sorghum |
| VEDSKEEV | Rice |
| GKDGKEEI | Amarathus |

FIG. 34 B

K T P moCas9 target sequence

GCTAAAGAGGAAGTGCAGCTCTTCTTGGGGAATGCTGGAACTGCAATGCGGCCATTGACAGCAGCTGTTACTGCTGCTGG

FIG. 34 C

R I S moCas9 target sequence

GCTAGAGAGGAAGTGCAGCTCTTCTTGGGGAATGCTGGAATCGCAATGCGGTCATTGACAGCAGCTGTTACTGCTGCTGG

FIG. 35 A

CATATCTG

FIG. 35 B

CATCTC...ACGATCAGAT..GCACCGCATGTCGCATGCCTA

FIG. 35 C

CATATCTGCACGATCAGATATGCACCGCATGTCGCATATCTG

FIG. 37

Intron Exon

GTTTTTGAACTTCAGTTACGTGCTTGATGGA (SEQ ID NO: 531)

GTTTTTGAACTTCAGGTACGTGCTTGATGGA (SEQ ID NO: 532)

Splicing site

U6 POLYMERASE III PROMOTER AND METHODS OF USE

CROSS-REFERENCE TO RELATED APPLICATIONS

This application is a Continuation of U.S. application Ser. No. 16/552,632 filed 27 Aug. 2019 now allowed as U.S. Pat. No. 11,427,830, which is a Continuation of U.S. application Ser. No. 14/913,630 filed 22 Feb. 2016 now allowed as U.S. Pat. No. 10,519,457, which is a 371 National Stage Entry of International Patent Application No. PCT/US14/51782 filed 20 Aug. 2014, which claims the benefit of U.S. Provisional Application No. 61/868,706, filed Aug. 22, 2013, U.S. Provisional Application No. 61/882,532, filed Sep. 25, 2013, U.S. Provisional Application No. 61/937,045, filed Feb. 7, 2014, and U.S. Provisional Application No. 62/023,239, filed Jul. 11, 2014; all of which are hereby incorporated herein in their entireties by reference.

FIELD

The disclosure relates to the field of plant molecular biology, in particular, to methods for altering the genome of a plant cell.

REFERENCE TO SEQUENCE LISTING SUBMITTED ELECTRONICALLY

The official copy of the sequence listing is submitted electronically via EFS-Web as an.XML formatted sequence listing with a file named BB2450-US-PCN3.XML created on Feb. 8, 2023 and having a size 926 KB and is filed concurrently with the specification. The sequence listing contained in this .XML formatted document is part of the specification and is herein incorporated by reference in its entirety.

BACKGROUND

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities can be incorporated properly into the plant's genome. The newly integrated gene (or genes) coding sequence can then be expressed in the plant cell to exhibit the desired new trait or characteristic. It is important that appropriate regulatory signals be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters", if the promoters direct RNA synthesis preferentially in certain tissues (RNA synthesis may occur in other tissues at reduced levels). Since patterns of expression of a nucleotides of interest introduced into a plant are controlled using promoters, there is an ongoing interest in the isolation of novel promoters that are capable of controlling the expression of nucleotides of interest at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a polynucleotide of interest such as but not limited to a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

BRIEF SUMMARY

This disclosure concerns a recombinant DNA construct comprising a nucleotide sequence comprising any of the sequences set forth in SEQ ID NO: 120 or SEQ ID NO: 295, or a functional fragment thereof, operably linked to at least one heterologous sequence, wherein said nucleotide sequence is a promoter.

In one embodiment, the disclosure concerns a recombinant DNA construct, wherein the nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:120 or SEQ ID NO: 295.

In one embodiment, the disclosure concerns a vector comprising said recombinant DNA construct.

In one embodiment, the disclosure concerns a cell comprising said recombinant DNA construct of claim 1. The cell can be a plant cell.

In one embodiment, the disclosure concerns a transgenic plant having stably incorporated into its genome said recombinant DNA construct. The transgenic plant can be a dicot plant, such as but not limited to a soybean plant.

In one embodiment, the disclosure concerns a transgenic seed produced by a transgenic plant, wherein the transgenic seed comprises said recombinant DNA construct.

In one embodiment, the disclosure concerns a recombinant DNA construct wherein the at least one heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

In one embodiment, the disclosure concerns a recombinant DNA construct of, wherein the at least one heterologous sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

In one embodiment, the disclosure concerns a method of expressing a coding sequence or a functional RNA in a plant comprising: a) introducing the recombinant DNA construct of claim A1 into the plant, wherein the at least one heterologous sequence comprises a coding sequence or encodes a functional RNA; b) growing the plant of step a); and c) selecting a plant displaying expression of the coding sequence or the functional RNA of the recombinant DNA construct.

In In one embodiment, the disclosure concerns a method of transgenically altering a marketable plant trait, comprising: a) introducing a recombinant DNA construct of claim A1 into the plant; b) growing a fertile, mature plant resulting from step a); and c) selecting a plant expressing the at least one heterologous sequence in at least one plant tissue based on the altered marketable trait. The marketable trait can be selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

In one embodiment, the disclosure concerns a method for altering expression of at least one heterologous sequence in a plant comprising: (a) transforming a plant cell with the recombinant DNA construct of claim 1; (b) growing fertile mature plants from transformed plant cell of step (a); and (c) selecting plants containing the transformed plant cell wherein the expression of the heterologous sequence is increased or decreased.

In one embodiment, the disclosure concerns a plant stably transformed with a recombinant DNA construct comprising a soybean promoter and a heterologous nucleic acid fragment operably linked to said promoter, wherein said promoter is a capable of controlling expression of said heterologous nucleic acid fragment in a plant cell, and further wherein said promoter comprises any of the sequences set forth in SEQ ID NO: 120 or SEQ ID NO: 295.

Additional embodiments of the methods and compositions of the present disclosure are shown herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

Figure 1B:
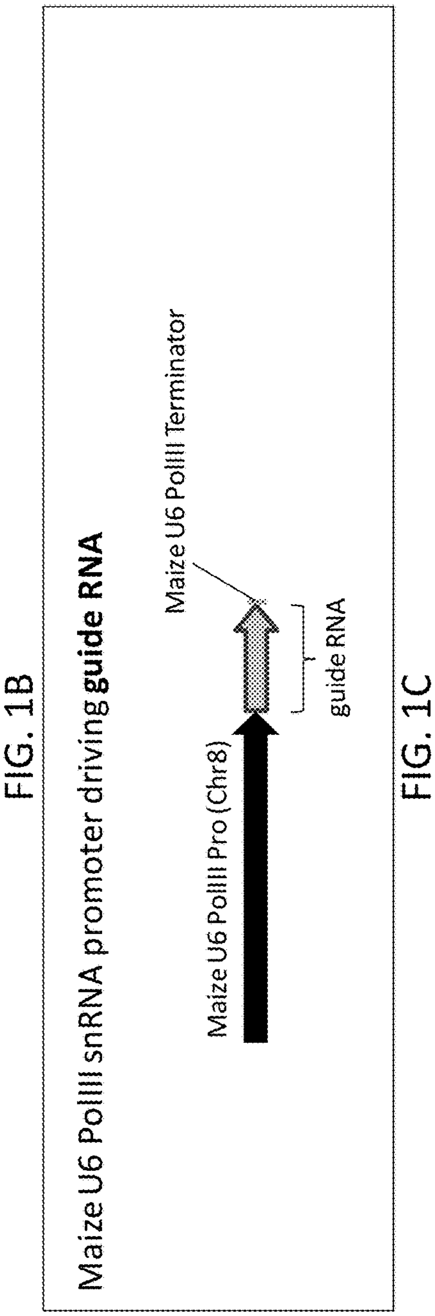
Figure 1C:
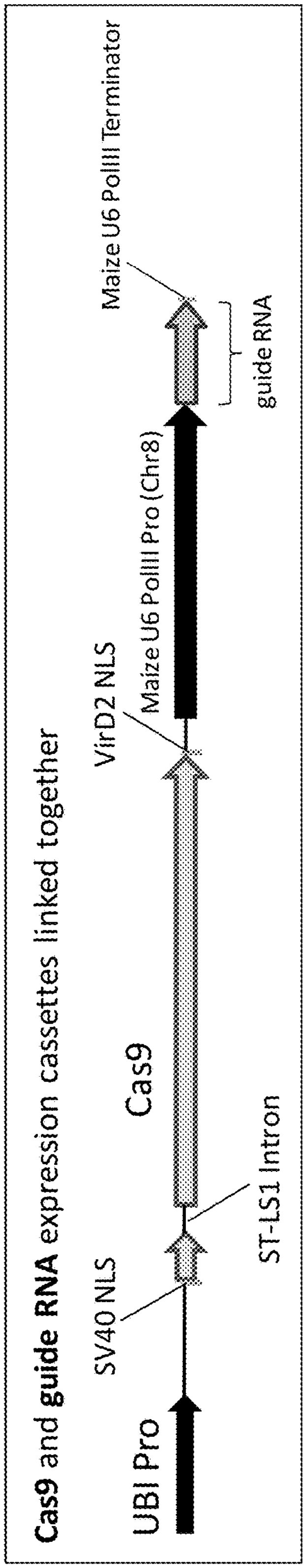

FIG. 1A shows a maize optimized Cas9 gene (encoding a Cas9 endonuclease) containing a potato ST-LS1 intron, a SV40 amino terminal nuclear localization sequence (NLS), and a VirD2 carboxyl terminal NLS, operably linked to a plant ubiquitin promoter (SEQ ID NO: 5). The maize optimized Cas9 gene (just Cas9 coding sequence, no NLSs) corresponds to nucleotide positions 2037-2411 and 2601-6329 of SEQ ID NO: 5 with the potato intron residing at positions 2412-2600 of SEQ ID NO: 5.SV40 NLS is at positions 2010-2036 of SEQ ID NO: 5. VirD2 NLS is at positions 6330-6386 of SEQ ID NO: 5. FIG. 1B shows a long guide RNA operably linked to a maize U6 polymerase III promoter terminating with a maize U6 terminator (SEQ ID NO: 12). The long guide RNA containing the variable targeting domain corresponding to the maize LIGCas-3 target site (SEQ ID NO: 8) is transcribed from/corresponds to positions 1001-1094 of SEQ ID NO: 12. FIG. 1C shows the maize optimized Cas9 and long guide RNA expression cassettes combined on a single vector DNA (SEQ ID NO: 102).

Figure 2A:
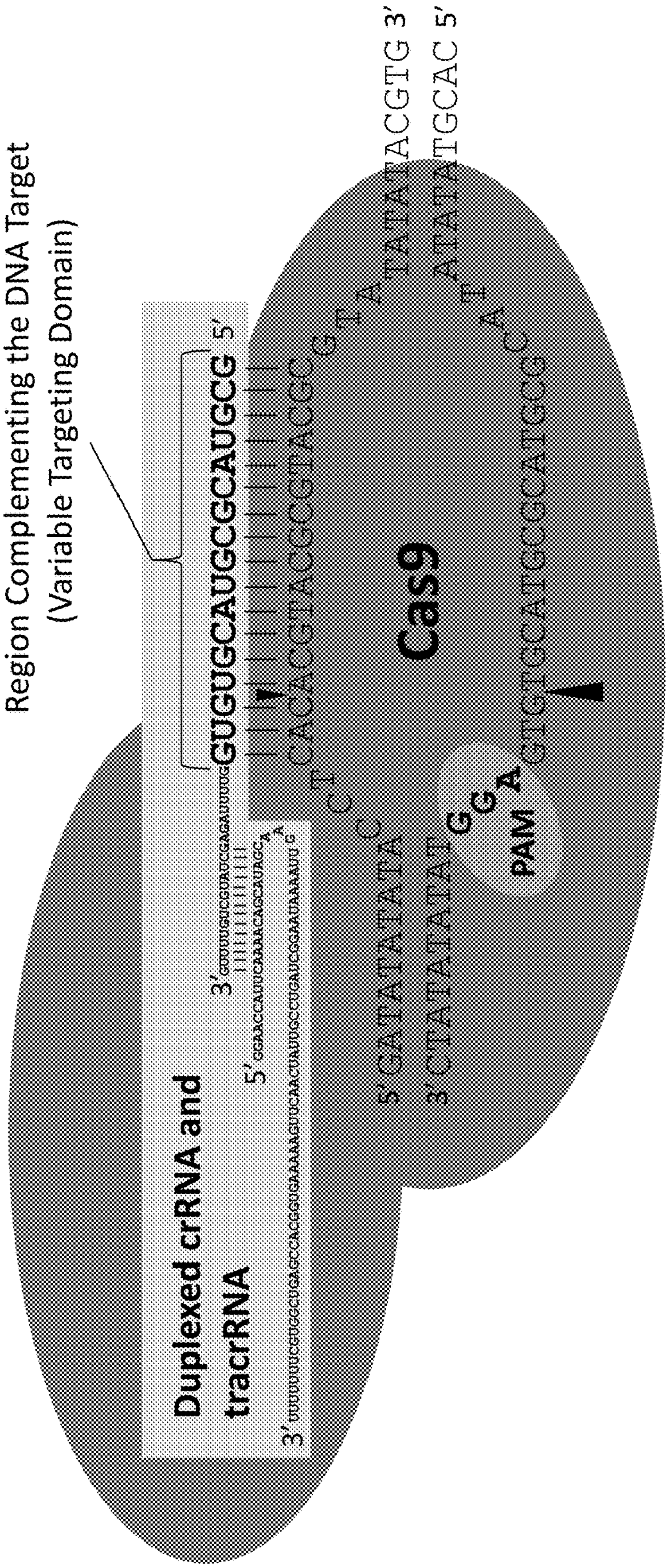
Figure 2B:
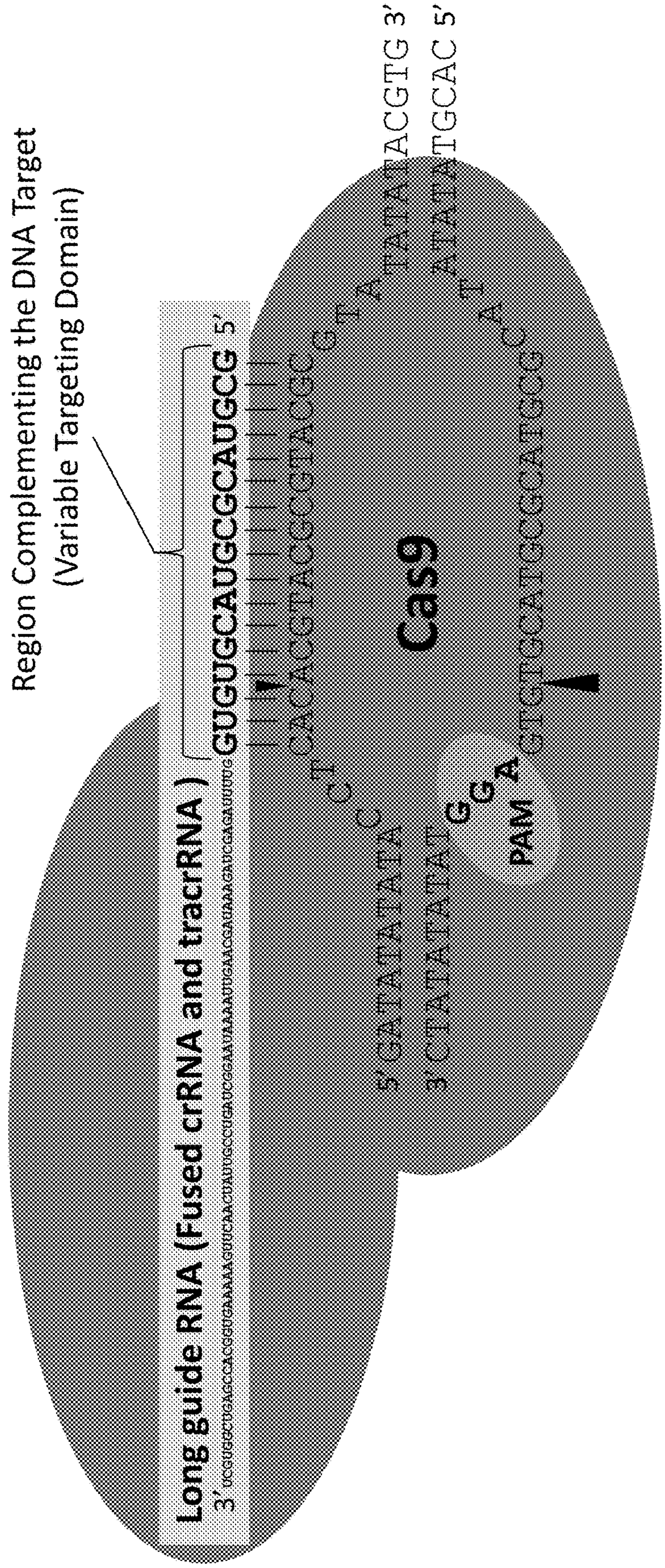

FIG. 2A illustrates the duplexed crRNA (SEQ ID NO:6)-tracrRNA (SEQ ID NO:7)/Cas9 endonuclease system and target DNA complex relative to the appropriately oriented PAM sequence at the maize LIGCas-3 (SEQ ID NO: 18, Table 1) target site with triangles pointing towards the expected site of cleavage on both sense and anti-sense DNA strands. FIG. 2B illustrates the guide RNA/Cas9 endonuclease complex interacting with the genomic target site relative to the appropriately oriented PAM sequence (GGA) at the maize genomic LIGCas-3 target site (SEQ ID NO:18, Table 1). The guide RNA (shown as boxed-in in light gray, SEQ ID NO:8) is a fusion between a crRNA and tracrRNA and comprises a variable targeting domain that is complementary to one DNA strand of the double strand DNA genomic target site. The Cas9 endonuclease is shown in dark gray. Triangles point towards the expected site of DNA cleavage on both sense and anti-sense DNA strands. The sense genome sequence shown in FIGS. 2A and 2B is listed in SEQ ID NO: 551, while the complementary genome sequence shown in FIGS. 2A and 2B is listed in SEQ ID NO: 552.

FIG. 3A-3B shows an alignment and count of the top 10 most frequent NHEJ mutations induced by the maize optimized guide RNA/Cas endonuclease system described herein compared to a LIG3-4 homing endonuclease control at the maize genomic Liguleless 1 locus. The mutations were identified by deep sequencing. The reference sequence represents the unmodified locus with each target site underlined. The PAM sequence and expected site of cleavage are also indicated. Deletions or insertions as a result of imperfect NHEJ are shown by a "-" or an italicized underlined nucleotide, respectively. FIG. 3A: The reference and mutations 1-10 of the LIGCas-1 target site correspond to SEQ ID NOs: 55-65, respectively. The reference and mutations 1-10 of the LIGCas-2 correspond to SEQ ID NOs: 55, 65-75, respectively. FIG. 3B: The reference and mutations 1-10 of the LIGCas-3 correspond to SEQ ID NOs: 76-86, respectively. The reference and mutations 1-10 of the LIG3-4 homing endonuclease target site correspond to SEQ ID NOs: 76, 87-96, respectively.

Figure 4:
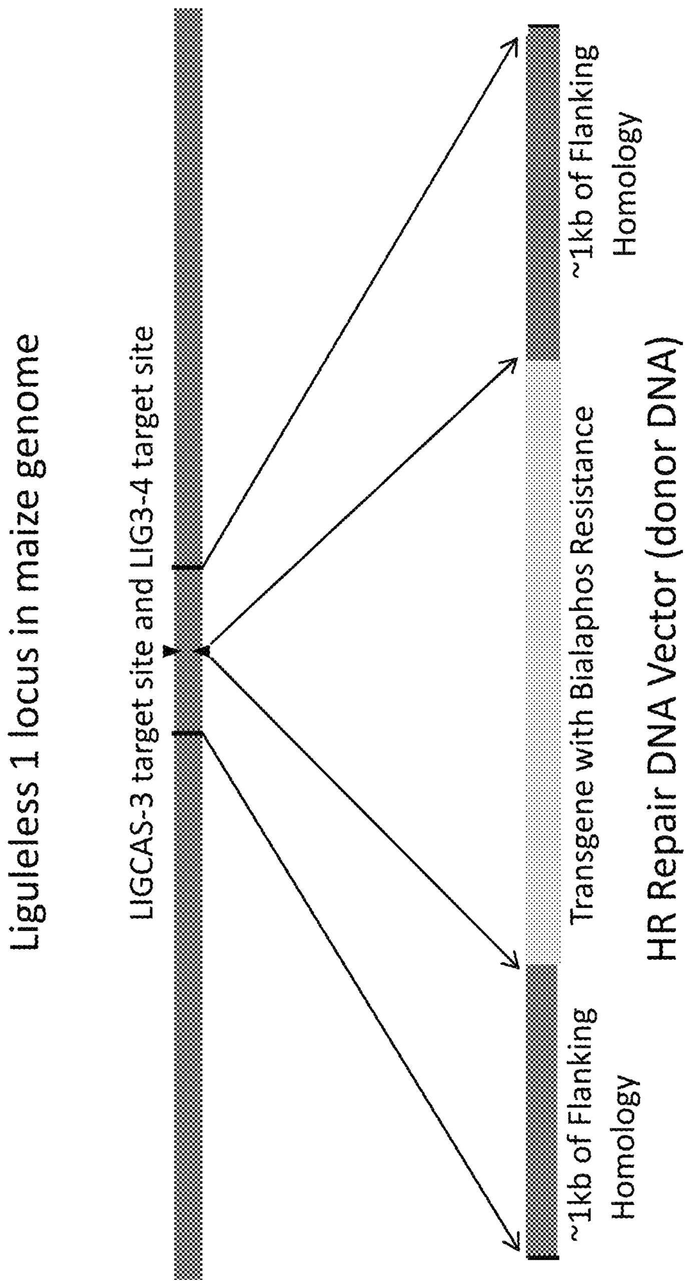

FIG. 4 illustrates how the homologous recombination (HR) repair DNA vector (SEQ ID NO: 97) was constructed. To promote site-specific transgene insertion by homologous recombination, the transgene (shown in light gray) was flanked on either side by approximately 1 kb of DNA with homology to the maize genomic regions immediately adjacent to the LIGCas3 and LIG3-4 homing endonuclease expected sites of cleavage.

Figure 5:
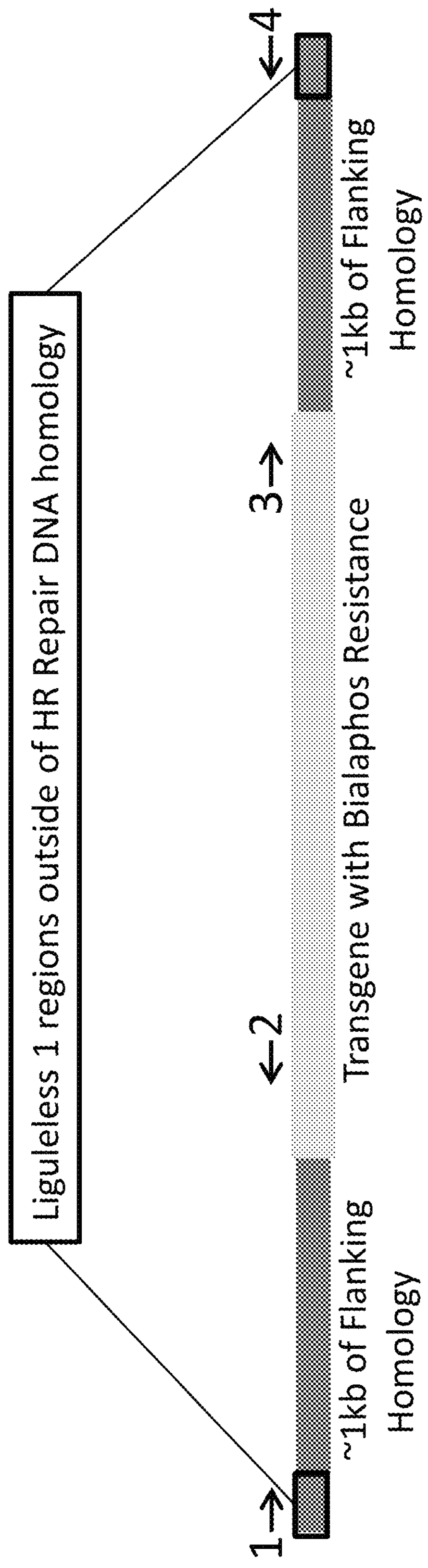

FIG. 5 illustrates how genomic DNA extracted from stable transformants was screened for site-specific transgene insertion by PCR. Genomic primers (corresponding to SEQ ID NOs: 98 and 101) within the Liguleless 1 locus were designed outside of the regions used in constructing the HR repair DNA vector (SEQ ID NO: 97) and were paired with primers inside the transgene (corresponding to SEQ ID NOs: 99 and 100) to facilitate PCR detection of unique genomic DNA junctions created by appropriately oriented site-specific transgene integration.

FIG. 6 shows an alignment of the NHEJ mutations induced by the maize optimized guide RNA/Cas endonuclease system, described herein, when the short guide RNA was delivered directly as RNA. The mutations were identified by deep sequencing. The reference illustrates the unmodified locus with the genomic target site underlined. The PAM sequence and expected site of cleavage are also indicated. Deletions or insertions as a result of imperfect NHEJ are shown by a "-" or an italicized underlined nucleotide, respectively. The reference and mutations 1-6 for 55CasRNA-1 correspond to SEQ ID NOs: 104-110, respectively.

Figure 7:
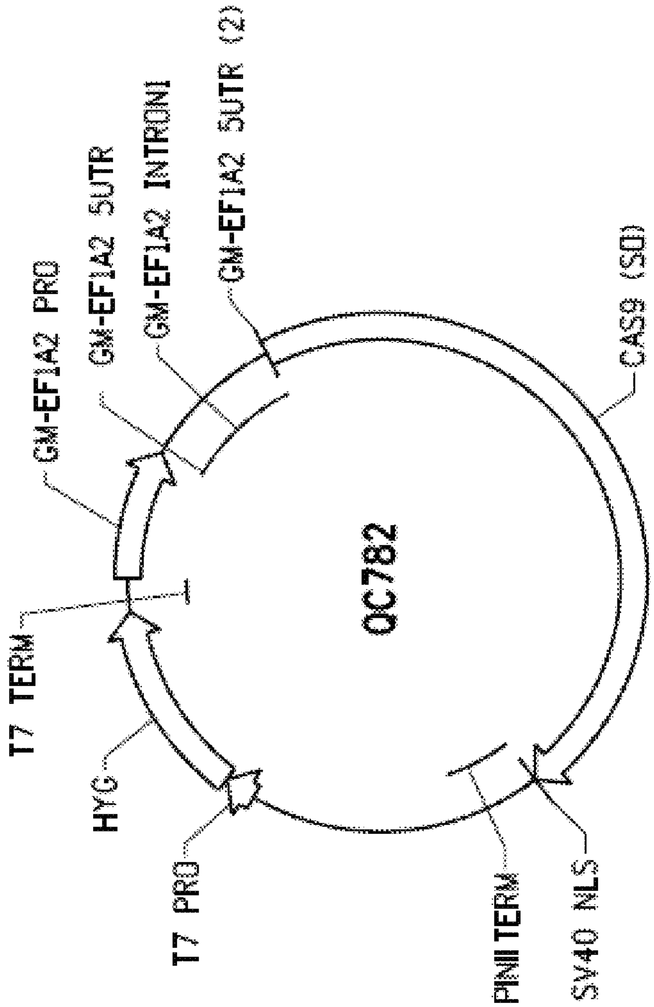

FIG. 7 shows the QC782 vector comprising the Cas9 expression cassette.

Figures 8A, 8B:
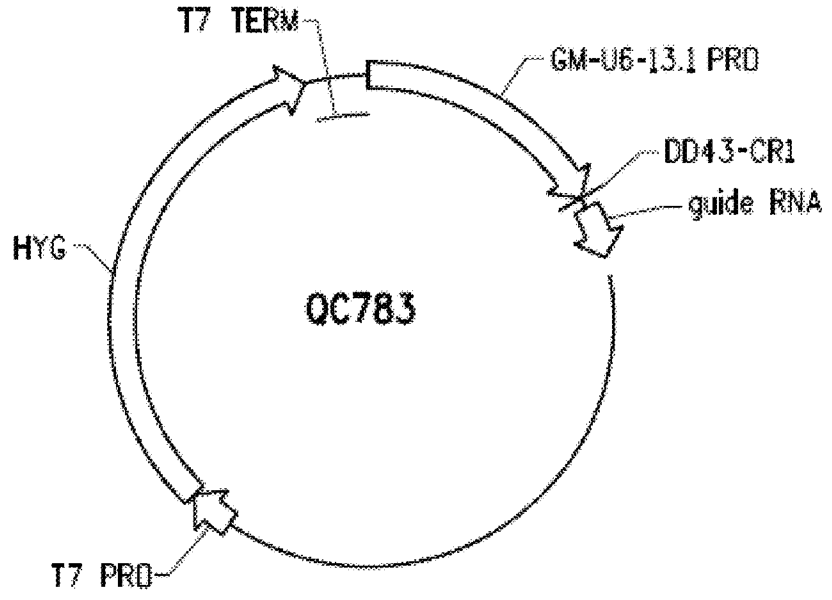

FIG. 8A shows the QC783 vector comprising the guide RNA expression cassette. FIG. 8B show the DNA sequence (coding sequence) of the DD43CR1 (20 bp) variable targeting domain of the guide RNA, as well as the terminator sequence linked to the guide RNA. The 20 bp variable targeting domain DD43CR1 is in bold. The sequence shown in FIG. 8B is listed in SEQ ID NO: 553.

Figure 9:
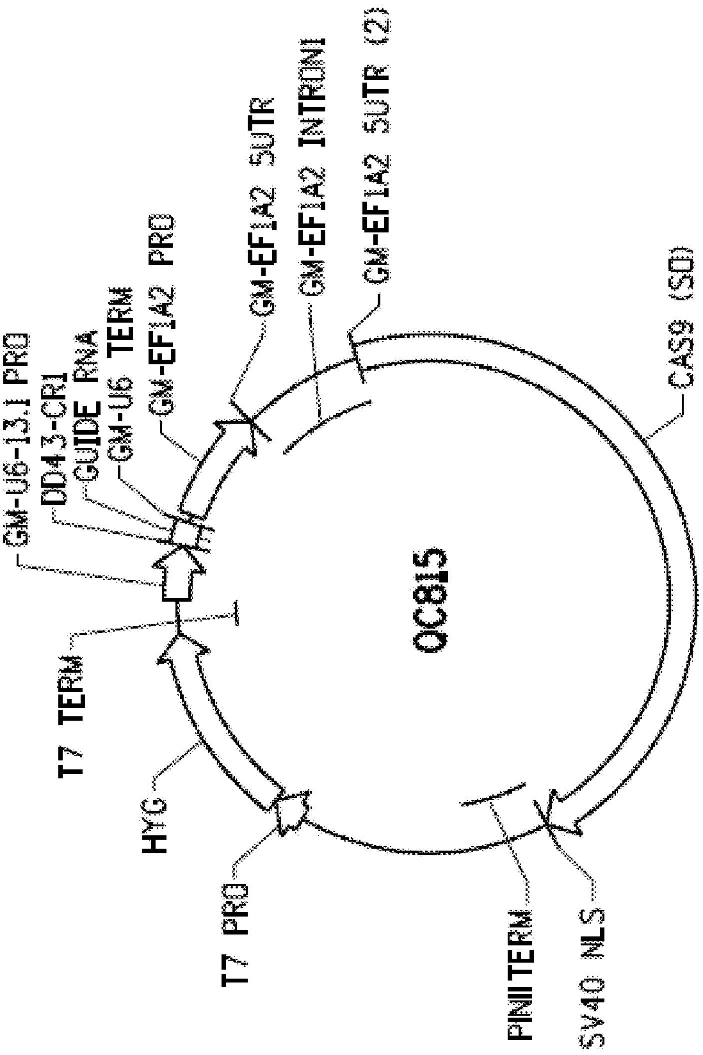

FIG. 9 shows the map of a linked soybean optimized Cas9 and guide RNA construct QC815.

Figure 10A:
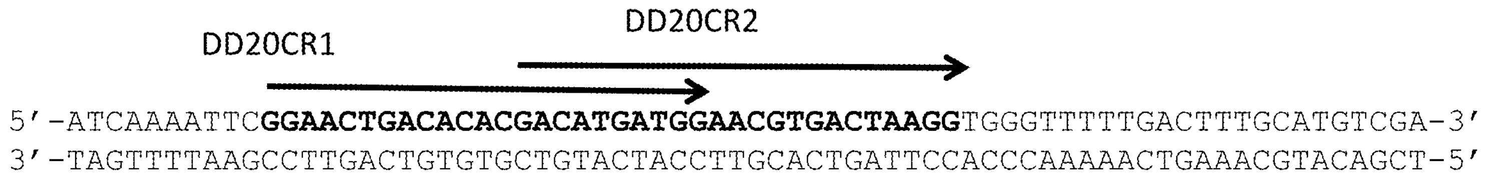
Figure 10B:
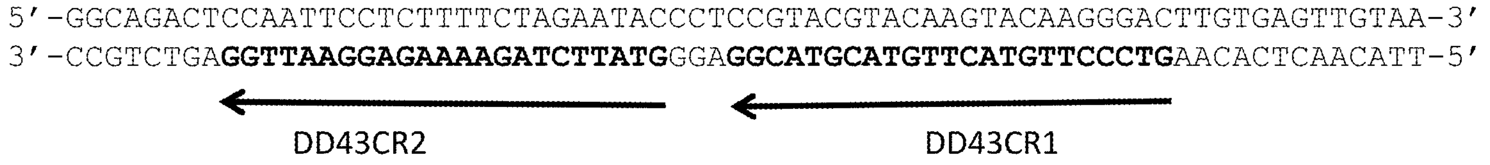

FIG. 10A shows the DD20 soybean locus on chromosome 4 and the DD2OCR1 and DD2OCR2 genomic target sites (indicated by bold arrows). The sense sequence shown in FIG. 10A is listed in SEQ ID NO: 554 and the complementary sequence shown in FIG. 10A is listed in SEQ ID NO: 555. FIG. 10B shows the DD43 soybean locus on chromosome 4 and the DD43CR1 and DD43CR2 genomic target sites (indicated by bold arrows). The sense sequence shown in FIG. 10B is listed in SEQ ID NO: 556 and the complementary sequence shown in FIG. 10B is listed in SEQ ID NO: 557.

FIG. 11A-11D. Alignments of expected target site sequences with mutant target sequences detected in four guide RNAs induced NHEJ experiments. FIG. 11A shows the DD2OCR1 PCR amplicon (reference sequence, SEQ ID NO:142, genomic target site is underlined) and the 10 mutations (SEQ ID NOs: 147-156) induced by the guideRNA/Cas endonuclease system at the DD2OCR1 genomic target site. FIG. 11B shows the DD2OCR2 PCR amplicon (reference sequence, SEQ ID NO:143) and the 10 mutations (SEQ ID NOs 157-166) induced by the guide RNA/Cas endonuclease system at the DD2OCR2 genomic target site. FIG. 11C shows the DD43CR1 PCR amplicon (reference sequence, SEQ ID NO:144) and the 10 mutations (SEQ ID NOs:167-176) induced by the guide RNA/Cas endonuclease system at the DD43CR1 genomic target site. FIG. 11D shows the DD43CR2 PCR amplicon (reference sequence, SEQ ID NO:145) and the 10 mutations (SEQ ID NOs: 177-191) induced by the guide RNA/Cas endonuclease system at the DD43CR2 genomic target site. The target sequences corresponding different guide RNAs are underlined. Each nucleotide deletions is indicated by "-". Inserted and replaced sequences are in bold. The total number of each mutant sequence is listed in the last column.

FIG. 12A-12B shows a schematic representation of the guide RNA/Cas endonuclease system used for editing a nucleotide sequence of interest. To enable specific nucleotide editing, a polynucleotide modification template that includes at least one nucleotide modification (when compared to the nucleotide sequence to be edited) is introduced into a cell together with the guide RNA and Cas endonuclease expression cassettes. For example, as shown herein, the nucleotide sequence to be edited is an endogenous wild type enolpyruvylshikimate-3-phosphate synthase (EPSPS) gene in maize cells. The Cas endonuclease (shaded circle) is a maize optimized Cas9 endonuclease that cleaves a moCas9 target sequence within the epsps genomic locus using a guide RNA of SEQ ID NO:194. FIG. 12-A shows a polynucleotide modification template that includes three nucleotide modifications (when compared to the wild type epsps locus depicted in FIG. 12-B) flanked by two homology regions HR-1 and HR-2. FIG. 12-B shows the guide RNA/maize optimized Cas9 endonuclease complex interacting with the epsps locus. The original nucleotide codons of the EPSPS gene that needed to be edited are show as aCT and Cca (FIG. 12-B). The nucleotide codons with modified nucleotides (shown in capitals) are shown as aTC and Tca (FIG. 12-B).

Figure 13:
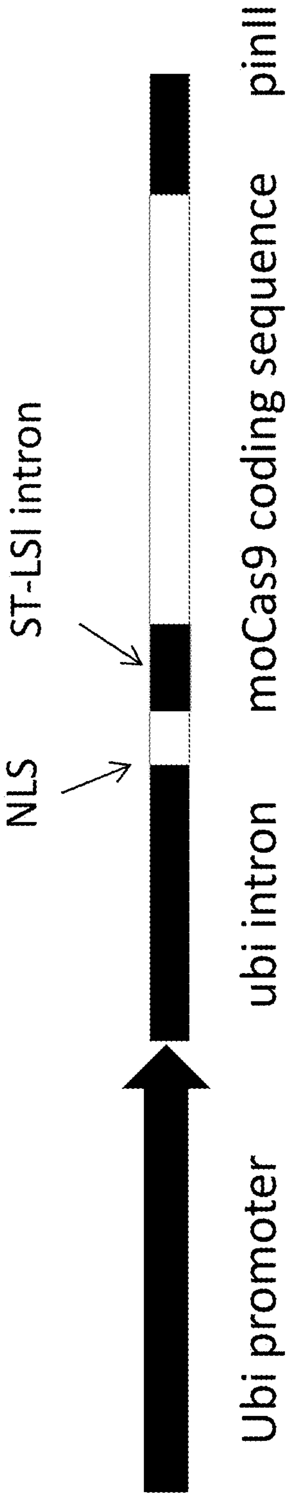

FIG. 13 shows a diagram of a maize optimized Cas9 endonuclease expression cassette. The bacterial cas9 coding sequence was codon optimized for expression in maize cells and supplemented with the ST-LS1 potato intron (moCas9 coding sequence, SEQ ID NO: 193). A DNA fragment encoding the SV40 nuclear localization signal (NLS) was fused to the 5'-end of the moCas9 coding sequence. A maize ubiquitin promoter (Ubi promoter) and its cognate intron (ubi intron) provided controlling elements for the expression of moCas9 in maize cells. The pinll transcription termination sequence (pinll) completed the maize moCAS9 gene design.

Figure 15:
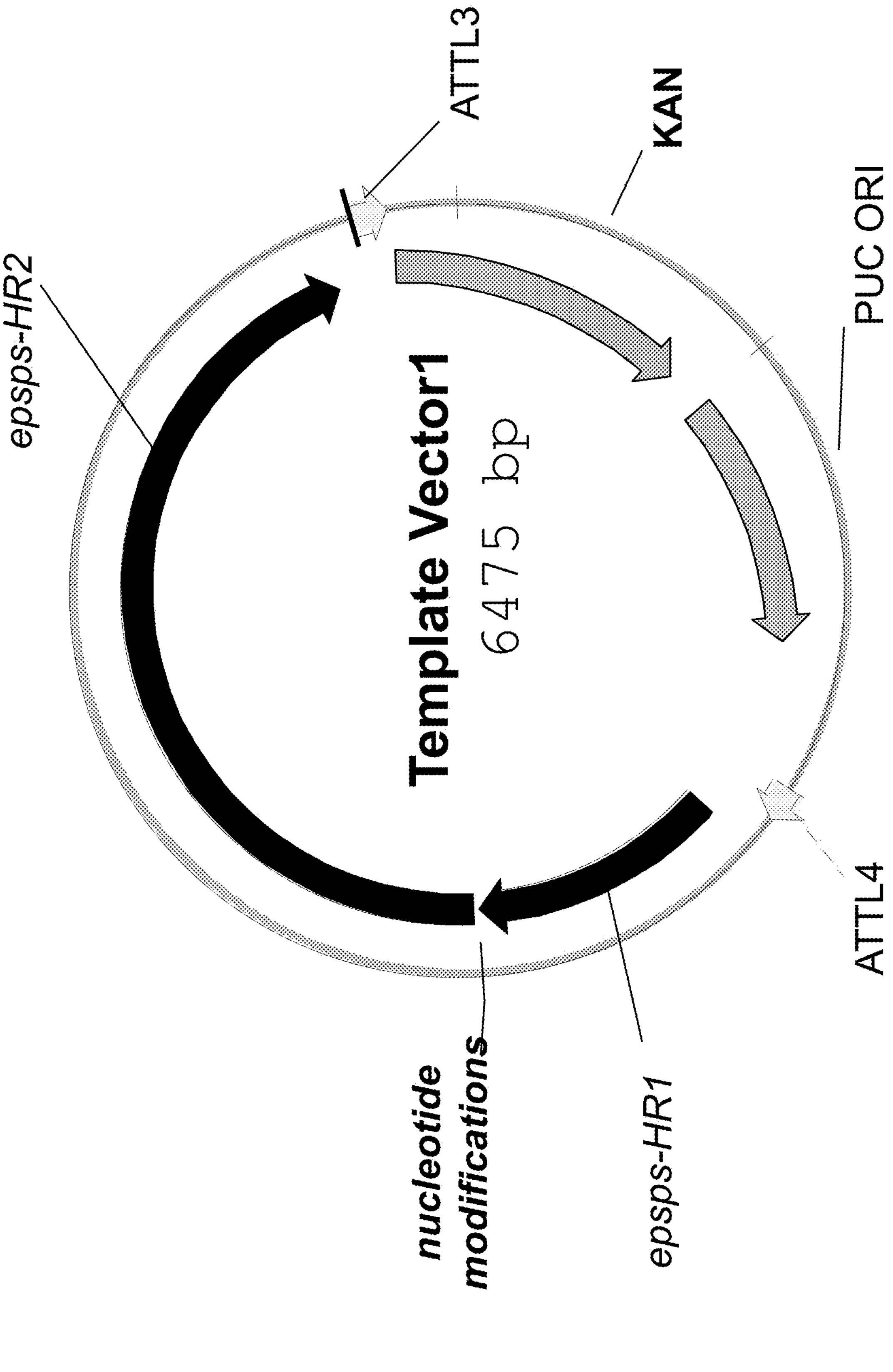

FIG. 14 shows some examples of the moCas9 target sequence (underlined), located on EPSPS DNA fragments, mutagenized by the introduction of double-strand breaks at the cleavage site of the moCas9 endonuclease (thick arrow) in maize cells. In SEQ ID NO: 206, three nucleotides were deleted (dashes) next to the moCas9 cleavage site. SEQ ID NOs: 207-208 indicate that the nucleotide deletion can expand beyond the moCAs9 cleavage site FIG. 15 depicts an EPSPS template vector used for delivery of the EPSPS polynucleotide modification template containing the three TIPS nucleotide modifications. The EPSP polynucleotide modification template includes a partial fragment of the EPSPS gene. The vector was 6,475 bp in length and consisted of two homology regions to the epsps locus (epsps-HR1 and epsps-HR2). Two Gateway cloning sites (ATTL4 and ATTL3), an antibiotic resistance gene (KAN), and the pUC origin of replication (PUC ORI) completed synthesis of the EPSPS template vector1.

Figure 16:
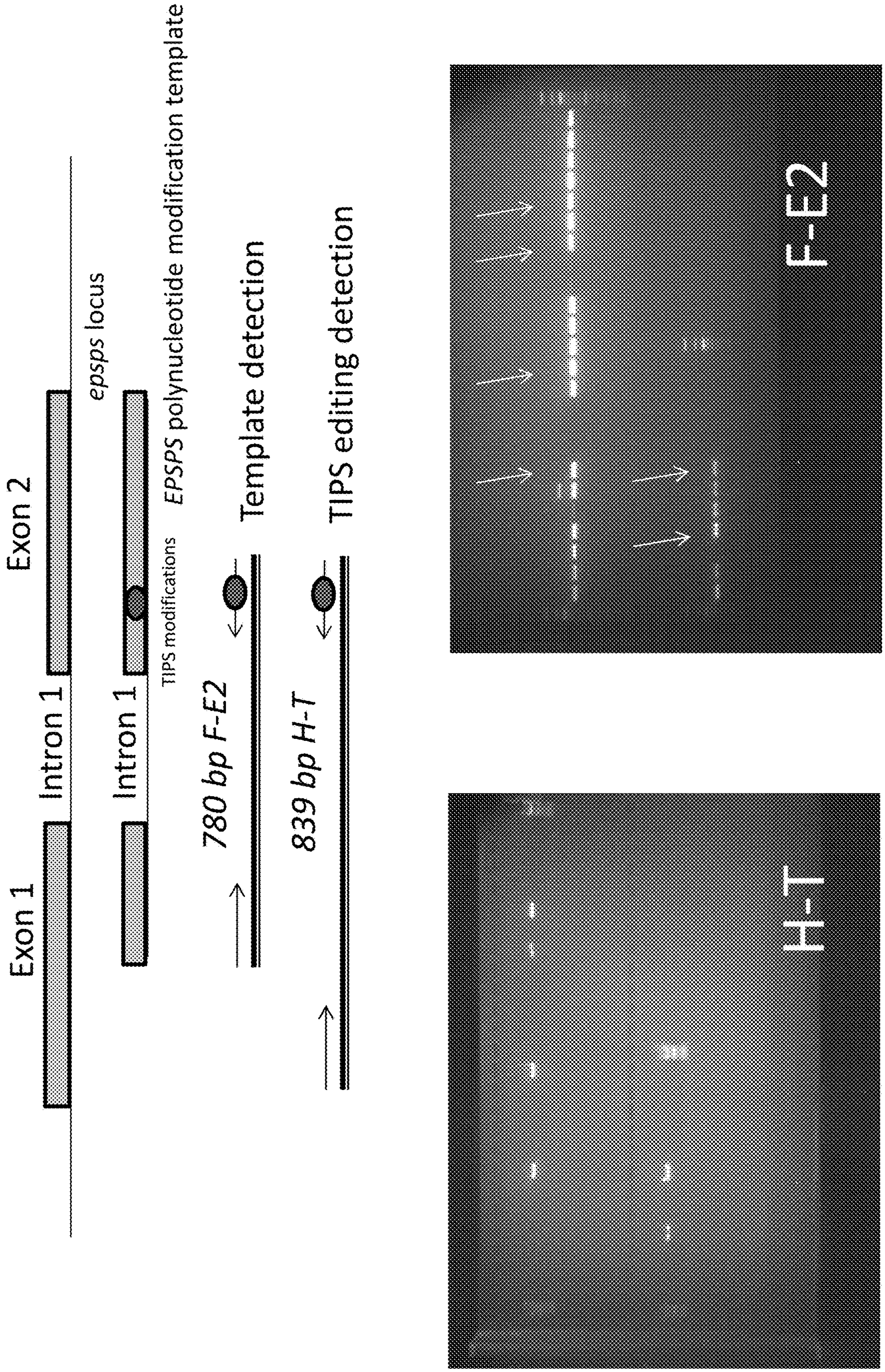

FIG. 16 illustrates the PCR-based screening strategy for the identification of maize events with TIPS nucleotide modifications in maize cells. Two pairs of PCR primers were used to amplify the genomic fragments of the epsps locus (upper section). Both of them contained the TIPS specific primers (an arrow with a dot indicating the site of the three TIPS modifications). The shorter fragment (780 bp F-E2) was produced by amplification of the EPSPS polynucleotide modification template fragment (template detection). The amplified EPSPS polynucleotide modification template fragment was found in all but 4 analyzed events (panel F-E2). The longer fragment (839 bp H-T) was produced by amplification of the genomic EPSPS sequence providing that the epsps locus contained the three nucleotide modifications responsible for the TIPS modifications. Six events were identified as containing the three nucleotide modifications (panel H-T). The white arrows point to events that contain both the amplified EPSPS polynucleotide modification template and the nucleotide modifications responsible for the TIPS modification.

Figure 17A:
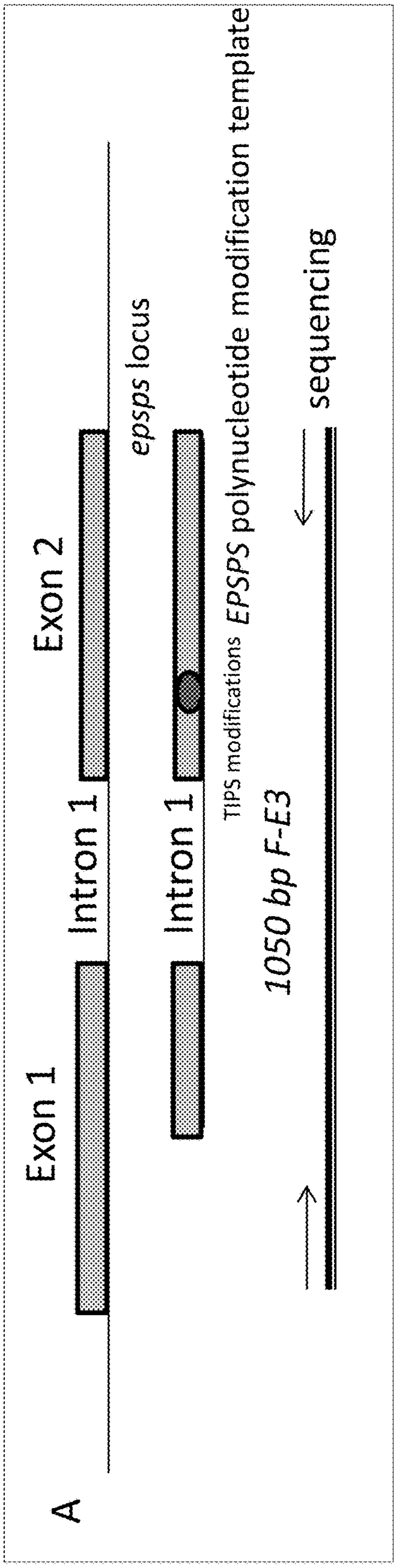
Figure 17B:
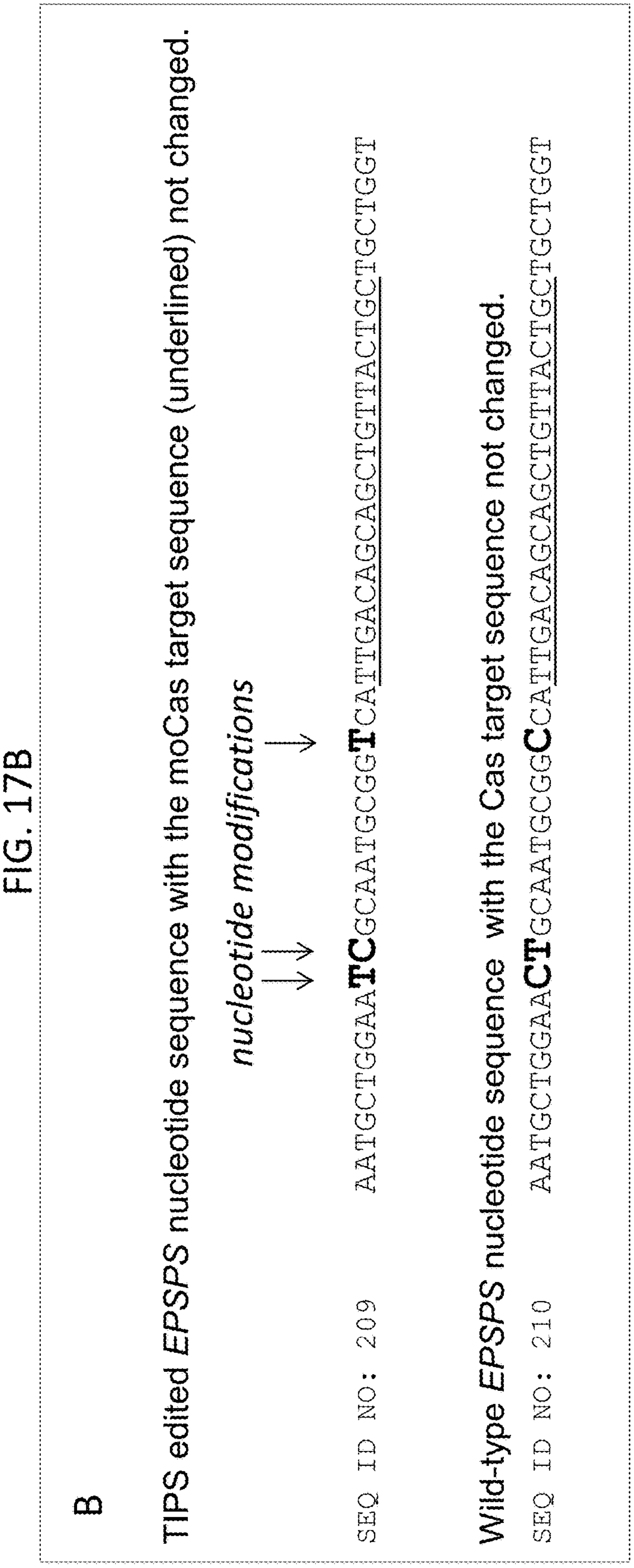

FIG. 17A shows a schematic diagram of the PCR protocol used to identify edited EPSPS DNA fragments in selected events. A partial genomic fragment, comprising parts of Exon1, Intron 1 and Exon2 of the epsps locus, was amplified regardless of the editing product (panel A, 1050 bp F-E3). The amplification products, representing only partial EPSPS gene sequences having one or more mutations, were cloned and sequenced. FIG. 17-B shows 2 examples of sequenced amplification products. In some amplification products, the epsps nucleotides and the moCas9 target sequence (underlined) were unchanged indicating that one EPSPS allele was not edited (wild type allele; SEQ ID NO: 210). In other amplification products, three specific nucleotide substitutions (representing the TIPS modifications) were identified with no mutations at the moCas9 target sequence (underlined) (SEQ ID NO: 209).

Figure 18:
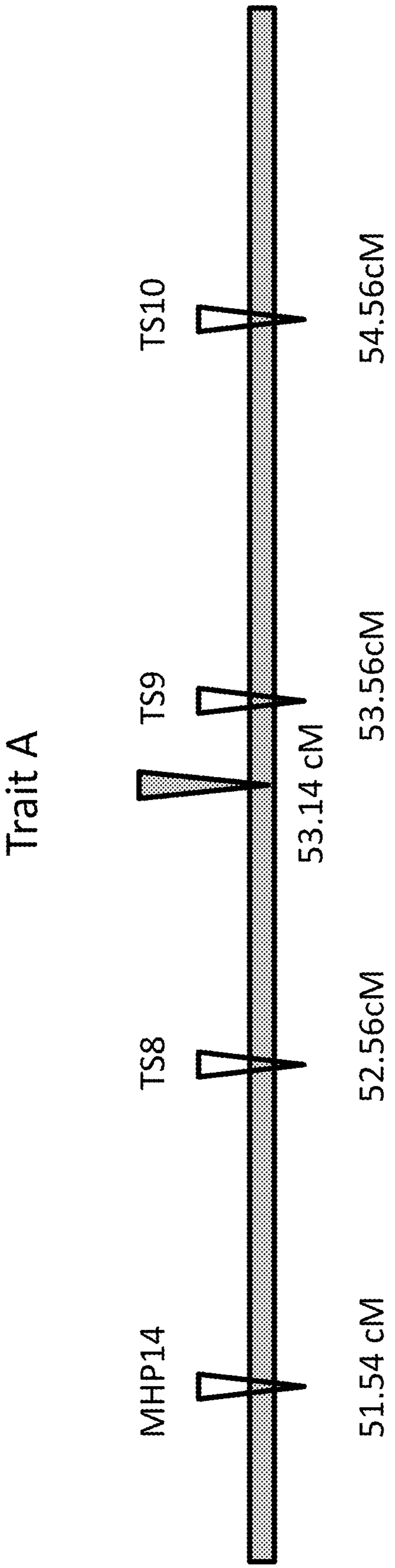

FIG. 18 shows the location of MHP14, TS8, TS9 and TS10 loci comprising target sites for the guide RNA/Cas endonuclease system near trait A (located at 53.14 cM) on chromosome 1 of maize.

FIG. 19A shows the location of the MHP14Cas1 maize genomic target sequence (SEQ ID NO: 229) and the MSP14Cas-3 maize genomic target sequence (SEQ ID NO: 230) on the MHP14 maize genomic DNA locus on chromosome1. The 5' to 3' sequence. FIG. 19B shows the location of the TS8Cas-1 (SEQ ID NO: 231) and TS8Cas-2 (SEQ ID NO: 232) maize genomic target sequences located on the TS8 locus. FIG. 19-C shows the location of the TS9Cas-2 (SEQ ID NO: 233) and TS9Cas-3 (SEQ ID NO: 234) maize genomic target sequences located on the TS8 locus. FIG. 19-D shows the location of the TS10Cas-1 (SEQ ID NO: 235), and TS10Cas-3 (SEQ ID NO: 236) maize genomic target sequences located on the TS10 locus. All these maize genomic target sites are recognized are recognized and cleaved by a guide RNA/Cas endonuclease system described herein. Each maize genomic target sequence (indicated by an arrow) is highlighted in bold and followed by the NGG PAM sequence shown boxed in.

Figure 20:
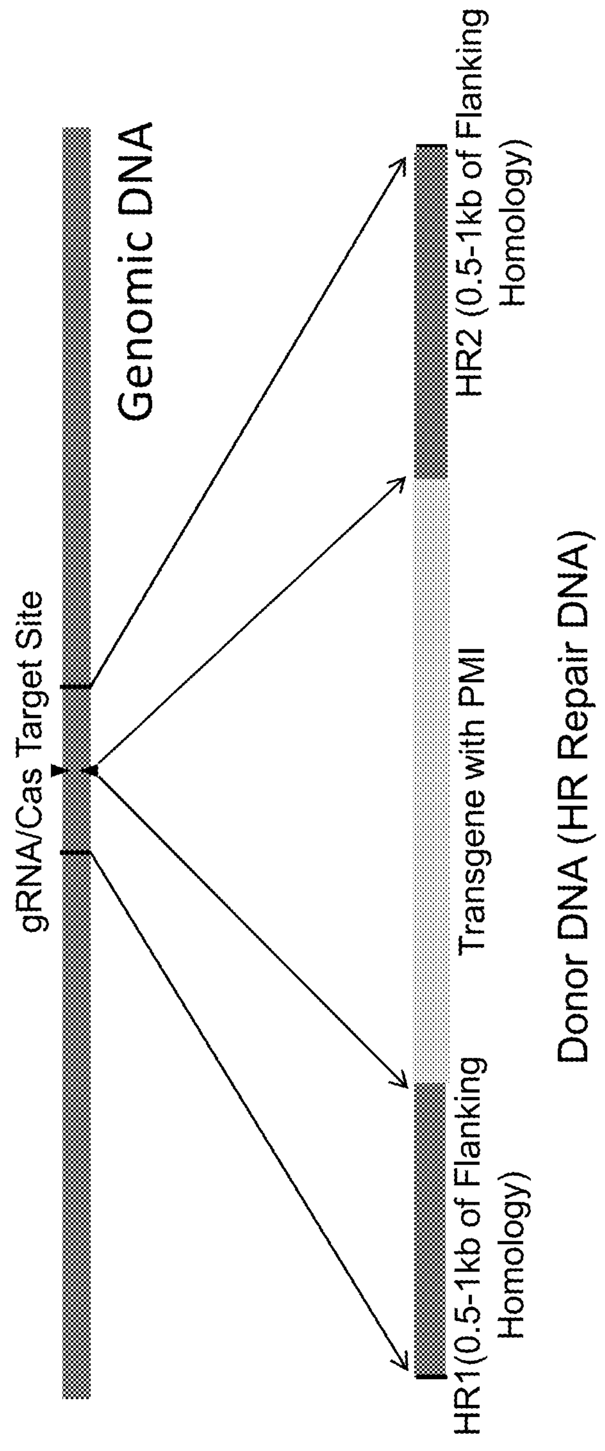

FIG. 20 shows a schematic of a donor DNA (also referred to as HR repair DNA) comprising a transgene cassette with a selectable marker (phosphomannose isomerase, depicted in grey), flanked by homologous recombination sequences (HR1 and HR2) of about 0.5 to 1 kb in length, used to introduce the transgene cassette into a genomic target site for the guide RNA/Cas endonuclease system. The arrows indicate the sections of the genomic DNA sequence on either side of the endonuclease cleavage site that corresponds to the homologous regions of the donor DNA. This schematic is representative for homologous recombination occurring at any one of the 8 target sites (4 loci) located on chromosome 1 from 51.54 cM to 54.56cM in maize genome.

Figure 21:
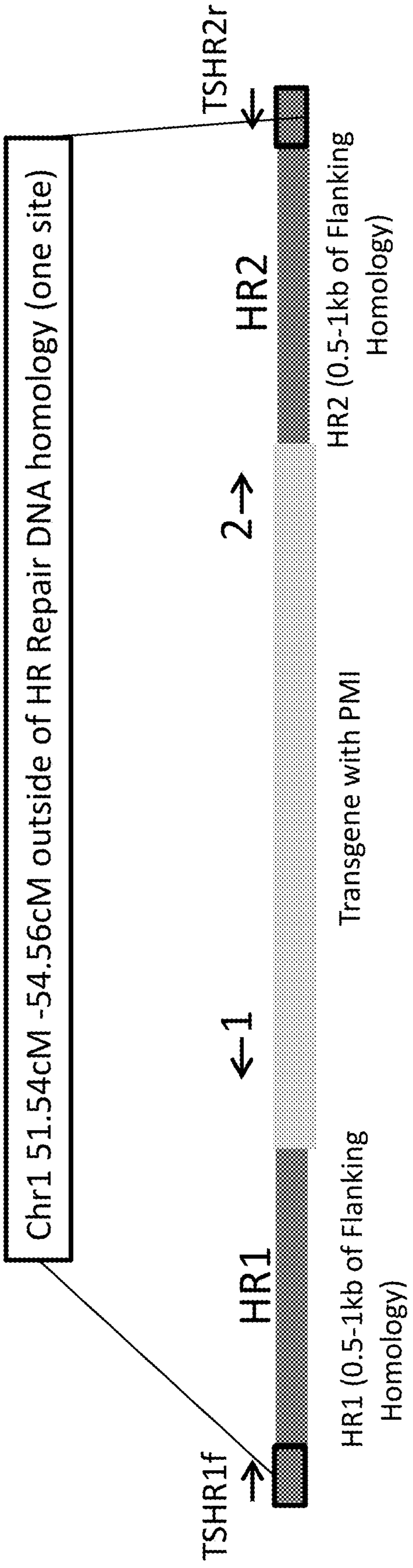

FIG. 21 shows the junction PCR screen for identification of insertion events. Primer 1 and 2 located on the transgene donor are common for all target sites. Primer TSHR1f is located on the genomic region outside of the homologous sequence HR1. Primer combination THR1f/primer1 amplify junction 1. Primer TSHR2r is located on the genomic region outside of the HR2 region. Primer combination primer2/TSHR2r amplify junction 2.

Figure 22:
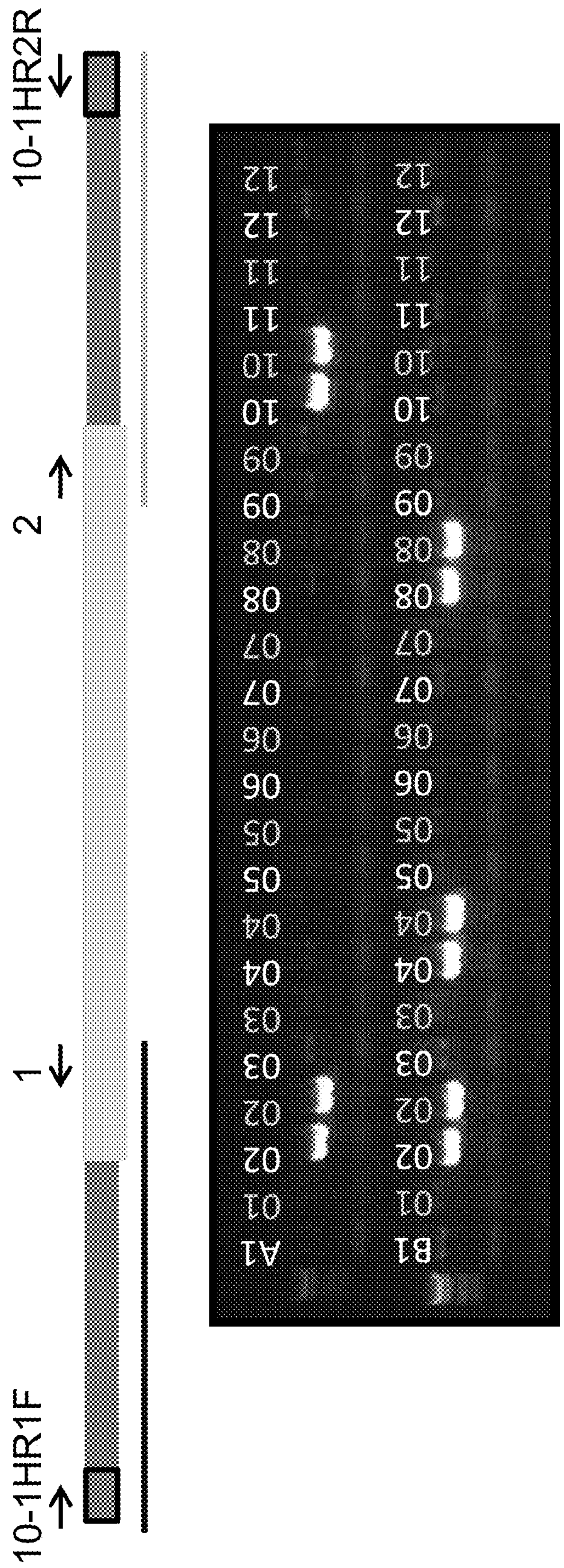

FIG. 22 shows a junction PCR screen for identification of insertion events at the TS10Cas10 locus. A gel picture indicates the presence of insertion events at the TS10Cas10-1 target site (lane 02 A1). PCR reaction of HR1 and HR2 junction loaded next to each other (lane 02-white label and lane 02-gray label), with white label representing HR1 junction PCR, gray label representing HR2 junction PCR.

FIG. 23A-B. DNA expression cassettes used in gRNA/Cas9 mediated genome modification experiments. FIG. 23A) The Cas9 endonuclease cassette (EF1A2:CAS9) comprising a soybean EF1A2 promoter (GM-EF1A2 PRO) driving the soybean codon optimized Cas9 endonucleases (CAS9(SO), a soybean optimized SV40 nuclear localization signal (SV40 NLS(SO)) and a PINII terminator (PINII TERM) was linked to a guide RNA expression cassette (U6-9.1:DD20CR1, comprising a soybean U6 promoter driving the DD2OCR1 guide RNA) used in experiment U6-9.1DD2OCR1 (Table 27). Other Guide RNA/Cas9 cassettes listed in Table 27 are identical except for the 20 bp variable targeting domains of the guide RNA targeting the genomic target sites DD2OCR2, DD43CR1, or DD43CR2. FIG. 23B) The donor DNA cassette (DD20HR1-SAMS:HPT-DD2OHR2) used in experiment U6-9.1DD2OCR1 (Table 27). DD2OHR1 and DD2OHR2 homologous DNA regions between the donor DNA cassette and the genomic DNA sequences flanking the DD20 target site). Other Donor DNA cassettes listed in Table 27 are identical except for the DD43HR1 and DD43HR2 regions in two of them.

FIG. 24A-C. DD20 and DD43 soybean genomic target sites locations and qPCR amplicons. FIG. 24A) Diagram of Glycine max chromosome 04 indicating relative positions of DD20 and DD43 target sites. Genetic mapping positions of DD20 and DD43 sites are the positions of the most nearby genes Glyma04g39780.1 and Glyma04g39550.1. FIG. 24B) DD20 qPCR 64 bp amplicon 45936307-45936370 from chromosome 04 (SEQ ID NO: 304). Relative positions of the target sites DD20-CR1 and DD20-CR2, qPCR primers and probe DD20-F, DD20-R, and DD2O-T are marked. FIG. 24C) DD43 qPCR 115 bp amplicon 45731879-45731993 from chromosome 04 (SEQ ID NO: 305). Relative positions of the target sites DD43-CR1 and DD43-CR2, qPCR primers and probe DD43-F2, DD43-F, DD43-R, and DD43-T are marked.

FIG. 25A-C. Schematic of guide RNA/Cas9 system mediated site-specific non-homologous end joining (NHEJ) and transgene insertion via homologous recombination (HR) at DD2OCR1 site. FIG. 25A) Soybean plants are co-transformed with guide RNA/Cas9 and donor DNA cassettes as listed in Table 27. The DD2OCR1 guide RNA/Cas9 complex transcribed from the linked guide RNA/Cas9 DNA cassettes will cleave specifically the DD2OCR1 target site on chromosome 04 to make DNA double strand breaks. The breaks can be repaired spontaneously as NHEJs or repaired as a HR event by the donor DNA facilitated by the flanking homologous regions DD2O-HR1 and DD2OHR2. FIG. 25B) NHEJs are detected by DD20-specific qPCR and the mutated sequences are assessed by sequencing cloned HR1-HR2 PCR fragments. FIG. 25C) HR events are revealed by two border-specific PCR analyses HR1-SAMS and NOS-HR2, noting that the primers are only able to amplify DNA recombined between the DD2OCR1 region of chromosome 04 and the donor DNA. Guide RNA/Cas9 mediated NHEJ and HR at DD20-CR2 site follow the same process except for using DD20-CR2 guide RNA. Guide RNA/Cas9 mediated site-specific NHEJ and HR at DD43CR1 and DD43CR2 sites follow the same process except for using guide RNA and homologous regions specific to the DD43 sites.

FIG. 26A-C. Sequences of gRNA/Cas9 system mediated NHEJs. Only 60 bp sequences surrounding the genomic target site shown in bold case are aligned to show the mutations. The PAM sequence is shown boxed in. Insertion sequences are indicated by symbol A marking the insertion position followed by the size of the insert. Actual insertion sequences are listed in the sequences listing. FIG. 26A) U6-9.1DD2OCR1 sequences. Three colonies were sequenced for each of 54 events from experiment U6-9.1DD2OCR1. A total of 150 sequences were returned, of which 26 were found to be short unique deletions while 2 of the events contained small insertions. FIG. 26B) U6-9.1DD2OCR2 sequences. Three colonies were sequenced for each of 28 events from experiment U6-9.1DD2OCR2. A total of 84 sequences were returned, of which 20 were found to be short unique deletions while 1 of the events contained a single bp insertion. FIG. 26C) U6-9.1DD43CR1 sequences. Three colonies were sequenced for each of 46 events from experiment U6-9.1DD43CR1. A total of 132 sequences were returned, of which 18 were found to be short unique deletions while 10 of the events contained small insertions. FIG. 26D) U6-9.1DD43CR2 sequences.

FIG. 27A-C shows the ten most prevalent types of NHEJ mutations recovered based on the crRNA/tracrRNA/Cas endonuclease system. FIG. 27A shows NHEJ mutations for LIGCas-1 target site, corresponding to SEQ ID NOs: 415-424), FIG. 27B shows NHEJ mutations for LIGCas-2 target site corresponding to SEQ ID NOs: 425-434) and FIG. 27V shows NHEJ mutations (for LIGCas-3 target site corresponding to SEQ ID NOs: 435-444).

Figure 28:
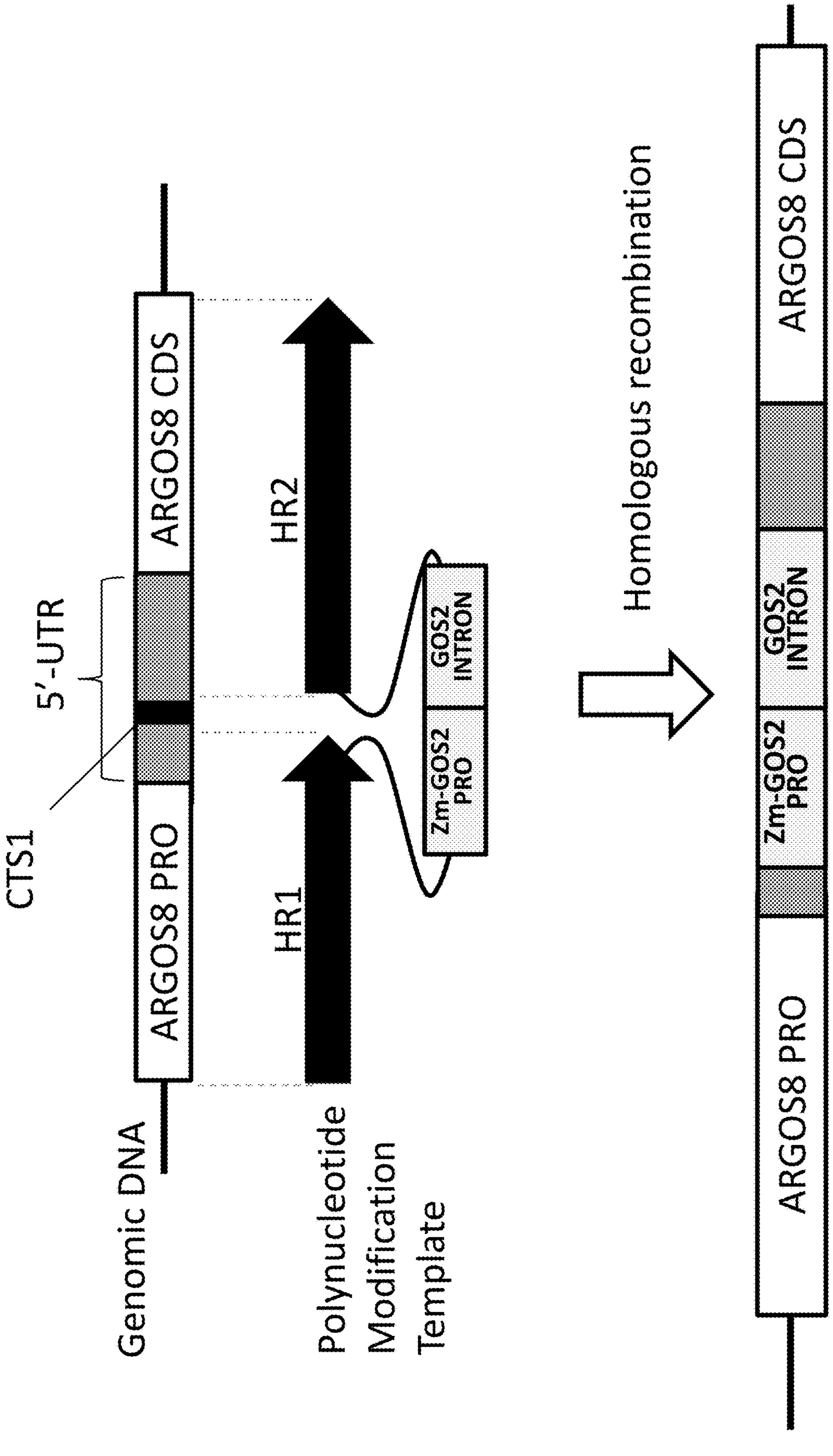

FIG. 28. Schematic representation of Zm-GOS2 PRO:GOS2 INTRON insertion in the 5'-UTR of maize ARGOS8 gene by targeting the guide RNA/Cas9 target sequence 1 (CTS1, SEQ ID NO: 1) with the gRNA1/Cas9 endonuclease system, described herein. HR1 and HR2 indicate homologous recombination regions.

Figure 29A:
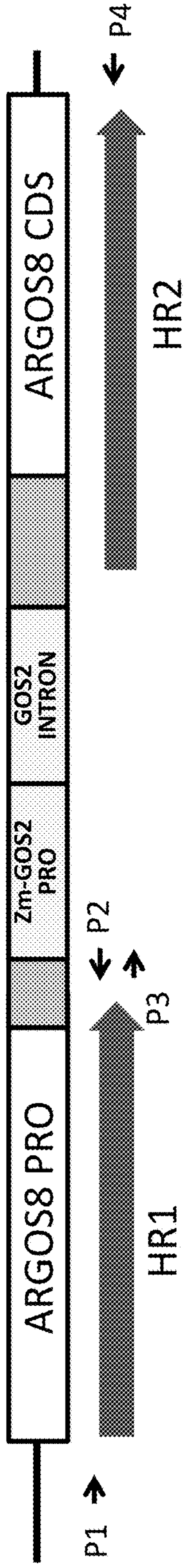
Figure 29B:
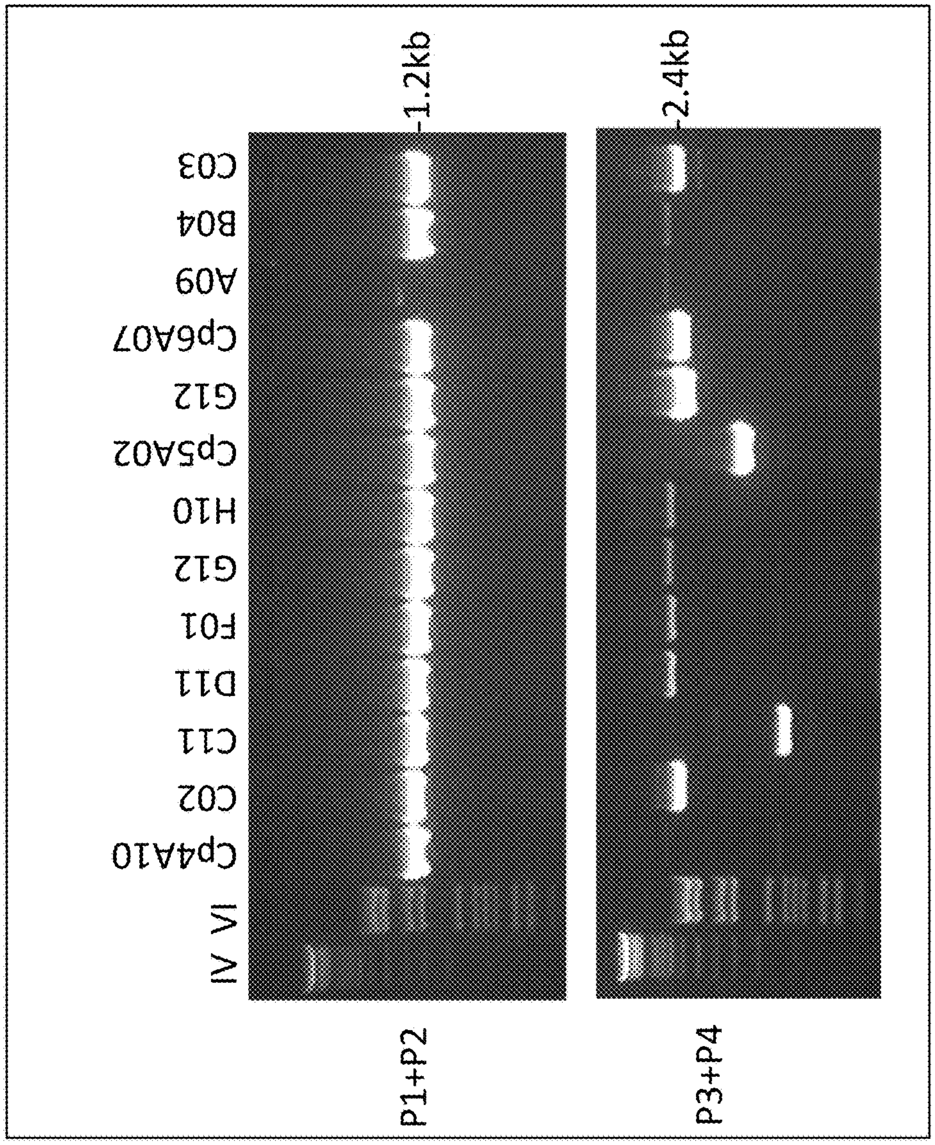
Figure 29C:
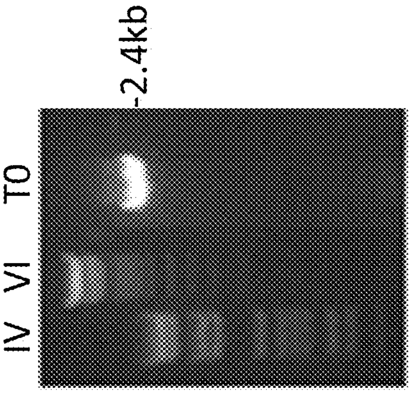

FIG. 29A-29C. Identification and analysis of Zm-GOS2 PRO:GOS2 INTRON insertion events in maize plants. (FIG. 29A) Schematic representation of Zm-GOS2 PRO:GOS2 INTRON insertion in the 5'-UTR of Zm-ARGOS8. CTS1 was targeted with the gRNA1/Cas9 endonuclease system, described herein. HR1 and HR2 indicate homologous recombination regions. P1 to P4 indicate PCR primers. (FIG. 29B) PCR screening of PMI-resistance calli to identify insertion events. PCR results are shown for 13 representative calli. The left and right junction PCRs were carried out with the primer pair P1+P2 and P3+P4, respectively. (FIG. 29C) PCR analysis of a T0 plant. A PCR product with the expected size (2.4 kb, Lane TO) was amplified with the primer P3 and P4.

Figure 30:
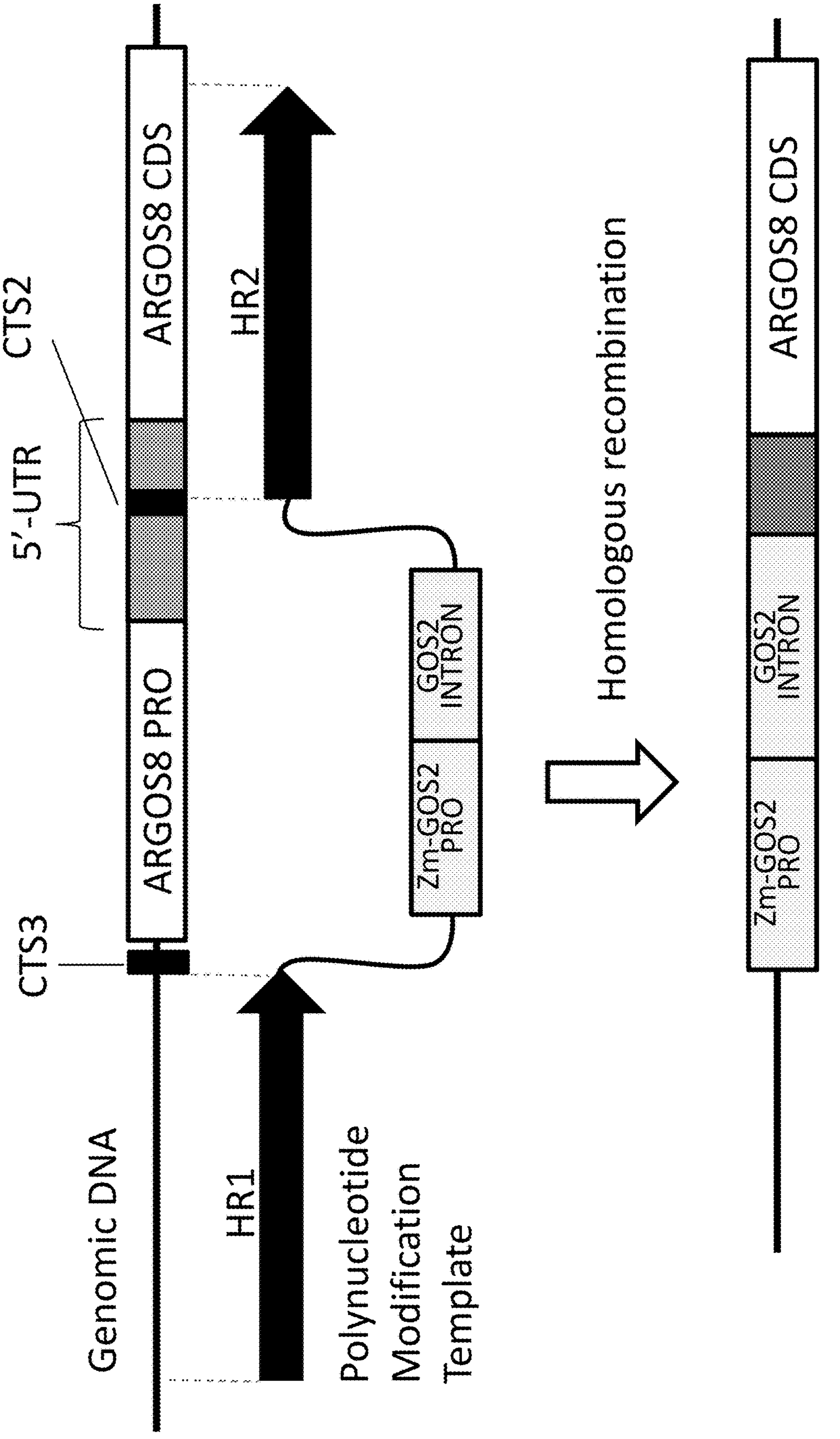

FIG. 30. Schematic representation of Zm-ARGOS8 promoter substitution with Zm-GOS2 PRO:GOS2 INTRON by targeting CTS3 (SEQ ID NO: 3) and CTS2 (SEQ ID NO:2). HR1 and HR2 indicate homologous recombination regions.

FIG. 31A-31D. Substitution of the native promoter of the ARGOS8 gene with Zm-GOS2 PRO:GOS2 INTRON in maize plants. (FIG. 31A) Schematic representation of the Zm-GOS2 PRO:GOS2 INTRON:ARGOS8 allele generated by promoter swap. Two guide RNA/Cas9 target sites, CTS3 (SEQ ID NO:3) and CTS2 (SEQ ID NO:2), were targeted with a gRNA3/gRNA2/Cas9 system. HR1 and HR2 indicate homologous recombination regions. P1 to P5 indicate PCR primers. (FIG. 31B) PCR screening of PMI-resistance calli to identify swap events. PCR results are shown for 10 representative calli. One callus sample, 12A09, is positive for both left junction (L, primer P1+P2) and right junction (R, primer P5+P4) PCR, indicating that 12A09 is a swap event. (FIG. 31C) PCR analysis of the callus events identified in primary screening. PCR products with the expected size (2.4 kb) were amplified using the primer P3 and P4 from event #3, 4, 6, 8 and 9, indicating presence of the Zm-GOS2 PRO:GOS2 INTRON:ARGOS8 allele. (FIG. 31D) PCR analysis of a T0 plant. A PCR product with the expected size (2.4 kb, Lane TO) was amplified with the primer P3 and P4.

Figure 32A:
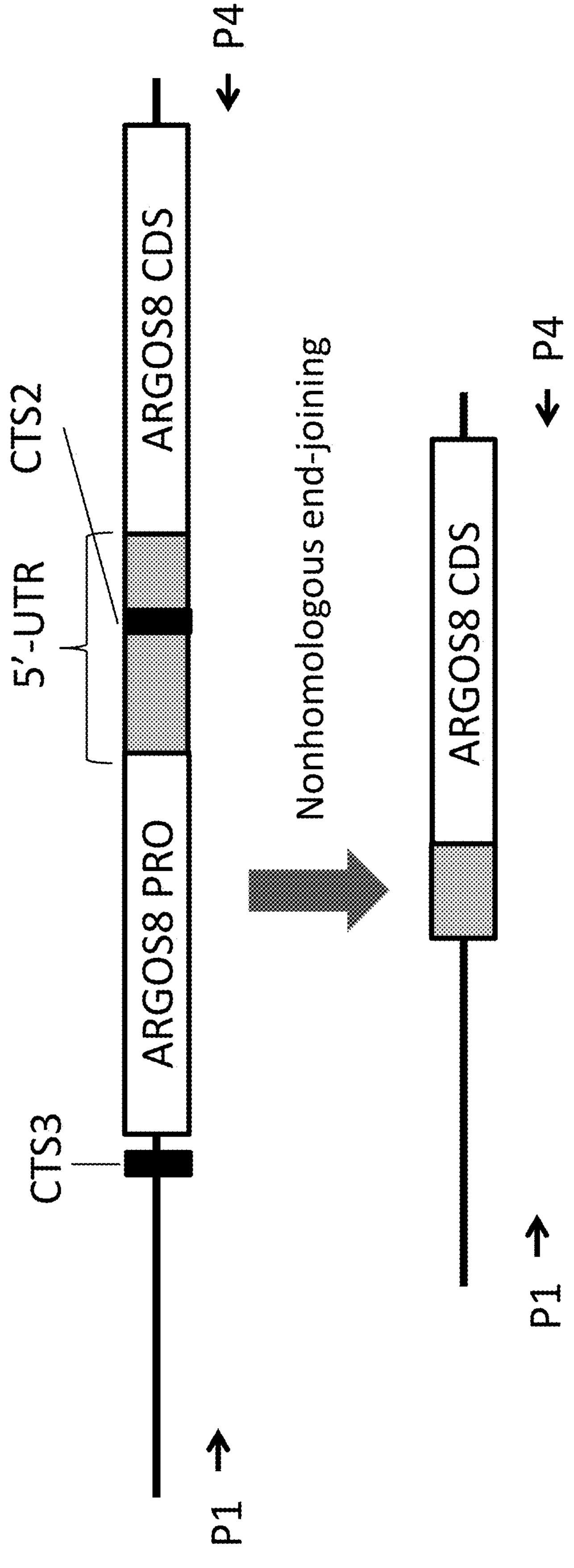
Figure 32B:
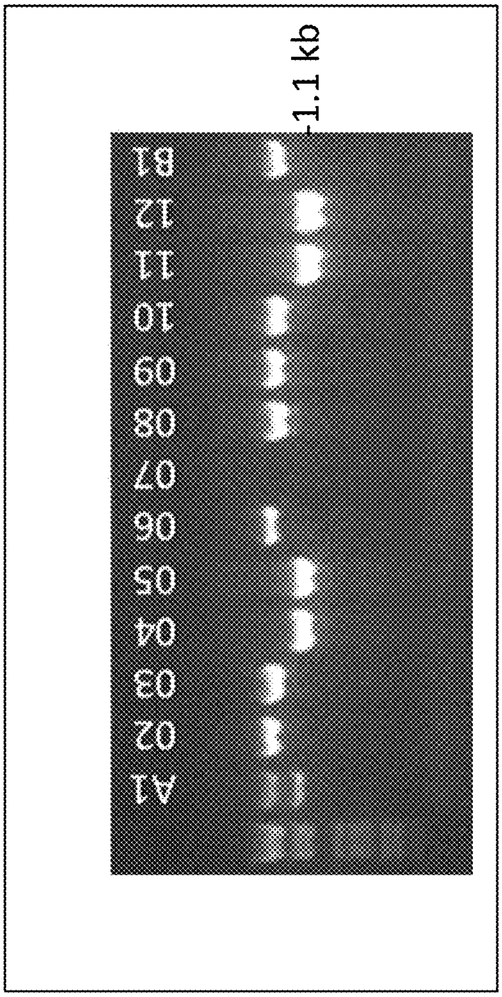

FIG. 32A-32B. Deletion of the native promoter of the ARGOS8 gene in maize plants. (FIG. 32A) Schematic representation of promoter deletion. Two guide RNA's and a Cas9 endonuclease system, referred to as a gRNA3/gRNA2/Cas9 system, were used to target the CTS3 and CTS2 sites in Zm-ARGOS8. P1 and P4 indicate PCR primers for deletion event screening. (FIG. 32B) PCR screening of PMI-resistance calli to identify deletion events. PCR results are shown for 15 representative calli. A 1.1-kp PCR product indicates deletion of the CTS3/CTS2 fragment.

Figure 33:
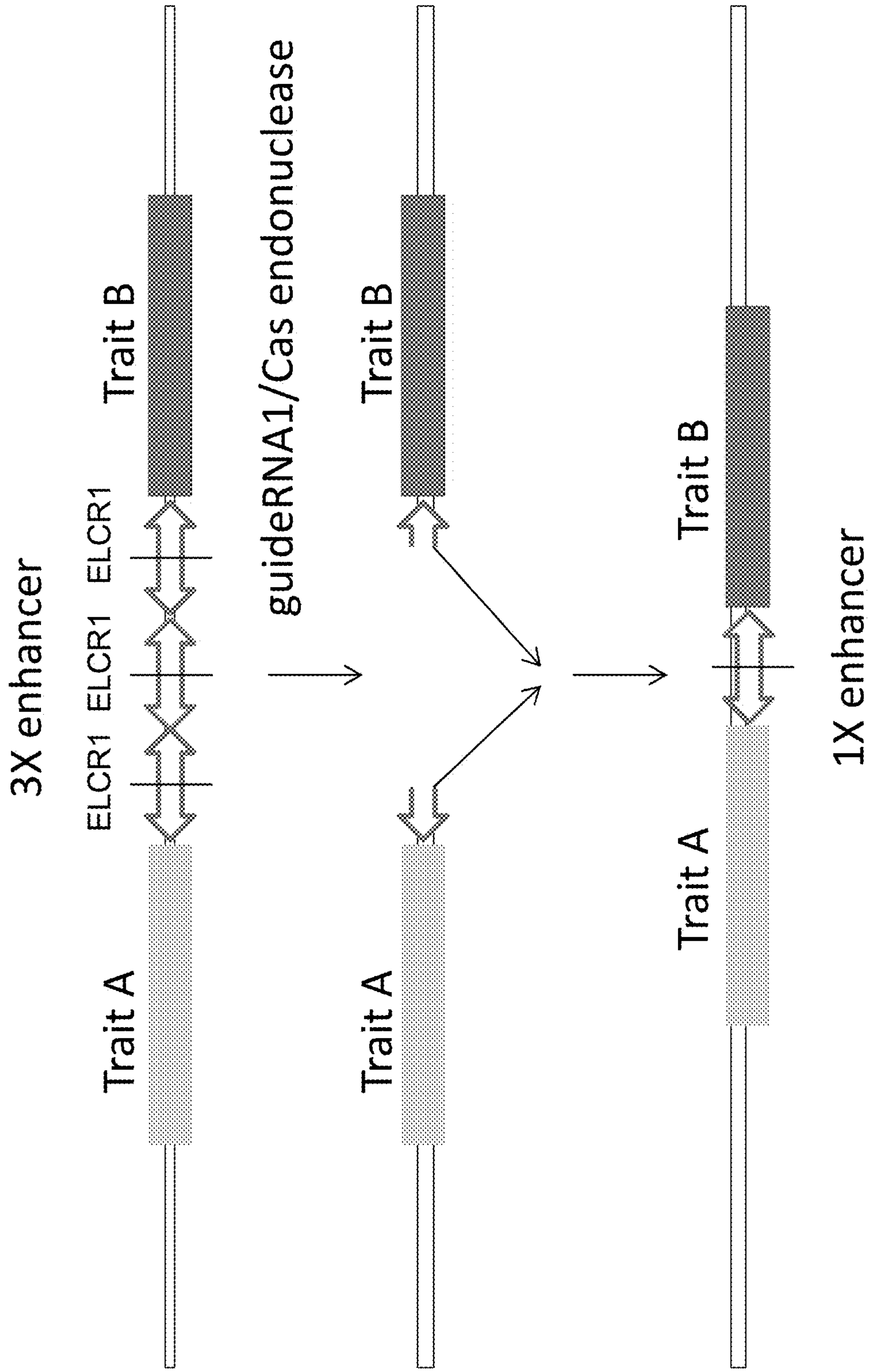

FIG. 33. Schematic representation of enhancer element deletions using the guide RNA/Cas9 target sequence. The enhancer element to be deleted can be, but is not limited to, a 35S enhancer element.

FIG. 34A-C. Modification of a maize EPSPS polyubiquitination site. (FIG. 34A) The selected maize EPSPS polyubiquitination site is compared to the analogous sites of other plant species (SEQ ID NOs: 558-563). (FIG. 34B) The nucleotides to be edited in the maize EPSPS coding sequence (underlined, encoded amino acid shown in bold). The sequence shown in FIG. 34B is listed in SEQ ID NO: 564 (FIG. 34C) The edited EPSPS coding sequence identified in the selected T0 plant. The sequence shown in FIG. 34C is listed in SEQ ID NO: 565.

FIG. 35A-C. The intron mediated enhanced element (FIG. 35A). The 5' section of the first intron of the EPSPS gene (editing: substitutions underlined and deletions represented by dots) (FIG. 35B) and its edited version conferring three IMEs elements (underlined). The edited nucleotides are shown in bold (FIG. 35C). The sequence shown in FIG. 35B is listed in SEQ ID NO: 566. The sequence shown in FIG. 35C is listed in SEQ ID NO: 567.

Figure 36:
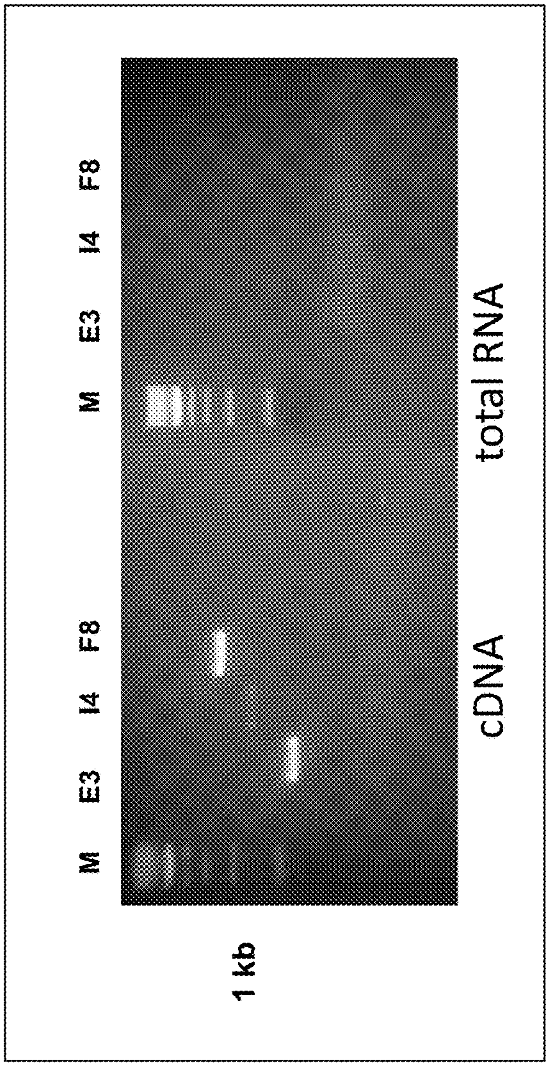
Figure 36:
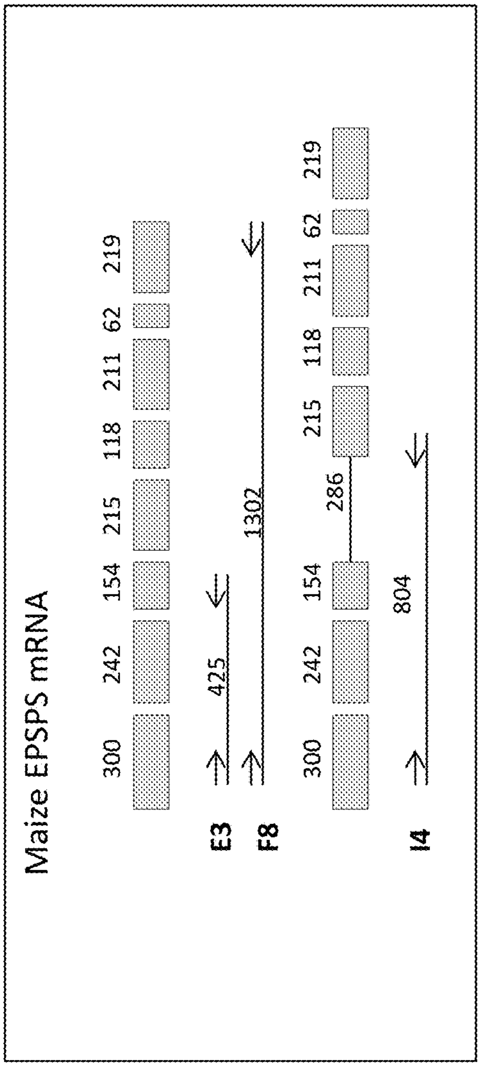

FIG. 36A-36B. Alternatively spliced EPSPS mRNA in maize cells. (FIG. 36A) left panel represents analysis of EPSPS cDNA. The lane 14 in FIG. 36A shows amplification of the EPSPS pre-mRNA containing the 3 rd intron unspliced (the 804 bp diagnostic fragment as shown in FIG. 36B indicates an alternate splicing event). Lanes E3 and F8 show the EPSPS PCR amplified fragments with spliced introns. These diagnostic fragments are not amplified unless cDNA is synthesized (as is evident by the absence of bands in lanes E3, 14, and F8 comprising total RNA (shown in the total RNA panel on right of FIG. 36A). The grey boxes in FIG. 36B represent the eight EPSPS exons (their sizes are indicated above each of them).

FIG. 37. Splicing site at the junction between the second EPSPS intron and the third exon (bolded). The nucleotide to be edited is underlined.

Figure 38:
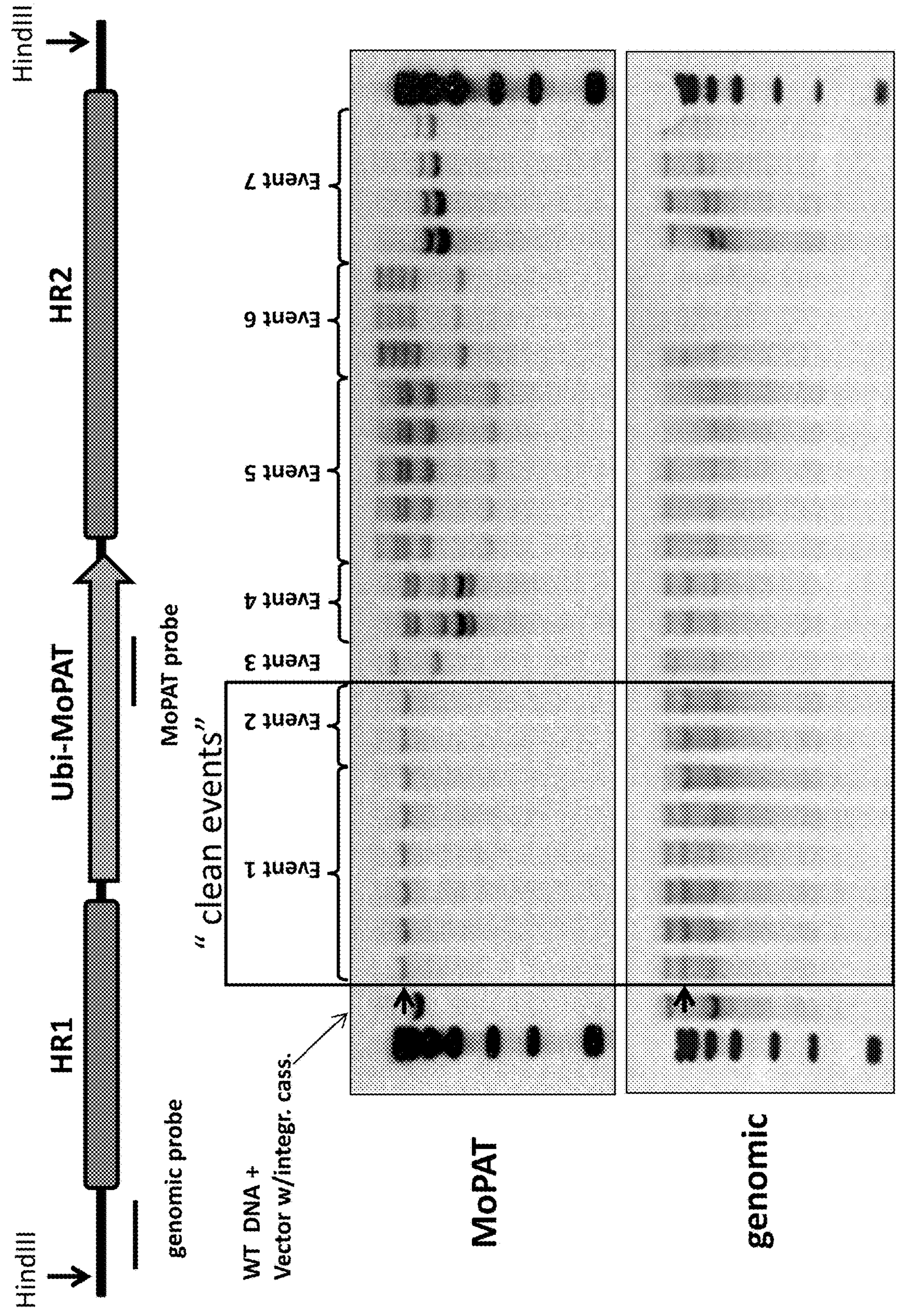

FIG. 38. Schematic representation of Southern hybridization analysis of TO and T1 maize plants.

SEQUENCES

SEQ ID NO: 1 is the nucleotide sequence of the Cas9 gene from *Streptococcus pyogenes* M1 GAS (SF370).

SEQ ID NO: 2 is the nucleotide sequence of the potato ST-LS1 intron.

SEQ ID NO: 3 is the amino acid sequence of SV40 amino N-terminal.

SEQ ID NO: 4 is the amino acid sequence of *Agrobacterium tumefaciens* bipartite VirD2 T-DNA border endonuclease carboxyl terminal.

SEQ ID NO: 5 is the nucleotide sequence of an expression cassette expressing the maize optimized Cas9.

SEQ ID NO: 6 is the nucleotide sequence of crRNA containing the LIGCas-3 target sequence in the variable targeting domain.

SEQ ID NO: 7 is the nucleotide sequence of the tracrRNA.

SEQ ID NO: 8 is the nucleotide sequence of a long guide RNA containing the LIGCas-3 target sequence in the variable targeting domain.

SEQ ID NO: 9 is the nucleotide sequence of the Chromosome 8 maize U6 polymerase III promoter.

SEQ ID NO: 10 list two copies of the nucleotide sequence of the maize U6 polymerase III terminator.

SEQ ID NO: 11 is the nucleotide sequence of the maize optimized short guide RNA containing the LIGCas-3 variable targeting domain.

SEQ ID NO: 12 is the nucleotide sequence of the maize optimized long guide RNA expression cassette containing the LIGCas-3 variable targeting domain.

SEQ ID NO: 13 is the nucleotide sequence of the Maize genomic target site MS26Cas-1 plus PAM sequence.

SEQ ID NO: 14 is the nucleotide sequence of the Maize genomic target site MS26Cas-2 plus PAM sequence.

SEQ ID NO: 15 is the nucleotide sequence of the Maize genomic target site MS26Cas-3 plus PAM sequence.

SEQ ID NO: 16 is the nucleotide sequence of the Maize genomic target site LIGCas-2 plus PAM sequence.

SEQ ID NO: 17 is the nucleotide sequence of the Maize genomic target site LIGCas-3 plus PAM sequence.

SEQ ID NO: 18 is the nucleotide sequence of the Maize genomic target site LIGCas-4 plus PAM sequence.

SEQ ID NO: 19 is the nucleotide sequence of the Maize genomic target site MS45Cas-1 plus PAM sequence.

SEQ ID NO: 20 is the nucleotide sequence of the Maize genomic target site MS45Cas-2 plus PAM sequence.

SEQ ID NO: 21 is the nucleotide sequence of the Maize genomic target site MS45Cas-3 plus PAM sequence.

SEQ ID NO: 22 is the nucleotide sequence of the Maize genomic target site ALSCas-1 plus PAM sequence.

SEQ ID NO: 23 is the nucleotide sequence of the Maize genomic target site ALSCas-2 plus PAM sequence.

SEQ ID NO: 24 is the nucleotide sequence of the Maize genomic target site ALSCas-3 plus PAM sequence.

SEQ ID NO: 25 is the nucleotide sequence of the Maize genomic target site EPSPSCas-1 plus PAM sequence.

SEQ ID NO: 26 is the nucleotide sequence of the Maize genomic target site EPSPSCas-2 plus PAM sequence.

SEQ ID NO: 27 is the nucleotide sequence of the Maize genomic target site EPSPSCas-3 plus PAM sequence.

SEQ ID NOs: 28-52 are the nucleotide sequence of target site specific forward primers for primary PCR as shown in Table 2.

SEQ ID NO: 53 is the nucleotide sequence of the forward primer for secondary PCR.

SEQ ID NO: 54 is the nucleotide sequence of Reverse primer for secondary PCR

SEQ ID NO: 55 is the nucleotide sequence of the unmodified reference sequence for LIGCas-1 and LIGCas-2 locus.

SEQ ID NOs: 56-65 are the nucleotide sequences of mutations 1-10 for LIGCas-1.

SEQ ID NOs: 66-75 are the nucleotide sequences of mutations 1-10 for LIGCas-2.

SEQ ID NO: 76 is the nucleotide sequence of the unmodified reference sequence for the LIGCas-3 and LIG3-4 homing endonuclease locus.

SEQ ID NOs: 77-86 are the nucleotide sequences of mutations 1-10 for LIGCas-3.

SEQ ID NOs: 88-96 are the nucleotide sequences of mutations 1-10 for LIG3-4 homing endonuclease locus.

SEQ ID NO: 97 is the nucleotide sequence of a donor vector referred to as an HR Repair DNA.

SEQ ID NO: 98 is the nucleotide sequence of forward PCR primer for site-specific transgene insertion at junction 1.

SEQ ID NO: 99 is the nucleotide sequence of reverse PCR primer for site-specific transgene insertion at junction 1.

SEQ ID NO: 100 is the nucleotide sequence of forward PCR primer for site-specific transgene insertion at junction 2.

SEQ ID NO: 101 is the nucleotide sequence of reverse PCR primer for site-specific transgene insertion at junction 2.

SEQ ID NO: 102 is the nucleotide sequence of the linked Cas9 endonuclease and LIGCas-3 long guide RNA expression cassettes SEQ ID NO: 103 is the nucleotide sequence of Maize genomic target site 55CasRNA-1 plus PAM sequence.

SEQ ID NO: 104 is the nucleotide sequence of the unmodified reference sequence for 55CasRNA-1 locus.

SEQ ID NOs: 105-110 are the nucleotide sequences of mutations 1-6 for 55CasRNA-1.

SEQ ID NO: 111 is the nucleotide sequence of LIG3-4 homing endonuclease target site SEQ ID NO: 112 is the nucleotide sequence of LIG3-4 homing endonuclease coding sequence.

SEQ ID NO: 113 is the nucleotide sequence of the MS26++ homing endonuclease target site.

SEQ ID NO: 114 is the nucleotide sequence of MS26++ homing endonuclease coding sequence SEQ ID NO: 115 is the nucleotide sequence of the soybean codon optimized Cas9 gene.

SEQ ID NO: 116 is the nucleotide sequence of the soybean constitutive promoter GM-EF1A2.

SEQ ID NO: 117 is the nucleotide sequence of linker SV40 NLS.

SEQ ID NO: 118 is the amino acid sequence of soybean optimized Cas9 with a SV40 NLS.

SEQ ID NO: 119 is the nucleotide sequence of vector QC782.

SEQ ID NO: 120 is the nucleotide sequence of soybean U6 polymerase III promoter described herein, GM-U6-13.1 PRO.

SEQ ID NO: 121 is the nucleotide sequence of the guide RNA in FIG. 8B.

SEQ ID NO: 122 is the nucleotide sequence of vector QC783.

SEQ ID NO: 123 is the nucleotide sequence of vector QC815.

SEQ ID NO: 124 is the nucleotide sequence of a Cas9 endonuclease (cas9-2) from *S. pyogenes.*

SEQ ID NO: 125 is the nucleotide sequence of the DD2OCR1 soybean target site

SEQ ID NO: 126 is the nucleotide sequence of the DD2OCR2 soybean target site

SEQ ID NO: 127 is the nucleotide sequence of the DD43CR1 soybean target site

SEQ ID NO: 128 is the nucleotide sequence of the DD43CR2 soybean target site

SEQ ID NO: 129 is the nucleotide sequence of the DD20 sequence in FIG. 10A.

SEQ ID NO: 130 is the nucleotide sequence of the DD20 sequence complementary in FIG. 10A.

SEQ ID NO: 131 is the nucleotide sequence of DD43 sequence.

SEQ ID NO: 132 is the nucleotide sequence of the DD43 complementary sequence.

SEQ ID NO: 133-141 are primer sequences.

SEQ ID NO: 142 is the nucleotide sequence of the DD2OCR1 PCR amplicon.

SEQ ID NO: 143 is the nucleotide sequence of the DD2OCR2 PCR amplicon.

SEQ ID NO: 144 is the nucleotide sequence of the DD43CR1 PCR amplicon.

SEQ ID NO: 145 is the nucleotide sequence of the DD43CR2 PCR amplicon.

SEQ ID NO: 146 is the nucleotide sequence of the DD43CR2 PCR amplicon.

SEQ ID NO: 147-156 are the nucleotide sequence of mutations 1 to 10 for the DD2OCR1 target site SEQ ID NO: 157-166 are the nucleotide sequence of mutations 1 to 10 for the DD2OCR2 target site SEQ ID NO: 167-176 are the nucleotide sequence of mutations 1 to 10 for the DD43CR1 target site SEQ ID NO: 177-191 are the nucleotide sequence of mutations 1 to 10 for the DD43CR2 target site.

SEQ ID NO: 192 is the amino acid sequence of a maize optimized version of the Cas9 protein.

SEQ ID NO: 193 is the nucleotide sequence of the maize optimized version of the Cas9 gene of SEQ ID NO: 192.

SEQ ID NO: 194 is the DNA version of guide RNA (EPSPS sgRNA).

SEQ ID NO: 195 is the EPSPS polynucleotide modification template.

SEQ ID NO: 196 is a nucleotide fragment comprising the TIPS nucleotide modifications.

SEQ ID NO: 197-204 are primer sequences shown in Table 15.

SEQ ID NO: 205-208 are nucleotide fragments shown in FIG. 14.

SEQ ID NO: 209 is an example of a TIPS edited EPSPS nucleotide sequence fragment shown in FIG. 17.

SEQ ID NO: 210 is an example of a Wild-type EPSPS nucleotide sequence fragment shown in FIG. 17.

SEQ ID NO: 211 is the nucleotide sequence of a maize enolpyruvylshikimate-3-phosphate synthase (epsps) locus SEQ ID NO: 212 is the nucleotide sequence of a Cas9 endonuclease (genbank CS571758.1) from S. thermophiles.

SEQ ID NO: 213 is the nucleotide sequence of a Cas9 endonuclease (genbank CS571770.1) from S. thermophiles.

SEQ ID NO: 214 is the nucleotide sequence of a Cas9 endonuclease (genbank CS571785.1) from *S. agalactiae.*

SEQ ID NO: 215 is the nucleotide sequence of a Cas9 endonuclease, (genbank CS571790.1) from *S. agalactiae.*

SEQ ID NO: 216 is the nucleotide sequence of a Cas9 endonuclease (genbank CS571790.1) from S. mutant.

SEQ ID NOs: 217-228 are primer and probe nucleotide sequences described in Example 17.

SEQ ID NOs: 229 is the nucleotide sequence of the MHP14Cas1 target site.

SEQ ID NOs: 230 is the nucleotide sequence of the MHP14Cas3 target site.

SEQ ID NOs: 231 is the nucleotide sequence of the TS8Cas1 target site.

SEQ ID NOs: 232 is the nucleotide sequence of the TS8Cas2 target site.

SEQ ID NOs: 233 is the nucleotide sequence of the TS9Cas2 target site.

SEQ ID NOs: 234 is the nucleotide sequence of the TS9Cas3 target site.

SEQ ID NOs: 235 is the nucleotide sequence of the TS10Cas1 target site.

SEQ ID NOs: 236 is the nucleotide sequence of the TS10Cas3 target site.

SEQ ID NOs: 237-244 are the nucleotide sequences shown in FIG. 19A-D.

SEQ ID NOs: 245-252 are the nucleotide sequences of the guide RNA expression cassettes described in Example 18.

SEQ ID NOs: 253-260 are the nucleotide sequences of donor DNA expression cassettes described in Example 18.

SEQ ID NOs: 261-270 are the nucleotide sequences of the primers described in Example 18.

SEQ ID NOs: 271-294 are the nucleotide sequences of the primers and probes described in Example 18.

SEQ ID NO: 295 is the nucleotide sequence of GM-U6-9.1 PRO, a soybean U6 polymerase III promoter described herein.

SEQ ID NOs: 298, 300, 301 and 303 are the nucleotide sequences of the linked guideRNA/Cas9 expression cassettes.

SEQ ID NOs: 299 and 302 are the nucleotide sequences of the donor DNA expression cassettes.

SEQ ID NOs: 271-294 are the nucleotide sequences of the primers and probes described in Example 18.

SEQ ID NO: 304 is the nucleotide sequence of the DD20 qPCR amplicon.

SEQ ID NO: 305 is the nucleotide sequence of the DD43 qPCR amplicon.

SEQ ID NOs: 306-328 are the nucleotide sequences of the primers and probes described herein.

SEQ ID NOs: 329-334 are the nucleotide sequences of PCR amplicons described herein.

SEQ ID NO: 335 is the nucleotide sequence of a soybean genomic region comprising the DD2OCR1 target site.

SEQ ID NO: 364 is the nucleotide sequence of a soybean genomic region comprising the DD2OCR2 target site.

SEQ ID NO: 386 is the nucleotide sequence of a soybean genomic region comprising the DD43CR1 target site.

SEQ ID NOs: 336-363, 365-385 and 387-414 are the nucleotide sequences of shown in FIG. 26A-C.

SEQ ID NOs: 415-444 are the nucleotide sequences of NHEJ mutations recovered based on the crRNA/tracrRNA/Cas endonuclease system shown in FIG. 27A-C.

SEQ ID NO: 445-447 are the nucleotide sequence of the LIGCas-1, LIGCas2 and LIGCas3 crRNA expression cassettes, respectively.

SEQ ID NO: 448 is the nucleotide sequence of the tracrRNA expression cassette.

SEQ ID NO: 449 is the nucleotide sequence of LIGCas-2 forward primer for primary PCR SEQ ID NO: 450 is the nucleotide sequence of LIGCas-3 forward primer for primary PCR.

SEQ ID NO: 451 is the nucleotide sequence of the maize genomic Cas9 endonuclease target site Zm-ARGOS8-CTS1.

SEQ ID NO: 452 is the nucleotide sequence of the maize genomic Cas9 endonuclease target site Zm-ARGOS8-CTS2.

SEQ ID NO: 453 is the nucleotide sequence of the maize genomic Cas9 endonuclease target site Zm-ARGOS8-CTS3

SEQ ID NOs: 454-458 are the nucleotide sequence of primers P1, P2, P3, P4, P5, respectively.

SEQ ID NO: 459 is the nucleotide sequence of a Primer Binding Site (PBS), a sequence to facilitate event screening.

SEQ ID NO: 460 is the nucleotide sequence of the Zm-GOS2 PRO-GOS2 INTRON, the maize GOS2 promoter and GOS2 intron1 including the promoter, 5'-UTR1, INTRON1 and 5'-UTR2.

SEQ ID NO:461 is the nucleotide sequence of the maize Zm-ARGOS8 promoter.

SEQ ID NO:462 is the nucleotide sequence of the maize Zm-ARGOS8 5'-UTR.

SEQ ID NO:463 is the nucleotide sequence of the maize Zm-ARGOS8 codon sequence

SEQ ID NO:464 is the nucleotide sequence of the maize Zm-GOS2 gene, including promoter, 5'-UTR, CDS, 3'-UTR and introns.

SEQ ID NO:465 is the nucleotide sequence of the maize Zm-GOS2 PRO promoter.

SEQ ID NO:466 is the nucleotide sequence of the maize GOS2 INTRON, maize GOS2 5'-UTR1 and intron1 and 5'-UTR2.

SEQ ID NOs: 467-468, 490-491, 503-504 are the nucleotide sequence of the soybean genomic Cas endonuclease target sequences soy EPSPS-CR1, soy EPSPS-CR2, soy EPSPS-CR4, soy EPSPS-CR5, soy EPSPS-CR6, soy EPSPS-CR7,respectively SEQ ID NO:469 is the nucleotide sequence of the soybean U6 small nuclear RNA promoter GM-U6-13.1.

SEQ ID NOs:470, 471 are the nucleotide sequences of the QC868, QC879 plasm ids, respectively.

SEQ ID NOs:472, 473, 492, 493, 494, 505, 506, 507 are the nucleotide sequences of the RTW1013A, RTW1012A, RTW1199, RTW1200, RTW1190A, RTW1201, RTW1202, RTW1192A respectively.

SEQ ID NOs:474-488, 495-402, 508-512 are the nucleotide sequences of primers and probes.

SEQ ID NO: 489 is the nucleotide sequence of the soybean codon optimized Cas9.

SEQ ID NO: 513 is the nucleotide sequence of the 35S enhancer.

SEQ ID NO: 514 is the nucleotide sequence of the 35S-CRTS for gRNA1 at 163-181 (including pam at 3' end).

SEQ ID NO: 515 is the nucleotide sequence of the 35S-CRTS for gRNA2 at 295-319 (including pam at 3' end).

SEQ ID NO: 516 is the nucleotide sequence of the 35S-CRT for gRNA3 at 331-350 (including pam at 3' end).

SEQ ID NO: 517 is the nucleotide sequence of the EPSPS-K9OR template.

SEQ ID NO: 518 is the nucleotide sequence of the EPSPS-IME template. S

SEQ ID NO: 519 is the nucleotide sequence of the EPSPS-Tspliced template.

SEQ ID NO: 520 is the amino acid sequence of ZM-RAP2.7 peptide

SEQ ID NO: 521 is the nucleotide sequence zM-RAP2.7 coding DNA sequence

SEQ ID NOs: 522 is the amino acid sequence of ZM-NPK1B peptide SEQ ID NO: 523 is the nucleotide sequence of the ZM-NPK1B coding DNA sequence SEQ ID NOs: 524 is the nucleotide sequence of the RAB17 promoter SEQ ID NOs: 525 is the amino acid sequence of the Maize FTM1.

SEQ ID NO: 526 is the nucleotide sequence of the Maize FTM1 coding DNA sequence.

SEQ ID NOs: 527-532 are the nucleotide sequences shown in FIGS. 34, 35 and 37.

SEQ ID NOs: 533-534 are the nucleotide sequences of the Southern genomic probe and Southern MoPAT probe of FIG. 38, respectively. SEQ ID NOs: 535-541 are the nucleotide sequences of the RF-FPCas-1, RF-FPCas-2, ALSCas-4, ALS modification repair template 804, ALS modification repair template 127, ALS Forward_primer and ALS Reverse_primer, respectively.

SEQ ID NOs: 542-549 are the nucleotide sequences of the soy ALS1-CR1, Cas9 target sequence, soy ALS2-CR2, Cas9 target sequence, QC880, QC881, RTW1026A, WOL900, Forward_primer, WOL578, Reverse_primer and WOL573, Forward_primer, respectively.

SEQ ID NO: 550 is the nucleotide sequence of a maize ALS protein.

DETAILED DESCRIPTION

The present disclosure includes compositions and methods for genome modification of a target sequence in the genome of a plant or plant cell, for selecting plants, for gene editing, and for inserting a polynucleotide of interest into the genome of a plant. The methods employ a guide RNA/Cas endonuclease system, wherein the Cas endonuclease is guided by the guide RNA to recognize and optionally introduce a double strand break at a specific target site into the genome of a cell. The guide RNA/Cas endonuclease system provides for an effective system for modifying target sites within the genome of a plant, plant cell or seed.

Further provided are methods and compositions employing a guide polynucleotide/Cas endonuclease system to provide an effective system for modifying target sites within the genome of a cell and for editing a nucleotide sequence in the genome of a cell. Once a genomic target site is identified, a variety of methods can be employed to further modify the target sites such that they contain a variety of polynucleotides of interest. Breeding methods utilizing a two component guide RNA/Cas endonuclease system are also disclosed. Compositions and methods are also provided for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times-also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060.

As described therein, 41 CRISP R-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell. As used herein, the tem "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence (FIG. 2A, FIG. 2B).

In one embodiment, the Cas endonuclease gene is a Cas9 endonuclease, such as but not limited to, Cas9 genes listed in SEQ ID NOs: 462, 474, 489, 494, 499, 505, and 518 of WO2007/025097published Mar. 1, 2007, and incorporated herein by reference. In another embodiment, the Cas endonuclease gene is plant, maize or soybean optimized Cas9 endonuclease (FIG. 1A). In another embodiment, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

In one embodiment, the Cas endonuclease gene is a Cas9 endonuclease gene of SEQ ID NO:1, 124, 212, 213, 214, 215, 216, 193 or nucleotides 2037-6329 of SEQ ID NO:5, or any functional fragment or variant thereof.

The terms "functional fragment ", "fragment that is functionally equivalent" and "functionally equivalent fragment" are used interchangeably herein. These terms refer to a portion or subsequence of the Cas endonuclease sequence of the present disclosure in which the ability to create a double-strand break is retained.

The terms "functional variant ", "Variant that is functionally equivalent" and "functionally equivalent variant" are used interchangeably herein. These terms refer to a variant of the Cas endonuclease of the present disclosure in which the ability create a double-strand break is retained. Fragments and variants can be obtained via methods such as site-directed mutagenesis and synthetic construction.

In one embodiment, the Cas endonuclease gene is a plant codon optimized *Streptococcus pyogenes* Cas9 gene that can recognize any genomic sequence of the form N(12-30)NGG can in principle be targeted.

In one embodiment, the Cas endonuclease is introduced directly into a cell by any method known in the art, for example, but not limited to transient introduction methods, transfection and/or topical application.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more.(patent application WO-PCT PCT/US12/30061 filed on Mar. 22, 2012) Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

TAL effector nucleases are a new class of sequence-specific nucleases that can be used to make double-strand breaks at specific target sequences in the genome of a plant or other organism. (Miller et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Bacteria and archaea have evolved adaptive immune defenses termed clustered regularly interspaced short palindromic repeats (CRISPR)/CRISPR-associated (Cas) systems that use short RNA to direct degradation of foreign nucleic acids ((WO2007/025097published Mar. 1, 2007). The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target (FIG. 2B).

As used herein, the term "guide RNA" includes a synthetic fusion of two RNA molecules, a crRNA (CRISPR RNA) comprising a variable targeting domain, and a tracrRNA (FIG. 2B). In one embodiment, the guide RNA comprises a variable targeting domain of 12 to 30 nucleotide sequences and a RNA fragment that can interact with a Cas endonuclease.

As used herein, the term "guide polynucleotide", includes a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA- combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA..

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site (FIGS. 2A and 2B). The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to nucleotides. The variable targeting domain can be composed of a DNA sequence, a RNA sequence, a modified DNA sequence, a modified RNA sequence, or any combination thereof.

The term "Cos endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In one embodiment, the guide RNA and Cas endonuclease are capable of forming a complex that enables the Cas endonuclease to introduce a double strand break at a DNA target site In one embodiment of the disclosure the variable target domain is 12, 13, 14, 15, 16, 17, 18, 19, 20, 21, 22, 23, 24, 25, 26, 27, 28, 29 or 30 nucleotides in length.

In one embodiment of the disclosure, the guide RNA comprises a cRNA (or cRNA fragment) and a tracrRNA (or tracrRNA fragment) of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

In one embodiment the guide RNA can be introduced into a plant or plant cell directly using any method known in the art such as, but not limited to, particle bombardment or topical applications.

In another embodiment the guide RNA can be introduced indirectly by introducing a recombinant DNA molecule comprising the corresponding guide DNA sequence operably linked to a plant specific promoter (as shown in FIG. 1B) that is capable of transcribing the guide RNA in said plant cell. The term "corresponding guide DNA" includes a DNA molecule that is identical to the RNA molecule but has a "T" substituted for each "U" of the RNA molecule.

In some embodiments, the guide RNA is introduced via particle bombardment or *Agrobacterium* transformation of a recombinant DNA construct comprising the corresponding guide DNA operably linked to a plant U6 polymerase III promoter.

In one embodiment, the RNA that guides the RNA/Cas9 endonuclease complex, is a duplexed RNA comprising a duplex crRNA-tracrRNA (as shown in FIG. 2B). One advantage of using a guide RNA versus a duplexed crRNA-tracrRNA is that only one expression cassette needs to be made to express the fused guide RNA.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

In one embodiments, the target site can be similar to a DNA recognition site or target site that that is specifically recognized and/or bound by a double-strand break inducing agent such as a LIG3-4 endonuclease (US patent publication 2009-0133152 A1 (published May 21, 2009) or a MS26++ meganuclease (U.S. patent application Ser. No. 13/526,912 filed Jun. 19, 2012).

An "artificial target site" or "artificial target sequence" are used interchangeably herein and refer to a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example:

(i) replacement of at least one nucleotide, (ii) a deletion of at least one nucleotide, (iii) an insertion of at least one nucleotide, or (iv) any combination of (i)-(iii).

Methods for modifying a plant genomic target site are disclosed herein. In one embodiment, a method for modifying a target site in the genome of a plant cell comprises introducing a guide RNA into a plant cell having a Cas endonuclease, wherein said guide RNA and Cas endonuclease are capable of forming a complex that enables the Cas endonuclease to introduce a double strand break at said target site.

Also provided is a method for modifying a target site in the genome of a plant cell, the method comprising introducing a guide RNA and a Cas endonuclease into said plant, wherein said guide RNA and Cas endonuclease are capable of forming a complex that enables the Cas endonuclease to introduce a double strand break at said target site.

Further provided is a method for modifying a target site in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest.

Further provided is a method for modifying a target site in the genome of a plant cell, the method comprising: a) introducing into a plant cell a guide RNA comprising a variable targeting domain and a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

Further provided, a method for modifying a target DNA sequence in the genome of a plant cell, the method comprising: a)introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

The length of the target site can vary, and includes, for example, target sites that are at least 12, 13, 14, 15, 16, 17, 18, 19, 20, 21, 22, 23, 24, 25, 26, 27, 28, 29, or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs.

In some embodiment, the genomic target site capable of being cleaved by a Cas endonuclease comprises a 12 to 30 nucleotide fragment of a male fertility gene such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676), ALS or ESPS genes.

Active variants of genomic target sites can also be used. Such active variants can comprise at least 65%, 70%, 75%, 80%, 85%, 90%, 91%, 92%, 93%, 94%, 95%, 96%, 97%, 98% 99 or more sequence identity to the given target site, wherein the active variants retain biological activity and hence are capable of being recognized and cleaved by an Cas endonuclease. Assays to measure the double-strand break of a target site by an endonuclease are known in the art and generally measure the overall activity and specificity of the agent on DNA substrates containing recognition sites.

Various methods and compositions can be employed to obtain a plant having a polynucleotide of interest inserted in a target site for a Cas endonuclease. Such methods can employ homologous recombination to provide integration of the polynucleotide of Interest at the target site. In one method provided, a polynucleotide of interest is provided to the plant cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the plant genome. By "homology" is meant DNA sequences that are similar. For example, a "region of homology to a genomic region" that is found on the donor DNA is a region of DNA that has a similar sequence to a given "genomic region" in the plant genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) *Current Protocols*, (Greene Publishing Associates, Inc. and John Wiley & Sons, Inc); and, Tijssen (1993) *Laboratory Techniques in Biochemistry and Molecular Biology—Hybridization with Nucleic Acid Probes*, (*Elsevier*, New York).

As used herein, a "genomic region" is a segment of a chromosome in the genome of a plant cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference. The guide polynucleotide/Cas9 endonuclease system described herein provides for an efficient system to generate double strand breaks and allows for traits to be stacked in a complex trait locus.

In one embodiment, the guide polynucleotide/Cas endonuclease system is used for introducing one or more polynucleotides of interest or one or more traits of interest into one or more target sites by providing one or more guide polynucleotides, one Cas endonuclease, and optionally one or more donor DNAs to a plant cell. A fertile plant can be produced from that plant cell that comprises an alteration at said one or more target sites, wherein the alteration is selected from the group consisting of (i) replacement of at least one nucleotide, (ii) a deletion of at least one nucleotide, (iii) an insertion of at least one nucleotide, and (iv) any combination of (i)-(iii). Plants comprising these altered target sites can be crossed with plants comprising at least one gene or trait of interest in the same complex trait locus, thereby further stacking traits in said complex trait locus. (see also US-2013-0263324-A1, published 3 Oct. 2013 and in PCT/US13/22891, published Jan. 24, 2013).

In one embodiment, the method comprises a method for producing in a plant a complex trait locus comprising at least two altered target sequences in a genomic region of interest, said method comprising: (a) selecting a genomic region in a plant, wherein the genomic region comprises a first target sequence and a second target sequence; (b) contacting at least one plant cell with at least a first guide polynucleotide, a second polynucleotide, and optionally at least one donor DNA, and a Cas endonuclease, wherein the first and second guide polynucleotide and the Cas endonuclease can form a complex that enables the Cas endonuclease to introduce a double strand break in at least a first and a second target sequence; (c) identifying a cell from (b) comprising a first alteration at the first target sequence and a second alteration at the second target sequence; and (d) recovering a first fertile plant from the cell of (c) said fertile plant comprising the first alteration and the second alteration, wherein the first alteration and the second alteration are physically linked.

In one embodiment, the method comprises a method for producing in a plant a complex trait locus comprising at least two altered target sequences in a genomic region of interest, said method comprising: (a) selecting a genomic region in a plant, wherein the genomic region comprises a first target sequence and a second target sequence; (b) contacting at least one plant cell with a first guide polynucleotide, a Cas endonuclease, and optionally a first donor DNA, wherein the first guide polynucleotide and the Cas endonuclease can form a complex that enables the Cas endonuclease to introduce a double strand break a first target sequence; (c) identifying a cell from (b) comprising a first alteration at the first target sequence; (d) recovering a first fertile plant from the cell of (c), said first fertile plant comprising the first alteration; (e) contacting at least one plant cell with a second guide polynucleotide, a Cas endonuclease and optionally a second Donor DNA; (f) identifying a cell from (e) comprising a second alteration at the second target sequence; (g) recovering a second fertile plant from the cell of (f), said second fertile plant comprising the second alteration; and, (h) obtaining a fertile progeny plant from the second fertile plant of (g), said fertile progeny plant comprising the first alteration and the second alteration, wherein the first alteration and the second alteration are physically linked.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of 10-4 to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) Genetics 147:689-99). Using FLP-mediated DNA integration at a target FRT in *Drosophila*, Golic et al., showed integration was approximately 10-fold more efficient when the donor and target shared 4.1 kb of homology as compared to 1.1 kb of homology (Golic et al., (1997) Nucleic Acids Res 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) Proc. Natl. Acad. Sci. USA 90:1262-6; Keeler and Gloor, (1997) Mol Cell Biol 17:627-34).

Homologous recombination has also been accomplished in other organisms. For example, at least 150-200 bp of homology was required for homologous recombination in the parasitic protozoan *Leishmania* (Papadopoulou and Dumas, (1997) Nucleic Acids Res 25:4278-86). In the filamentous fungus *Aspergillus nidulans*, gene replacement has been accomplished with as little as 50 bp flanking homology (Chaveroche et al., (2000) Nucleic Acids Res 28:e97). Targeted gene replacement has also been demonstrated in the ciliate Tetrahymena *thermophila* (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically offspring. By interbreeding siblings, homozygous mice carrying the selected genes can be obtained. An overview of the process is provided in Watson et al., (1992) Recombinant DNA, 2nd Ed., (Scientific American Books distributed by WH Freeman & Co.); Capecchi, (1989) Trends Genet 5:70-6; and Bronson, (1994) J Biol Chem 269:27155-8. Homologous recombination in mammals other than mouse has been limited by the lack of stem cells capable of being transplanted to oocytes or developing embryos. However, McCreath et al., Nature 405:1066-9 (2000) reported successful homologous recombination in sheep by transformation and selection in primary embryo fibroblast cells.

Error-prone DNA repair mechanisms can produce mutations at double-strand break sites. The nonhomologous end-joining (NHEJ) pathways are the most common repair mechanism to bring the broken ends together (Bleuyard et al., (2006) DNA Repair 5:1-12). The structural integrity of chromosomes is typically preserved by the repair, but deletions, insertions, or other rearrangements are possible. The two ends of one double-strand break are the most prevalent substrates of NHEJ (Kirik et al., (2000) EMBO J 19:5562-6), however if two different double-strand breaks occur, the free ends from different breaks can be ligated and result in chromosomal deletions (Siebert and Puchta, (2002) Plant Cell 14:1121-31), or chromosomal translocations between different chromosomes (Pacher et al., (2007) Genetics 175: 21-9).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152: 1173-81).

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Alternatively, the double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152:1173-81).

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

In one embodiment provided herein, the method comprises contacting a plant cell with the donor DNA and the endonuclease. Once a double-strand break is introduced in the target site by the endonuclease, the first and second regions of homology of the donor DNA can undergo homologous recombination with their corresponding genomic regions of homology resulting in exchange of DNA between the donor and the genome. As such, the provided methods result in the integration of the polynucleotide of interest of the donor DNA into the double-strand break in the target site in the plant genome, thereby altering the original target site and producing an altered genomic target site.

The donor DNA may be introduced by any means known in the art. For example, a plant having a target site is provided. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed plant's genome.

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould et al., (2006) J Mol Biol 355:443-58; Ashworth et al., (2006) Nature 441:656-9; Doyon et al., (2006) J Am Chem Soc 128:2477-84; Rosen et al., (2006) Nucleic Acids Res 34:4791-800; and Smith et al., (2006) Nucleic Acids Res 34:e149; Lyznik et al., (2009) U.S. Patent Application Publication No. 20090133152A1; Smith et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang et al., (2009) Plant Mol Biol 70:669-79). More practically, the maize liguleless locus was targeted using an engineered single-chain endonuclease designed based on the I-CreI meganuclease sequence. Mutations of the selected liguleless locus recognition sequence were detected in 3% of the T0 transgenic plants when the designed homing nuclease was introduced by *Agrobacterium*-mediated transformation of immature embryos (Gao et al., (2010) Plant J 61:176-87).

Polynucleotides of interest are further described herein and are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

Genome Editing Using the Guide RNA/Cas Endonuclease System

As described herein, the guide RNA/Cas endonuclease system can be used in combination with a co-delivered polynucleotide modification template to allow for editing of a genomic nucleotide sequence of interest. Also, as described herein, for each embodiment that uses a guide RNA/Cas endonuclease system, a similar guide polynucleotide/Cas endonuclease system can be deployed where the guide polynucleotide does not solely comprise ribonucleic acids but wherein the guide polynucleotide comprises a combination of RNA-DNA molecules or solely comprise DNA molecules.

While numerous double-strand break-making systems exist, their practical applications for gene editing may be restricted due to the relatively low frequency of induced double-strand breaks (DSBs). To date, many genome modification methods rely on the homologous recombination system. Homologous recombination (HR) can provide molecular means for finding genomic DNA sequences of interest and modifying them according to the experimental specifications. Homologous recombination takes place in plant somatic cells at low frequency. The process can be enhanced to a practical level for genome engineering by introducing double-strand breaks (DSBs) at selected endonuclease target sites. The challenge has been to efficiently make DSBs at genomic sites of interest since there is a bias in the directionality of information transfer between two interacting DNA molecules (the broken one acts as an acceptor of genetic information). Described herein is the use of a guide RNA/Cas system which provides flexible genome cleavage specificity and results in a high frequency of double-strand breaks at a DNA target site, thereby enabling efficient gene editing in a nucleotide sequence of interest, wherein the nucleotide sequence of interest to be edited can be located within or outside the target site recognized and cleaved by a Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure describes a method for editing a nucleotide sequence in the genome of a cell, the method comprising providing a guide RNA, a polynucleotide modification template, and at least one Cas endonuclease to a cell, wherein the Cas endonuclease is capable of introducing a double-strand break at a target sequence in the genome of said cell, wherein said polynucleotide modification template includes at least one nucleotide modification of said nucleotide sequence. Cells include, but are not limited to, human, animal, bacterial, fungal, insect, and plant cells as well as plants and seeds produced by the methods described herein. The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In another embodiment, the disclosure describes a method for editing a nucleotide sequence in the genome of a plant cell, the method comprising providing a guide RNA, a polynucleotide modification template, and at least one maize optimized Cas9 endonuclease to a plant cell, wherein the maize optimized Cas9 endonuclease is capable of providing a double-strand break at a moCas9 target sequence in the plant genome, wherein said polynucleotide modification template includes at least one nucleotide modification of said nucleotide sequence.

In another embodiment, the disclosure describes a method for editing a nucleotide sequence in the genome of a cell, the method comprising providing a guide RNA, a polynucleotide modification template and at least one Cas endonuclease to a cell, wherein said guide RNA and Cas endonuclease are capable of forming a complex that enables the Cas endonuclease to introduce a double strand break at a target site, wherein said polynucleotide modification template comprises at least one nucleotide modification of said nucleotide sequence.

In another embodiment of genome editing, editing of the endogenous enolpyruvylshikimate-3-phosphate synthase (EPSPS) gene is disclosed herein (Example 16). In this embodiment, the polynucleotide modification template (EPSPS polynucleotide modification template) includes a partial fragment of the EPSPS gene (and therefore does not encode a fully functional EPSPS polypeptide by itself). The EPSPS polynucleotide modification template contained three point mutations that were responsible for the creation of the T1021/P106S (TIPS) double mutant (Funke, T et al., J. Biol. Chem. 2009, 284:9854-9860), which provide glyphosate tolerance to transgenic plants expressing as EPSPS double mutant transgene.

As defined herein "Glyphosate" includes any herbicidally effective form of N-phosphonomethylglycine (including any salt thereof), other forms which result in the production of the glyphosate anion in plants and any other herbicides of the phosphonomethylglycine family.

In one embodiment of the disclosure, an epsps mutant plant is produced by the method described herein, said method comprising: a) providing a guide RNA, a polynucleotide modification template and at least one Cas endonuclease to a plant cell, wherein the Cas endonuclease introduces a double strand break at a target site within an epsps (enolpyruvylshikimate-3-phosphate synthase) genomic sequence in the plant genome, wherein said polynucleotide modification template comprises at least one nucleotide modification of said epsps genomic sequence; b) obtaining a plant from the plant cell of (a); c) evaluating the plant of (b) for the presence of said at least one nucleotide modification and d) selecting a progeny plant that shows resistance to glyphosate.

Increased resistance to a herbicide is demonstrated when plants which display the increased resistance to a herbicide are subjected to the herbicide and a dose/response curve is shifted to the right when compared with that provided by an appropriate control plant. Such dose/response curves have "dose" plotted on the x-axis and "percentage injury", "herbicidal effect" etc. plotted on the y-axis. Plants which are substantially resistant to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field. The terms resistance and tolerance may be used interchangeably.

FIG. 12 shows a schematic representation of components used in the genome editing procedure. A maize optimized Cas endonuclease, a guide RNA and a polynucleotide modification template were provided to a plant cell. For example, as shown in FIG. 12, the polynucleotide modification template included three nucleotide modifications (indicated by arrows) when compared to the EPSPS genomic sequence to be edited. These three nucleotide modifications are referred to as TIPS mutations as these nucleotide modifications result in the amino acid changes T-102 to 1-102 and γ-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon ATC, the third point mutation results from the substitution of the first C nucleotide in the codon sequence CCA with a T nucleotide in order to form a serine codon TCA (FIG. 12).

In one embodiment, the disclosure describes a method for producing an epsps (enolpyruvylshikimate-3-phosphate synthase) mutant plant, the method comprising: a) providing a guide RNA, a polynucleotide modification template and at least one Cas endonuclease to a plant cell, wherein the Cas endonuclease introduces a double strand break at a target site within an epsps genomic sequence in the plant genome, wherein said polynucleotide modification template comprises at least one nucleotide modification of said epsps genomic sequence; b) obtaining a plant from the plant cell of (a); c) evaluating the plant of (b) for the presence of said at least one nucleotide modification; and, d) screening a progeny plant of (c) that is void of said guide RNA and Cas endonuclease.

The nucleotide sequence to be edited can be a sequence that is endogenous, artificial, pre-existing, or transgenic to the cell that is being edited. For example, the nucleotide sequence in the genome of a cell can be a native gene, a mutated gene, a non-native gene, a foreign gene, or a transgene that is stably incorporated into the genome of a cell. Editing of such nucleotide may result in a further desired phenotype or genotype.

Regulatory Sequence Modifications Using the Guide Polynucleotide/Cas Endonuclease System In one embodiment the nucleotide sequence to be modified can be a regulatory sequence such as a promoter wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers (U.S. Pat. No. 5,837,850 issued Nov. 17, 1998), a mutation of DNA binding elements and/or a deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

In one embodiment the nucleotide sequence can be a promoter wherein the editing of the promoter comprises replacing an ARGOS 8 promoter with a *Zea mays* GOS2 PRO:GOS2-intron promoter.

In one embodiment the nucleotide sequence can be a promoter wherein the editing of the promoter comprises replacing a native EPSPS1 promoter from with a plant ubiquitin promoter.

In one embodiment the nucleotide sequence can be a promoter wherein the editing of the promoter comprises replacing an endogenous maize NPK1 promoter with a stress inducible maize RAB17 promoter.

In one embodiment the nucleotide sequence can be a promoter wherein the promoter to be edited is selected from the group comprising *Zea mays*-PEPC1 promoter (Kausch et al, Plant Molecular Biology, 45: 1-15, 2001), *Zea mays* Ubiquitin promoter (UBI1ZM PRO, Christensen et al, plant Molecular Biology 18: 675-689, 1992), *Zea mays*-Rootmet2 promoter (U.S. Pat. No. 7,214,855), Rice actin promoter (OS-ACTIN PRO, U.S. Pat. No. 5,641,876; McElroy et al, The Plant Cell, Vol 2, 163-171, Feb. 1990), Sorghum RCC3 promoter (US 2012/0210463 filed on 13 Feb. 2012), *Zea mays*-GOS2 promoter (U.S. Pat. No. 6,504,083), *Zea mays*-ACO2 promoter(U.S. application Ser. No. 14/210,711 filed 14 Mar. 2014) or *Zea mays*-oleosin promoter (U.S. Pat. No. 8,466,341 B2). In another embodiment, the guide polynucleotide/Cas endonuclease system can be used in combination with a co-delivered polynucleotide modification template or donor DNA sequence to allow for the insertion of a promoter or promoter element into a genomic nucleotide sequence of interest, wherein the promoter insertion (or promoter element insertion) results in any one of the following or any one combination of the following: an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression a mutation of DNA binding elements and/or an addition of DNA binding elements. Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or sulphonylurea (Su) repressor/operator/inducer elements. The dehydration-responsive element (DRE) was first identified as a cis-acting promoter element in the promoter of the drought-responsive gene rd29A, which contains a 9 bp conserved core sequence, TACCGACAT (Yamaguchi-Shinozaki, K., and Shinozaki, K. (1994) *Plant Cell* 6, 251-264). Insertion of DRE into an endogenous promoter may confer a drought inducible expression of the downstream gene. Another example is ABA-responsive elements (ABREs) which contains a (C/T) ACGTGGC consensus sequence found to be present in numerous ABA and/or stress-regulated genes (Busk P. K., Pages M.(1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

In one embodiment, the guide polynucleotide/Cas endonuclease system can be used to insert an enhancer element, such as but not limited to a Cauliflower Mosaic Virus 35 S enhancer, in front of an endogenous FMT1 promoter to enhance expression of the FTM1.

In one embodiment, the guide polynucleotide/Cas endonuclease system can be used to insert a component of the TET operator repressor/operator/inducer system, or a component of the sulphonylurea (Su) repressor/operator/inducer system into plant genomes to generate or control inducible expression systems.

In another embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements and/or an addition of DNA binding elements. Promoter elements to be deleted can be, but are not limited to, promoter core elements, promoter enhancer elements or 35 S enhancer elements (as described in Example 32) The promoter or promoter fragment to be deleted can be endogenous, artificial, pre-existing, or transgenic to the cell that is being edited.

In one embodiment, the guide polynucleotide/Cas endonuclease system can be used to delete the ARGOS 8 promoter present in a maize genome as described herein.

In one embodiment, the guide polynucleotide/Cas endonuclease system can be used to delete a 35S enhancer element present in a plant genome as described herein.

Terminator Modifications Using the Guide Polynucleotide/Cas Endonuclease System

In one embodiment the nucleotide sequence to be modified can be a terminator wherein the editing of the terminator comprises replacing the terminator (also referred to as a "terminator swap" or "terminator replacement") or terminator fragment with a different terminator (also referred to as replacement terminator) or terminator fragment (also referred to as replacement terminator fragment), wherein the terminator replacement results in any one of the following or any one combination of the following: an increased terminator activity, an increased terminator tissue specificity, a decreased terminator activity, a decreased terminator tissue specificity, a mutation of DNA binding elements and/or a deletion or addition of DNA binding elements." The terminator (or terminator fragment) to be modified can be a terminator (or terminator fragment) that is endogenous, artificial, pre-existing, or transgenic to the cell that is being edited. The replacement terminator (or replacement terminator fragment) can be a terminator (or terminator fragment) that is endogenous, artificial, pre-existing, or transgenic to the cell that is being edited.

In one embodiment the nucleotide sequence to be modified can be a terminator wherein the terminator to be edited is selected from the group comprising terminators from maize Argos 8 or SRTF18 genes, or other terminators, such as potato PinII terminator, sorghum actin terminator (SB-ACTIN TERM, WO 2013/184537 A1 published Dec. 2013), sorghum SB-GKAF TERM (WO2013019461), rice T28 terminator (OS-T28 TERM,WO 2013/012729 A2), AT-T9 TERM (WO 2013/012729 A2) or GZ-W64A TERM (U.S. Pat. No. 7,053,282).

In one embodiment, the guide polynucleotide/Cas endonuclease system can be used in combination with a co-delivered polynucleotide modification template or donor DNA sequence to allow for the insertion of a terminator or terminator element into a genomic nucleotide sequence of interest, wherein the terminator insertion (or terminator element insertion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements.

The terminator (or terminator element) to be inserted can be a terminator (or terminator element) that is endogenous, artificial, pre-existing, or transgenic to the cell that is being edited.

In another embodiment, the guide polynucleotide/Cas endonuclease system can be used to allow for the deletion of a terminator or terminator element, wherein the terminator deletion (or terminator element deletion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements. The terminator or terminator fragment to be deleted can be endogenous, artificial, pre-existing, or transgenic to the cell that is being edited.

Additional Regulatory Sequence Modifications Using the Guide Polynucleotide/Cas Endonuclease System In one embodiment, the guide polynucleotide/Cas endonuclease system can be used to modify or replace a regulatory sequence in the genome of a cell. A regulatory sequence is a segment of a nucleic acid molecule which is capable of increasing or decreasing the expression of specific genes within an organism and/or is capable of altering tissue specific expression of genes within an organism. Examples of regulatory sequences include, but are not limited to, 3' UTR (untranslated region) region, 5' UTR region, transcription activators, transcriptional enhancers transcriptions repressors, translational repressors, splicing factors, miRNAs, siRNA, artificial miRNAs, promoter elements, CAMV 35 S enhancer, MMV enhancer elements (PCT/US14/23451 filed Mar. 11, 2013), SECIS elements, polyadenylation signals, and polyubiquitination sites. In some embodiments the editing (modification) or replacement of a regulatory element results in altered protein translation, RNA cleavage, RNA splicing, transcriptional termination or post translational modification. In one embodiment, regulatory elements can be identified within a promoter and these regulatory elements can be edited or modified do to optimize these regulatory elements for up or down regulation of the promoter.

In one embodiment, the genomic sequence of interest to be modified is a polyubiquitination site, wherein the modification of the polyubiquitination sites results in a modified rate of protein degradation. The ubiquitin tag condemns proteins to be degraded by proteasomes or autophagy. Proteasome inhibitors are known to cause a protein overproduction. Modifications made to a DNA sequence encoding a protein of interest can result in at least one amino acid modification of the protein of interest, wherein said modification allows for the polyubiquitination of the protein (a post translational modification) resulting in a modification of the protein degradation In one embodiment, the genomic sequence of interest to be modified is a polyubiquitination site on a maize EPSPS gene, wherein the polyubiquitination site modified resulting in an increased protein content due to a slower rate of EPSPS protein degradation.

In one embodiment, the genomic sequence of interest to be modified is a an intron site, wherein the modification consist of inserting an intron enhancing motif into the intron which results in modulation of the transcriptional activity of the gene comprising said intron.

In one embodiment, the genomic sequence of interest to be modified is a an intron site, wherein the modification consist of replacing a soybean EPSP1 intron with a soybean ubiquitin intron 1 as described herein (Example 25)

In one embodiment, the genomic sequence of interest to be modified is a an intron or UTR site, wherein the modification consist of inserting at least one microRNA into said intron or UTR site, wherein expression of the gene comprising the intron or UTR site also results in expression of said microRNA, which in turn can silence any gene targeted by the microRNA without disrupting the gene expression of the native/transgene comprising said intron.

In one embodiment, the guide polynucleotide/Cas endonuclease system can be used to allow for the deletion or mutation of a Zinc Finger transcription factor, wherein the deletion or mutation of the Zinc Finger transcription factor results in or allows for the creation of a dominant negative Zinc Finger transcription factor mutant (Li et al 2013 Rice zinc finger protein DST enhances grain production through controlling Gn1a/OsCKX2 expression PNAS 110:3167-3172). Insertion of a single base pair downstream zinc finger domain will result in a frame shift and produces a new protein which still can bind to DNA without transcription activity. The mutant protein will compete to bind to cytokinin oxidase gene promoters and block the expression of cytokinin oxidase gene. Reduction of cytokinin oxidase gene expression will increase cytokinin level and promote panicle growth in rice and ear growth in maize, and increase yield under normal and stress conditions.

Modifications of Splicing Sites and/or Introducing Alternate Splicing Sites Using the Guide Polynucleotide/Cas Endonuclease System Protein synthesis utilizes mRNA molecules that emerge from pre-mRNA molecules subjected to the maturation process. The pre-mRNA molecules are capped, spliced and stabilized by addition of polyA tails. Eukaryotic cells developed a complex process of splicing that result in alternative variants of the original pre-mRNA molecules. Some of them may not produce functional templates for protein synthesis. In maize cells, the splicing process is affected by splicing sites at the exon-intron junction sites. An example of a canonical splice site is AGGT. Gene coding sequences can contains a number of alternate splicing sites that may affect the overall efficiency of the pre-mRNA maturation process and as such may limit the protein accumulation in cells. The guide polynucleotide/Cas endonuclease system can be used in combination with a co-delivered polynucleotide modification template to edit a gene of interest to introduce a canonical splice site at a described junction or any variant of a splicing site that changes the splicing pattern of pre-mRNA molecules.

In one embodiment, the nucleotide sequence of interest to be modified is a maize EPSPS gene, wherein the modification of the gene consists of modifying alternative splicing sites resulting in enhanced production of the functional gene transcripts and gene products (proteins).

In one embodiment, the nucleotide sequence of interest to be modified is a gene, wherein the modification of the gene consists of editing the intron borders of alternatively spliced genes to alter the accumulation of splice variants.

Modifications of Nucleotide Sequences Encoding a Protein of Interest Using the Guide Polynucleotide/Cas Endonuclease System In one embodiment, the guide polynucleotide/Cas endonuclease system can be used to modify or replace a coding sequence in the genome of a cell, wherein the modification or replacement results in any one of the following, or any one combination of the following: an increased protein (enzyme) activity, an increased protein functionality, a decreased protein activity, a decreased protein functionality, a site specific mutation, a protein domain swap, a protein knock-out, a new protein functionality, a modified protein functionality.

In one embodiment the protein knockout is due to the introduction of a stop codon into the coding sequence of interest.

In one embodiment the protein knockout is due to the deletion of a start codon into the coding sequence of interest.

Amino Acid and/or Protein Fusions Using the Guide Polynucleotide/Cas Endonuclease System In one embodiment, the guide polynucleotide/Cas endonuclease system can be used with or without a co-delivered polynucleotide sequence to fuse a first coding sequence encoding a first protein to a second coding sequence encoding a second protein in the genome of a cell, wherein the protein fusion results in any one of the following or any one combination of the following: an increased protein (enzyme) activity, an increased protein functionality, a decreased protein activity, a decreased protein functionality, a new protein functionality, a modified protein functionality, a new protein localization, a new timing of protein expression, a modified protein expression pattern, a chimeric protein, or a modified protein with dominant phenotype functionality.

In one embodiment, the guide polynucleotide/Cas endonuclease system can be used with or without a co-delivered polynucleotide sequence to fuse a first coding sequence encoding a chloroplast localization signal to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding a chloroplast localization signal to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding a chloroplast localization signal (e.g., a chloroplast transit peptide) to a second coding sequence, wherein the protein fusion results in a modified protein with dominant phenotype functionality Gene Silencing by Expressing an Inverted Repeat into a Gene of Interest Using the Guide Polynucleotide/Cas Endonuclease System In one embodiment, the guide polynucleotide/Cas endonuclease system can be used in combination with a co-delivered polynucleotide sequence to insert an inverted gene fragment into a gene of interest in the genome of an organism, wherein the insertion of the inverted gene fragment can allow for an in-vivo creation of an inverted repeat (hairpin) and results in the silencing of said endogenous gene.

In one embodiment the insertion of the inverted gene fragment can result in the formation of an in-vivo created inverted repeat (hairpin) in a native (or modified) promoter of a gene and/or in a native 5' end of the native gene. The inverted gene fragment can further comprise an intron which can result in an enhanced silencing of the targeted gene.

Genome Deletion for Trait Locus Characterization

Trait mapping in plant breeding often results in the detection of chromosomal regions housing one or more genes controlling expression of a trait of interest. For a qualitative trait, the guide polynucleotide/Cas endonuclease system can be used to eliminate candidate genes in the identified chromosomal regions to determine if deletion of the gene affects expression of the trait. For quantitative traits, expression of a trait of interest is governed by multiple quantitative trait loci (QTL) of varying effect-size, complexity, and statistical significance across one or more chromosomes. In cases of negative effect or deleterious QTL regions affecting a complex trait, the guide polynucleotide/Cas endonuclease system can be used to eliminate whole regions delimited by marker-assisted fine mapping, and to target specific regions for their selective elimination or rearrangement. Similarly, presence/absence variation (PAV) or copy number variation (CNV) can be manipulated with selective genome deletion using the guide polynucleotide/Cas endonuclease system.

In one embodiment, the region of interest can be flanked by two independent guide polynucleotide/CAS endonuclease target sequences. Cutting would be done concurrently. The deletion event would be the repair of the two chromosomal ends without the region of interest. Alternative results would include inversions of the region of interest, mutations at the cut sites and duplication of the region of interest.

Methods for identifying at least one plant cell comprising in its genome a polynucleotide of Interest integrated at the target site.

Further provided are methods for identifying at least one plant cell comprising in its genome a polynucleotide of Interest integrated at the target site. A variety of methods are available for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering a plant from the plant cell comprising a polynucleotide of Interest integrated into its genome. The plant may be sterile or fertile. It is recognized that any polynucleotide of interest can be provided, integrated into the plant genome at the target site, and expressed in a plant.

Polynucleotides/polypeptides of interest include, but are not limited to, herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with glyphosate resistance described herein.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) Eur. J. Biochem. 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) J. Bacteriol. 170:5837-5847) facilitate expression of polyhydroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) Proceedings of the World Congress on Vegetable Protein Utilization in Human Foods and Animal Feedstuffs, ed. Applewhite (American Oil Chemists Society, Champaign, Illinois), pp. 497-502; herein incorporated by reference); corn (Pedersen et al. (1986) J. Biol. Chem. 261:6279; Kirihara et al. (1988) Gene 71:359; both of which are herein incorporated by reference); and rice (Musumura et al. (1989) Plant Mol. Biol. 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) Nature 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

Polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) Science 266:789; Martin et al. (1993) Science 262:1432; and Mindrinos et al. (1994) Cell 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g., the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference. The bar gene encodes resistance to the herbicide basta, the nptll gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male fertility genes such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676). Maize plants (*Zea mays* L.) can be bred by both self-pollination and cross-pollination techniques. Maize has male flowers, located on the tassel, and female flowers, located on the ear, on the same plant. It can self-pollinate ("selfing") or cross pollinate. Natural pollination occurs in maize when wind blows pollen from the tassels to the silks that protrude from the tops of the incipient ears. Pollination may be readily controlled by techniques known to those of skill in the art. The development of maize hybrids requires the development of homozygous inbred lines, the crossing of these lines, and the evaluation of the crosses. Pedigree breeding and recurrent selections are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated F1. The F1 hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid (F1) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used as a hybrid parent. Mutations that cause male sterility in maize have been produced by a variety of methods such as X-rays or UV-irradiations, chemical treatments, or transposable element insertions (ms23, ms25, ms26, ms32) (Chaubal et al. (2000) Am J Bot 87:1193-1201). Conditional regulation of fertility genes through fertility/sterility "molecular switches" could enhance the options for designing new male-sterility systems for crop improvement (Unger et al. (2002) Transgenic Res 11:455-465).

Besides identification of novel genes impacting male fertility, there remains a need to provide a reliable system of producing genetic male sterility.

In U.S. Pat. No. 5,478,369, a method is described by which the Ms45 male fertility gene was tagged and cloned on maize chromosome 9. Previously, there had been described a male fertility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" Canadian Journal of Genetics & Cytology 23:195-208 (Jan. 1981). The only fertility gene cloned before that had been the *Arabidopsis* gene described at Aarts, et al., supra.

Examples of genes that have been discovered subsequently that are important to male fertility are numerous and include the *Arabidopsis* ABORTED MICROSPORES (AMS) gene, Sorensen et al., The Plant Journal (2003) 33(2):413-423); the *Arabidopsis* MS1 gene (Wilson et al., The Plant Journal (2001) 39(2):170-181); the NEF1 gene (Ariizumi et al., The Plant Journal (2004) 39(2):170-181); *Arabidopsis* AtGPAT1 gene (Zheng et al., The Plant Cell (2003) 15:1872-1887); the *Arabidopsis* dde2-2 mutation was shown to be defective in the allene oxide syntase gene (Malek et al., Planta (2002)216:187-192); the *Arabidopsis* faceless pollen-1 gene (flp1) (Ariizumi et al, Plant Mol. Biol. (2003) 53:107-116); the *Arabidopsis* MALE MEIOCYTE DEATH1 gene (Yang et al., The Plant Cell (2003) 15: 1281-1295); the tapetum-specific zinc finger gene, TAZ1 (Kapoor et al., The Plant Cell (2002) 14:2353-2367); and the TAPETUM DETERMINANT1 gene (Lan et al, The Plant Cell (2003) 15:2792-2804).

Other known male fertility mutants or genes from *Zea mays* are listed in U.S. Pat. No. 7,919,676 incorporated herein by reference.

Other genes include kinases and those encoding compounds toxic to either male or female gametophytic development.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) Proc. Natl. Acad. Sci. USA 89:6314-8; Yao et al., (1992) Cell 71:63-72; Reznikoff, (1992) Mol Microbiol 6:2419-22; Hu et al., (1987) Cell 48:555-66; Brown et al., (1987) Cell 49:603-12; Figge et al., (1988) Cell 52:713-22; Deuschle et al., (1989) Proc. Natl. Acad. Sci. USA 86:5400-4; Fuerst et al., (1989) Proc. Natl. Acad. Sci. USA 86:2549-53; Deuschle et al., (1990) Science 248:480-3; Gossen, (1993) Ph.D. Thesis, University of Heidelberg; Reines et al., (1993) Proc. Natl. Acad. Sci. USA 90:1917-21; Labow et al., (1990) Mol Cell Biol 10:3343-56; Zambretti et al., (1992) Proc. Natl. Acad. Sci. USA 89:3952-6; Bairn et al., (1991) Proc. Natl. Acad. Sci. USA 88:5072-6; Wyborski et al., (1991) Nucleic Acids Res 19:4647-53; Hillen and Wissman, (1989) Topics Mol Struc Biol 10:143-62; Degenkolb et al., (1991) Antimicrob Agents Chemother 35:1591-5; Kleinschnidt et al., (1988) Biochemistry 27:1094-104; Bonin, (1993) Ph.D. Thesis, University of Heidelberg; Gossen et al., (1992) Proc. Natl. Acad. Sci. USA 89:5547-51; Oliva et al., (1992) Antimicrob Agents Chemother 36:913-9; Hlavka et al., (1985) Handbook of Experimental Pharmacology, Vol. 78 (Springer-Verlag, Berlin); Gill et al., (1988) Nature 334:721-4. Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) J. Bacteriol. 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

"Open reading frame" is abbreviated ORF.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, WI). Within the context of this application it will be understood that where sequence analysis software is used for analysis, that the results of the analysis will be based on the "default values" of the program referenced, unless otherwise specified. As used herein "default values"

will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992) *Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) Proc. Natl. Acad. Sci. USA 89:10915). GAP uses the algorithm of Needleman and Wunsch, (1970) J Mol Biol 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%72%, 73%, 74%, 75%, 76%, 77%, 78%, 79%, 80%, 81% 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

In one embodiment, the targeted mutation is the result of a guideRNA/Cas endonuclease induced gene editing as described herein. The guide RNA/Cas endonuclease induced targeted mutation can occur in a nucleotide sequence that is located within or outside a genomic target site that is recognized and cleaved by a Cas endonuclease.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage.

Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures. Thus, "a plant-optimized nucleotide sequence" of the present disclosure comprises one or more of such sequence modifications.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Some embodiments of the disclosures relate to newly discovered U6 RNA polymerase III promoters, GM-U6-13.1 (SEQ ID NO: 120) as described in Example 12 and GM-U6-9.1 (SEQ ID NO: 295) described in Example 19.

Non-limiting examples of methods and compositions relating to the soybean promoters described herein are as follows:

A1. A recombinant DNA construct comprising a nucleotide sequence comprising any of the sequences set forth in SEQ ID NO:120 or SEQ ID NO:295, or a functional fragment thereof, operably linked to at least one heterologous sequence, wherein said nucleotide sequence is a promoter.

A2. The recombinant DNA construct of embodiment A1, wherein the nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:120 or SEQ ID NO: 295..

A3. A vector comprising the recombinant DNA construct of embodiment A1.

A4. A cell comprising the recombinant DNA construct of embodiment A1.

A5. The cell of embodiment A4, wherein the cell is a plant cell.

A6. A transgenic plant having stably incorporated into its genome the recombinant DNA construct of embodiment A1.

A7. The transgenic plant of embodiment A6 wherein said plant is a dicot plant.

A8. The transgenic plant of embodiment A7 wherein the plant is soybean.

A9. A transgenic seed produced by the transgenic plant of embodiment A7, wherein the transgenic seed comprises the recombinant DNA construct.

A10. The recombinant DNA construct of embodiment A1 wherein the at least one heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

A11. The recombinant DNA construct of embodiment A1, wherein the at least one heterologous sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

A12. A method of expressing a coding sequence or a functional RNA in a plant comprising:

a) introducing the recombinant DNA construct of embodiment A1 into the plant, wherein the at least one heterologous sequence comprises a coding sequence or encodes a functional RNA;
b) growing the plant of step a); and
c) selecting a plant displaying expression of the coding sequence or the functional RNA of the recombinant DNA construct.

A13. A method of transgenically altering a marketable plant trait, comprising:

a) introducing a recombinant DNA construct of embodiment A1 into the plant;

b) growing a fertile, mature plant resulting from step a); and c) selecting a plant expressing the at least one heterologous sequence in at least one plant tissue based on the altered marketable trait.

A14. The method of embodiment A13 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

A15. A method for altering expression of at least one heterologous sequence in a plant comprising:

(a) transforming a plant cell with the recombinant DNA construct of embodiment A1;

(b) growing fertile mature plants from transformed plant cell of step (a); and (c) selecting plants containing the transformed plant cell wherein the expression of the heterologous sequence is increased or decreased.

A16. The method of Embodiment A15 wherein the plant is a soybean plant.

A17. A plant stably transformed with a recombinant DNA construct comprising a soybean promoter and a heterologous nucleic acid fragment operably linked to said promoter, wherein said promoter is a capable of controlling expression of said heterologous nucleic acid fragment in a plant cell, and further wherein said promoter comprises any of the sequences set forth in SEQ ID NO: 120 or SEQ ID NO:295.

New promoters of various types useful in plant cells are constantly being discovered; numerous examples may be found in the compilation by Okamuro and Goldberg, (1989) *In The Biochemistry of Plants*, Vol. 115, Stumpf and Conn, eds (New York, NY: Academic Press), pp. 1-82.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) Mol Biotechnol 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) Plant Cell 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre mRNAt. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense"

RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook et al., Molecular Cloning: A Laboratory Manual; Cold Spring Harbor Laboratory: Cold Spring Harbor, NY (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) EMBO J 4:2411-2418; De Almeida et al., (1989) Mol Gen Genetics 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA, guide RNA, or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different genes of interest.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male- fertile, respectively. It is further recognized that a male fertile (but female sterile) plant can produce viable progeny when crossed with a female fertile plant and that a female fertile (but male sterile) plant can produce viable progeny when crossed with a male fertile plant.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to an 1 average recombination frequency between the two linked genes, markers, target sites, loci, or any pair thereof.

Breeding Methods and Methods for Selecting Plants Utilizing a Two Component RNA Guide and Cas Endonuclease System The present disclosure finds use in the breeding of plants comprising one or more transgenic traits. Most commonly, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

The currently used systems for precision genetic engineering of eukaryotic genomes, e.g. plant genomes, rely upon homing endonucleases, meganucleases, zinc finger nucleases, and transcription activator—like effector nucleases (TALENs), which require de novo protein engineering for every new target locus. The highly specific, RNA-directed DNA nuclease, guide RNA/Cas9 endonuclease system described herein, is more easily customizable and therefore more useful when modification of many different target sequences is the goal. This disclosure takes further advantage of the two component nature of the guide RNA/Cas system, with its constant protein component, the Cas endonuclease, and its variable and easily reprogrammable targeting component, the guide RNA or the crRNA.

The guide RNA/Cas system described herein is especially useful for genome engineering, especially plant genome engineering, in circumstances where nuclease off-target cutting can be toxic to the targeted cells. In one embodiment of the guide RNA/Cas system described herein, the constant component, in the form of an expression-optimized Cas9 gene, is stably integrated into the target genome, e.g. plant genome. Expression of the Cas9 gene is under control of a promoter, e.g. plant promoter, which can be a constitutive promoter, tissue-specific promoter or inducible promoter, e.g. temperature-inducible, stress-inducible, developmental stage inducible, or chemically inducible promoter. In the absence of the variable component, i.e. the guide RNA or crRNA, the Cas9 protein is not able to cut DNA and therefore its presence in the plant cell should have little or no consequence. Hence a key advantage of the guide RNA/Cas system described herein is the ability to create and maintain a cell line or transgenic organism capable of efficient expression of the Cas9 protein with little or no consequence to cell viability. In order to induce cutting at desired genomic sites to achieve targeted genetic modifications, guide RNAs or crRNAs can be introduced by a variety of methods into cells containing the stably-integrated and expressed cas9 gene. For example, guide RNAs or crRNAs can be chemically or enzymatically synthesized, and introduced into the Cas9 expressing cells via direct delivery methods such a particle bombardment or electroporation.

Alternatively, genes capable of efficiently expressing guide RNAs or crRNAs in the target cells can be synthesized chemically, enzymatically or in a biological system, and these genes can be introduced into the Cas9 expressing cells via direct delivery methods such a particle bombardment, electroporation or biological delivery methods such as *Agrobacterium* mediated DNA delivery.

One embodiment of the disclosure is a method for selecting a plant comprising an altered target site in its plant genome, the method comprising: a) obtaining a first plant comprising at least one Cas endonuclease capable of introducing a double strand break at a target site in the plant genome; b) obtaining a second plant comprising a guide RNA that is capable of forming a complex with the Cas endonuclease of (a), c) crossing the first plant of (a) with the second plant of (b); d) evaluating the progeny of (c) for an alteration in the target site and e) selecting a progeny plant that possesses the desired alteration of said target site.

Another embodiment of the disclosure is a method for selecting a plant comprising an altered target site in its plant genome, the method comprising: a) obtaining a first plant comprising at least one Cas endonuclease capable of introducing a double strand break at a target site in the plant genome; b) obtaining a second plant comprising a guide RNA and a donor DNA, wherein said guide RNA is capable of forming a complex with the Cas endonuclease of (a), wherein said donor DNA comprises a polynucleotide of interest; c) crossing the first plant of (a) with the second plant of (b); d) evaluating the progeny of (c) for an alteration in the target site and e) selecting a progeny plant that comprises the polynucleotide of interest inserted at said target site.

Another embodiment of the disclosure is a method for selecting a plant comprising an altered target site in its plant genome, the method comprising selecting at least one progeny plant that comprises an alteration at a target site in its plant genome, wherein said progeny plant was obtained by crossing a first plant expressing at least one Cas endonuclease to a second plant comprising a guide RNA and a donor DNA, wherein said Cas endonuclease is capable of introducing a double strand break at said target site, wherein said donor DNA comprises a polynucleotide of interest.

As disclosed herein, a guide RNA/Cas system mediating gene targeting can be used in methods for directing transgene insertion and/or for producing complex transgenic trait loci comprising multiple transgenes in a fashion similar as disclosed in WO2013/0198888 (published Aug. 1, 2013) where instead of using a double strand break inducing agent to introduce a gene of interest, a guide RNA/Cas system or a guide polynucleotide/Cas system as disclosed herein is used. In one embodiment, a complex transgenic trait locus is a genomic locus that has multiple transgenes genetically linked to each other. By inserting independent transgenes within 0.1, 0.2, 0.3, 04, 0.5, 1, 2, or even 5 centimorgans (cM) from each other, the transgenes can be bred as a single genetic locus (see, for example, U.S. patent application Ser. No. 13/427,138) or PCT application PCT/US2012/030061. After selecting a plant comprising a transgene, plants containing (at least) one transgenes can be crossed to form an F1 that contains both transgenes. In progeny from these F1 (F2 or BC1) 1/500 progeny would have the two different transgenes recombined onto the same chromosome. The complex locus can then be bred as single genetic locus with both transgene traits. This process can be repeated to stack as many traits as desired.

Chromosomal intervals that correlate with a phenotype or trait of interest can be identified. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. In one embodiment, the chromosomal interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (*MacMillan Publishing Company, New York*) *and the references* cited therein. Guidance regarding amino acid substitutions not likely to affect biological activity of the protein is found, for example, in the model of Dayhoff et al., (1978) *Atlas of Protein Sequence and Structure* (Natl *Biomed Res* Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

A variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "*Direct DNA Transfer into Intact Plant Cells via Microprojectile Bombardment*" *in* Plant Cell, Tissue, and Organ Culture: Fundamental Methods, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in The Experimental Manipulation of Ovule Tissues, ed. Chapman et al., (*Longman*, New York), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

The term “dicot” refers to the subclass of angiosperm plants also knows as “dicotyledoneae” and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term “crossed” or “cross” or “crossing” in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term “introgression” refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasm ids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

The present disclosure further provides expression constructs for expressing in a plant, plant cell, or plant part a guide RNA/cas system that is capable of binding to and creating a double strand break in a target site. In one embodiment, the expression constructs of the disclosure comprise a promoter operably linked to a nucleotide sequence encoding a cas gene and a promoter operably linked to a guide RNA of the present disclosure. The promoter is capable of driving expression of an operably linked nucleotide sequence in a plant cell.

A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1, 3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) Mol Gen Genet 254:337-43; Russell et al., (1997) *Transgenic Res* 6:157-68; Rinehart et al., (1996) *Plant Physiol* 112:1331-41; Van Camp et al., (1996) *Plant Physiol* 112:525-35; Canevascini et al., (1996) *Plant Physiol* 112:513-524; Lam, (1994) *Results Probl Cell Differ* 20:181-96; and Guevara-Garcia et al., (1993) *Plant J* 4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) *Plant J* 3:509-18; Orozco et al., (1993) *Plant Mol Biol* 23:1129-38; Matsuoka et al., (1993) *Proc. Natl. Acad. Sci.* USA 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS));

Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* roIC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean [3-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) *Proc. Natl. Acad. Sci. USA* 89:6314-8; Yao et al., (1992) *Cell* 71:63-72; Reznikoff, (1992) Mo/Microbio/6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) Ph.D. Thesis, University of Heidelberg; Reines et al., (1993) *Proc. Natl. Acad. Sci. USA* 90:1917-21; Labow et al., (1990) *Mo/Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) Topics Mol Struc Biol 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci*. USA 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (Musa spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), *Arabidopsis* (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant.

Marker Assisted Selection and Breeding of Plants

A primary motivation for development of molecular markers in crop species is the potential for increased efficiency in plant breeding through marker assisted selection (MAS). Genetic marker alleles, or alternatively, quantitative trait loci (QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. It will be appreciated that for the purposes of MAS, the term marker can encompass both marker and QTL loci.

After a desired phenotype and a polymorphic chromosomal locus, e.g., a marker locus or QTL, are determined to segregate together, it is possible to use those polymorphic loci to select for alleles corresponding to the desired phenotype-a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, southern blot analysis, northern blot analysis, in situ hybridization, hybridization of primers followed by PCR amplification of a region of the marker or the like. A variety of procedures for detecting markers are well known in the art. After the presence (or absence) of a particular marker in the biological sample is verified, the plant is selected, i.e., used to make progeny plants by selective breeding.

Plant breeders need to combine traits of interest with genes for high yield and other desirable traits to develop improved plant varieties. Screening for large numbers of samples can be expensive, time consuming, and unreliable. Use of markers, and/or genetically-linked nucleic acids is an effective method for selecting plant having the desired traits in breeding programs. For example, one advantage of marker-assisted selection over field evaluations is that MAS can be done at any time of year regardless of the growing season. Moreover, environmental effects are irrelevant to marker-assisted selection.

When a population is segregating for multiple loci affecting one or multiple traits, the efficiency of MAS compared to phenotypic screening becomes even greater because all the loci can be processed in the lab together from a single sample of DNA.

The DNA repair mechanisms of cells are the basis to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be routinely used in gene targeting or gene editing until it has been found that the process can be stimulated by DNA double-strand breaks (Bibikova et al., (2001) *Mol. Cell Biol.* 21:289-297; Puchta and Baltimore, (2003) *Science* 300:763; Wright et al., (2005) *Plant J.* 44:693-705).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "pg" means microgram(s), "ng" means nanogram(s), "U" means unit(s), "bp" means base pair(s) and "kb" means kilobase(s).

Also, as described herein, for each example or embodiment that cites a guide RNA, a similar guide polynucleotide can be designed wherein the guide polynucleotide does not solely comprise ribonucleic acids but wherein the guide polynucleotide comprises a combination of RNA-DNA molecules or solely comprises DNA molecules.

Non-limiting examples of compositions and methods disclosed herein are as follows:

1. A method for selecting a plant comprising an altered target site in its plant genome, the method comprising:
   a) obtaining a first plant comprising at least one Cas endonuclease capable of introducing a double strand break at a target site in the plant genome;
   b) obtaining a second plant comprising a guide RNA that is capable of forming a complex with the Cas endonuclease of (a);
   c) crossing the first plant of (a) with the second plant of (b);
   d) evaluating the progeny of (c) for an alteration in the target site; and,
   e) selecting a progeny plant that possesses the desired alteration of said target site.
2. A method for selecting a plant comprising an altered target site in its plant genome, the method comprising selecting at least one progeny plant that comprises an alteration at a target site in its plant genome, wherein said progeny plant was obtained by crossing a first plant comprising at least one a Cas endonuclease with a second plant comprising a guide RNA, wherein said Cas endonuclease is capable of introducing a double strand break at said target site.
3. A method for selecting a plant comprising an altered target site in its plant genome, the method comprising:
   a) obtaining a first plant comprising at least one Cas endonuclease capable of introducing a double strand break at a target site in the plant genome;
   b) obtaining a second plant comprising a guide RNA and a donor DNA, wherein said guide RNA is capable of forming a complex with the Cas endonuclease of (a), wherein said donor DNA comprises a polynucleotide of interest;
   c) crossing the first plant of (a) with the second plant of (b);
   d) evaluating the progeny of (c) for an alteration in the target site; and,
   e) selecting a progeny plant that comprises the polynucleotide of interest inserted at said target site.
4. A method for selecting a plant comprising an altered target site in its plant genome, the method comprising selecting at least one progeny plant that comprises an alteration at a target site in its plant genome, wherein said progeny plant was obtained by crossing a first plant expressing at least one Cas endonuclease to a second plant comprising a guide RNA and a donor DNA, wherein said Cas endonuclease is capable of introducing a double strand break at said target site, wherein said donor DNA comprises a polynucleotide of interest.
5. A method for modifying a target site in the genome of a plant cell, the method comprising introducing a guide RNA into a plant cell having a Cas endonuclease, wherein said guide RNA and Cas endonuclease are capable of forming a complex that enables the Cas endonuclease to introduce a double strand break at said target site.
6. A method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site.

7 A method for modifying a target site in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest.

8. A method for modifying a target site in the genome of a plant cell, the method comprising:
  a) introducing into a plant cell a guide RNA and a Cas endonuclease, wherein said guide RNA and Cas endonuclease are capable of forming a complex that enables the Cas endonuclease to introduce a double strand break at said target site; and,
  b) identifying at least one plant cell that has a modification at said target, wherein the modification includes at least one deletion or substitution of one or more nucleotides in said target site.

9. A method for modifying a target DNA sequence in the genome of a plant cell, the method comprising:
  a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and,
  b) identifying at least one plant cell that has a modification at said target, wherein the modification includes at least one deletion or substitution of one or more nucleotides in said target site.

10. A method for introducing a polynucleotide of Interest into a target site in the genome of a plant cell, the method comprising:
  a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site;
  b) contacting the plant cell of (a) with a donor DNA comprising a polynucleotide of Interest; and,
  c) identifying at least one plant cell from (b) comprising in its genome the polynucleotide of Interest integrated at said target site.

10-B A method for introducing a polynucleotide of Interest into a target site in the genome of a plant cell, the method comprising:
  a) introducing into a plant cell a guide RNA and a Cas endonuclease, wherein said guide RNA and Cas endonuclease are capable of forming a complex that enables the Cas endonuclease to introduce a double strand break at said target site;
  b) contacting the plant cell of (a) with a donor DNA comprising a polynucleotide of Interest; and,
  c) identifying at least one plant cell from (b) comprising in its genome the polynucleotide of Interest integrated at said target site.

11. The method of any one of embodiments 5-8, wherein the guide RNA is introduced directly by particle bombardment.

12. The method of any one of embodiments 5-9, wherein the guide RNA is introduced via particle bombardment or *Agrobacterium* transformation of a recombinant DNA construct comprising the corresponding guide DNA operably linked to a plant U6 polymerase III promoter.

13. The method of any one of embodiments 1-10, wherein the Cas endonuclease gene is a plant optimized Cas9 endonuclease.

14. The method of any one of embodiments 1-10, wherein the Cas endonuclease gene is operably linked to a SV40 nuclear targeting signal upstream of the Cas codon region and a VirD2 nuclear localization signal downstream of the Cas codon region.

15. The method of any one of embodiments 1-14, wherein the plant is a monocot or a dicot.

16. The method of embodiment 15, wherein the monocot is selected from the group consisting of maize, rice, sorghum, rye, barley, wheat, millet, oats, sugarcane, turfgrass, or switchgrass.

17. The method of embodiment 16, wherein the dicot is selected from the group consisting of soybean, canola, alfalfa, sunflower, cotton, tobacco, peanut, potato, tobacco, *Arabidopsis*, or safflower.

18. The method of any one of embodiments 1-17 wherein the target site is located in the gene sequence of an acetolactate synthase (ALS) gene, an Enolpyruvylshikimate Phosphate Synthase Gene (ESPSP) gene, a male fertility (MS45, MS26 or MSCA1).

19. A plant or seed produced by any one of embodiments 1-17.

20. A plant comprising a recombinant DNA construct, said recombinant DNA construct comprising a promoter operably linked to a nucleotide sequence encoding a plant optimized Cas9 endonuclease, wherein said plant optimized Cas9 endonuclease is capable of binding to and creating a double strand break in a genomic target sequence said plant genome.

21. A plant comprising a recombinant DNA construct and a guide RNA, wherein said recombinant DNA construct comprises a promoter operably linked to a nucleotide sequence encoding a plant optimized Cas9 endonuclease, wherein said plant optimized Cas9 endonuclease and guide RNA are capable of forming a complex and creating a double strand break in a genomic target sequence said plant genome.

22. A recombinant DNA construct comprising a promoter operably linked to a nucleotide sequence encoding a plant optimized Cas9 endonuclease, wherein said plant optimized Cas9 endonuclease is capable of binding to and creating a double strand break in a genomic target sequence said plant genome.

23. A recombinant DNA construct comprising a promoter operably linked to a nucleotide sequence expressing a guide RNA, wherein said guide RNA is capable of forming a complex with a plant optimized Cas9 endonuclease, and wherein said complex is capable of binding to and creating a double strand break in a genomic target sequence said plant genome.

24. A method for selecting a male sterile plant, the method comprising selecting at least one progeny plant that comprises an alteration at a genomic target site located in a male fertility gene locus, wherein said progeny plant is obtained by crossing a first plant expressing a Cas9 endonuclease to a second plant comprising a guide RNA, wherein said Cas endonuclease is capable of introducing a double strand break at said genomic target site.

25. A method for producing a male sterile plant, the method comprising:
   a) obtaining a first plant comprising at least one Cas endonuclease capable of introducing a double strand break at a genomic target site located in a male fertility gene locus in the plant genome;
   b) obtaining a second plant comprising a guide RNA that is capable of forming a complex with the Cas endonuclease of (a);
   c) crossing the first plant of (a) with the second plant of (b);
   d) evaluating the progeny of (c) for an alteration in the target site; and,
   e) selecting a progeny plant that is male sterile.
26. The method of any of embodiments 23-24 wherein the male fertility gene is selected from the list comprising MS26, MS45, M.
27. The method of any one of embodiments 24-26, wherein the plant is a monocot or a dicot.
28. The method of embodiment 27, wherein the monocot is selected from the group consisting of maize, rice, sorghum, rye, barley, wheat, millet, oats, sugarcane, turfgrass, or switchgrass.
29. A method for editing a nucleotide sequence in the genome of a cell, the method comprising introducing a guide RNA, a polynucleotide modification template and at least one Cas endonuclease into a cell, wherein the Cas endonuclease introduces a double-strand break at a target site in the genome of said cell, wherein said polynucleotide modification template comprises at least one nucleotide modification of said nucleotide sequence.
30. The method of embodiment 29, wherein the cell is a plant cell.
31. The method of embodiment 29 wherein the nucleotide sequence is a promoter, a regulatory sequence or a gene of interest of interest.
32. The method of embodiment 31 wherein the gene of interest is an EPSPS gene.
33. The method of embodiment 30 wherein the plant cell is a monocot or dicot plant cell.
34. A method for producing an epsps mutant plant, the method comprising:
   a) providing a guide RNA, a polynucleotide modification template and at least one Cas endonuclease to a plant cell, wherein the Cas endonuclease introduces a double strand break at a target site within an epsps genomic sequence in the plant genome, wherein said_polynucleotide modification template comprises at least one nucleotide modification of said epsps genomic sequence.
   b) obtaining a plant from the plant cell of (a);
   c) evaluating the plant of (b) for the presence of said at least one nucleotide modification; and,
   c) selecting a progeny plant that shows tolerance to glyphosate.
35. A method for producing an epsps mutant plant, the method comprising:
   a) providing a guide RNA, a polynucleotide modification template and at least one Cas endonuclease into a plant cell, wherein the Cas endonuclease introduces a double strand break at a target site within an epsps genomic sequence in the plant genome, wherein said polynucleotide modification template comprises at least one nucleotide modification of said epsps genomic sequence.
   b) obtaining a plant from the plant cell of (a);
   c) evaluating the plant of (b) for the presence of said at least one nucleotide modification; and,
   d) screening a progeny plant of (c) that is void of said guide RNA and Cas endonuclease.
36. The method of embodiment 35 further comprising selecting a plant that shows resistance to glyphosate.
37. A plant, plant cell or seed produced by any one of embodiments 29-36
38. The method of any one of embodiments 29-36 wherein the Cas endonuclease is a Cas9 endonuclease.
39. The method of embodiment 38 wherein the Cas9 endonuclease is expressed by SEQ ID NO:5.
40. The method of embodiment 38 wherein the Cas9 endonuclease is encoded by any one of SEQ ID NOs: 1, 124, 212, 213, 214, 215, 216, 193 or nucleotides 2037-6329 of SEQ ID NO:5, or any functional fragment or variant thereof.
41. The plant or plant cell of embodiment 37, wherein said plant cell shows resistance to glyphosate.
42. A plant cell comprising a modified nucleotide sequence, wherein the modified nucleotide sequence was produced by providing a guide RNA, a polynucleotide modification template and at least one Cas endonuclease to a plant cell, wherein the Cas endonuclease is capable of introducing a double-strand break at a target site in the plant genome wherein said polynucleotide modification template comprises at least one nucleotide modification of said nucleotide sequence.
43. The method of embodiments 29, 34 and 35 wherein the at least one nucleotide modification is not a modification at said target site.
44. A method for producing a male sterile plant, the method comprising:
   a) introducing into a plant cell a guide RNA and a Cas endonuclease, wherein said guide RNA and Cas endonuclease are capable of forming a complex that enables the Cas endonuclease to introduce a double strand break at a target site located in or near a male fertility gene;
   b) identifying at least one plant cell that has a modification in said male fertility gene, wherein the modification includes at least one deletion or substitution of one or more nucleotides in said male sterility gene; and,
   c) obtaining a plant from the plant cell of b).
45. The method of embodiment 43, further comprising selecting a progeny plant from the plant of c) wherein said progeny plant is male sterile.
46. The method of embodiment 43, wherein the male fertility gene is selected from the group comprising MS26, MS45 and MSCA1.
47. A plant comprising at least one altered target site, wherein the at least one altered target site originated from a corresponding target site that was recognized and cleaved by a guide RNA/Cas endonuclease system, and wherein the at least one altered target site is in a genomic region of interest that extends from the target sequence set forth in SEQ ID NO: 229 to the target site set forth in SEQ ID NO: 235.
48. The plant of embodiment 47, wherein the at least one altered target site has an alteration selected from the group consisting of (i) replacement of at least one nucleotide, (ii) a deletion of at least one nucleotide, (iii) an insertion of at least one nucleotide, and (iv) any combination of (i)-(iii).

49. The plant of embodiment 47, wherein the at least one altered target site comprises a recombinant DNA molecule.
50. The plant of embodiment 47, wherein the plant comprises at least two altered target sites, wherein each of the altered target site originated from corresponding target site that was recognized and cleaved by a guide RNA/Cas endonuclease system, wherein the corresponding target site is selected from the group consisting of SEQ ID NOs: 229, 230, 231, 232, 233, 234, 235 and 236. 51. A recombinant DNA construct comprising a nucleotide sequence set forth in SEQ ID NO: 120 or SEQ ID NO:295, or a functional fragment thereof, operably linked to at least one heterologous sequence, wherein said nucleotide sequence is a promoter.
52. A plant stably transformed with a recombinant DNA construct comprising a soybean promoter and a heterologous nucleic acid fragment operably linked to said soybean promoter, wherein said promoter is a capable of controlling expression of said heterologous nucleic acid fragment in a plant cell, and further wherein said promoter comprises any of the sequences set forth in SEQ ID NO: 120 or SEQ ID NO: 295.
53. A method for editing a nucleotide sequence in the genome of a cell, the method comprising introducing a guide polynucleotide, a Cas endonuclease, and optionally a polynucleotide modification template, into a cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said nucleotide sequence.
54. The method of embodiment 53, wherein the nucleotide sequence in the genome of a cell is selected from the group consisting of a promoter sequence, a terminator sequence, a regulatory element sequence, a splice site, a coding sequence, a polyubiquitination site, an intron site and an intron enhancing motif.
55. A method for editing a promoter sequence in the genome of a cell, the method comprising introducing a guide polynucleotide, a polynucleotide modification template and at least one Cas endonuclease into a cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said nucleotide sequence.
56. A method for replacing a first promoter sequence in a cell, the method comprising introducing a guide RNA, a polynucleotide modification template, and a Cas endonuclease into said cell, wherein said guide RNA and Cas endonuclease are capable of forming a complex that enables the Cas endonuclease to introduce a double strand break at a target site in the genome of said cell, wherein said polynucleotide modification template comprises a second promoter or second promoter fragment that is different from said first promoter sequence.
57. The method of embodiment 56, wherein the replacement of the first promoter sequence results in any one of the following, or any one combination of the following: an increased promoter activity, an increased promoter tissue specificity, a decreased promoter activity, a decreased promoter tissue specificity, a new promoter activity, an inducible promoter activity, an extended window of gene expression, or a modification of the timing or developmental progress of gene expression in the same cell layer or other cell layer
58. The method of embodiment 56, wherein the first promoter sequence is selected from the group consisting of *Zea mays* ARGOS 8 promoter, a soybean EPSPS1 promoter, a maize EPSPS promoter, maize NPK1 promoter, wherein the second promoter sequence is selected from the group consisting of a *Zea mays* GOS2 PRO:GOS2-intron promoter, a soybean ubiquitin promoter, a stress inducible maize RAB17 promoter, a *Zea mays*-PEPC1 promoter, a *Zea mays* Ubiquitin promoter, a *Zea mays*-Rootmet2 promoter, a rice actin promoter, a sorghum RCC3 promoter, a *Zea mays*-GOS2 promoter, a *Zea mays*-ACO2 promoter and a *Zea mays* oleosin promoter.
59. A method for deleting a promoter sequence in the genome of a cell, the method comprising introducing a guide polynucleotide, a Cas endonuclease into a cell, wherein said guide RNA and Cas endonuclease are capable of forming a complex that enables the Cas endonuclease to introduce a double strand break in at least one target site located inside or outside said promoter sequence.
60. A method for inserting a promoter or a promoter element in the genome of a cell, the method comprising introducing a guide polynucleotide, a polynucleotide modification template comprising the promoter or the promoter element, and a Cas endonuclease into a cell, wherein said guide RNA and Cas endonuclease are capable of forming a complex that enables the Cas endonuclease to introduce a double strand break at a target site in the genome of said cell.
61. The method of embodiment 60, wherein the insertion of the promoter or promoter element results in any one of the following, or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements, or an addition of DNA binding elements.
62. A method for editing a Zinc Finger transcription factor, the method comprising introducing a guide polynucleotide, a Cas endonuclease, and optionally a polynucleotide modification template, into a cell, wherein the Cas endonuclease introduces a double-strand break at a target site in the genome of said cell, wherein said polynucleotide modification template comprises at least one nucleotide modification or deletion of said Zinc Finger transcription factor, wherein the deletion or modification of said Zinc Finger transcription factor results in the creation of a dominant negative Zinc Finger transcription factor mutant.
63. A method for creating a fusion protein, the method comprising introducing a guide polynucleotide, a Cas endonuclease, and a polynucleotide modification template, into a cell, wherein the Cas endonuclease introduces a double-strand break at a target site located inside or outside a first coding sequence in the genome of said cell, wherein said polynucleotide modification template comprises a second coding sequence encoding a protein of interest, wherein the protein fusion results in any one of the following, or any one combination of the following: a targeting of the fusion protein to the chloroplast of said cell, an increased protein activity, an increased protein functionality, a decreased protein activity, a decreased protein functionality, a new protein functionality, a modified protein functionality, a new protein localization, a new timing of protein expression, a modified protein expression pattern, a chimeric protein, or a modified protein with dominant phenotype functionality.

64. A method for producing in a plant a complex trait locus comprising at least two altered target sequences in a genomic region of interest, said method comprising:
(a) selecting a genomic region in a plant, wherein the genomic region comprises a first target sequence and a second target sequence;
(b) contacting at least one plant cell with at least a first guide polynucleotide, a second polynucleotide, and optionally at least one Donor DNA, and a Cas endonuclease, wherein the first and second guide polynucleotide and the Cas endonuclease can form a complex that enables the Cas endonuclease to introduce a double strand break in at least a first and a second target sequence;
(c) identifying a cell from (b) comprising a first alteration at the first target sequence and a second alteration at the second target sequence; and,
(d) recovering a first fertile plant from the cell of (c) said fertile plant comprising the first alteration and the second alteration, wherein the first alteration and the second alteration are physically linked.

65. A method for producing in a plant a complex trait locus comprising at least two altered target sequences in a genomic region of interest, said method comprising:
(a) selecting a genomic region in a plant, wherein the genomic region comprises a first target sequence and a second target sequence;
(b) contacting at least one plant cell with a first guide polynucleotide, a Cas endonuclease, and optionally a first Donor DNA, wherein the first guide polynucleotide and the Cas endonuclease can form a complex that enables the Cas endonuclease to introduce a double strand break a first target sequence;
(c) identifying a cell from (b) comprising a first alteration at the first target sequence;
(d) recovering a first fertile plant from the cell of (c), said first fertile plant comprising the first alteration;
(e) contacting at least one plant cell with a second guide polynucleotide, a Cas endonuclease, and optionally a second Donor DNA;
(f) identifying a cell from (e) comprising a second alteration at the second target sequence;
(g) recovering a second fertile plant from the cell of (f), said second fertile plant comprising the second alteration; and,
(h) obtaining a fertile progeny plant from the second fertile plant of (g), said fertile progeny plant comprising the first alteration and the second alteration, wherein the first alteration and the second alteration are physically linked.

66. A method for editing a nucleotide sequence in the genome of a cell, the method comprising introducing at least one guide RNA, at least one polynucleotide modification template and at least one Cas endonuclease into a cell, wherein the Cas endonuclease introduces a double-strand break at a target site in the genome of said cell, wherein said polynucleotide modification template comprises at least one nucleotide modification of said nucleotide sequence.

67. The method of embodiment 66 wherein the editing of said nucleotide sequence renders said nucleotide sequence capable of conferring herbicide resistance to said cell.

68. The method of embodiment 67, wherein the cell is a plant cell.

69. The method of embodiment 66 wherein the nucleotide sequence is a promoter, a regulatory sequence or a gene of interest of interest.

70. The method of embodiment 69 wherein the gene of interest is an enolpyruvylshikimate-3-phosphate synthase (EPSPS) gene or an ALS gene.

71. The method of embodiment 66 wherein the plant cell is a monocot or dicot plant cell.

72. A method for producing an acetolactate synthase (ALS) mutant plant, the method comprising:
a) providing a guide RNA, a polynucleotide modification template, and a Cas endonuclease to a plant cell comprising an ALS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said ALS nucleotide sequence;
b) obtaining a plant from the plant cell of (a);
c) evaluating the plant of (b) for the presence of said at least one nucleotide modification; and,
d) selecting a progeny plant that shows resistance to sulphonylurea.

73. A method for producing an acetolactate synthase (ALS) mutant plant, the method comprising:
a) providing a guide RNA and a polynucleotide modification template to a plant cell comprising a Cas endonuclease and an ALS nucleotide sequence, wherein said Cas endonuclease introduces a double strand break at a target site in the genome of said plant cell, wherein said polynucleotide modification template comprises at least one nucleotide modification of said ALS nucleotide sequence;
b) obtaining a plant from the plant cell of (a);
c) evaluating the plant of (b) for the presence of said at least one nucleotide modification; and,
d) selecting a progeny plant that shows resistance to sulphonylurea.

74. The method of any of embodiments 72-73, wherein said polynucleotide modification template comprises a non-functional or partial fragment of the ALS nucleotide sequence.

75. The method of any of embodiments 72-73, wherein the target site is located within the ALS nucleotide sequence.

76. The method of any of embodiments 72-73, further comprising selecting a progeny plant that is void of said guide RNA and Cas endonuclease.

77. A method for producing an acetolactate synthase (ALS) mutant plant, the method comprising:
a) obtaining a plant or a seed thereof, wherein the plant or the seed comprises a modification in an endogenous ALS gene, the modification generated by a Cas endonuclease, a guide RNA and a polynucleotide modification template, wherein the plant or the seed is resistant to sulphonylurea; and, b) producing a progeny plant that is void of said guide RNA and Cas endonuclease.

78. The method of embodiment 77 further comprising selecting a plant that shows resistance to sulphonylurea.

79. The method of any one of embodiments 72-78, wherein the plant is a monocot or a dicot.

80. The method of embodiment 79, wherein the monocot is selected from the group consisting of maize, rice, sorghum, rye, barley, wheat, millet, oats, sugarcane, turfgrass, or switchgrass.

81. The method of embodiment 79, wherein the dicot is selected from the group consisting of soybean, canola, alfalfa, sunflower, cotton, tobacco, peanut, potato, tobacco, *Arabidopsis*, or safflower.

82. A method of generating a sulphonylurea resistant plant, the method comprising providing a plant cell wherein its endogenous chromosomal ALS gene by has been modified through a guide RNA/Cas endonuclease system to produce a sulphonylurea resistant ALS protein and growing a plant from said maize plant cell, wherein said plant is resistant to sulphonylurea.

83. The method of embodiment 82, wherein the plant is a monocot or a dicot.

84. A plant produced by the method of embodiment 82.

85. A seed produced by the plant of embodiment 84.

86. A guide RNA wherein the variable targeting domain targets a fragment of a plant EPSPS or ALS nucleotide sequence.

87. A method for producing an acetolactate synthase (ALS) mutant plant cell, the method comprising:

a) providing to a cell comprising an ALS nucleotide sequence, a guide RNA, a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said ALS nucleotide sequence; and, b) obtaining at least one plant cell of (a) that has at least one nucleotide modification at said ALS nucleotide sequence, wherein the modification includes at least one deletion, insertion or substitution of one or more nucleotides in said ALS nucleotide sequence.

88. A method for producing an acetolactate synthase (ALS) mutant plant cell, the method comprising:

a) providing a guide RNA and a polynucleotide modification template to a plant cell comprising a Cas endonuclease and a ALS nucleotide sequence, wherein said Cas endonuclease introduces a double strand break at a target site in the genome of said plant cell, wherein said polynucleotide modification template comprises at least one nucleotide modification of said ALS nucleotide sequence; and, b) identifying at least one plant cell of (a) that has at least one nucleotide modification at said ALS nucleotide sequence, wherein the modification includes at least one deletion, insertion or substitution of one or more nucleotides in said ALS nucleotide sequence.

89. A method for producing an acetolactate synthase (ALS) mutant cell, the method comprising:

a) providing to a cell comprising an ALS nucleotide sequence, a first recombinant DNA construct capable of expressing a guide RNA, a second recombinant DNA construct capable of expressing a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises a non-functional fragment of the ALS gene and at least one nucleotide modification of said ALS nucleotide sequence; and, b) identifying at least one cell of (a) that has at least one nucleotide modification at said ALS nucleotide sequence, wherein the modification includes at least one deletion, insertion or substitution of one or more nucleotides in said ALS nucleotide sequence.

90. A recombinant DNA construct comprising a soybean U6 polymerase III promoter driving a heterologous nucleic acid fragment encoding a guide polynucleotide.

91. The recombinant DNA construct of embodiment 90, wherein said promoter comprises any of the sequences set forth in SEQ ID NO: 120 or SEQ ID NO: 295, or a functional fragment thereof.

92. A method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site, wherein said guide RNA is generated by a recombinant DNA construct comprising a promoter comprising any of the sequences set forth in SEQ ID NO: 120 or SEQ ID NO:295, or a functional fragment thereof.

93. A recombinant DNA construct comprising a soybean U6 polymerase III promoter driving a heterologous nucleic acid fragment encoding a guide polynucleotide comprising:

(i) a first nucleotide sequence domain that is complementary to a nucleotide sequence in a target DNA; and, (ii) a second nucleotide sequence domain that interacts with a Cas endonuclease, wherein the first nucleotide sequence domain and the second nucleotide sequence domain are composed of deoxyribonucleic acids (DNA), ribonucleic acids (RNA), or a combination thereof, wherein the guide polynucleotide does not solely comprise ribonucleic acids.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Maize Optimized Expression Cassettes for Guide RNA/Cas Endonuclease Based Genome Modification in Maize Plants For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) *Proc. Natl. Acad. Sci.USA* 109:E2579-86, Jinek et al. (2012) *Science* 337:816-21, Mali et al. (2013) *Science* 339:823-26, and Cong et al. (2013) *Science* 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into said target site.

To test the guide RNA/Cas endonuclease system in maize, the Cas9 gene from *Streptococcus pyogenes* M1 GAS (SF370) (SEQ ID NO: 1) was maize codon optimized per standard techniques known in the art and the potato ST-LS1 intron (SEQ ID NO: 2) was introduced in order to eliminate its expression in *E. coli* and *Agrobacterium* (FIG. 1A). To facilitate nuclear localization of the Cas9 protein in maize cells, Simian virus 40 (SV40) monopartite amino terminal nuclear localization signal (MAPKKKRKV, SEQ ID NO: 3) and *Agrobacterium tumefaciens* bipartite VirD2 T-DNA border endonuclease carboxyl terminal nuclear localization signal (KRPRDRHDGELGGRKRAR, SEQ ID NO: 4) were incorporated at the amino and carboxyl-termini of the Cas9 open reading frame (FIG. 1A), respectively. The maize optimized Cas9 gene was operably linked to a maize constitutive or regulated promoter by standard molecular biological techniques. An example of the maize optimized Cas9 expression cassette (SEQ ID NO: 5) is illustrated in FIG. 1A. FIG. 1A shows a maize optimized Cas9 gene containing the ST-LS1 intron, SV40 amino terminal nuclear localization signal (NLS) and VirD2 carboxyl terminal NLS driven by a plant Ubiquitin promoter.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in maize, the maize U6 polymerase III promoter (SEQ ID NO: 9) and maize U6 polymerase III terminator (first 8 bases of SEQ ID NO: 10) residing on chromosome 8 were isolated and operably fused to the termini of a guide RNA (FIG. 1B) using standard molecular biology techniques. Two different guide RNA configurations were developed for testing in maize, a short guide RNA (SEQ ID NO: 11) based on Jinek et al. (2012) *Science* 337:816-21 and a long guide RNA (SEQ ID NO: 8) based on *Mali* et al. (2013) *Science* 339:823-26. An example expression cassette (SEQ ID NO: 12) is shown in FIG. 1B which illustrates a maize U6 polymerase III promoter driving expression of a long guide RNA terminated with a U6 polymerase III terminator.

As shown in FIGS. 2A and 2B, the guide RNA or crRNA molecule contains a region complementary to one strand of the double strand DNA target (referred to as the variable targeting domain) that is approximately 12-30 nucleotides in length and upstream of a PAM sequence (5'NGG3' on antisense strand of FIG. 2A-2B, corresponding to 5'CCN3' on sense strand of FIG. 2A-2B) for target site recognition and cleavage (Gasiunas et al. (2012) *Proc. Natl. Acad. Sci. USA* 109:E2579-86, Jinek et al. (2012) *Science* 337:816-21, Mali et al. (2013) *Science* 339:823-26, and Cong et al. (2013) *Science* 339:819-23). To facilitate the rapid introduction of maize genomic DNA target sequences into the crRNA or guide RNA expression constructs, two Type IIS Bbsl restriction endonuclease target sites were introduced in an inverted tandem orientation with cleavage orientated in an outward direction as described in Cong et al. (2013) *Science* 339:819-23. Upon cleavage, the Type IIS restriction endonuclease excises its target sites from the crRNA or guide RNA expression plasmid, generating overhangs allowing for the in-frame directional cloning of duplexed oligos containing the desired maize genomic DNA target site into the variable targeting domain. In this example, only target sequences starting with a G nucleotide were used to promote favorable polymerase III expression of the guide RNA or crRNA.

Expression of both the Cas endonuclease gene and the guide RNA then allows for the formation of the guide RNA/Cas complex depicted in FIG. 2B (SEQ ID NO: 8). Alternatively, expression of the Cas endonucleases gene, crRNA, and tracrRNA allow for the formation of the crRNA/tracrRNA/Cas complex as depicted in FIG. 2A, (SEQ ID NOs: 6-7).

Example 2

The Guide RNA/Cas Endonuclease System Cleaves Chromosomal DNA in Maize and Introduces Mutations by Imperfect Non-Homologous End-Joining To test whether the maize optimized guide RNA/Cas endonuclease described in example 1 could recognize, cleave, and mutate maize chromosomal DNA through imprecise non-homologous end-joining (NHEJ) repair pathways, three different genomic target sequences in 5 maize loci were targeted for cleavage (see Table 1) and examined by deep sequencing for the presence of NHEJ mutations.

TABLE 1

Maize genomic target sites targeted by a guideRNA/Cas endonuclease system.

| Locus | Location | Guide RNA Used | Target Site Designation | Maize Genomic Target Site Sequence | PAM Sequence | SEQ ID NO: |
|---|---|---|---|---|---|---|
| MS26 | Chr. 1: | Long | MS26Cas-1 | GTACTCCATCCGCCCCATCGAGTA | GGG | 13 |
| | 51.81 cM | Long | MS26Cas-2 | GCACGTACGTCACCATCCCGC | CGG | 14 |
| | | Long | MS26Cas-3 | GACGTACGTGCCCTACTCGAT | GGG | 15 |
| LIG | Chr. 2: | Long | LIGCas-1 | GTACCGTACGTGCCCCGGCGG | AGG | 16 |
| | 28.45 cM | Long | LIGCas-2 | GGAATTGTACCGTACGTGCCC | CGG | 17 |
| | | Long | LIGCas-3 | GCGTACGCGTACGTGTG | AGG | 18 |
| MS45 | Chr. 9: | Long | MS45Cas-1 | GCTGGCCGAGGTCGACTAC | CGG | 19 |
| | 119.15 cM | Long | MS45Cas-2 | GGCCGAGGTCGACTACCGGC | CGG | 20 |
| | | Long | MS45Cas-3 | GGCGCGAGCTCGTGCTTCAC | CGG | 21 |

TABLE 1-continued

Maize genomic target sites targeted by a guideRNA/Cas endonuclease system.

| Locus | Location | Guide RNA Used | Target Site Designation | Maize Genomic Target Site Sequence | PAM Sequence | SEQ ID NO: |
|---|---|---|---|---|---|---|
| ALS | Chr. 4: 107.73 cM and Chr. 5: 115.49 cM | Long | ALSCas-1 | GGTGCCAATCATGCGTCG | CGG | 22 |
| | | Long | ALSCas-2 | GGTCGCCATCACGGGAC | AGG | 23 |
| | | Long | ALSCas-3 | GTCGCGGCACCTGTCCCGTGA | TGG | 24 |
| EPSPS | Chr. 9: 69.43 cM | Long | EPSPSCas-1 | GGAATGCTGGAACTGCAATG | CGG | 25 |
| | | Long | EPSPSCas-2 | GCAGCTCTTCTTGGGGAATGC | TGG | 26 |
| | | Long | EPSPSCas-3 | GCAGTAACAGCTGCTGTCAA | TGG | 27 |

MS26 = Male Sterility Gene 26, LIG = Liguleless 1 Gene Promoter, MS45 = Male Sterility Gene 45, ALS = Acetolactate Synthase Gene, EPSPS = Enolpyruvylshikimate Phosphate Synthase Gene The maize optimized Cas9 endonuclease and long guide RNA expression cassettes containing the specific maize variable targeting domains were co-delivered to 60-90 Hi-II immature maize embryos by particle-mediated delivery (see Example 10) in the presence of BBM and WUS2 genes (see Example 11). Hi-II maize embryos transformed with either the LIG3-4 or MS26++ homing endonucleases (see Example 9) targeting the same maize genomic loci as the LIGCas or MS26Cas target sites served as a positive control and embryos transformed with only the Cas9 or guide RNA expression cassette served as negative controls. After 7 days, the 20-30 most uniformly transformed embryos from each treatment were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 2 and the primers used in the secondary PCR reaction were AATGATACGGCGACCACCGAGATCTACACTCTTTCCCTACACG (forward, SEQ ID NO: 53) and CAAGCAGAAGACGGCATA (reverse, SEQ ID NO: 54).

TABLE 2

PCR primer sequences

| Target Site | Primer Orientation | Primary PCR Primer Sequence | SEQ ID NO: |
|---|---|---|---|
| MS26Cas-1 | Forward | CTACACTCTTTCCCTACACGACGCTCTTCCGATCTAGGACCGGAAGCTCGCCGCGT | 28 |
| MS26Cas-1 | Reverse | CAAGCAGAAGACGGCATACGAGCTCTTCCGATCTTCCTGGAGGACGACGTGCTG | 29 |
| MS26Cas-2 | Forward | CTACACTCTTTCCCTACACGACGCTCTTCCGATCTAAGGTCCTGGAGGACGACGTGCTG | 30 |
| MS26Cas-2 | Reverse | CAAGCAGAAGACGGCATACGAGCTCTTCCGATCTCCGGAAGCTCGCCGCGT | 31 |
| MS26Cas-3 | Forward | CTACACTCTTTCCCTACACGACGCTCTTCCGATCTTCCTCCGGAAGCTCGCCGCGT | 32 |
| MS26Cas-3 | Reverse | CAAGCAGAAGACGGCATACGAGCTCTTCCGATCTTCCTGGAGGACGACGTGCTG | 29 |
| MS26 Meganuclease | Forward | CTACACTCTTTCCCTACACGACGCTCTTCCGATCTTTCCTCCTGGAGGACGACGTGCTG | 33 |
| MS26 Meganuclease | Reverse | CAAGCAGAAGACGGCATACGAGCTCTTCCGATCTCCGGAAGCTCGCCGCGT | 31 |
| LIGCas-1 | Forward | CTACACTCTTTCCCTACACGACGCTCTTCCGATCTAGGACTGTAACGATTTACGCACCTGCTG | 34 |
| LIGCas-1 | Reverse | CAAGCAGAAGACGGCATACGAGCTCTTCCGATCTGCAAATGAGTAGCAGCGCACGTAT | 35 |
| LIGCas-2 | Forward | CTACACTCTTTCCCTACACGACGCTCTTCCGATCTTCCTCTGTAACGATTTACGCACCTGCTG | 36 |

TABLE 2-continued

PCR primer sequences

| Target Site | Primer Orientation | Primary PCR Primer Sequence | SEQ ID NO: |
|---|---|---|---|
| LIGCas-2 | Reverse | CAAGCAGAAGACGGCATACGAGCTCTTCCGATCTG CAAATGAGTAGCAGCGCACGTAT | 35 |
| LIGCas-3 | Forward | CTACACTCTTTCCCTACACGACGCTCTTCCGATCTA AGGCGCAAATGAGTAGCAGCGCAC | 37 |
| LIGCas-3 | Reverse | CAAGCAGAAGACGGCATACGAGCTCTTCCGATCTC ACCTGCTGGGAATTGTACCGTA | 38 |
| LIG3-4 Meganuclease | Forward | CTACACTCTTTCCCTACACGACGCTCTTCCGATCTC CTTCGCAAATGAGTAGCAGCGCAC | 39 |
| LIG3-4 Meganuclease | Reverse | CAAGCAGAAGACGGCATACGAGCTCTTCCGATCTC ACCTGCTGGGAATTGTACCGTA | 38 |
| MS45Cas-1 | Forward | CTACACTCTTTCCCTACACGACGCTCTTCCGATCTA GGAGGACCCGTTCGGCCTCAGT | 40 |
| MS45Cas-1 | Reverse | CAAGCAGAAGACGGCATACGAGCTCTTCCGATCTG CCGGCTGGCATTGTCTCTG | 41 |
| MS45Cas-2 | Forward | CTACACTCTTTCCCTACACGACGCTCTTCCGATCTT CCTGGACCCGTTCGGCCTCAGT | 42 |
| MS45Cas-2 | Reverse | CAAGCAGAAGACGGCATACGAGCTCTTCCGATCTG CCGGCTGGCATTGTCTCTG | 41 |
| MS45Cas-3 | Forward | CTACACTCTTTCCCTACACGACGCTCTTCCGATCT GAAGGGACCCGTTCGGCCTCAGT | 43 |
| MS45Cas-3 | Reverse | CAAGCAGAAGACGGCATACGAGCTCTTCCGATCTG CCGGCTGGCATTGTCTCTG | 41 |
| ALSCas-1 | Forward | CTACACTCTTTCCCTACACGACGCTCTTCCGATCTA AGGCGACGATGGGCGTCTCCTG | 44 |
| ALSCas-1 | Reverse | CAAGCAGAAGACGGCATACGAGCTCTTCCGATCTG CGTCTGCATCGCCACCTC | 45 |
| ALSCas-2 | Forward | CTACACTCTTTCCCTACACGACGCTCTTCCGATCTT TCCCGACGATGGGCGTCTCCTG | 46 |
| ALSCas-2 | Reverse | CAAGCAGAAGACGGCATACGAGCTCTTCCGATCTG CGTCTGCATCGCCACCTC | 45 |
| ALSCas-3 | Forward | CTACACTCTTTCCCTACACGACGCTCTTCCGATCT GGAACGACGATGGGCGTCTCCTG | 47 |
| ALSCas-3 | Reverse | CAAGCAGAAGACGGCATACGAGCTCTTCCGATCTG CGTCTGCATCGCCACCTC | 45 |
| EPSPSCas-1 | Forward | CTACACTCTTTCCCTACACGACGCTCTTCCGATCT GGAAGAGGAAACATACGTTGCATTTCCA | 48 |
| EPSPSCas-1 | Reverse | CAAGCAGAAGACGGCATACGAGCTCTTCCGATCTG GTGGAAAGTTCCCAGTTGAGGA | 49 |
| EPSPSCas-2 | Forward | CTACACTCTTTCCCTACACGACGCTCTTCCGATCTA AGCGGTGGAAAGTTCCCAGTTGAGGA | 50 |
| EPSPSCas-2 | Reverse | CAAGCAGAAGACGGCATACGAGCTCTTCCGATCTG AGGAAACATACGTTGCATTTCCA | 51 |
| EPSPSCas-3 | Forward | CTACACTCTTTCCCTACACGACGCTCTTCCGATCTC CTTGAGGAAACATACGTTGCATTTCCA | 52 |
| EPSPSCas-3 | Reverse | CAAGCAGAAGACGGCATACGAGCTCTTCCGATCTG GTGGAAAGTTCCCAGTTGAGGA | 49 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the % mutant reads based on the total number of reads of an appropriate length containing a perfect match to the barcode and forward primer.

The frequency of NHEJ mutations recovered by deep sequencing for the guide RNA/Cas endonuclease system targeting the three LIGCas targets (SEQ ID NOS: 16, 17, 18) compared to the LIG3-4 homing endonuclease targeting the same locus is shown in Table 3. The ten most prevalent types of NHEJ mutations recovered based on the guide RNA/Cas endonuclease system compared to the LIG3-4 homing endonuclease are shown in FIG. 3A (corresponding to SEQ ID NOs: 55-75) and FIG. 3B (corresponding to SEQ ID NOs: 76-96). Approximately, 12-23 fold higher frequencies of NHEJ mutations were observed when using a guide RNA/Cas system to introduce a double strand break at a maize genomic target site (Cas target sites), relative to the LIG3-4 homing endonuclease control. As shown in Table 4, a similar difference between the guide RNA/Cas system and meganuclease double-strand break technologies was observed at the MS26 locus with approximately 14-25 fold higher frequencies of NHEJ mutations when a guide RNA/Cas endonuclease system was used. High frequencies of NHEJ mutations were also recovered at the MS45, ALS and EPSPS Cas targets (see Table 5) when using a guide RNA/Cas endonuclease system. This data indicates that the guide RNA/Cas9 endonuclease system described herein can be effectively used to introduce an alteration at genomic sites of interest such as those related to male fertility, wherein an alteration results in the creation of a male sterile gene locus and male sterile plants. Altering the EPSPS target can result in the production of plants that are tolerant and/or resistant against glyphosate based herbicides. Altering the acetolactate synthase (ALS) gene target site can result in the production of plants that are tolerant and/or resistant to imidazolinone and sulphonylurea herbicides.

TABLE 3

Percent (%) mutant reads at maize Liguleless 1 target locus produced by a guide RNA/Cas system versus a homing endonuclease system.

| System | Total Number of Reads | Number of Mutant Reads | % Mutant Reads |
|---|---|---|---|
| Cas9 Only Control | 640,063 | 1 | 0.00% |
| guide RNA Only Control | 646,774 | 1 | 0.00% |
| LIG3-4 Homing Endonuclease | 616,536 | 1,211 | 0.20% |
| LIGCas-1 guide/Cas9 | 716,854 | 33,050 | 4.61% |

TABLE 3-continued

Percent (%) mutant reads at maize Liguleless 1 target locus produced by a guide RNA/Cas system versus a homing endonuclease system.

| System | Total Number of Reads | Number of Mutant Reads | % Mutant Reads |
|---|---|---|---|
| LIGCas-2 guide/Cas9 | 711,047 | 16,675 | 2.35% |
| LIGCas-3 guide/Cas9 | 713,183 | 27,959 | 3.92% |

TABLE 4

Percent (%) mutant reads at maize Male Sterility 26 target locus produced by a guide RNA/Cas system versus a homing endonuclease.

| System | Total Number of Reads | Number of Mutant Reads | % Mutant Reads |
|---|---|---|---|
| Cas9 Only Control | 403,123 | 15 | 0.00% |
| MS26++ Homing Endonuclease | 512,784 | 642 | 0.13% |
| MS26Cas-1 guide/Cas9 | 575,671 | 10,073 | 1.75% |
| MS26Cas-2 guide/Cas9 | 543,856 | 16,930 | 3.11% |
| MS26Cas-3 guide/Cas9 | 538,141 | 13,879 | 2.58% |

TABLE 5

Percent (%) mutant reads at maize Male Sterility 45, Acetolactate Synthase and Enolpyruvylshikimate Phosphate Synthase target loci produced by the guide RNA/Cas system.

| System | Total Number of Reads | Number of Mutant Reads | % Mutant Reads |
|---|---|---|---|
| Cas9 Only Control (MS45) | 899,500 | 27 | 0.00% |
| MS45Cas-1 guide/Cas9 | 812,644 | 3,795 | 0.47% |
| MS45Cas-2 guide/Cas9 | 785,183 | 14,704 | 1.87% |
| MS45Cas-3 guide/Cas9 | 728,023 | 9,203 | 1.26% |
| Cas9 Only Control (ALS) | 534,764 | 19 | 0.00% |
| ALSCas-1 guide/Cas9 | 434,452 | 9,669 | 2.23% |
| ALSCas-2 guide/Cas9 | 472,351 | 6,352 | 1.345% |
| ALSCas-3 guide/Cas9 | 497,786 | 8,535 | 1.715% |
| Cas9 Only Control (EPSPS) | 1,347,086 | 6 | 0.00% |
| EPSPSCas-1 guide/Cas9 | 1,420,274 | 13,051 | 0.92% |
| EPSPSCas-2 guide/Cas9 | 1,225,082 | 26,340 | 2.15% |
| EPSPSCas-3 guide/Cas9 | 1,406,905 | 53,603 | 3.81% |

Taken together, our data indicate that the maize optimized guide RNA/Cas endonuclease system described herein using a long guide RNA expression cassette efficiently cleaves maize chromosomal DNA and generates imperfect NHEJ mutations at frequencies greater than the engineered LIG3-4 and MS26++ homing endonucleases.

Example 3

Long Guide RNA of the Maize Optimized Guide RNA/Cas Endonuclease System Cleaves Maize Chromosomal DNA More Efficiently than the Short Guide RNA To determine the most effective guide RNA (comprising a fusion of the crRNA and tracrRNA) for use in maize, the recovery of NHEJ mutations using a short guide RNA (SEQ ID NO: 11) based on Jinek et al. (2012) *Science* 337:816-21 and a long guide RNA (SEQ ID NO: 8) based on *Mali* et al. (2013) *Science* 339:823-26 was examined.

The variable targeting domains of the guide RNA targeting the maize genomic target sites at the LIG locus (LIGCas-1, LIGCas-2 and LIGCas-3, SEQ ID NOs: 16, 17 and 18, Table1) were introduced into both the maize optimized long and short guide RNA expression cassettes as described in Example 1 and co-transformed along with the maize optimized Cas9 endonuclease expression cassette into immature maize embryos and deep sequenced for NHEJ mutations as described in Example 2. Embryos transformed with only the Cas9 endonuclease expression cassette served as a negative control.

As shown in Table 6 below, the frequency of NHEJ mutations recovered with the long guide RNA far exceeded those obtained with the short guide RNA. This data indicates that the long guide RNA paired with the maize optimized Cas9 endonuclease gene described herein more efficiently cleaves maize chromosomal DNA.

TABLE 6

Percent (%) mutant reads at the maize Liguleless 1 target locus produced by a guide RNA/Cas system with a long versus a short guide RNA.

| System | guide RNA Used | Total Number of Reads | Number of Mutant Reads | % Mutant Reads |
|---|---|---|---|---|
| Cas9 Only | N/A | 640,063 | 1 | 0.00% |
| LIGCas-1 guide/Cas9 | Short | 676,870 | 43 | 0.01% |
| LIGCas-2 guide/Cas9 | Short | 747,945 | 91 | 0.01% |
| LIGCas-3 guide/Cas9 | Short | 655,157 | 10 | 0.00% |
| LIGCas-1 guide/Cas9 | Long | 716,854 | 33,050 | 4.61% |
| LIGCas-2 guide/cas9 | Long | 711,047 | 16,675 | 2.35% |
| LIGCas-3 guide/Cas9 | Long | 713,183 | 27,959 | 3.92% |

Example 4

The Guide RNA/Cas Endonuclease System May be Multiplexed to Simultaneously Target Multiple Chromosomal Loci in Maize for Mutagenesis by Imperfect Non-Homologous End-Joining To test if multiple chromosomal loci may be simultaneously mutagenized with the guide RNA/maize optimized Cas endonuclease system described herein, the long guide RNA expression cassettes targeting the MS26Cas-2 target site (SEQ ID NO: 14), the LIGCas-3 target site (SEQ ID NO: 18) and the MS45Cas-2 target site (SEQ ID NO: 20), were co-transformed into maize embryos either in duplex or in triplex along with the Cas9 endonuclease expression cassette and examined by deep sequencing for the presence of imprecise NHEJ mutations as described in Example 2. Hi-II maize embryos co-transformed with the Cas9 expression cassette and the corresponding guide RNA expression cassette singly served as a positive control and embryos transformed with only the Cas9 expression cassette served as a negative control.

As shown in Table 7 below, mutations resulting from imprecise NHEJ were recovered at all relevant loci when multiple guide RNA expression cassettes were simultaneously introduced either in duplex or triplex with frequencies of mutant reads near those of the positive control. Thus, demonstrating that the maize optimized guide RNA/Cas endonuclease system described herein may be used to simultaneously introduce imprecise NHEJ mutations at multiple loci in maize.

TABLE 7

Percent (%) mutant reads at maize target loci produced by a multiplexed guide RNA/Cas system.

| Target Site Examined for NHEJ Mutations | guide RNAs Co-transformed Individually, in Duplex, or in Triplex with Cas9 | Total Number of Reads | Number of Mutant Reads | % Mutant Reads |
|---|---|---|---|---|
| LIGCas-3, MS26Cas-2, MS45Cas-2 | None (Cas9 Only control) | 527,691 | 9 | 0.00% |
| LIGCas-3 | LIGCas-3 | 645,107 | 12,631 | 1.96% |
| | LIGCas-3 MS26Cas-2 | 579,992 | 10,348 | 1.78% |
| | LIGCas-3 MS26Cas-2 MS45Cas-2 | 648,901 | 12,094 | 1.86% |
| MS26Cas-2 | MS26 Cas 2 | 699,154 | 17,247 | 2.47% |
| | LIGCas-3 MS26Cas-2 | 717,158 | 10,256 | 1.43% |
| | MS26Cas-2 MS45Cas-2 | 613,431 | 9,931 | 1.62% |
| | LIGCas-3 MS26Cas-2 MS45Cas-2 | 471,890 | 7,311 | 1.55% |
| MS45Cas-2 | MS45Cas-2 | 503,423 | 10,034 | 1.99% |
| | MS26Cas-2 MS45Cas-2 | 480,178 | 8,008 | 1.67% |
| | LIGCas-3 MS26Cas-2 MS45Cas-2 | 416,711 | 7,190 | 1.73% |

Example 5

Guide RNA/Cas Endonuclease Mediated DNA Cleavage in Maize Chromosomal Loci can Stimulate Homologous Recombination Repair-Mediated Transgene Insertion To test the utility of the maize optimized guide RNA/Cas system described herein to cleave maize chromosomal loci and stimulate homologous recombination (HR) repair pathways to site-specifically insert a transgene, a HR repair DNA vector (also referred to as a donor DNA) (SEQ ID NO: 97) was constructed as illustrated in FIG. 4 using standard molecular biology techniques and co-transformed with a long guide RNA expression cassette, comprising a variable targeting domain corresponding to the LIGCas-3 genomic target site, and a Cas9 endonuclease expression cassette into immature maize embryos as described in Example 2.

Maize embryos co-transformed with the HR repair DNA vector and LIG3-4 homing endonuclease (see Example 9) targeting the same genomic target site as LIGCas-3 served as a positive control. Since successful delivery of the HR repair DNA vector confers bialaphos herbicide resistance, callus events containing putative HR-mediated transgenic insertions were selected by placing the callus on herbicide containing media. After selection, stable callus events were sampled, total genomic DNA extracted, and using the primer pairs shown in FIG. 5 (corresponding to SEQ ID NOs: 98-101), PCR amplification was carried out at both possible transgene genomic DNA junctions to identify putative HR-mediated transgenic insertions. The resulting amplifications were sequenced for confirmation.

Sequence confirmed PCR amplifications indicating site-specific transgene insertion for the guide RNA/Cas system were detected for 37 out of 384 stable transformants with 15 containing amplifications across both transgene genomic DNA junctions indicating near perfect site-specific transgene insertion. The LIG3-4 homing endonuclease positive control yielded PCR amplifications indicating site-specific transgene insertion for 3 out of 192 stable transformants with 1 containing amplifications across both transgene genomic DNA junctions. The data clearly demonstrates that maize chromosomal loci cleaved with the maize optimized guide RNA/Cas system described herein can be used to stimulate HR repair pathways to site-specifically insert transgenes at frequencies greater than the LIG3-4 homing endonuclease.

Example 6

Guide RNA/Cas Endonuclease System Transformed Together on a Single Vector Results in Greater Recovery of Imperfect Non-Homologous End-Joining Mutations To evaluate different delivery methods for the maize optimized guide RNA/Cas endonuclease system described herein, the recovery of NHEJ mutations when the guide RNA/Cas expression cassettes were either co-transformed as separate DNA vectors as in Examples 2, 3, 4 and 5 or transformed as a single vector DNA (comprising both guide RNA and Cas endonuclease expression cassettes, as shown in FIG. 1C) was examined.

The long guide RNA expression cassette for LIGCas-3 and the Cas9 expression cassette were consolidated onto a single vector DNA (FIG. 1C, SEQ ID NO: 102) by standard molecular biology techniques and transformed into immature Hi-II maize embryos as described in Examples 10 and 11 by particle-mediated delivery. Hi-II embryos co-transformed with the Cas9 and LIGCas-3 long guide RNA expression cassettes served as a positive control while embryos transformed with only the Cas9 expression cassette served as a negative control. Deep sequencing for NHEJ mutations was performed as described in Example 2.

As shown in Table 8 below, the frequency of NHEJ mutations recovered when the Cas endonuclease and long guide RNA expression cassettes were delivered together as a single vector DNA was approximately 2-fold greater than that observed from the equivalent co-transformation experiment. This indicates that delivery of the guide RNA/Cas system expression cassettes together on a single vector DNA results in a greater recovery of imperfect non-homologous end-joining mutations.

TABLE 8

Percent (%) mutant reads at the maize Liguleless 1 target locus produced by a guide RNA/Cas system with Cas9 and guide RNA expression cassettes combined into one DNA vector versus two separate DNA vectors.

| System | Total Number of Reads | Number of Mutant Reads | % Mutant Reads |
|---|---|---|---|
| Cas9 Only Control | 1,519,162 | 97 | 0.01% |
| LIGCas-3 guide/Cas9 (Two vector DNAs) | 1,515,0607 | 36,346 | 2.40% |
| LIGCas-3 guide/Cas9 (Single vector DNA) | 1,860,031 | 105,854 | 5.69% |

Example 7

Delivery Methods for Plant Genome Editing Using the Guide RNA/Cas Endonuclease System This example describes methods to deliver or maintain and express the Cas9 endonuclease and guide RNA (or individual crRNA and tracrRNAs) into, or within plants, respectively, to enable directed DNA modification or gene insertion via homologous recombination. More specifically this example describes a variety of methods which include, but are not limited to, delivery of the Cas9 endonuclease as a DNA, RNA (5'-capped and polyadenylated) or protein molecule. In addition, the guide RNA may be delivered as a DNA or RNA molecule.

Shown in Example 2, a high mutation frequency was observed when Cas9 endonuclease and guide RNA were delivered as DNA vectors by biolistic transformation of immature corn embryos. Other embodiments of this disclosure can be to deliver the Cas9 endonuclease as a DNA, RNA or protein and the guide RNA as a DNA or RNA molecule or as a duplex crRNA/tracrRNA molecule as RNA or DNA or a combination. Various combinations of Cas9 endonuclease, guide RNA and crRNA/tracrRNA delivery methods can be, but are not limited to, the methods shown in Table 9.

TABLE 9

Various combinations of delivery of the cas9 endonuclease, guide RNA or CRNA + tracrRNA.

| combination | Components delivered. (Delivery method is shown between brackets) |
|---|---|
| 1 | Cas9 (DNA vector), guide RNA (DNA vector) |
| 2 | Cas9 (DNA vector), guide RNA (RNA) |
| 3 | Cas9 (RNA), guide RNA (DNA) |
| 4 | Cas9 (RNA), guide RNA (RNA) |
| 5 | Cas9 (Protein), guide RNA (DNA) |
| 6 | Cas9 (Protein), guide RNA (RNA) |
| 7 | Cas9 (DNA vector), crRNA (DNA), tracrRNA (DNA) |
| 8 | Cas9 (DNA vector), crRNA (RNA), tracrRNA (DNA) |
| 9 | Cas9 (DNA vector), crRNA (RNA), tracrRNA (RNA) |
| 10 | Cas9 (DNA vector) crRNA (DNA), tracrRNA (RNA) |
| 11 | Cas9 (RNA), crRNA (DNA), tracrRNA (DNA) |
| 12 | Cas9 (RNA), crRNA (RNA), tracrRNA (DNA) |
| 13 | Cas9 (RNA), crRNA (RNA), tracrRNA (RNA) |
| 14 | Cas9 (RNA), crRNA (DNA), tracrRNA (RNA) |
| 15 | Cas9 (Protein), crRNA (DNA), tracrRNA (DNA) |
| 16 | Cas9 (Protein), crRNA (RNA), tracrRNA (DNA) |
| 17 | Cas9 (Protein), crRNA (RNA), tracrRNA 18(RNA) |
| 18 | Cas9 (Protein), crRNA (DNA), tracrRNA (RNA) |

Delivery of the Cas9 (as DNA vector) and guide RNA (as DNA vector) example (Table 9, combination1) can also be accomplished by co-delivering these DNA cassettes on a single or multiple *Agrobacterium* vectors and transforming plant tissues by *Agrobacterium* mediated transformation. In addition, a vector containing a constitutive, tissue-specific or conditionally regulated Cas9 gene can be first delivered to plant cells to allow for stable integration into the plant genome to establish a plant line that contains only the Cas9 gene in the plant genome. In this example, single or multiple guide RNAs, or single or multiple crRNA and a tracrRNA can be delivered as either DNA or RNA, or combination, to the plant line containing the genome-integrated version of the Cas9 gene for the purpose of generating mutations or promoting homologous recombination when HR repair DNA vectors for targeted integration are co-delivered with the guide RNAs. As extension of this example, plant line containing the genome-integrated version of the Cas9 gene and a tracrRNA as a DNA molecule can also be established. In this example single or multiple crRNA molecules can be delivered as RNA or DNA to promote the generation of mutations or to promote homologous recombination when HR repair DNA vectors for targeted integration are co-delivered with crRNA molecule(s) enabling the targeted mutagenesis or homologous recombination at single or multiple sites in the plant genome.

Example 8

Components of the Guide RNA/Cas Endonuclease System Delivered Directly as RNA in Plants This example illustrates the use of the methods as described in Table 9 configuration of Example 7 [Cas9 (DNA vector), guide RNA (RNA)] for modification or mutagenesis of chromosomal loci in plants. The maize optimized Cas9 endonuclease expression cassette described in Example 1 was co-delivered by particle gun as described in Example 2 along with single stranded RNA molecules (synthesized by Integrated DNA Technologies, Inc.) constituting a short guide RNA targeting the maize locus and sequence shown in Table 10. Embryos transformed with only the Cas9 expression cassette or short guide RNA molecules served as negative controls. Seven days post-bombardment, the immature embryos were harvested and analyzed by deep sequencing for NHEJ mutations as described in Example 2. Mutations not present in the negative controls were found at the site (FIG. 6, corresponding to SEQ ID NOs: 104-110). These mutations were similar to those found in Examples 2, 3, 4 and 6. This data indicates that component(s) of the maize optimized guide RNA/Cas endonuclease system described herein may be delivered directly as RNA.

TABLE 10

Maize genomic target site and location for short guide RNA delivered as RNA.

| Locus | Location | Guide RNA Used | Designation | Maize Target Site | PAM Sequence | SEQ ID NO |
|---|---|---|---|---|---|---|
| 55 | Chr. 1: 51.78 cM | Short | 55CasRNA-1 | TGGGCAGGTCTCACGACGGT | TGG | 103 |

Example 9

Creation of Rare Cutting Engineered Meganucleases

LIG3-4 Meganuclease and LIG3-4 Intended Recognition Sequence

An endogenous maize genomic target site comprising the LIG3-4 intended recognition sequence (SEQ ID NO: 111) was selected for design of a rare-cutting double-strand break inducing agent (SEQ ID NO: 112) as described in US patent publication 2009-0133152 A1 (published May 21, 2009). The LIG3-4 intended recognition sequence is a 22 bp polynucleotide having the following sequence: ATATACCTCACACGTACGCGTA (SEQ ID NO: 111).

MS 26++ meganuclease

An endogenous maize genomic target site designated "TS-M526" (SEQ ID NO: 113) was selected for design of a custom double-strand break inducing agent MS26++as described in U.S. patent application Ser. No. 13/526,912 filed Jun. 19, 2012). The TS-MS26 target site is a 22 bp polynucleotide positioned 62 bps from the 5' end of the fifth exon of the maize MS26 gene and having the following sequence: gatggtgacqtacAgtgccctac (SEQ ID NO: 113). The double strand break site and overhang region is underlined, the enzyme cuts after C13, as indicated by the A. Plant optimized nucleotide sequences for an engineered endonuclease (SEQ ID NO: 114) encoding an engineered MS26++ endonuclease were designed to bind and make double-strand breaks at the selected TS-MS26 target site.

Example 10

Transformation of Maize Immature Embryos

Transformation can be accomplished by various methods known to be effective in plants, including particle-mediated delivery, *Agrobacterium*-mediated transformation, PEG-mediated delivery, and electroporation.

a. Particle-Mediated Delivery

Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560L (Initiation medium) and placed in the dark at temperatures ranging from 26° C. to 37° C. for 8 to 24 hours prior to placing on 560Y for 4 hours at 26° C. prior to bombardment as described above.

Plasmids containing the double strand brake inducing agent and donor DNA are constructed using standard molecular biology techniques and co-bombarded with plasmids containing the developmental genes ODP2 (AP2 domain transcription factor ODP2 (Ovule development protein 2); US20090328252 A1) and Wushel (US2011/0167516).

The plasm ids and DNA of interest are precipitated onto 0.6 μm (average diameter) gold pellets using a water-soluble cationic lipid transfection reagent as follows. DNA solution is prepared on ice using 1 pg of plasmid DNA and optionally other constructs for co-bombardment such as 50 ng (0.5 μl)

of each plasmid containing the developmental genes ODP2 (AP2 domain transcription factor ODP2 (Ovule development protein 2); US20090328252 A1) and Wushel. To the pre-mixed DNA, 20 µl of prepared gold particles (15 mg/ml) and 5 µl of the a water-soluble cationic lipid transfection reagent is added in water and mixed carefully. Gold particles are pelleted in a microfuge at 10,000 rpm for 1 min and supernatant is removed. The resulting pellet is carefully rinsed with 100 ml of 100% EtOH without resuspending the pellet and the EtOH rinse is carefully removed. 105 µl of 100% EtOH is added and the particles are resuspended by brief sonication. Then, 10 µl is spotted onto the center of each macrocarrier and allowed to dry about 2 minutes before bombardment.

Alternatively, the plasm ids and DNA of interest are precipitated onto 1.1 µm (average diameter) tungsten pellets using a calcium chloride ($CaCl_2$)) precipitation procedure by mixing 100 µl prepared tungsten particles in water, 10 µl (1 µg) DNA in Tris EDTA buffer (1 µg total DNA), 100 µl 2.5 M CaCl2, and 10 µl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 µl 100% ethanol is added to the final tungsten particle pellet. For particle gun bombardment, the tungsten/DNA particles are briefly sonicated. 10 µl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26° C. to 37° C., and then placed at 26° C. After 5 to 7 days the embryos are transferred to 560R selection medium containing 3 mg/liter Bialaphos, and subcultured every 2 weeks at 26° C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560L) comprises 4.0 g/l N6 basal salts (SIGMA C-1416), 1.0 ml/I Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/I Eriksson's Vitamin Mix (1000× SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/I Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/I Eriksson's Vitamin Mix (1000× SIGMA-1511), 0.5 mg/l thiamine HCl, 30.0 g/I sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/I MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) *Physiol. Plant.* 15:473), 100 mg/l myo-inositol, 0.5 mg/l zeatin, 60 g/l sucrose, and 1.0 ml/I of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/I MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 μM ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 11

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI. In one example, the BBM plasmid is precipitated onto gold particles with PEI, while the transgenic expression cassette (UBI::moPAT-GFPm::Pinll; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 μl of the washed gold particle/EtOH mix was centrifuged and the EtOH discarded. The particles were washed once in 100 μl ddH2O to remove residual ethanol, 250 μl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 μl aliquots of 2.5 mM HEPES buffer, pH 7.1, with 1× pulse-sonication, and then a quick vortex before each centrifugation. The particles were then suspended in a final volume of 250 μl HEPES buffer. A 25 μl aliquot of the particles was added to fresh tubes before attaching DNA. To attach uncoated DNA, the particles were pulse-sonicated, then 1 μg of DNA (in 5 μl water) was added, followed by mixing by pipetting up and down a few times with a Pipetteman and incubated for 10 minutes. The particles were spun briefly (i.e. 10 seconds), the supernatant removed, and 60 μl EtOH added. The particles with PEI-precipitated DNA-1 were washed twice in 60 μl of EtOH. The particles were centrifuged, the supernatant discarded, and the particles were resuspended in 45 μl water. To attach the second DNA (DNA-2), precipitation using a water-soluble cationic lipid transfection reagent was used. The 45 μl of particles/DNA-1 suspension was briefly sonicated, and then 5 μl of 100 ng/μl of DNA-2 and 2.5 μl of the water-soluble cationic lipid transfection reagent were added. The solution was placed on a rotary shaker for 10 minutes, centrifuged at 10,000 g for 1 minute. The supernatant was removed, and the particles resuspended in 60 μl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasm id contained a UBI::RFP::pinll expression cassette, and DNA-2 contained a UBI::CFP::pinll expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI::BBM::pinll using PEI, then coated with UBI::moPAT-YFP using a water-soluble cationic lipid transfection reagent, and then bombarded into scutellar cells on the surface of immature embryos. PEI-mediated precipitation results in a high frequency of transiently expressing cells on the surface of the immature embryo and extremely low frequencies of recovery of stable transformants Thus, it is expected that the PEI-precipitated BBM cassette expresses transiently and stimulates a burst of embryogenic growth on the bombarded surface of the tissue (i.e. the scutellar surface), but this plasmid will not integrate. The PAT-GFP plasmid released from the Ca++/gold particles is expected to integrate and express the selectable marker at a frequency that results in substantially improved recovery of transgenic events. As a control treatment, PEI-precipitated particles containing a UBI::GUS::pinll (instead of BBM) are mixed with the PAT-GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBLmoPAT-GFPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT-GFPm::PinII. It is expected that the cells receiving the RNA will immediately begin dividing more rapidly and a large portion of these will have integrated the agronomic gene. These events can further be validated as being transgenic clonal colonies because they will also express the PAT-GFP fusion protein (and thus will display green fluorescence under appropriate illumination). Plants regenerated from these embryos can then be screened for the presence of the polynucleotide of interest.

Example 12

DNA Constructs to Test the Guide RNA/Cas Endonuclease System for Soybean Genome Modifications To test if a guide RNA/Cas endonuclease system, similar to that described in Example 1 for maize, is functional in a dicot such as soybean, a Cas9 (SO) gene (SEQ ID NO:115) soybean codon optimized from *Streptococcus pyogenes* M1 GAS (SF370) was expressed with a strong soybean constitutive promoter GM-EF1A2 (US patent application 20090133159 (SEQ ID NO: 116). A simian vacuolating virus (SV40) large T-antigen nuclear localization signal (SEQ ID NO:117), representing the amino acid molecules of PKKKRKV (with a linker SRAD (SRADPKKKRKV), was added to the carboxyl terminus of the codon optimized Cas9 to facilitate transporting the codon optimized Cas9 protein (SEQ ID NO:118) to the nucleus. The codon optimized Cas9 gene was synthesized as two pieces by GenScript USA Inc. (Piscataway, NJ) and cloned in frame downstream of the GM-EF1A2 promoter to make DNA construct QC782 shown in FIG. 7 (SEQ ID NO:119).

Plant U6 RNA polymerase III promoters have been cloned and characterized from such as *Arabidopsis* and *Medicago truncatula* (Waibel and Filipowicz, NAR 18:3451-3458 (1990); Li et al., *J. Integrat. Plant Biol.* 49:222-229 (2007); *Kim and Nam, Plant Mol. Biol. Rep.* 31:581-593 (2013); Wang et al., *RNA* 14:903-913 (2008)). Soybean U6 small nuclear RNA (snRNA) genes were identified herein by searching public soybean variety Williams82 genomic sequence using *Arabidopsis U*6 gene coding sequence. Approximately 0.5 kb genomic DNA sequence upstream of the first G nucleotide of a U6 gene was selected to be used as a RNA polymerase III promoter for example, GM-U6-13.1 promoter (SEQ ID NO:120), to express guide RNA to direct Cas9 nuclease to designated genomic site. The guide RNA coding sequence was 76 bp long (FIG. 8B) and comprised a 20 bp variable targeting domain from a chosen soybean genomic target site on the 5' end and a tract of 4 or more T residues as a transcription terminator on the 3' end. (SEQ ID NO:121, FIG. 8B). The first nucleotide of the 20 bp variable targeting domain was a G residue to be used by RNA polymerase III for transcription. The U6 gene promoter and the complete guide RNA was synthesized and then cloned into an appropriate vector to make, for example, DNA construct QC783 shown in FIG. 8A (SEQ ID NO:122). Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct, for example, QC815 in FIG. 9A (SEQ ID NO:123), which was then used to transform soybean cells to test the soybean optimized guide RNA/Cas system for genome modification. Similar DNA constructs were made to target different genomic sites using guide RNAs containing different target sequences.

Example 13

Selection of Soybean Genomic Sites to be Cleaved by the Guide RNA/Cas Endonuclease System A region of the soybean chromosome 4 (Gm04) was selected to test if the soybean optimized guide RNA/Cas endonuclease system could recognize, cleave, and mutate soybean chromosomal DNA through imprecise non-homologous end-joining (NHEJ) repair. Two genomic target sites were selected one close to a predicted gene Glyma04g39780.1 at 114.13 cM herein named DD20 locus (FIG. 10A) and another close to Glyma04g39550.1 at 111.95 cM herein named DD43 locus (FIG. 10B). Each of the 20 bp variable targeting domain of the guide RNA started with a G residue required by RNA polymerase III and was followed in the soybean genome by a 3 bp PAM motif (Table 11). The chromosome positions of the soybean genomic targets sites in close proximity to the PAM sequences were determined by blast searching the public soybean variety Williams82 genomic sequence. The soybean genomic target sites DD2OCR1(SEQ ID NO: 125), DD2OCR2 (SEQ ID NO: 126), and DD43CR1 (SEQ ID NO: 127) were identified as all unique in soybean genome while a second identical 23 bp genomic target site DD43CR2 (SEQ ID NO: 128) was found at Gm06:12072339-12072361 so there are two potential cleavage sites targeted by DD43CR2 guide RNA. Both DD43CR1 and DD43CR2 are complementary strand sequences indicated by "c" after the positions.

TABLE 11

Soybean genomic target sites for a guide RNA/Cas endonuclease system.

| Chromosome | Positions | Designation | Genomic Target Sites | PAM |
|---|---|---|---|---|
| Gm04, | 45936311-45936333 | DD20CR1 | GGAACTGACACACGACATGA | TGG |
| 114.13 CM | 45936324-45936346 | DD20CR2 | GACATGATGGAACGTGACTA | AGG |
| Gm04, | 45731921-45731943c | DD43CR1 | GTCCCTTGTACTTGTACGTA | CGG |
| 111.95 CM | 45731895-45731917c | DD43CR2 | GTATTCTAGAAAAGAGGAAT | TGG |

Guide RNA expression cassette comprising a variable targeting domain targeting one of DD2OCR1, DD2OCR2, DD43CR2 genomic target sites were similarly constructed and linked to the soybean Cas9 expression cassette to make DNA constructs QC817, QC818, and QC816 that are similar to QC815 in FIG. 9A (SEQ ID NO:123) except for the 20 bp variable targeting domain of the guide RNA Since up to six continuous mismatches in the 5' regions of the genomic target site (protospacer) with the 20 bp variable targeting domain can be tolerated, i.e., a continuous stretch of 14 base pairs between the variable targeting domain and the crRNA sequence proximate to the PAM is necessarily enough for efficient targets cleavage any 23 bp genomic DNA sequence following the pattern N(20)NGG can be selected as a target site for the guide RNA/Cas endonuclease system. The last NGG is the PAM sequence that should not be included in the 20 bp variable targeting domain of the guide RNA. If the first N is not endogenously a G residue it must be replaced with a G residue in guide RNA target sequence to accommodate RNA polymerase III, which should not sacrifice recognition specificity of the target site by the guide RNA.

Example 14

Delivery of the Guide RNA/Cas Endonuclease System DNA to Soybean by Transient Transformation The soybean optimized Cas9 endonuclease and guide RNA expression cassettes were delivered to young soybean somatic embryos in the form of embryogenic suspension cultures by particle gun bombardment. Soybean embryogenic suspension cultures were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 μl of a 60 mg/ml 1.0 mm gold particle suspension were added (in order): 30 μl of 30 ng/μl QC815 DNA fragment U6-13.1:DD43CR1+EF1A2:CAS9 as an example, 20 μl of 0.1 M spermidine, and 25 μl of 5 M $CaCl_2$). The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. Then 5 μl of the DNA-coated gold particles was loaded on each macro carrier disk.

Approximately 100 mg of a two-week-old suspension cultures were placed in an empty 60×15 mm Petri dish and the residual liquid removed from the tissue with a pipette. Membrane rupture pressure was set at 1100 psi and the chamber was evacuated to a vacuum of 28 inches mercury. The tissue was placed approximately 3.5 inches away from the retaining screen and bombarded once. The tissue clumps were rearranged and bombarded another time. Minimum amount of liquid MS media without 2,4-D supplement was added to the tissue to prevent the cultures from drying or overgrowing. The 60×15 mm Petri dish was sealed in a 100×25 mm Petri dish containing agar solid MS media to as another measure to keep the tissues from drying up. The tissues were harvested seven days after and genomic DNA was extracted for PCR analysis.

Example 15

Analysis of Guide RNA/Cas Endonuclease System Mediated Site-Specific NHEJ by Deep Sequencing To evaluate DNA double strand cleavage at a soybean genomic target site mediated by the guide RNA/Cas endonuclease system, a region of approximately 100 bp genomic DNA surrounding the target site was amplified by PCR and the PCR product was then sequenced to check mutations at the target site as results of NHEJs. The region was first amplified by 20 cycles of PCR with Phusion High Fidelity mastermix (New England Biolabs) from 100 ng genomic DNA using gene-specific primers that also contain adaptors and amplicon-specific barcode sequences needed for a second round PCR and subsequence sequence analysis. For examples, the first PCR for the four experiments listed in Table 2 were done using primers DD2O-S3 (SEQ ID NO:133)/DD20-A (SEQ ID NO:134), DD20-54 (SEQ ID NO:135)/DD20-A, DD43-S3 (SEQ ID NO:136)/DD43-A (SEQ ID NO:137) and DD43-S4 (SEQ ID NO:138)/DD43-A. One micro liter of the first round PCR products was further amplified by another 20 cycles of PCR using universal primers (SEQ ID NOs:140, 141) with Phusion High Fidelity mastermix. The resulting PCR products were separated on 1.5% agarose gel and the specific DNA bands were purified with Qiagen gel purification spin columns. DNA concentrations were measured with a DNA Bioanalyzer (Agilent) and equal molar amounts of DNA for up to 12 different samples each with specific barcode were mixed as one sample for Illumina deep sequencing analysis. Single read 100 nucleotide-length deep sequencing was performed at a DuPont core facility on a Illumnia's MiSeq Personal Sequencer with a 40% (v/v) spike of PhiX control v3 (Illumina, FC-110-3001) to off-set sequence bias.

Since the genomic target site is located in the middle of the ~100 bp long PCR amplicon (SEQ ID NOs: 142, 143, 144, 145), the 100 nucleotide-length deep sequencing is sufficient to cover the targets site region. A window of 10 nucleotides centered over the expected cleavage site, i.e., 3 bp upstream of the PAM, was selected for sequence analysis. Only those reads with one or more nucleotide indel arising within the 10 nucleotide window and not found in a similar level in negative controls were classified as NHEJ mutations. NHEJ mutant reads of different lengths but with the same mutation were counted into a single read and up to 10 most prevalent mutations were visually confirmed to be specific mutations before they were then used to calculate the % mutant reads based on the total analyzed reads containing specific barcode and forward primer.

The frequencies of NHEJ mutations revealed by deep sequencing for four target sites DD2OCR1, DD2OCR2, DD43CR1, DD43CR2 with one RNA polymerase III promoter GM-U6-13.1 are shown in Table 2. The visually confirmed most prevalent NHEJ mutations are shown in FIG. 11A-11D. The mutant sequences in FIG. 11A-11E are listed as SEQ ID NOs:147-201. The top row is the original reference sequence with the target site sequence underlined. Deletions in the mutated sequences are indicated by "—-" while additions and replacements are indicated by bold letters. Total count of each mutation of different reads is given in the last column. Cas9 nuclease construct only, guide RNA construct only, and no DNA bombardment negative controls were similarly performed and analyzed but data not shown since no-specific mutations were detected. Other targets sites and guide RNAs were also tested with similar positive results and data not shown.

TABLE 12

Target site-specific mutations introduced by guide RNA/Cas endonuclease mediated NHEJ.

| Experiment | DNA | Mutant reads | Total reads | % Mutants |
|---|---|---|---|---|
| U6-13.1:DD20CR1 + EF1A2:CAS9 | QC817 | 339 | 710,339 | 0.048% |
| U6-13.1:DD20CR2 + EF1A2:CAS9 | QC818 | 419 | 693,483 | 0.060% |
| U6-13.1:DD43CR1 + EF1A2:CAS9 | QC815 | 489 | 682,207 | 0.072% |
| U6-13.1:DD43CR2 + EF1A2:CAS9 | QC816 | 917** | 539,681 | 0.170% |

**At least the top 15 reads are specific mutations but only the top 10 are counted in the table to be consistent with other experiments. If all top 15 mutations are counted, the total Mutant reads is 1080 and the % Mutants is 0.200%.

In conclusion, our data indicate that the soybean optimized guide RNA/Cas endonuclease system is able to effectively cleave soybean endogenous genomic DNA and create imperfect NHEJ mutations at the specified genomic target sites.

Example 16

The Guide RNA/Cas Endonuclease System Delivers Double-Strand Breaks (DBSs) to the Maize Epsps Locus Resulting in Desired Point Mutations Two maize optimized Cas9 endonucleases were developed and evaluated for their ability to introduce a double-strand break at a genomic target sequence. A first Cas9 endonuclease was as described in FIG. 1A (Example 2 and expression cassette SEQ ID NO:5). A second maize optimized Cas9 endonuclease (moCas9 endonuclease; SEQ ID NO:192) was supplemented with the SV40 nuclear localization signal by adding the signal coding sequence to the 5' end of the moCas9 coding sequence (FIG. 13). The plant moCas9 expression cassette was subsequently modified by the insertion of the ST-LS1 intron into the moCas9 coding sequence in order to enhance its expression in maize cells and to eliminate its expression in *E. coli* and *Agrobacterium*. The maize ubiquitin promoter and the potato proteinase inhibitor II gene terminator sequences complemented the moCas9 endonuclease gene designs. The structural elements of the moCas9 expression cassette are shown in FIG. 13 and its amino acid and nucleotide sequences are listed as SEQ ID Nos: 192 and 193.

A single guide RNA (sgRNA) expression cassette was essentially as described in Example 1 and shown in FIG. 1B. It consists of the U6 polymerase III maize promoter (SEQ ID NO: 9) and its cognate U6 polymerase III termination sequences (TTTTTTTT). The guide RNA (SEQ ID NO: 194) comprised a 20 nucleotide variable targeting domain (nucleotide)-20 of SEQ ID NO: 194) followed by a RNA sequence capable of interacting with the double strand break inducing endonuclease.

A maize optimized Cas9 endonuclease target sequence (moCas9 target sequence) within the EPSPS codon sequence was complementary to the 20 nucleotide variable sequence of the guide sgRNA determined the site of the Cas9 endonuclease cleavage within the EPSPS coding sequence.

The moCAS9 target sequence (nucleotides 25-44 of SEQ ID NO:209) was synthesized and cloned into the guide RNA-Cas9 expression vector designed for delivery of the components of the guide RNA-Cas9 system to the BMS (Black Mexican Sweet) cells through *Agrobacterium*-mediated transformation. *Agrobacterium* T-DNA delivered also the yeast FLP site-specific recombinase and the WDV (wheat dwarf virus) replication-associated protein (replicase). Since the moCas9 target sequences were flanked by the FLP recombination targets (FRT), they were excised by FLP in maize cells forming episomal (chromosome-like) structures. Such circular DNA fragments were replicated by the WDV replicase (the origin of replication was embedded into the WDV promoter) allowing their recovery in *E. coli* cells. If the maize optimizedCas9 endonuclease made a double-strand break at the moCas9 target sequence, its repair might produce mutations. The procedure is described in detail in: Lyznik, L. A., Djukanovic, V., Yang, M. and Jones, S. (2012) Double-strand break-induced targeted mutagenesis in plants. In: *Transgenic plants: Methods and Protocols* (Dunwell, J. M. and Wetten, A. C. eds). New York Heidelberg Dordrecht London: Springer, pp. 399-416.

The guideRNA/Cas endonuclease systems using either one of the maize optimized Cas9 endonucleases described herein, generated double-strand breaks in the moCas9 target sequence (Table 13). Table 13 shows the percent of the moCas9 target sequences mutagenized in the maize BMS cells using the moCas9 endonuclease of SEQ ID NO: 192 or the maize optimized cas9 endonuclease described in FIG. 1A and expressed by the expression cassette of SEQ ID NO:5. Both guideRNA/Cas endonuclease systems generated double-strand breaks (as judged by the number of targeted mutagenesis events) ranging from 67 to 84% of the moCas9 target sequences available on episomal DNA molecules in maize BMS cells. A sample of mutagenized EPSPS target sequences is shown in FIG. 14. This observation indicates that the maize optimized Cas9 endonuclease described herein is functional in maize cells and efficiently generates double-strand breaks at the moCas9 target sequence.

TABLE 13

Percent of the moCas9 target sequences mutagenized in the maize BMS cells by maize optimized Cas9 endonucleases.

| Cas9 endonuclease version | # of moCas9 target sequences analyzed | # of intact moCas9 target sequences recovered | # of mutagenized moCas9 target sequences found | Percent mutagenesis (%) |
|---|---|---|---|---|
| SEQ ID NO: 193 (FIG. 13) | 81 | 13 | 68 | 84% |
| SEQ ID NO: 5 (FIG. 1A) | 93 | 31 | 62 | 67% |

In order to accomplish targeted genome editing of the maize chromosomal EPSPS gene, a polynucleotide modification template which provided genetic information for editing the EPSPS coding sequence was created (SEQ ID NO:195) and co-delivered with the guide RNA/Cas9 system components..

As shown in FIG. 12, the polynucleotide modification template comprised three nucleotide modifications (indicated by arrows) when compared to the EPSPS genomic sequence to be edited. These three nucleotide modifications are referred to as TIPS mutations as these nucleotide modifications result in the amino acid changes T-102 to 1-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon (ATC), the third point mutation results from the substitution of the first C nucleotide in the codon sequence CCA with a T nucleotide in order to form a serine codon, TCA.(FIG. 12). Both codon sequences were located within 9 nucleotides of each other as shown in SEQ ID NO: 196: atcgcaatgcggtca. The three nucleotide modifications are shown in bold. The nucleotides between the two codon sequences were homologous to the non-edited EPSPS gene on the epsps locus. The polynucleotide modification template further comprised DNA fragments of maize EPSPS genomic sequence that were used as homologous sequence for the EPSPS gene editing. The short arm of homologous sequence (HR1-FIG. 12) was 810 base pairs long and the long arm of homologous sequence (HR2-FIG. 12) was 2,883 base pairs long (SEQ ID NO: 195).

In this example, the EPSPS polynucleotide modification template was co-delivered using particle gun bombardment as a plasmid (see template vector 1, FIG. 15) together with the guide sgRNA expression cassette and a maize optimized-Cas9 endonuclease expression vector which contained the maize optimized Cas9 endonuclease expression cassette described in FIG. 1A (Example 1, SEQ ID NO:5) and also contained a moPA T selectable marker gene. Ten to eleven day-old immature embryos were placed, embryo-axis down, onto plates containing the N6 medium (Table 14) and incubated at 28° C. for 4-6 hours before bombardment. The plates were placed on the third shelf from the bottom in the PDS-1000 apparatus and bombarded at 200 psi. Post-bombardment, embryos were incubated in the dark overnight at 28° C. and then transferred to plates containing the N6-2 media for 6-8 days at 28° C. The embryos were then transferred to plates containing the N6-3 media for three weeks, followed by transferring the responding callus to plates containing the N6-4 media for an additional three-week selection. After six total weeks of selection at 28° C., a small amount of selected tissue was transferred onto the MS regeneration medium and incubated for three weeks in the dark at 28° C.

TABLE 14

Composition of Culture Media.

| Culture medium | Composition |
|---|---|
| N6 | 4.0 g/L $N_6$ Basal Salts (Sigma C-1416; Sigma-Aldrich Co., St. Louis, MO, USA), 1.0 ml/L Ericksson's Vitamin Mix (Sigma E-1511), 0.5 mg/L thiamine HCl, 190 g/L sucrose, 1.0 mg/L 2,4-dichlorophenoxyacetic acid (2,4-D), 2.88 g/L L-proline, 8.5 mg/L silver nitrate, 25 mg/L cefotaxime, and 6.36 g/L Sigma agar at pH 5.8 |
| N6-2 | 4.0 g/L $N_6$ Basal Salts (Sigma C-1416), 1.0 ml/L Ericksson's Vitamin Mix (Sigma E-1511), 0.5 mg/L thiamine HCl, 20 g/L sucrose, 1.0 mg/L 2,4-D, 2.88 g/L L-proline, 8.5 mg/L silver nitrate, 25 mg/L cefotaxime, and 8.5 g/L Sigma agar at pH 5.8 |
| N6-3 | 4.0 g/L $N_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L 2-(N-morpholino)ethanesulphonic acid (MES) buffer, 0.85 mg/L silver nitrate, 5 mg/L glufosinate $NH_4$, and 8.0 g/L Sigma agar at pH 5.8 |
| N6-4 | 4.0 g/L $N_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L MES buffer, 0.85 mg/L silver nitrate, 3 mg/L bialophos, and 8.0 g/L Sigma agar at pH 5.8 |
| MS | 4.3 g/L Murashige and Skoog (MS) salts (Gibco 11117; Gibco, Grand Island, NY), 5.0 ml/L MS Vitamins Stock Solution (Sigma M3900), 100 mg/L myo-inositol, 0.1 μmol abscisic acid (ABA), 1 mg/L indoleacetic acid (IAA), 0.5 mg/L zeatin, 60.0 g/L sucrose, 3.0 mg/L Bialaphos, and 8.0 g/L Sigma agar at pH 5.6 |

DNA was extracted by placing callus cell samples, two stainless-steel beads, and 450 ul of extraction buffer (250 mM NaCl, 200 mM Tris-HCl pH 7.4, 25 mM EDTA, 4.2 M Guanidine HCl) into each tube of a Mega titer rack. The rack was shaken in the Genogrinder at 1650 r.p.m. for 60 seconds and centrifuged at 3000× g for 20 min at 4° C. Three hundred μl of supernatant was transferred to the wells of the Unifilter 96-well DNA Binding GF/F Microplate (770-2810, Whatman, GE Healthcare). The plate was placed on the top of a Multi-well plate vacuum manifold (5017, Pall Life Sciences). A vacuum pressure was applied until the wells were completely dried. The vacuum filtration procedure was repeated one time with 100 ul extraction buffer and two times with 250 ul washing buffer (50 mM Tris-HCl pH 7.4, 200 mM NaCl, 70% ethanol). The residual ethanol was removed by placing the GF/F filter plate on an empty waste collection plate and centrifuged for 10 min at 3000× g. The DNA was eluted in 100 ul Elution Buffer (10 mM Tns-FICI, pH 8.3) and centrifuged at 3000×g for 1 min. For each sample, four PCR reactions were run. They included approximately 40 ng genomic DNA, 10 ul REDExtract-N-Amp PCR ReadyMix (R4775, Sigma-Aldrich Co.), and 5 picomoles of each primer in a total volume of 20 ul. Primer combinations for each PCR reaction are listed in the Table 15.

TABLE 15

Primer combinations for PCR reactions.

| PCR reaction | Primer sequence | SEQ ID NO: | PCR product |
|---|---|---|---|
| F-E2 | CCGAGGAGATCGTGCTGCA<br>CAATGGCCGCATTGCAGTTC | 197<br>198 | Template randomly integrated or gene editing event |

TABLE 15-continued

Primer combinations for PCR reactions.

| PCR reaction | Primer sequence | SEQ ID NO: | PCR product |
|---|---|---|---|
| F-T | CCGAGGAGATCGTGCTGCA<br>TGACCGCATTGCGATTCCAG | 199<br>200 | Wild-type EPSPS allele |
| H-T | TCCAAGTCGCTTTCCAACAGGATC<br>TGACCGCATTGCGATTCCAG | 201<br>202 | TIPS editing event |
| F-E3 | CCGAGGAGATCGTGCTGCA<br>ACCAAGCTGCTTCAATCCGACAAC | 203<br>204 | A fragment of the epsps locus for cloning and sequencing |

The same PCR reactions were done on five samples of genomic DNA obtained from untransformed maize inbred plantlets. After an initial denaturation at 95° C. for 5 minutes, each PCR amplification was carried out over 35 cycles using DNA Engine Tetrad2 Thermal Cycler (BioRad Laboratories, Hercules, CA) at 94° C. for 30 sec denaturation, 68° C. for 30 sec annealing, and 72° C. for 1 min extension. PCR products F-E2, F-T and H-T were separated in 1% agarose gel at 100 Volts for 45 minutes, with 100 bp DNA Ladder (N0467S, NewEngland Biolabs). For sequencing, the F-F3 PCR amplified fragments from selected calli were cloned into pCR 2.1-TOPO vectors using the TOPO TA Cloning Kit (Invitrogen Corp, Carlsbad, CA). DNA sequencing was done with BigDye Terminator chemistry on ABI 3700 capillary sequencing machines (Applied Biosystems, Foster City, CA). Each sample contained about 0.5 ug Topo plasmid DNA and 6.4 μmole primer E3-EPex3 Rev (ACCAAGCTGCTTCAATCCGACAAC, SEQ ID NO: 204). Sequences were analyzed using the Sequencer program.

A sample of thirty one callus events selected on media containing bialophos (the moPAT selectable marker gene was part of the guide RNA- moCas9 expression vector) were screened for the presence of the TIPS point mutations. Twenty four events contained the TIPS point mutations integrated into genomic DNA (FIG. 16, the F-E2 treatment). Among them, six events showed the PCR amplification product of the chromosomal EPSPS gene with TIPS mutations (FIG. 16, the H-T treatment). The pair of PCR primers (one that can hybridize to the genomic epsps sequence not present in the EPSPS polynucleotide modification template and the other one binding to the edited EPSPS sequence present in the EPSPS polynucleotide modification template) distinguished the EPSPS-TIPS editing products from the wild-type epsps alleles or random insertions of the TIPS mutations. If one EPSPS allele was edited to contain the TIPS substitutions, it should be detected as a DNA fragment originating from the genomic epsps locus, regardless whether the TIPS substitutions were selected for during the PCR amplification process. The TIPS primer was replaced with the wild-type EPSPS primer (Table 15, the F-E3 pair of primers) and the PCR amplification products were cloned into the TOPO cloning vectors and sequenced. The sequencing data represented a random sample of the genomic epsps locus sequences in one of the selected events (FIG. 17, callus A12 3360.92). FIG. 17 shows that the method disclosed herein resulted in the successful nucleotide editing of three nucleotides (FIG. 17 bold) responsible for the TIPS mutations without altering any of the other epsps nucleotides, while the moCas9 target sequence (the site of guide RNA binding underlined in FIG. 17) was not mutagenized.

Also, the other EPSPS allele was not edited indicating that only one EPSPS allele was edited in this particular event (FIG. 17, lower section).

This data further shows that the present disclosure of the use of the guide RNA/Cas system for the gene editing demonstrates the ability to recover gene editing events at a high efficiency of 1 out of fewer than 10 selected events.

Example 17

The Guide RNA/Cas Endonuclease System Delivers Double-Strand Breaks to the Maize Epsps Locus Resulting in Maize Plants Containing an EPSPS-TIPS Edited Gene.

The EPSPS gene edited events were produced and selected as described in the Example 16. In short, the EPSPS polynucleotide modification template was co-delivered using particle gun bombardment as a plasmid (see template vector 1, FIG. 15) together with the guide RNA expression cassette and a maize optimized Cas9 endonuclease expression vector which contained the maize optimized Cas9 endonuclease expression cassette described in FIG. 1A (Example 1, SEQ ID NO:5) and also contained a moPAT selectable marker gene.

After six weeks of selection at 28° C., a small amount of selected tissue was transferred onto the MS regeneration medium and incubated for three weeks in the dark at 28° C. After the three week incubation visible shoots were transferred to plates containing the MS-1 medium and incubated at 26° C. in the light for 1-2 weeks until they were ready to be sent to a greenhouse and transferred into soil flats. The Ms-1 medium contained: 4.3 g/L MS salts (Gibco 11117), 5.0 ml/L MS Vitamins Stock Solution (Sigma M3900), 100 mg/L myo-inositol, 40.0 g/L sucrose, and 6.0 g/L Bacto-Agar at pH 5.6.

Using the procedures described above, 390 T0 maize plants were produced originating from 3282 embryos, resulting in an overall transformation efficiency of 12%, further indicating that the guide RNA/Cas system used herein results in low or no toxicity (Table 16).

TABLE 16

Transformation efficiency of the EPSPS editing.

| Treatment | # Embryos | # Calli selected | Selection efficiency | T0 plants to GH | Overall Efficiency |
|---|---|---|---|---|---|
| Particle bombardment | 3282 | 489 | 15% | 390 | 12% |

DNA was extracted from each T0 plantlet 7-10 days after transfer to the greenhouse and PCR procedures were conducted as described in the Example 16 to screen the T0 plants for mutations at the epsps locus.

Seventy two percent of analyzed T0 plants (270/375, Table 17) contained mutagenized EPSPS alleles as determined by the end-point PCR procedure described in the Example 16. Most of the mutations (230/375 or 89%) were produced as a result of error-prone non-homologous end joining (NHEJ) while forty T0 plants (40/375 or 11%) contained the TIPS edited EPSPS alleles indicating the involvement of a templated double-strand break repair mechanism (Table 17).

TABLE 17

Mutations at the epsps locus.

| Transformation | TO Plants Analyzed | Mutations at the epsps locus | Mutation rate | TIPS editing | Gene Editing Rate (TIPS ) |
|---|---|---|---|---|---|
| Particle bombardment | 375 | 270 | 72% | 40 | 11 % |

A pair of primers (Table 15, the F-E3 pair of primers) was used to amplify a native, endogenous fragment of the epsps locus containing the moCas6 target sequence and the EPSPS editing site from the genomic DNA of selected T0 plants. The PCR amplification products were cloned into the TOPO cloning vectors and sequenced as described in Example 16. The sequencing data represent a random sample of the genomic epsps locus sequences from a particular T0 plant (Table 18) and indicate the genotype of the selected T0 plants. The list of the EPSPS-TIPS allele-containing T0 plants transferred to the pots is presented in Table 18 (a selected set of T0 plants from the original 40 TIPS-containing events).

TABLE 18

The epsps locus genotypes observed in T0 plants. TIPS refers to a clone comprising the TIPS edited EPSPS sequence. NHEJ refers to the presence of a NHEJ mutation and WT refers to the presence of a wild-type EPSPS sequence amplified from the native epsps locus.

| Event (T0 plant) | Observed Sequences found at the epsps locus |
|---|---|
| E1 | 16 TIPS, 13 NHEJ |
| E2 | 28 TIPS, 0 NHEJ |
| E3 | 2 TIPS, 20 WT |

TABLE 18-continued

The epsps locus genotypes observed in T0 plants. TIPS refers to a clone comprising the TIPS edited EPSPS sequence. NHEJ refers to the presence of a NHEJ mutation and WT refers to the presence of a wild-type EPSPS sequence amplified from the native epsps locus.

| Event (T0 plant) | Observed Sequences found at the epsps locus |
|---|---|
| E4 | 1 TIPS, 28 NHEJ |
| E5 | 2 TIPS, 2 NHEJ, 9 WT |
| E6 | 10 TIPS, 17 NHEJ |
| E7 | 12 TIPS, 17 NHEJ |
| E8 | 11 TIPS, 15 NHEJ |
| E9 | 17 TIPS, 10 NHEJ |

As presented in Table 18, the selected plants of E1 and E3 to E9 contained the EPSPS-TIPS edited version of the EPSPS gene either accompanied by a wild-type EPSPS allele (WT) or a NHEJ mutagenized EPSPS allele (NHEJ). The numbers before TIPS, WT, NHEJ in Table18 indicate the frequency at which a particular version of the EPSPS allele was identified. If all clones contained the TIPS-edited EPSPS sequence, the analyzed plant was likely to be homozygous for the EPSPS-TIPS allele (see for example E2). If only about 50% of clones contained a TIPS-edited EPSPS sequence, the analyzed plant was likely to be hemizygous for the EPSPS-TIPS allele (see for example E1). Other plants, such as E3 or E4, were likely to be chimeric for TIPS. In one event, E2, the T0 plant contained only TIPS-edited sequence at the epsps locus indicating that the guide RNA/Cas endonuclease system disclosed herein resulted in the successful nucleotide editing of three nucleotides (FIG. 17 bold) responsible for the two EPSPS-TIPS alleles at the epsps locus in maize plants.

A qPCR analysis was performed on the selected T0 plants to estimate the copy number of the wild-type EPSPS genes and the moCas9 endonuclease sequences. Multiplex qPCR amplifications of the maize EPSPS gene and the ADH housekeeping gene were carried out on the DNA samples from T0 plants. The primers and probes used in the PCR reaction are shown in Table 19.

TABLE 19

Primers used in qPCR analysis of T0 plants.

| Primer/probe | Primary PCR Primer Sequence | SEQ ID NO: |
|---|---|---|
| primer qADH F | 5'-CAAGTCGCGGTTTTCAATCA-3 | SEQ ID NO: 217 |
| Primer qADH R | 5'-TGAAGGTGGAAGTCCCAACAA-3' | SEQ ID NO: 218 |
| probe ADH-VIC | VIC-TGGGAAGCCTATCTACCAC | SEQ ID NO: 219 |
| Probe wtEPSPS | 6FAM-CGGCCATTGACAGCA-MGB-NFQ | SEQ ID NO: 220 |
| Forward primer qEPSPS F | 5'-TCTTGGGGAATGCTGGAACT-3' | ,SEQ ID NO: 221 |
| reverse primer qEPSPSR | 5'-CACCAGCAGCAGTAACAGCTG-3' | SEQ ID NO: 222 |
| FAM-wtEPSPS R probe | 6FAM-TGCTGTCAATGGCCGCA | SEQ ID NO: 223 |

TABLE 19-continued

| Primers used in qPCR analysis of T0 plants. | | |
|---|---|---|
| Primer/probe | Primary PCR Primer Sequence | SEQ ID NO: |
| forward primer qEPSPS F | 5'-TCTTGGGGAATGCTGGAACT-3' | SEQ ID NO: 224 |
| reverse primer qwtEPSPS RA | 5'-CCACCAGCAGCAGTAACAGC-3 | SEQ ID NO: 225) |

All analyses were conducted using the LightCycler 480 Real-Time PCR System (Roche Diagnostics). A threshold value for the wtEPSPS genotype was set at 1.76. Every sample showing less than 1.76 copies of EPSPS, with the end-point florescence measurements up to two times lower than the wild-type control, was categorized as the One Allele EPSPS genotype (hemizygous for the wild-type EPSPS allele).

A qPCR method was used to estimate the TIPS sequence copy number. The primers and probes used in the qPCR reaction are shown in Table 20.

TABLE 20

| Primers used in qPCR analysis to estimate the TIPS sequence copy number. | | |
|---|---|---|
| Primer/probe | Primary PCR Primer Sequence | SEQ ID NO: |
| forward primer qepTIPS F | 5'-GGAAGTGCAGCTCTTCTTGGG-3' | SEQ ID NO: 226 |
| reverse primer qepTIPS R | 5'-AGCTGCTGTCAATGACCGC-3' | SEQ ID NO: 227 |
| TIPS probe | 6FAM-AATGCTGGAATCGCA | SEQ ID NO: 228) |

A comparative Ct method with Delta Ct values normalized to the average Delta Ct from the bi-allelic TIPS genotypes provided a copy number estimation for the TIPS sequence detected in the analyzed plant samples.

TABLE 21 qPCR genotyping and copy number of selected T0 plants.

| Event name | TIPS EPSPS allele | Wild-type EPSPS allele # | TIPS copy # | moCas9 coding sequence |
|---|---|---|---|---|
| E1 | positive | Null | 5 | positive |
| E2 | positive | Null | 2 | positive |
| E7 | positive | Null | 6 | positive |
| E8 | positive | Null | 1 | positive |
| E9 | positive | Null | 3 | positive |

The qPCR genotyping indicated that no wild-type EPSPS alleles were detected in the selected T0 plants of Events E1, E2, E7, E8 and E9 (Table 21). Both, the TIPS template sequences and the moCas9 coding sequence were found in the selected T0 plants, presumably, as a result of random insertions associated with the transformation process (Table 21: for the TIPS template sequences E1, E7, and E9 T0 plants). Both genetic elements (the randomly inserted TIPS templates and the moCas9 expression cassette) can be segregated out by standard breeding procedures in the T1 progeny generation, if not linked to the edited EPSPS-TIPS gene.

T0 plants grew well in the greenhouse and were fertile. A sample of T0 plants was sprayed with a 1× dose of glyphosate (Roundup Powermax) at V3 growth stage using the spray booth setting of 20 gallons per acre. The 1× dose of glyphosate was prepared as follow: 2.55 ml Powermax in 300 ml water (active ingredient: glyphosate, N-(phosphonomethyl) glycine, in the form of its potassium salt at 48.7%). Seven days after glyphosate application, no leaf tissue damage was observed in some of the T0 plants. These plantlets were hemizygous for the EPSPS-TIPS alleles, while other plantlets were severely damaged. One plant showing no damage to the leaf tissue 14 days after herbicide application contained 21 EPSPS-TIPS alleles among 44 genomic clones of the epsps locus (cloned and sequenced as described in the Example 16).

These data indicate that a guide RNA/Cas system can be used to create a TIPS-edited EPSPS allele in maize. Maize plants homozygous at the epsps-tips locus (two EPSPS alleles edited) with no additional insertion of the TIPS template (plant E2) were obtained. Furthermore, some EPSPS-TIPS edited maize plants did show some level of tolerance against a 1× dose of glyphosate.

Example 18

Guide RNA/Cas Endonuclease Mediated DNA Cleavage in Maize Chromosomal Loci Enables Transgene Insertion in an Elite Maize Line To test whether a maize optimized guide RNA/Cas system can cleave an maize chromosomal locus and enable homologous recombination (HR) mediated pathways to site-specifically insert a transgene in an elite maize line, 4 loci were selected on the maize chromosome 1 located between 51.54 cM to 54.56 cM (FIG. 18). Two target sites for a Cas endonuclease were identified at each of the four loci and are referred to as MHP14Cas-1, MHP14Cas-3, TS8Cas-1, TS8Cas2, TS9Cas-2, TS9Cas-3, TS10Cas-1 and TS10Cas-3 (FIG. 19, Table 22, SEQ ID NOs:229-236).

Table 22. Maize Genomic Target Sites Targeted by a Guide RNA/Cas Endonuclease.

TABLE 22

Maize genomic target sites targeted by a guide RNA/Cas endonuclease.

| Locus | Location | Target Site | Maize Genomic Target Site Sequence | PAM | SEQ ID NO: |
|---|---|---|---|---|---|
| MHP14 | Chr.1: | MHP14Cas-1 | gttaaatctgacgtgaatctgtt | TGG | 229 |
| | 51.54cM | MHP14Cas-3 | acaaacattgaagcgacatag | TGG | 230 |
| TS8 | Chr.1: | TS8Cas-1 | gtacgtaacgtgcagtac | TGG | 231 |
| | 52.56cM | TS8Cas-2 | gctcatcagtgatcagctgg | TGG | 232 |
| TS9 | Chr.1: | TS9Cas-2 | ggctgtttgcggcctcg | AGG | 233 |
| | 53.56cM | TS9Cas-3 | gcctcgaggttgcacgcacgt | CGG | 234 |
| TS10 | Chr.1: | TS10Cas-1 | gcctcgccttcgctagttaa | GGG | 235 |
| | 54.56cM | TS10Cas-3 | gctcgtgttggagataca | GGG | 236 |

The maize optimized Cas endonuclease cassette (SEQ ID NO: 5 was as prepared as describe in Example 1. Long guide RNA expression cassettes comprising a variable targeting domain targeting one of the 8 genomic target sites, driven by a maize U6 polymerase III promoter, and terminated by a maize U6 polymerase III terminator were designed as described in Example 1 and 3 and listed in Table 23. A donor DNA (HR repair DNA) containing a selectable marker (a phosphomannose-isomerase (PMI) expression cassette) flanked by two homologous regions was constructed using standard molecular biology techniques (FIG. 20).

TABLE 23

List of guide RNA (gRNA) and Donor DNA expression cassettes

| Locus | Target Site | gRNA (SEQ ID NO:) | Donor DNA (SEQ ID NO:) |
|---|---|---|---|
| MHP14 | MHP14Cas-1 | 245 | 253 |
| | MHP14Cas-3 | 246 | 254 |
| TS8 | TS8Cas-1 | 247 | 255 |
| | TS8Cas-2 | 248 | 256 |
| TS9 | TS9Cas-2 | 249 | 257 |
| | TS9Cas-3 | 250 | 258 |

TABLE 23-continued

List of guide RNA (gRNA) and Donor DNA expression cassettes

| Locus | Target Site | gRNA (SEQ ID NO:) | Donor DNA (SEQ ID NO:) |
|---|---|---|---|
| TS10 | TS10Cas-1 | 251 | 259 |
| | TS10Cas-3 | 252 | 260 |

A vector containing the maize optimized Cas9 endonuclease of SEQ ID NO: 5, a vector containing one of eight long guide RNA expression cassettes of SEQ ID NOs: 245-252, and a vector containing one of eight donor DNAs of SEQ ID NOs: 253-260 were co-delivered to maize elite line immature embryos by particle-mediated delivery as described in Example 10. About 1000 embryos were bombarded for each target site. Since the donor DNA contained a selectable marker, PMI, successful delivery of the donor DNA allowed for callus growth on mannose media. Putative HR-mediated transgenic insertions were selected by placing the callus on mannose containing media. After selection, stable shoots on maturation plates were sampled, total genomic DNA extracted, and using the primer pairs shown in Table 24 (corresponding to SEQ ID NOs: 261-270), PCR amplification was carried out at both possible transgene genomic DNA junctions to identify putative HR-mediated transgenic insertions.

TABLE 24

Primer sequences used for integration event screening at each target site.

| Locus | Target Site | Junction | Primer | SEQ ID NO: |
|---|---|---|---|---|
| UBIR | donor | 1 | CCATGTCTAACTGTTCATTTATATGATTCTCT | 261 |
| PSBF | donor | 2 | GCTCGTGTCCAAGCGTCACTTACGATTAGCT | 262 |
| MHP14 | MHP14Cas-1<br>MHP14Cas-3 | 14-1HR1f | CTCACATGAGGCTCTTCTTTGCTTGCT | 263 |
| | | 14-1HR2r | AGGATCCTATTCCCCAATTTGTAGAT | 264 |
| CHR1-8 | TS8Cas-1 | 8HR1f | CAGTCCGTGGATTGAAGCCAT | 265 |
| | TS8Cas-2 | 8HR2r | CTCTGTCTCCGAGACGTGCTTA | 266 |
| CHR1-9 | TS9Cas-2<br>TS9Cas-3 | 9HR1f | GGAGCAAATGTTTTAGGTATGAAATG | 267 |
| | | 9HR2r | CGGATTCTAAAGATCATACGTAAATGAA | 268 |

TABLE 24-continued

Primer sequences used for integration event screening at each target site.

| Locus | Target Site | Junction | Primer | SEQ ID NO: |
|---|---|---|---|---|
| CHR1-10 | TS10Cas-1 | 10HR1f | TGGCTTGTCTATGCGCATCTC | 269 |
| | TS10Cas-3 | 10HR2r | CCAGACCCAAACAGCAGGTT | 270 |

The same genomic primers were used for each of the two target sites at one locus. The resulting amplifications were sequenced to determine if these sites were mutated or contained a transgene insertion.

The "Event Recovery frequency" was calculated using the number of events recovered divided by the total number of embryos bombarded, and may indicate if an endonuclease has some toxic effect or not (Table 26). Hence, if 1000 embryos were bombarded and 240 were recovered, the Event Recovery frequency is 24%. Table 26 indicates that for all target sites analyzed the Event Recovery frequency ranged between 17 and 28%, indicating that the guide RNA/Cas system used herein results in low or no toxicity.

Cas endonuclease activity was measured in-planta by determining the "Target Site Mutation frequency "(Table 26) is defined as: (number of events with target site modification/total number recovered events)*100%. Hence, if 240 events were recovered and 180 events showed a mutation, the Target Site Mutation frequency is 75%. The target site mutation frequency was measured using target site allele copy number as described in Example 9 of U.S. application Ser. No. 13/886,317, filed on May 3, 2013. The primers and probes for obtaining the target site copy number using qPCR at each site were as listed in Table 25 (SEQ ID NO: 271-294).

TABLE 25

Primer and probe sequences used to assess DNA cleavage at 8 maize genomic target sites

| Target Site Designation | Probe primers | Primer sequence | SEQ ID NO: |
|---|---|---|---|
| MHP14Cas-1 | probe | CAGATTCACGTCAGATTT | 271 |
| | forward | CATAGTGGTGTATGAAAGGAAGCACTT | 272 |
| | reverse | CATTTTGGATTGTAATATGTGTACCTCATA | 273 |
| MHP14Cas-3 | probe | CACCACTATGTCGCTTC | 274 |
| | forward | CGGATGCACGAAAATTGTAGGA | 275 |
| | reverse | CTGACGTGAATCTGTTTGGAATTG | 276 |
| TS8Cas-1 | probe | TACGTAACGTGCAGTACT | 277 |
| | forward | ACGGACGGACCATACGTTATG | 278 |
| | reverse | TCAGCTGGTGGAGTATATTAGTTCGT | 279 |
| TS8Cas-2 | probe | CCAGCTGATCACTGATGA | 280 |
| | forward | ACGGACGGACCATACGTTATG | 281 |
| | reverse | CGCACATGTTATAAATTACAATGCAT | 282 |
| TS9Cas-2 | probe | CTGTTTGCGGCCTC | 283 |
| | forward | CTGCGGAGCTGCTGGCGAT | 284 |
| | reverse | CTTGCTGGCTTCGTCTGTCA | 285 |
| TS9Cas-3 | probe | CCGACGTGCGTGCAA | 286 |
| | forward | CTGCGGAGCTGCTGGCGAT | 287 |
| | reverse | CTTGCTGGCTTCGTCTGTCA | 288 |
| TS10Cas-1 | probe | TCGCCTTCGCTAGTTAA | 289 |
| | forward | AAGACCTGGCCGGTTTTCCA | 290 |
| | reverse | TAGCGGCCATTGCCATCA | 291 |
| TS10Cas-3 | probe | CTGTATCTCCAACACGAGC | 292 |
| | forward | AAGACCTGGCCGGTTTTCCA | 293 |
| | reverse | TAGCGGCCATTGCCATCA | 294 |

As shown in Table 26, all 8 guide RNA/Cas9 systems were very efficient in cleaving their target DNA and inducing mutations (by non-homologous end joining (NHEJ) as is evidenced by a mutation frequency ranging from 33-90%.

All events were also screened for the presence of an inserted transgene. The insertion event screening for each target site is illustrated in FIG. 21. The primers used for insertion PCR analysis at each site are listed in Table 24. FIG. 22 shows one example of an insertion event screening PCR result. The frequency of transgene insertion was determined by calculating the "Insertion frequency" which is defined as: (number of events with target site insertion/total number recovered events)*100%. Hence, if 240 events were recovered and 21 events showed a transgene insertion, the Insertion frequency was 9%.

TABLE 26

Activity of the guide RNA/Cas 9 system at 8 target sites as determined by target site mutation frequency and transgene insertion frequency at the desired target site in maize plant tissue

| Target Site | Event Recovery (%) | Target Site Mutation (%) | Insertion frequency (%) |
|---|---|---|---|
| TS10Cas-1 | 24% | 75% | 9% (7*) |
| TS10Cas-3 | 22% | 83% | 16% (20*) |
| TS8Cas-1 | 17% | 90% | 14% (9*) |
| TS8Cas-2 | 27% | 84% | 8% (10*) |
| MHP14Cas-1 | 17% | 33% | 2% (2*) |
| MHP14Cas-3 | 28% | 68% | 4% (1*) |
| TS9Cas-2 | 23% | 62% | 8%** |
| TS9Cas-3 | 28% | 84% | 8%** |

*Number of events with HR1 and HR2 both junctions positive

**only HR2 junction available

Sequence—confirmed-PCR amplifications indicated a site-specific transgene insertion for each of the 8 target sites as shown in Table 26 (column Insertion frequency). A transgene cassette was inserted at all 8 target sites with high efficiency (2-16%). The number of events containing amplifications across both transgene genomic DNA junctions, indicating near perfect site-specific transgene insertion, are show in brackets in Table 26.

Taken together, these data demonstrates that maize chromosomal loci cleaved with the maize optimized guide RNA/Cas system described herein can be used to insert transgenes at high frequencies in maize elite inbred line.

Example 19

Delivery of the Guide RNA/Cas9 Endonuclease System DNA to Soybean by Stable Transformation A soybean U6 small nuclear RNA promoter (GM-U6-9.1; SEQ ID NO: 295) was identified in a similar manner as the soybean promoter GM-U6-13.1 (SEQ ID NO:120) described in Example 12. The GM-U6-9.1 promoter was used to express guide RNA to direct Cas9 nuclease to designated genomic target site.

A soybean codon optimized Cas9 endonuclease expression cassette (such as for example EF1A2:CAS9, SEQ ID NO: 296) and a guide RNA expression cassette (such as for example U6-9.1:DD2OCR1; SEQ ID NO: 297) were linked (such as U6-9.1: DD2OCR1+EF1A2:CAS9; SEQ ID NO: 298, FIG. 23A) and integrated into a DNA plasm id that was co-delivered with another plasm id comprising a donor DNA (repair DNA) cassette (such as DD2OHR1-SAMS:HPT-DD2OHR2; SEQ ID NO: 299) to young soybean somatic embryos in the form of embryogenic suspension cultures by particle gun bombardment (FIGS. 23A and 23B). Other guide RNA/Cas9 DNA constructs targeting various soybean genomic sites and donor DNA constructs for site-specific transgene integration through homologous recombination were similarly configured and are listed in Table 27. The four gRNA/Cas9 constructs differed only in the 20 bp guide RNA targeting domain (variable targeting domain) targeting the soybean genomic target sites DD2OCR1 (SEQ ID NO: 125), DD2OCR2 (SEQ ID NO: 126), DD43CR1 (SEQ ID NO: 127), or DD43CR2 (SEQ ID NO: 128). The two donor DNA constructs differed only in the homologous regions such as DD2OHR1 and DD2OHR (FIG. 23B), or DD43HR1 and DD43HR2. These guide RNA/Cas9 DNA constructs and donor DNAs were co-delivered to an elite (93B86) or a non-elite (Jack) soybean genome by the stable transformation procedure described below.

TABLE 27

Guide RNA/Cas9 Mediated Soybean Stable Transformation

| Experiment | Guide RNA/Cas9 | Donor DNA | SEQ ID NOs: |
|---|---|---|---|
| U6-9.1DD20CR1 | U6-9.1:DD20CR1 + EF1A2:CAS9 | DD20HR1-SAMS:HPT-DD20HR2 | 298, 299 |
| U6-9.1DD20CR2 | U6-9.1:DD20CR2 + EF1A2:CAS9 | DD20HR1-SAMS:HPT-DD20HR2 | 300, 299 |
| U6-9.1DD43CR1 | U6-9.1:DD43CR1 + EF1A2:CAS9 | DD43HR1-SAMS:HPT-DD43HR2 | 301, 302 |
| U6-9.1DD43CR2 | U6-9.1:DD43CR2 + EF1A2:CAS9 | DD43HR1-SAMS:HPT-DD43HR2 | 303, 302 |

Soybean somatic embryogenic suspension cultures were induced from a DuPont Pioneer proprietary elite cultivar 93686 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 μl of a 60 mg/ml 1.0 mm gold particle suspension were added in order: 30 μl of equal amount (30 ng/μl) plasmid DNA comprising, for example, U6-9.1:DD2OCR1+EF1A2:CAS9 (SEQ ID NO:298) and plasmid DNA comprising, for example, (DD2OHR1-SAMS:HPT-DD2OHR2, SEQ ID NO: 299) (Experiment U6-9.1DD2OCR1 listed in Table 27) 20 μl of 0.1 M spermidine, and 25 μl of 5 M $CaCl_2$). The particle preparation was then agitated for 3 minutes, spun in a centrifuge for 10 seconds and the supernatant removed. The DNA-coated particles were then washed once in 400 μl 100% ethanol and resuspended in 45 μl of 100% ethanol. The DNA/particle suspension was sonicated three times for one second each. Then 5 μl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or T0 leaf stage for molecular analysis.

Similar transformation experiments (U6-9.1DD2OCR2, U6-9.1DD43CR1, U6-9.1DD43CR2) with the components listed in Table 27 and using the elite cultivar 93686 were performed as described above.

Two transformation experiments, U6-9.1DD2OCR1 and U6-9.1DD43CR1 listed in Table 27, were also performed in a non-elite soybean cultivar "Jack" to test the gRNA/Cas9 system performance in different soybean genotypes.

Example 20

Detection of Site-Specific NHEJ Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, CA) with target site-specific primers and FAM-labeled fluorescence probe to check copy number changes of the target site DD20 or DD43 (FIG. 24A-C). The qPCR analysis was done in duplex reactions with a heat shock protein (HSP) gene as the endogenous controls and a wild type 93686 genomic DNA sample that contains one copy of the target site with 2 alleles, as the single copy calibrator. The HSP endogenous control qPCR employed primer probe set HSP-F/HSP-T/HSP-R. The DD20-CR1 (SEQ ID NO:306) and DD20-CR2 (SEQ ID NO:307) specific qPCR employed primer probe set DD2O-F (SEQ ID NO:308)/DD2O-T(SEQ ID NO:309)/DD2O-R(SEQ ID NO:310). The DD43-CR1 (SEQ ID NO:311) specific qPCR employed primer probe set DD43-F(SEQ ID NO:313)/DD43-T(SEQ ID NO:315)/DD43-R (SEQ ID NO:316) while the DD43-CR2 (SEQ ID NO:312) specific qPCR employed primer probe set DD43-F2(SEQ ID NO:314)/DD43-T/DD43-R. The guide RNA/Cas9 DNA (SEQ ID NOs: 298, 300, 301, and 303) specific qPCR employed primer probe set Cas9-F (SEQ ID NO:317/Cas9-T(SEQ ID NO:318)/Cas-9-R(SEQ ID NO:319). The donor DNA (SEQ ID NOS: 299, and 302) specific qPCR employed primer probe set Sams-76° F. (SEQ ID NO:320)/FRT1I63-T (SEQ ID NO:321)/FRT1I-41 F (SEQ ID NO:322). The endogenous control probe HSP-T was labeled with VIC and the gene-specific probes DD2O-T, DD43-T, Cas9-T, and FRT1I63-T were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93686 genomic DNA with two alleles of the target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). The wide range of the qPCR values suggested that most of the events contained mixed mutant and wild type sequences of the target site. High percentage of NHEJ-Hemi (ranging from 10.1 to 33.5%, Table 28) and NHEJ-Null (ranging from 32.3 to 46.4%, Table 21) were detected in all four experiments with combined NHEJ average frequencies of more than 60% (Table 28).

TABLE 28

Target Site Mutations and Site Specific Gene Integration Induced by the Guide RNA/Cas9 system in elite soybean germplasm. Numbers indicate no. of events (numbers in parentheses are %).

| Project | Total event | Wt-Homo (%) | NHEJ-Hemi (%) | NHEJ-Null (%) | Insertion Frequency (%) |
|---|---|---|---|---|---|
| U6-9.1DD20CR1 | 239 | 85 (35.6%) | 77 (32.2%) | 77 (32.2%) | 11 (4.6%) |
| U6-9.1DD20CR2 | 79 | 43 (54.4%) | 8 (10.1%) | 28 (35.4%) | NA |
| U6-9.1DD43CR1 | 263 | 53 (20.2%) | 88 (33.5%) | 122 (46.4%) | 10 (3.8%) |

NA = not analyzed.

TABLE 29

Target Site Mutations and Site Specific Gene Inegration Induced by the Guide RNA/Cas9 system in non-elite soybean germplasm. Numbers indicate no. of events (numbers in parentheses are % of the total analyzed events).

| Project | Total event | Wt-Homo (%) | NHEJ-Hemi (%) | NHEJ-Null (%) | Insertion frequency (%) |
|---|---|---|---|---|---|
| U6-9.1DD20CR1-Jack | 149 | 99 (66.4%) | 34 (22.8%) | 16 (10.7%) | 0 (0%) |
| U6-9.1DD43CR1-Jack | 141 | 84 (59.6%) | 27 (19.1%) | 30 (21.3%) | 1 (0.7%) |

Both NHEJ-Hemi and NHEJ-Null were detected in the two experiments U6-9.1DD2OCR1-Jack and U6-9.1DD43CR1-Jack repeated in "Jack" genotype though at lower frequencies (Table 29). The differences between NHEJ frequencies were likely caused by variations between transformation experiments.

The target region of NHEJ-Null events were amplified by regular PCR from the same genomic DNA samples using DD20-LB (SEQ ID NO: 323) and DD20-RB (SEQ ID NO: 326) primers specific respectively to DD2O-HR1 and DD2O-HR2 for DD20 target site specific HR1-HR2 PCR amplicon (FIG. 25A-C; SEQ ID NO: 329), or DD43-LB (SEQ ID NO: 327) and DD43-RB (SEQ ID NO: 328) primers specific respectively to DD43-HR1 and DD43-HR2 for DD43 target site specific HR1-HR2 PCR amplicon (SEQ ID NO: 332). The PCR bands were cloned into pCR2.1 vector using a TOPO-TA cloning kit (Invitrogen) and multiple clones were sequenced to check for target site sequence changes as the results of NHEJ. Various small deletions at the Cas9 cleavage site, 3 bp upstream of the PAM, were revealed at all four tested target sites (FIG. 26A-C). Small insertions were also detected in some sequences. Different mutated sequences were identified from some of the same events indicating the chimeric nature of these events. Some of the same mutated sequences were also identified from different events suggesting that the same mutations could have happened independently or some of the events could be clonal events. These sequence analysis confirmed the occurrence of NHEJ mediated by the guide RNA/Cas9 system at the specific Cas9 target sites.

Example 21

Identification of Site-Specific Gene Integration Via Homologous Recombination Mediated by the Guide RNA/Cas9 System in Stably Transformed Soybean Site-specific gene integration via guide RNA/Cas9 system mediated DNA homologous recombination was determined by border-specific PCR analysis. The 5' end borders of DD2OCR1 and DD2OCR2 events were amplified as a 1204 bp DD20 HR1-SAMS PCR amplicon (SEQ ID NO: 330) by PCR with primers DD20-LB (SEQ ID NO: 323) and Sams-A1 (SEQ ID NO: 324) while the 3' borders of the same events were amplified as a 1459 bp DD20 NOS-HR2 PCR amplicon (SEQ ID NO: 331) with primers QC498A-S1 and DD20-RB (FIG. 25A-C). Any events with both the 5' border and 3' border-specific bands amplified are considered as site-specific integration events through homologous recombination containing the transgene from the donor DNA fragment DD2OHR1-SAMS:HPT-DD20HR2 or its circular form (FIG. 23). The 5' end borders of DD43CR1 and DD43CR2 events were amplified as a 1202 bp DD43 HR1-SAMS PCR amplicon (SEQ ID NO: 333) by PCR with primers DD43-LB and Sams-A1 while the 3' borders of the same events were amplified as a 1454 bp DD43 NOS-HR2 PCR amplicon (SEQ ID NO: 334) with primers QC498A-S1 (SEQ ID NO: 325) and DD43-RB (SEQ ID NO: 328). Any events with both the 5' border and 3' border-specific bands amplified are considered as site-specific integration events through homologous recombination containing the transgene from repair DNA fragment DD43HR1-SAMS:HPT-DD43HR2 or its circular form. Some of the border-specific PCR fragments were sequenced and were all confirmed to be recombined sequences as expected from homologous recombination. On average, gene integration through the guide RNA/Cas9 mediated homologous recombination occurred at approximately 4% of the total transgenic events (Insertion frequency, Table 28 and Table 29). One homologous recombination event was identified from experiment U6-9.1DD43CR1-Jack repeated in "Jack" genotype (Table 29).

Example 22

The crRNA/tracrRNA/Cas Endonuclease System Cleaves Chromosomal DNA in Maize and Introduces Mutations by Imperfect Non-Homologous End-Joining To test whether the maize optimized crRNA/tracrRNA/Cas endonuclease system described in Example 1 could recognize, cleave, and mutate maize chromosomal DNA through imprecise non-homologous end-joining (NHEJ) repair pathways, three different genomic target sequences were targeted for cleavage (see Table 30) and examined by deep sequencing for the presence of NHEJ mutations.

TABLE 30

Maize genomic target sequences targeted by a crRNA/tracrRNA/Cas endonuclease system.

| Locus | Location | Cas RNA System Used | Target Site Designation | Maize Genomic Site Target Sequence | PAM Sequence | SEQ ID NO: |
|---|---|---|---|---|---|---|
| LIG | Chr.2. 28.45cM | crRNA/ tracrRNA | LIGCas-1 | GTACCGTACGTGCCCCGGCGG | AGG | 16 |
| | | crRNA/ tracrRNA | LIGCas-2 | GGAATTGTACCGTACGTGCCC | CGG | 17 |
| | | crRNA/ tracrRNA | LIGCas-3 | GCGTACGCGTACGTGTG | AGG | 18 |

LIG = Liguleless 1 Gene Promoter

The maize optimized Cas9 endonuclease expression cassette, crRNA expression cassettes containing the specific maize variable targeting domains (SEQ ID NOs: 445-447) complementary to the antisense strand of the maize genomic target sequences listed in Table 30 and tracrRNA expression cassette (SEQ ID NO: 448) were co-delivered to 60-90 Hi-II immature maize embryos by particle-mediated delivery (see Example 5) in the presence of BBM and WUS2 genes (see Example 6). Hi-II maize embryos transformed with the Cas9 and long guide RNA expression cassettes targeting the LIGCas-3 genomic target site (SEQ ID NO: 18) for cleavage served as a positive control and embryos transformed with only the Cas9 expression cassette served as a negative control. After 7 days, the 20-30 most uniformly transformed embryos from each treatment were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 31 and the primers used in the secondary PCR reaction were AATGATACGGCGACCACCGAGATCTACACTCTTTCCCTACACG (forward, SEQ ID NO: 53) and CAAGCAGAAGACGGCATA (reverse, SEQ ID NO: 54).

TABLE 31

PCR primer sequences

| Target Site | Cas RNA System Used | Primer Orientation | Primary PCR Primer Sequence | SEQ ID NO: |
|---|---|---|---|---|
| LIGCas-1 | crRNA/ tracrRNA | Forward | CTACACTCTTTCCCTACACGACGCTCTTC CGATCTTCCTCTGTAACGATTTACGCACC TGCTG | 36 |
| LIGCas-1 | crRNA/ tracrRNA | Reverse | CAAGCAGAAGACGGCATACGAGCTCTTC CGATCTGCAAATGAGTAGCAGCGCACGTA T | 35 |
| LIGCas-2 | crRNA/ tracrRNA | Forward | CTACACTCTTTCCCTACACGACGCTCTTC CGATCTGAAGCTGTAACGATTTACGCACC TGCTG | 449 |
| LIGCas-2 | crRNA/ tracrRNA | Reverse | CAAGCAGAAGACGGCATACGAGCTCTTC CGATCTGCAAATGAGTAGCAGCGCACGTA T | 35 |
| LIGCas-3 | crRNA/ tracrRNA | Forward | CTACACTCTTTCCCTACACGACGCTCTTC CGATCTAAGGCGCAAATGAGTAGCAGCG CAC | 37 |
| LIGCas-3 | crRNA/ tracrRNA | Reverse | CAAGCAGAAGACGGCATACGAGCTCTTC CGATCTCACCTGCTGGGAATTGTACCGTA | 38 |
| LIGCas-3 | Long guide RNA | Forward | CTACACTCTTTCCCTACACGACGCTCTTC CGATCTTTCCCGCAAATGAGTAGCAGCGC AC | 450 |
| LIGCas-3 | Long guide RNA | Reverse | CAAGCAGAAGACGGCATACGAGCTCTTC CGATCTCACCTGCTGGGAATTGTACCGTA | 38 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the % mutant reads based on the total number of reads of an appropriate length containing a perfect match to the barcode and forward primer.

The frequency of NHEJ mutations recovered by deep sequencing for the crRNA/tracrRNA/Cas endonuclease system targeting the three LIGCas targets (SEQ ID NOS: 16, 17, 18) compared to the long guide RNA/Cas endonuclease system targeting the same locus is shown in Table 32.

TABLE 32

Percent (%) mutant reads at maize Liguleless 1 target locus produced by crRNA/tracrRNA/Cas endonuclease system compared to the long guide RNA/Cas endonuclease system

| System | Total Number of Reads | Number of Mutant Reads | % Mutant Reads |
|---|---|---|---|
| Cas9 Only Control | 1,744,427 | 0 | 0.00% |
| LIGCas-3 long guide RNA | 1,596,955 | 35,300 | 2.21% |
| LIGCas-1 crRNA/tracrRNA | 1,803,163 | 4,331 | 0.24% |
| LIGCas-2 crRNA/tracrRNA | 1,648,743 | 3,290 | 0.20% |
| LIGCas-3 crRNA/tracrRNA | 1,681,130 | 2,409 | 0.14% |

The ten most prevalent types of NHEJ mutations recovered based on the crRNA/tracrRNA/Cas endonuclease system are shown in FIG. 27A (for LIGCas-1 target site, corresponding to SEQ ID NOs:415-424), FIG. 27B (for LIGCas-2 target site corresponding to SEQ ID NOs: 425-434) and FIG. 27C (for LIGCas-3 target site corresponding to SEQ ID NOs:435-444). Approximately, 9-16 fold lower frequencies of NHEJ mutations were observed when using a crRNA/tracrRNA/Cas endonuclease system to introduce a double strand break at a maize genomic target site, relative to the long guide RNA/Cas endonuclease system control.

Taken together, our data indicate that the maize optimized crRNA/tracrRNA/Cas endonuclease system described herein cleaves maize chromosomal DNA and generates imperfect NHEJ mutations.

Example 23

Modifying the ARGOS8 Gene to Improve Drought Tolerance and Nitrogen Use Efficiency in Maize Plants ARGOS is a negative regulator for ethylene responses in plants (WO 2013/066805 A1, published 10 May 2013). ARGOS proteins target the ethylene signal transduction pathway. When over-expressed in maize plants, ARGOS reduces plant sensitivity to ethylene and promotes organ growth, leading to increased drought tolerance (DRT) and improved nitrogen use efficiency (NUE) ((WO 2013/066805 A1, published 10 May 2013). To achieve optimal ethylene sensitivity, promoters have been tested for driving Zm-ARGOS8 over-expression in transgenic maize plants. Field trials showed that a maize promoter, Zm-GOS2 PRO:GOS2 INTRON (SEQ ID NO:460, U.S. Pat. No. 6,504,083 patent issued on Jan. 7, 2003; Zm-GOS2 is a maize homologous gene of rice GOS2. Rice GOS2 stands for Gene from *Oryza Sativa* 2), provided a favorable expression level and tissue coverage for Zm-ARGOS8 and the transgenic plants have a higher grain yield than non-transgenic controls under drought stress and low nitrogen conditions (WO 2013/066805 A1, published 10 May 2013). However, these transgenic plants contain two ARGOS8 genes, the endogenous gene and the transgene. ARGOS8 protein levels, therefore, are determined by these two genes. Because the endogenous ARGOS8 gene varies in sequence and the expression level among different inbred lines, the ARGOS8 protein level will be different when the transgene is integrated into different inbreds. Here we present a mutagenization (gene editing) method to modify the promoter region of the endogenous ARGOS8 gene to attain desired expression patterns and eliminate the need for a transgene.

The promoter Zm-GOS2 PRO:GOS2 INTRON (SEQ ID NO:460; U.S. Pat. No. 6,504,083 patent issued on Jan. 7, 2003) was inserted into the 5'-UTR of Zm-ARGOS8 (SEQ ID NO:462) by using a guideRNA/Cas9 system. The Zm-GOS2 PRO:GOS2 INTRON fragment also included a primer binding site (SEQ ID NO:459) at its 5' end to facilitate event screening with PCR. We also substituted the native promoter of Zm-ARGOS8 (SEQ ID NO:461) with Zm-GOS2 PRO::GOS2 INTRON (SEQ ID NO:460). Resulted maize lines carry a new ARGOS8 allele whose expression levels and tissue specificity will differ from the native form. We expect that these lines will recapitulate the phenotype of increased drought tolerance and improved NUE as observed in the Zm-GOS2 PRO:Zm-ARGOS8 transgenic plants (WO 2013/066805 A1, published 10 May 2013). These maize lines are different from those conventional transgenic events: (1) there is only one ARGOS8 gene in the genome; (2) this modified version of Zm-ARGOS8 resides at its native locus; (3) the ARGOS8 protein level and the tissue specificity of gene expression are entirely controlled by the edited allele. The DNA reagents used during the mutagenization, such as guideRNA, Cas9endonuclease, transformation selection marker and other DNA fragments are not required for function of the newly generated ARGOS8 allele and can be eliminated from the genome by segregation through standard breeding methods. Because the promoter Zm-GOS2 PRO:GOS2 INTRON was copied from maize GOS2 gene (SEQ ID NO:464) and inserted into the ARGOS8 locus through homologous recombination, this ARGOS8 allele is indistinguishable from natural mutant alleles.

A. Insertion of *Zea mays*-GOS2 PRO:GOS2 INTRON into Maize-ARGOS 8 Promoter

To insert Zm-GOS2 PRO:GOS2 INTRON into the 5'-UTR of maize ARGOS8 gene, a guideRNA construct, gRNA1, was made using maize U6 promoter and terminator as described herein. The 5'-end of the guide RNA contained a 19-bp variable targeting domain targeting the genomic target sequence 1 (CTS1; SEQ ID NO; 451) in the 5'-UTR of Zm-ARGOS8 (FIG. 28). A polynucleotide modification template containing the Zm-GOS2 PRO:GOS2 INTRON that was flanked by two genomic DNA fragments (HR1 and HR2, 370 and 430-bp in length, respectively) derived from the upstream and downstream region of the CTS1 (FIG. 28). The gRNA1 construct, the polynucleotide modification template, a Cas9 cassette and transformation selection marker phosphomannose isomerase (PMI) were introduced into maize immature embryo cells by using a particle bombardment method. PMI-resistant calli were screened with PCR for Zm-GOS2 PRO:GOS2 INTRON insertion (FIGS. 29A and 29B). Multiple callus events were identified and plants were regenerated. The insertion events were confirmed by amplifying the Zm-ARGOS8 region in T0 plants with PCR (FIG. 29C) and sequencing the PCR products.

B. Replacement of Zm-ARGOS 8 Promoter with Zm-GOS2 PRO:GOS2 INTRON Promoter (Promoter Swap).

Figure 31A:
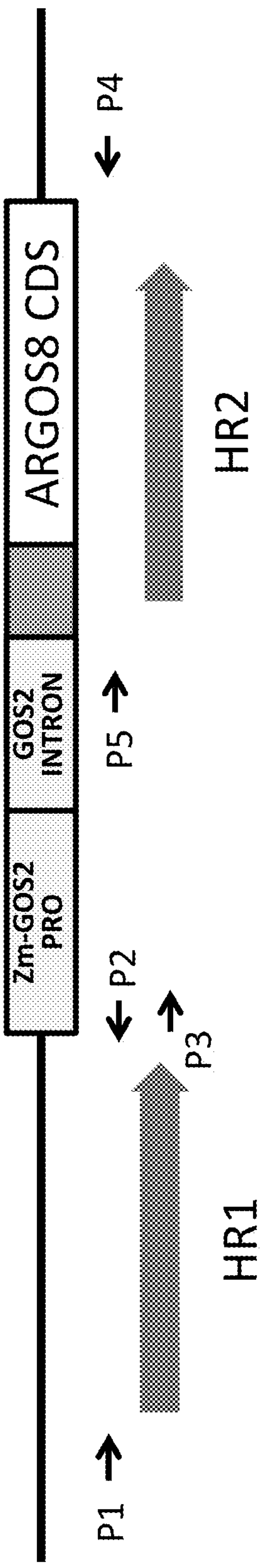
Figure 31B:
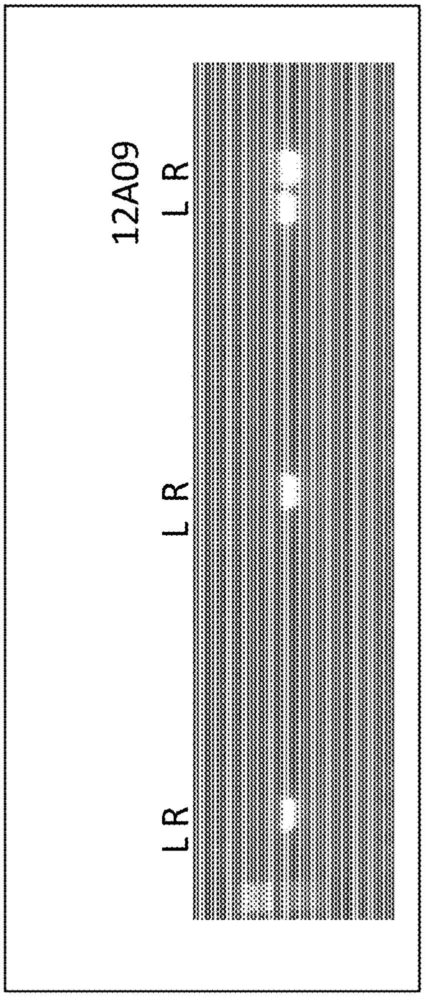
Figure 31C:
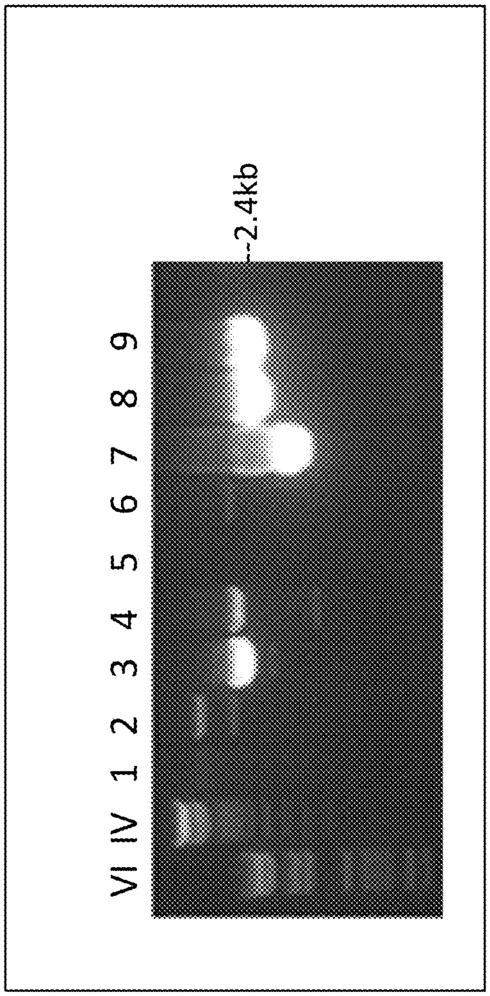
Figure 31D:
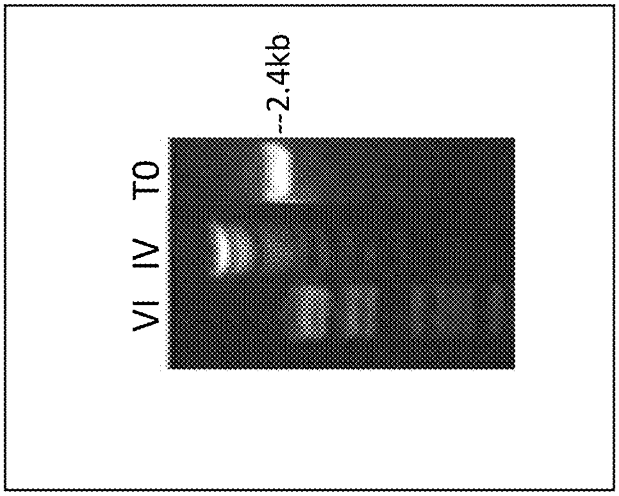

To substitute (replace) the native promoter of Zm-ARGOS8 with Zm-GOS2 PRO:GOS2 INTRON, a guide RNA construct, gRNA3, was made for targeting the genomic target site CTS3 (SEQ ID NO:453), located 710-bp upstream of the Zm-ARGOS8 start codon (FIG. 30). Another guide RNA, gRNA2, was designed to target the genomic target site CTS2 (SEQ ID NO:452) located in the 5'-UTR of Zm-ARGOSO8 (FIG. 30). The polynucleotide modification template contained a 400-bp genomic DNA fragment derived from the upstream region of CTS3, Zm-GOS2 PRO:GOS2 INTRON and a 360-bp genomic DNA fragment derived from the downstream region of CTS2 (FIG. 30). The gRNA3 and gRNA2, the Cas9 cassette, the polynucleotide modification template and the PMI selection marker were used to transform immature embryo cells. Multiple promoter swap (promoter replacement) events were identified by PCR screening of the PMI-resistance calli (FIGS. 31A, 31B & 31C) and plants were regenerated. The swap events were confirmed by PCR analysis of the Zm-ARGOS8 region in T0 plants (FIG. 31D).

C. Deletion of Zm-ARGOS 8 Promoter

To delete the promoter of Zm-ARGOS8, we screened the PMI-resistance calli obtained from the above gRNA3/gRNA2 experiment to look for events that produce a 1.1-kb PCR product (FIG. 32A). Multiple deletion events were identified (FIG. 32B) and plants were regenerated. The deletion events were confirmed by amplifying the Zm-ARGOS8 region in T0 plants with PCR and sequencing of the PCR products.

Example 24

Gene Editing of the Soybean EPSPS1 Gene Using the Guide RNA/Cas Endonuclease System A. guideRNA/Cas9 Endonuclease Target Site Design on the Soybean EPSPS Genes.

Two guideRNA/Cas9 endonuclease target sites (soy EPSPS-CR1 and soy EPSPS-CR2) were identified in the-Exon2 of the soybean EPSPS1 gene Glyma01g33660 (Table 33).

TABLE 33

Guide RNA/Cas9 endonuclease target sites on soybean EPSPS1 gene

| Name of gRNA-Cas9 endonuclease target site | Cas endonuclease target sequence (SEQ ID NO:) | Physical location |
|---|---|---|
| soy EPSPS-CR1 | 467 | Gm01:45865337 . . . 45865315 |
| soy EPSPS-CR2 | 468 | Gm01: 45865311 . . . 45865333 |

B. Guide-RNA expression cassettes, Cas9 endonuclease expression cassettes and polynucleotide modification templates for introduction of specific amino acid changes in the soybean EPSPS1 gene The soybean U6 small nuclear RNA promoter, GM-U6-13.1 (SEQ ID. NO: 469), was used to express guide RNAs to direct Cas9 nuclease to designated genomic target sites (Table 34). A soybean codon optimized Cas9 endonuclease (SEQ ID NO: 489) expression cassette and a guide RNA expression cassette were linked in a first plasm id that was co-delivered with a polynucleotide modification template. The polynucleotide modification template contained specific nucleotide changes that encoded for amino acid changes in the EPSPS1 polypeptide (Glyma01g33660), such as the T183I and P187S (TIPS) in the Exon2. Other amino acid changes in the EPSPS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 34

Guide RNA/Cas9 expression cassettes and polynucleotide modification templates used in soybean stable transformation for the specific amino acid modifications of the EPSPS1 gene.

| Experiment | Guide RNA/Cas9 (plasmid name) | SEQ ID NO: | polynucleotide modification template | SEQ ID NO: |
|---|---|---|---|---|
| soy EPSPS-CR1 | U6-13.1: EPSPS CR1 + EF1A2:CAS9 (QC878) | 470 | RTW1013A | 472 |
| soy EPSPS-CR2 | U6-13.1: EPSPS CR2 + EF1A2:CAS9 (QC879) | 471 | RTW1012A | 473 |

C. Detection of site-specific non-homologous-end-joining (NHEJ) mediated by the guide RNA/Cas9 system in stably transformed soybean Genomic DNA was extracted from somatic embryo samples and analyzed by quantitative PCR using a 7500 real time PCR system (Applied Biosystems, Foster City, CA) with target site-specific primers and FAM-labeled fluorescence probe to check copy number changes of the double strand break target sites. The qPCR analysis was done in duplex reactions with a syringolide induced protein (SIP) as the endogenous controls and a wild type 93686 genomic DNA sample that contains one copy of the target site with 2 alleles, as the single copy calibrator. The presence or absence of the guide RNA—Cas9 expression cassette in the transgenic events was also analyzed with the qPCR primer/probes for guideRNA/Cas9 (SEQ IDs: 477-479) and for PinII (SEQ ID: 480-482).he qPCR primers/probes are listed in Table 35.

TABLE 35

Primers/Probes used in qPCR analyses of transqenic soybean events.

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGAA ATCA | 474 |
| | Soy1-R2 | CCTGCAGCAACCACAGCTGCTGTC | 475 |
| | Soy1-T1 (FAM-MGB) | CTGCAATGCGTCCTT | 476 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pinII | pINII-99F | TGATGCCCACATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

The endogenous control probe SIP-T was labeled with VIC and the gene-specific probes for all the target sites were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93686 genomic DNA with two alleles of the double strand break target site was used as the single copy calibrator, events without any change of the target site would be detected as one copy herein termed Wt-Homo (qPCR value >=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). As shown in Table 36, both guideRNA/Cas endonuclease systems targeting the soy EPSPS-CR1 and EPSPS-CR2 sites can introduce efficient Double Strand Break (DSB) efficiency at their designed target sites. Both NHEJ-Hemi and NHEJ-Null were detected in the 93686 genotype. NHEJ (Non-Homologous-End-Joining) mutations mediated by the guide RNA/Cas9 system at the specific Cas9 target sites were confirmed by PCR/topo cloning/sequencing.

TABLE 36

Target Site Double Strand Break Rate Mutations Induced by the Guide RNA/Cas9 system on soybean EPSPS1 gene. Numbers indicate no. of events (numbers in parentheses are %).

| Project | Total event | Wt-Homo (%) | NHEJ-Hemi (%) | NHEJ-Null (%) |
|---|---|---|---|---|
| U6-13.1 EPSPS-CR1 | 168 | 63 (38%) | 66 (39%) | 39 (23%) |
| U6-13.1 EPSPS-CR2 | 111 | 50 (45%) | 21 (19%) | 40 (36%) |

D. Detection of the TIPS mutation in the soybean EPSPS gene

In order to edit specific amino acids at the native EPSPS gene (such as those resulting in a TIPS modification), a polynucleotide modification template, such as RTW1013A or RTW1012A (Table 34), was co-delivered with the guideRNA/Cas9 expression cassettes into soybean cells.

The modification of the native EPSPS1 gene via guide RNA/Cas9 system mediated DNA homologous recombination was determined by specific PCR analysis. A specific PCR assay with primer pair WOL569 (SEQ ID NO: 486) and WOL876 (SEQ ID NO: 487) was used to detect perfect TIPS modification at the native EPSPS1 gene. A second primer pair WOL569 (SEQ ID NO: 486) and WOL570 (SEQ ID NO: 488) was used to amplify both TIPS modified EPSPS1 allele and WT (wild type)/NHEJ mutated allele. Topo cloning/sequencing was used to verify the sequences.

Example 25

Intron Replacement of Soybean Genes Using the guideRNA/Cas Endonuclease System

A. guideRNA/Cas9 Endonuclease Target Site Design.

Four guideRNA/Cas9 endonuclease target sites were identified in the soybean EPSPS1 gene Glyma01g33660 (Table 37). Two of the target sites (soy EPSPS-CR1 and soy EPSPS-CR2) were identified to target the Exon2 of the soybean EPSPS gene as described in Example 24. Another two target sites (soy EPSPS-CR4 and soy EPSPS-CR5) were designed near the 5' end of the intron1 of the soybean EPSPS gene.

TABLE 37

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 467 | Gm01:45865337 . . . 45865315 |
| soy EPSPS-CR2 | 468 | Gm01: 45865311 . . . 45865333 |
| soy EPSPS-CR4 | 490 | Gm01: 45866302 . . . 45866280 |
| soy EPSPS-CR5 | 491 | Gm01:45866295 . . . 45866274 |

B. Guide RNA/Cas9 endonuclease expression cassettes and polynucleotide modification templates used in soybean stable transformation for the replacement of the Intron1 of the soybean EPSPS1 gene with the soybean ubiquitin (UBQ) intron1

The soybean U6 small nuclear RNA promoter GM-U6-13.1 (SEQ ID. NO: 469) was used to express two guide RNAs (soy-EPSPS-CR1 and soy-EPSPS-CR4, or soy-EPSPS-CR1 and soy-EPSPS-CR5) to direct Cas9 endonuclease to designated genomic target sites (Table 38). One of the target sites (soy-EPSPS-CR1) was located in the exon2, as described in Example 24, and a second target site (soy-EPSPS-CR4 or soy-EPSPS-CR5) was located near the 5' end of intron1 of the native EPSPS1 gene. A soybean codon optimized Cas9 endonuclease expression cassette and a guide RNA expression cassette were linked in the expression plasmids QC878/RTW1199 (SEQ ID NO:470/492) or QC878/RTW1200 (SEQ ID NO:470/493) that was co-delivered with a polynucleotide modification template. The polynucleotide modification template, RTW1190A (SEQ ID NO:494), contained 532 bp intron1 of the soybean UBQ gene and the TIPS modified Exon2. Soybean EPSPS1 intron 1 replacement with the soybean UBQ intron1 can be achieved with the guide RNA/Cas system by homologous recombination between the genomic DNA and the polynucleotide modification template, resulting in enhancement of the native or modified soy EPSPS1 gene expression.

TABLE 38

Guide RNA/Cas9 endonuclease expression cassettes and polynucleotide modification templates used in soybean stable transformation for the replacement of the Intron1 of the soybean EPSPS1 gene with the soybean ubiquitin (UBQ) intron1

| Experiment | Guide RNA/Cas9 | SEQ ID NO: | polynucleotide modification template | SEQ ID NO: |
|---|---|---|---|---|
| soy EPSPS-CR1 and soy EPSPS-CR4 | U6-13.1: EPSPS CR1 + CR4 + EF1A2:CAS9 (QC878/RTW1199) | 470/492 | RTW1190A | 494 |
| soy EPSPS-CR1 and soy EPSPS-CR5 | U6-13.1: EPSPS CR1 + CR5 + EF1A2:CAS9 (QC878/RTW1200) | 470/493 | RTW1190A | 494 |

C. Detection of site-specific NHEJ mediated by the guide RNA/Cas9 system in stably transformed soybean Site-specific NHEJ was detected as described in Example 24 C, using the qPCR primers/probes listed in Table 39.

TABLE 39

Primers/Probes used in qPCR analyses of transdenic soybean events.

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGA AATCA | 474 |
| | Soy1-R2 | CCTGCAGCAACCACAGCTGCTGTC | 475 |
| | Soy1-T1 (FAM-MGB) | CTGCAATGCGTCCTT | 476 |
| EPSPS-CR4 | Soy1-F3 | GTTTGTTTGTTGTTGGGTGTGGG | 495 |
| | Soy1-R3 | GACATGATGCTTCATTTTCACAGAA | 496 |
| | Soy-T2 (FAM-MGB) | TGTGTAGAGTGGATTTTG | 497 |
| EPSPS-CR5 | Soy1-F2 | TGTTGTTGGGTGTGGGAATAGG | 498 |
| | Soy1-R3 | GACATGATGCTTCATTTTCACAGAA | 496 |
| | Soy1-T2 (FAM-MGB) | TGTGTAGAGTGGATTTTG | 497 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pinII | pINII-99F | TGATGCCCACATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

D. Detection of the replacement of the soybean EPSPS1 intron1 with the soybean UBQ intron1 using the guide RNA/Cas9 endonuclease system.

In order to replace the soybean EPSPS1 intron1 with the soybean UBQ intron1 at the native EPSPS1 gene, two guideRNA expression vectors were used as shown in Table 38. The QC878 vector (SEQ ID NO: 470) was targeting the exon2 and the RTW1199 (SEQ ID NO:492) or RTW1200 (SEQ ID NO:493) was targeting the 5' end of the intron1. The double cleavage of soybean EPSPS gene with the two guide RNA/Cas systems resulted in the removal of the native EPSPS1 intron1/partial Exon2 fragment. At the same time, a polynucleotide modification template RTW1190A (SEQ ID NO:494) was co-delivered into soybean cells and homologous recombination between the polynucleotide modification template and the genomic DNA resulted in the replacement of EPSPS1 intron1 with the soybean UBQ intron1 and the desired amino acid modifications in exon2 as evidenced by PCR analysis. PCR assays with primer WOL1001/WOL1002 pair (SEQ ID NO: 499 and 500) and WOL1003/WOL1004 pair (SEQ ID NO: 501 and 502) were used to detect the intron replacement events.

Example 26

Promoter Replacement (Promoter Swap) of Soybean Genes Using the guideRNA/Cas Endonuclease System A. guideRNA/Cas9 Endonuclease Target Site Design.

Four guideRNA/Cas9 endonuclease target sites were identified in the soybean EPSPS1 gene Glyma01g33660 (Table 40). Two of the target sites (soy EPSPS-CR1 and soy EPSPS-CR2) were identified to target the Exon2 of the soybean EPSPS gene as described in Example 24. The soy EPSPS-CR6 and soy EPSPS-CR7 were identified near the 5' end of the −798 bp of the native EPSPS promoter.

TABLE 40

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 467 | Gm01:45865337 . . . 45865315 |
| soy EPSPS-CR2 | 468 | Gm01: 45865311 . . . 45865333 |
| soy EPSPS-CR6 | 503 | Gm01:45867471 . . . 45867493 |
| soy EPSPS-CR7 | 504 | Gm01:45867459 . . . 45867481 |

B. Guide RNA/Cas9 endonuclease expression cassettes and polynucleotide modification templates used in soybean stable transformation for the replacement of the −798 bp soybean EPSPS1 promoter with the soybean UBQ promoter.

The soybean U6 small nuclear RNA promoter GM-U6-13.1 (SEQ ID. NO: 469) was used to express two guide RNAs (soyEPSPS-CR1 and soyEPSPS-CR6, or soyEPSPS-CR1 and soyEPSPS-CR7) to direct Cas9 nuclease to designated genomic target sites (Table 41). One of the target sites (soy-EPSPS-CR1) was located in the exon2 as described in Example 24 and a second target site (soy-EPSPS-CR6 or soy-EPSPS-CR7) was located near 5' end of the −798 bp of the native EPSPS1 promoter. A soybean codon optimized Cas9 endonuclease expression cassette and a guide RNA expression cassette were linked in the expression plasm ids QC878/RTW1201 (SEQ ID NO:470/505) or QC878/RTW1202 (SEQ ID NO:470/506) that was co-delivered with a polynucleotide modification template, RTW1192A (SEQ ID NO:507). The polynucleotide modification template contained 1369 bp of the soybean UBQ gene promoter, 47 bp SUTR and 532 bp UBQ intron1. Specific soybean EPSPS1 promoter replacement with the soybean UBQ promoter can be achieved with the guide RNA/Cas system by homologous recombination between the genomic DNA and the polynucleotide modification template, resulting enhancement of the native or modified soy EPSPS1 gene expression

TABLE 41

Guide RNA/Cas9 endonuclease expression cassettes and polynucleotide modification templates used in soybean stable transformation for the replacement of the −798 bp soybean EPSPS1 promoter with the soybean UBQ promoter

| Experiment | Guide RNA/Cas9 | SEQ ID NO: | polynucleotide modification template | SEQ ID NO: |
|---|---|---|---|---|
| soy EPSPS-CR1 and soy EPSPS-CR6 | U6-13.1: EPSPS CR1 + CR6 + EF1A2:CAS9 (QC878/RTW1201) | 470, 505 | RTW1192A | 507 |
| soy EPSPS-CR1 and soy EPSPS-CR7 | U6-13.1: EPSPS CR1 + CR7 + EF1A2:CAS9 (QC878/RTW1202) | 470, 506 | RTW1192A | 507 |

C. Detection of site-specific NHEJ mediated by the guide RNA/Cas9 system in stably transformed soybean Site-specific NHEJ was detected as described in Example 24 C, using the qPCR primers/probes listed in Table 42.

TABLE 42

Primers/Probes used in qPCR analyses of transdenic soybean events

| Target Site | Primer/Probe Name | Sequences | SEQ ID NOs: |
|---|---|---|---|
| EPSPS-CR1 & EPSPS-CR12 | Soy1-F1 | CCACTAGTAAGGAATCTAAAGATGAA ATCA | 474 |
| | Soy1-R2 | CCTGCAGCAACCACAGCTGCTGTC | 475 |
| | Soy1-T1 (FAM-MGB) | CTGCAATGCGTCCTT | 476 |
| EPSPS-CR6 & EPSPS-CR7 | Soy1-F4 | TCAATAATACTACTCTCTTAGACACCA AACAA | 508 |
| | Soy1-R4 | CAAGGAAAATGAATGATGGCTTT | 509 |
| | Soy1-T3 (FAM-MGB) | CCTTCCCAAACTATAATC | 510 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pinII | pINII-99F | TGATGCCCACATTATAGTGATTAGC | 480 |
| | pINII-13R | CATCTTCTGGATTGGCCAACTT | 481 |
| | pIN11-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

D. Detection of the replacement of the soybean EPSPS1 intron1 with the soybean UBQ intron1 using the guide RNA/Cas9 endonuclease system.

In order to replace the soybean EPSPS1 promoter with the soybean UBQ promoter at the native EPSPS1 gene, two guideRNA expression vectors were used in each soybean transformation experiment as shown in Table 41. The QC878 (SEQ ID NO: 470) was targeting the exon2 and the RTW1201(SEQ ID NO: 505) or RTW1202 (SEQ ID NO: 506) was targeting the 5' end of the soybean −798 bp promoter. The double cleavage of the soybean EPSPS1 gene with the two guide RNA/Cas systems resulted in removal of the native EPSPS1 promoter/5'UTR-Exon1/Intron1/partial Exon2 fragment at the native EPSPS gene. At the same time, a polynucleotide modification template RTW1192A (SEQ ID NO: 507) was co-delivered into soybean cells. This RTW1192A DNA contained 1369 bp soybean UBQ promoter, its 47 bp 5-UTR and 532 bp UBQ intron1 in front of the EPSPS1 exon1-Intron1-modified Exon2. Homologous recombination between the polynucleotide modification template and the genomic DNA resulted in the replacement of EPSPS1 promoter/5'UTR with the soybean UBQ promoter/5'UTR/Intron1 and the desired amino acid modifications evidenced by PCR analysis. PCR assays with primer WOL1005/WOL1006 pair (SEQ ID NO: 511 and 512) and WOL1003/WOL1004 pair (SEQ ID NO: 501 and 502) were used to detect the promoter replacement events.

Example 27

Enhancer Element Deletions Using the guideRNA/Cas Endonuclease System

The guide RNA/Cas endonuclease system described herein can be used to allow for the deletion of a promoter element from either a transgenic (pre-existing, artificial) or endogenous gene. Promoter elements, such enhancer elements, or often introduced in promoters driving gene expression cassettes in multiple copies (3×=3 copies of enhancer element, FIG. 33) for trait gene testing or to produce transgenic plants expressing specific trait. Enhancer elements can be, but are not limited to, a 35S enhancer element (Benfey et al, *EMBO J*, Aug. 1989; 8(8): 2195-2202, SEQ ID NO:513). In some plants (events), the enhancer elements can cause an unwanted phenotype, a yield drag, or a change in expression pattern of the trait of interest that is not desired. For example, as shown in FIG. 33, a plant comprising multiple enhancer elements (3 copies, 3×) in its genomic DNA located between two trait cassettes (Trait A en TraitB) was characterized to show an unwanted phenotype. It is desired to remove the extra copies of the enhancer element while keeping the trait gene cassettes intact at their integrated genomic location. The guide RNA/Cas endonuclease system described herein can be used to removing the unwanted enhancing element from the plant genome. A guide RNA can be designed to contain a variable targeting region targeting a target site sequence of 12-30 bps adjacent to a NGG (PAM) in the enhancer. If a Cas endonuclease target site sequence is present in all copies of the enhancer elements (such as the three Cas endonuclease target sites 35S-CRTS1 (SEQ ID NO:514), 35S-CRTS2 (SEQ ID NO:515), 35S-CRTS3 (SEQ ID NO:516)), only one guide RNA is needed to guide the Cas endonuclease to the target sites and induce a double strand break in all the enhancer elements at once. The Cas endonuclease can make cleavage to remove one or multiple enhancers. The guideRNA/Cas endonuclease system can introduced by either *agrobacterium* or particle gun bombardment. Alternatively, two different guide RNAs (targeting two different genomic target sites) can be used to remove all 3× enhancer elements from the genome of an organism, in a manner similar to the removal of a (transgenic or endogenous) promoter described herein.

Example 28

Regulatory Sequence Modifications Using the Guide RNA/Cas Endonuclease System

A. Modification of Polyubiquitination Sites

There are defined ubiquitination sites on proteins to be degraded and they were found within the maize EPSPS protein by using dedicated computer programs (for example, the CKSAAP_UbSite (Ziding Zhang's Laboratory of Protein Bioinformatics College of Biological Sciences, China Agricultural University, 100193 Beijing, China). One of the selected polyubiquitination site within the maize EPSPS coding sequence is shown in FIG. 34A and its amino acid signature sequence is compared to the equivalent EPSPS sites from the other plants (FIG. 34A). The lysine amino acid (K) at position 90 (highly conserved in other plant species) was selected as a potential site of the EPSPS protein polyubiquitination. The polynucleotide modification template (referred to as EPSPS polynucleotide maize K9OR template) used to edit the epsps locus is listed as SEQ ID NO: 517. This template allowed for editing the epsps locus to contain the lysine (K) to arginine (R) substitution at position 90 (K9OR) and two additional TIPS substitutions at positions 102 and 106 (FIGS. 34B and 34C). Maize genomic DNA was edited using the guideRNA/Cas endonuclease system described herein and T0 plants were produced as described herein. The T0 plants that contained the nucleotide modifications, as specified by the information provided on the K9OR template (FIG. 34C), were selected by the genotyping methods described herein. F1 EPSPS-K9OR plants can be selected for elevated protein content due to a slower rate of the EPSPS protein degradation.

B. Editing Intron Elements to Introduce Intron Mediated Enhancer Elements (IMEs)

Transcriptional activity of the native EPSPS gene can be modulated by transcriptional enhancers positioned in the vicinity of other transcription controlling elements. Introns are known to contain enhancer elements affecting the overall rate of transcription from native promoters including the EPSPS promoter. For example, the first intron of the maize ubiquitin 5'UTR confers a high level of expression in monocot plants as specified in the WO 2011/156535 A1 patent application. An intron enhancing motif CATATCTG (FIG. 35A), also referred to as a intron-mediated enhancer element, IME) was identified by proprietary analysis (WO2011/156535 A1, published on Dec. 15, 2011) and appropriate nucleotide sites at the 5' end of the EPSPS first intron were selected for editing in order to introduce the intron-mediated enhancer elements (IMEs) (FIG. 35B-35C). The polynucleotide modification template (referred to as EPSPS polynucleotide maize IME template) is listed as SEQ ID No: 518. The polynucleotide modification template allows for editing of the epsps locus to contain three IMEs (two on one strand of the DNA, one on the reverse strand) in the first EPSPS intron and the TIPS substitutions at positions 102 and 106. The genomic DNA of maize plants was edited using the guideRNA/Cas endonuclease system described herein. Maize plants containing the IME edited EPSPS coding sequence can be selected by genotyping the T0 plants and can be further evaluated for elevated EPSPS-TIPS protein content due to the enhanced transcription rate of the native EPSPS gene.

Example 29

Modifications of Splicing Sites and/or Introducing Alternate Splicing Sites Using the Guide RNA/Cas Endonuclease System In maize cells, the splicing process is affected by splicing sites at the exon-intron junction sites as illustrated in the EPSPS mRNA production (FIG. 36A-36B).

FIG. 36A shows analysis of EPSPS amplified pre-mRNA (cDNA panel on left). Lane 14 in FIG. 36A shows amplification of the EPSPS pre-mRNA containing the 3 rd intron unspliced, resulting in a 804 bp diagnostic fragment indicative for an alternate splicing event. Lanes E3 and F8 show the EPSPS PCR amplified fragments resulting from regular spliced introns. Diagnostic fragments such as the 804 bp fragment of lane 14 are not amplified unless cDNA is synthesized (as is evident by the absence of bands in lanes E3, 14, and F8 comprising total RNA (shown in the total RNA panel on right of FIG. 36A). The canonical splice site in the maize EPSPS gene and genes from other species is AGGT, while other (alterative) variants of the splice sites may lead to the aberrant processing of pre-mRNA molecules. The EPSPS coding sequence contains a number of alternate splicing sites that may affect the overall efficiency of the pre-mRNA maturation process and as such may limit the EPSPS protein accumulation in maize cells.

In order to limit the occurrence of alternate splicing events during EPSPS gene expression, a guideRNA/Cas endonuclease system as described herein can be used to edit splicing sites. The splicing site at the junction of the second native EPSPS intron and the third exon is AGTT and can be edited in order to introduce the canonical AGGT splice site at this junction (FIG. 37). The T>G substitution does not affect the native EPSPS open reading frame and it does not change the EPSPS amino acid sequence. The polynucleotide modification template (referred to as EPSPS polynucleotide maize Tspliced template) is listed as SEQ ID NO: 519. This polynucleotide modification template allows for editing of the epsps locus to contain the canonical AGGT splice site at the 2 nd intron-3rd exon junction site and the TIPS substitutions at positions 102 and 106. Maize plants are edited using the procedures described herein. F1 EPSPS-Tspliced maize plants can be evaluated for increased protein content due to the enhanced production of functional EPSPS mRNA messages.

Example 30

Shortening Maturity Via Manipulation of Early Flowering Phenotype with ZmRap2.7 Down-Regulation Using the Guide RNA/Cas Endonuclease System Overall plant maturity can be shortened by modulating the flowering time phenotype of plants through modulation of a maize ZmRap2.7 gene. Shortening of plant maturity can be obtained by an early flowering phenotype.

RAP2.7 is an acronym for Related to APETALA 2.7. RAPL means RAP2.7 LIKE and RAP2.7 functions as an AP2-family transcription factor that suppresses floral transition (SEQ ID NOs:520 and 521). Transgenic phenotype upon silencing or knock-down of Rap2.7 resulted in early flowering, reduced plant height, but surprisingly developed normal ear and tassel as compared the wild-type plants (PCT/US14/26279 application, filed Mar. 13, 2014). The guide RNA/Cas endonuclease system described herein can be used to target and induce a double strand break at a Cas endonuclease target site located within the RAP2.7 gene. Plants comprising NHEJ within the RAP2.7 gene can be selected and evaluated for the presence of a shortened maturity phenotype.

Example 31

Modulating Expression of a Maize NPK1B Gene for Engineering Frost Tolerance in Maize Using a Guide RNA/Cas Endonuclease System Nicotiana Protein Kinase1 (NPK1) is a mitogen activated protein kinase kinase kinase that is involved in cytokinesis regulation and oxidative stress signal transduction. The ZM-NPK1B (SEQ ID NO: 522 and SEQ ID NO: 523) which has about 70% amino acid similarity to rice NPKL3 has been tested for frost tolerance in maize seedlings and reproductive stages (PCT/US14/26279 application, filed Mar. 13, 2014). Transgenic seedlings and plants comprising a ZM-NPK1B driven by an inducible promoter Rab17, had significantly higher frost tolerance than control seedlings and control plants. The gene seemed inducted after cold acclimation and during −3° C. treatment period in most of the events but at low levels. (PCT/US14/26279 application, filed Mar. 13, 2014).

A guide RNA/Cas endonuclease system described herein can be used to replace the endogenous promoter of NPK1 gene, with a stress-inducible promoter such as the maize RAB17 promoter stages (SEQ ID NO: 524; PCT/US14/26279 application, filed Mar. 13, 2014), thus modulate NPK1B expression in a stress-responsive manner and provide frost tolerance to the modulated maize plants.

Example 32

Shortening Maturity Via Manipulation of Early Flowering Phenotype with FTM1 Expression Using a Guide RNA/Cas Endonuclease Systems Overall plant maturity can shortened by modulating the flowering time phenotype of plants through expressing a transgene. Such a phenotype modification can also be achieved with additional transgenes or through a breeding approach.

FTM1 stands for Floral Transition MADS 1 transcription factor (SEQ ID NOs: 525 and 526). It is a MADS Box transcriptional factor and induces floral transition. Upon expression of FTM1 under a constitutive promoter, transgenic plants exhibited early flowering and shortened maturity, but surprisingly ear and tassel developed normally as compared to the wild-type plants (PCT/US14/26279 application, filed Mar. 13, 2014).

FTM1-expressing maize plants demonstrated that by manipulating a floral transition gene, time to flowering can be reduced significantly, leading to a shortened maturity for the plant. As maturity can be generally described as time from seeding to harvest, a shorter maturity is desired for ensuring that a crop can finish in the northern continental dry climatic environment (PCT/US14/26279 application, filed Mar. 13, 2014).

A guide RNA/Cas endonuclease system described herein can be used to introduce enhancer elements such as the CaMV35S enhancers (Benfey et al, EMBO J, Aug 1989; 8(8): 2195-2202, SEQ ID NO:512), specifically targeted in front of the endogenous promoter of FTM1, in order to enhance the expression of FTM1 while preserving most of the tissue and temporal specificities of native expression, providing shortened maturity to the modulated plants.

Example 33

Inserting Inducible Responsive Elements in Plant Genomes

Inducible expression systems controlled by an external stimulus are desirable for functional analysis of cellular proteins as well as trait development as changes in the expression level of the gene of interest can lead to an accompanying phenotype modification. Ideally such a system would not only mediate an "on/off" status for gene expression but would also permit limited expression of a gene at a defined level.

The guide RNA/Cas endonuclease system described herein can be used to introduce components of repressor/operator/inducer systems to regulate gene expression of an organism. Repressor/operator/inducer systems and their components are well known I the art (US 2003/0186281 published Oct. 2, 2003; U.S. Pat. No. 6,271,348). For example, nut not limited to, components of the tetracycline (Tc) resistance system of *E. coli* have been found to function in eukaryotic cells and have been used to regulate gene expression (U.S. Pat. No. 6,271,348).Nucleotide sequences of tet operators of different classes are known in the art see for example: classA, classB, classC, classD, classE TET operator sequences listed as SEQ ID NOs:11 15 of U.S. Pat. No. 6,271,348.

Components of a sulfonylurea-responsive repressor system (as described in U.S. Pat. No. 8,257,956, issued on Sep. 4,2012) can also be introduced into plant genomes to generate a repressor/operator/inducer systems into said plant where polypeptides can specifically bind to an operator, wherein the specific binding is regulated by a sulfonylurea compound.

Example 34

Genome Deletion for Trait Locus Characterization

Trait mapping in plant breeding often results in the detection of chromosomal regions housing one or more genes controlling expression of a trait of interest. For quantitative traits, expression of a trait of interest is governed by multiple quantitative trait loci (QTL) of varying effect-size, complexity, and statistical significance across one or more chromosomes. A QTL or haplotype that is associated with suppression of kernel-row number in the maize ear can be found to be endemic in elite breeding germ plasm. The negative effect of this QTL for kernel row number can be fine-mapped to an acceptable resolution to desire selective elimination of this negative QTL segment within specific recipient germ plasm. Two flanking cut sites for the guide polynucleotide/Cas endonuclease system are designed via haplotype, marker, and/or DNA sequence context at the targeted QTL region, and the two guide polynucleotide/Cas endonuclease systems are deployed simultaneously or sequentially to produce the desired end product of two independent double strand breaks (cuts) that liberate the intervening region from the chromosome. Individuals harboring the desired deletion event would result by the NHEJ repair of the two chromosomal ends and eliminating the intervening DNA region. Assays to identify these individuals is based on the presence of flanking DNA marker regions, but absence of intervening DNA markers. A proprietary haplotype for kernel-row-number is created that is not extant in the previously defined elite breeding germplasm pool.

An alternative approach would be to delete a region containing a fluorescent gene. Recovery of plants with, and without, fluorescence would give an approximate indication of the efficiency of the deletion process.

Example 35

Engineering Drought Tolerance and Nitrogen Use Efficiency into Maize Via Gene Silencing by Expressing an Inverted Repeat into an ACS6 Gene Using the Guide RNA/Cas Endonuclease System ACC (1-aminocyclopropane-1-carboxylic acid) synthase (ACS) genes encode enzymes that catalyze the rate limiting step in ethylene biosynthesis. A construct containing one of the maize ACS genes, ZM-ACS6, in an inverted repeat configuration, has been extensively tested for improved abiotic stress tolerance in maize (PCT/US2010/051358, filed Oct. 4, 2010; PCT/US2010/031008, filed Apr. 14, 2010). Multiple transgenic maize events containing a ZM-ACS6 RNAi sequence driven by a ubiquitin constitutive promoter had reduced ethylene emission, and a concomitant increase in grain yield relative to controls under both drought and low nitrogen field conditions (Plant Biotechnology Journal: 12 Mar. 2014, DOI: 10.1111/pbi.12172).

In one embodiment, the guide RNA/Cas endonuclease system can be used in combination with a co-delivered polynucleotide sequence to insert an inverted ZM-ACS6 gene fragment into the genome of maize, wherein the insertion of the inverted gene fragment allows for the in-vivo creation of an inverted repeat (hairpin) and results in the silencing of the endogenous ethylene biosynthesis gene.

In an embodiment the insertion of the inverted gene fragment can result in the formation of an in-vivo created inverted repeat (hairpin) in a native (or modified) promoter of an ACS6 gene and/or in a native 5' end of the native ACS6 gene. The inverted gene fragment can further comprise an intron which can result in an enhanced silencing of the targeted ethylene biosynthetic gene.

Example 36

T0 Plants from the Multiplexed Guide RNA/Cas Experiment Carried High Frequency of Bi-Allelic Mutations and Demonstrated Proper Inheritance of Mutagenized Alleles in the T1 Population.

This example demonstrates the high efficiency of the guide RNA/Cas endonuclease system in generating maize plants with multiple mutagenized loci and their inheritance in the consecutive generation(s).

Mutated events generated in the multiplexed experiment described in Example 4 were used to regenerate T0 plants with mutations at 3 different target sites: MS26Cas-2 target site (SEQ ID NO: 14), LIGCas-3 target site (SEQ ID NO: 18) and MS45Cas-2 target site (SEQ ID NO: 20).

For further analysis, total genomic DNA was extracted from leaf tissue of individual T0 plants. Fragments spanning all 3 target sites were PCR amplified using primer pairs for the corresponding target sites, cloned into the pCR2.1-TOPO cloning vector (Invitrogen), and sequenced. Table 43 shows examples of mutations detected in four T0 plants resulting from imprecise NHEJ at all relevant loci when multiple guide RNA expression cassettes were simultaneously introduced either in duplex (see TS=Lig34/MS26) or triplex (see TS=Lig34/MS26/MS45), respectively.

TABLE 43

Examples of mutations at maize target loci produced by a multiplexed guide RNA/Cas system

| Target sites (TS) | T0 plant | qPCR data | Sequencing data Lig3/4 TS | Ms26 TS | Ms45 TS |
|---|---|---|---|---|---|
| Lig34/MS26 | 1 | NULL/NULL* | 1 bp ins/2 bp del+1 bp ins | 1 bp ins/19 bp del | |
| | 2 | NULL/NULL | 1 bp ins/1 bp del | 1 bp ins/1 bp ins | |
| Lig34/MS26/MS45 | 1 | NULL/NULL/NULL | 1 bp ins/large del | 1 bp ins/1 bp del | 15 bp del/large del |
| | 2 | INDEL**/NULL/NULL | 1 bp ins/WT | 1 bp (T) ins/1 bp (C) ins | 1 bp ins/large del |

*NULL indicates that both alleles are mutated

**INDEL indicates mutation in one of the two alleles.

del = deletion, ins = insertion, bp = base pair

All T0 plants were crossed with wild type maize plants to produce T1 seeds. T1 progeny plants (32 plants) of the second T0 plant from the triplex experiment (see Table 43, Lig34/MS26/MS45) were analyzed by sequencing to evaluate segregation frequencies of the mutated alleles. Our results demonstrated proper inheritance and expected (1:1) segregation of the mutated alleles as well as between mutated and wild type alleles at all three target sites.

The data clearly demonstrate that the guide RNA/maize optimized Cas endonuclease system described herein, can be used to simultaneously mutagenize multiple chromosomal loci and produce progeny plants containing the stably inherited multiple gene knock-outs.

Example 37

Guide RNA/Cas Endonuclease Mediated DNA Cleavage in Maize Chromosomal Loci can Stimulate Homologous Recombination Repair-Mediated Transgene Insertion and Resulting T1 Progeny Plants Demonstrated Proper Inheritance of the Modified Alleles.

Maize events generated in the experiment described in Example 5 were used to regenerate T0 plants. T0 plants were regenerated from 7 independent callus events with correct amplifications across both transgene genomic DNA junctions and analyzed. Leaf tissue was sampled, total genomic DNA extracted, and PCR amplification at both transgene genomic DNA junctions was carried out using the primer pairs (corresponding to SEQ ID NOs: 98-101). The resulting amplification products were sequenced for confirmation. Plants with confirmed junctions at both ends were further analyzed by Southern hybridization (FIG. 38) using two probes, genomic (outside HR1 region, SEQ ID: 533) and transgenic (within MoPAT gene, SEQ ID: 534). PCR, sequencing and Southern hybridization data demonstrated that plants regenerated from two of the 7 events (events 1 and 2) demonstrated perfect, clean, single copy transgene integration at the expected target site via homologous recombination. Plants regenerated from the remaining 5 events contained either additional, randomly integrated copies of the transgene (events 4, 5, and 6) or rearranged copies of the transgene integrated into the target site (events 3 and 7).

T0 plants from events 1 and 2 were crossed with wild type maize plants to produce T1 seeds. Ninety-six T1 plants from events 1 and 2 were analyzed by Southern hybridization (using the same probes as above) to evaluate segregation frequencies of the transgene locus. Southern results demonstrated proper inheritance and expected (1:1) segregation of the transgene and wild type loci.

The data clearly demonstrate that maize chromosomal loci cleaved with the maize optimized guide RNA/Cas system described herein can be used to stimulate HR repair pathways to site-specifically insert transgenes and produce progeny plants that have the inserted transgene stably inherited.

Example 38

Production of Maize Transgenic Lines with Pre-Integrated Cas9 for Transient Delivery of Guide RNA This example describes the rationale, production, and testing of maize transgenic lines with an integrated Cas9 gene under constitutive and temperature inducible promoters.

As demonstrated in Example 2, a high mutation frequency was observed when Cas9 endonuclease and guide RNA were delivered as DNA vectors by biolistic transformation to immature corn embryo cells. When Cas9 endonuclease was delivered as a DNA vector and guide RNA as RNA molecules, a reduced mutation frequency was observed (Table 44).

TABLE 44

Mutant reads at LigCas-3 target site produced by transiently delivered guide RNA.

| Target Site Examined for Mutations | Transient Delivery | Expression Cassette | Mutant Reads | Total Reads |
|---|---|---|---|---|
| LIGCas-3 | — | Cas9 | 24.2 | 1,599,492 |
| LIGCas-3 | — | Cas9/guide RNA | 44170 | 1,674,825 |
| LIGCas-3 | 35 ng guide RNA | Cas9 | 418 | 1,622,180 |
| LIGCas-3 | 70 ng guide RNA | Cas9 | 667 | 1,791,388 |
| LIGCas-3 | 140ng guide RNA | Cas9 | 239 | 1,632,137 |

Increased efficiency (increased mutant reads) may occur when the Cas9 protein and guide RNA are present in the cell at the same time. To facilitate the presence of both Cas9 endonuclease and guide RNA in the same cell, a vector containing a constitutive and conditionally regulated Cas9 gene can be first delivered to plant cells to allow for stable integration into the plant genome to establish a plant line that contains only the Cas9 gene in the plant genome. Then, single or multiple guide RNAs can be delivered as either DNA or RNA, or combination, to the embryo cells of the plant line containing the genome-integrated version of the Cas9 gene.

Transgenic maize (genotype Hi-II) lines with an integrated Cas9 gene driven by either a constitutive (Ubi) or an inducible (CAS) promoter were generated via *Agrobacterium*-mediated transformation. Besides the Cas9 gene, the Agro vector also contained a visible marker (END2:Cyan) and a Red Fluorescent Protein sequence interrupted with a 318 bp long linker (H2B:RF-FP). The linker sequence was flanked with 370 bp long direct repeats to promote recombination and restoration of a functional RFP gene sequence upon double strand break within the linker.

Lines with single copies of the transgene were identified and used for further experiments. Two guide RNA constructs targeting 2 different sites (Table 45 in the linker sequence, were delivered into immature embryo cells via particle bombardment. Meganuclease variant LIG3-4 B65 with very high cutting activity previously used in similar experiments was used as the positive control.

TABLE 45

Target sites in the RF-FP linker for guideRNA/Cas endonuclease system.

| Locus | Guide RNA Used | Target Site Designation | Target Site Sequence | PAM Sequence | SEQ ID NO: |
|---|---|---|---|---|---|
| RF-FP linker | Long | RF-FPCas-1 | GCAGGTCTCACGACGGT | TGG | 535 |
| | Long | RF-FPCas-2 | GTAAAGTACGCGTACGTGTG | AGG | 536 |

After transformation, embryos with Cas9 gene under Ubiquitin promoter were incubated at 28° C. while embryos with Cas9 gene under temperature inducible CAS promoter were first incubated at 37° C. for 15-20 hours and then transferred to 28° C. Embryos were examined 3-5 days after bombardment under luminescent microscope. Expression and activity of the pre-integrated Cas9 protein was visually evaluated based on the number of embryo cells with RFP protein expression. In most lines, the guide RNA/Cas endonuclease system demonstrated similar or higher frequency of RFP repair than LIG3-4 B65 meganuclease indicating high level of Cas9 protein expression and activity in the generated transgenic lines.

This example describes the production of transgenic lines with a pre-integrated Cas9 gene that can be used in further experiments to evaluate efficiency of mutagenesis at a target site upon transient delivery of guide RNA in the form of RNA molecules.

Example 39

The Guide RNA/Cas Endonuclease System Delivers Double-Strand Breaks to the Maize ALS Locus and Facilitates Editing of the ALS Gene This example demonstrates that the guide RNA/Cas endonuclease system can be efficiently used to introduce specific changes into the nucleotide sequence of the maize ALS gene resulting in resistance to sulfonylurea class herbicides, specifically, chlorsulfuron.

Endogenous ALS protein is the target site of ALS inhibitor sulfonylurea class herbicides. Expression of the herbicide tolerant version of ALS protein in crops confers tolerance to this class of herbicides. The ALS protein contains N-terminal transit peptides, and the mature protein is formed following transport into the chloroplast and subsequent cleavage of the transit peptide. The mature protein starts at residue S41, resulting in a mature protein of 598 amino acids with a predicted molecular weight of 65 kDa (SEQ ID NO: 550).

TABLE 46

Deduced Amino Acid Sequence of the Full-Length ZM-ALS Protein (SEQ ID NO: 550)

```
1   MATAAAASTA LTGATTAAPK ARRRAHLLAT RRALAAPIRC SAASPAMPMA
51  PPATPLRPWG PTEPRKGADI LVESLERCGV RDVFAYPGGA SMEIHQALTR
101 SPVIANHLER HEQGEAFAAS GYARSSGRVG VCIATSGPGA TNLVSALADA
151 LLDSVPMVAI TGQVPRRMIG TDAFQETPIV EVTRSITKHN YLVLDVDDIP
201 RVVQEAFFLA SSGRPGPVLV DIPKDIQQQM AVPVWDKPMS LPGYIARLPK
251 PPATELLEQV LRLVGESRRP VLYVGGGCAA SGEELRREVE LTGIPVTTTL
301 MGLGNFPSDD PLSLRMLGMH GTVYANYAVD KADLLLALGV REDDRVTGKI
351 EAFASRAKIV HVDIDPAEIG KNKQPHVSIC ADVKLALQGM NALLEGSTSK
401 KSFDFGSWND ELDQQKREFP LGYKTSNEEI QPQYAIQVLD ELTKGEAIIG
451 TGVGQHQMWA AQYYTYKRPR QWLSSAGLGA MGFGLPAAAG ASVANPGVTV
501 VDIDGDGSEL MNVQELAMIR IENLPVKVFV LNNQHLGMVV QWEDREYKAN
551 RAHTYLGNPE NESEIYPDFV TIAKGENIPA VRVTKKNEVR AAIKKMLETP
601 GPYLLDIIVP HQEHVLPMIP SGGAFKDMIL DGDGRTVY
```

Modification of a single amino acid residue (P165A or P165S, shown in bold) from the endogenous maize acetoacetate synthase protein provides resistance to herbicides in maize.

There are two ALS genes in maize, ALS1 and ALS2, located on chromosomes 5 and 4, respectively. As described in Example 2, guide RNA expressing constructs for 3 different target sites within the ALS genes were tested. Based on polymorphism between ALS1 and ALS2 nucleotide sequences, ALS1-specific and ALSCas-4 target site were identified and tested. ALSCas-1 guide RNA expressing construct targeting both ALS1 and ALS2 genes was used as control (Table 47)

TABLE 47

Maize ALS genomic target sites tested.

| Locus | Location | Guide RNA | Target Site Designation | Maize Genomic Site Target Sequence | PAM Sequence | SEQ ID NO: |
|---|---|---|---|---|---|---|
| ALS | Chr.4: 107.73cM and Chr.5: 115.49cM | Long | ALSCas-1 | GGTGCCAATCATGC GTCG | CGG | 22 |
|  |  | Long | ALSCas-4 | GCTGCTCGATTC CGTCCCCA | TGG* | 537 |

*Target site in the ALS1 gene; bolded nucleotides are different in the ALS2 gene.

The experiment was conducted and mutation frequency determined as described in Example 2 and results are shown in Table 48.

TABLE 48

Frequencies of NHEJ mutations at the two ALS target sites recovered by deep sequencing.

| TS | Total Reads | Mutant reads (ALS1) | Mutant reads (ALS2) |
|---|---|---|---|
| ALSCas-1 | 204,230 | 5072 (2.5%) | 2704 (1.3%) |
| ALSCas-4 | 120,766 | 3294 (2.7%) | 40 (0.03%) |

The results demonstrated that ALSCas-4 guide RNA/Cas9 system mutates the ALS1 gene with approximately 90 times higher efficiency than the ALS2 gene. Therefore, the ALS-Cas-4 target site and the corresponding guide RNA were selected for the ALS gene editing experiment.

To produce edited events, the ALS polynucleotide modification repair template was co-delivered using particle bombardment as a plasmid with an 804 bp long homologous region (SEQ ID NO: 538) or as a single-stranded 127 bp DNA fragment (SEQ ID NO: 539), the maize optimized Cas9 endonuclease expression vector described in Example 1, the guide RNA expression cassette (targeting ALSCas-4 site), a moPAT-DsRed fusion as selectable and visible markers, and developmental genes (ODP-2 and WUS). Approximately 1000 Hi-II immature embryos were bombarded with each of the two repair templates described above. Forty days after bombardment, 600 young callus events (300 for each repair template) were collected and transferred to the media with bialaphos selection. The embryos with remaining events were transferred to the media with 100 ppm of chlorsulfuron for selection. A month later, events that continued growing under chlorsulfuron selection were collected and used for analysis.

A small amount of callus tissue from each selected event was used for total DNA extraction. A pair of genomic primers outside the repair/donor DNA fragment (SEQ ID NO:540 and SEQ ID NO:541) was used to amplify an endogenous fragment of the ALS1 locus containing the ALSCas4 target sequence. The PCR amplification products were gel purified, cloned into the pCR2.1 TOPO cloning vector (Invitrogen) and sequenced. A total of 6 events demonstrated the presence of the specifically edited ALS1 allele as well as either a wild type or a mutagenized second allele.

These data indicate that a guide RNA/Cas system can be successfully used to create edited ALS allele in maize. The data further demonstrates that the guide RNA/maize optimized Cas endonuclease system described herein, can be used to produce progeny plants containing gene edits that are stably inherited.

Example 40

Gene Editing of the Soybean ALS1 Gene and Use as a Transformation Selectable Marker for Soybean Transformation with the Guide RNA/Cas Endonuclease System A. guideRNA/Cas9 endonuclease target site design on the Soybean ALS1 gene.

There are four ALS genes in soybean (Glyma04g37270, Glyma06g17790, Glyma13g31470 and Glyma15g07860). Two guideRNA/Cas9 endonuclease target sites (soy ALS1-CR1 and soy ALS1-CR2) were designed near the Proline 178 of the soybean ALS1 gene Glyma04g37270 (Table 49).

TABLE 49

Guide RNA/Cas9 endonuclease target sites on soybean ALS1 gene

| Name of gRNA-Cas9 endonuclease target site | Cas endonuclease target sequence (SEQ ID NO:) | Physical location |
|---|---|---|
| soy ALS1-CR1 | 542 | Gm04:43645633 ... 43645612 |
| soy ALS1-CR2 | 543 | Gm04: 43645594 ... 43645615 |

B. Guide-RNA expression cassettes, Cas9 endonuclease expression cassettes, polynucleotide modification templates for introduction of specific amino acid changes and use the P178S modified ALS1 allele as a soybean transformation selectable marker The soybean U6 small nuclear RNA promoter, GM-U6-13.1 (SEQ ID. NO: 469), was used to express guide RNAs to direct Cas9 nuclease to designated genomic target sites (Table 50). A soybean codon optimized Cas9 endonuclease (SEQ ID NO:489) expression cassette and a guide RNA expression cassette were linked in a first plasm id that was co-delivered with a polynucleotide modification template. The polynucleotide modification template contained specific nucleotide changes that encoded for amino acid changes in the soy ALS1 polypeptide (Glyma04g37270), such as the P178S. Other amino acid changes in the ALS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 50

Guide RNA/Cas9 expression cassettes and polynucleotide modification templates used in soybean stable transformation for the specific amino acid modifications of the soy ALS1 gene.

| Experiment | Guide RNA/Cas9 (plasmid name) | SEQ ID NO: | polynucleotide modification template | SEQ ID NO: |
|---|---|---|---|---|
| soy ALS1-CR1 | U6-13.1:ALS1-CR1 + EF1A2:CAS9 (QC880) | 544 | RTW1026A | 546 |
| soy ALS-CR2 | U6-13.1:ALS1-CR2 + EF1A2:CAS9 (QC881) | 545 | RTW1026A | 546 |

C. Detection of the P178S mutation in the soybean ALS1 gene in the event selected by chlorsulfuron In order to edit specific amino acids at the native ALS1 gene (such as the P178S modification), a polynucleotide modification template such as RTW1026A (Table 50), was co-delivered with the guideRNA/Cas9 expression cassettes into soybean cells. Chlorsulfuron (100 ppb) was used to select the P178S ALS1 gene editing events in soybean transformation process.

The modification of the native ALS1 gene via guide RNA/Cas9 system mediated DNA homologous recombination was determined by specific PCR analysis. A specific PCR assay with primer pair WOL900 (SEQ ID NO: 547) and WOL578 (SEQ ID NO: 548) was used to detect perfect P178S modification at the native ALS1 gene. A second primer pair WOL573 (SEQ ID NO: 549) and WOL578 (SEQ ID NO: 548) was used to amplify both a P178S modified Soy ALS1 allele and a NHEJ mutated allele. A chlorsulfuron tolerant event (MSE3772-18) was generated from the soy ALS1-CR2 experiment. The event contained a perfect P178S modified allele and a 2 nd allele with a 5 bp deletion at the soyALS1-CR2 cleavage site. Topo cloning/sequencing was used to verify the sequences. Our results demonstrated one P178S modified ALS1 allele is sufficient to provide chlorsulfuron selection in soybean transformation process.

That which is claimed:

1. A recombinant DNA construct comprising a promoter nucleotide sequence of homology of at least 98% sequence identity with SEQ ID NO: 295, operably linked to at least one heterologous sequence, wherein said nucleotide sequence drives constitutive expression of the heterologous sequence.

2. The recombinant DNA construct of claim 1, wherein the nucleotide sequence comprises a fragment of at least 98% sequence identity, based on the Clustal V method of alignment with pairwise alignment default parameters KTUPLE=2, GAP PENALTY=5, WINDOW=4 and DIAGONALS SAVED=4, to the sequence set forth in SEQ ID NO: 295.

3. A vector comprising the recombinant DNA construct of claim 1.

4. A cell comprising the recombinant DNA construct of claim 1.

5. The cell of claim 4, wherein the cell is a plant cell.

6. A transgenic plant comprising the recombinant DNA construct of claim 1.

7. The transgenic plant of claim 6, wherein said plant is a monocot plant.

8. The transgenic plant of claim 7, wherein the plant is a maize plant.

9. A transgenic seed produced by the transgenic plant of claim 7, wherein the transgenic seed comprises the recombinant DNA construct.

10. The recombinant DNA construct of claim 1, wherein the at least one heterologous sequence is selected from the group consisting of: a reporter coding sequence, a selection marker, a functional RNA, a disease resistance conferring coding sequence, a herbicide resistance conferring coding sequence, an insect resistance conferring coding sequence, a carbohydrate metabolism coding sequence, a fatty acid metabolism coding sequence, an amino acid metabolism coding sequence, a drought resistance coding sequence, a cold resistance coding sequence, a heat resistance coding sequence, and a salt resistance coding sequence.

11. The recombinant DNA construct of claim 1, wherein the at least one heterologous sequence encodes a sequence selected from the group consisting of: a reporter protein, a selection marker, a functional RNA, a protein conferring disease resistance, a protein conferring herbicide resistance, a protein conferring insect resistance, a carbohydrate metabolism protein, a fatty acid metabolism protein, an amino acid metabolism protein, a drought resistance protein, a cold resistance protein, a heat resistance protein, and a salt resistance protein.

12. A method of expressing a coding sequence or a functional RNA in a plant comprising:

(a) introducing the recombinant DNA construct of claim 1 into the plant, wherein the at least one heterologous sequence comprises a coding sequence or encodes a functional RNA;

(b) growing the plant of step (a); and (c) selecting a plant displaying expression of the coding sequence or the functional RNA of the recombinant DNA construct.

13. A method of transgenically altering a plant trait, comprising:

(a) introducing the recombinant DNA construct of claim 1 into the plant;

(b) growing a fertile, mature plant resulting from step (a); and (c) selecting a plant expressing the at least one heterologous sequence in at least one plant tissue having the altered trait.

14. The method of claim 13, wherein the trait is selected from the group consisting of disease resistance, herbicide resistance, insect resistance carbohydrate metabolism, fatty acid metabolism, amino acid metabolism, plant development, drought resistance, cold resistance, heat resistance, and salt resistance.

15. A method for altering expression of at least one heterologous sequence in a plant comprising:

(a) transforming a plant cell with the recombinant DNA construct of claim 1;

(b) growing fertile mature plants from the transformed plant cell of step (a); and (c) selecting plants containing the transformed plant cell wherein the expression of the heterologous sequence is increased or decreased.

16. The method of claim 15 wherein the plant is a maize plant.

17. A plant transformed with a recombinant DNA construct comprising a promoter and a heterologous nucleic acid fragment operably linked to said promoter, wherein said promoter drives expression of said heterologous nucleic acid fragment in a plant cell, and further wherein said promoter comprises a nucleotide sequence of at least 98% sequence identity with SEQ ID NO: 295.

18. A recombinant DNA construct comprising a promoter comprising a nucleotide sequence of at least 98% sequence identity with SEQ ID NO: 295, wherein said promoter is operably linked to a heterologous nucleic acid fragment, and wherein said heterologous nucleic acid fragment expresses a guide RNA.

* * * * *

SEQUENCE LISTING

```
Sequence total quantity: 567
SEQ ID NO: 1           moltype = DNA  length = 4107
FEATURE                Location/Qualifiers
source                 1..4107
                       mol_type = genomic DNA
                       organism = Streptococcus pyogenes
SEQUENCE: 1
atggataaga aatactcaat aggcttagat atcggcacaa atagcgtcgg atgggcggtg  60
atcactgatg aatataaggt tccgtctaaa aagttcaagg ttctgggaaa tacagaccgc  120
cacagtatca aaaaaaatct tataggggct cttttatttg acagtggaga gacagcggaa  180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt cttttttggt ggaagaagac aagaagcatg aacgtcatcc tatttttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca tttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga  1020
caacaacttc cagaaaagta taaagaaatc ttttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga gaagacaaga agacttttat ccatttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gtttgatag tgttgaaatt  1740
tcaggagttg aagatagatt taatgcttca ttaggtacct accatgattt gctaaaaatt  1800
attaaagata aagatttttt ggataatgaa gaaaatgaag atatcttaga ggatattgtt  1860
ttaacattga ccttatttga agatagggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgg cacgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
```

-continued

```
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctggttttat caaacgccaa  2760
ttggttgaaa ctcgccaaat cactaagcat gtggcacaaa ttttggatag tcgcatgaat  2820
actaaatacg atgaaaatga taaacttatt cgagaggtta aagtgattac cttaaaatct  2880
aaattagttt ctgacttccg aaaagatttc caattctata aagtacgtga gattaacaat  2940
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
atgattgcta agtctgagca agaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aattatggaa agaagttcct ttgaaaaaaa tccgattgac  3540
tttttagaag ctaaaggata taaggaagtt aaaaaagact taatcattaa actacctaaa  3600
tatagtcttt ttgagttaga aaacggtcgt aaacggatgc tggctagtgc cggagaatta  3660
caaaaaggaa atgagctggc tctgccaagc aaatatgtga atttttttata tttagctagt  3720
cattatgaaa agttgaaggg tagtccagaa gataacgaac aaaaacaatt gtttgtggag  3780
cagcataagc attatttaga tgagattatt gagcaaatca gtgaattttc taagcgtgtt  3840
attttagcag atgccaattt agataaagtt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg gtctttatga aacacgcatt  4080
gatttgagtc agctaggagg tgactga                                      4107

SEQ ID NO: 2            moltype = DNA  length = 189
FEATURE                 Location/Qualifiers
source                  1..189
                        mol_type = genomic DNA
                        organism = Solanum tuberosum
SEQUENCE: 2
gtaagtttct gcttctacct ttgatatata tataataatt atcattaatt agtagtaata  60
taatatttca aatatttttt tcaaaataaa agaatgtagt atatagcaat tgcttttctg  120
tagtttataa gtgtgtatat tttaatttat aacttttcta atatatgacc aaaacatggt  180
gatgtgcag                                                          189

SEQ ID NO: 3            moltype = AA  length = 9
FEATURE                 Location/Qualifiers
source                  1..9
                        mol_type = protein
                        organism = Simian virus 40 (SV40)
SEQUENCE: 3
MAPKKKRKV                                                          9

SEQ ID NO: 4            moltype = AA  length = 18
FEATURE                 Location/Qualifiers
source                  1..18
                        mol_type = protein
                        organism = Agrobacterium tumefaciens
SEQUENCE: 4
KRPRDRHDGE LGGRKRAR                                                18

SEQ ID NO: 5            moltype = DNA  length = 6717
FEATURE                 Location/Qualifiers
misc_feature            1..6717
                        note = synthesized sequence-Maize optimized Cas9 expression
                         cassette
source                  1..6717
                        mol_type = other DNA
                        organism = synthetic construct
SEQUENCE: 5
gtgcagcgtg acccggtcgt gcccctctct agagataatg agcattgcat gtctaagtta  60
taaaaaatta ccacatattt tttttgtcac acttgtttga agtgcagttt atctatcttt  120
atacatatat ttaaacttta ctctacgaat aatataatct atagtactac aataatatca  180
gtgttttaga gaatcatata aatgaacagt tagacatggt ctaaaggaca attgagtatt  240
ttgacaacag gactctacag ttttatcttt ttagtgtgca tgtgttctcc tttttttttg  300
caaatagctt cacctatata atacttcatc cattttatta gtacatccat ttagggttta  360
gggttaatgg tttttataga ctaatttttt tagtacatct attttattct attttagcct  420
ctaaattaag aaaactaaaa ctctatttta gtttttttat ttaataattt agatataaaa  480
tagaataaaa taaagtgact aaaaattaaa caaataccct ttaagaaatt aaaaaaacta  540
aggaaacatt tttcttgttt cgagtagata atgccagcct gttaaacgcc gtcgacgagt  600
ctaacggaca ccaaccagcg aaccagcagc gtcgcgtcgg gccaagcgaa gcagacggca  660
cggcatctct gtcgctgcct ctggacccct ctcgagagtt ccgctccacc gttggacttg  720
ctccgctgtc ggcatccaga aattgcgtgg cggagcggca gacgtgagcc ggcacggcag  780
gcggcctcct cctcctctca cggcaccggc agctacgggg gattcctttc ccaccgctcc  840
ttcgctttcc cttcctcgcc cgccgtaata aatagacacc ccctccacac cctctttccc  900
caacctcgtg ttgttcggag cgcacacaca cacaaccaga tctcccccaa atccacccgt  960
```

-continued cggcacctcc gcttcaaggt acgccgctcg tcctcccccc ccccccctctc taccttctct 1020
agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt ttttttgttt cgttgcatag 1260
ggtttggttt gccctttttcc tttatttcaa tatatgccgt gcacttgttt gtcgggtcat 1320
cttttcatgc ttttttttgt cttggttgtg atgatgtggt ctggttgggc ggtcgttcta 1380
gatcggagta gaattctgtt tcaaactacc tggtggattt attaattttg gatctgtatg 1440
tgtgtgccat acatattcat agttacgaat tgaagatgat ggatggaaat atcgatctag 1500
gataggtata catgttgatg cgggttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgga ttttttttagc cctgccttca 1920
tacgctattt atttgcttgg tactgtttct tttgtcgatg ctcaccctgt tgtttggtgt 1980
tacttctgca ggtcgactct agaggatcca tggcaccgaa gaagaagcgc aaggtgatgg 2040
acaagaagta cagcatcggc ctcgacatcg gcaccaactc ggtgggctgg gccgtcatca 2100
cggacgaata taaggtcccg tcgaagaagt tcaaggtcct cggcaataca gaccgccaca 2160
gcatcaagaa aaacttgatc ggcgccctcc tgttcgatag cggcgagacc gcggaggcga 2220
ccaggctcaa gaggaccgcc aggagacggt acactaggcg caagaacagg atctgctacc 2280
tgcaggagat cttcagcaac gagatggcga aggtggacga ctccttcttc caccgcctgg 2340
aggaatcatt cctggtggag gaggacaaga agcatgagcg gcacccaatc ttcggcaaca 2400
tcgtcgacga ggtaagtttc tgcttctacc tttgatatat atataataat tatcattaat 2460
tagtagtaat ataatatttc aaatattttt ttcaaaataa aagaatgtag tatatagcaa 2520
ttgcttttct gtagtttata agtgtgtata ttttaattta taacttttct aatatatgac 2580
caaaacatgg tgatgtgcag gtggcctacc acgagaagta cccgacaatc taccacctcc 2640
ggaagaaact ggtggacagc acagacaagg cggacctccg gctcatctac cttgccctcg 2700
cgcatatgat caagttccgc ggccacttcc tcatcgaggg cgacctgaac ccggacaact 2760
ccgacgtgga caagctgttc atccagctcg tgcagacgta caatcaactg ttcgaggaga 2820
accccataaa cgctagcggc gtggacgcca aggccatcct ctcggccagg ctctcgaaat 2880
caagaaggct ggagaacctt atcgcgcagt tgccaggcga aaagaagaac ggcctcttcg 2940
gcaaccttat tgcgctcagc ctcggcctga cgccgaactt caaatcaaac ttcgacctcg 3000
cggaggacgc caagctccag ctctcaaagg acacctacga cgacgacctc gacaacctcc 3060
tggcccagat aggagaccag tacgcggacc tcttcctcgc cgccaagaac ctctccgacg 3120
ctatcctgct cagcgacatc cttcgggtca acaccgaaat taccaaggca ccgctgtccg 3180
ccagcatgat taaacgctac gacgagcacc atcaggacct cacgctgctc aaggcactcg 3240
tccgccagca gctccccgag aagtacaagg agatcttctt cgaccaatca aaaaacggct 3300
acgcgggata tatcgacggc ggtgccagcc aggaagagtt ctacaagttc atcaaaccaa 3360
tcctggagaa gatggacggc accgaggagt tgctggtcaa gctcaacagg gaggacctcc 3420
tcaggaagca gaggaccttc gacaacggct ccatcccgca tcagatccac ctgggcgaac 3480
tgcatgccat cctgcggcgc caggaggact tctacccgtt cctgaaggat aaccgggaga 3540
agatcgagaa gatcttgacg ttccgcatcc catactacgt gggcccgctg gctcgcggca 3600
actcccggtt cgcctggatg acccggaagt cggaggagac catcacaccc tggaactttg 3660
aggaggtggt cgataagggc gctagcgctc agagcttcat cgagcgcatg accaacttcg 3720
ataaaaacct gcccaatgaa aaagtcctcc ccaagcactc gctgctctac gagtacttca 3780
ccgtgtacaa cgagctcacc aaggtcaaat acgtcaccga gggcatgcgg aagccggcgt 3840
tcctgagcgg cgagcagaag aaggcgatag tggacctcct cttcaagacc aacaggaagg 3900
tgaccgtgaa gcaattaaaa gaggactact tcaagaaaat agagtgcttc gactccgtgg 3960
agatctcggg cgtggaggat cggttcaacg cctcactcgg cacgtatcac gacctcctca 4020
agatcattaa agacaaggac ttcctcgaca acgaggagaa cgaggacatc ctcgaggaca 4080
tcgtcctcac cctgaccctg ttcgaggacc gcgaaatgat cgaggagagg ctgaagacct 4140
acgcgcacct gttcgacgac aaggtcatga aacagctcaa gaggcgccgc tacactggtt 4200
ggggaaggct gtcccgcaag ctcattaatg gcatcaggga caagcagagc ggcaagacca 4260
tcctggactt cctcaagtcc gacgggttcg ccaaccgcaa cttcatgcag ctcattcacg 4320
acgactcgct cacgttcaag gaagacatcc agaaggcaca ggtgagcggg cagggtgact 4380
ccctccacga acacatcgcc aacctggccg gctcgccggc cattaaaaag ggcatcctgc 4440
agacggtcaa ggtcgtcgac gagctcgtga aggtgatggg ccggcacaag cccgaaaata 4500
tcgtcataga gatggccagg gagaaccaga ccacccaaaa agggcagaag aactcgcgcg 4560
agcggatgaa acggatcgag gagggcatta aagagctcgg gtcccagatc ctgaaggagc 4620
accccgtgga aaatacccag ctccagaatg aaaagctcta cctctactac ctgcagaacg 4680
gccgcgacat gtacgtggac caggagctgg acattaatcg gctatcggac tacgacgtcg 4740
accacatcgt gccgcagtcg ttcctcaagg acgatagcat cgacaacaag gtgctcaccc 4800
ggtcggataa aaatcggggc aagagcgaca acgtgcccag cgaggaggtc gtgaagaaga 4860
tgaaaaacta ctggcgccag ctcctcaacg cgaaactgat cacccagcgc aagttcgaca 4920
acctgacgaa ggcggaacgc ggtggcttga gcgaactcga taaggcgggc ttcataaaaa 4980
ggcagctggt cgagacgcgc cagatcacga agcatgtcgc ccagatcctg gacagccgca 5040
tgaatactaa gtacgatgaa aacgacaagc tgatccggga ggtgaaggtg atcacgctga 5100
agtccaagct cgtgtcggac ttccgcaagg acttccagtt ctacaaggtc cgcgagatca 5160
acaactacca ccacgcccac gacgcctacc tgaatgcggt ggtcgggacc gccctgatca 5220
agaagtaccc gaagctggag tcggagttcg tgtacggcga ctacaaggtc tacgacgtgc 5280
gcaaaatgat cgccaagtcc gagcaggaga tcggcaaggc cacggcaaaa tacttcttct 5340
actcgaacat catgaacttc ttcaagaccg agatcaccct cgcgaacggc gagatccgca 5400
agcgcccgct catcgaaacc aacggcgaga cgggcgagat cgtctgggat aagggccggg 5460
atttcgcgac ggtccgcaag gtgctctcca tgccgcaagt caatatcgtg aaaaagacgg 5520
aggtccagac gggcgggttc agcaaggagt ccatcctccc gaagcgcaac tccgacaagc 5580
tcatcgcgag gaagaaggat tggacccga aaaaatatgg cggcttcgac agcccgaccg 5640
tcgcatacag cgtcctcgtc gtggcgaagg tggagaaggg caagtcaaag aagctcaagt 5700

```
ccgtgaagga gctgctcggg atcacgatta tggagcggtc ctccttcgag aagaacccga  5760
tcgacttcct agaggccaag ggatataagg aggtcaagaa ggacctgatt attaaactgc  5820
cgaagtactc gctcttcgag ctggaaaacg gccgcaagag gatgctcgcc tccgcaggcg  5880
agttgcagaa gggcaacgag ctcgccctcc cgagcaaata cgtcaatttc ctgtacctcg  5940
ctagccacta tgaaaagctc aagggcagcc cggaggacaa cgagcagaag cagctcttcg  6000
tggagcagca caagcattac ctggacgaga tcatcgagca gatcagcgag ttctcgaagc  6060
gggtgatcct cgccgacgcg aacctggaca aggtgctgtc ggcatataac aagcaccgcg  6120
acaaaccaat acgcgagcag gccgaaaata tcatccacct cttcaccctc accaacctcg  6180
gcgctccggc agccttcaag tacttcgaca ccacgattga ccggaagcgg tacacgagca  6240
cgaaggaggt gctcgatgcg acgctgatcc accagagcat cacagggctc tatgaaacac  6300
gcatcgacct gagccagctg ggcggagaca agagaccacg ggaccgccac gatggcgagc  6360
tgggaggccg caagcgggca aggtaggtac cgttaaccta gacttgtcca tcttctggat  6420
tggccaactt aattaatgta tgaaataaaa ggatgcacac atagtgacat gctaatcact  6480
ataatgtggg catcaaagtt gtgtgttatg tgtaattact agttatctga ataaaagaga  6540
aagagatcat ccatatttct tatcctaaat gaatgtcacg tgtctttata attctttgat  6600
gaaccagatg catttcatta accaaatcca tatacatata aatattaatc atatataatt  6660
aatatcaatt gggttagcaa aacaaatcta gtctaggtgt gttttgcgaa tgcggcc     6717

SEQ ID NO: 6           moltype = RNA  length = 39
FEATURE                Location/Qualifiers
misc_feature           1..39
                       note = synthesized sequence-crRNA containing the LIGCas-3
                        target sequence in the variable targeting domain
source                 1..39
                       mol_type = other RNA
                       organism = synthetic construct
SEQUENCE: 6
gcgtacgcgt acgtgtggtt ttagagctat gctgttttg                         39

SEQ ID NO: 7           moltype = RNA  length = 86
FEATURE                Location/Qualifiers
misc_feature           1..86
                       note = tracrRNA
source                 1..86
                       mol_type = unassigned RNA
                       organism = Streptococcus pyogenes
SEQUENCE: 7
ggaaccattc aaaacagcat agcaagttaa aataaggcta gtccgttatc aacttgaaaa  60
agtggcaccg agtcggtgct tttttt                                       86

SEQ ID NO: 8           moltype = RNA  length = 94
FEATURE                Location/Qualifiers
misc_feature           1..94
                       note = synthesized sequence- Long guide RNA containing the
                        LIGCas-3 target sequence in the variable targeting domain
source                 1..94
                       mol_type = other RNA
                       organism = synthetic construct
SEQUENCE: 8
gcgtacgcgt acgtgtggtt ttagagctag aaatagcaag ttaaaataag gctagtccgt  60
tatcaacttg aaaaagtggc accgagtcgg tgct                              94

SEQ ID NO: 9           moltype = DNA  length = 1000
FEATURE                Location/Qualifiers
source                 1..1000
                       mol_type = genomic DNA
                       organism = Zea mays
SEQUENCE: 9
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcga agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt   720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt                        1000

SEQ ID NO: 10          moltype = DNA  length = 16
FEATURE                Location/Qualifiers
source                 1..16
```

```
                          mol_type = genomic DNA
                          organism = Zea mays
SEQUENCE: 10
tttttttttt tttttt                                                   16

SEQ ID NO: 11             moltype = RNA  length = 59
FEATURE                   Location/Qualifiers
misc_feature              1..59
                          note = synthesized sequence- Short guide RNA containing the
                           LIGCas-3 variable targeting domain
source                    1..59
                          mol_type = other RNA
                          organism = synthetic construct
SEQUENCE: 11
gcgtacgcgt acgtgtggtt ttagagctag aaatagcaag ttaaaataag gctagtccg   59

SEQ ID NO: 12             moltype = DNA  length = 1102
FEATURE                   Location/Qualifiers
misc_feature              1..1102
                          note = synthesized sequence- Maize optimized long guide RNA
                           expression cassette containing the LIGCas-3 variable
                           targeting domain
source                    1..1102
                          mol_type = other DNA
                          organism = synthetic construct
SEQUENCE: 12
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta ttttttttata taccttttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc cacccttgact aatcacaaga  960
gtggagcgta ccttataaac cgagccgcaa gcaccgaatt gcgtacgcgt acgtgtggtt  1020
ttagagctag aaatagcaag ttaaaataag gctagtccgt tatcaacttg aaaaagtggc  1080
accgagtcgg tgcttttttt tt                                           1102

SEQ ID NO: 13             moltype = DNA  length = 27
FEATURE                   Location/Qualifiers
source                    1..27
                          mol_type = genomic DNA
                          organism = Zea mays
SEQUENCE: 13
gtactccatc cgccccatcg agtaggg                                      27

SEQ ID NO: 14             moltype = DNA  length = 24
FEATURE                   Location/Qualifiers
source                    1..24
                          mol_type = genomic DNA
                          organism = Zea mays
SEQUENCE: 14
gcacgtacgt caccatcccg ccgg                                         24

SEQ ID NO: 15             moltype = DNA  length = 24
FEATURE                   Location/Qualifiers
source                    1..24
                          mol_type = genomic DNA
                          organism = Zea mays
SEQUENCE: 15
gacgtacgtg ccctactcga tggg                                         24

SEQ ID NO: 16             moltype = DNA  length = 24
FEATURE                   Location/Qualifiers
source                    1..24
                          mol_type = genomic DNA
                          organism = Zea mays
SEQUENCE: 16
gtaccgtacg tgccccggcg gagg                                         24

SEQ ID NO: 17             moltype = DNA  length = 24
```

```
FEATURE                Location/Qualifiers
source                 1..24
                       mol_type = genomic DNA
                       organism = Zea mays
SEQUENCE: 17
ggaattgtac cgtacgtgcc ccgg                                              24

SEQ ID NO: 18          moltype = DNA  length = 20
FEATURE                Location/Qualifiers
source                 1..20
                       mol_type = genomic DNA
                       organism = Zea mays
SEQUENCE: 18
gcgtacgcgt acgtgtgagg                                                   20

SEQ ID NO: 19          moltype = DNA  length = 22
FEATURE                Location/Qualifiers
source                 1..22
                       mol_type = genomic DNA
                       organism = Zea mays
SEQUENCE: 19
gctggccgag gtcgactacc gg                                                22

SEQ ID NO: 20          moltype = DNA  length = 23
FEATURE                Location/Qualifiers
source                 1..23
                       mol_type = genomic DNA
                       organism = Zea mays
SEQUENCE: 20
ggccgaggtc gactaccggc cgg                                               23

SEQ ID NO: 21          moltype = DNA  length = 23
FEATURE                Location/Qualifiers
source                 1..23
                       mol_type = genomic DNA
                       organism = Zea mays
SEQUENCE: 21
ggcgcgagct cgtgcttcac cgg                                               23

SEQ ID NO: 22          moltype = DNA  length = 21
FEATURE                Location/Qualifiers
source                 1..21
                       mol_type = genomic DNA
                       organism = Zea mays
SEQUENCE: 22
ggtgccaatc atgcgtcgcg g                                                 21

SEQ ID NO: 23          moltype = DNA  length = 20
FEATURE                Location/Qualifiers
source                 1..20
                       mol_type = genomic DNA
                       organism = Zea mays
SEQUENCE: 23
ggtcgccatc acgggacagg                                                   20

SEQ ID NO: 24          moltype = DNA  length = 24
FEATURE                Location/Qualifiers
source                 1..24
                       mol_type = genomic DNA
                       organism = Zea mays
SEQUENCE: 24
gtcgcggcac ctgtcccgtg atgg                                              24

SEQ ID NO: 25          moltype = DNA  length = 23
FEATURE                Location/Qualifiers
source                 1..23
                       mol_type = genomic DNA
                       organism = Zea mays
SEQUENCE: 25
ggaatgctgg aactgcaatg cgg                                               23

SEQ ID NO: 26          moltype = DNA  length = 24
FEATURE                Location/Qualifiers
source                 1..24
                       mol_type = genomic DNA
                       organism = Zea mays
SEQUENCE: 26
gcagctcttc ttggggaatg ctgg                                              24
```

-continued

```
SEQ ID NO: 27          moltype = DNA  length = 23
FEATURE                Location/Qualifiers
source                 1..23
                       mol_type = genomic DNA
                       organism = Zea mays
SEQUENCE: 27
gcagtaacag ctgctgtcaa tgg                                          23

SEQ ID NO: 28          moltype = DNA  length = 56
FEATURE                Location/Qualifiers
misc_feature           1..56
                       note = synthesized sequence- MS26Cas-1 forward primer
source                 1..56
                       mol_type = other DNA
                       organism = synthetic construct
SEQUENCE: 28
ctacactctt tccctacacg acgctcttcc gatctaggac cggaagctcg ccgcgt      56

SEQ ID NO: 29          moltype = DNA  length = 54
FEATURE                Location/Qualifiers
misc_feature           1..54
                       note = synthesized sequence- MS26Cas-1 and MS26Cas-3
                        reverse primer
source                 1..54
                       mol_type = other DNA
                       organism = synthetic construct
SEQUENCE: 29
caagcagaag acggcatacg agctcttccg atcttcctgg aggacgacgt gctg        54

SEQ ID NO: 30          moltype = DNA  length = 59
FEATURE                Location/Qualifiers
misc_feature           1..59
                       note = synthesized sequence- MS26Cas-2 forward primer
source                 1..59
                       mol_type = other DNA
                       organism = synthetic construct
SEQUENCE: 30
ctacactctt tccctacacg acgctcttcc gatctaaggt cctggaggac gacgtgctg   59

SEQ ID NO: 31          moltype = DNA  length = 51
FEATURE                Location/Qualifiers
misc_feature           1..51
                       note = synthesized sequence- MS26Cas-2 and MS26
                        meganuclease reverse primer
source                 1..51
                       mol_type = other DNA
                       organism = synthetic construct
SEQUENCE: 31
caagcagaag acggcatacg agctcttccg atctccggaa gctcgccgcg t           51

SEQ ID NO: 32          moltype = DNA  length = 56
FEATURE                Location/Qualifiers
misc_feature           1..56
                       note = synthesized sequence- MS26Cas-3 forward primer
source                 1..56
                       mol_type = other DNA
                       organism = synthetic construct
SEQUENCE: 32
ctacactctt tccctacacg acgctcttcc gatcttcctc cggaagctcg ccgcgt      56

SEQ ID NO: 33          moltype = DNA  length = 59
FEATURE                Location/Qualifiers
misc_feature           1..59
                       note = synthesized sequence- MS26 Meganuclease forward
                        primer
source                 1..59
                       mol_type = other DNA
                       organism = synthetic construct
SEQUENCE: 33
ctacactctt tccctacacg acgctcttcc gatctttcct cctggaggac gacgtgctg   59

SEQ ID NO: 34          moltype = DNA  length = 63
FEATURE                Location/Qualifiers
misc_feature           1..63
                       note = synthesized sequence- LIGCas-1 forward primer
source                 1..63
                       mol_type = other DNA
                       organism = synthetic construct
SEQUENCE: 34
```

-continued

```
ctacactctt tccctacacg acgctcttcc gatctaggac tgtaacgatt tacgcacctg  60
ctg                                                                63

SEQ ID NO: 35          moltype = DNA  length = 58
FEATURE                Location/Qualifiers
misc_feature           1..58
                       note = synthesized sequence- LIGCas-1 and LIGCas-2 reverse
                        primer
source                 1..58
                       mol_type = other DNA
                       organism = synthetic construct
SEQUENCE: 35
caagcagaag acggcatacg agctcttccg atctgcaaat gagtagcagc gcacgtat    58

SEQ ID NO: 36          moltype = DNA  length = 63
FEATURE                Location/Qualifiers
misc_feature           1..63
                       note = synthesized sequence- LIGCas-2 forward primer
source                 1..63
                       mol_type = other DNA
                       organism = synthetic construct
SEQUENCE: 36
ctacactctt tccctacacg acgctcttcc gatcttcctc tgtaacgatt tacgcacctg  60
ctg                                                                63

SEQ ID NO: 37          moltype = DNA  length = 60
FEATURE                Location/Qualifiers
misc_feature           1..60
                       note = synthesized sequence- LIGCas-3 forward primer
source                 1..60
                       mol_type = other DNA
                       organism = synthetic construct
SEQUENCE: 37
ctacactctt tccctacacg acgctcttcc gatctaaggc gcaaatgagt agcagcgcac  60

SEQ ID NO: 38          moltype = DNA  length = 57
FEATURE                Location/Qualifiers
misc_feature           1..57
                       note = synthesized sequence- LIGCas-3 and LIG3-4
                        meganuclease reverse primer
source                 1..57
                       mol_type = other DNA
                       organism = synthetic construct
SEQUENCE: 38
caagcagaag acggcatacg agctcttccg atctcacctg ctgggaattg taccgta     57

SEQ ID NO: 39          moltype = DNA  length = 60
FEATURE                Location/Qualifiers
misc_feature           1..60
                       note = synthesized sequence- LIG3-4 meganuclease forward
                        primer
source                 1..60
                       mol_type = other DNA
                       organism = synthetic construct
SEQUENCE: 39
ctacactctt tccctacacg acgctcttcc gatctccttc gcaaatgagt agcagcgcac  60

SEQ ID NO: 40          moltype = DNA  length = 58
FEATURE                Location/Qualifiers
misc_feature           1..58
                       note = synthesized sequence- MS45Cas-1 forward primer
source                 1..58
                       mol_type = other DNA
                       organism = synthetic construct
SEQUENCE: 40
ctacactctt tccctacacg acgctcttcc gatctaggag gacccgttcg gcctcagt    58

SEQ ID NO: 41          moltype = DNA  length = 54
FEATURE                Location/Qualifiers
misc_feature           1..54
                       note = synthesized sequence- MS45Cas-1, MS45Cas-2 and
                        MS45Cas-3 reverse primer
source                 1..54
                       mol_type = other DNA
                       organism = synthetic construct
SEQUENCE: 41
caagcagaag acggcatacg agctcttccg atctgccggc tggcattgtc tctg        54

SEQ ID NO: 42          moltype = DNA  length = 58
```

-continued

```
FEATURE                Location/Qualifiers
misc_feature           1..58
                       note = synthesized sequence- MS45Cas-2 forward primer
source                 1..58
                       mol_type = other DNA
                       organism = synthetic construct
SEQUENCE: 42
ctacactctt tccctacacg acgctcttcc gatcttcctg gacccgttcg gcctcagt    58

SEQ ID NO: 43          moltype = DNA  length = 58
FEATURE                Location/Qualifiers
misc_feature           1..58
                       note = synthesized sequence- MS45Cas-3 forward primer
source                 1..58
                       mol_type = other DNA
                       organism = synthetic construct
SEQUENCE: 43
ctacactctt tccctacacg acgctcttcc gatctgaagg gacccgttcg gcctcagt    58

SEQ ID NO: 44          moltype = DNA  length = 58
FEATURE                Location/Qualifiers
misc_feature           1..58
                       note = synthesized sequence- ALSCas-1 forward primer
source                 1..58
                       mol_type = other DNA
                       organism = synthetic construct
SEQUENCE: 44
ctacactctt tccctacacg acgctcttcc gatctaaggc gacgatgggc gtctcctg    58

SEQ ID NO: 45          moltype = DNA  length = 53
FEATURE                Location/Qualifiers
misc_feature           1..53
                       note = synthesized sequence- ALSCas-1, ALSCas-2 and
                        ALSCas-3 reverse primer
source                 1..53
                       mol_type = other DNA
                       organism = synthetic construct
SEQUENCE: 45
caagcagaag acggcatacg agctcttccg atctgcgtct gcatcgccac ctc         53

SEQ ID NO: 46          moltype = DNA  length = 58
FEATURE                Location/Qualifiers
misc_feature           1..58
                       note = synthesized sequence- ALSCas-2 forward primer
source                 1..58
                       mol_type = other DNA
                       organism = synthetic construct
SEQUENCE: 46
ctacactctt tccctacacg acgctcttcc gatctttccc gacgatgggc gtctcctg    58

SEQ ID NO: 47          moltype = DNA  length = 58
FEATURE                Location/Qualifiers
misc_feature           1..58
                       note = synthesized sequence- ALSCas-3 forward primer
source                 1..58
                       mol_type = other DNA
                       organism = synthetic construct
SEQUENCE: 47
ctacactctt tccctacacg acgctcttcc gatctggaac gacgatgggc gtctcctg    58

SEQ ID NO: 48          moltype = DNA  length = 63
FEATURE                Location/Qualifiers
misc_feature           1..63
                       note = synthesized sequence- EPSPSCas-1 forward primer
source                 1..63
                       mol_type = other DNA
                       organism = synthetic construct
SEQUENCE: 48
ctacactctt tccctacacg acgctcttcc gatctggaag aggaaacata cgttgcattt  60
cca                                                                63

SEQ ID NO: 49          moltype = DNA  length = 57
FEATURE                Location/Qualifiers
misc_feature           1..57
                       note = synthesized sequence- PSPSCas-1 and EPSPSCas-3
                        reverse primer
source                 1..57
                       mol_type = other DNA
                       organism = synthetic construct
```

```
SEQUENCE: 49
caagcagaag acggcatacg agctcttccg atctggtgga aagttcccag ttgagga     57

SEQ ID NO: 50          moltype = DNA  length = 62
FEATURE                Location/Qualifiers
misc_feature           1..62
                       note = synthesized sequence- PSPSCas-2 forward primer
source                 1..62
                       mol_type = other DNA
                       organism = synthetic construct
SEQUENCE: 50
ctacactctt tccctacacg acgctcttcc gatctaagcg gtggaaagtt cccagttgag  60
ga                                                                 62

SEQ ID NO: 51          moltype = DNA  length = 58
FEATURE                Location/Qualifiers
misc_feature           1..58
                       note = synthesized sequence- EPSPSCas-2 reverse primer
source                 1..58
                       mol_type = other DNA
                       organism = synthetic construct
SEQUENCE: 51
caagcagaag acggcatacg agctcttccg atctgaggaa acatacgttg catttcca    58

SEQ ID NO: 52          moltype = DNA  length = 63
FEATURE                Location/Qualifiers
misc_feature           1..63
                       note = synthesized sequence- EPSPSCas-3 forward primer
source                 1..63
                       mol_type = other DNA
                       organism = synthetic construct
SEQUENCE: 52
ctacactctt tccctacacg acgctcttcc gatctccttg aggaaacata cgttgcattt  60
cca                                                                63

SEQ ID NO: 53          moltype = DNA  length = 43
FEATURE                Location/Qualifiers
misc_feature           1..43
                       note = synthesized sequence- Forward primer for secondary
                        PCR
source                 1..43
                       mol_type = other DNA
                       organism = synthetic construct
SEQUENCE: 53
aatgatacgg cgaccaccga gatctacact ctttccctac acg                    43

SEQ ID NO: 54          moltype = DNA  length = 18
FEATURE                Location/Qualifiers
misc_feature           1..18
                       note = synthesized sequence- Reverse primer for secondary
                        PCR
source                 1..18
                       mol_type = other DNA
                       organism = synthetic construct
SEQUENCE: 54
caagcagaag acggcata                                                18

SEQ ID NO: 55          moltype = DNA  length = 93
FEATURE                Location/Qualifiers
source                 1..93
                       mol_type = genomic DNA
                       organism = Zea mays
SEQUENCE: 55
ctgtaacgat ttacgcacct gctgggaatt gtaccgtacg tgccccggcg gaggatatat  60
atacctcaca cgtacgcgta cgcgtatata tac                               93

SEQ ID NO: 56          moltype = DNA  length = 98
FEATURE                Location/Qualifiers
source                 1..98
                       mol_type = genomic DNA
                       organism = Zea mays
SEQUENCE: 56
aggactgtaa cgatttacgc acctgctggg aattgtaccg tacgtgcccc ggtcggagga  60
tatatatacc tcacacgtac gcgtacgcgt atatatac                          98

SEQ ID NO: 57          moltype = DNA  length = 98
FEATURE                Location/Qualifiers
source                 1..98
                       mol_type = genomic DNA
```

-continued

```
                       organism = Zea mays
SEQUENCE: 57
aggactgtaa cgatttacgc acctgctggg aattgtaccg tacgtgcccc ggacggagga  60
tatatatacc tcacacgtac gcgtacgcgt atatatac                          98

SEQ ID NO: 58          moltype = DNA  length = 98
FEATURE                Location/Qualifiers
source                 1..98
                       mol_type = genomic DNA
                       organism = Zea mays
SEQUENCE: 58
aggactgtaa cgatttacgc acctgctggg aattgtaccg tacgtgcccc gggcggagga  60
tatatatacc tcacacgtac gcgtacgcgt atatatac                          98

SEQ ID NO: 59          moltype = DNA  length = 95
FEATURE                Location/Qualifiers
source                 1..95
                       mol_type = genomic DNA
                       organism = Zea mays
SEQUENCE: 59
aggactgtaa cgatttacgc acctgctggg aattgtaccg tacgtgcggt cggaggatat  60
atatacctca cacgtacgcg tacgcgtata tatac                             95

SEQ ID NO: 60          moltype = DNA  length = 98
FEATURE                Location/Qualifiers
source                 1..98
                       mol_type = genomic DNA
                       organism = Zea mays
SEQUENCE: 60
aggactgtaa cgatttacgc acctgctggg aattgtaccg tacgtgcccc ggccggagga  60
tatatatacc tcacacgtac gcgtacgcgt atatatac                          98

SEQ ID NO: 61          moltype = DNA  length = 96
FEATURE                Location/Qualifiers
source                 1..96
                       mol_type = genomic DNA
                       organism = Zea mays
SEQUENCE: 61
aggactgtaa cgatttacgc acctgctggg aattgtaccg tacgtgcccc gcggaggata  60
tatatacctc acacgtacgc gtacgcgtat atatac                            96

SEQ ID NO: 62          moltype = DNA  length = 96
FEATURE                Location/Qualifiers
source                 1..96
                       mol_type = genomic DNA
                       organism = Zea mays
SEQUENCE: 62
aggactgtaa cgatttacgc acctgctggg aattgtaccg tacgtgcccc ggggaggata  60
tatatacctc acacgtacgc gtacgcgtat atatac                            96

SEQ ID NO: 63          moltype = DNA  length = 94
FEATURE                Location/Qualifiers
source                 1..94
                       mol_type = genomic DNA
                       organism = Zea mays
SEQUENCE: 63
aggactgtaa cgatttacgc acctgctggg aattgtaccg tacgtgcccc ggaggatata  60
tatacctcac acgtacgcgt acgcgtatat atac                              94

SEQ ID NO: 64          moltype = DNA  length = 94
FEATURE                Location/Qualifiers
source                 1..94
                       mol_type = genomic DNA
                       organism = Zea mays
SEQUENCE: 64
aggactgtaa cgatttacgc acctgctggg aattgtaccg tacgtgcgtc ggaggatata  60
tatacctcac acgtacgcgt acgcgtatat atac                              94

SEQ ID NO: 65          moltype = DNA  length = 43
FEATURE                Location/Qualifiers
source                 1..43
                       mol_type = genomic DNA
                       organism = Zea mays
SEQUENCE: 65
aggactgtaa cgatttacgc acctgctggg aattgtaccg tac                    43

SEQ ID NO: 66          moltype = DNA  length = 98
FEATURE                Location/Qualifiers
source                 1..98
```

```
                        mol_type = genomic DNA
                        organism = Zea mays
SEQUENCE: 66
tcctctgtaa cgatttacgc acctgctggg aattgtaccg tacgtgaccc cggcggagga  60
tatatatacc tcacacgtac gcgtacgcgt atatatac                          98

SEQ ID NO: 67           moltype = DNA  length = 96
FEATURE                 Location/Qualifiers
source                  1..96
                        mol_type = genomic DNA
                        organism = Zea mays
SEQUENCE: 67
tcctctgtaa cgatttacgc acctgctggg aattgtaccg tacgtccccg gcggaggata  60
tatatacctc acacgtacgc gtacgcgtat atatac                            96

SEQ ID NO: 68           moltype = DNA  length = 98
FEATURE                 Location/Qualifiers
source                  1..98
                        mol_type = genomic DNA
                        organism = Zea mays
SEQUENCE: 68
tcctctgtaa cgatttacgc acctgctggg aattgtaccg tacgtgtccc cggcggagga  60
tatatatacc tcacacgtac gcgtacgcgt atatatac                          98

SEQ ID NO: 69           moltype = DNA  length = 94
FEATURE                 Location/Qualifiers
source                  1..94
                        mol_type = genomic DNA
                        organism = Zea mays
SEQUENCE: 69
tcctctgtaa cgatttacgc acctgctggg aattgtaccg tacccccggc ggaggatata  60
tatacctcac acgtacgcgt acgcgtatat atac                              94

SEQ ID NO: 70           moltype = DNA  length = 93
FEATURE                 Location/Qualifiers
source                  1..93
                        mol_type = genomic DNA
                        organism = Zea mays
SEQUENCE: 70
tcctctgtaa cgatttacgc acctgctggg aattgtaccg taccccggcg gaggatatat  60
atacctcaca cgtacgcgta cgcgtatata tac                               93

SEQ ID NO: 71           moltype = DNA  length = 98
FEATURE                 Location/Qualifiers
source                  1..98
                        mol_type = genomic DNA
                        organism = Zea mays
SEQUENCE: 71
tcctctgtaa cgatttacgc acctgctggg aattgtaccg tacgtggccc cggcggagga  60
tatatatacc tcacacgtac gcgtacgcgt atatatac                          98

SEQ ID NO: 72           moltype = DNA  length = 92
FEATURE                 Location/Qualifiers
source                  1..92
                        mol_type = genomic DNA
                        organism = Zea mays
SEQUENCE: 72
tcctctgtaa cgatttacgc acctgctggg aattgtaccg tacccggcgg aggatatata  60
tacctcacac gtacgcgtac gcgtatatat ac                                92

SEQ ID NO: 73           moltype = DNA  length = 99
FEATURE                 Location/Qualifiers
source                  1..99
                        mol_type = genomic DNA
                        organism = Zea mays
SEQUENCE: 73
tcctctgtaa cgatttacgc acctgctggg aattgtaccg tacgtgaacc ccggcggagg  60
atatatatac ctcacacgta cgcgtacgcg tatatatac                         99

SEQ ID NO: 74           moltype = DNA  length = 61
FEATURE                 Location/Qualifiers
source                  1..61
                        mol_type = genomic DNA
                        organism = Zea mays
SEQUENCE: 74
tcctctgtaa cgatttacgc acctgctggg aattgtaccg tacgtgtacg cgtatatata  60
c                                                                  61

SEQ ID NO: 75           moltype = DNA  length = 95
```

```
FEATURE                Location/Qualifiers
source                 1..95
                       mol_type = genomic DNA
                       organism = Zea mays
SEQUENCE: 75
tcctctgtaa cgatttacgc acctgctggg aattgtaccg tacgccccgg cggaggatat  60
atatacctca cacgtacgcg tacgcgtata tatac                             95

SEQ ID NO: 76          moltype = DNA  length = 93
FEATURE                Location/Qualifiers
source                 1..93
                       mol_type = genomic DNA
                       organism = Zea mays
SEQUENCE: 76
cgcaaatgag tagcagcgca cgtatatata cgcgtacgcg tacgtgtgag gtatatatat  60
cctccgccgg ggcacgtacg gtacaattcc cag                               93

SEQ ID NO: 77          moltype = DNA  length = 98
FEATURE                Location/Qualifiers
source                 1..98
                       mol_type = genomic DNA
                       organism = Zea mays
SEQUENCE: 77
aaggcgcaaa tgagtagcag cgcacgtata tatacgcgta cgcgtacgtt gtgaggtata  60
tatatcctcc gccggggcac gtacggtaca attcccag                          98

SEQ ID NO: 78          moltype = DNA  length = 96
FEATURE                Location/Qualifiers
source                 1..96
                       mol_type = genomic DNA
                       organism = Zea mays
SEQUENCE: 78
aaggcgcaaa tgagtagcag cgcacgtata tatacgcgta cgcgtacggt gaggtatata  60
tatcctccgc cggggcacgt acggtacaat tcccag                            96

SEQ ID NO: 79          moltype = DNA  length = 96
FEATURE                Location/Qualifiers
source                 1..96
                       mol_type = genomic DNA
                       organism = Zea mays
SEQUENCE: 79
aaggcgcaaa tgagtagcag cgcacgtata tatacgcgta cgcgtactgt gaggtatata  60
tatcctccgc cggggcacgt acggtacaat tcccag                            96

SEQ ID NO: 80          moltype = DNA  length = 95
FEATURE                Location/Qualifiers
source                 1..95
                       mol_type = genomic DNA
                       organism = Zea mays
SEQUENCE: 80
aaggcgcaaa tgagtagcag cgcacgtata tatacgcgta cgcgtacgtg aggtatatat  60
atcctccgcc ggggcacgta cggtacaatt cccag                             95

SEQ ID NO: 81          moltype = DNA  length = 68
FEATURE                Location/Qualifiers
source                 1..68
                       mol_type = genomic DNA
                       organism = Zea mays
SEQUENCE: 81
aaggcgcaaa tgagtagcag cgcacgtata tatatcctcc gccggggcac gtacggtaca  60
attcccag                                                           68

SEQ ID NO: 82          moltype = DNA  length = 55
FEATURE                Location/Qualifiers
source                 1..55
                       mol_type = genomic DNA
                       organism = Zea mays
SEQUENCE: 82
aaggcgcaaa tgagtagcag cgcacgtata tatacgcgta cggtacaatt cccag       55

SEQ ID NO: 83          moltype = DNA  length = 93
FEATURE                Location/Qualifiers
source                 1..93
                       mol_type = genomic DNA
                       organism = Zea mays
SEQUENCE: 83
aaggcgcaaa tgagtagcag cgcacgtata tatacgcgta cgcgtgtgag gtatatatat  60
cctccgccgg ggcacgtacg gtacaattcc cag                               93
```

```
SEQ ID NO: 84          moltype = DNA  length = 69
FEATURE                Location/Qualifiers
source                 1..69
                       mol_type = genomic DNA
                       organism = Zea mays
SEQUENCE: 84
aaggcgcaaa tgagtagcag cgcacgtata tatacgcgta cgccggggca cgtacggtac  60
aattcccag                                                           69

SEQ ID NO: 85          moltype = DNA  length = 66
FEATURE                Location/Qualifiers
source                 1..66
                       mol_type = genomic DNA
                       organism = Zea mays
SEQUENCE: 85
aaggcgcaaa tgagtagcag cgcacgtata tatcctccgc cggggcacgt acggtacaat  60
tcccag                                                              66

SEQ ID NO: 86          moltype = DNA  length = 95
FEATURE                Location/Qualifiers
source                 1..95
                       mol_type = genomic DNA
                       organism = Zea mays
SEQUENCE: 86
aaggcgcaaa tgagtagcag cgcacgtata tatacgcgta cgcgtatgtg aggtatatat  60
atcctccgcc ggggcacgta cggtacaatt cccag                              95

SEQ ID NO: 87          moltype = DNA  length = 95
FEATURE                Location/Qualifiers
source                 1..95
                       mol_type = genomic DNA
                       organism = Zea mays
SEQUENCE: 87
ccttcgcaaa tgagtagcag cgcacgtata tatacgcgta cgcgtacgtg aggtatatat  60
atcctccgcc ggggcacgta cggtacaatt cccag                              95

SEQ ID NO: 88          moltype = DNA  length = 68
FEATURE                Location/Qualifiers
source                 1..68
                       mol_type = genomic DNA
                       organism = Zea mays
SEQUENCE: 88
ccttcgcaaa tgagtagcag cgcacgtata tatatcctcc gccggggcac gtacggtaca  60
attcccag                                                            68

SEQ ID NO: 89          moltype = DNA  length = 65
FEATURE                Location/Qualifiers
source                 1..65
                       mol_type = genomic DNA
                       organism = Zea mays
SEQUENCE: 89
ccttcgcaaa tgagtagcag cgcacgtata tatacgcgta cgcgtacgta cggtacaatt  60
cccag                                                               65

SEQ ID NO: 90          moltype = DNA  length = 55
FEATURE                Location/Qualifiers
source                 1..55
                       mol_type = genomic DNA
                       organism = Zea mays
SEQUENCE: 90
ccttcgcaaa tgagtagcag cgcacgtata tatacgcgta cggtacaatt cccag        55

SEQ ID NO: 91          moltype = DNA  length = 69
FEATURE                Location/Qualifiers
source                 1..69
                       mol_type = genomic DNA
                       organism = Zea mays
SEQUENCE: 91
ccttcgcaaa tgagtagcag cgcacgtata tatacgcgta cgccggggca cgtacggtac  60
aattcccag                                                           69

SEQ ID NO: 92          moltype = DNA  length = 85
FEATURE                Location/Qualifiers
source                 1..85
                       mol_type = genomic DNA
                       organism = Zea mays
SEQUENCE: 92
ccttcgcaaa tgagtagcag cgcacgtata tatacgtgtg aggtatatat atcctccgcc  60
ggggcacgta cggtacaatt cccag                                         85
```

```
SEQ ID NO: 93          moltype = DNA  length = 93
FEATURE                Location/Qualifiers
source                 1..93
                       mol_type = genomic DNA
                       organism = Zea mays
SEQUENCE: 93
ccttcgcaaa tgagtagcag cgcacgtata tatacgcgta cgcgtgtgag gtatatatat  60
cctccgccgg ggcacgtacg gtacaattcc cag                               93

SEQ ID NO: 94          moltype = DNA  length = 66
FEATURE                Location/Qualifiers
source                 1..66
                       mol_type = genomic DNA
                       organism = Zea mays
SEQUENCE: 94
ccttcgcaaa tgagtagcag cgcacgtata tatcctccgc cggggcacgt acggtacaat  60
tcccag                                                             66

SEQ ID NO: 95          moltype = DNA  length = 95
FEATURE                Location/Qualifiers
source                 1..95
                       mol_type = genomic DNA
                       organism = Zea mays
SEQUENCE: 95
ccttcgcaaa tgagtagcag cgcacgtata tatacgcgta cgcgtacgtg tggtatatat  60
atcctccgcc ggggcacgta cggtacaatt cccag                             95

SEQ ID NO: 96          moltype = DNA  length = 102
FEATURE                Location/Qualifiers
source                 1..102
                       mol_type = genomic DNA
                       organism = Zea mays
SEQUENCE: 96
ccttcgcaaa tgagtagcag cgcacgtata tatacgcgta cggtatatat acgtgtgagg  60
tatatatatc ctccgccggg gcacgtacgg tacaattccc ag                     102

SEQ ID NO: 97          moltype = DNA  length = 5424
FEATURE                Location/Qualifiers
misc_feature           1..5424
                       note = synthesized sequence- donor DNA -HR Repair DNA
source                 1..5424
                       mol_type = other DNA
                       organism = synthetic construct
SEQUENCE: 97
cccatagaaa actgtgtgct ataatacacc aaaaggaaag caaagtgaaa aggaaacttt  60
gaatagccaa gaagactcgg agtgcttcac gccttcacct atcccacata ggtgatgagc  120
taagagtaaa atgtagattc tctcgagtac tgaatattgc ctgcactttt ccttgcagta  180
aatacacctt taatccatga cgagagtcca ctctttgagt ccgtcttgag attcttccat  240
tgatcataca acatgacctc gaagtcctga tggagaacaa cttatataat taaaactaca  300
atacagaaag ttcctgacaa ttaaaacctt tggtggtggc atgccgtagg ttaaaaaaaa  360
tagataatga caacacaact ggagacacgc tctttgccga gtgctcacac gtttgctgag  420
agcgagcact cggcaaatat atgatttgcc gaataccacc ctcctcggca aaacaataca  480
ctaggcaaaa aggtagtttc ccatcaccat gatgcccgcc gttaatgtac cttctatgcc  540
gagtatgttg gcgctcagca aagagatcgt taccggcgtt tgtttcacca agagctcttt  600
gacgagtgtg gcacacgaca aaaccttttg ccgagtgtaa ttagtcgttt gccaagtgac  660
tggtgcagtt ggcaaaggag tcgtttatta tgtgtgggca aaatgatata tggtgccagt  720
tagggctagc aaattaaagg gggggggggg ggggttaggt tgaagaaggt gacgagtaat  780
aaggtctcgg acggccgcgc gcatatatat cagatccgat ccaatggcac acggtgcaaa  840
cgaaaagcac gaaatttcca ccagcttaat tagggagaga aaaatagagc accagctgat  900
gagtgaatga atgagataga cgggacacag agggtccagc aggctagcct actctggccg  960
ccctaaatag aagtcagtgc cgtgacgacg cgcaaacttc ttttgatcgg ctgcggaaat  1020
aatatactgt aacgatttac gcacctgctg ggaattgtac cgtacgtgcc ccggcggagg  1080
atatatatac ctcacacaag ggcgaattgt actagttagt tagctagtcg gtcctagatg  1140
ccgtaatcat tagctaatcg taagtgacgc ttggacacga gcggcttgag ctaggaacct  1200
acgaagtcat cggaatcagc tcaggtgtac agaagttcct atactttctg gagaatagga  1260
acttcggaat aggaacttcg tatacgctag ggccgcattc gcaaaacaca cctagactag  1320
atttgttttg ctaacccaat tgatattaat tatatatgat taatatttat atgtatatgg  1380
atttggttaa tgaaatgcat ctggttcatc aaagaattat aaagacacgt gacattcatt  1440
taggataaga aatatggatg atctctttct cttttattca gataactagt aattacacat  1500
aacacacaac tttgatgccc acattatagt gattagcatg tcactatgtg tgcatccttt  1560
tatttcatac attaattaag ttggccaatc cagaagatgg acaagtctag gtttcgactc  1620
agatctgcgt caccgggcgc accgggcgcg gcggggccgg cagctcgaag tcgcgctgcc  1680
agaagccgac gtcgtgccag ccgccgtgct tgtagccggc ggcgcggagg gtgccgcggg  1740
cggtgtagcc gagggcctcg tggaggcgca cggacgggtc gttcgggagg ccgatcacgg  1800
ccaccacgga cttgaagccc tgggcctcca tgctcttgag gaggtgggtg tagagggtgg  1860
agccgaggcc gaggcgctgg tggcggtggg acacgtacac ggtggactcc acggtccagt  1920
cgtaggcgtt gcgggccttc cacgggccgg cgtaggcgat gccggccacc acgccctcca  1980
cctcggccac gagccacggg tagcggtcct ggaggcgctc caggtcgtcg atccactcct  2040
```

-continued

```
gcggggtctg cggctcggtg cggaagttca cggtggaggt ctcgatgtag tggttcacga  2100
tgtcgcacac ggcggccatg tcggcggcgg tggccgggcg gatctcgacg gggcggcgct  2160
cgggggacat ggtgtcgtgt ggatcccggt ggatctgaag ttcctatact ttctagagaa  2220
taggaacttc ggaataggaa cttcgctagc gaattgatcc tctagagtcg acctgcagaa  2280
gtaacaccaa acaacagggt gagcatcgac aaaagaaaca gtaccaagca aataaatagc  2340
gtatgaaggc agggctaaaa aaatccacat atagctgctg catatgccat catccaagta  2400
tatcaagatc aaaataatta taaaacatac ttgtttatta taatagatag gtactcaagg  2460
ttagagcata tgaatagatg ctgcatatgc catcatgtat atgcatcagt aaaacccaca  2520
tcaacatgta tacctatcct agatcgatat ttccatccat cttaaactcg taactatgaa  2580
gatgtatgac acacacatac agttccaaaa ttaataaata caccaggtag tttgaaacag  2640
tattctactc cgatctagaa cgaatgaacg accgcccaac cacaccacat catcacaacc  2700
aagcgaacaa aaagcatctc tgtatatgca tcagtaaaac ccgcatcaac atgtatacct  2760
atcctagatc gatatttcca tccatcatct tcaattcgta actatgaata tgtatggcac  2820
acacatacag atccaaaatt aataaatcca ccaggtagtt tgaaacagaa ttctactccg  2880
atctagaacg accgcccaac cagaccacat catcacaacc aagacaaaaa aaagcatgaa  2940
aagatgaccc gacaaacaag tgcacggcat atattgaaat aaaggaaaag ggcaaaccaa  3000
accctatgca acgaaacaaa aaaaatcatg aaatcgatcc cgtctgcgga acggctagag  3060
ccatcccagg attccccaaa gagaaacact ggcaagttag caatcagaac gtgtctgacg  3120
tacaggtcgc atccgtgtac gaacgctagc agcacggatc taacacaaac acggatctaa  3180
cacaaacatg aacagaagta gaactaccgg gccctaacca tgcatggacc ggaacgccga  3240
tctagagaag gtagagaggg gggggggga ggacgagcgg cgtaccttga agcggaggtg  3300
ccgacgggtg gatttggggg agatctggtt gtgtgtgtgt gcgctccgaa caacacgagg  3360
ttggggaaag agggtgtgga gggggtgtct atttattacg gcgggcgagg aagggaaagc  3420
gaaggagcgg tgggaaagga atccccgta gctgccggtg ccgtgagagg aggaggaggc  3480
cgcctgccgt gccggctcac gtctgccgct ccgccacgca atttctggat gccgacagcg  3540
gagcaagtcc aacggtggag cggaactctc gagaggggtc cagaggcagc gacagagatg  3600
ccgtgccgtc tgcttcgctt ggcccgacgc gacgctgctg gttcgctggt tggtgtccgt  3660
tagactcgtc gacggcgttt aacaggctgg cattatctac tcgaaacaag aaaaatgttt  3720
ccttagtttt tttaatttct taaagggtat ttgtttaatt tttagtcact ttattttatt  3780
ctattttata tctaaattat taaataaaaa aactaaaata gagttttagt tttcttaatt  3840
tagaggctaa aatagaataa aatagatgta ctaaaaaaat tagtctataa aaaccattaa  3900
ccctaaaccc taaatggatg tactaataaa atggatgaag tattatatag gtgaagctat  3960
ttgcaaaaaa aaaggagaac acatgcacac taaaaagata aaactgtaga gtcctgttgt  4020
caaaatactc aattgtcctt tagaccatgt ctaactgttc atttatatga ttctctaaaa  4080
cactgatatt attgtagtac tatagattat attattcgta gagtaaagtt taaatatatg  4140
tataaagata gataaactgc acttcaaaca agtgtgacaa aaaaaatatg tggtaatttt  4200
ttataactta gacatgcaat gctcattatc tctagagagg ggcacgaccg ggtcacgctg  4260
cactgcaggc tagcggcgaa ttcgcccttg tacgcgtacg cgtatatata cgtgcgctgc  4320
tactcatttg cgcgggaata cagctcagtc tgctgtgcgc tgcaggatgt acatacatac  4380
atgcgcaggt gcaaagtcta cgcgcgcggg caatgcaagc ccctggcgta gttgggccat  4440
gactgagatc acgcctcatg gtcatggaac gaaacaccgc gtccggccgg gctgcccctg  4500
gcgtcacgcg ggaggcagct gctagcgtta gcgtacgtac ccaccgtctc gtacacacca  4560
ccgcagggag agagaagagc gatgcaatgc acatgtacag catccgcatc atgcatagat  4620
actcatatct tcaaggccac acatgcagca gtgtcgtacg ctacgttgtt tcaacggagg  4680
aggaggatac atacatagac acccacagcc agcctagcat atagcagata gcatacggac  4740
tcccgggtga ggaaaaatgg agggcgaacc aaaccaacca caaagaagca gcagcagcag  4800
cagcagcagc tgcggctgct atcaccactc accaactcca attaaagatc tctctctctc  4860
tctctactgg ccggccctgt cagtgccagc gcccggtttg ttgctagctg agctgcgggc  4920
gtcgctctta gatatagccc aaaactcact ccaccaccac tcgttccatg gaaccctaga  4980
ccaaaagtac tcgcgctctc ggccctcgct ctcgccctct ccctctccgc agcaaaagag  5040
atccggccgg ccgagaaggg cgcgcgctag ctgcccggct actagctggc gcccgcccgc  5100
gcatatatct gtgtcatcgc catcacccac accatggccc ggccggccaa caccgccgta  5160
ttagctctgt ctgtcgctcg tccacctgcg accgactgag cgatcgatct ccaccgagct  5220
ctccgctaag cgctgtcctt gccgccgtcc tcccctccgt cccctacgca tccatttccg  5280
tgtgctcgtg tgtgcgcgcg cgggcactcc tgctcctgct ccctccggcc cctcctcccc  5340
tcccaggctc ccagctagcc gcgcccgccc gcgcgacctg cacctgcaca gatcgggcgg  5400
ccgggccgac cgatcgatcg agat                                         5424

SEQ ID NO: 98          moltype = DNA  length = 24
FEATURE                Location/Qualifiers
misc_feature           1..24
                       note = synthesized sequence- Forward PCR primer
source                 1..24
                       mol_type = other DNA
                       organism = synthetic construct
SEQUENCE: 98
cccgttattg tatgaggtaa tgac                                         24

SEQ ID NO: 99          moltype = DNA  length = 31
FEATURE                Location/Qualifiers
misc_feature           1..31
                       note = synthesized sequence- Reverse PCR primer for
                        site-specific transgene insertion at junction 1
source                 1..31
                       mol_type = other DNA
                       organism = synthetic construct
SEQUENCE: 99
gctcgtgtcc aagcgtcact tacgattagc t                                 31
```

-continued

```
SEQ ID NO: 100         moltype = DNA  length = 32
FEATURE                Location/Qualifiers
misc_feature           1..32
                       note = synthesized sequence- Forward PCR primer for
                        site-specific transgene insertion at junction 2
source                 1..32
                       mol_type = other DNA
                       organism = synthetic construct
SEQUENCE: 100
ccatgtctaa ctgttcattt atatgattct ct                                32

SEQ ID NO: 101         moltype = DNA  length = 24
FEATURE                Location/Qualifiers
misc_feature           1..24
                       note = synthesized sequence- Reverse PCR primer for
                        site-specific transgene insertion at junction 2
source                 1..24
                       mol_type = other DNA
                       organism = synthetic construct
SEQUENCE: 101
gcagccgata ggttcatcat cttc                                         24

SEQ ID NO: 102         moltype = DNA  length = 7850
FEATURE                Location/Qualifiers
misc_feature           1..7850
                       note = synthesized sequence- Linked Cas9 and LIGCas-3 long
                        guide RNA expression cassettes
source                 1..7850
                       mol_type = other DNA
                       organism = synthetic construct
SEQUENCE: 102
gtgcagcgtg acccggtcgt gcccctctct agagataatg agcattgcat gtctaagtta  60
taaaaaatta ccacatattt tttttgtcac acttgtttga agtgcagttt atctatcttt  120
atacatatat ttaaacttta ctctacgaat aatataatct atagtactac aataatatca  180
gtgttttaga gaatcatata aatgaacagt tagacatggt ctaaaggaca attgagtatt  240
ttgacaacag gactctacag ttttatcttt ttagtgtgca tgtgttctcc tttttttttg  300
caaatagctt cacctatata atacttcatc cattttatta gtacatccat ttagggttta  360
gggttaatgg tttttataga ctaatttttt tagtacatct attttattct attttagcct  420
ctaaattaag aaaactaaaa ctctatttta gtttttttat ttaataattt agatataaaa  480
tagaataaaa taaagtgact aaaaattaaa caaataccct ttaagaaatt aaaaaaacta  540
aggaaacatt tttcttgttt cgagtagata atgccagcct gttaaacgcc gtcgacgagt  600
ctaacggaca ccaaccagcg aaccagcagc gtcgcgtcgg gccaagcgaa gcagacggca  660
cggcatctct gtcgctgcct ctggacccct ctcgagagtt ccgctccacc gttggacttg  720
ctccgctgtc ggcatccaga aattgcgtgg cggagcggca gacgtgagcc ggcacggcag  780
gcggcctcct cctcctctca cggcaccggc agctacgggg gattcctttc ccaccgctcc  840
ttcgctttcc cttcctcgcc cgccgtaata aatagacacc ccctccacac cctctttccc  900
caacctcgtg ttgttcggag cgcacacaca cacaaccaga tctcccccaa atccacccgt  960
cggcacctcc gcttcaaggt acgccgctcg tcctcccccc cccccctctc taccttctct  1020
agatcggcgt tccggtccat gcatggttag ggcccggtag ttctacttct gttcatgttt  1080
gtgttagatc cgtgtttgtg ttagatccgt gctgctagcg ttcgtacacg gatgcgacct  1140
gtacgtcaga cacgttctga ttgctaactt gccagtgttt ctctttgggg aatcctggga  1200
tggctctagc cgttccgcag acgggatcga tttcatgatt ttttttgttt cgttgcatag  1260
ggtttggttt gccctttttcc tttatttcaa tatatgccgt gcacttgttt gtcgggtcat  1320
cttttcatgc ttttttttgt cttggttgtg atgatgtggt ctggttgggc ggtcgttcta  1380
gatcggagta gaattctgtt tcaaactacc tggtggattt attaattttg gatctgtatg  1440
tgtgtgccat acatattcat agttacgaat tgaagatgat ggatggaaat atcgatctag  1500
gataggtata catgttgatg cgggttttac tgatgcatat acagagatgc tttttgttcg  1560
cttggttgtg atgatgtggt gtggttgggc ggtcgttcat tcgttctaga tcggagtaga  1620
atactgtttc aaactacctg gtgtatttat taattttgga actgtatgtg tgtgtcatac  1680
atcttcatag ttacgagttt aagatggatg gaaatatcga tctaggatag gtatacatgt  1740
tgatgtgggt tttactgatg catatacatg atggcatatg cagcatctat tcatatgctc  1800
taaccttgag tacctatcta ttataataaa caagtatgtt ttataattat tttgatcttg  1860
atatacttgg atgatggcat atgcagcagc tatatgtgga tttttttagc cctgccttca  1920
tacgctattt atttgcttgg tactgtttct tttgtcgatg ctcaccctgt tgtttggtgt  1980
tacttctgca ggtcgactct agaggatcca tggcaccgaa gaagaagcgc aaggtgatgg  2040
acaagaagta cagcatcggc ctcgacatcg gcaccaactc ggtgggctgg gccgtcatca  2100
cggacgaata taaggtcccg tcgaagaagt tcaaggtcct cggcaataca gaccgccaca  2160
gcatcaagaa aaacttgatc ggcgccctcc tgttcgatag cggcgagacc gcggaggcga  2220
ccaggctcaa gaggaccgcc aggagacggt acactaggcg caagaacagg atctgctacc  2280
tgcaggagat cttcagcaac gagatggcga aggtggacga ctccttcttc caccgcctgg  2340
aggaatcatt cctggtggag gaggacaaga agcatgagcg gcacccaatc ttcggcaaca  2400
tcgtcgacga ggtaagtttc tgcttctacc tttgatatat atataataat tatcattaat  2460
tagtagtaat ataatatttc aaatattttt ttcaaaataa aagaatgtag tatatagcaa  2520
ttgcttttct gtagtttata agtgtgtata ttttaattta taacttttct aatatatgac  2580
caaaacatgg tgatgtgcag gtggcctacc acgagaagta cccgacaatc taccacctcc  2640
ggaagaaact ggtggacagc acagacaagg cggacctccg gctcatctac cttgccctcg  2700
cgcatatgat caagttccgc ggccacttcc tcatcgaggg cgacctgaac ccggacaact  2760
ccgacgtgga caagctgttc atccagctcg tgcagacgta caatcaactg ttcgaggaga  2820
accccataaa cgctagcggc gtggacgcca aggccatcct ctcggccagg ctctcgaaat  2880
```

-continued

```
caagaaggct ggagaacctt atcgcgcagt tgccaggcga aaagaagaac ggcctcttcg  2940
gcaaccttat tgcgctcagc ctcggcctga cgccgaactt caaatcaaac ttcgacctcg  3000
cggaggacgc caagctccag ctctcaaagg acacctacga cgacgacctc gacaacctcc  3060
tggcccagat aggagaccag tacgcggacc tcttcctcgc cgccaagaac ctctccgacg  3120
ctatcctgct cagcgacatc cttcgggtca acaccgaaat taccaaggca ccgctgtccg  3180
ccagcatgat taaacgctac gacgagcacc atcaggacct cacgctgctc aaggcactcg  3240
tccgccagca gctccccgag aagtacaagg agatcttctt cgaccaatca aaaaacggct  3300
acgcgggata tatcgacggc ggtgccagcc aggaagagtt ctacaagttc atcaaaccaa  3360
tcctggagaa gatggacggc accgaggagt tgctggtcaa gctcaacagg gaggacctcc  3420
tcaggaagca gaggaccttc gacaacggct ccatcccgca tcagatccac ctgggcgaac  3480
tgcatgccat cctgcggcgc caggaggact tctacccgtt cctgaaggat aaccgggaga  3540
agatcgagaa gatcttgacg ttccgcatcc catactacgt gggcccgctg gctcgcggca  3600
actcccggtt cgcctggatg acccggaagt cggaggagac catcacaccc tggaactttg  3660
aggaggtggt cgataagggc gctagcgctc agagcttcat cgagcgcatg accaacttcg  3720
ataaaaacct gcccaatgaa aaagtcctcc ccaagcactc gctgctctac gagtacttca  3780
ccgtgtacaa cgagctcacc aaggtcaaat acgtcaccga gggcatgcgg aagccggcgt  3840
tcctgagcgg cgagcagaag aaggcgatag tggacctcct cttcaagacc aacaggaagg  3900
tgaccgtgaa gcaattaaaa gaggactact tcaagaaaat agagtgcttc gactccgtgg  3960
agatctcggg cgtggaggat cggttcaacg cctcactcgg cacgtatcac gacctcctca  4020
agatcattaa agacaaggac ttcctcgaca acgaggagaa cgaggacatc ctcgaggaca  4080
tcgtcctcac cctgaccctg ttcgaggacc gcgaaatgat cgaggagagg ctgaagacct  4140
acgcgcacct gttcgacgac aaggtcatga aacagctcaa gaggcgccgc tacactggtt  4200
ggggaaggct gtcccgcaag ctcattaatg gcatcaggga caagcagagc ggcaagacca  4260
tcctggactt cctcaagtcc gacgggttcg ccaaccgcaa cttcatgcag ctcattcacg  4320
acgactcgct cacgttcaag gaagacatcc agaaggcaca ggtgagcggg cagggtgact  4380
ccctccacga acacatcgcc aacctggccg gctcgccggc cattaaaaag ggcatcctgc  4440
agacggtcaa ggtcgtcgac gagctcgtga aggtgatggg ccggcacaag cccgaaaata  4500
tcgtcataga gatggccagg gagaaccaga ccacccaaaa agggcagaag aactcgcgcg  4560
agcggatgaa acggatcgag gagggcatta aagagctcgg gtcccagatc ctgaaggagc  4620
accccgtgga aaatacccag ctccagaatg aaaagctcta cctctactac ctgcagaacg  4680
gccgcgacat gtacgtggac caggagctgg acattaatcg gctatcggac tacgacgtcg  4740
accacatcgt gccgcagtcg ttcctcaagg acgatagcat cgacaacaag gtgctcaccc  4800
ggtcggataa aaatcggggc aagagcgaca acgtgcccag cgaggaggtc gtgaagaaga  4860
tgaaaaacta ctggcgccag ctcctcaacg cgaaactgat cacccagcgc aagttcgaca  4920
acctgacgaa ggcggaacgc ggtggcttga gcgaactcga taaggcgggc ttcataaaaa  4980
ggcagctggt cgagacgcgc cagatcacga agcatgtcgc ccagatcctg gacagccgca  5040
tgaatactaa gtacgatgaa aacgacaagc tgatccggga ggtgaaggtg atcacgctga  5100
agtccaagct cgtgtcggac ttccgcaagg acttccagtt ctacaaggtc cgcgagatca  5160
acaactacca ccacgcccac gacgcctacc tgaatgcggt ggtcgggacc gccctgatca  5220
agaagtaccc gaagctggag tcggagttcg tgtacggcga ctacaaggtc tacgacgtgc  5280
gcaaaatgat cgccaagtcc gagcaggaga tcggcaaggc cacggcaaaa tacttcttct  5340
actcgaacat catgaacttc ttcaagaccg agatcaccct cgcgaacggc gagatccgca  5400
agcgcccgct catcgaaacc aacggcgaga cgggcgagat cgtctgggat aagggccggg  5460
atttcgcgac ggtccgcaag gtgctctcca tgccgcaagt caatatcgtg aaaaagacgg  5520
aggtccagac gggcgggttc agcaaggagt ccatcctccc gaagcgcaac tccgacaagc  5580
tcatcgcgag gaagaaggat tgggacccga aaaaatatgg cggcttcgac agcccgaccg  5640
tcgcatacag cgtcctcgtc gtggcgaagg tggagaaggg caagtcaaag aagctcaagt  5700
ccgtgaagga gctgctcggg atcacgatta tggagcggtc ctccttcgag aagaacccga  5760
tcgacttcct agaggccaag ggatataagg aggtcaagaa ggacctgatt attaaactgc  5820
cgaagtactc gctcttcgag ctggaaaacg gccgcaagag gatgctcgcc tccgcaggcg  5880
agttgcagaa gggcaacgag ctcgccctcc cgagcaaata cgtcaatttc ctgtacctcg  5940
ctagccacta tgaaaagctc aagggcagcc cggaggacaa cgagcagaag cagctcttcg  6000
tggagcagca caagcattac ctggacgaga tcatcgagca gatcagcgag ttctcgaagc  6060
gggtgatcct cgccgacgcg aacctggaca aggtgctgtc ggcatataac aagcaccgcg  6120
acaaaccaat acgcgagcag gccgaaaata tcatccacct cttcaccctc accaacctcg  6180
gcgctccggc agccttcaag tacttcgaca ccacgattga ccggaagcgg tacacgagca  6240
cgaaggaggt gctcgatgcg acgctgatcc accagagcat cacagggctc tatgaaacac  6300
gcatcgacct gagccagctg ggcggagaca agagaccacg ggaccgccac gatggcgagc  6360
tgggaggccg caagcgggca aggtaggtac cgttaaccta gacttgtcca tcttctggat  6420
tggccaactt aattaatgta tgaaataaaa ggatgcacac atagtgacat gctaatcact  6480
ataatgtggg catcaaagtt gtgtgttatg tgtaattact agttatctga ataaaagaga  6540
aagagatcat ccatatttct tatcctaaat gaatgtcacg tgtctttata attctttgat  6600
gaaccagatg catttcatta accaaatcca tatacatata aatattaatc atatataatt  6660
aatatcaatt gggttagcaa aacaaatcta gtctaggtgt gttttgcgaa tgcggccccc  6720
cctcgaggtc gacggtatcg ataagctttg agagtacaat gatgaaccta gattaatcaa  6780
tgccaaagtc tgaaaaatgc accctcagtc tatgatccag aaaatcaaga ttgcttgagg  6840
ccctgttcgg ttgttccgga ttagagcccc ggattaattc ctagccggat tacttctcta  6900
atttatatag attttgatga gctggaatga atcctggctt attccggtac aaccgaacag  6960
gccctgaagg ataccagtaa tcgctgagct aaattggcat gctgtcagag tgtcagtatt  7020
gcagcaaggt agtgagataa ccggcatcat ggtgccagtt tgatggcacc attagggtta  7080
gagatggtgg ccatgggcgc atgtcctggc caactttgta tgatatatgg cagggtgaat  7140
aggaaagtaa aattgtattg taaaaaggga tttcttctgt ttgttagcgc atgtacaagg  7200
aatgcaagtt ttgagcgagg gggcatcaaa gatctggctg tgtttccagc tgtttttgtt  7260
agccccatcg aatccttgac ataatgatcc cgcttaaata agcaacctcg cttgtatagt  7320
tccttgtgct ctaacacacg atgatgataa gtcgtaaaat agtggtgtcc aaagaatttc  7380
caggcccagt tgtaaaagct aaaatgctat tcgaatttct actagcagta agtcgtgttt  7440
agaaattatt tttttatata cctttttttcc ttctatgtac agtaggacac agtgtcagcg  7500
ccgcgttgac ggagaatatt tgcaaaaaag taaaagagaa agtcatagcg gcgtatgtgc  7560
caaaaacttc gtcacagaga gggccataag aaacatggcc cacggcccaa tacgaagcac  7620
```

-continued

```
cgcgacgaag cccaaacagc agtccgtagg tggagcaaag cgctgggtaa tacgcaaacg  7680
ttttgtccca ccttgactaa tcacaagagt ggagcgtacc ttataaaccg agccgcaagc  7740
accgaattgc gtacgcgtac gtgtggtttt agagctagaa atagcaagtt aaaataaggc  7800
tagtccgtta tcaacttgaa aaagtggcac cgagtcggtg cttttttttt            7850

SEQ ID NO: 103         moltype = DNA  length = 23
FEATURE                Location/Qualifiers
source                 1..23
                       mol_type = genomic DNA
                       organism = Zea mays
SEQUENCE: 103
tgggcaggtc tcacgacggt tgg                                          23

SEQ ID NO: 104         moltype = DNA  length = 91
FEATURE                Location/Qualifiers
source                 1..91
                       mol_type = genomic DNA
                       organism = Zea mays
SEQUENCE: 104
ccggtttcgc gtgctctggc tttacattac atgggcaggt ctcacgacgg ttgggctgga  60
gagccggctg gtaggggagg acctcaacgg c                                 91

SEQ ID NO: 105         moltype = DNA  length = 90
FEATURE                Location/Qualifiers
source                 1..90
                       mol_type = genomic DNA
                       organism = Zea mays
SEQUENCE: 105
ccggtttcgc gtgctctggc tttacattac atgggcaggt ctcacgaggt tgggctggag  60
agccggctgg taggggagga cctcaacggc                                   90

SEQ ID NO: 106         moltype = DNA  length = 90
FEATURE                Location/Qualifiers
source                 1..90
                       mol_type = genomic DNA
                       organism = Zea mays
SEQUENCE: 106
ccggtttcgc gtgctctggc tttacattac atgggcaggt ctcacacggt tgggctggag  60
agccggctgg taggggagga cctcaacggc                                   90

SEQ ID NO: 107         moltype = DNA  length = 92
FEATURE                Location/Qualifiers
source                 1..92
                       mol_type = genomic DNA
                       organism = Zea mays
SEQUENCE: 107
ccggtttcgc gtgctctggc tttacattac atgggcaggt ctcacgacgg tttgggctgg  60
agagccggct ggtaggggag gacctcaacg gc                                92

SEQ ID NO: 108         moltype = DNA  length = 89
FEATURE                Location/Qualifiers
source                 1..89
                       mol_type = genomic DNA
                       organism = Zea mays
SEQUENCE: 108
ccggtttcgc gtgctctggc tttacattgc atgagcaggt cgtgacggtt gggctggaga  60
gccggctggt aggggaggac ctcaacggc                                    89

SEQ ID NO: 109         moltype = DNA  length = 57
FEATURE                Location/Qualifiers
source                 1..57
                       mol_type = genomic DNA
                       organism = Zea mays
SEQUENCE: 109
gggcaggtct cgacggttgg gctggagagc cggctggtag gggaggacct caacggc     57

SEQ ID NO: 110         moltype = DNA  length = 57
FEATURE                Location/Qualifiers
source                 1..57
                       mol_type = genomic DNA
                       organism = Zea mays
SEQUENCE: 110
ccggtttcgc gtgctcttgg gctggagagc cggctggtag gggaggacct caacggc     57

SEQ ID NO: 111         moltype = DNA  length = 22
FEATURE                Location/Qualifiers
source                 1..22
                       mol_type = genomic DNA
                       organism = Zea mays
```

-continued

```
SEQUENCE: 111
atatacctca cacgtacgcg ta                                          22

SEQ ID NO: 112         moltype = DNA  length = 1053
FEATURE                Location/Qualifiers
source                 1..1053
                       mol_type = genomic DNA
                       organism = Zea mays
SEQUENCE: 112
atgaacacca agtacaacaa ggagttcctg ctctacctgg ccggcttcgt ggacggcgac  60
ggctccatca aggcgcagat caagccgaac cagtcctgca agttcaagca ccagctctcc  120
ctgaccttcc aggtgaccca gaagacgcag aggcgctggt tcctcgacaa gctggtcgac  180
gagatcgggg tgggctacgt ctacgaccgc gggtcggtgt ccgactacga gctctcccag  240
atcaagcccc tgcacaactt cctcacccag ctccagccgt tcctcaagct gaagcagaag  300
caggcgaacc tcgtcctgaa gatcatcgag cagctcccct cggccaagga gtccccggac  360
aagttcctgg aggtgtgcac gtgggtcgac cagatcgcgg ccctcaacga cagcaagacc  420
cgcaagacga cctcggagac ggtgcgggcg gtcctggact ccctcccagg atccgtggga  480
ggtctatcgc catctcaggc atccagcgcc gcatcctcgg cttcctcaag cccgggttca  540
gggatctccg aagcactcag agctggagca actaagtcca aggaattcct gctctacctg  600
gccggcttcg tggacggcga cggctccatc atcgcgtcca tcaagccgcg ccagtgctac  660
aagttcaagc acgagctccg cctggagttc accgtgaccc agaagacgca gaggcgctgg  720
ttcctcgaca agctggtcga cgagatcggg gtgggctacg tctacgaccg cgggtcggtg  780
tccgactacc gcctctccca gatcaagccc ctgcacaact tcctcaccca gctccagccg  840
ttcctcaagc tgaagcagaa gcaggcgaac ctcgtcctga agatcatcga gcagctcccc  900
tcggccaagg agtccccgga caagttcctg gaggtgtgca cgtgggtcga ccagatcgcg  960
gccctcaacg acagcaagac ccgcaagacg acctcggaga cggtgcgggc ggtcctggac  1020
tccctcagcg agaagaagaa gtcgtccccc tga                              1053

SEQ ID NO: 113         moltype = DNA  length = 22
FEATURE                Location/Qualifiers
source                 1..22
                       mol_type = genomic DNA
                       organism = Zea mays
SEQUENCE: 113
gatggtgacg tacgtgccct ac                                          22

SEQ ID NO: 114         moltype = DNA  length = 1053
FEATURE                Location/Qualifiers
source                 1..1053
                       mol_type = genomic DNA
                       organism = Zea mays
SEQUENCE: 114
atgaacacca agtacaacaa ggagttcctc ctctacctgg caggtttcgt ggacggcgat  60
gggtctatca tcgcccagat taccccgcaa cagtcctaca agttcaagca cgccctgcgg  120
ctgaggttca cggtcactca gaagacgcag cgcaggtggt tcctcgataa gctggtcgac  180
gaaatcggag tcggcaaggt gcgggacagg ggctctgtca gcgactacat cctctcccag  240
aagaagccgc tccacaactt cctgacccag ctgcagccct tcctcaagct caagcagaag  300
caggccaacc tggtgctcaa gatcatcgag cagctgccat ctgccaagga gtcaccagac  360
aagttccttg aggtctgcac ctgggtcgat cagatcgctg ccctgaacga ctccaagacg  420
aggaagacca cctccgagac cgtcagggct gtgctggact cactcccagg atccgttggc  480
ggtctcagcc cttctcaggc tagctcggct gcttcctcag ccagcagctc acctggctcc  540
ggtatcagcg aggctctcag agcaggtgcc accaagtcca aggagttcct cctgtacctg  600
gcaggcttcg ttgacggcga cggctcgatc atggcgtcca ttaccccgaa ccagtcgtgt  660
aagttcaagc atcagctgcg cctgcgcttt accgtcacgc agaagaccca gaggcgctgg  720
ttcctggaca aactggtgga cgagatcggg gtcgggaagg tgtacgacag agggagcgtt  780
agcgactacc ggctgtccca gaagaagccg ctccacaact tcctgacgca gctccaaccc  840
ttcctgaagc tgaagcagaa gcaggcgaac cttgtgctga agatcattga gcagctgccg  900
agcgccaagg agagccctga caagttcctg gaggtctgca cctgggtcga ccagatcgct  960
gccctcaacg actccaagac caggaagacc acgagcgaga ccgttcgggc tgtcctggac  1020
agcctctccg agaagaagaa gtcgagcccg tag                              1053

SEQ ID NO: 115         moltype = DNA  length = 4104
FEATURE                Location/Qualifiers
misc_feature           1..4104
                       note = synthesized sequence- soybean codon optimized Cas9
source                 1..4104
                       mol_type = other DNA
                       organism = synthetic construct
SEQUENCE: 115
atggacaaaa agtactcaat agggctcgac atagggacta actccgttgg atgggccgtc  60
atcaccgacg agtacaaggt gccctccaag aagttcaagg tgttgggaaa caccgacagg  120
cacagcataa agaagaattt gatcggtgcc ctcctcttcg actccggaga gaccgctgag  180
gctaccaggc tcaagaggac cgctagaagg cgctacacca gaaggaagaa cagaatctgc  240
tacctgcagg agatcttctc caacgagatg gccaaggtgg acgactcctt cttccaccgc  300
cttgaggaat cattcctggt ggaggaggat aaaaagcacg agagacaccc aatcttcggg  360
aacatcgtcg acgaggtggc ctaccatgaa aagtacccta ccatctacca cctgaggaag  420
aagctggtcg actctaccga caaggctgac ttgcgcttga tttacctggc tctcgctcac  480
atgataaagt tccgcggaca cttcctcatt gagggagacc tgaacccaga caactccgac  540
gtggacaagc tcttcatcca gctcgttcag acctacaacc agcttttcga ggagaaccca  600
```

-continued

```
atcaacgcca gtggagttga cgccaaggct atcctctctg ctcgtctgtc aaagtccagg  660
aggcttgaga acttgattgc ccagctgcct ggcgaaaaga agaacggact gttcggaaac  720
ttgatcgctc tctccctggg attgactccc aacttcaagt ccaacttcga cctcgccgag  780
gacgctaagt tgcagttgtc taaagacacc tacgacgatg acctcgacaa cttgctggcc  840
cagataggcg accaatacgc cgatctcttc ctcgccgcta agaacttgtc cgacgcaatc  900
ctgctgtccg acatcctgag agtcaacact gagattacca aagctcctct gtctgcttcc  960
atgattaagc gctacgacga gcaccaccaa gatctgaccc tgctcaaggc cctggtgaga  1020
cagcagctgc ccgagaagta caaggagatc tttttcgacc agtccaagaa cggctacgcc  1080
ggatacattg acggaggcgc ctcccaggaa gagttctaca agttcatcaa gcccatcctt  1140
gagaagatgg acggtaccga ggagctgttg gtgaagttga acagagagga cctgttgagg  1200
aagcagagaa ccttcgacaa cggaagcatc cctcaccaaa tccacctggg agagctccac  1260
gccatcttga ggaggcagga ggatttctat cccttcctga aggacaaccg cgagaagatt  1320
gagaagatct tgaccttcag aattccttac tacgtcgggc cactcgccag aggaaactct  1380
aggttcgcct ggatgacccg caaatctgaa gagaccatta ctccctggaa cttcgaggaa  1440
gtcgtggaca agggcgcttc cgctcagtct ttcatcgaga ggatgaccaa cttcgataaa  1500
aatctgccca acgagaaggt gctgcccaag cactccctgt tgtacgagta tttcacagtg  1560
tacaacgagc tcaccaaggt gaagtacgtc acagagggaa tgaggaagcc tgccttcttg  1620
tccggagagc agaagaaggc catcgtcgac ctgctcttca agaccaacag gaaggtgact  1680
gtcaagcagc tgaaggagga ctacttcaag aagatcgagt gcttcgactc cgtcgagatc  1740
tctggtgtcg aggacaggtt caacgcctcc cttgggactt accacgatct gctcaagatt  1800
attaaagaca aggacttcct ggacaacgag gagaacgagg acatccttga ggacatcgtg  1860
ctcaccctga ccttgttcga agacagggaa atgatcgaag agaggctcaa gacctacgcc  1920
cacctcttcg acgacaaggt gatgaaacag ctgaagagac gcagatatac cggctgggga  1980
aggctctccc gcaaattgat caacgggatc agggacaagc agtcagggaa gactatactc  2040
gacttcctga agtccgacgg attcgccaac aggaacttca tgcagctcat tcacgacgac  2100
tccttgacct tcaaggagga catccagaag gctcaggtgt ctggacaggg tgactccttg  2160
catgagcaca ttgctaactt ggccggctct cccgctatta agaagggcat tttgcagacc  2220
gtgaaggtcg ttgacgagct cgtgaaggtg atggacgcc acaagccaga gaacatcgtt  2280
attgagatgg ctcgcgagaa ccaaactacc cagaaagggc agaagaattc ccgcgagagg  2340
atgaagcgca ttgaggaggg cataaaagag cttggctctc agatcctcaa ggagcacccc  2400
gtcgagaaca ctcagctgca gaacgagaag ctgtacctgt actacctcca aaacggaagg  2460
gacatgtacg tggaccagga gctggacatc aacaggttgt ccgactacga cgtcgaccac  2520
atcgtgcctc agtccttcct gaaggatgac tccatcgaca ataaagtgct gacacgctcc  2580
gataaaaata gaggcaagtc cgacaacgtc ccctccgagg aggtcgtgaa gaagatgaaa  2640
aactactgga gacagctctt gaacgccaag ctcatcaccc agcgtaagtt cgacaacctg  2700
actaaggctg agagaggagg attgtccgag ctcgataagg ccggattcat caagagacag  2760
ctcgtcgaaa cccgccaaat taccaagcac gtggcccaaa ttctggattc ccgcatgaac  2820
accaagtacg atgaaaatga caagctgatc cgcgaggtca aggtgatcac cttgaagtcc  2880
aagctggtct ccgacttccg caaggacttc cagttctaca aggtgaggga gatcaacaac  2940
taccaccacg cacacgacgc ctacctcaac gctgtcgttg gaaccgccct catcaaaaaa  3000
tatcctaagc tggagtctga gttcgtctac ggcgactaca aggtgtacga cgtgaggaag  3060
atgatcgcta agtctgagca ggagatcggc aaggccaccg ccaagtactt cttctactcc  3120
aacatcatga acttcttcaa gaccgagatc actctcgcca acggtgagat caggaagcgc  3180
ccactgatcg agaccaacgg tgagactgga gagatcgtgt gggacaaagg gagggatttc  3240
gctactgtga ggaaggtgct ctccatgcct caggtgaaca tcgtcaagaa gaccgaagtt  3300
cagaccggag gattctccaa ggagtccatc ctccccaaga gaaactccga caagctgatc  3360
gctagaaaga aagactggga ccctaagaag tacggaggct tcgattctcc taccgtggcc  3420
tactctgtgc tggtcgtggc caaggtggag aagggcaagt ccaagaagct gaaatccgtc  3480
aaggagctcc tcgggattac catcatggag aggagttcct tcgagaagaa ccctatcgac  3540
ttcctggagg ccaagggata taaagaggtg aagaaggacc tcatcatcaa gctgcccaag  3600
tactccctct tcgagttgga gaacggaagg aagaggatgc tggcttctgc cggagagttg  3660
cagaagggaa atgagctcgc ccttccctcc aagtacgtga acttcctgta cctcgcctct  3720
cactatgaaa agttgaaggg ctctcctgag gacaacgagc agaagcagct cttcgtggag  3780
cagcacaagc actacctgga cgaaattatc gagcagatct ctgagttctc caagcgcgtg  3840
atattggccg acgccaacct cgacaaggtg ctgtccgcct acaacaagca cagggataag  3900
cccattcgcg agcaggctga aaacattatc cacctgttta ccctcacaaa cttgggagcc  3960
cctgctgcct tcaagtactt cgacaccacc attgacagga agagatacac ctccaccaag  4020
gaggtgctcg acgcaacact catccaccaa tccatcaccg gcctctatga aacaaggatt  4080
gacttgtccc agctgggagg cgac                                        4104

SEQ ID NO: 116         moltype = DNA  length = 1503
FEATURE                Location/Qualifiers
source                 1..1503
                       mol_type = genomic DNA
                       organism = Glycine max
SEQUENCE: 116
ccgggtttac ttattttgtg ggtatctata cttttattag atttttaatc aggctcctga  60
tttcttttta tttcgattga attcctgaac ttgtattatt cagtagatcg aataaattat  120
aaaaagataa aatcataaaa taatatttta tcctatcaat catattaaag caatgaatat  180
gtaaaattaa tcttatcttt attttaaaaa atcatatagg tttagtattt ttttaaaaat  240
aaagatagga ttagttttac tattcactgc ttattacttt taaaaaaatc ataaaggttt  300
agtatttttt taaaataaat ataggaatag ttttactatt cactgcttta atagaaaaat  360
agtttaaaat ttaagatagt tttaatccca gcatttgcca cgtttgaacg tgagccgaaa  420
cgatgtcgtt acattatctt aacctagctg aaacgatgtc gtcataatat cgccaaatgc  480
caactggact acgtcgaacc cacaaatccc acaaagcgcg tgaaatcaaa tcgctcaaac  540
cacaaaaaag aacaacgcgt ttgttacacg ctcaatccca cgcgagtaga gcacagtaac  600
cttcaaataa gcgaatgggg cataatcaga aatccgaaat aaacctaggg gcattatcgg  660
aaatgaaaag tagctcactc aatataaaaa tctaggaacc ctagttttcg ttatcactct  720
gtgctccctc gctctatttc tcagtctctg tgtttgcggc tgaggattcc gaacgagtga  780
```

```
ccttcttcgt ttctcgcaaa ggtaacagcc tctgctcttg tctcttcgat tcgatctatg  840
cctgtctctt atttacgatg atgtttcttc ggttatgttt ttttatttat gctttatgct  900
gttgatgttc ggttgtttgt ttcgctttgt ttttgtggtt cagtttttta ggattctttt  960
ggtttttgaa tcgattaatc ggaagagatt ttcgagttat ttggtgtgtt ggaggtgaat  1020
cttttttttg aggtcataga tctgttgtat ttgtgttata aacatgcgac tttgtatgat  1080
tttttacgag gttatgatgt tctggttgtt ttattatgaa tctgttgaga cagaaccatg  1140
atttttgttg atgttcgttt acactattaa aggtttgttt taacaggatt aaaagttttt  1200
taagcatgtt gaaggagtct tgtagatatg taaccgtcga tagttttttt gtgggtttgt  1260
tcacatgtta tcaagcttaa tcttttacta tgtatgcgac catatctgga tccagcaaag  1320
gcgatttttt aattccttgt gaaacttttg taatatgaag ttgaaatttt gttattggta  1380
aactataaat gtgtgaagtt ggagtatacc tttaccttct tatttggctt tgtgatagtt  1440
taatttatat gtattttgag ttctgacttg tatttctttg aattgattct agtttaagta  1500
atc                                                                1503

SEQ ID NO: 117         moltype = DNA  length = 33
FEATURE                Location/Qualifiers
misc_feature           1..33
                       note = synthesized sequence- inker SV40 NLS
source                 1..33
                       mol_type = other DNA
                       organism = synthetic construct
SEQUENCE: 117
tctagagccg atcccaagaa gaagagaaag gtg                               33

SEQ ID NO: 118         moltype = AA  length = 1379
FEATURE                Location/Qualifiers
REGION                 1..1379
                       note = synthesized sequence- Cas9 with a SV40 NLS
source                 1..1379
                       mol_type = protein
                       organism = synthetic construct
SEQUENCE: 118
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGDSR ADPKKKRKV   1379

SEQ ID NO: 119         moltype = DNA  length = 8519
FEATURE                Location/Qualifiers
misc_feature           1..8519
                       note = synthesized sequence- QC782
source                 1..8519
                       mol_type = other DNA
                       organism = synthetic construct
SEQUENCE: 119
ccgggtttac ttattttgtg ggtatctata cttttattag atttttaatc aggctcctga  60
tttcttttta tttcgattga attcctgaac ttgtattatt cagtagatcg aataaattat  120
aaaaagataa aatcataaaa taatatttta tcctatcaat catattaaag caatgaatat  180
gtaaaattaa tcttatcttt attttaaaaa atcatatagg tttagtattt ttttaaaaat  240
aaagatagga ttagttttac tattcactgc ttattacttt taaaaaaatc ataaaggttt  300
agtatttttt taaaataaat ataggaatag ttttactatt cactgcttta atagaaaaat  360
agtttaaaat ttaagatagt tttaatccca gcatttgcca cgtttgaacg tgagccgaaa  420
cgatgtcgtt acattatctt aacctagctg aaacgatgtc gtcataatat cgccaaatgc  480
caactggact acgtcgaacc cacaaatccc acaaagcgcg tgaaatcaaa tcgctcaaac  540
cacaaaaaag aacaacgcgt ttgttacacg ctcaatccca cgcgagtaga gcacagtaac  600
cttcaaataa gcgaatgggg cataatcaga aatccgaaat aaacctaggg gcattatcgg  660
aaatgaaaag tagctcactc aatataaaaa tctaggaacc ctagttttcg ttatcactct  720
gtgctccctc gctctatttc tcagtctctg tgtttgcggc tgaggattcc gaacgagtga  780
ccttcttcgt ttctcgcaaa ggtaacagcc tctgctcttg tctcttcgat tcgatctatg  840
cctgtctctt atttacgatg atgtttcttc ggttatgttt ttttatttat gctttatgct  900
```

-continued

```
gttgatgttc ggttgtttgt ttcgctttgt ttttgtggtt cagtttttta ggattctttt  960
ggtttttgaa tcgattaatc ggaagagatt ttcgagttat ttggtgtgtt ggaggtgaat  1020
cttttttttg aggtcataga tctgttgtat ttgtgttata aacatgcgac tttgtatgat  1080
tttttacgag gttatgatgt tctggttgtt ttattatgaa tctgttgaga cagaaccatg  1140
atttttgttg atgttcgttt acactattaa aggtttgttt taacaggatt aaaagttttt  1200
taagcatgtt gaaggagtct tgtagatatg taaccgtcga tagttttttt gtgggtttgt  1260
tcacatgtta tcaagcttaa tcttttacta tgtatgcgac catatctgga tccagcaaag  1320
gcgatttttt aattccttgt gaaacttttg taatatgaag ttgaaatttt gttattggta  1380
aactataaat gtgtgaagtt ggagtatacc tttaccttct tatttggctt tgtgatagtt  1440
taatttatat gtattttgag ttctgacttg tatttctttg aattgattct agtttaagta  1500
atccatggac aaaaagtact caatagggct cgacataggg actaactccg ttggatgggc  1560
cgtcatcacc gacgagtaca aggtgccctc caagaagttc aaggtgttgg gaaacaccga  1620
caggcacagc ataaagaaga atttgatcgg tgccctcctc ttcgactccg gagagaccgc  1680
tgaggctacc aggctcaaga ggaccgctag aaggcgctac accagaagga agaacagaat  1740
ctgctacctg caggagatct tctccaacga gatggccaag gtggacgact ccttcttcca  1800
ccgccttgag gaatcattcc tggtggagga ggataaaaag cacgagagac acccaatctt  1860
cgggaacatc gtcgacgagg tggcctacca tgaaaagtac cctaccatct accacctgag  1920
gaagaagctg gtcgactcta ccgacaaggc tgacttgcgc ttgatttacc tggctctcgc  1980
tcacatgata aagttccgcg gacacttcct cattgaggga gacctgaacc cagacaactc  2040
cgacgtggac aagctcttca tccagctcgt tcagacctac aaccagcttt tcgaggagaa  2100
cccaatcaac gccagtggag ttgacgccaa ggctatcctc tctgctcgtc tgtcaaagtc  2160
caggaggctt gagaacttga ttgcccagct gcctggcgaa aagaagaacg gactgttcgg  2220
aaacttgatc gctctctccc tgggattgac tcccaacttc aagtccaact tcgacctcgc  2280
cgaggacgct aagttgcagt tgtctaaaga cacctacgac gatgacctcg acaacttgct  2340
ggcccagata ggcgaccaat acgccgatct cttcctcgcc gctaagaact tgtccgacgc  2400
aatcctgctg tccgacatcc tgagagtcaa cactgagatt accaaagctc ctctgtctgc  2460
ttccatgatt aagcgctacg acgagcacca ccaagatctg accctgctca aggccctggt  2520
gagacagcag ctgcccgaga agtacaagga gatctttttc gaccagtcca agaacggcta  2580
cgccggatac attgacggag gcgcctccca ggaagagttc tacaagttca tcaagcccat  2640
ccttgagaag atggacggta ccgaggagct gttggtgaag ttgaacagag aggacctgtt  2700
gaggaagcag agaaccttcg acaacggaag catccctcac caaatccacc tgggagagct  2760
ccacgccatc ttgaggaggc aggaggattt ctatcccttc ctgaaggaca accgcgagaa  2820
gattgagaag atcttgacct tcagaattcc ttactacgtc gggccactcg ccagaggaaa  2880
ctctaggttc gcctggatga cccgcaaatc tgaagagacc attactccct ggaacttcga  2940
ggaagtcgtg gacaagggcg cttccgctca gtctttcatc gagaggatga ccaacttcga  3000
taaaaatctg cccaacgaga aggtgctgcc caagcactcc ctgttgtacg agtatttcac  3060
agtgtacaac gagctcacca aggtgaagta cgtcacagag ggaatgagga agcctgcctt  3120
cttgtccgga gagcagaaga aggccatcgt cgacctgctc ttcaagacca acaggaaggt  3180
gactgtcaag cagctgaagg aggactactt caagaagatc gagtgcttcg actccgtcga  3240
gatctctggt gtcgaggaca ggttcaacgc ctcccttggg acttaccacg atctgctcaa  3300
gattattaaa gacaaggact tcctggacaa cgaggagaac gaggacatcc ttgaggacat  3360
cgtgctcacc ctgaccttgt tcgaagacag ggaaatgatc gaagagaggc tcaagaccta  3420
cgcccacctc ttcgacgaca aggtgatgaa acagctgaag agacgcagat ataccggctg  3480
gggaaggctc tcccgcaaat tgatcaacgg gatcagggac aagcagtcag ggaagactat  3540
actcgacttc ctgaagtccg acggattcgc caacaggaac ttcatgcagc tcattcacga  3600
cgactccttg accttcaagg aggacatcca gaaggctcag gtgtctggac agggtgactc  3660
cttgcatgag cacattgcta acttggccgg ctctcccgct attaagaagg gcattttgca  3720
gaccgtgaag gtcgttgacg agctcgtgaa ggtgatggga cgccacaagc cagagaacat  3780
cgttattgag atggctcgcg agaaccaaac tacccagaaa gggcagaaga attcccgcga  3840
gaggatgaag cgcattgagg agggcataaa agagcttggc tctcagatcc tcaaggagca  3900
ccccgtcgag aacactcagc tgcagaacga gaagctgtac ctgtactacc tccaaaacgg  3960
aagggacatg tacgtggacc aggagctgga catcaacagg ttgtccgact acgacgtcga  4020
ccacatcgtg cctcagtcct tcctgaagga tgactccatc gacaataaag tgctgacacg  4080
ctccgataaa aatagaggca agtccgacaa cgtcccctcc gaggaggtcg tgaagaagat  4140
gaaaaactac tggagacagc tcttgaacgc caagctcatc acccagcgta agttcgacaa  4200
cctgactaag gctgagagag gaggattgtc cgagctcgat aaggccggat tcatcaagag  4260
acagctcgtc gaaacccgcc aaattaccaa gcacgtggcc caaattctgg attcccgcat  4320
gaacaccaag tacgatgaaa atgacaagct gatccgcgag gtcaaggtga tcaccttgaa  4380
gtccaagctg gtctccgact tccgcaagga cttccagttc tacaaggtga gggagatcaa  4440
caactaccac cacgcacacg acgcctacct caacgctgtc gttggaaccg ccctcatcaa  4500
aaaatatcct aagctggagt ctgagttcgt ctacggcgac tacaaggtgt acgacgtgag  4560
gaagatgatc gctaagtctg agcaggagat cggcaaggcc accgccaagt acttcttcta  4620
ctccaacatc atgaacttct tcaagaccga gatcactctc gccaacggtg agatcaggaa  4680
gcgcccactg atcgagacca acggtgagac tggagagatc gtgtgggaca aagggaggga  4740
tttcgctact gtgaggaagg tgctctccat gcctcaggtg aacatcgtca agaagaccga  4800
agttcagacc ggaggattct ccaaggagtc catcctcccc aagagaaact ccgacaagct  4860
gatcgctaga aagaaagact gggaccctaa gaagtacgga ggcttcgatt ctcctaccgt  4920
ggcctactct gtgctggtcg tggccaaggt ggagaagggc aagtccaaga agctgaaatc  4980
cgtcaaggag ctcctcggga ttaccatcat ggagaggagt tccttcgaga agaaccctat  5040
cgacttcctg gaggccaagg gatataaaga ggtgaagaag gacctcatca tcaagctgcc  5100
caagtactcc ctcttcgagt tggagaacgg aaggaagagg atgctggctt ctgccggaga  5160
gttgcagaag ggaaatgagc tcgcccttcc ctccaagtac gtgaacttcc tgtacctcgc  5220
ctctcactat gaaaagttga agggctctcc tgaggacaac gagcagaagc agctcttcgt  5280
ggagcagcac aagcactacc tggacgaaat tatcgagcag atctctgagt tctccaagcg  5340
cgtgatattg gccgacgcca acctcgacaa ggtgctgtcc gcctacaaca agcacaggga  5400
taagcccatt cgcgagcagg ctgaaaacat tatccacctg tttaccctca caaacttggg  5460
agcccctgct gccttcaagt acttcgacac caccattgac aggaagagat acacctccac  5520
caaggaggtg ctcgacgcaa cactcatcca ccaatccatc accggcctct atgaaacaag  5580
gattgacttg tcccagctgg gaggcgactc tagagccgat cccaagaaga agagaaaggt  5640
```

-continued

```
gtaggttaac ctagacttgt ccatcttctg gattggccaa cttaattaat gtatgaaata  5700
aaaggatgca cacatagtga catgctaatc actataatgt gggcatcaaa gttgtgtgtt  5760
atgtgtaatt actagttatc tgaataaaag agaaagagat catccatatt tcttatccta  5820
aatgaatgtc acgtgtcttt ataattcttt gatgaaccag atgcatttca ttaaccaaat  5880
ccatatacat ataaatatta atcatatata attaatatca attgggttag caaaacaaat  5940
ctagtctagg tgtgttttgc gaatgcggcc gctcgagggg gggcccggta ccggcgcgcc  6000
gttctatagt gtcacctaaa tcgtatgtgt atgatacata aggttatgta ttaattgtag  6060
ccgcgttcta acgacaatat gtccatatgg tgcactctca gtacaatctg ctctgatgcc  6120
gcatagttaa gccagccccg acacccgcca acacccgctg acgcgccctg acgggcttgt  6180
ctgctcccgg catccgctta cagacaagct gtgaccgtct ccgggagctg catgtgtcag  6240
aggttttcac cgtcatcacc gaaacgcgcg agacgaaagg gcctcgtgat acgcctattt  6300
ttataggtta atgtcatgac caaaatccct taacgtgagt tttcgttcca ctgagcgtca  6360
gaccccgtag aaaagatcaa aggatcttct tgagatcctt tttttctgcg cgtaatctgc  6420
tgcttgcaaa caaaaaaacc accgctacca gcggtggttt gtttgccgga tcaagagcta  6480
ccaactcttt ttccgaaggt aactggcttc agcagagcgc agataccaaa tactgtcctt  6540
ctagtgtagc cgtagttagg ccaccacttc aagaactctg tagcaccgcc tacatacctc  6600
gctctgctaa tcctgttacc agtggctgct gccagtggcg ataagtcgtg tcttaccggg  6660
ttggactcaa gacgatagtt accggataag gcgcagcggt cgggctgaac ggggggttcg  6720
tgcacacagc ccagcttgga gcgaacgacc tacaccgaac tgagatacct acagcgtgag  6780
cattgagaaa gcgccacgct tcccgaaggg agaaaggcgg acaggtatcc ggtaagcggc  6840
agggtcggaa caggagagcg cacgagggag cttccagggg gaaacgcctg gtatctttat  6900
agtcctgtcg ggtttcgcca cctctgactt gagcgtcgat ttttgtgatg ctcgtcaggg  6960
gggcggagcc tatggaaaaa cgccagcaac gcggcctttt tacggttcct ggccttttgc  7020
tggccttttg ctcacatgtt ctttcctgcg ttatcccctg attctgtgga taaccgtatt  7080
accgcctttg agtgagctga taccgctcgc cgcagccgaa cgaccgagcg cagcgagtca  7140
gtgagcgagg aagcggaaga gcgcccaata cgcaaaccgc ctctccccgc gcgttggccg  7200
attcattaat gcaggttgat cagatctcga tcccgcgaaa ttaatacgac tcactatagg  7260
gagaccacaa cggtttccct ctagaaataa ttttgtttaa ctttaagaag gagatatacc  7320
catggaaaag cctgaactca ccgcgacgtc tgtcgagaag tttctgatcg aaaagttcga  7380
cagcgtctcc gacctgatgc agctctcgga gggcgaagaa tctcgtgctt tcagcttcga  7440
tgtaggaggg cgtggatatg tcctgcgggt aaatagctgc gccgatggtt tctacaaaga  7500
tcgttatgtt tatcggcact ttgcatcggc cgcgctcccg attccggaag tgcttgacat  7560
tggggaattc agcgagagcc tgacctattg catctcccgc cgtgcacagg gtgtcacgtt  7620
gcaagacctg cctgaaaccg aactgcccgc tgttctgcag ccggtcgcgg aggctatgga  7680
tgcgatcgct gcggccgatc ttagccagac gagcgggttc ggcccattcg gaccgcaagg  7740
aatcggtcaa tacactacat ggcgtgattt catatgcgcg attgctgatc cccatgtgta  7800
tcactggcaa actgtgatgg acgacaccgt cagtgcgtcc gtcgcgcagg ctctcgatga  7860
gctgatgctt tgggccgagg actgccccga agtccggcac ctcgtgcacg cggatttcgg  7920
ctccaacaat gtcctgacgg acaatggccg cataacagcg gtcattgact ggagcgaggc  7980
gatgttcggg gattcccaat acgaggtcgc caacatcttc ttctggaggc cgtggttggc  8040
ttgtatggag cagcagacgc gctacttcga gcggaggcat ccggagcttg caggatcgcc  8100
gcggctccgg gcgtatatgc tccgcattgg tcttgaccaa ctctatcaga gcttggttga  8160
cggcaatttc gatgatgcag cttgggcgca gggtcgatgc gacgcaatcg tccgatccgg  8220
agccgggact gtcgggcgta cacaaatcgc ccgcagaagc gcggccgtct ggaccgatgg  8280
ctgtgtagaa gtactcgccg atagtggaaa ccgacgcccc agcactcgtc cgagggcaaa  8340
ggaatagtga ggtacagctt ggatcgatcc ggctgctaac aaagcccgaa aggaagctga  8400
gttggctgct gccaccgctg agcaataact agcataaccc cttggggcct ctaaacgggt  8460
cttgaggggt tttttgctga aaggaggaac tatatccgga tgatcgggcg cgccggtac   8519

SEQ ID NO: 120         moltype = DNA  length = 434
FEATURE                Location/Qualifiers
source                 1..434
                       mol_type = genomic DNA
                       organism = Glycine max
SEQUENCE: 120
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaa                                                   434

SEQ ID NO: 121         moltype = DNA  length = 104
FEATURE                Location/Qualifiers
misc_feature           1..104
                       note = synthesized sequence- Guide RNA for DD43CR1
source                 1..104
                       mol_type = other DNA
                       organism = synthetic construct
SEQUENCE: 121
gtcccttgta cttgtacgta gttttagagc tagaaatagc aagttaaaat aaggctagtc  60
cgttatcaac ttgaaaaagt ggcaccgagt cggtgctttt tttt                  104

SEQ ID NO: 122         moltype = DNA  length = 3098
FEATURE                Location/Qualifiers
misc_feature           1..3098
                       note = synthesized sequence- QC783
```

```
source                  1..3098
                        mol_type = other DNA
                        organism = synthetic construct
SEQUENCE: 122
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg tcccttgtac ttgtacgtag ttttagagct agaaatagca  480
agttaaaata aggctagtcc gttatcaact tgaaaaagtg gcaccgagtc ggtgcttttt  540
tttgcggccg ctcgaggggg ggcccggtac cggcgcgccg ttctatagtg tcacctaaat  600
cgtatgtgta tgatacataa ggttatgtat taattgtagc cgcgttctaa cgacaatatg  660
tccatatggt gcactctcag tacaatctgc tctgatgccg catagttaag ccagccccga  720
cacccgccaa cacccgctga cgcgccctga cgggcttgtc tgctcccggc atccgcttac  780
agacaagctg tgaccgtctc cgggagctgc atgtgtcaga ggttttcacc gtcatcaccg  840
aaacgcgcga gacgaaaggg cctcgtgata cgcctatttt tataggttaa tgtcatgacc  900
aaaatccctt aacgtgagtt ttcgttccac tgagcgtcag accccgtaga aaagatcaaa  960
ggatcttctt gagatccttt ttttctgcgc gtaatctgct gcttgcaaac aaaaaaacca  1020
ccgctaccag cggtggtttg tttgccggat caagagctac caactctttt tccgaaggta  1080
actggcttca gcagagcgca gataccaaat actgtccttc tagtgtagcc gtagttaggc  1140
caccacttca agaactctgt agcaccgcct acatacctcg ctctgctaat cctgttacca  1200
gtggctgctg ccagtggcga taagtcgtgt cttaccgggt tggactcaag acgatagtta  1260
ccggataagg cgcagcggtc gggctgaacg gggggttcgt gcacacagcc cagcttggag  1320
cgaacgacct acaccgaact gagataccta cagcgtgagc attgagaaag cgccacgctt  1380
cccgaaggga gaaaggcgga caggtatccg gtaagcggca gggtcggaac aggagagcgc  1440
acgagggagc ttccaggggg aaacgcctgg tatctttata gtcctgtcgg gtttcgccac  1500
ctctgacttg agcgtcgatt tttgtgatgc tcgtcagggg ggcggagcct atggaaaaac  1560
gccagcaacg cggccttttt acggttcctg gccttttgct ggccttttgc tcacatgttc  1620
tttcctgcgt tatcccctga ttctgtggat aaccgtatta ccgcctttga gtgagctgat  1680
accgctcgcc gcagccgaac gaccgagcgc agcgagtcag tgagcgagga agcggaagag  1740
cgcccaatac gcaaaccgcc tctccccgcg cgttggccga ttcattaatg caggttgatc  1800
agatctcgat cccgcgaaat taatacgact cactataggg agaccacaac ggtttccctc  1860
tagaaataat tttgtttaac tttaagaagg agatataccc atggaaaagc ctgaactcac  1920
cgcgacgtct gtcgagaagt ttctgatcga aaagttcgac agcgtctccg acctgatgca  1980
gctctcggag ggcgaagaat ctcgtgcttt cagcttcgat gtaggagggc gtggatatgt  2040
cctgcgggta aatagctgcg ccgatggttt ctacaaagat cgttatgttt atcggcactt  2100
tgcatcggcc gcgctcccga ttccggaagt gcttgacatt ggggaattca gcgagagcct  2160
gacctattgc atctcccgcc gtgcacaggg tgtcacgttg caagacctgc ctgaaaccga  2220
actgcccgct gttctgcagc cggtcgcgga ggctatggat gcgatcgctg cggccgatct  2280
tagccagacg agcgggttcg gcccattcgg accgcaagga atcggtcaat acactacatg  2340
gcgtgatttc atatgcgcga ttgctgatcc ccatgtgtat cactggcaaa ctgtgatgga  2400
cgacaccgtc agtgcgtccg tcgcgcaggc tctcgatgag ctgatgcttt gggccgagga  2460
ctgccccgaa gtccggcacc tcgtgcacgc ggatttcggc tccaacaatg tcctgacgga  2520
caatggccgc ataacagcgg tcattgactg gagcgaggcg atgttcgggg attcccaata  2580
cgaggtcgcc aacatcttct tctggaggcc gtggttggct tgtatggagc agcagacgcg  2640
ctacttcgag cggaggcatc cggagcttgc aggatcgccg cggctccggg cgtatatgct  2700
ccgcattggt cttgaccaac tctatcagag cttggttgac ggcaatttcg atgatgcagc  2760
ttgggcgcag ggtcgatgcg acgcaatcgt ccgatccgga gccgggactg tcgggcgtac  2820
acaaatcgcc cgcagaagcg cggccgtctg gaccgatggc tgtgtagaag tactcgccga  2880
tagtggaaac cgacgcccca gcactcgtcc gagggcaaag gaatagtgag gtacagcttg  2940
gatcgatccg gctgctaaca aagcccgaaa ggaagctgag ttggctgctg ccaccgctga  3000
gcaataacta gcataacccc ttggggcctc taaacgggtc ttgaggggtt ttttgctgaa  3060
aggaggaact atatccggat gatcgggcgc gccggtac                          3098

SEQ ID NO: 123          moltype = DNA  length = 9093
FEATURE                 Location/Qualifiers
misc_feature            1..9093
                        note = synthesized sequence- QC815
source                  1..9093
                        mol_type = other DNA
                        organism = synthetic construct
SEQUENCE: 123
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg tcccttgtac ttgtacgtag ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
```

-continued

```
aaaaaatcat aaaggtttag tatttttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gtttttttagg attcttttgg tttttgaatc gattaatcgg aagagatttt cgagttattt  1560
ggtgtgttgg aggtgaatct tttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gtttttttgt gggtttgttc acatgttatc aagcttaatc ttttactatg tatgcgacca  1860
tatctggatc cagcaaaggc gatttttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggacaa aaagtactca atagggctcg acatagggac  2100
taactccgtt ggatgggccg tcatcaccga cgagtacaag gtgccctcca agaagttcaa  2160
ggtgttggga aacaccgaca ggcacagcat aaagaagaat ttgatcggtg ccctcctctt  2220
cgactccgga gagaccgctg aggctaccag gctcaagagg accgctagaa ggcgctacac  2280
cagaaggaag aacagaatct gctacctgca ggagatcttc tccaacgaga tggccaaggt  2340
ggacgactcc ttcttccacc gccttgagga atcattcctg gtggaggagg ataaaaagca  2400
cgagagacac ccaatcttcg ggaacatcgt cgacgaggtg gcctaccatg aaaagtaccc  2460
taccatctac cacctgagga agaagctggt cgactctacc gacaaggctg acttgcgctt  2520
gatttacctg gctctcgctc acatgataaa gttccgcgga cacttcctca ttgagggaga  2580
cctgaaccca gacaactccg acgtggacaa gctcttcatc cagctcgttc agacctacaa  2640
ccagcttttc gaggagaacc caatcaacgc cagtggagtt gacgccaagg ctatcctctc  2700
tgctcgtctg tcaaagtcca ggaggcttga gaacttgatt gcccagctgc ctggcgaaaa  2760
gaagaacgga ctgttcggaa acttgatcgc tctctccctg ggattgactc ccaacttcaa  2820
gtccaacttc gacctcgccg aggacgctaa gttgcagttg tctaaagaca cctacgacga  2880
tgacctcgac aacttgctgg cccagatagg cgaccaatac gccgatctct tcctcgccgc  2940
taagaacttg tccgacgcaa tcctgctgtc cgacatcctg agagtcaaca ctgagattac  3000
caaagctcct ctgtctgctt ccatgattaa gcgctacgac gagcaccacc aagatctgac  3060
cctgctcaag gccctggtga gacagcagct gcccgagaag tacaaggaga tctttttcga  3120
ccagtccaag aacggctacg ccggatacat tgacggaggc gcctcccagg aagagttcta  3180
caagttcatc aagcccatcc ttgagaagat ggacggtacc gaggagctgt tggtgaagtt  3240
gaacagagag gacctgttga ggaagcagag aaccttcgac aacggaagca tccctcacca  3300
aatccacctg ggagagctcc acgccatctt gaggaggcag gaggatttct atcccttcct  3360
gaaggacaac cgcgagaaga ttgagaagat cttgaccttc agaattcctt actacgtcgg  3420
gccactcgcc agaggaaact ctaggttcgc ctggatgacc cgcaaatctg aagagaccat  3480
tactccctgg aacttcgagg aagtcgtgga caagggcgct tccgctcagt ctttcatcga  3540
gaggatgacc aacttcgata aaaatctgcc caacgagaag gtgctgccca agcactccct  3600
gttgtacgag tatttcacag tgtacaacga gctcaccaag gtgaagtacg tcacagaggg  3660
aatgaggaag cctgccttct tgtccggaga gcagaagaag gccatcgtcg acctgctctt  3720
caagaccaac aggaaggtga ctgtcaagca gctgaaggag gactacttca agaagatcga  3780
gtgcttcgac tccgtcgaga tctctggtgt cgaggacagg ttcaacgcct cccttgggac  3840
ttaccacgat ctgctcaaga ttattaaaga caaggacttc ctggacaacg aggagaacga  3900
ggacatcctt gaggacatcg tgctcaccct gaccttgttc gaagacaggg aaatgatcga  3960
agagaggctc aagacctacg cccacctctt cgacgacaag gtgatgaaac agctgaagag  4020
acgcagatat accggctggg gaaggctctc ccgcaaattg atcaacggga tcagggacaa  4080
gcagtcaggg aagactatac tcgacttcct gaagtccgac ggattcgcca acaggaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaagggc attttgcaga ccgtgaaggt cgttgacgag ctcgtgaagg tgatgggacg  4320
ccacaagcca gagaacatcg ttattgagat ggctcgcgag aaccaaacta cccagaaagg  4380
gcagaagaat tcccgcgaga ggatgaagcg cattgaggag ggcataaaag agcttggctc  4440
tcagatcctc aaggagcacc ccgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tcccctccga  4680
ggaggtcgtg aagaagatga aaaactactg gagacagctc ttgaacgcca agctcatcac  4740
ccagcgtaag ttcgacaacc tgactaaggc tgagagagga ggattgtccg agctcgataa  4800
ggccggattc atcaagagac agctcgtcga aacccgccaa attaccaagc acgtggccca  4860
aattctggat tcccgcatga acaccaagta cgatgaaaat gacaagctga tccgcgaggt  4920
caaggtgatc accttgaagt ccaagctggt ctccgacttc cgcaaggact tccagttcta  4980
caaggtgagg gagatcaaca actaccacca cgcacacgac gcctacctca acgctgtcgt  5040
tggaaccgcc ctcatcaaaa aatatcctaa gctggagtct gagttcgtct acggcgacta  5100
caaggtgtac gacgtgagga agatgatcgc taagtctgag caggagatcg gcaaggccac  5160
cgccaagtac ttcttctact ccaacatcat gaacttcttc aagaccgaga tcactctcgc  5220
caacggtgag atcaggaagc gcccactgat cgagaccaac ggtgagactg gagagatcgt  5280
gtgggacaaa gggagggatt tcgctactgt gaggaaggtg ctctccatgc ctcaggtgaa  5340
catcgtcaag aagaccgaag ttcagaccgg aggattctcc aaggagtcca tcctccccaa  5400
gagaaactcc gacaagctga tcgctagaaa gaaagactgg gaccctaaga agtacggagg  5460
cttcgattct cctaccgtgg cctactctgt gctggtcgtg gccaaggtgg agaagggcaa  5520
gtccaagaag ctgaaatccg tcaaggagct cctcgggatt accatcatgg agaggagttc  5580
```

```
cttcgagaag aaccctatcg acttcctgga ggccaaggga tataaagagg tgaagaagga  5640
cctcatcatc aagctgccca agtactccct cttcgagttg gagaacggaa ggaagaggat  5700
gctggcttct gccggagagt tgcagaaggg aaatgagctc gcccttccct ccaagtacgt  5760
gaacttcctg tacctcgcct ctcactatga aaagttgaag ggctctcctg aggacaacga  5820
gcagaagcag ctcttcgtgg agcagcacaa gcactacctg gacgaaatta tcgagcagat  5880
ctctgagttc tccaagcgcg tgatattggc cgacgccaac ctcgacaagg tgctgtccgc  5940
ctacaacaag cacagggata agcccattcg cgagcaggct gaaaacatta tccacctgtt  6000
taccctcaca aacttgggag cccctgctgc cttcaagtac ttcgacacca ccattgacag  6060
gaagagatac acctccacca aggaggtgct cgacgcaaca ctcatccacc aatccatcac  6120
cggcctctat gaaacaagga ttgacttgtc ccagctggga ggcgactcta gagccgatcc  6180
caagaagaag agaaaggtgt aggttaacct agacttgtcc atcttctgga ttggccaact  6240
taattaatgt atgaaataaa aggatgcaca catagtgaca tgctaatcac tataatgtgg  6300
gcatcaaagt tgtgtgttat gtgtaattac tagttatctg aataaaagag aaagagatca  6360
tccatatttc ttatcctaaa tgaatgtcac gtgtctttat aattctttga tgaaccagat  6420
gcatttcatt aaccaaatcc atatacatat aaatattaat catatataat taatatcaat  6480
tgggttagca aaacaaatct agtctaggtg tgttttgcga attcgatatc aagcttatcg  6540
ataccgtcga ggggggcccc ggtaccggcg cgccgttcta tagtgtcacc taaatcgtat  6600
gtgtatgata cataaggtta tgtattaatt gtagccgcgt tctaacgaca atatgtccat  6660
atggtgcact ctcagtacaa tctgctctga tgccgcatag ttaagccagc cccgacaccc  6720
gccaacaccc gctgacgcgc cctgacgggc ttgtctgctc ccggcatccg cttacagaca  6780
agctgtgacc gtctccggga gctgcatgtg tcagaggttt tcaccgtcat caccgaaacg  6840
cgcgagacga aagggcctcg tgatacgcct atttttatag gttaatgtca tgaccaaaat  6900
cccttaacgt gagttttcgt tccactgagc gtcagacccc gtagaaaaga tcaaaggatc  6960
ttcttgagat cctttttttc tgcgcgtaat ctgctgcttg caaacaaaaa aaccaccgct  7020
accagcggtg gtttgtttgc cggatcaaga gctaccaact ctttttccga aggtaactgg  7080
cttcagcaga gcgcagatac caaatactgt ccttctagtg tagccgtagt taggccacca  7140
cttcaagaac tctgtagcac cgcctacata cctcgctctg ctaatcctgt taccagtggc  7200
tgctgccagt ggcgataagt cgtgtcttac cgggttggac tcaagacgat agttaccgga  7260
taaggcgcag cggtcgggct gaacgggggg ttcgtgcaca cagcccagct tggagcgaac  7320
gacctacacc gaactgagat acctacagcg tgagcattga gaaagcgcca cgcttcccga  7380
agggagaaag gcggacaggt atccggtaag cggcagggtc ggaacaggag agcgcacgag  7440
ggagcttcca gggggaaacg cctggtatct ttatagtcct gtcgggtttc gccacctctg  7500
acttgagcgt cgatttttgt gatgctcgtc aggggggcgg agcctatgga aaaacgccag  7560
caacgcggcc tttttacggt tcctggcctt ttgctggcct tttgctcaca tgttctttcc  7620
tgcgttatcc cctgattctg tggataaccg tattaccgcc tttgagtgag ctgataccgc  7680
tcgccgcagc cgaacgaccg agcgcagcga gtcagtgagc gaggaagcgg aagagcgccc  7740
aatacgcaaa ccgcctctcc ccgcgcgttg gccgattcat taatgcaggt tgatcagatc  7800
tcgatcccgc gaaattaata cgactcacta tagggagacc acaacggttt ccctctagaa  7860
ataattttgt ttaactttaa gaaggagata tacccatgga aaagcctgaa ctcaccgcga  7920
cgtctgtcga gaagtttctg atcgaaaagt tcgacagcgt ctccgacctg atgcagctct  7980
cggagggcga agaatctcgt gctttcagct tcgatgtagg agggcgtgga tatgtcctgc  8040
gggtaaatag ctgcgccgat ggtttctaca aagatcgtta tgtttatcgg cactttgcat  8100
cggccgcgct cccgattccg gaagtgcttg acattgggga attcagcgag agcctgacct  8160
attgcatctc ccgccgtgca cagggtgtca cgttgcaaga cctgcctgaa accgaactgc  8220
ccgctgttct gcagccggtc gcggaggcta tggatgcgat cgctgcggcc gatcttagcc  8280
agacgagcgg gttcggccca ttcggaccgc aaggaatcgg tcaatacact acatggcgtg  8340
atttcatatg cgcgattgct gatccccatg tgtatcactg gcaaactgtg atggacgaca  8400
ccgtcagtgc gtccgtcgcg caggctctcg atgagctgat gctttgggcc gaggactgcc  8460
ccgaagtccg gcacctcgtg cacgcggatt tcggctccaa caatgtcctg acggacaatg  8520
gccgcataac agcggtcatt gactggagcg aggcgatgtt cggggattcc caatacgagg  8580
tcgccaacat cttcttctgg aggccgtggt tggcttgtat ggagcagcag acgcgctact  8640
tcgagcggag gcatccggag cttgcaggat cgccgcggct ccgggcgtat atgctccgca  8700
ttggtcttga ccaactctat cagagcttgg ttgacggcaa tttcgatgat gcagcttggg  8760
cgcagggtcg atgcgacgca atcgtccgat ccggagccgg gactgtcggg cgtacacaaa  8820
tcgcccgcag aagcgcggcc gtctggaccg atggctgtgt agaagtactc gccgatagtg  8880
gaaaccgacg ccccagcact cgtccgaggg caaaggaata gtgaggtaca gcttggatcg  8940
atccggctgc taacaaagcc cgaaaggaag ctgagttggc tgctgccacc gctgagcaat  9000
aactagcata accccttggg gcctctaaac gggtcttgag gggttttttg ctgaaaggag  9060
gaactatatc cggatgatcg ggcgcgccgg tac                                9093

SEQ ID NO: 124          moltype = DNA  length = 4107
FEATURE                 Location/Qualifiers
source                  1..4107
                        mol_type = genomic DNA
                        organism = Steptococcus pyogenes
SEQUENCE: 124
atggataaga aatactcaat aggcttagat atcggcacaa atagcgtcgg atgggcggtg  60
atcactgatg attataaggt tccgtctaaa aagctcaagg gtctgggaaa tacagaccgc  120
cacggtatca aaaaaaatct tataggggct cttttatttg acagtggaga gacagcggaa  180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt ctttttggt ggaagaagac aagaagcatg aacgtcatcc tatttttgga  360
aatatagtag atgaagttgc ttatcatgag aaatatccaa ctatctatca tctgcgaaaa  420
aaattggcag attctactga taaagtggat ttgcgcttaa tctatttggc cttagcgcat  480
atgattaagt ttcgtggtca ttttttgatt gagggagatt taaatcctga taatagtgat  540
gtggacaaac tatttatcca gttggtacaa acctacaatc aattatttga agaaaaccct  600
attaacgcaa gtagagtaga tgctaaagcg attctttctg cacgattgag taaatcaaga  660
cgattagaaa atctcattgc tcagctcccc ggtgagaaga aaaatggatt gtttgggaat  720
ctcattgctt tgtcattggg attgacccct aattttaaat caaattttga tttggcagaa  780
```

-continued

```
gatgctaaat tacagctttc aaaagatact tacgatgatg atttagataa tttattggcg  840
caaattggag atcaatatgc tgatttgttt ttggcagcta agaatttatc agatgctact  900
ttactttcag atatcctaag agtaaatagt gaaataacta aggctcccct atcagcttca  960
atgattaagc gctacgatga acatcatcaa gacttgactc ttttaaaagc tttagttcga  1020
caacaacttc cagaaaagta taaagaaatc ttttttgatc aatcaaaaaa cggatatgca  1080
ggttatattg atgggggagc tagccaagaa gaattttata aatttatcaa accaatttta  1140
gaaaaaatgg atggtactga ggaattattg gcgaaactaa atcgtgaaga tttgctgcgc  1200
aagcaacgga cctttgacaa cggctctatt ccctatcaaa ttcacttggg tgagctgcat  1260
gctattttga gaagacaaga agacttttat ccattttttaa aagacaatcg tgagaagatt  1320
gaaaaaatct tgacttttcg aattccttat tatgttggtc cattggcgcg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaagt caaatatgtt actgagggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggtacct accatgattt gctaaaaatt  1800
attaaagata aagatttttt ggataatgaa gaaaacgaag atatcttaga ggatattgtt  1860
ttaacattga ccttatttga agatagggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gatttttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgg cacgtgaaaa tcagacaact caaaagggcc agaaaaattc gcgtgagcgt  2340
atgaaacgta ttgaagaagg aataaaagaa ctaggaagtg atattctaaa ggagtatcct  2400
gttgaaaaca ctcaattaca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acaaaagctg aacgtggagg tttgagtgaa cttgataaag ttggttttat caaacgccaa  2760
ttggttgaaa ctcgccaaat cactaagcat gtggcacaaa ttttggatag tcgcatgaat  2820
actaaatacg atgaaaatga taaacttatt cgagaggtta gagtgattac cttaaaatct  2880
aaattagttt ctgacttccg aaaagatttc caattctata aagtacgtga gattaacaat  2940
taccatcatg cccatgatgc gtatcttaat gccgtcgttg gaactgcttt gattaagaaa  3000
tatccaaaac ttgaatcgga gtttgtctat ggtgattata aagtttatga tgttcgtaaa  3060
atgattgcta agtctgagca ggaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aataatggaa agaagctctt ttgaaaaaga tccgattgac  3540
tttttagaag ctaaaggata taaggaagtt agaaaagact taatcattaa actacctaaa  3600
tatagtcttt ttgagttaga aaacggtcgt aaacggatgc tggctagtgc cggagaattg  3660
caaaaaggaa atgagctagc tctgccaagc aaatatgtga attttttata tttagctagt  3720
cattatgaaa agttgaaggg tagtccagaa gataacgaac aaaaacaatt gtttgtggag  3780
cagcataagc attatttaga tgagattatt gagcaaatca gtgaattttc taagcgtgtt  3840
attttagcag atgccaattt agataaagtt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg gtctttatga aacacgcatt  4080
gatttgagtc agctaggagg tgactga                                      4107

SEQ ID NO: 125          moltype = DNA  length = 20
FEATURE                 Location/Qualifiers
source                  1..20
                        mol_type = genomic DNA
                        organism = Glycine max
SEQUENCE: 125
ggaactgaca cacgacatga                                              20

SEQ ID NO: 126          moltype = DNA  length = 20
FEATURE                 Location/Qualifiers
source                  1..20
                        mol_type = genomic DNA
                        organism = Glycine max
SEQUENCE: 126
gacatgatgg aacgtgacta                                              20

SEQ ID NO: 127          moltype = DNA  length = 20
FEATURE                 Location/Qualifiers
source                  1..20
                        mol_type = genomic DNA
                        organism = Glycine max
SEQUENCE: 127
```

-continued

```
gtcccttgta cttgtacgta                                                  20

SEQ ID NO: 128         moltype = DNA  length = 20
FEATURE                Location/Qualifiers
source                 1..20
                       mol_type = genomic DNA
                       organism = Glycine max
SEQUENCE: 128
gtattctaga aaagaggaat                                                  20

SEQ ID NO: 129         moltype = DNA  length = 70
FEATURE                Location/Qualifiers
source                 1..70
                       mol_type = genomic DNA
                       organism = Glycine max
SEQUENCE: 129
atcaaaattc ggaactgaca cacgacatga tggaacgtga ctaaggtggg tttttgactt  60
tgcatgtcga                                                             70

SEQ ID NO: 130         moltype = DNA  length = 70
FEATURE                Location/Qualifiers
source                 1..70
                       mol_type = genomic DNA
                       organism = Glycine max
SEQUENCE: 130
tcgacatgca aagtcaaaaa cccaccttag tcacgttcca tcatgtcgtg tgtcagttcc  60
gaattttgat                                                             70

SEQ ID NO: 131         moltype = DNA  length = 70
FEATURE                Location/Qualifiers
source                 1..70
                       mol_type = genomic DNA
                       organism = Glycine max
SEQUENCE: 131
ggcagactcc aattcctctt ttctagaata ccctccgtac gtacaagtac aagggacttg  60
tgagttgtaa                                                             70

SEQ ID NO: 132         moltype = DNA  length = 70
FEATURE                Location/Qualifiers
source                 1..70
                       mol_type = genomic DNA
                       organism = Glycine max
SEQUENCE: 132
ttacaactca caagtccctt gtacttgtac gtacggaggg tattctagaa aagaggaatt  60
ggagtctgcc                                                             70

SEQ ID NO: 133         moltype = DNA  length = 71
FEATURE                Location/Qualifiers
misc_feature           1..71
                       note = synthesized sequence-primer DD20-S3
source                 1..71
                       mol_type = other DNA
                       organism = synthetic construct
SEQUENCE: 133
ctacactctt tccctacacg acgctcttcc gatctggaat ttacagcaca agtagatcac  60
ttgtacttat c                                                           71

SEQ ID NO: 134         moltype = DNA  length = 59
FEATURE                Location/Qualifiers
misc_feature           1..59
                       note = synthesized sequence-primer DD20-A
source                 1..59
                       mol_type = other DNA
                       organism = synthetic construct
SEQUENCE: 134
caagcagaag acggcatacg agctcttccg atctaaatca ctctcacttc gacatgcaa   59

SEQ ID NO: 135         moltype = DNA  length = 71
FEATURE                Location/Qualifiers
misc_feature           1..71
                       note = synthesized sequence-primer DD20-S4
source                 1..71
                       mol_type = other DNA
                       organism = synthetic construct
SEQUENCE: 135
ctacactctt tccctacacg acgctcttcc gatctttcct ttacagcaca agtagatcac  60
ttgtacttat c                                                           71

SEQ ID NO: 136         moltype = DNA  length = 68
```

-continued

```
FEATURE                Location/Qualifiers
misc_feature           1..68
                       note = synthesized sequence-primer DD43-S3
source                 1..68
                       mol_type = other DNA
                       organism = synthetic construct
SEQUENCE: 136
ctacactctt tccctacacg acgctcttcc gatctagctg taaatacagc cttacaactc  60
acaagtcc                                                           68

SEQ ID NO: 137         moltype = DNA  length = 63
FEATURE                Location/Qualifiers
misc_feature           1..63
                       note = synthesized sequence-Primer, DD43-A
source                 1..63
                       mol_type = other DNA
                       organism = synthetic construct
SEQUENCE: 137
caagcagaag acggcatacg agctcttccg atctttaatt taggactaaa agaagaggca  60
gac                                                                63

SEQ ID NO: 138         moltype = DNA  length = 68
FEATURE                Location/Qualifiers
misc_feature           1..68
                       note = synthesized sequence- Primer, DD43-S4
source                 1..68
                       mol_type = other DNA
                       organism = synthetic construct
SEQUENCE: 138
ctacactctt tccctacacg acgctcttcc gatctctagg taaatacagc cttacaactc  60
acaagtcc                                                           68

SEQ ID NO: 139         moltype = DNA  length = 68
FEATURE                Location/Qualifiers
misc_feature           1..68
                       note = synthesized sequence- Primer, DD43-S5
source                 1..68
                       mol_type = other DNA
                       organism = synthetic construct
SEQUENCE: 139
ctacactctt tccctacacg acgctcttcc gatctgatcg taaatacagc cttacaactc  60
acaagtcc                                                           68

SEQ ID NO: 140         moltype = DNA  length = 43
FEATURE                Location/Qualifiers
misc_feature           1..43
                       note = synthesized sequence- Primer, JKY557
source                 1..43
                       mol_type = other DNA
                       organism = synthetic construct
SEQUENCE: 140
aatgatacgg cgaccaccga gatctacact ctttccctac acg                    43

SEQ ID NO: 141         moltype = DNA  length = 18
FEATURE                Location/Qualifiers
misc_feature           1..18
                       note = synthesized sequence- primer, JKY558
source                 1..18
                       mol_type = other DNA
                       organism = synthetic construct
SEQUENCE: 141
caagcagaag acggcata                                                18

SEQ ID NO: 142         moltype = DNA  length = 117
FEATURE                Location/Qualifiers
misc_feature           1..117
                       note = synthesized sequence- DD20CR1 PCR amplicon
source                 1..117
                       mol_type = other DNA
                       organism = synthetic construct
SEQUENCE: 142
ggaatttaca gcacaagtag atcacttgta cttatcaaaa ttcggaactg acacacgaca  60
tgatggaacg tgactaaggt gggtttttga ctttgcatgt cgaagtgaga gtgattt     117

SEQ ID NO: 143         moltype = DNA  length = 117
FEATURE                Location/Qualifiers
misc_feature           1..117
                       note = synthesized sequence- DD20CR2 PCR amplicon
source                 1..117
```

```
                        mol_type = other DNA
                        organism = synthetic construct
SEQUENCE: 143
ttcctttaca gcacaagtag atcacttgta cttatcaaaa ttcggaactg acacacgaca  60
tgatggaacg tgactaaggt gggtttttga ctttgcatgt cgaagtgaga gtgattt     117

SEQ ID NO: 144          moltype = DNA  length = 108
FEATURE                 Location/Qualifiers
misc_feature            1..108
                        note = synthesized sequence- DD43CR1 PCR amplicon
source                  1..108
                        mol_type = other DNA
                        organism = synthetic construct
SEQUENCE: 144
agctgtaaat acagccttac aactcacaag tcccttgtac ttgtacgtac ggagggtatt  60
ctagaaaaga ggaattggag tctgcctctt cttttagtcc taaattaa               108

SEQ ID NO: 145          moltype = DNA  length = 108
FEATURE                 Location/Qualifiers
misc_feature            1..108
                        note = synthesized sequence- DD43CR2 PCR amplicon
source                  1..108
                        mol_type = other DNA
                        organism = synthetic construct
SEQUENCE: 145
ctaggtaaat acagccttac aactcacaag tcccttgtac ttgtacgtac ggagggtatt  60
ctagaaaaga ggaattggag tctgcctctt cttttagtcc taaattaa               108

SEQ ID NO: 146          moltype = DNA  length = 108
FEATURE                 Location/Qualifiers
misc_feature            1..108
                        note = synthesized sequence- amplicon
source                  1..108
                        mol_type = other DNA
                        organism = synthetic construct
SEQUENCE: 146
ctaggtaaat acagccttac aactcacaag tcccttgtac ttgtacgtac ggagggtatt  60
ctagaaaaga ggaattggag tctgcctctt cttttagtcc taaattaa               108

SEQ ID NO: 147          moltype = DNA  length = 101
FEATURE                 Location/Qualifiers
source                  1..101
                        mol_type = genomic DNA
                        organism = Glycine max
SEQUENCE: 147
ggaatttaca gcacaagtag atcacttgta cttatcaaaa ttcggaactg acacacgatg  60
atggaacgtg actaaggtgg gtttttgact ttgcatgtcg a                      101

SEQ ID NO: 148          moltype = DNA  length = 101
FEATURE                 Location/Qualifiers
source                  1..101
                        mol_type = genomic DNA
                        organism = Glycine max
SEQUENCE: 148
ggaatttaca gcacaagtag atcacttgta cttatcaaaa ttcggaactg acacacgatg  60
gaacgtgact aaggtgggtt tttgactttg catgtcgaag t                      101

SEQ ID NO: 149          moltype = DNA  length = 101
FEATURE                 Location/Qualifiers
source                  1..101
                        mol_type = genomic DNA
                        organism = Glycine max
SEQUENCE: 149
ggaatttaca gcacaagtag atcacttgta cttatcaaaa ttcggaactg acacacgact  60
gatggaacgt gactaaggtg ggtttttgac tttgcatgtc g                      101

SEQ ID NO: 150          moltype = DNA  length = 101
FEATURE                 Location/Qualifiers
source                  1..101
                        mol_type = genomic DNA
                        organism = Glycine max
SEQUENCE: 150
ggaatttaca gcacaagtag atcacttgta cttatcaaaa ttcggaactg acacacatgg  60
aacgtgacta aggtgggttt ttgactttgc atgtcgaagt g                      101

SEQ ID NO: 151          moltype = DNA  length = 101
FEATURE                 Location/Qualifiers
source                  1..101
                        mol_type = genomic DNA
```

```
                          organism = Glycine max
SEQUENCE: 151
ggaatttaca gcacaagtag atcacttgta cttatcaaaa ttcggaactg acacatgatg  60
gaacgtgact aaggtgggtt tttgactttg catgtcgaag t                      101

SEQ ID NO: 152            moltype = DNA  length = 101
FEATURE                   Location/Qualifiers
source                    1..101
                          mol_type = genomic DNA
                          organism = Glycine max
SEQUENCE: 152
ggaatttaca gcacaagtag atcacttgta cttatcaaaa ttcggaactg acacagacat  60
gatggaacgt gactaaggtg ggtttttgac tttgcatgtc g                      101

SEQ ID NO: 153            moltype = DNA  length = 101
FEATURE                   Location/Qualifiers
source                    1..101
                          mol_type = genomic DNA
                          organism = Glycine max
SEQUENCE: 153
ggaatttaca gcacaagtag atcacttgta cttatcaaaa ttcggaactg acacgacatg  60
atggaacgtg actaaggtgg gtttttgact ttgcatgtcg a                      101

SEQ ID NO: 154            moltype = DNA  length = 101
FEATURE                   Location/Qualifiers
source                    1..101
                          mol_type = genomic DNA
                          organism = Glycine max
SEQUENCE: 154
ggaatttaca gcacaagtag atcacttgta cttatcaaaa ttcggaactg acacaagaaa  60
tgatggaacg tgactaaggt gggtttttga ctttgcatgt c                      101

SEQ ID NO: 155            moltype = DNA  length = 101
FEATURE                   Location/Qualifiers
source                    1..101
                          mol_type = genomic DNA
                          organism = Glycine max
SEQUENCE: 155
ggaatttaca gcacaagtag atcacttgta cttatcaaaa ttcggaactg acacacgatt  60
gaacgtgact aaggtgggtt tttgactttg catgtcgaag t                      101

SEQ ID NO: 156            moltype = DNA  length = 101
FEATURE                   Location/Qualifiers
source                    1..101
                          mol_type = genomic DNA
                          organism = Glycine max
SEQUENCE: 156
ggaatttaca gcacaagtag atcacttgta cttatcaaaa ttcggaactg acacacattg  60
aacgtgacta aggtgggttt ttgactttgc atgtcgaagt g                      101

SEQ ID NO: 157            moltype = DNA  length = 101
FEATURE                   Location/Qualifiers
source                    1..101
                          mol_type = genomic DNA
                          organism = Glycine max
SEQUENCE: 157
ttcctttaca gcacaagtag atcacttgta cttatcaaaa ttcggaactg acacacgaca  60
tgatggaacg tctaaggtgg gtttttgact ttgcatgtcg a                      101

SEQ ID NO: 158            moltype = DNA  length = 101
FEATURE                   Location/Qualifiers
source                    1..101
                          mol_type = genomic DNA
                          organism = Glycine max
SEQUENCE: 158
ttcctttaca gcacaagtag atcacttgta cttatcaaaa ttcggaactg acacacgaca  60
tgatggaacc taaggtgggt ttttgacttt gcatgtcgaa g                      101

SEQ ID NO: 159            moltype = DNA  length = 101
FEATURE                   Location/Qualifiers
source                    1..101
                          mol_type = genomic DNA
                          organism = Glycine max
SEQUENCE: 159
ttcctttaca gcacaagtag atcacttgta cttatcaaaa ttcggaactg acacacgaca  60
tgatggaacg tgactaggtg ggtttttgac tttgcatgtc g                      101

SEQ ID NO: 160            moltype = DNA  length = 101
FEATURE                   Location/Qualifiers
```

```
source                  1..101
                        mol_type = genomic DNA
                        organism = Glycine max
SEQUENCE: 160
ttcctttaca gcacaagtag atcacttgta cttatcaaaa ttcggaactg acacacgaca  60
tgatggaact aaggtgggtt tttgactttg catgtcgaag t                      101

SEQ ID NO: 161          moltype = DNA  length = 101
FEATURE                 Location/Qualifiers
source                  1..101
                        mol_type = genomic DNA
                        organism = Glycine max
SEQUENCE: 161
ttcctttaca gcacaagtag atcacttgta cttatcaaaa ttcggaactg acacacgaca  60
tgatggaacg aaggtgggtt tttgactttg catgtcgaag t                      101

SEQ ID NO: 162          moltype = DNA  length = 101
FEATURE                 Location/Qualifiers
source                  1..101
                        mol_type = genomic DNA
                        organism = Glycine max
SEQUENCE: 162
ttcctttaca gcacaagtag atcacttgta cttatcaaaa ttcggaactg acacacgaca  60
tgatggaagg tgggtttttg actttgcatg tcgaagtgag a                      101

SEQ ID NO: 163          moltype = DNA  length = 101
FEATURE                 Location/Qualifiers
source                  1..101
                        mol_type = genomic DNA
                        organism = Glycine max
SEQUENCE: 163
ttcctttaca gcacaagtag atcacttgta cttatcaaaa ttcggaactg acacacgaca  60
tgatggacgt gactaaggtg ggtttttgac tttgcatgtc g                      101

SEQ ID NO: 164          moltype = DNA  length = 101
FEATURE                 Location/Qualifiers
source                  1..101
                        mol_type = genomic DNA
                        organism = Glycine max
SEQUENCE: 164
ttcctttaca gcacaagtag atcacttgta cttatcaaaa ttcggaactg acacacgaca  60
tgatggaact ttactaaggt gggtttttga ctttgcatgt c                      101

SEQ ID NO: 165          moltype = DNA  length = 101
FEATURE                 Location/Qualifiers
source                  1..101
                        mol_type = genomic DNA
                        organism = Glycine max
SEQUENCE: 165
ttcctttaca gcacaagtag atcacttgta cttatcaaaa ttcggaactg acacacgaca  60
tgatggaacg tgacaaggtg ggtttttgac tttgcatgtc g                      101

SEQ ID NO: 166          moltype = DNA  length = 101
FEATURE                 Location/Qualifiers
source                  1..101
                        mol_type = genomic DNA
                        organism = Glycine max
SEQUENCE: 166
ttcctttaca gcacaagtag atcacttgta cttatcaaaa ttcggaactg acacactaca  60
ttatttaact ttactaaggt gggtttttga ctttgcatgt c                      101

SEQ ID NO: 167          moltype = DNA  length = 108
FEATURE                 Location/Qualifiers
source                  1..108
                        mol_type = genomic DNA
                        organism = Glycine max
SEQUENCE: 167
agctgtaaat acagccttac aactcacaag tcccttgtac ttgtacgtac ggagggtatt  60
ctagaaaaga ggaattggag tctgcctctt cttttagtcc taaattaa               108

SEQ ID NO: 168          moltype = DNA  length = 101
FEATURE                 Location/Qualifiers
source                  1..101
                        mol_type = genomic DNA
                        organism = Glycine max
SEQUENCE: 168
agctgtaaat acagccttac aactcacaag tcccttgtac ggagggtatt ctagaaaaga  60
ggaattggag tctgcctctt cttttagtcc taaattaaag a                      101
```

-continued

```
SEQ ID NO: 169          moltype = DNA  length = 101
FEATURE                 Location/Qualifiers
source                  1..101
                        mol_type = genomic DNA
                        organism = Glycine max
SEQUENCE: 169
agctgtaaat acagccttac aactcacaag tcccttgtac ttgtacggag ggtattctag  60
aaaagaggaa ttggagtctg cctcttcttt tagtcctaaa t                      101

SEQ ID NO: 170          moltype = DNA  length = 101
FEATURE                 Location/Qualifiers
source                  1..101
                        mol_type = genomic DNA
                        organism = Glycine max
SEQUENCE: 170
agctgtaaat acagccttac aactcacaag tcccttacgg agggtattct agaaaagagg  60
aattggagtc tgcctcttct tttagtccta aattaaagat c                      101

SEQ ID NO: 171          moltype = DNA  length = 101
FEATURE                 Location/Qualifiers
source                  1..101
                        mol_type = genomic DNA
                        organism = Glycine max
SEQUENCE: 171
agctgtaaat acagccttac aactcacaag tcccttgtac ttgtaccgta cggagggtat  60
tctagaaaag aggaattgga gtctgcctct tcttttagtc c                      101

SEQ ID NO: 172          moltype = DNA  length = 101
FEATURE                 Location/Qualifiers
source                  1..101
                        mol_type = genomic DNA
                        organism = Glycine max
SEQUENCE: 172
agctgtaaat acagccttac aactcacaag tcccttgtac tgtacggagg gtattctaga  60
aaagaggaat tggagtctgc ctcttctttt agtcctaaat t                      101

SEQ ID NO: 173          moltype = DNA  length = 101
FEATURE                 Location/Qualifiers
source                  1..101
                        mol_type = genomic DNA
                        organism = Glycine max
SEQUENCE: 173
agctgtaaat acagccttac aactcacaag tcccttgtag tacggagggt attctagaaa  60
agaggaattg gagtctgcct cttcttttag tcctaaatta a                      101

SEQ ID NO: 174          moltype = DNA  length = 101
FEATURE                 Location/Qualifiers
source                  1..101
                        mol_type = genomic DNA
                        organism = Glycine max
SEQUENCE: 174
agctgtaaat acagccttac aactcacaag tcccttgtac ttgtacgtag ggtattctag  60
aaaagaggaa ttggagtctg cctcttcttt tagtcctaaa t                      101

SEQ ID NO: 175          moltype = DNA  length = 100
FEATURE                 Location/Qualifiers
source                  1..100
                        mol_type = genomic DNA
                        organism = Glycine max
SEQUENCE: 175
agctgtaaat acagccttac aactcacaag tcctacactc tttccctaca cgacgctctt  60
cttttagtcc taaattaaag atcggaagat ctcgtatgcc                        100

SEQ ID NO: 176          moltype = DNA  length = 101
FEATURE                 Location/Qualifiers
source                  1..101
                        mol_type = genomic DNA
                        organism = Glycine max
SEQUENCE: 176
agctgtaaat acagccttac aactcacaag tcccttgtac ttgtacctta cggagggtat  60
tctagaaaag aggaattgga gtctgcctct tcttttagtc c                      101

SEQ ID NO: 177          moltype = DNA  length = 101
FEATURE                 Location/Qualifiers
source                  1..101
                        mol_type = genomic DNA
                        organism = Glycine max
SEQUENCE: 177
ctaggtaaat acagccttac aactcacaag tcccttgtac ttgtacgtac ggagggtatt  60
```

```
ctagaaaatt ggagtctgcc tcttctttta gtcctaaatt a                      101

SEQ ID NO: 178         moltype = DNA  length = 101
FEATURE                Location/Qualifiers
source                 1..101
                       mol_type = genomic DNA
                       organism = Glycine max
SEQUENCE: 178
ctaggtaaat acagccttac aactcacaag tcccttgtac ttgtacgtac ggagggtatt  60
ctagaaaaga attggagtct gcctcttctt ttagtcctaa a                      101

SEQ ID NO: 179         moltype = DNA  length = 101
FEATURE                Location/Qualifiers
source                 1..101
                       mol_type = genomic DNA
                       organism = Glycine max
SEQUENCE: 179
ctaggtaaat acagccttac aactcacaag tcccttgtac ttgtacgtac ggagggtatt  60
ctagaattgg agtctgcctc ttcttttagt cctaaattaa a                      101

SEQ ID NO: 180         moltype = DNA  length = 101
FEATURE                Location/Qualifiers
source                 1..101
                       mol_type = genomic DNA
                       organism = Glycine max
SEQUENCE: 180
ctaggtaaat acagccttac aactcacaag tcccttgtac ttgtacgtac ggagggtatt  60
ctagaaaaga aattggagtc tgcctcttct tttagtccta a                      101

SEQ ID NO: 181         moltype = DNA  length = 101
FEATURE                Location/Qualifiers
source                 1..101
                       mol_type = genomic DNA
                       organism = Glycine max
SEQUENCE: 181
ctaggtaaat acagccttac aactcacaag tcccttgtac ttgtacgtac ggagggtatt  60
ctagaaaaat tggagtctgc ctcttctttt agtcctaaat t                      101

SEQ ID NO: 182         moltype = DNA  length = 101
FEATURE                Location/Qualifiers
source                 1..101
                       mol_type = genomic DNA
                       organism = Glycine max
SEQUENCE: 182
ctaggtaaat acagccttac aactcacaag tcccttgtac ttgtacgtac ggagggtatt  60
ctagaaaaga ggattggagt ctgcctcttc ttttagtcct a                      101

SEQ ID NO: 183         moltype = DNA  length = 101
FEATURE                Location/Qualifiers
source                 1..101
                       mol_type = genomic DNA
                       organism = Glycine max
SEQUENCE: 183
ctaggtaaat acagccttac aactcacaag tcccttgtac ttgtacgtac ggagggtatt  60
ctagaaattg gagtctgcct cttcttttag tcctaaatta a                      101

SEQ ID NO: 184         moltype = DNA  length = 101
FEATURE                Location/Qualifiers
source                 1..101
                       mol_type = genomic DNA
                       organism = Glycine max
SEQUENCE: 184
ctaggtaaat acagccttac aactcacaag tcccttgtac ttgtacgtac ggagggtatt  60
ctattggagt ctgcctcttc ttttagtcct aaattaaaga t                      101

SEQ ID NO: 185         moltype = DNA  length = 101
FEATURE                Location/Qualifiers
source                 1..101
                       mol_type = genomic DNA
                       organism = Glycine max
SEQUENCE: 185
ctaggtaaat acagccttac aactcacaag tcccttgtac ttgtacgtac ggagggtatt  60
ctagtctgcc tcttctttta gtcctaaatt aaagatcgga a                      101

SEQ ID NO: 186         moltype = DNA  length = 101
FEATURE                Location/Qualifiers
source                 1..101
                       mol_type = genomic DNA
                       organism = Glycine max
```

```
SEQUENCE: 186
ctaggtaaat acagccttac aactcacaag tcccttgtac ttgtacgtac ggagggtatt  60
ctagaaaagt ctgcctcttc ttttagtcct aaattaaaga t                      101

SEQ ID NO: 187         moltype = DNA  length = 101
FEATURE                Location/Qualifiers
source                 1..101
                       mol_type = genomic DNA
                       organism = Glycine max
SEQUENCE: 187
ctaggtaaat acagccttac aactcacaag tcccttgtac ttgtacgtac ggagggtatt  60
ctagaaaaga gaattggagt ctgcctcttc ttttagtcct a                      101

SEQ ID NO: 188         moltype = DNA  length = 101
FEATURE                Location/Qualifiers
source                 1..101
                       mol_type = genomic DNA
                       organism = Glycine max
SEQUENCE: 188
ctaggtaaat acagccttac aactcacaag tcccttgtac ttgtacgtac ggagggtatt  60
ctagaaaaga ggagtctgcc tcttctttta gtcctaaatt a                      101

SEQ ID NO: 189         moltype = DNA  length = 101
FEATURE                Location/Qualifiers
source                 1..101
                       mol_type = genomic DNA
                       organism = Glycine max
SEQUENCE: 189
ctaggtaaat acagccttac aactcacaag tcccttgtac ttgtacgtac ggagggtatt  60
ctaattggag tctgcctctt cttttagtcc taaattaaag a                      101

SEQ ID NO: 190         moltype = DNA  length = 101
FEATURE                Location/Qualifiers
source                 1..101
                       mol_type = genomic DNA
                       organism = Glycine max
SEQUENCE: 190
ctaggtaaat acagccttac aactcacaag tcccttgtac ttgtacgtac ggagggtatt  60
ctagaaaaga ggaaattgga gtctgcctct tcttttagtc c                      101

SEQ ID NO: 191         moltype = DNA  length = 101
FEATURE                Location/Qualifiers
source                 1..101
                       mol_type = genomic DNA
                       organism = Glycine max
SEQUENCE: 191
ctaggtaaat acagccttac aactcacaag tcccttgtac ttgtacgtac ggagggtatt  60
ctagaaagag gaattggagt ctgcctcttc ttttagtcct a                      101

SEQ ID NO: 192         moltype = AA  length = 1377
FEATURE                Location/Qualifiers
REGION                 1..1377
                       note = synthesized sequence- maize optimized moCAS9
                        endonuclease
source                 1..1377
                       mol_type = protein
                       organism = synthetic construct
SEQUENCE: 192
MAPKKKRKVM DKKYSIGLDI GTNSVGWAVI TDEYKVPSKK FKVLGNTDRH SIKKNLIGAL  60
LFDSGETAEA TRLKRTARRR YTRRKNRICY LQEIFSNEMA KVDDSFFHRL EESFLVEEDK  120
KHERHPIFGN IVDEVAYHEK YPTIYHLRKK LVDSTDKADL RLIYLALAHM IKFRGHFLIE  180
GDLNPDNSDV DKLFIQLVQT YNQLFEENPI NASGVDAKAI LSARLSKSRR LENLIAQLPG  240
EKKNGLFGNL IALSLGLTPN FKSNFDLAED AKLQLSKDTY DDDLDNLLAQ IGDQYADLFL  300
AAKNLSDAIL LSDILRVNTE ITKAPLSASM IKRYDEHHQD LTLLKALVRQ QLPEKYKEIF  360
FDQSKNGYAG YIDGGASQEE FYKFIKPILE KMDGTEELLV KLNREDLLRK QRTFDNGSIP  420
HQIHLGELHA ILRRQEDFYP FLKDNREKIE KILTFRIPYY VGPLARGNSR FAWMTRKSEE  480
TITPWNFEEV VDKGASAQSF IERMTNFDKN LPNEKVLPKH SLLYEYFTVY NELTKVKYVT  540
EGMRKPAFLS GEQKKAIVDL LFKTNRKVTV KQLKEDYFKK IECFDSVEIS GVEDRFNASL  600
GTYHDLLKII KDKDFLDNEE NEDILEDIVL TLTLFEDREM IEERLKTYAH LFDDKVMKQL  660
KRRRYTGWGR LSRKLINGIR DKQSGKTILD FLKSDGFANR NFMQLIHDDS LTFKEDIQKA  720
QVSGQGDSLH EHIANLAGSP AIKKGILQTV KVVDELVKVM GRHKPENIVI EMARENQTTQ  780
KGQKNSRERM KRIEEGIKEL GSQILKEHPV ENTQLQNEKL YLYYLQNGRD MYVDQELDIN  840
RLSDYDVDHI VPQSFLKDDS IDNKVLTRSD KNRGKSDNVP SEEVVKKMKN YWRQLLNAKL  900
ITQRKFDNLT KAERGGLSEL DKAGFIKRQL VETRQITKHV AQILDSRMNT KYDENDKLIR  960
EVKVITLKSK LVSDFRKDFQ FYKVREINNY HHAHDAYLNA VVGTALIKKY PKLESEFVYG  1020
DYKVYDVRKM IAKSEQEIGK ATAKYFFYSN IMNFFKTEIT LANGEIRKRP LIETNGETGE  1080
IVWDKGRDFA TVRKVLSMPQ VNIVKKTEVQ TGGFSKESIL PKRNSDKLIA RKKDWDPKKY  1140
GGFDSPTVAY SVLVVAKVEK GKSKKLKSVK ELLGITIMER SSFEKNPIDF LEAKGYKEVK  1200
KDLIIKLPKY SLFELENGRK RMLASAGELQ KGNELALPSK YVNFLYLASH YEKLKGSPED  1260
```

-continued

```
NEQKQLFVEQ HKHYLDEIIE QISEFSKRVI LADANLDKVL SAYNKHRDKP IREQAENIIH  1320
LFTLTNLGAP AAFKYFDTTI DRKRYTSTKE VLDATLIHQS ITGLYETRID LSQLGGD     1377

SEQ ID NO: 193         moltype = DNA  length = 6677
FEATURE                Location/Qualifiers
misc_feature           1..6677
                       note = synthesized sequence- maize optimized moCAS9
                        endonuclease
source                 1..6677
                       mol_type = other DNA
                       organism = synthetic construct
SEQUENCE: 193
ctgcagtgca gcgtgacccg gtcgtgcccc tctctagaga taatgagcat tgcatgtcta  60
agttataaaa aattaccaca tattttttt gtcacacttg tttgaagtgc agtttatcta  120
tctttataca tatatttaaa ctttactcta cgaataatat aatctatagt actacaataa  180
tatcagtgtt ttagagaatc atataaatga acagttagac atggtctaaa ggacaattga  240
gtattttgac aacaggactc tacagtttta tctttttagt gtgcatgtgt tctccttttt  300
ttttgcaaat agcttcacct atataatact tcatccattt tattagtaca tccatttagg  360
gtttagggtt aatggttttt atagactaat ttttttagta catctatttt attctatttt  420
agcctctaaa ttaagaaaac taaaactcta ttttagtttt tttatttaat aatttagata  480
taaaatagaa taaaataaag tgactaaaaa ttaaacaaat accctttaag aaattaaaaa  540
aactaaggaa acatttttct tgtttcgagt agataatgcc agcctgttaa acgccgtcga  600
cgagtctaac ggacaccaac cagcgaacca gcagcgtcgc gtcgggccaa gcgaagcaga  660
cggcacggca tctctgtcgc tgcctctgga cccctctcga gagttccgct ccaccgttgg  720
acttgctccg ctgtcggcat ccagaaattg cgtggcggag cggcagacgt gagccggcac  780
ggcaggcggc ctcctcctcc tctcacggca cggcagctac gggggattcc tttcccaccg  840
ctccttcgct ttcccttcct cgcccgccgt aataaataga cacccccctcc acaccctctt  900
tccccaacct cgtgttgttc ggagcgcaca cacacacaac cagatctccc ccaaatccac  960
ccgtcggcac ctccgcttca aggtacgccg ctcgtcctcc cccccccccc tctctacctt  1020
ctctagatcg gcgttccggt ccatgcatgg ttagggcccg gtagttctac ttctgttcat  1080
gtttgtgtta gatccgtgtt tgtgttagat ccgtgctgct agcgttcgta cacggatgcg  1140
acctgtacgt cagacacgtt ctgattgcta acttgccagt gtttctcttt ggggaatcct  1200
gggatggctc tagccgttcc gcagacggga tcgatttcat gatttttttt gtttcgttgc  1260
atagggtttg gtttgccctt ttcctttatt tcaatatatg ccgtgcactt gtttgtcggg  1320
tcatcttttc atgctttttt ttgtcttggt tgtgatgatg tggtctggtt gggcggtcgt  1380
tctagatcgg agtagaattc tgtttcaaac tacctggtgg atttattaat tttggatctg  1440
tatgtgtgtg ccatacatat tcatagttac gaattgaaga tgatggatgg aaatatcgat  1500
ctaggatagg tatacatgtt gatgcgggtt ttactgatgc atatacagag atgctttttg  1560
ttcgcttggt tgtgatgatg tggtgtggtt gggcggtcgt tcattcgttc tagatcggag  1620
tagaatactg tttcaaacta cctggtgtat ttattaattt tggaactgta tgtgtgtgtc  1680
atacatcttc atagttacga gtttaagatg gatggaaata tcgatctagg ataggtatac  1740
atgttgatgt gggttttact gatgcatata catgatggca tatgcagcat ctattcatat  1800
gctctaacct tgagtaccta tctattataa taaacaagta tgttttataa ttattttgat  1860
cttgatatac ttggatgatg gcatatgcag cagctatatg tggatttttt tagccctgcc  1920
ttcatacgct atttatttgc ttggtactgt ttcttttgtc gatgctcacc ctgttgtttg  1980
gtgttacttc tgcaggtcga ctctagagga tccccatggc cccgaagaag aagaggaagg  2040
tgcacatgga taagaagtac agcatcggcc tcgacatcgg gaccaacagc gtcggctggg  2100
ccgtcatcac cgacgaatat aaggtgccca gcaagaagtt caaggtgctc gggaatacag  2160
accgccacag catcaagaag aacctgatcg gcgccctcct gttcgactcg ggcgagaccg  2220
ctgaggccac cagactaaag aggaccgctc gccgccgcta cacccgccgc aagaaccgca  2280
tatgctacct ccaggagatc ttcagcaacg agatggccaa ggtggacgac agcttcttcc  2340
accgccttga ggagtcgttc ctcgtggagg aggacaagaa gcatgagagg cacccgatct  2400
tcgggaacat cgtggacgag gtaagtttct gcttctacct ttgatatata tataataatt  2460
atcattaatt agtagtaata taatatttca aatatttttt tcaaaataaa agaatgtagt  2520
atatagcaat tgcttttctg tagtttataa gtgtgtatat tttaatttat aacttttcta  2580
atatatgacc aaaacatggt gatgtgcagg tggcgtacca cgagaagtac ccgacgatct  2640
accacctccg caagaagctg gtcgactcca cagacaaggc cgacctcaga ctgatctacc  2700
tggccctcgc gcacatgatc aagttccgcg ggcacttcct catcgagggc gacctgaacc  2760
cggacaactc cgacgtcgac aagctcttca tccagctggt ccagacctac aatcaactgt  2820
tcgaggagaa cccgatcaac gcgtccggcg tggacgcgaa ggccatcctc agcgcgaggc  2880
tcagcaaatc aagacggctg gagaacctga tcgcccagct cccaggcgag aagaaaaacg  2940
gcttgttcgg caacctgatc gcgctctcgc tcggcctcac gcccaacttc aaatcaaact  3000
tcgacctggc cgaggacgcg aaactgcagc tgtccaagga cacttacgac gacgacctcg  3060
acaacctgct ggcgcaaatc ggtgaccagt acgcagacct cttcctggcc gccaagaacc  3120
tctcggacgc catcctgctg tccgatatcc tgagagtgaa tacggagatc accaaggcgc  3180
cgctcagcgc ctccatgatt aaaaggtacg acgagcacca ccaggacctg acgctgctca  3240
aggccctggt gcgccagcag ctccccgaga agtacaagga gatcttcttc gaccaatcaa  3300
aaaacggcta cgccggctac atcgacgggg gcgcctccca ggaggagttc tacaagttca  3360
tcaaaccaat tctcgagaag atggacggca cggaggagct tctcgtgaag ctcaaccggg  3420
aggacctcct gaggaagcag aggacgttcg acaacggctc gataccgcat cagatccacc  3480
tgggcgagct ccacgccatc ctgcgccggc aggaggattt ctatccgttc ctcaaggaca  3540
acagggagaa gatcgagaaa attctgacgt tccgcatccc gtactacgtg ggccctctcg  3600
cgcgcgggaa cagccggttc gcctggatga ctcggaagtc ggaggagacg atcacgccgt  3660
ggaacttcga ggaggtggtg gacaagggcg cctccgccca gtcgttcatc gagcgcatga  3720
cgaacttcga taaaaatctg cccaatgaaa aagtgctccc gaagcacagc ctcctctacg  3780
agtacttcac ggtgtacaac gagctcacga aggtgaagta cgtgaccgag ggtatgcgga  3840
agccggcgtt cctgagcggc gagcagaaga aggccatcgt ggacctcctc ttcaagacga  3900
accggaaagt caccgtgaag caattaaagg aggactactt caagaaaata gagtgcttcg  3960
acagcgtcga gatctcgggc gtcgaggaca ggttcaacgc gtcgctgggc acataccacg  4020
```

-continued

```
acctcctcaa gatcattaaa gacaaggact tcctggacaa cgaggagaac gaggacatcc  4080
tcgaggacat cgtgctgacc ctcaccctgt ttgaggaccg ggagatgatc gaggagcgcc  4140
tcaagacgta cgctcacctt ttcgacgaca aggtgatgaa acagctgaag cggcgccgct  4200
acaccggatg ggccggctc tcccgcaagc tcattaatgg gatcagggac aagcagtccg  4260
gcaagaccat actcgatttc ctgaagagcg acggcttcgc caaccggaac ttcatgcagc  4320
tcatccacga cgactccctc actttcaagg aggacatcca gaaggcccag gtcagcggac  4380
agggcgactc gctccacgaa cacatcgcca acctggccgg gtcgcctgcg attaaaaagg  4440
gaatccttca gaccgtcaag gtcgtggacg agctggtgaa ggtgatgggc aggcacaagc  4500
ccgaaaatat cgtcattgag atggcccggg agaaccagac cacgcagaaa ggccagaaga  4560
acagccggga gcgcatgaaa cggatcgagg agggtatcaa ggagctgggc tcgcagatcc  4620
tcaaggagca ccctgtggaa aatacccagc tgcagaatga aaagctctac ctctactacc  4680
tccagaacgg ccgcgacatg tacgtggacc aggagctgga cattaatcgc ctctcggact  4740
acgacgtcga ccacatcgtc ccgcagtcct tcctgaagga cgacagcatc gacaacaagg  4800
tcttgacccg ctccgataaa aatcgcggga agtccgacaa cgtgccgtcg gaggaggtgg  4860
tcaagaagat gaaaaactac tggcgccagc tgctcaacgc caagctaatc acgcagcgca  4920
agttcgacaa cctcaccaag gccgaacgcg gcggtctctc cgagcttgat aaggctgggt  4980
tcatcaagag acagctggtg gagacccggc agatcaccaa gcatgtcgcc cagatcctgg  5040
actcgcgcat gaatactaag tacgatgaaa acgacaagct catccgcgag gtgaaggtga  5100
tcaccctgaa gagcaagctg gtctcggact tccggaagga cttccagttc tacaaggtcc  5160
gggagatcaa caactaccac cacgcgcacg acgcctacct gaacgcggtg gtgggcacag  5220
cccttataaa gaagtaccct aagctcgagt ccgagttcgt gtacggcgac tacaaggtgt  5280
acgacgtccg caagatgatc gcgaagagcg agcaggagat cgggaaggcc accgcaaaat  5340
acttcttcta ctccaacatc atgaacttct tcaagaccga gatcaccctg gccaacgggg  5400
agatccgcaa gcgcccgctg attgagacga acggagagac aggcgagata gtctgggaca  5460
agggcaggga cttcgccacc gtgcgcaagg ttctgtccat gccgcaggtg aacatcgtga  5520
agaagactga ggtgcagaca ggcggcttct cgaaggagtc catcctgccc aagcggaaca  5580
gcgacaagct catcgcgcgg aagaaggact gggaccctaa aaaatatggc gggttcgact  5640
cgcccaccgt ggcttactcg gtcctcgtgg tggccaaggt cgagaagggc aaaagcaaga  5700
agctgaagag cgtcaaggag ctcctcggca tcaccatcat ggagcggtcc agcttcgaga  5760
agaacccgat cgacttcctc gaggcgaagg gatataagga ggtgaagaag gacctcatca  5820
ttaaactgcc gaagtactcg ctattcgaac tggagaatgg tcgcaagagg atgctcgcga  5880
gcgctggcga gctgcagaaa gggaacgagc tggctctccc gagcaagtac gtcaacttcc  5940
tctacctggc ctcccactat gaaaagctca agggctcgcc ggaggacaac gagcagaagc  6000
agctgttcgt cgagcagcac aagcattacc tcgacgagat catcgagcag atctcggagt  6060
tcagcaagcg cgtgatcctg gccgacgcca acctcgacaa ggtgctgtcc gcatataaca  6120
agcaccgcga caaaccaata cgggagcagg ccgaaaatat catccacctg ttcaccctca  6180
cgaacctggg cgcccccgcc gcgttcaagt acttcgacac aaccatcgac cgcaagcggt  6240
acacgagcac gaaggaggtg ctggacgcca cgttgattca ccagtccatc acgggcctgt  6300
atgaaacaag gatcgatctc agccagctcg gcggcgacta ggtaccacat ggttaaccta  6360
gacttgtcca tcttctggat tggccaactt aattaatgta tgaaataaaa ggatgcacac  6420
atagtgacat gctaatcact ataatgtggg catcaaagtt gtgtgttatg tgtaattact  6480
agttatctga ataaaagaga aagagatcat ccatatttct tatcctaaat gaatgtcacg  6540
tgtctttata attctttgat gaaccagatg catttcatta accaaatcca tatacatata  6600
aatattaatc atatataatt aatatcaatt gggttagcaa aacaaatcta gtctaggtgt  6660
gttttgcgaa ttgcggc                                                 6677
```

```
SEQ ID NO: 194          moltype = DNA  length = 100
FEATURE                 Location/Qualifiers
misc_feature            1..100
                        note = synthesized sequence- DNA version of guide RNA
                         (EPSPS sgRNA)
source                  1..100
                        mol_type = other DNA
                        organism = synthetic construct
SEQUENCE: 194
gcagtaacag ctgctgtcaa gttttagagc tagaaatagc aagttaaaat aaggctagtc  60
cgttatcaac ttgaaaaagt ggcaccgagt cggtgctttt                        100
```

```
SEQ ID NO: 195          moltype = DNA  length = 3708
FEATURE                 Location/Qualifiers
misc_feature            1..3708
                        note = synthesized sequence- EPSPS polynucleotide template
source                  1..3708
                        mol_type = other DNA
                        organism = synthetic construct
SEQUENCE: 195
ctgcagccca tcaaggagat ctccggcacc gtcaagctgc cggggtccaa gtcgctttcc  60
aacaggatcc tcctgctcgc cgccctgtcc gaggtgagcg attttggtgc ttgctgcgct  120
gccctgtctc actgctacct aaatgttttg cctgtcgaat accatggatt ctcggtgtaa  180
tccatctcac gatcagatgc accgcatgtc gcatgcctag ctctctctaa tttgtctagt  240
agtttgtata cggattaaga ttgataaatc ggtaccgcaa aagctaggtg taaataaaca  300
ctacaaaatt ggatgttccc ctatcggcct gtactcggct actcgttctt gtgatggcat  360
gttatttctt cttggtgttt ggtgaactcc cttatgaaat ttgggcgcaa agaaatcgcc  420
ctcaagggtt gatcttatgc catcgtcatg ataaacagtg aagcacggat gatcctttac  480
gttgttttta acaaactttg tcagaaaact agcaatgtta acttcttaat gatgatttca  540
caacaaaaaa ggtaaccttg ctactaacat aacaaaagac ttgttgctta ttaattatat  600
gttttttttaa tctttgatca ggggacaaca gtggttgata acctgttgaa cagtgaggat  660
gtccactaca tgctcggggc cttgaggact cttggtctct ctgtcgaagc ggacaaagct  720
gccaaaagag ctgtagttgt tggctgtggt ggaaagttcc cagttgagga tgctaaagag  780
```

-continued

```
gaagtgcagc tcttcttggg gaatgctgga atcgcaatgc ggtcattgac agcagctgtt  840
actgctgctg gtggaaatgc aacgtatgtt tcctctctct ctctacaata cttgttggag  900
ttagtatgaa acccatgtgt atgtctagtg gcttatggtg tattggtttt tgaacttcag  960
ttacgtgctt gatggagtac caagaatgag ggagagaccc attggcgact tggttgtcgg  1020
attgaagcag cttggtgcag atgttgattg tttccttggc actgactgcc cacctgttcg  1080
tgtcaatgga atcggagggc tacctggtgg caaggttagt tactaagggc cacatgttac  1140
attcttctgt aaatggtaca actattgtcg agcttttgca tttgtaagga aaacattgat  1200
tgatctgaat ttgatgctac accacaaaat atctacaaat ggtcatccct aactagcaaa  1260
ccatgtctcc attaagctca atgaagtaat acttggcatg tgtttatcaa cttaatttcc  1320
atcttctggg gtattgcctg ttttctagtc taatagcatt tgtttttaga attagctctt  1380
acaactgtta tgttctacag gtcaagctgt ctggctccat cagcagtcag tacttgagtg  1440
ccttgctgat ggctgctcct ttggctcttg gggatgtgga gattgaaatc attgataaat  1500
taatctccat tccctacgtc gaaatgacat tgagattgat ggagcgtttt ggtgtgaaag  1560
cagagcattc tgatagctgg gacagattct acattaaggg aggtcaaaaa tacaagtaag  1620
ctctgtaatg tatttcacta ctttgatgcc aatgtttcag ttttcagttt tccaaacagt  1680
cgcatcaata tttgaataga tgcactgtag aaaaaaatca ttgcagggaa aaactagtac  1740
tgagtatttt gactgtaaat tatttaacca gtcggaatat agtcagtcta ttggagtcaa  1800
gagcgtgaac cgaaatagcc agttaattat cccattatac agaggacaac catgtatact  1860
attgaaactt ggtttaagag aatctaggta gctggactcg tagctgcttg gcatggatac  1920
cttcttatct ttaggaaaag acacttgatt ttttttctgt ggccctctat gatgtgtgaa  1980
cctgcttctc tattgcttta gaaggatata tctatgtcgt tatgcaacat gcttccctta  2040
gtcatttgta ctgaaatcag tttcataagt tcgttagtgg ttccctaaac gaaaccttgt  2100
ttttctttgc aatcaacagg tcccctaaaa atgcctatgt tgaaggtgat gcctcaagcg  2160
caagctattt cttggctggt gctgcaatta ctggagggac tgtgactgtg gaaggttgtg  2220
gcaccaccag tttgcaggta aagatttctt ggctggtgct acgataactg cttttgtctt  2280
tttggtttca gcattgttct cagagtcact aaataacatt atcatctgca aacgtcaaat  2340
agacatactt aggtgaatgg atattcatgt aaccgtttcc ttacaaattt gctgaaacct  2400
cagggtgatg tgaagtttgc tgaggtactg gagatgatgg gagcgaaggt tacatggacc  2460
gagactagcg taactgttac tggcccaccg cgggagccat ttgggaggaa acacctcaag  2520
gcgattgatg tcaacatgaa caagatgcct gatgtcgcca tgactcttgc tgtggttgcc  2580
ctctttgccg atggcccgac agccatcaga gacggtaaaa cattctcagc cctacaacca  2640
tgcctcttct acatcactac ttgacaagac taaaaactat tggctcgttg gcagtggctt  2700
cctggagagt aaaggagacc gagaggatgg ttgcgatccg gacggagcta accaaggtaa  2760
ggctacatac ttcacatgtc tcacgtcgtc tttccatagc tcgctgcctc ttagcggctt  2820
gcctgcggtc gctccatcct cggttgctgt ctgtgttttc cacagctggg agcatctgtt  2880
gaggaagggc cggactactg catcatcacg ccgccggaga agctgaacgt gacggcgatc  2940
gacacgtacg acgaccacag gatggccatg gccttctccc ttgccgcctg tgccgaggtc  3000
cccgtgacca tccgggaccc tgggtgcacc cggaagacct tccccgacta cttcgatgtg  3060
ctgagcactt tcgtcaagaa ttaataaagc gtgcgatact accacgcagc ttgattgaag  3120
tgataggctt gtgctgagga aatacatttc ttttgttctg ttttttctct ttcacgggat  3180
taagttttga gtctgtaacg ttagttgttt gtagcaagtt tctatttcgg atcttaagtt  3240
tgtgcactgt aagccaaatt tcatttcaag agtggttcgt tggaataata agaataataa  3300
attacgtttc agtggctgtc aagcctgctg ctacgtttta ggagatggca ttagacattc  3360
atcatcaaca acaataaaac cttttagcct caaacaataa tagtgaagtt attttttagt  3420
cctaaacaag ttgcattagg atatagttaa aacacaaaag aagctaaagt tagggtttag  3480
acatgtggat attgttttcc atgtatagta tgttctttct ttgagtctca tttaactacc  3540
tctacacata ccaactttag ttttttttct acctcttcat gttactatgg tgccttctta  3600
tcccactgag cattggtata tttagaggtt tttgttgaac atgcctaaat catctcaatc  3660
aacgatggac aatcttttct tcgattgagc tgaggtacgt catctaga              3708
```

```
SEQ ID NO: 196         moltype = DNA  length = 15
FEATURE                Location/Qualifiers
misc_feature           1..15
                       note = synthesized sequence- TIPS nucleotide modifications
source                 1..15
                       mol_type = other DNA
                       organism = synthetic construct
SEQUENCE: 196
atcgcaatgc ggtca                                               15
```

```
SEQ ID NO: 197         moltype = DNA  length = 19
FEATURE                Location/Qualifiers
misc_feature           1..19
                       note = synthesized sequence- Primer Seqeunce-1 F-E2
source                 1..19
                       mol_type = other DNA
                       organism = synthetic construct
SEQUENCE: 197
ccgaggagat cgtgctgca                                           19
```

```
SEQ ID NO: 198         moltype = DNA  length = 20
FEATURE                Location/Qualifiers
misc_feature           1..20
                       note = synthesized sequence- Primer Seqeunce-2 F-E2
source                 1..20
                       mol_type = other DNA
                       organism = synthetic construct
SEQUENCE: 198
caatggccgc attgcagttc                                          20
```

```
SEQ ID NO: 199          moltype = DNA  length = 19
FEATURE                 Location/Qualifiers
misc_feature            1..19
                        note = synthesized sequence- Primer Seqeunce-1 F-T
source                  1..19
                        mol_type = other DNA
                        organism = synthetic construct
SEQUENCE: 199
ccgaggagat cgtgctgca                                              19

SEQ ID NO: 200          moltype = DNA  length = 20
FEATURE                 Location/Qualifiers
misc_feature            1..20
                        note = synthesized sequence- Primer Seqeunce-2 F-T
source                  1..20
                        mol_type = other DNA
                        organism = synthetic construct
SEQUENCE: 200
tgaccgcatt gcgattccag                                             20

SEQ ID NO: 201          moltype = DNA  length = 24
FEATURE                 Location/Qualifiers
misc_feature            1..24
                        note = synthesized sequence- Primer Seqeunce-1 H-T
source                  1..24
                        mol_type = other DNA
                        organism = synthetic construct
SEQUENCE: 201
tccaagtcgc tttccaacag gatc                                        24

SEQ ID NO: 202          moltype = DNA  length = 20
FEATURE                 Location/Qualifiers
misc_feature            1..20
                        note = synthesized sequence- Primer Seqeunce-2 H-T
source                  1..20
                        mol_type = other DNA
                        organism = synthetic construct
SEQUENCE: 202
tgaccgcatt gcgattccag                                             20

SEQ ID NO: 203          moltype = DNA  length = 19
FEATURE                 Location/Qualifiers
misc_feature            1..19
                        note = synthesized sequence- Primer Seqeunce-1 F-E3
source                  1..19
                        mol_type = other DNA
                        organism = synthetic construct
SEQUENCE: 203
ccgaggagat cgtgctgca                                              19

SEQ ID NO: 204          moltype = DNA  length = 24
FEATURE                 Location/Qualifiers
misc_feature            1..24
                        note = synthesized sequence- Primer Seqeunce-2 F-E3
source                  1..24
                        mol_type = other DNA
                        organism = synthetic construct
SEQUENCE: 204
accaagctgc ttcaatccga caac                                        24

SEQ ID NO: 205          moltype = DNA  length = 63
FEATURE                 Location/Qualifiers
source                  1..63
                        mol_type = genomic DNA
                        organism = Zea mays
SEQUENCE: 205
ggggaatgct ggaactgcaa tgcggccatt gacagcagct gttactgctg ctggtggaaa  60
tgc                                                               63

SEQ ID NO: 206          moltype = DNA  length = 60
FEATURE                 Location/Qualifiers
source                  1..60
                        mol_type = genomic DNA
                        organism = Zea mays
SEQUENCE: 206
ggggaatgct ggaactgcaa tgcggccatt ggcagctgtt actgctgctg gtggaaatgc  60

SEQ ID NO: 207          moltype = DNA  length = 50
```

-continued

```
FEATURE                Location/Qualifiers
source                 1..50
                       mol_type = genomic DNA
                       organism = Zea mays
SEQUENCE: 207
ggggaatgct ggaactgcac agcagctgtt actgctgctg gtggaaatgc            50

SEQ ID NO: 208         moltype = DNA  length = 33
FEATURE                Location/Qualifiers
source                 1..33
                       mol_type = genomic DNA
                       organism = Zea mays
SEQUENCE: 208
ggggaatgct gttactgctg ctggtggaaa tgc                              33

SEQ ID NO: 209         moltype = DNA  length = 51
FEATURE                Location/Qualifiers
source                 1..51
                       mol_type = genomic DNA
                       organism = Zea mays
SEQUENCE: 209
aatgctggaa tcgcaatgcg gtcattgaca gcagctgtta ctgctgctgg t          51

SEQ ID NO: 210         moltype = DNA  length = 51
FEATURE                Location/Qualifiers
source                 1..51
                       mol_type = genomic DNA
                       organism = Zea mays
SEQUENCE: 210
aatgctggaa ctgcaatgcg gccattgaca gcagctgtta ctgctgctgg t          51

SEQ ID NO: 211         moltype = DNA  length = 5124
FEATURE                Location/Qualifiers
source                 1..5124
                       mol_type = genomic DNA
                       organism = Zea mays
SEQUENCE: 211
atggcggcca tggcgaccaa ggccgccgcg ggcaccgtgt cgctggacct cgccgcgccg  60
ccggcggcgg cagcggcggc ggcggtgcag gcgggtgccg aggagatcgt gctgcagccc  120
atcaaggaga tctccggcac cgtcaagctg ccggggtcca agtcgctttc caacaggatc  180
ctcctgctcg ccgccctgtc cgaggtgagc gattttggtg cttgctgcgc tgccctgtct  240
cactgctacc taaatgtttt gcctgtcgaa taccatggat tctcggtgta atccatctca  300
cgatcagatg caccgcatgt cgcatgccta gctctctcta atttgtctag tagtttgtat  360
acggattaag attgataaat cggtaccgca aaagctaggt gtaaataaac actacaaaat  420
tggatgttcc cctatcggcc tgtactcggc tactcgttct tgtgatggca tgttatttct  480
tcttggtgtt tggtgaactc ccttatgaaa tttgggcgca aagaaatcgc cctcaagggt  540
tgatcttatg ccatcgtcat gataaacagt gaagcacgga tgatccttta cgttgttttt  600
aacaaacttt gtcagaaaac tagcaatgtt aacttcttaa tgatgatttc acaacaaaaa  660
aggtaacctt gctactaaca taacaaaaga cttgttgctt attaattata tgttttttta  720
atctttgatc aggggacaac agtggttgat aacctgttga acagtgagga tgtccactac  780
atgctcgggg ccttgaggac tcttggtctc tctgtcgaag cggacaaagc tgccaaaaga  840
gctgtagttg ttggctgtgg tggaaagttc ccagttgagg atgctaaaga ggaagtgcag  900
ctcttcttgg ggaatgctgg aactgcaatg cggccattga cagcagctgt tactgctgct  960
ggtggaaatg caacgtatgt ttcctctctc tctctacaat acttgttgga gttagtatga  1020
aacccatgtg tatgtctagt ggcttatggt gtattggttt ttgaacttca gttacgtgct  1080
tgatggagta ccaagaatga gggagagacc cattggcgac ttggttgtcg gattgaagca  1140
gcttggtgca gatgttgatt gtttccttgg cactgactgc ccacctgttc gtgtcaatgg  1200
aatcggaggg ctacctggtg gcaaggttag ttactaaggg ccacatgtta cattcttctg  1260
taaatggtac aactattgtc gagcttttgc atttgtaagg aaaacattga ttgatctgaa  1320
tttgatgcta caccacaaaa tatctacaaa tggtcatccc taactagcaa accatgtctc  1380
cattaagctc aatgaagtaa tacttggcat gtgtttatca acttaatttc catcttctgg  1440
ggtattgcct gttttctagt ctaatagcat ttgtttttag aattagctct tacaactgtt  1500
atgttctaca ggtcaagctg tctggctcca tcagcagtca gtacttgagt gccttgctga  1560
tggctgctcc tttggctctt ggggatgtgg agattgaaat cattgataaa ttaatctcca  1620
ttccctacgt cgaaatgaca ttgagattga tggagcgttt tggtgtgaaa gcagagcatt  1680
ctgatagctg ggacagattc tacattaagg gaggtcaaaa atacaagtaa gctctgtaat  1740
gtatttcact actttgatgc caatgtttca gttttcagtt ttccaaacag tcgcatcaat  1800
atttgaatag atgcactgta gaaaaaaatc attgcaggga aaaactagta ctgagtattt  1860
tgactgtaaa ttatttaacc agtcggaata tagtcagtct attggagtca agagcgtgaa  1920
ccgaaatagc cagttaatta tcccattata cagaggacaa ccatgtatac tattgaaact  1980
tggtttaaga gaatctaggt agctggactc gtagctgctt ggcatggata ccttcttatc  2040
tttaggaaaa gacacttgat tttttttctg tggccctcta tgatgtgtga acctgcttct  2100
ctattgcttt agaaggatat atctatgtcg ttatgcaaca tgcttccctt agtcatttgt  2160
actgaaatca gtttcataag ttcgttagtg gttccctaaa cgaaaccttg tttttctttg  2220
caatcaacag gtcccctaaa aatgcctatg ttgaaggtga tgcctcaagc gcaagctatt  2280
tcttggctgg tgctgcaatt actggaggga ctgtgactgt ggaaggttgt ggcaccacca  2340
gtttgcaggt aaagatttct tggctggtgc tacgataact gcttttgtct tttggtttc  2400
agcattgttc tcagagtcac taaataacat tatcatctgc aaacgtcaaa tagacatact  2460
taggtgaatg gatattcatg taaccgtttc cttacaaatt tgctgaaacc tcagggtgat  2520
```

-continued

```
gtgaagtttg ctgaggtact ggagatgatg ggagcgaagg ttacatggac cgagactagc  2580
gtaactgtta ctggcccacc gcgggagcca tttgggagga aacacctcaa ggcgattgat  2640
gtcaacatga acaagatgcc tgatgtcgcc atgactcttg ctgtggttgc cctctttgcc  2700
gatggcccga cagccatcag agacggtaaa acattctcag ccctacaacc atgcctcttc  2760
tacatcacta cttgacaaga ctaaaaacta ttggctcgtt ggcagtggct tcctggagag  2820
taaaggagac cgagaggatg gttgcgatcc ggacggagct aaccaaggta aggctacata  2880
cttcacatgt ctcacgtcgt ctttccatag ctcgctgcct cttagcggct tgcctgcggt  2940
cgctccatcc tcggttgctg tctgtgtttt ccacagctgg gagcatctgt tgaggaaggg  3000
ccggactact gcatcatcac gccgccggag aagctgaacg tgacggcgat cgacacgtac  3060
gacgaccaca ggatggccat ggccttctcc cttgccgcct gtgccgaggt ccccgtgacc  3120
atccgggacc ctgggtgcac ccggaagacc ttccccgact acttcgatgt gctgagcact  3180
ttcgtcaaga attaataaag cgtgcgatac taccacgcag cttgattgaa gtgataggct  3240
tgtgctgagg aaatacattt cttttgttct gtttttctc tttcacggga ttaagttttg  3300
agtctgtaac gttagttgtt tgtagcaagt ttctatttcg gatcttaagt ttgtgcactg  3360
taagccaaat ttcatttcaa gagtggttcg ttggaataat aagaataata aattacgttt  3420
cagtggctgt caagcctgct gctacgtttt aggagatggc attagacatt catcatcaac  3480
aacaataaaa ccttttagcc tcaaacaata atagtgaagt tattttttag tcctaaacaa  3540
gttgcattag gatatagtta aaacacaaaa gaagctaaag ttagggttta gacatgtgga  3600
tattgtttc catgtatagt atgttctttc tttgagtctc atttaactac ctctacacat  3660
accaacttta gtttttttc tacctcttca tgttactatg gtgccttctt atcccactga  3720
gcattggtat atttagaggt ttttgttgaa catgcctaaa tcatctcaat caacgatgga  3780
caatcttttc ttcgattgag ctgaggtacg tcatctagag gataggacct tgagaatatg  3840
tgtccgtcaa tagctaaccc tctactaatt ttttcaatca agcaacctat tggcttgact  3900
ttaattcgta ccggcttcta ctacttctac agtattttgt ctctataaat tgcagctaca  3960
acagtcagaa cggctggctt taaaatcaaa tggcctaagg atcattgaaa ggcatcttag  4020
caatgtctaa aattattacc ttctctagac gttgatatct ttgctccgga ttcgatccct  4080
tgttgtatga ccacaaatcc aacaccaaat acgcatttct gcaacacacc caaacacccc  4140
ttccaaataa gtggaatggt tgagaaattt gctattttga ttaaatattg gtgaaggggc  4200
aaggctgagg aaacgagacg aaggttcctt gacagctgaa aaatggaaca ctctagaggc  4260
ggagggagcg aggcgagctg tgtgaattgc cacccattga ttaagaatcc aacaacttga  4320
ctagcaaatg ccgacatggg tagcctacaa aggcgagttt tggagctggt ttcgtaataa  4380
ggaaatttct caaccaacta ctttccttag aaaagagttg cttgaccgga tcaacatctc  4440
cccctaaacc ccttggaggg ggaggggggct aagattttaa tctacaagtt agatctaact  4500
gtccacctca atccccctca aggaggtttt tgtattattt gttagtgtag aatgataaag  4560
tggatgtatt gataggagat ggggtacaca tatttatagg gactcaaccc taaccctaat  4620
gggtcggcag cccaacagtg gtgtccggcc cacacacaca ctcacacaca cagtctaaca  4680
tcccccgcag tcgcaacggg gacaccacac acgatgagac tggagtagag gccgaaggta  4740
ggagccgacg ggttgaaatc cccccctagtc gcagcgtcgt gatagtacga atgttgcggc  4800
tggagtagag accggtgtgt gctccaagaa gacgatagcc cctagatgcc gaggtagccg  4860
aagtcgaggt ggtcgcggtc ggaagacgcg cagcaaaagc ctgatcttcg ggatggtcga  4920
cgttcgagcg tcaacgatcg gtagggcgac acaataaaag ggcaccagca ggtcgacctt  4980
cctgcttctt cgatcgtcca gacgtcaagg agcctcgcta gggaggccga cggcagcgca  5040
cgcggctacg ccggtcatgg tgtcctcacc cgcggcagaa aagaagggga atgtcggatc  5100
cgaccgagaa ggccacggca gcga                                          5124
```

```
SEQ ID NO: 212          moltype = DNA  length = 3387
FEATURE                 Location/Qualifiers
source                  1..3387
                        mol_type = genomic DNA
                        organism = Streptococcus thermophilus
SEQUENCE: 212
atgagtgact tagttttagg acttgatatc ggtataggtt ctgttggtgt aggtatcctt  60
aacaaagtga caggagaaat tatccataaa aactcacgca tcttcccagc agctcaagca  120
gaaaataacc tagtacgtag aacgaatcgt caaggaagac gcttgacacg acgtaaaaaa  180
catcgtatag ttcgtttaaa tcgtctattt gaggaaagtg gattaatcac cgattttacg  240
aagatttcaa ttaatcttaa cccatatcaa ttacgagtta agggcttgac cgatgaattg  300
tctaatgaag aactgtttat cgctcttaaa aatatggtga aacaccgtgg gattagttac  360
ctcgatgatg ctagtgatga cggaaattca tcagtaggag actatgcaca aattgttaag  420
gaaaatagta aacaattaga aactaagaca ccgggacaga tacagttgga acgctaccaa  480
acatatggtc aattacgtgg tgattttact gttgagaaag atggcaaaaa acatcgcttg  540
attaatgtct ttccaacatc agcttatcgt tcagaagcct taaggatact gcaaactcaa  600
caagaattta atccacagat tacagatgaa tttattaatc gttatctcga aattttaact  660
ggaaaacgga aatattatca tggacccgga aatgaaaagt cacggactga ttatggtcgt  720
tacagaacga gtggagaaac tttagacaat atttttggaa ttctaattgg gaaatgtaca  780
ttttatccag aagagtttag agcagcaaaa gcttcctaca cggctcaaga attcaatttg  840
ctaaatgatt tgaacaatct aacagttcct actgaaacca aaaagttgag caaagaacag  900
aagaatcaaa tcattaatta tgtcaaaaat gaaaaggcaa tggggccagc gaaacttttt  960
aaatatatcg ctaagttact ttcttgtgat gttgcagata tcaagggata ccgtatcgac  1020
aaatcaggta aggctgagat tcatactttc gaagcctatc gaaaaatgaa aacgcttgaa  1080
accttagata ttgaacaaat ggatagagaa acgcttgata aattagccta tgtcttaaca  1140
ttaaacactg agagggaagg tattcaagaa gccttagaac atgaatttgc tgatggtagc  1200
tttagccaga agcaagttga cgaattggtt caattccgca aagcaaatag ttccattttt  1260
ggaaaaggat ggcataattt ttctgtcaaa ctgatgatgg agttaattcc agaattgtat  1320
gagacgtcag aagagcaaat gactatcctg acacgacttg gaaaacaaaa acgacttcgt  1380
cttcaaataa aacaaaatat ttcaaataaa acaaaatata tagatgagaa actattaact  1440
gaagaaatct ataatcctgt tgttgctaag tctgttcgcc aggctataaa aatcgtaaat  1500
gcggcgatta aagaatacgg agactttgac aatattgtca tcgaaatggc tcgtgaaaca  1560
aatgaagatg atgaaaagaa agctattcaa aagattcaaa aagccaacaa agatgaaaaa  1620
gatgcagcaa tgcttaaggc tgctaaccaa tataatggaa aggctgaatt accacatagt  1680
```

-continued

```
gttttccacg gtcataagca attagcgact aaaatccgcc tttggcatca gcaaggagaa  1740
cgttgccttt atactggtaa gacaatctca atccatgatt tgataaataa tcctaatcag  1800
tttgaagtag atcatatttt acctctttct atcacattcg atgatagcct tgcaaataag  1860
gttttggttt atgcaactgc taaccaagaa aaaggacaac gaacacctta tcaggcttta  1920
gatagtatgg atgatgcgtg gtctttccgt gaattaaaag cttttgtacg tgagtcaaaa  1980
acactttcaa acaagaaaaa agaatacctc cttacagaag aagatatttc aaagtttgat  2040
gttcgaaaga aatttattga acgaaatctt gtagatacaa gatacgcttc aagagttgtc  2100
ctcaatgccc ttcaagaaca ctttagagct cacaagattg atacaaaagt ttccgtggtt  2160
cgtggccaat ttacatctca attgagacgc cattggggaa ttgagaagac tcgtgatact  2220
tatcatcacc atgctgtcga tgcattgatt attgccgcct caagtcagtt gaatttgtgg  2280
aaaaaacaaa agaataccct tgtaagttat tcagaagaac aactccttga tattgaaaca  2340
ggtgaactta ttagtgatga tgagtacaag gaatctgtgt tcaaagcccc ttatcaacat  2400
tttgttgata cattgaagag taaagaattt gaagacagta tcttattctc atatcaagtg  2460
gattctaagt ttaatcgtaa aatatcagat gccactattt atgcgacaag acaggctaaa  2520
gtgggaaaag ataagaagga tgaaacttat gtcttaggga aatcaaaga tatctatact  2580
caggatggtt atgatgcctt tatgaagatt tataagaagg ataagtcaaa attcctcatg  2640
tatcgtcacg acccacaaac ctttgagaaa gttatcgagc caattttaga gaactatcct  2700
aataagcaaa tgaatgaaaa aggaaaagag gtaccatgta atcctttcct aaaatataaa  2760
gaagaacatg gctatattcg taaatatagt aaaaaaggca atggtcctga aatcaagagt  2820
cttaaatact atgatagtaa gcttttaggt aatcctattg atattactcc agagaatagt  2880
aaaaataaag ttgtcttaca gtcattaaaa ccttggagaa cagatgtcta tttcaataag  2940
gctactggaa aatacgaaat ccttggatta aaatatgctg atctacaatt tgagaaaggg  3000
acaggaacat ataagatttc ccaggaaaaa tacaatgaca ttaagaaaaa agagggtgta  3060
gattctgatt cagaattcaa gtttacactt tataaaaatg atttgttact cgttaaagat  3120
acagaaacaa aagaacaaca gcttttccgt tttctttctc gaactttacc taaacaaaag  3180
cattatgttg aattaaaacc ttatgataaa cagaaatttg aaggaggtga ggcgttaatt  3240
aaagtgttgg gtaacgttgc taatggtggt caatgcataa aaggactagc aaaatcaaat  3300
atttctattt ataaagtaag aacagatgtc ctaggaaatc agcatatcat caaaaatgag  3360
ggtgataagc ctaagctaga tttttaa                                      3387

SEQ ID NO: 213         moltype = DNA  length = 3369
FEATURE                Location/Qualifiers
source                 1..3369
                       mol_type = genomic DNA
                       organism = Streptococcus thermophilus
SEQUENCE: 213
atgagtgact tagttttagg acttgatatc ggtataggtt ctgttggtgt aggtatcctt  60
aacaaagtga caggagaaat tatccataaa aactcacgca tcttcccagc agctcaagca  120
gaaaataacc tagtacgtag aacgaatcgt caaggaagac gcttgacacg acgtaaaaaa  180
catcgtatag ttcgtttaaa tcgtctattt gaggaaagtg gattaatcac cgattttacg  240
aagatttcaa ttaatcttaa cccatatcaa ttacgagtta agggcttgac cgatgaattg  300
tctaatgaag aactgtttat cgctcttaaa aatatggtga aacaccgtgg gattagttac  360
ctcgatgatg ctagtgatga cggaaattca tcagtaggag actatgcaca aattgttaag  420
gaaaatagta aacaattaga aactaagaca ccgggacaga tacagttgga acgctaccaa  480
acatatggtc aattacgtgg tgattttact gttgagaaag atggcaaaaa acatcgcttg  540
attaatgtct ttccaacatc agcttatcgt tcagaagcct taaggatact gcaaactcaa  600
caagaattta attcacagat tacagatgaa tttattaatc gttatctcga aattttaact  660
ggaaaacgga aatattatca tggacccgga aatgaaaagt cacggactga ttatggtcgt  720
tacagaacga atggagaaac tttagacaat atttttggaa ttctaattgg gaaatgtaca  780
ttttatccag acgagtttag agcagcaaaa gcttcctaca cggctcaaga attcaatttg  840
ctaaatgatt tgaacaatct aacagttcct actgaaacca aaaagttgag caaagaacag  900
aagaatcaaa tcattaatta tgtcaaaaat gaaaaggtaa tggggccagc gaaacttttt  960
aaatatatcg ctaaattact ttcttgtgat gttgcagata tcaagggaca ccgtatcgac  1020
aaatcaggta aggctgagat tcatactttc gaagcctatc gaaaaatgaa aacgcttgaa  1080
accttagata ttgagcaaat ggatagagaa acgcttgata aattagccta tgtcttaaca  1140
ttaaacactg agagggaagg tattcaagaa gctttagaac atgaatttgc tgatggtagc  1200
tttagccaga agcaagttga cgaattggtt caattccgca aagcaaatag ttccattttt  1260
ggaaaaggat ggcataattt ttctgtcaaa ctgatgatgg agttaattcc agaattgtat  1320
gagacgtcag aagagcaaat gactatcctg acacgacttg gaaaacaaaa aacaacttcg  1380
tcttcaaata aaacaaaata tatagatgag aaactattaa ctgaagaaat ctataatcct  1440
gttgttgcta agtctgttcg ccaggctata aaaatcgtaa atgcggcgat taaagaatac  1500
ggagactttg acaatattgt catcgaaatg gctcgtgaaa caaatgaaga tgatgaaaag  1560
aaagctattc aaaagattca aaaagccaac aaagatgaaa aagatgcagc aatgcttaag  1620
gctgctaacc aatataatgg aaaggctgaa ttaccacata gtgttttcca cggtcataag  1680
caattagcga ctaaaatccg cctttggcat cagcaaggag aacgttgcct ttatactggt  1740
aagacaatct caatccatga tttgataaat aatcctaatc agtttgaagt agatcatatt  1800
ttacctcttt ctatcacatt cgatgatagc cttgcaaata aggttttggt ttatgcaact  1860
gctaaccaag aaaaaggaca acgaacacct tatcaggctt tagatagtat ggatgatgcg  1920
tggtctttcc gtgaattaaa agcttttgta cgtgagtcaa aaacactttc aaacaagaaa  1980
aaagaatacc tccttacaga agaagatatt tcaaagtttg atgttcgaaa gaaatttatt  2040
gaacgaaatc ttgtagatac aagatacgct tcaagagttg tcctcaatgc ccttcaagaa  2100
cactttagag ctcacaagat tgatacaaaa gtttccgtgg ttcgtggcca atttacatct  2160
caattgagac gccattgggg aattgagaag actcgtgata cttatcatca ccatgctgtc  2220
gatgcattga ttattgccgc ctcaagtcag ttgaatttgt ggaaaaaaca aaagaatacc  2280
cttgtaagtt attcagaaga acaactcctt gatattgaaa caggtgaact tattagtgat  2340
gatgagtaca aggaatctgt gttcaaagcc ccttatcaac attttgttga tacattgaag  2400
agtaaagaat ttgaagacag tatcttattc tcatatcaag tggattctaa gtttaatcgt  2460
aaaatatcag atgccactat ttatgcgaca agacaggcta aagtgggaaa agataagaag  2520
gatgaaactt atgtcttagg gaaaatcaaa gatatctata ctcaggatgg ttatgatgcc  2580
```

-continued

```
tttatgaaga tttataagaa ggataagtca aaattcctca tgtatcgtca cgacccacaa  2640
acctttgaga aagttatcga gccaatttta gagaactatc ctaataagga aatgaatgaa  2700
aaagggaaag aagtaccatg taatcctttc ctaaaatata aagaagaaca tggctatatt  2760
cgtaaatata gtaaaaaagg caatggtcct gaaatcaaga gtcttaaata ctatgatagt  2820
aagcttttag gtaatcctat tgatattact ccagagaata gtaaaaataa agttgtctta  2880
cagtcattaa aaccttggag aacagatgtc tatttcaata aaaatactgg taaatatgaa  2940
attttaggac tgaaatatgc tgatttacaa tttgaaaaga agacaggaac atataagatt  3000
tcccaggaaa aatacaatgg cattatgaaa gaagagggtg tagattctga ttcagaattc  3060
aagtttacac tttataaaaa tgatttgtta ctcgttaaag atacagaaac aaaagaacaa  3120
cagcttttcc gttttctttc tcgaactatg cctaatgtga aatattatgt agagttaaag  3180
ccttattcaa aagataaatt tgagaagaat gagtcactta ttgaaatttt aggttctgca  3240
gataagtcag gacgatgtat aaaagggcta ggaaaatcaa atatttctat ttataaggta  3300
agaacagatg tcctaggaaa tcagcatatc atcaaaaatg agggtgataa gcctaagcta  3360
gatttttaa                                                          3369
```

```
SEQ ID NO: 214          moltype = DNA  length = 4113
FEATURE                 Location/Qualifiers
source                  1..4113
                        mol_type = genomic DNA
                        organism = Streptococcus agalactiae
SEQUENCE: 214
atgaataagc catattcaat aggccttgac atcggtacta attccgtcgg atggagcatt  60
attacagatg attataaagt acctgctaag aagatgagag ttttagggaa cactgataaa  120
gaatatatta agaagaatct cataggtgct ctgcttttttg atggcgggaa tactgctgca  180
gatagacgct tgaagcgaac tgctcgtcgt cgttatacac gtcgtagaaa tcgtattcta  240
tatttacaag aaatttttgc agaggaaatg agtaaagttg atgatagttt ctttcatcga  300
ttagaggatt cttttctagt tgaggaagat aagagaggga gcaagtatcc tatctttgca  360
acattgcagg aagagaaaga ttatcatgaa aaattttcga caatctatca tttgagaaaa  420
gaattagctg acaagaaaga aaaagcagac cttcgtctta tttatattgc tctagctcat  480
atcattaaat ttagagggca tttcctaatt gaggatgata gctttgatgt caggaataca  540
gacatttcaa aacaatatca agatttttta gaaatcttta atacaacttt tgaaaataat  600
gatttgttat ctcaaaacgt tgacgtagag gcaatactaa cagataagat tagcaagtct  660
gcgaagaaag atcgtatttt agcgcagtat cctaaccaaa aatctactgg catttttgca  720
gaatttttga aattgattgt cggaaatcaa gctgacttca agaaatattt caatttggag  780
gataaaacgc cgcttcaatt cgctaaggat agctacgatg aagatttaga aaatcttctt  840
ggacagattg gtgatgaatt tgcagactta ttctcagcag cgaaaaagtt atatgatagt  900
gtccttttgt ctggcattct tacagtaatc gacctcagta ccaaggcgcc actttcagct  960
tctatgattc agcgttatga tgaacataga gaggacttga aacagttaaa acaattcgta  1020
aaagcttcat tgccggaaaa atatcaagaa atatttgctg attcatcaaa agatggctac  1080
gctggttata ttgaaggtaa aactaatcaa gaagcttttt ataaatacct gtcaaaattg  1140
ttgaccaagc aagaagatag cgagaatttt cttgaaaaaa tcaagaatga agatttcttg  1200
agaaaacaaa ggacctttga taatggctca attccacacc aagtccattt gacagagctg  1260
aaagctatta tccgccgtca atcagaatac tatcccttct tgaaagagaa tcaagatagg  1320
attgaaaaaa tccttacctt tagaattcct tattatatcg ggccactagc acgtgagaag  1380
agtgattttg catggatgac tcgcaaaaca gatgacagta ttcgaccttg gaattttgaa  1440
gacttggttg ataaagaaaa atctgcggaa gcttttatcc atcgtatgac caacaatgat  1500
ttttatcttc ctgaagaaaa agttttacca aagcatagtc ttatttatga aaaatttacg  1560
gtctataatg agttgactaa ggttagatat aaaaatgagc aaggtgagac ttatttttttt  1620
gatagcaata ttaaacaaga aatctttgat ggagtattca aggaacatcg taaggtatcc  1680
aagaagaagt tgctagattt tctggctaaa gaatatgagg agtttaggat agtagatgtt  1740
attggtctag ataaagaaaa taaagctttc aacgcctcat tgggaactta ccacgatctc  1800
gaaaaaatac tagacaaaga ttttctagat aatccagata atgagtctat tctggaagat  1860
atcgtccaaa ctctaacatt atttgaagac agagaaatga ttaagaagcg tcttgaaaac  1920
tataaagatc tttttacaga gtcacaacta aaaaaactct atcgtcgtca ctatactggc  1980
tggggacgat tgtctgctaa gttaatcaat ggtattcgag ataaagagag tcaaaaaaca  2040
atcttggact atcttattga tgatggtaga tctaatcgca actttatgca gttgataaat  2100
gatgatggtc tatctttcaa atcaattatc agtaaggcac aggctggtag tcattcagat  2160
aatctaaaag aagttgtagg tgagcttgca ggtagccctg ctattaaaaa gggaattcta  2220
caaagtttga aaattgttga tgagcttgtt aaagtcatgg gatacgaacc tgaacaaatt  2280
gtggttgaga tggcgcgtga gaatcaaaca acaaatcaag gtcgtcgtaa ctctcgacaa  2340
cgctataaac ttcttgatga tggcgttaag aatctagcta gtgacttgaa tggcaatatt  2400
ttgaaagaat atcctacgga taatcaagcg ttgcaaaatg aaagactttt cctttactac  2460
ttacaaaacg gaagagatat gtatacaggg gaagctctag atattgacaa tttaagtcaa  2520
tatgatattg accacattat tcctcaagct ttcataaaag atgattctat tgataatcgt  2580
gttttggtat catctgctaa aaatcgtgga aagtcagatg atgttcctag ccttgaaatt  2640
gtaaaagatt gtaaagtttt ctggaaaaaa ttacttgatg ctaagttaat gagtcagcgt  2700
aagtatgata atttgactaa ggcagagcgc ggaggcctaa cttccgatga taaggcaaga  2760
tttatccaac gtcagttggt tgagacacga caaattacca agcatgttgc ccgtatcttg  2820
gatgaacgct ttaataatga gcttgatagt aaaggtagaa ggatccgcaa agttaaaatt  2880
gtaaccttga agtcaaattt ggtttcaaat ttccgaaaag aatttggatt ctataaaatt  2940
cgtgaagtta acaattatca ccatgcacat gatgcctatc ttaatgcagt agttgctaaa  3000
gctattctaa ccaaatatcc tcagttagag ccagaatttg tctacggcga ctatccaaaa  3060
tataatagtt acaaaacgcg taaatccgct acagaaaagc tatttttcta ttcaaatatt  3120
atgaacttct ttaaaactaa ggtaacttta gcggatggaa ccgttgttgt aaaagatgat  3180
attgaagtta ataatgatac gggtgaaatt gtttgggata aaaagaaaca ctttgcgaca  3240
gttagaaaag tcttgtcata ccctcagaac aatatcgtga agaagacaga gattcagaca  3300
ggtggtttct ctaaggaatc aatcttggcg catggtaact cagataagtt gattccaaga  3360
aaaacgaagg atatttattt agatcctaag aaatatggag gttttgatag tccgatagta  3420
gcttactctg ttttagttgt agctgatatc aaaaagggta aagcacaaaa actaaaaaca  3480
```

```
gttacggaac ttttaggaat taccatcatg gagaggtcca gatttgagaa aaatccatca  3540
gctttccttg aatcaaaagg ctatttaaat attagggctg ataaactaat tattttgccc  3600
aagtatagtc tgttcgaatt agaaaatggg cgtcgtcgat tacttgctag tgctggtgaa  3660
ttacaaaaag gtaatgagct agccttacca acacaattta tgaagttctt ataccttgca  3720
agtcgttata atgagtcaaa aggtaaacca gaggagattg agaagaaaca agaatttgta  3780
aatcaacatg tctcttattt tgatgacatc cttcaattaa ttaatgattt ttcaaaacga  3840
gttattctag cagatgctaa tttagagaaa atcaataagc tttaccaaga taataaggaa  3900
aatatatcag tagatgaact tgctaataat attatcaatc tatttacttt taccagtcta  3960
ggagctccag cagcttttaa attttttgat aaaatagttg atagaaaacg ctatacatca  4020
actaaagaag tacttaattc taccctaatt catcaatcta ttactggact ttatgaaaca  4080
cgtattgatt tgggtaagtt aggagaagat tga                               4113

SEQ ID NO: 215         moltype = DNA  length = 4134
FEATURE                Location/Qualifiers
source                 1..4134
                       mol_type = genomic DNA
                       organism = Streptococcus agalactiae
SEQUENCE: 215
atgaataagc catattcaat aggccttgac atcggtacta attccgtcgg atggagcatt  60
attacagatg attataaagt acctgctaag aagatgagag ttttagggaa cactgataaa  120
gaatatatta agaagaatct cataggtgct ctgcttttttg atggcgggaa tactgctgca  180
gatagacgct tgaagcgaac tgctcgtcgt cgttatacac gtcgtagaaa tcgtattcta  240
tatttacaag aaatttttgc agaggaaatg agtaaagttg atgatagttt ctttcatcga  300
ttagaggatt cttttctagt tgaggaagat aagagaggta gcaagtatcc tatctttgca  360
acaatgcagg aggagaaata ttatcatgaa aaatttccga caatctatca tttgagaaaa  420
gaattggctg acaagaaaga aaaagcagac cttcgtcttg tttatctggc tctagctcat  480
atcattaaat tcagagggca tttcctaatt gaggatgata gatttgatgt gaggaatacc  540
gatattcaaa aacaatatca agccttttta gaaatttttg atactacctt tgaaaataat  600
catttgttat ctcaaaatgt agatgtagaa gcaattctaa cagataagat tagcaagtct  660
gcgaagaagg atcgcatctt agcgcagtat cctaaccaaa aatctactgg tatttttgca  720
gaattttga aattgattgt cggaaatcaa gctgacttca agaaacattt caatttggag  780
gataaaacac cgcttcaatt cgctaaggat agctacgatg aagatttaga aaatcttctt  840
ggacagattg gtgatgaatt tgcagactta ttctcagtag cgaaaaagct atatgatagt  900
gttcttttat ctggcattct tacagtaact gatctcagta ccaaggcgcc actttctgcc  960
tctatgattc agcgttatga tgaacatcat gaggacttaa agcatctaaa acaattcgta  1020
aaagcttcat tacctgaaaa ttatcgggaa gtatttgctg attcatcaaa agatggctac  1080
gctggctata ttgaaggcaa aactaatcaa gaagcttttt ataaatatct gttaaaattg  1140
ttgaccaaac aagaaggtag cgagtatttt cttgagaaaa ttaagaatga agatttttttg  1200
agaaaacaga gaacctttga taatggctca atcccgcatc aagtccattt gacagaattg  1260
agggctatta ttcgacgtca atcagaatac tatccattct tgaaagagaa tcaagatagg  1320
attgaaaaaa tccttacctt tagaattcct tattatgtcg ggccactagc acgtgagaag  1380
agtgattttg catggatgac tcgcaaaaca gatgacagta ttcgaccttg gaattttgaa  1440
gacttggttg ataaagaaaa atctgcggaa gcttttatcc atcgcatgac caacaatgac  1500
ctctatcttc cagaagaaaa agttttacca aagcatagtc ttatttatga aaaatttact  1560
gtttacaatg aattaacgaa ggttagattt ttggcagaag gctttaaaga ttttcaattt  1620
ttaaatagga agcaaaaaga aactatcttt aacagcttgt ttaaggaaaa acgtaaagta  1680
actgaaaagg atattattag ttttttgaat aaagttgatg gatatgaagg aattgcaatc  1740
aaaggaattg agaaacagtt taacgctagc ctttcaacct atcatgatct taaaaaaata  1800
cttggcaagg atttccttga taatacagat aacgagctta ttttggaaga tatcgtccaa  1860
actctaacct tatttgaaga tagagaaatg attaagaagt gtcttgacat ctataaagat  1920
ttttttacag agtcacagct taaaaagctc tatcgccgtc actatactgg ctggggacga  1980
ttgtctgcta agctaataaa tggcatccga aataaagaga atcaaaaaac aatcttggac  2040
tatcttattg atgatggaag tgcaaaccga aacttcatgc agttgataaa tgatgatgat  2100
ctatcattta aaccaattat tgacaaggca cgaactggta gtcattcgga taatctgaaa  2160
gaagttgtag gtgaacttgc tggtagccct gctattaaaa aagggattct acaaagtttg  2220
aaaatagttg atgagctggt taaagtcatg ggctatgaac ctgaacaaat cgtggttgaa  2280
atggcacgtg agaaccaaac gacagcaaaa ggattaagtc gttcacgaca acgcttgaca  2340
accttgagag aatctcttgc taatttgaag agtaatattt tggaagagaa aaagcctaag  2400
tatgtgaaag atcaagttga aaatcatcat ttatctgatg accgtctttt cctttactac  2460
ttacaaaacg gaagagatat gtatacaaaa aaggctctgg atattgataa tttaagtcaa  2520
tatgatattg accacattat tcctcaagct ttcataaaag atgattctat tgataatcgt  2580
gttttggtat catctgctaa aaatcgtgga aaatcagatg atgttcctag cattgaaatt  2640
gtaaaagctc gcaaaatgtt ctggaaaaat ttactggatg ctaagttaat gagtcagcgt  2700
aagtatgata atttgactaa ggcagagcgc ggaggcctaa cttccgatga taaggcaaga  2760
tttatccaac gtcagttggt tgagactcga caaattacca agcatgtagc tcgtatcttg  2820
gatgaacgct tcaataatga agttgataat ggtaaaaaga tttgcaaggt taaaattgta  2880
accttgaagt caaatttggt ttcaaatttc cgaaaagaat ttggattcta taaaattcgt  2940
gaagttaatg attatcacca tgcacacgat gcttatctta atgcagtagt tgccaaagct  3000
attctaacca aatatccaca gttagagcca gagtttgtct acggaatgta tagacagaaa  3060
aaactttcga aaatcgttca tgaggataag gaagaaaaat atagtgaagc aaccaggaaa  3120
atgtttttct actccaactt gatgaatatg ttcaaaagag ttgtgaggtt agcagatggt  3180
tctattgttg taagaccagt aatagaaact ggtagatata tgagaaaaac tgcatgggat  3240
aaaaagaaac actttgcgac agttagaaaa gtcttgtcat accctcagaa caatatcgtg  3300
aagaagacag agattcagac aggtggtttc tctaaggaat caatcttggc gcatggtaac  3360
tcagataagt tgattccaag aaaaacgaag gatatttatt tagatcctaa gaaatatgga  3420
ggttttgata gtccgatagt agcttactct gttttagttg tagctgatat caaaaaaggt  3480
aaagcacaaa aactaaaaac agttacggaa cttttaggaa ttaccatcat ggagaggtcc  3540
agatttgaga aaaatccatc agctttcctt gaatcaaaag gttatttaaa tattagggac  3600
gataaattaa tgattttacc gaagtatagt ctgttcgaat tagaaaatgg gcgtcgtcga  3660
```

-continued

```
ttacttgcta gtgctggtga attacaaaaa ggtaacgagc tagccttacc aacacaattt  3720
atgaagttct tataccttgc aagtcgttat aatgagtcaa aaggtaaacc agaggagatt  3780
gagaagaaac aagaatttgt aaatcaacat gtctcttatt ttgatgacat ccttcaatta  3840
attaatgatt tttcaaaacg agttattcta gcagatgcta atttagagaa aatcaataag  3900
ctttaccagg ataataagga aaatatacca gtagatgaac ttgctaataa tattatcaat  3960
ctatttactt ttaccagtct aggagctcca gcagctttta aatttttga taaaatagtt  4020
gatagaaaac gctatacatc aactaaagaa gtacttaatt ctactctaat ccatcaatct  4080
attactggac tttatgaaac acgtattgat ttgggtaaat taggagaaga ttga        4134

SEQ ID NO: 216         moltype = DNA  length = 4038
FEATURE                Location/Qualifiers
source                 1..4038
                       mol_type = genomic DNA
                       organism = Streptococcus mutans
SEQUENCE: 216
atgaaaaaac cttactctat tggacttgat attggaacca attctgttgg ttgggctgtt  60
gtgacagatg actacaaagt tcctgctaag aagatgaagg ttctgggaaa tacagataaa  120
agtcatatcg agaaaaattt gcttggcgct ttattatttg atagcgggaa tactgcagaa  180
gacagacggt taaagagaac tgctcgccgt cgttacacac gtcgcagaaa tcgtatttta  240
tatttgcaag agatttttc agaagaaatg ggcaaggtag atgatagttt ctttcatcgt  300
ttagaggatt cttttcttgt tactgaggat aaacgaggag agcgccatcc catttttggg  360
aatcttgaag aagaagttaa gtatcatgaa aattttccaa ccatttatca tttgcggcaa  420
tatcttgcgg ataatccaga aaaagttgat ttgcgtttag tttatttggc tttggcacat  480
ataattaagt ttagaggtca ttttttaatt gaaggaaagt ttgatacacg caataatgat  540
gtacaaagac tgtttcaaga atttttagca gtctatgata atacttttga gaatagttcg  600
cttcaggagc aaaatgttca agttgaagaa attctgactg ataaaaatcag taaatctgct  660
aagaaagata gagttttgaa actttttcct aatgaaaagt ctaatggccg ctttgcagaa  720
tttctaaaac taattgttgg taatcaagct gattttaaaa agcattttga attagaagag  780
aaagcaccat tgcaatttc taaagatact tatgaagaag agttagaagt actattagct  840
caaattggag ataattacgc agagctcttt ttatcagcaa agaaactgta tgatagtatc  900
cttttatcag ggattttaac agttactgat gttggtacca aagcgccttt atctgcttcg  960
atgattcagc gatataatga acatcagatg gatttagctc agcttaaaca attcattcgt  1020
cagaaattat cagataaata taacgaagtt ttttctgatg tttcaaaaga cggctatgcg  1080
ggttatattg atgggaaaac aaatcaagaa gctttttata aataccttaa aggtctatta  1140
aataagattg agggaagtgg ctatttcctt gataaaattg agcgtgaaga ttttctaaga  1200
aagcaacgta cctttgacaa tggctctatt ccacatcaga ttcatcttca agaaatgcgt  1260
gctatcattc gtagacaggc tgaattttat ccgtttttag cagacaatca agataggatt  1320
gagaaattat tgactttccg tattccctac tatgttggtc cattagcgcg cggaaaaagt  1380
gattttgctt ggttaagtcg gaaatcggct gataaaatta caccatggaa ttttgatgaa  1440
atcgttgata aagaatcctc tgcagaagct tttatcaatc gtatgacaaa ttatgatttg  1500
tacttgccaa atcaaaaagt tcttcctaaa catagtttat tatacgaaaa atttactgtt  1560
tacaatgaat taacaaaggt taaatataaa acagagcaag gaaaaacagc atttttgat  1620
gccaatatga agcaagaaat ctttgatggc gtatttaagg tttatcgaaa agtaactaaa  1680
gataaattaa tggatttcct tgaaaaagaa tttgatgaat ttcgtattgt tgatttaaca  1740
ggtctggata aagaaaataa agtatttaac gcttcttatg gaacttatca tgatttgtgt  1800
aaaattttag ataaagattt tctcgataat tcaaagaatg aaaagatttt agaagatatt  1860
gtgttgacct taacgttatt tgaagataga gaaatgatta gaaaacgtct agaaaattac  1920
agtgatttat tgaccaaaga acaagtgaaa aagctggaaa gacgtcatta tactggttgg  1980
ggaagattat cagctgagtt aattcatggt attcgcaata aagaaagcag aaaaacaatt  2040
cttgattatc tcattgatga tggcaatagc aatcggaact ttatgcaact gattaacgat  2100
gatgctcttt ctttcaaaga agagattgct aaggcacaag ttattggaga aacagacaat  2160
ctaaatcaag ttgttagtga tattgctggc agccctgcta ttaaaaaagg aattttacaa  2220
agcttgaaga ttgttgatga gcttgtcaaa attatgggac atcaacctga aaatatcgtc  2280
gtggagatgg cgcgtgaaaa ccagtttacc aatcagggac gacgaaattc acagcaacgt  2340
ttgaaaggtt tgacagattc tattaaagaa tttggaagtc aaattcttaa agaacatccg  2400
gttgagaatt cacagttaca aaatgataga ttgtttctat attatttaca aaacggcaga  2460
gatatgtata ctggagaaga attggatatt gattatctaa gccagtatga tatagaccat  2520
attatcccgc aagcttttat aaaggataat tctattgata atagagtatt gactagctca  2580
aaggaaaatc gtggaaaatc ggatgatgta ccaagtaaag atgttgttcg taaaatgaaa  2640
tcctattgga gtaagctact ttcggcaaag cttattacac aacgtaaatt tgataatttg  2700
acaaaagctg aacgaggtgg attgaccgac gatgataaag ctggattcat caagcgtcaa  2760
ttagtagaaa cacgacaaat taccaaacat gtagcacgta ttctggacga acgatttaat  2820
acagaaacag atgaaaacaa caagaaaatt cgtcaagtaa aaattgtgac cttgaaatca  2880
aatcttgttt ccaatttccg taaagagttt gaactctaca aagtgcgtga aattaatgac  2940
tatcatcatg cacatgatgc ctatctcaat gctgtaattg gaaaggcttt actaggtgtt  3000
tacccacaat tggaacctga atttgtttat ggtgattatc ctcattttca tggacataaa  3060
gaaaataaag caactgctaa gaaatttttc tattcaaata ttatgaactt ctttaaaaaa  3120
gatgatgtcc gtactgataa aaatggtgaa attatctgga aaaaagatga gcatatttct  3180
aatattaaaa aagtgctttc ttatccacaa gttaatattg ttaagaaagt agaggagcaa  3240
acgggaggat tttctaaaga atctatcttg ccgaaaggta attctgacaa gcttattcct  3300
cgaaaaacga agaaatttta ttgggatacc aagaaatatg gaggatttga tagcccgatt  3360
gttgcttatt ctattttagt tattgctgat attgaaaaag gtaaatctaa aaaattgaaa  3420
acagtcaaag ccttagttgg tgtcactatt atggaaaaga tgacttttga aagggatcca  3480
gttgcttttc ttgagcgaaa aggctatcga aatgttcaag aagaaaatat tataaagtta  3540
ccaaaatata gtttatttaa actagaaaac ggacgaaaaa ggctattggc aagtgctagg  3600
gaacttcaaa agggaaatga aatcagtttg ccaaatcatt taggaacctt gctttatcac  3660
gctaaaaata ttcataaagt tgatgaacca aagcatttgg actatgttga taaacataaa  3720
gatgaattta aggagttgct agatgttgtg tcaaactttt ctaaaaaata tactttagca  3780
gaaggaaatt tagaaaaaat caaagaatta tatgcacaaa ataatggtga agatcttaaa  3840
```

```
gaattagcaa gttcatttat caacttatta acatttactg ctataggagc accggctact  3900
tttaaattct ttgataaaaa tattgatcga aaacgatata cttcaactac tgaaattctc  3960
aacgctaccc tcatccacca atccatcacc ggtctttatg aaacgcggat tgatctcaat  4020
aagttaggag gagactaa                                                4038

SEQ ID NO: 217         moltype = DNA  length = 20
FEATURE                Location/Qualifiers
misc_feature           1..20
                       note = synthesized sequence- Mprimer qADH-F
source                 1..20
                       mol_type = other DNA
                       organism = synthetic construct
SEQUENCE: 217
caagtcgcgg ttttcaatca                                              20

SEQ ID NO: 218         moltype = DNA  length = 21
FEATURE                Location/Qualifiers
misc_feature           1..21
                       note = synthesized sequence- Primer qADH-R
source                 1..21
                       mol_type = other DNA
                       organism = synthetic construct
SEQUENCE: 218
tgaaggtgga agtcccaaca a                                            21

SEQ ID NO: 219         moltype = DNA  length = 19
FEATURE                Location/Qualifiers
misc_feature           1..19
                       note = synthesized sequence- probe ADH-VIC
source                 1..19
                       mol_type = other DNA
                       organism = synthetic construct
SEQUENCE: 219
tgggaagcct atctaccac                                               19

SEQ ID NO: 220         moltype = DNA  length = 15
FEATURE                Location/Qualifiers
misc_feature           1..15
                       note = synthesized sequence- Probe wtEPSPS
source                 1..15
                       mol_type = other DNA
                       organism = synthetic construct
SEQUENCE: 220
cggccattga cagca                                                   15

SEQ ID NO: 221         moltype = DNA  length = 20
FEATURE                Location/Qualifiers
misc_feature           1..20
                       note = synthesized sequence- Forward primer qEPSPS-F
source                 1..20
                       mol_type = other DNA
                       organism = synthetic construct
SEQUENCE: 221
tcttggggaa tgctggaact                                              20

SEQ ID NO: 222         moltype = DNA  length = 21
FEATURE                Location/Qualifiers
misc_feature           1..21
                       note = synthesized sequence- reverse primer qEPSPSR
source                 1..21
                       mol_type = other DNA
                       organism = synthetic construct
SEQUENCE: 222
caccagcagc agtaacagct g                                            21

SEQ ID NO: 223         moltype = DNA  length = 17
FEATURE                Location/Qualifiers
misc_feature           1..17
                       note = synthesized sequence- FAM-wtEPSPS R probe
source                 1..17
                       mol_type = other DNA
                       organism = synthetic construct
SEQUENCE: 223
tgctgtcaat ggccgca                                                 17

SEQ ID NO: 224         moltype = DNA  length = 20
FEATURE                Location/Qualifiers
misc_feature           1..20
                       note = synthesized sequence- forward primer qEPSPS-F
```

-continued

```
source                  1..20
                        mol_type = other DNA
                        organism = synthetic construct
SEQUENCE: 224
tcttggggaa tgctggaact                                              20

SEQ ID NO: 225          moltype = DNA  length = 20
FEATURE                 Location/Qualifiers
misc_feature            1..20
                        note = synthesized sequence- reverse primer q wtEPSPS RA
source                  1..20
                        mol_type = other DNA
                        organism = synthetic construct
SEQUENCE: 225
ccaccagcag cagtaacagc                                              20

SEQ ID NO: 226          moltype = DNA  length = 21
FEATURE                 Location/Qualifiers
misc_feature            1..21
                        note = synthesized sequence- forward primer q epTIPS F
source                  1..21
                        mol_type = other DNA
                        organism = synthetic construct
SEQUENCE: 226
ggaagtgcag ctcttcttgg g                                            21

SEQ ID NO: 227          moltype = DNA  length = 19
FEATURE                 Location/Qualifiers
misc_feature            1..19
                        note = synthesized sequence- reverse primer q epTIPS R
source                  1..19
                        mol_type = other DNA
                        organism = synthetic construct
SEQUENCE: 227
agctgctgtc aatgaccgc                                               19

SEQ ID NO: 228          moltype = DNA  length = 15
FEATURE                 Location/Qualifiers
misc_feature            1..15
                        note = synthesized sequence- TIPS probe
source                  1..15
                        mol_type = other DNA
                        organism = synthetic construct
SEQUENCE: 228
aatgctggaa tcgca                                                   15

SEQ ID NO: 229          moltype = DNA  length = 23
FEATURE                 Location/Qualifiers
misc_feature            1..23
                        note = MHP14Cas1 target site
source                  1..23
                        mol_type = genomic DNA
                        organism = Zea mays
SEQUENCE: 229
gttaaatctg acgtgaatct gtt                                          23

SEQ ID NO: 230          moltype = DNA  length = 21
FEATURE                 Location/Qualifiers
misc_feature            1..21
                        note = MHP14Cas3 target site
source                  1..21
                        mol_type = genomic DNA
                        organism = Zea mays
SEQUENCE: 230
acaaacattg aagcgacata g                                            21

SEQ ID NO: 231          moltype = DNA  length = 18
FEATURE                 Location/Qualifiers
misc_feature            1..18
                        note = TS8Cas1 target site
source                  1..18
                        mol_type = genomic DNA
                        organism = Zea mays
SEQUENCE: 231
gtacgtaacg tgcagtac                                                18

SEQ ID NO: 232          moltype = DNA  length = 20
FEATURE                 Location/Qualifiers
misc_feature            1..20
```

```
                        note = TS8Cas2 target site
source                  1..20
                        mol_type = genomic DNA
                        organism = Zea mays
SEQUENCE: 232
gctcatcagt gatcagctgg                                                 20

SEQ ID NO: 233          moltype = DNA  length = 17
FEATURE                 Location/Qualifiers
misc_feature            1..17
                        note = TS9Cas2 target site
source                  1..17
                        mol_type = genomic DNA
                        organism = Zea mays
SEQUENCE: 233
ggctgtttgc ggcctcg                                                    17

SEQ ID NO: 234          moltype = DNA  length = 21
FEATURE                 Location/Qualifiers
misc_feature            1..21
                        note = TS9Cas3 target site
source                  1..21
                        mol_type = genomic DNA
                        organism = Zea mays
SEQUENCE: 234
gcctcgaggt tgcacgcacg t                                               21

SEQ ID NO: 235          moltype = DNA  length = 20
FEATURE                 Location/Qualifiers
misc_feature            1..20
                        note = TS10Cas1 target site
source                  1..20
                        mol_type = genomic DNA
                        organism = Zea mays
SEQUENCE: 235
gcctcgcctt cgctagttaa                                                 20

SEQ ID NO: 236          moltype = DNA  length = 18
FEATURE                 Location/Qualifiers
misc_feature            1..18
                        note = TS10Cas3 target site
source                  1..18
                        mol_type = genomic DNA
                        organism = Zea mays
SEQUENCE: 236
gctcgtgttg gagataca                                                   18

SEQ ID NO: 237          moltype = DNA  length = 80
FEATURE                 Location/Qualifiers
source                  1..80
                        mol_type = genomic DNA
                        organism = Zea mays
SEQUENCE: 237
gttaaatctg acgtgaatct gtttggaatt gaaaaacaag tgcttccttt catacaccac  60
tatgtcgctt caatgtttgt                                                 80

SEQ ID NO: 238          moltype = DNA  length = 80
FEATURE                 Location/Qualifiers
source                  1..80
                        mol_type = genomic DNA
                        organism = Zea mays
SEQUENCE: 238
acaaacattg aagcgacata gtggtgtatg aaaggaagca cttgtttttc aattccaaac  60
agattcacgt cagatttaac                                                 80

SEQ ID NO: 239          moltype = DNA  length = 66
FEATURE                 Location/Qualifiers
source                  1..66
                        mol_type = genomic DNA
                        organism = Zea mays
SEQUENCE: 239
ccagtactgc acgttacgta cgtacgaact aatatactcc accagctgat cactgatgag  60
ccgagc                                                                66

SEQ ID NO: 240          moltype = DNA  length = 66
FEATURE                 Location/Qualifiers
source                  1..66
                        mol_type = genomic DNA
                        organism = Zea mays
```

```
SEQUENCE: 240
gctcggctca tcagtgatca gctggtggag tatattagtt cgtacgtacg taacgtgcag  60
tactgg                                                             66

SEQ ID NO: 241         moltype = DNA  length = 35
FEATURE                Location/Qualifiers
source                 1..35
                       mol_type = genomic DNA
                       organism = Zea mays
SEQUENCE: 241
ccgacgtgcg tgcaacctcg aggccgcaaa cagcc                             35

SEQ ID NO: 242         moltype = DNA  length = 35
FEATURE                Location/Qualifiers
source                 1..35
                       mol_type = genomic DNA
                       organism = Zea mays
SEQUENCE: 242
ggctgtttgc ggcctcgagg ttgcacgcac gtcgg                             35

SEQ ID NO: 243         moltype = DNA  length = 68
FEATURE                Location/Qualifiers
source                 1..68
                       mol_type = genomic DNA
                       organism = Zea mays
SEQUENCE: 243
gctcgtgttg gagatacagg gacagcaagt acttggccct taactagcga aggcgaggcg  60
gccatgga                                                           68

SEQ ID NO: 244         moltype = DNA  length = 68
FEATURE                Location/Qualifiers
source                 1..68
                       mol_type = genomic DNA
                       organism = Zea mays
SEQUENCE: 244
tccatggccg cctcgccttc gctagttaag ggccaagtac ttgctgtccc tgtatctcca  60
acacgagc                                                           68

SEQ ID NO: 245         moltype = DNA  length = 1108
FEATURE                Location/Qualifiers
misc_feature           1..1108
                       note = synthesized sequence- MHP14Cas-1 guideRNA cassette
source                 1..1108
                       mol_type = other DNA
                       organism = synthetic construct
SEQUENCE: 245
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta ttttttttata taccttttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gttaaatctg acgtgaatct  1020
gttgttttag agctagaaat agcaagttaa aataaggcta gtccgttatc aacttgaaaa  1080
agtggcaccg agtcggtgct tttttttt                                     1108

SEQ ID NO: 246         moltype = DNA  length = 1106
FEATURE                Location/Qualifiers
misc_feature           1..1106
                       note = synthesized sequence- MHP14Cas-3 gRNA cassette
source                 1..1106
                       mol_type = other DNA
                       organism = synthetic construct
SEQUENCE: 246
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
```

```
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt   720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gcaaacattg aagcgacata  1020
ggttttagag ctagaaatag caagttaaaa taaggctagt ccgttatcaa cttgaaaaag  1080
tggcaccgag tcggtgcttt tttttt                                       1106
```

```
SEQ ID NO: 247          moltype = DNA  length = 1103
FEATURE                 Location/Qualifiers
misc_feature            1..1103
                        note = synthesized sequence- TS8Cas-1 guideRNA cassette
source                  1..1103
                        mol_type = other DNA
                        organism = synthetic construct
SEQUENCE: 247
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt   720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gtacgtaacg tgcagtacgt  1020
tttagagcta gaaatagcaa gttaaaataa ggctagtccg ttatcaactt gaaaaagtgg  1080
caccgagtcg gtgctttttt ttt                                          1103
```

```
SEQ ID NO: 248          moltype = DNA  length = 1105
FEATURE                 Location/Qualifiers
misc_feature            1..1105
                        note = synthesized sequence- TS8Cas-2 guideRNA cassette
source                  1..1105
                        mol_type = other DNA
                        organism = synthetic construct
SEQUENCE: 248
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt   720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gctcatcagt gatcagctgg  1020
gttttagagc tagaaatagc aagttaaaat aaggctagtc cgttatcaac ttgaaaaagt  1080
ggcaccgagt cggtgctttt ttttt                                        1105
```

```
SEQ ID NO: 249          moltype = DNA  length = 1102
FEATURE                 Location/Qualifiers
misc_feature            1..1102
                        note = synthesized sequence- TS9Cas-2 guideRNA cassette
source                  1..1102
                        mol_type = other DNA
                        organism = synthetic construct
SEQUENCE: 249
```

-continued

```
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt ggctgtttgc ggcctcggtt  1020
ttagagctag aaatagcaag ttaaaataag gctagtccgt tatcaacttg aaaaagtggc  1080
accgagtcgg tgcttttttt tt                                          1102
```

```
SEQ ID NO: 250          moltype = DNA  length = 1106
FEATURE                 Location/Qualifiers
misc_feature            1..1106
                        note = synthesized sequence- TS9Cas-3 guideRNA cassette
source                  1..1106
                        mol_type = other DNA
                        organism = synthetic construct
SEQUENCE: 250
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gcctcgaggt tgcacgcacg  1020
tgttttagag ctagaaatag caagttaaaa taaggctagt ccgttatcaa cttgaaaaag  1080
tggcaccgag tcggtgcttt tttttt                                      1106
```

```
SEQ ID NO: 251          moltype = DNA  length = 1105
FEATURE                 Location/Qualifiers
misc_feature            1..1105
                        note = synthesized sequence- TS10Cas-1 guideRNA cassette
source                  1..1105
                        mol_type = other DNA
                        organism = synthetic construct
SEQUENCE: 251
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gcctcgcctt cgctagttaa  1020
gttttagagc tagaaatagc aagttaaaat aaggctagtc cgttatcaac ttgaaaaagt  1080
ggcaccgagt cggtgctttt ttttt                                       1105
```

```
SEQ ID NO: 252          moltype = DNA  length = 1103
FEATURE                 Location/Qualifiers
misc_feature            1..1103
```

```
                        note = synthesized sequence- TSCas-3 guideRNA cassette
source                  1..1103
                        mol_type = other DNA
                        organism = synthetic construct
SEQUENCE: 252
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta tttttttata taccttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gctcgtgttg gagatacagt  1020
tttagagcta gaaatagcaa gttaaaataa ggctagtccg ttatcaactt gaaaaagtgg  1080
caccgagtcg gtgctttttt ttt                                         1103

SEQ ID NO: 253          moltype = DNA  length = 4928
FEATURE                 Location/Qualifiers
misc_feature            1..4928
                        note = synthesized sequence- MHP14Cas1 donor
source                  1..4928
                        mol_type = other DNA
                        organism = synthetic construct
SEQUENCE: 253
gccatgtcat cttgtagtta gggcttggag ctagtcgacc gttggaggct ttgtcctcat  60
gcggcaccgg acagtctggt gctacaccgg acagtccggt gcccctctga ccatctgctc  120
tgacatctga attgcactgt tcactttgca gagtcgacca ttgcgtgcag gtagccattg  180
ctccgctggt gcaccggaca gtccagtggc acaccggaca gtccgatgaa ttatagcgga  240
gctgcgcctg ggaaacccga agctgaggag tttgagctga ttcaccctgg tgcaccggac  300
actgtccggt ggcacactgg acagtccggt gcgccggacc agggcacact tcggtttcct  360
ttttgctcct ttcttttgaa gcctaacttg ttcttttgat tggtttgtgt tgaacctta  420
gcacctgtag aatgtatgat ctagagcaaa ctagttagtc caattatttg tgttgggcaa  480
ttcaaccacc aaaaacattt aggaaaatgt ttgatcttat ttccctttca tattctcta  540
ttgctagttg tcggggtgaa gttgagctct tgcttaggtt ttaattagtg ttgattttta  600
gaaaaaccca attcaccccc ctcttgggca tcgtgatcct tttagcaaca aaatgtgcac  660
acatcaaaac aagcgcttct accatatgta gttgttgcac aataatggtc ctccttagga  720
tttgcaaccg tttaacaata gctatgtgac cacagattta tgtcggatgc acgaaaattg  780
taggatttta catttcttta ccttggttca caaacattga agcgacatag tggtgtatga  840
aaggaagcac ttgtttttca attccaaacc gcggtaccat ttaaatctta agcctaggat  900
aacttcgtat agcatacatt atacgaagtt atggcgccgc tagcctgcag tgcagcgtga  960
cccggtcgtg cccctctcta gagataatga gcattgcatg tctaagttat aaaaaattac  1020
cacatatttt ttttgtcaca cttgtttgaa gtgcagttta tctatcttta tacatatatt  1080
taaactttac tctacgaata atataatcta tagtactaca ataatatcag tgttttagag  1140
aatcatataa atgaacagtt agacatggtc taaaggacaa ttgagtattt tgacaacagg  1200
actctacagt tttatctttt tagtgtgcat gtgttctcct tttttttgc aaatagcttc  1260
acctatataa tacttcatcc atttattag tacatccatt tagggtttag ggttaatggt  1320
ttttatagac taatttttt agtacatcta ttttattcta ttttagcctc taaattaaga  1380
aaactaaaac tctattttag tttttttatt taataattta gatataaaat agaataaaat  1440
aaagtgacta aaaattaaac aaataccctt taagaaatta aaaaaactaa ggaaacattt  1500
ttcttgtttc gagtagataa tgccagcctg ttaaacgccg tcgacgagtc taacggacac  1560
caaccagcga accagcagcg tcgcgtcggg ccaagcgaag cagacggcac ggcatctctg  1620
tcgctgcctc tggacccctc tcgagagttc cgctccaccg ttggacttgc tccgctgtcg  1680
gcatccagaa attgcgtggc ggagcggcag acgtgagccg gcacggcagg cggcctcctc  1740
ctcctctcac ggcaccggca gctacggggg attcctttcc caccgctcct tcgctttccc  1800
ttcctcgccc gccgtaataa atagacaccc cctccacacc ctctttcccc aacctcgtgt  1860
tgttcggagc gcacacacac acaaccagat ctcccccaaa tccacccgtc ggcacctccg  1920
cttcaaggta cgccgctcgt cctccccccc cccctctct accttctcta gatcggcgtt  1980
ccggtccatg catggttagg gcccggtagt tctacttctg ttcatgtttg tgttagatcc  2040
gtgtttgtgt tagatccgtg ctgctagcgt tcgtacacgg atgcgacctg tacgtcagac  2100
acgttctgat tgctaacttg ccagtgtttc tctttgggga atcctgggat ggctctagcc  2160
gttccgcaga cgggatcgat ttcatgattt tttttgtttc gttgcatagg gtttggtttg  2220
ccctttcct ttatttcaat atatgccgtg cacttgtttg tcgggtcatc ttttcatgct  2280
ttttttgtc ttggttgtga tgatgtggtc tggttgggcg gtcgttctag atcggagtag  2340
aattctgttt caaactacct ggtggattta ttaattttgg atctgtatgt gtgtgccata  2400
catattcata gttacgaatt gaagatgatg gatggaaata tcgatctagg ataggtatac  2460
atgttgatgc gggttttact gatgcatata cagagatgct tttgttcgc ttggttgtga  2520
tgatgtggtg tggttgggcg gtcgttcatt cgttctagat cggagtagaa tactgtttca  2580
aactacctgg tgtatttatt aattttggaa ctgtatgtgt gtgtcataca tcttcatagt  2640
tacgagttta agatggatgg aaatatcgat ctaggatagg tatacatgtt gatgtgggtt  2700
ttactgatgc atatacatga tggcatatgc agcatctatt catatgctct aaccttgagt  2760
```

-continued

```
acctatctat tataataaac aagtatgttt tataattatt ttgatcttga tatacttgga  2820
tgatggcata tgcagcagct atatgtggat ttttttagcc ctgccttcat acgctattta  2880
tttgcttggt actgtttctt ttgtcgatgc tcaccctgtt gtttggtgtt acttctgcag  2940
gtcgactcta gaggatcaat tcgctagcga agttcctatt ccgaagttcc tattctctag  3000
aaagtatagg aacttcagat ccaccgggat ccccgatcat gcaaaaactc attaactcag  3060
tgcaaaacta tgcctggggc agcaaaacgg cgttgactga actttatggt atggaaaatc  3120
cgtccagcca gccgatggcc gagctgtgga tgggcgcaca tccgaaaagc agttcacgag  3180
tgcagaatgc cgccggagat atcgtttcac tgcgtgatgt gattgagagt gataaatcga  3240
ctctgctcgg agaggccgtt gccaaacgct ttggcgaact gcctttcctg ttcaaagtat  3300
tatgcgcagc acagccactc tccattcagg ttcatccaaa caaacacaat tctgaaatcg  3360
gttttgccaa agaaaatgcc gcaggtatcc cgatggatgc cgccgagcgt aactataaag  3420
atcctaacca caagccggag ctggtttttg cgctgacgcc tttccttgcg atgaacgcgt  3480
ttcgtgaatt ttccgagatt gtctccctac tccagccggt cgcaggtgca catccggcga  3540
ttgctcactt tttacaacag cctgatgccg aacgtttaag cgaactgttc gccagcctgt  3600
tgaatatgca gggtgaagaa aaatcccgcg cgctggcgat tttaaaatcg gccctcgata  3660
gccagcaggg tgaaccgtgg caaacgattc gtttaatttc tgaattttac ccggaagaca  3720
gcggtctgtt ctccccgcta ttgctgaatg tggtgaaatt gaaccctggc gaagcgatgt  3780
tcctgttcgc tgaaacaccg cacgcttacc tgcaaggcgt ggcgctggaa gtgatggcaa  3840
actccgataa cgtgctgcgt gcgggtctga cgcctaaata cattgatatt ccggaactgg  3900
ttgccaatgt gaaattcgaa gccaaaccgg ctaaccagtt gttgacccag ccggtgaaac  3960
aaggtgcaga actggacttc ccgattccag tggatgattt tgccttctcg ctgcatgacc  4020
ttagtgataa agaaaccacc attagccagc agagtgccgc cattttgttc tgcgtcgaag  4080
gcgatgcaac gttgtggaaa ggttctcagc agttacagct taaaccgggt gaatcagcgt  4140
ttattgccgc caacgaatca ccggtgactg tcaaaggcca cggccgttta gcgcgtgttt  4200
acaacaagct gtaagagctt actgaaaaaa ttaacatctc ttgctaagct gggggtggaa  4260
cctagacttg tccatcttct ggattggcca acttaattaa tgtatgaaat aaaaggatgc  4320
acacatagtg acatgctaat cactataatg tgggcatcaa agttgtgtgt tatgtgtaat  4380
tactagttat ctgaataaaa gagaaagaga tcatccatat ttcttatcct aaatgaatgt  4440
cacgtgtctt tataattctt tgatgaacca gatgcatttc attaaccaaa tccatataca  4500
tataaatatt aatcatatat aattaatatc aattgggtta gcaaaacaaa tctagtctag  4560
gtgtgttttg cgaatgcggc cctagcgtat acgaagttcc tattccgaag ttcctattct  4620
ccagaaagta taggaacttc tgtacacctg agctgattcc gatgacttcg taggttccta  4680
gctcaagccg ctcgtgtcca agcgtcactt acgattagct aatgattacg gcatctagga  4740
ccgactagct aactaactag taccgaggcc ggccccgcgg gagctcggcg cgccagattc  4800
acgtcagatt taaccaaaac tatattatga ggtacacata ttacaatcca aaatgaatta  4860
tctagttctc gagttgtaca cagtttatca cgtgttttac acattccaac cctaaactcc  4920
aaccgtgg                                                           4928
```

```
SEQ ID NO: 254          moltype = DNA  length = 4570
FEATURE                 Location/Qualifiers
misc_feature            1..4570
                        note = synthesized sequence- MHP14Cas3 donor
source                  1..4570
                        mol_type = other DNA
                        organism = synthetic construct
SEQUENCE: 254
acacttcggt ttccttttg ctcctttctt ttgaagccta acttgttctt ttgattggtt  60
tgtgttgaac ctttagcacc tgtagaatgt atgatctaga gcaaactagt tagtccaatt  120
atttgtgttg ggcaattcaa ccaccaaaaa catttaggaa aatgtttgat cttatttccc  180
tttcatattc tcttattgct agttgtcggg gtgaagttga gctcttgctt aggttttaat  240
tagtgttgat ttttagaaaa acccaattca ccccccctctt gggcatcgtg atcctttttag  300
caacaaaatg tgcacacatc aaaacaagcg cttctaccat atgtagttgt tgcacaataa  360
tggtcctcct taggatttgc aaccgtttaa caatagctat gtgaccacag atttatgtcg  420
gatgcacgaa aattgtagga ttttacattt ctttaccttg gttcacaaac attgaagcga  480
caggtaccat ttaaatctta agcctaggat aacttcgtat agcatacatt atacgaagtt  540
atggcgccgc tagcctgcag tgcagcgtga cccggtcgtg cccctctcta gagataatga  600
gcattgcatg tctaagttat aaaaaattac cacatatttt ttttgtcaca cttgtttgaa  660
gtgcagttta tctatcttta tacatatatt taaactttac tctacgaata atataatcta  720
tagtactaca ataatatcag tgttttagag aatcatataa atgaacagtt agacatggtc  780
taaaggacaa ttgagtattt tgacaacagg actctacagt tttatctttt tagtgtgcat  840
gtgttctcct ttttttttgc aaatagcttc acctatataa tacttcatcc attttattag  900
tacatccatt tagggtttag ggttaatggt ttttatagac taattttttt agtacatcta  960
ttttattcta ttttagcctc taaattaaga aaactaaaac tctattttag ttttttttatt  1020
taataattta gatataaaat agaataaaat aaagtgacta aaaattaaac aaataccctt  1080
taagaaatta aaaaaactaa ggaaacattt ttcttgtttc gagtagataa tgccagcctg  1140
ttaaacgccg tcgacgagtc taacggacac caaccagcga accagcagcg tcgcgtcggg  1200
ccaagcgaag cagacggcac ggcatctctg tcgctgcctc tggacccctc tcgagagttc  1260
cgctccaccg ttggacttgc tccgctgtcg gcatccagaa attgcgtggc ggagcggcag  1320
acgtgagccg gcacggcagg cggcctcctc ctcctctcac ggcaccggca gctacggggg  1380
attcctttcc caccgctcct tcgctttccc ttcctcgccc gcccgtaataa atagacaccc  1440
cctccacacc ctctttcccc aacctcgtgt tgttcggagc gcacacacac acaaccagat  1500
ctcccccaaa tccacccgtc ggcacctccg cttcaaggta cgccgctcgt cctccccccc  1560
ccccctctct accttctcta gatcggcgtt ccggtccatg catggttagg gcccggtagt  1620
tctacttctg ttcatgtttg tgttagatcc gtgtttgtgt tagatccgtg ctgctagcgt  1680
tcgtacacgg atgcgacctg tacgtcagac acgttctgat tgctaacttg ccagtgtttc  1740
tctttgggga atcctgggat ggctctagcc gttccgcaga cgggatcgat ttcatgattt  1800
tttttgtttc gttgcatagg gtttggtttg ccctttttcct ttatttcaat atatgccgtg  1860
cacttgtttg tcgggtcatc ttttcatgct ttttttgtc ttggttgtga tgatgtggtc  1920
tggttgggcg gtcgttctag atcggagtag aattctgttt caaactacct ggtggattta  1980
```

-continued

```
ttaattttgg atctgtatgt gtgtgccata catattcata gttacgaatt gaagatgatg  2040
gatggaaata tcgatctagg ataggtatac atgttgatgc gggttttact gatgcatata  2100
cagagatgct ttttgttcgc ttggttgtga tgatgtggtg tggttgggcg gtcgttcatt  2160
cgttctagat cggagtagaa tactgtttca aactacctgg tgtatttatt aattttggaa  2220
ctgtatgtgt gtgtcataca tcttcatagt tacgagttta agatggatgg aaatatcgat  2280
ctaggatagg tatacatgtt gatgtgggtt ttactgatgc atatacatga tggcatatgc  2340
agcatctatt catatgctct aaccttgagt acctatctat tataataaac aagtatgttt  2400
tataattatt ttgatcttga tatacttgga tgatggcata tgcagcagct atatgtggat  2460
ttttttagcc ctgccttcat acgctattta tttgcttggt actgtttctt ttgtcgatgc  2520
tcaccctgtt gtttggtgtt acttctgcag gtcgactcta gaggatcaat tcgctagcga  2580
agttcctatt ccgaagttcc tattctctag aaagtatagg aacttcagat ccaccgggat  2640
ccccgatcat gcaaaaactc attaactcag tgcaaaacta tgcctggggc agcaaaacgg  2700
cgttgactga actttatggt atggaaaatc cgtccagcca gccgatggcc gagctgtgga  2760
tgggcgcaca tccgaaaagc agttcacgag tgcagaatgc cgccggagat atcgtttcac  2820
tgcgtgatgt gattgagagt gataaatcga ctctgctcgg agaggccgtt gccaaacgct  2880
ttggcgaact gcctttcctg ttcaaagtat tatgcgcagc acagccactc tccattcagg  2940
ttcatccaaa caaacacaat tctgaaatcg gttttgccaa agaaaatgcc gcaggtatcc  3000
cgatggatgc cgccgagcgt aactataaag atcctaacca caagccggag ctggtttttg  3060
cgctgacgcc tttccttgcg atgaacgcgt ttcgtgaatt ttccgagatt gtctccctac  3120
tccagccggt cgcaggtgca catccggcga ttgctcactt tttacaacag cctgatgccg  3180
aacgtttaag cgaactgttc gccagcctgt tgaatatgca gggtgaagaa aaatcccgcg  3240
cgctggcgat tttaaaatcg gccctcgata gccagcaggg tgaaccgtgg caaacgattc  3300
gtttaatttc tgaattttac ccggaagaca gcggtctgtt ctccccgcta ttgctgaatg  3360
tggtgaaatt gaaccctggc gaagcgatgt tcctgttcgc tgaaacaccg cacgcttacc  3420
tgcaaggcgt ggcgctggaa gtgatggcaa actccgataa cgtgctgcgt gcgggtctga  3480
cgcctaaata cattgatatt ccggaactgg ttgccaatgt gaaattcgaa gccaaaccgg  3540
ctaaccagtt gttgacccag ccggtgaaac aaggtgcaga actggacttc ccgattccag  3600
tggatgattt tgccttctcg ctgcatgacc ttagtgataa agaaaccacc attagccagc  3660
agagtgccgc cattttgttc tgcgtcgaag gcgatgcaac gttgtggaaa ggttctcagc  3720
agttacagct taaaccgggt gaatcagcgt ttattgccgc caacgaatca ccggtgactg  3780
tcaaaggcca cggccgttta gcgcgtgttt acaacaagct gtaagagctt actgaaaaaa  3840
ttaacatctc ttgctaagct gggggtggaa cctagacttg tccatcttct ggattggcca  3900
acttaattaa tgtatgaaat aaaaggatgc acacatagtg acatgctaat cactataatg  3960
tgggcatcaa agttgtgtgt tatgtgtaat tactagttat ctgaataaaa gagaaagaga  4020
tcatccatat ttcttatcct aaatgaatgt cacgtgtctt tataattctt tgatgaacca  4080
gatgcatttc attaaccaaa tccatataca tataaatatt aatcatatat aattaatatc  4140
aattgggtta gcaaaacaaa tctagtctag gtgtgttttg cgaatgcggc cctagcgtat  4200
acgaagttcc tattccgaag ttcctattct ccagaaagta taggaacttc tgtacacctg  4260
agctgattcc gatgacttcg taggttccta gctcaagccg ctcgtgtcca agcgtcactt  4320
acgattagct aatgattacg gcatctagga ccgactagct aactaactag taccgaggcc  4380
ggcccgcgg gagctcggcg cgcctagtgg tgtatgaaag gaagcacttg tttttcaatt  4440
ccaaacagat tcacgtcaga tttaaccaaa actatattat gaggtacaca tattacaatc  4500
caaaatgaat tatctagttc tcgagttgta cacagtttat cacgtgtttt acacattcca  4560
accctaaact                                                  4570
```

```
SEQ ID NO: 255          moltype = DNA  length = 5091
FEATURE                 Location/Qualifiers
misc_feature            1..5091
                        note = synthesized sequence- TS8Cas-1 donor
source                  1..5091
                        mol_type = other DNA
                        organism = synthetic construct
SEQUENCE: 255
cacacatgac tgcctgagaa tctgctgccg ttgcctctca tattatattc gatcccctga  60
ctaaaaaaac tcggggccgg ctaatacgta ctgtacgtac gcagaattta cggtccagca  120
cgggcatgcc gcgcgggctg actttgctcc actgactcga tcatgtgcgg attccatcgc  180
ggcgtagcgt agccaaccgc aacgcaaacc gacttcatct ttttttttta ttatgaacaa  240
aaggagatcg agagaaacgt gaacggtaaa taatatatct gatcccatgc atgcacgctg  300
cctgggtcga tctcgctctc gctccgccca gacgaacatg catgctggtc aggctcaacg  360
ctcaggcggg caagctgtgg gaggacatgg gatgggagag gaggacacat gcatgctggc  420
cagtcaggca ctgtgctggc acatgaggta gggatagggg ggccctcggc cagtgtccag  480
gccgcatgca tgcatgcccc ccctgctgct cgaccgaaca acgttggatg cctggattga  540
tgcaacagtt tggacggacg gaccatacgt tatgtaccag taggtaccat ttaaatctta  600
agcctaggat aacttcgtat agcatacatt atacgaagtt atggcgccgc tagcctgcag  660
tgcagcgtga cccggtcgtg cccctctcta gagataatga gcattgcatg tctaagttat  720
aaaaaattac cacatatttt ttttgtcaca cttgtttgaa gtgcagttta tctatcttta  780
tacatatatt taaactttac tctacgaata atataatcta tagtactaca ataatatcag  840
tgttttagag aatcatataa atgaacagtt agacatggtc taaaggacaa ttgagtattt  900
tgacaacagg actctacagt tttatctttt tagtgtgcat gtgttctcct ttttttttgc  960
aaatagcttc acctatataa tacttcatcc attttattag tacatccatt tagggtttag  1020
ggttaatggt ttttatagac taattttttt agtacatcta ttttattcta ttttagcctc  1080
taaattaaga aaactaaaac tctattttag tttttttatt taataattta gatataaaat  1140
agaataaaat aaagtgacta aaaattaaac aaataccctt taagaaatta aaaaaactaa  1200
ggaaacattt ttcttgtttc gagtagataa tgccagcctg ttaaacgccg tcgacgagtc  1260
taacggacac caaccagcga accagcagcg tcgcgtcggg ccaagcgaag cagacggcac  1320
ggcatctctg tcgctgcctc tggacccctc tcgagagttc cgctccaccg ttggacttgc  1380
tccgctgtcg gcatccagaa attgcgtggc ggagcggcag acgtgagccg gcacggcagg  1440
cggcctcctc ctcctctcac ggcaccggca gctacggggg attcctttcc caccgctcct  1500
tcgctttccc ttcctcgccc gccgtaataa atagacaccc cctccacacc ctctttcccc  1560
```

```
aacctcgtgt tgttcggagc gcacacacac acaaccagat ctcccccaaa tccacccgtc  1620
ggcacctccg cttcaaggta cgccgctcgt cctccccccc ccccctctct accttctcta  1680
gatcggcgtt ccggtccatg catggttagg gcccggtagt tctacttctg ttcatgtttg  1740
tgttagatcc gtgtttgtgt tagatccgtg ctgctagcgt tcgtacacgg atgcgacctg  1800
tacgtcagac acgttctgat tgctaacttg ccagtgtttc tctttgggga atcctgggat  1860
ggctctagcc gttccgcaga cgggatcgat ttcatgattt tttttgtttc gttgcatagg  1920
gtttggtttg cccttttcct ttatttcaat atatgccgtg cacttgtttg tcgggtcatc  1980
ttttcatgct tttttttgtc ttggttgtga tgatgtggtc tggttgggcg gtcgttctag  2040
atcggagtag aattctgttt caaactacct ggtggattta ttaattttgg atctgtatgt  2100
gtgtgccata catattcata gttacgaatt gaagatgatg gatggaaata tcgatctagg  2160
ataggtatac atgttgatgc gggttttact gatgcatata cagagatgct ttttgttcgc  2220
ttggttgtga tgatgtggtg tggttgggcg gtcgttcatt cgttctagat cggagtagaa  2280
tactgtttca aactacctgg tgtatttatt aattttggaa ctgtatgtgt gtgtcataca  2340
tcttcatagt tacgagttta agatggatgg aaatatcgat ctaggatagg tatacatgtt  2400
gatgtgggtt ttactgatgc atatacatga tggcatatgc agcatctatt catatgctct  2460
aaccttgagt acctatctat tataataaac aagtatgttt tataattatt ttgatcttga  2520
tatacttgga tgatggcata tgcagcagct atatgtggat ttttttagcc ctgccttcat  2580
acgctattta tttgcttggt actgtttctt ttgtcgatgc tcaccctgtt gtttggtgtt  2640
acttctgcag gtcgactcta gaggatcaat tcgctagcga agttcctatt ccgaagttcc  2700
tattctctag aaagtatagg aacttcagat ccaccgggat ccccgatcat gcaaaaactc  2760
attaactcag tgcaaaacta tgcctggggc agcaaaacgg cgttgactga actttatggt  2820
atggaaaatc cgtccagcca gccgatggcc gagctgtgga tgggcgcaca tccgaaaagc  2880
agttcacgag tgcagaatgc cgccggagat atcgtttcac tgcgtgatgt gattgagagt  2940
gataaatcga ctctgctcgg agaggccgtt gccaaacgct ttggcgaact gcctttcctg  3000
ttcaaagtat tatgcgcagc acagccactc tccattcagg ttcatccaaa caaacacaat  3060
tctgaaatcg gttttgccaa agaaaatgcc gcaggtatcc cgatggatgc cgccgagcgt  3120
aactataaag atcctaacca caagccggag ctggtttttg cgctgacgcc tttccttgcg  3180
atgaacgcgt ttcgtgaatt ttccgagatt gtctccctac tccagccggt cgcaggtgca  3240
catccggcga ttgctcactt tttacaacag cctgatgccg aacgtttaag cgaactgttc  3300
gccagcctgt tgaatatgca gggtgaagaa aaatcccgcg cgctggcgat tttaaaatcg  3360
gccctcgata gccagcaggg tgaaccgtgg caaacgattc gtttaatttc tgaattttac  3420
ccggaagaca gcggtctgtt ctccccgcta ttgctgaatg tggtgaaatt gaaccctggc  3480
gaagcgatgt tcctgttcgc tgaaacaccg cacgcttacc tgcaaggcgt ggcgctggaa  3540
gtgatggcaa actccgataa cgtgctgcgt gcgggtctga cgcctaaata cattgatatt  3600
ccggaactgg ttgccaatgt gaaattcgaa gccaaaccgg ctaaccagtt gttgacccag  3660
ccggtgaaac aaggtgcaga actggacttc ccgattccag tggatgattt tgccttctcg  3720
ctgcatgacc ttagtgataa agaaaccacc attagccagc agagtgccgc catttgttc   3780
tgcgtcgaag gcgatgcaac gttgtggaaa ggttctcagc agttacagct taaaccgggt  3840
gaatcagcgt ttattgccgc caacgaatca ccggtgactg tcaaaggcca cggccgttta  3900
gcgcgtgttt acaacaagct gtaagagctt actgaaaaaa ttaacatctc ttgctaagct  3960
gggggtggaa cctagacttg tccatcttct ggattggcca acttaattaa tgtatgaaat  4020
aaaaggatgc acacatagtg acatgctaat cactataatg tgggcatcaa agttgtgtgt  4080
tatgtgtaat tactagttat ctgaataaaa gagaaagaga tcatccatat ttcttatcct  4140
aaatgaatgt cacgtgtctt tataattctt tgatgaacca gatgcatttc attaaccaaa  4200
tccatataca tataaatatt aatcatatat aattaatatc aattgggtta gcaaaacaaa  4260
tctagtctag gtgtgttttg cgaatgcggc cctagcgtat acgaagttcc tattccgaag  4320
ttcctattct ccagaaagta taggaacttc tgtacacctg agctgattcc gatgacttcg  4380
taggttccta gctcaagccg ctcgtgtcca agcgtcactt acgattagct aatgattacg  4440
gcatctagga ccgactagct aactaactag taccgaggcc ggccccgcgg actgcacgtt  4500
acgtacgtac gaactaatat actccaccag ctgatcactg atgagccgag ccgccatgca  4560
ttgtaattta taacatgtgc ggctgtacgc ttccatctca aataccttt  tatatatata  4620
ttgtacttta tagtctacga cataatctgc catggtaatt tataagatgt gctttattgc  4680
tcgttgttct gttctcatct gtgtccatgg catggcatgg atacaaaatg tatgtatggc  4740
cacgcatcca atctgtgacg ttgtcaaggc agaggtccaa ccgtccaaga ccctcttgtg  4800
ccgccctgta cttgcagtca gtgacgttgt gagaaaaagc tgtgggtggt ctccgcagag  4860
cgcgcgggcc acgagaggga gccccatctc tcggccgagg ggtacggggg ctccagacac  4920
ggtcctttgg tttcttctgc ctgtagcgag cggccccgcc ccccaccgcg ctgctagcct  4980
agccgatgct gatccatcca ccacccacaa gggattgttc cacgacttgt ggacctgacc  5040
atgacgtgac ttcacgccat gtacgctcag ccgctcacta gcttttttt  c           5091
```

```
SEQ ID NO: 256          moltype = DNA  length = 5237
FEATURE                 Location/Qualifiers
misc_feature            1..5237
                        note = synthesized sequence- TS8Cas-2 donor
source                  1..5237
                        mol_type = other DNA
                        organism = synthetic construct
SEQUENCE: 256
tctctttcag ggcttgttcg tttacgttgg attgcacccg gaatcgttac agctaatcaa  60
agtttatata aattagagaa gcaaccggat aggaatcgtt ccgacccacc aattcgacac  120
aaacgaacaa ggcctcaatc cttctcaatc cacctccaac ccaataagct cttggaggcg  180
gcggcgggag agcagccaca cacatgactg cctgagaatc tgctgccgtt gcctctcata  240
ttatattcga tcccctgact aaaaaaactc ggggccggct aatacgtact gtacgtacgc  300
agaatttacg gtccagcacg ggcatgccgc gcgggctgac tttgctccac tgactcgatc  360
atgtgcggat tccatcgcgg cgtagcgtag ccaaccgcaa cgcaaaccga cttcatcttt  420
tttttttatt atgaacaaaa ggagatcgag agaaacgtga acggtaaata atatatctga  480
tcccatgcat gcacgctgcc tgggtcgatc tcgctctcgc tccgcccaga cgaacatgca  540
tgctggtcag gctcaacgct caggcgggca agctgtggga ggacatggga tgggagagga  600
ggacacatgc atgctggcca gtcaggcact gtgctggcac atgaggtagg gatagggggg  660
```

```
ccctcggcca gtgtccaggc cgcatgcatg catgcccccc ctgctgctcg accgaacaac  720
gttggatgcc tggattgatg caacagtttg gacggacgga ccatacgtta tgtaccagta  780
ctgcacgtta cgtacgtacg aactaatata ctccaccagg taccatttaa atcttaagcc  840
taggataact tcgtatagca tacattatac gaagttatgg cgccgctagc ctgcagtgca  900
gcgtgacccg gtcgtgcccc tctctagaga taatgagcat tgcatgtcta agttataaaa  960
aattaccaca tattttttt gtcacacttg tttgaagtgc agtttatcta tctttataca  1020
tatatttaaa ctttactcta cgaataatat aatctatagt actacaataa tatcagtgtt  1080
ttagagaatc atataaatga acagttagac atggtctaaa ggacaattga gtattttgac  1140
aacaggactc tacagtttta tctttttagt gtgcatgtgt tctccttttt ttttgcaaat  1200
agcttcacct atataatact tcatccattt tattagtaca tccatttagg gtttagggtt  1260
aatggttttt atagactaat ttttttagta catctatttt attctatttt agcctctaaa  1320
ttaagaaaac taaaactcta ttttagtttt tttatttaat aatttagata taaaatagaa  1380
taaaataaag tgactaaaaa ttaaacaaat accctttaag aaattaaaaa aactaaggaa  1440
acatttttct tgtttcgagt agataatgcc agcctgttaa acgccgtcga cgagtctaac  1500
ggacaccaac cagcgaacca gcagcgtcgc gtcgggccaa gcgaagcaga cggcacggca  1560
tctctgtcgc tgcctctgga cccctctcga gagttccgct ccaccgttgg acttgctccg  1620
ctgtcggcat ccagaaattg cgtggcggag cggcagacgt gagccggcac ggcaggcggc  1680
ctcctcctcc tctcacggca ccggcagcta cgggggattc ctttcccacc gctccttcgc  1740
tttcccttcc tcgcccgccg taataaatag acaccccctc cacaccctct ttccccaacc  1800
tcgtgttgtt cggagcgcac acacacacaa ccagatctcc cccaaatcca cccgtcggca  1860
cctccgcttc aaggtacgcc gctcgtcctc cccccccccc ctctctacct tctctagatc  1920
ggcgttccgg tccatgcatg gttagggccc ggtagttcta cttctgttca tgtttgtgtt  1980
agatccgtgt ttgtgttaga tccgtgctgc tagcgttcgt acacggatgc gacctgtacg  2040
tcagacacgt tctgattgct aacttgccag tgtttctctt tggggaatcc tgggatggct  2100
ctagccgttc cgcagacggg atcgatttca tgattttttt tgtttcgttg catagggttt  2160
ggtttgccct tttcctttat ttcaatatat gccgtgcact tgtttgtcgg gtcatctttt  2220
catgcttttt tttgtcttgg ttgtgatgat gtggtctggt tgggcggtcg ttctagatcg  2280
gagtagaatt ctgtttcaaa ctacctggtg gatttattaa ttttggatct gtatgtgtgt  2340
gccatacata ttcatagtta cgaattgaag atgatggatg gaaatatcga tctaggatag  2400
gtatacatgt tgatgcgggt tttactgatg catatacaga gatgcttttt gttcgcttgg  2460
ttgtgatgat gtggtgtggt tgggcggtcg ttcattcgtt ctagatcgga gtagaatact  2520
gtttcaaact acctggtgta tttattaatt ttggaactgt atgtgtgtgt catacatctt  2580
catagttacg agtttaagat ggatggaaat atcgatctag gataggtata catgttgatg  2640
tgggttttac tgatgcatat acatgatggc atatgcagca tctattcata tgctctaacc  2700
ttgagtacct atctattata ataaacaagt atgttttata attattttga tcttgatata  2760
cttggatgat ggcatatgca gcagctatat gtggattttt ttagccctgc cttcatacgc  2820
tatttatttg cttggtactg tttcttttgt cgatgctcac cctgttgttt ggtgttactt  2880
ctgcaggtcg actctagagg atcaattcgc tagcgaagtt cctattccga agttcctatt  2940
ctctagaaag tataggaact tcagatccac cgggatcccc gatcatgcaa aaactcatta  3000
actcagtgca aaactatgcc tggggcagca aaacggcgtt gactgaactt tatggtatgg  3060
aaaatccgtc cagccagccg atggccgagc tgtggatggg cgcacatccg aaaagcagtt  3120
cacgagtgca gaatgccgcc ggagatatcg tttcactgcg tgatgtgatt gagagtgata  3180
aatcgactct gctcggagag gccgttgcca aacgctttgg cgaactgcct ttcctgttca  3240
aagtattatg cgcagcacag ccactctcca ttcaggttca tccaaacaaa cacaattctg  3300
aaatcggttt tgccaaagaa aatgccgcag gtatcccgat ggatgccgcc gagcgtaact  3360
ataaagatcc taaccacaag ccggagctgg tttttgcgct gacgcctttc cttgcgatga  3420
acgcgtttcg tgaattttcc gagattgtct ccctactcca gccggtcgca ggtgcacatc  3480
cggcgattgc tcacttttta caacagcctg atgccgaacg tttaagcgaa ctgttcgcca  3540
gcctgttgaa tatgcagggt gaagaaaaat cccgcgcgct ggcgatttta aaatcggccc  3600
tcgatagcca gcagggtgaa ccgtggcaaa cgattcgttt aatttctgaa ttttacccgg  3660
aagacagcgg tctgttctcc ccgctattgc tgaatgtggt gaaattgaac cctggcgaag  3720
cgatgttcct gttcgctgaa acaccgcacg cttacctgca aggcgtggcg ctggaagtga  3780
tggcaaactc cgataacgtg ctgcgtgcgg gtctgacgcc taaatacatt gatattccgg  3840
aactggttgc caatgtgaaa ttcgaagcca aaccggctaa ccagttgttg acccagccgg  3900
tgaaacaagg tgcagaactg gacttcccga ttccagtgga tgattttgcc ttctcgctgc  3960
atgaccttag tgataaagaa accaccatta gccagcagag tgccgccatt ttgttctgcg  4020
tcgaaggcga tgcaacgttg tggaaaggtt ctcagcagtt acagcttaaa ccgggtgaat  4080
cagcgtttat tgccgccaac gaatcaccgg tgactgtcaa aggccacggc cgtttagcgc  4140
gtgtttacaa caagctgtaa gagcttactg aaaaaattaa catctcttgc taagctgggg  4200
gtggaaccta gacttgtcca tcttctggat tggccaactt aattaatgta tgaaataaaa  4260
ggatgcacac atagtgacat gctaatcact ataatgtggg catcaaagtt gtgtgttatg  4320
tgtaattact agttatctga ataaaagaga aagagatcat ccatatttct tatcctaaat  4380
gaatgtcacg tgtctttata attctttgat gaaccagatg catttcatta accaaatcca  4440
tatacatata aatattaatc atatataatt aatatcaatt gggttagcaa aacaaatcta  4500
gtctaggtgt gttttgcgaa tgcggcccta gcgtatacga agttcctatt ccgaagttcc  4560
tattctccag aaagtatagg aacttctgta cacctgagct gattccgatg acttcgtagg  4620
ttcctagctc aagccgctcg tgtccaagcg tcacttacga ttagctaatg attacggcat  4680
ctaggaccga ctagctaact aactagtacc gaggccggcc ccgcgggagc tcgctgatca  4740
ctgatgagcc gagccgccat gcattgtaat ttataacatg tgcggctgta cgcttccatc  4800
tcaaatacct ttttatatat atattgtact ttatagtcta cgacataatc tgccatggta  4860
atttataaga tgtgctttat tgctcgttgt tctgttctca tctgtgtcca tggcatggca  4920
tggatacaaa atgtatgtat ggccacgcat ccaatctgtg acgttgtcaa ggcagaggtc  4980
caaccgtcca agaccctctt gtgccgccct gtacttgcag tcagtgacgt tgtgagaaaa  5040
agctgtgggt ggtctccgca gagcgcgcgg gccacgagag ggagccccat ctctcggccg  5100
aggggtacgg gggctccaga cacggtcctt tggtttcttc tgcctgtagc gagcggcccc  5160
gccccccacc gcgctgctag cctagccgat gctgatccat ccaccaccca caagggattg  5220
ttccacgact tgtggac                                                 5237
```

SEQ ID NO: 257 moltype = DNA length = 5427

-continued

FEATURE Location/Qualifiers
misc_feature 1..5427
note = synthesized sequence- TS9Cas-2 donor
source 1..5427
mol_type = other DNA
organism = synthetic construct

SEQUENCE: 257 agcaaggaac taaactgtta ttggacgcta aagtttagta ctttatcttt aacatctttc 60
agcatttcta tgtagatatt taagggctaa attttagcaa gtgtgctgat aaattttagc 120
ctaaatgttt ctgttgggct aaattttagc aagtgtactg ttaaatttta gcatattcct 180
tttagagtgg tatgggtgtg catagactaa atgtttccgt tgggccctaa tttaacgatg 240
tgtacgcagg cctgtttaga tgacttggta ccggcatatg gcctcgtact gtttcatttg 300
atgacgcgag cgtgcggccc atgcagcagc agcacgccgg gaaggcagcg gattttgaag 360
tactattgga cagcgcggcg cggggaccgg gtcgttggcg cgcggtggag tgggggtggg 420
tggtcctggc gtcctgccct gcgcgatggt cgatggatgc cccatgcgcg tgtaaccgcc 480
cagccgtcgc catccgacca ggtgggcaga cgtacgtacg gtggcacgcc cacggcccat 540
cggccatcgc gatcgcgttc gtatcgtgtc ctcaataacg aaagcgccaa cggaaggcgc 600
tgtcgtcgtc agttcaccgc gcgccggcgc cctgtgtcct cgtccctctc gacttctcga 660
ccagtaagaa ctctcgcgag ctgcggagct gctggcgatg gccggccggt gggatccgac 720
gtgcgtgcaa cctcgaattt aaatcttaag cctaggataa cttcgtatag catacattat 780
acgaagttat ggcgccgcta gcctgcagtg cagcgtgacc cggtcgtgcc cctctctaga 840
gataatgagc attgcatgtc taagttataa aaaattacca catatttttt ttgtcacact 900
tgtttgaagt gcagtttatc tatctttata catatattta aactttactc tacgaataat 960
ataatctata gtactacaat aatatcagtg ttttagagaa tcatataaat gaacagttag 1020
acatggtcta aaggacaatt gagtattttg acaacaggac tctacagttt tatcttttta 1080
gtgtgcatgt gttctccttt ttttttgcaa atagcttcac ctatataata cttcatccat 1140
tttattagta catccattta gggtttaggg ttaatggttt ttatagacta atttttttag 1200
tacatctatt ttattctatt ttagcctcta aattaagaaa actaaaactc tattttagtt 1260
tttttattta ataatttaga tataaaatag aataaaataa agtgactaaa aattaaacaa 1320
atacccttta agaaattaaa aaaactaagg aaacattttt cttgtttcga gtagataatg 1380
ccagcctgtt aaacgccgtc gacgagtcta acggacacca accagcgaac cagcagcgtc 1440
gcgtcgggcc aagcgaagca gacggcacgg catctctgtc gctgcctctg gacccctctc 1500
gagagttccg ctccaccgtt ggacttgctc cgctgtcggc atccagaaat tgcgtggcgg 1560
agcggcagac gtgagccggc acggcaggcg gcctcctcct cctctcacgg caccggcagc 1620
tacgggggat tcctttccca ccgctccttc gctttccctt cctcgcccgc cgtaataaat 1680
agacaccccc tccacaccct ctttccccaa cctcgtgttg ttcggagcgc acacacacac 1740
aaccagatct cccccaaatc cacccgtcgg cacctccgct tcaaggtacg ccgctcgtcc 1800
tccccccccc ccctctctac cttctctaga tcggcgttcc ggtccatgca tggttagggc 1860
ccggtagttc tacttctgtt catgtttgtg ttagatccgt gtttgtgtta gatccgtgct 1920
gctagcgttc gtacacggat gcgacctgta cgtcagacac gttctgattg ctaacttgcc 1980
agtgtttctc tttggggaat cctgggatgg ctctagccgt tccgcagacg ggatcgattt 2040
catgattttt tttgtttcgt tgcatagggt ttggtttgcc cttttccttt atttcaatat 2100
atgccgtgca cttgtttgtc gggtcatctt ttcatgcttt tttttgtctt ggttgtgatg 2160
atgtggtctg gttgggcggt cgttctagat cggagtagaa ttctgtttca aactacctgg 2220
tggatttatt aattttggat ctgtatgtgt gtgccataca tattcatagt tacgaattga 2280
agatgatgga tggaaatatc gatctaggat aggtatacat gttgatgcgg gttttactga 2340
tgcatataca gagatgcttt ttgttcgctt ggttgtgatg atgtggtgtg gttgggcggt 2400
cgttcattcg ttctagatcg gagtagaata ctgtttcaaa ctacctggtg tatttattaa 2460
ttttggaact gtatgtgtgt gtcatacatc ttcatagtta cgagtttaag atggatggaa 2520
atatcgatct aggataggta tacatgttga tgtgggtttt actgatgcat atacatgatg 2580
gcatatgcag catctattca tatgctctaa ccttgagtac ctatctatta taataaacaa 2640
gtatgtttta taattatttt gatcttgata tacttggatg atggcatatg cagcagctat 2700
atgtggattt ttttagccct gccttcatac gctatttatt tgcttggtac tgtttctttt 2760
gtcgatgctc accctgttgt ttggtgttac ttctgcaggt cgactctaga ggatcaattc 2820
gctagcgaag ttcctattcc gaagttccta ttctctagaa agtataggaa cttcagatcc 2880
accgggatcc ccgatcatgc aaaaactcat taactcagtg caaaactatg cctggggcag 2940
caaaacggcg ttgactgaac tttatggtat ggaaaatccg tccagccagc cgatggccga 3000
gctgtggatg ggcgcacatc cgaaaagcag ttcacgagtg cagaatgccg ccggagatat 3060
cgtttcactg cgtgatgtga ttgagagtga taaatcgact ctgctcggag aggccgttgc 3120
caaacgcttt ggcgaactgc ctttcctgtt caaagtatta tgcgcagcac agccactctc 3180
cattcaggtt catccaaaca aacacaattc tgaaatcggt tttgccaaag aaaatgccgc 3240
aggtatcccg atggatgccg ccgagcgtaa ctataaagat cctaaccaca agccggagct 3300
ggtttttgcg ctgacgcctt tccttgcgat gaacgcgttt cgtgaatttt ccgagattgt 3360
ctccctactc cagccggtcg caggtgcaca tccggcgatt gctcactttt tacaacagcc 3420
tgatgccgaa cgtttaagcg aactgttcgc cagcctgttg aatatgcagg gtgaagaaaa 3480
atcccgcgcg ctggcgattt taaaatcggc cctcgatagc cagcagggtg aaccgtggca 3540
aacgattcgt ttaatttctg aattttaccc ggaagacagc ggtctgttct ccccgctatt 3600
gctgaatgtg gtgaaattga accctggcga agcgatgttc ctgttcgctg aaacaccgca 3660
cgcttacctg caaggcgtgg cgctggaagt gatggcaaac tccgataacg tgctgcgtgc 3720
gggtctgacg cctaaataca ttgatattcc ggaactggtt gccaatgtga aattcgaagc 3780
caaaccggct aaccagttgt tgacccagcc ggtgaaacaa ggtgcagaac tggacttccc 3840
gattccagtg gatgatttg ccttctcgct gcatgacctt agtgataaag aaaccaccat 3900
tagccagcag agtgccgcca ttttgttctg cgtcgaaggc gatgcaacgt tgtggaaagg 3960
ttctcagcag ttacagctta aaccgggtga atcagcgttt attgccgcca acgaatcacc 4020
ggtgactgtc aaaggccacg gccgtttagc gcgtgtttac aacaagctgt aagagcttac 4080
tgaaaaaatt aacatctctt gctaagctgg gggtggaacc tagacttgtc catcttctgg 4140
attggccaac ttaattaatg tatgaaataa aaggatgcac acatagtgac atgctaatca 4200
ctataatgtg ggcatcaaag ttgtgtgtta tgtgtaatta ctagttatct gaataaaaga 4260
gaaagagatc atccatattt cttatcctaa atgaatgtca cgtgtcttta taattctttg 4320

-continued

```
atgaaccaga tgcatttcat taaccaaatc catatacata taaatattaa tcatatataa  4380
ttaatatcaa ttgggttagc aaaacaaatc tagtctaggt gtgttttgcg aatgcggccc  4440
tagcgtatac gaagttccta ttccgaagtt cctattctcc agaaagtata ggaacttctg  4500
tacacctgag ctgattccga tgacttcgta ggttcctagc tcaagccgct cgtgtccaag  4560
cgtcacttac gattagctaa tgattacggc atctaggacc gactagctaa ctaactagta  4620
ccgaggccgg ccccgcggga gctcggccgc aaacagcctg gtgacagacg aagccagcaa  4680
gcacgtacgt acgcacgtct ctgctggtct ggatgtgtat ggatatggac gtctcacgtc  4740
tggacgtcgt cgtcgccgtt gtattgtatc atgccaacca cttccgtacc gtaccccctc  4800
gcgtgccaac atgaccaccg ccggtacgtc tccatcgtcg gccgtcggcg tctcaggcag  4860
ctctcaatta agcggacgtg ttttggtaat ctggtggaac gccgcgcgca ctgagggttt  4920
gggggccccg gcggacgagc gagcgagaga cggtgcatgc atgccaaatg gcaacgaggg  4980
cccgcccgcc catccaataa ccaacccaga cgtagcgcaa ccaacgtacg agtcctgtgc  5040
tggcgcgtac gactaccacg ctagctgccg cgacatgcga actacggtcc accaggcacc  5100
agccatgaca atatatactg tatatatatt tttcttcttc tttttgtttc cgctctctca  5160
agttcctgct ctgctcctgc ctgtccgcgg tgccgatcgg cgagagagca tgcatggaca  5220
tggaccacgc gagatccagg aaccggcacg ggcccatgcg tggcaggcgg ccgtttcgtc  5280
aggttccccg aaatgcccca actgcgcggc tgcaggatgg ctcatggctg gctgcctagc  5340
tggcccgtga caccgatcga tcggtaacga cgacgcacgc acctgaagca caggaaggag  5400
cctccctctc gcatgcacgt tagtact                                      5427

SEQ ID NO: 258          moltype = DNA  length = 5426
FEATURE                 Location/Qualifiers
misc_feature            1..5426
                        note = synthesized sequence- TS9Cas-3 donor
source                  1..5426
                        mol_type = other DNA
                        organism = synthetic construct
SEQUENCE: 258
agcaaggaac taaactgtta ttggacgcaa agtttagtac tttatcttta acatctttca  60
gcatttctat gtagatattt aagggctaaa ttttagcaag tgtgctgata aattttagcc  120
taaatgtttc tgttgggcta aattttagca agtgtactgt taaattttag catattcctt  180
ttagagtggt atgggtgtgc atagactaaa tgtttccgtt gggccctaat ttaacgatgt  240
gtacgcaggc ctgtttagat gacttggtac cggcatatgg cctcgtactg tttcatttga  300
tgacgcgagc gtgcggccca tgcagcagca gcacgccggg aaggcagcgg attttgaagt  360
actattggac agcgcggcgc ggggaccggg tcgttggcgc gcggtggagt gggggtgggt  420
ggtcctggcg tcctgccctg cgcgatggtc gatggatgcc ccatgcgcgt gtaaccgccc  480
agccgtcgcc atccgaccag gtgggcagac gtacgtacgg tggcacgccc acggcccatc  540
ggccatcgcg atcgcgttcg tatcgtgtcc tcaataacga aagcgccaac ggaaggcgct  600
gtcgtcgtca gttcaccgcg cgccggcgcc ctgtgtcctc gtccctctcg acttctcgac  660
cagtaagaac tctcgcgagc tgcggagctg ctggcgatgg ccggccggtg ggatccgacg  720
atttaaatct taagcctagg ataacttcgt atagcataca ttatacgaag ttatggcgcc  780
gctagcctgc agtgcagcgt gacccggtcg tgcccctctc tagagataat gagcattgca  840
tgtctaagtt ataaaaaatt accacatatt ttttttgtca cacttgtttg aagtgcagtt  900
tatctatctt tatacatata tttaaacttt actctacgaa taatataatc tatagtacta  960
caataatatc agtgttttag agaatcatat aaatgaacag ttagacatgg tctaaaggac  1020
aattgagtat tttgacaaca ggactctaca gttttatctt tttagtgtgc atgtgttctc  1080
cttttttttt gcaaatagct tcacctatat aatacttcat ccattttatt agtacatcca  1140
tttagggttt agggttaatg gtttttatag actaattttt ttagtacatc tattttattc  1200
tattttagcc tctaaattaa gaaaactaaa actctatttt agttttttta tttaataatt  1260
tagatataaa atagaataaa ataaagtgac taaaaattaa acaaataccc tttaagaaat  1320
taaaaaaact aaggaaacat ttttcttgtt tcgagtagat aatgccagcc tgttaaacgc  1380
cgtcgacgag tctaacggac accaaccagc gaaccagcag cgtcgcgtcg ggccaagcga  1440
agcagacggc acggcatctc tgtcgctgcc tctggacccc tctcgagagt tccgctccac  1500
cgttggactt gctccgctgt cggcatccag aaattgcgtg gcggagcggc agacgtgagc  1560
cggcacggca ggcggcctcc tcctcctctc acggcaccgg cagctacggg ggattccttt  1620
cccaccgctc cttcgctttc ccttcctcgc ccgccgtaat aaatagacac cccctccaca  1680
ccctctttcc ccaacctcgt gttgttcgga gcgcacacac acacaaccag atctccccca  1740
aatccacccg tcggcacctc cgcttcaagg tacgccgctc gtcctccccc cccccccctct  1800
ctaccttctc tagatcggcg ttccggtcca tgcatggtta gggcccggta gttctacttc  1860
tgttcatgtt tgtgttagat ccgtgtttgt gttagatccg tgctgctagc gttcgtacac  1920
ggatgcgacc tgtacgtcag acacgttctg attgctaact tgccagtgtt tctctttggg  1980
gaatcctggg atggctctag ccgttccgca gacgggatcg atttcatgat tttttttgtt  2040
tcgttgcata gggttttggtt tgccctttttc ctttatttca atatatgccg tgcacttgtt  2100
tgtcgggtca tcttttcatg cttttttttg tcttggttgt gatgatgtgg tctggttggg  2160
cggtcgttct agatcggagt agaattctgt ttcaaactac ctggtggatt tattaatttt  2220
ggatctgtat gtgtgtgcca tacatattca tagttacgaa ttgaagatga tggatggaaa  2280
tatcgatcta ggataggtat acatgttgat gcgggtttta ctgatgcata tacagagatg  2340
ctttttgttc gcttggttgt gatgatgtgg tgtggttggg cggtcgttca ttcgttctag  2400
atcggagtag aatactgttt caaactacct ggtgtattta ttaattttgg aactgtatgt  2460
gtgtgtcata catcttcata gttacgagtt taagatggat ggaaatatcg atctaggata  2520
ggtatacatg ttgatgtggg ttttactgat gcatatacat gatggcatat gcagcatcta  2580
ttcatatgct ctaaccttga gtacctatct attataataa acaagtatgt tttataatta  2640
ttttgatctt gatatacttg gatgatggca tatgcagcag ctatatgtgg atttttttag  2700
ccctgccttc atacgctatt tatttgcttg gtactgtttc ttttgtcgat gctcaccctg  2760
ttgtttggtg ttacttctgc aggtcgactc tagaggatca attcgctagc gaagttccta  2820
ttccgaagtt cctattctct agaaagtata ggaacttcag atccaccggg atccccgatc  2880
atgcaaaaac tcattaactc agtgcaaaac tatgcctggg gcagcaaaac ggcgttgact  2940
gaactttatg gtatggaaaa tccgtccagc cagccgatgg ccgagctgtg gatgggcgca  3000
catccgaaaa gcagttcacg agtgcagaat gccgccggag atatcgtttc actgcgtgat  3060
```

-continued

```
gtgattgaga gtgataaatc gactctgctc ggagaggccg ttgccaaacg ctttggcgaa  3120
ctgcctttcc tgttcaaagt attatgcgca gcacagccac tctccattca ggttcatcca  3180
aacaaacaca attctgaaat cggttttgcc aaagaaaatg ccgcaggtat cccgatggat  3240
gccgccgagc gtaactataa agatcctaac cacaagccgg agctggtttt tgcgctgacg  3300
cctttccttg cgatgaacgc gtttcgtgaa ttttccgaga ttgtctccct actccagccg  3360
gtcgcaggtg cacatccggc gattgctcac tttttacaac agcctgatgc cgaacgttta  3420
agcgaactgt tcgccagcct gttgaatatg cagggtgaag aaaaatcccg cgcgctggcg  3480
attttaaaat cggccctcga tagccagcag ggtgaaccgt ggcaaacgat tcgtttaatt  3540
tctgaatttt acccggaaga cagcggtctg ttctccccgc tattgctgaa tgtggtgaaa  3600
ttgaaccctg gcgaagcgat gttcctgttc gctgaaacac cgcacgctta cctgcaaggc  3660
gtggcgctgg aagtgatggc aaactccgat aacgtgctgc gtgcgggtct gacgcctaaa  3720
tacattgata ttccggaact ggttgccaat gtgaaattcg aagccaaacc ggctaaccag  3780
ttgttgaccc agccggtgaa acaaggtgca gaactggact tcccgattcc agtggatgat  3840
tttgccttct cgctgcatga ccttagtgat aaagaaacca ccattagcca gcagagtgcc  3900
gccattttgt tctgcgtcga aggcgatgca acgttgtgga aaggttctca gcagttacag  3960
cttaaaccgg gtgaatcagc gtttattgcc gccaacgaat caccggtgac tgtcaaaggc  4020
cacggccgtt tagcgcgtgt ttacaacaag ctgtaagagc ttactgaaaa aattaacatc  4080
tcttgctaag ctgggggtgg aacctagact tgtccatctt ctggattggc caacttaatt  4140
aatgtatgaa ataaaaggat gcacacatag tgacatgcta atcactataa tgtgggcatc  4200
aaagttgtgt gttatgtgta attactagtt atctgaataa aagagaaaga gatcatccat  4260
atttcttatc ctaaatgaat gtcacgtgtc tttataattc tttgatgaac cagatgcatt  4320
tcattaacca aatccatata catataaata ttaatcatat ataattaata tcaattgggt  4380
tagcaaaaca aatctagtct aggtgtgttt tgcgaatgcg gccctagcgt atacgaagtt  4440
cctattccga agttcctatt ctccagaaag tataggaact tctgtacacc tgagctgatt  4500
ccgatgactt cgtaggttcc tagctcaagc cgctcgtgtc caagcgtcac ttacgattag  4560
ctaatgatta cggcatctag gaccgactag ctaactaact agtaccgagg ccggccccgc  4620
gggagctctg cgtgcaacct cgaggccgca aacagcctgg tgacagacga agccagcaag  4680
cacgtacgta cgcacgtctc tgctggtctg gatgtgtatg gatatggacg tctcacgtct  4740
ggacgtcgtc gtcgccgttg tattgtatca tgccaaccac ttccgtaccg taccccctcg  4800
cgtgccaaca tgaccaccgc cggtacgtct ccatcgtcgg ccgtcggcgt ctcaggcagc  4860
tctcaattaa gcggacgtgt tttggtaatc tggtggaacg ccgcgcgcac tgagggtttg  4920
ggggccccgg cggacgagcg agcgagagac ggtgcatgca tgccaaatgg caacgagggc  4980
ccgcccgccc atccaataac caacccagac gtagcgcaac caacgtacga gtcctgtgct  5040
ggcgcgtacg actaccacgc tagctgccgc gacatgcgaa ctacggtcca ccaggcacca  5100
gccatgacaa tatatactgt atatatattt ttcttcttct ttttgtttcc gctctctcaa  5160
gttcctgctc tgctcctgcc tgtccgcggt gccgatcggc gagagagcat gcatggacat  5220
ggaccacgcg agatccagga accggcacgg gcccatgcgt ggcaggcggc cgtttcgtca  5280
ggttccccga aatgccccaa ctgcgcggct gcaggatggc tcatggctgg ctgcctagct  5340
ggcccgtgac accgatcgat cggtaacgac gacgcacgca cctgaagcac aggaaggagc  5400
ctccctctcg catgcacgtt agtact                                        5426
```

```
SEQ ID NO: 259          moltype = DNA  length = 5152
FEATURE                 Location/Qualifiers
misc_feature            1..5152
                        note = synthesized sequence- TS10Cas-1 donor
source                  1..5152
                        mol_type = other DNA
                        organism = synthetic construct
SEQUENCE: 259
ggtaccaaat agtaaacggg aggggaggtc gctagtagta aacgctaggt agctaggata  60
atccgtctcg tgttggacgg aaggttttgg acgcatctgc gtgcacagcc cgctgataca  120
gatctgatcg actagctagc tagatgccga ggccccagag caaggcccgg atactcctgc  180
acagtccctg agatttcagc acagcaggtg ctgttgcatc aatatataaa tccctgcttt  240
attaatttaa tctctgtgca tgtatccata catcgtcagc ggctcagcgc tatcacactg  300
cagtgcacgc agctagttga gcgcctgggt cagtatatat atagctagta gggacaaagg  360
ggggcactgt acgttggttt ggtttggcac gcacgcgatc gagagtggtg gaatggactg  420
cagatcatcg atcgctgcac tgtacgcacg cgcaccggac tgcatttgca tgcccctgaa  480
ggaggaaagg ggaaggaaag aaaagaaata ggagaaagaa gaagaagcag agaaatacgt  540
cacagtccaa gaagagtgag ccgccctagc tagcttcaac cctgacgaac ccggcagcca  600
cacttccggc catgtatgca tgcatgcatg gcttagcttc agatgtccaa tcgaatccat  660
caagacctgg ccggttttcc atggccgcct cgccttcgct agtggtacca tttaaatctt  720
aagcctagga taacttcgta tagcatacat tatacgaagt tatggcgccg ctagcctgca  780
gtgcagcgtg acccggtcgt gcccctctct agagataatg agcattgcat gtctaagtta  840
taaaaaatta ccacatattt tttttgtcac acttgtttga agtgcagttt atctatcttt  900
atacatatat ttaaacttta ctctacgaat aatataatct atagtactac aataatatca  960
gtgttttaga gaatcatata aatgaacagt tagacatggt ctaaaggaca attgagtatt  1020
ttgacaacag gactctacag ttttatcttt ttagtgtgca tgtgttctcc tttttttttg  1080
caaatagctt cacctatata atacttcatc cattttatta gtacatccat ttagggttta  1140
gggttaatgg tttttataga ctaatttttt tagtacatct attttattct attttagcct  1200
ctaaattaag aaaactaaaa ctctatttta gttttttat ttaataattt agatataaaa  1260
tagaataaaa taaagtgact aaaaattaaa caaataccct ttaagaaatt aaaaaaacta  1320
aggaaacatt tttcttgttt cgagtagata atgccagcct gttaaacgcc gtcgacgagt  1380
ctaacggaca ccaaccagcg aaccagcagc gtcgcgtcgg gccaagcgaa gcagacggca  1440
cggcatctct gtcgctgcct ctggacccct ctcgagagtt ccgctccacc gttggacttg  1500
ctccgctgtc ggcatccaga aattgcgtgg cggagcggca gacgtgagcc ggcacggcag  1560
gcggcctcct cctcctctca cggcaccggc agctacgggg gattcctttc ccaccgctcc  1620
ttcgctttcc cttcctcgcc cgccgtaata aatagacacc ccctccacac cctctttccc  1680
caacctcgtg ttgttcggag cgcacacaca cacaaccaga tctcccccaa atccacccgt  1740
cggcacctcc gcttcaaggt acgccgctcg tcctcccccc ccccctctc taccttctct  1800
```

-continued

```
agatcggcgt tccggtccat gcatggttag ggcccggtag ttctacttct gttcatgttt  1860
gtgttagatc cgtgtttgtg ttagatccgt gctgctagcg ttcgtacacg gatgcgacct  1920
gtacgtcaga cacgttctga ttgctaactt gccagtgttt ctctttgggg aatcctggga  1980
tggctctagc cgttccgcag acgggatcga tttcatgatt ttttttgttt cgttgcatag  2040
ggtttggttt gccctttcc tttatttcaa tatatgccgt gcacttgttt gtcgggtcat  2100
cttttcatgc ttttttttgt cttggttgtg atgatgtggt ctggttgggc ggtcgttcta  2160
gatcggagta gaattctgtt tcaaactacc tggtggattt attaattttg gatctgtatg  2220
tgtgtgccat acatattcat agttacgaat tgaagatgat ggatggaaat atcgatctag  2280
gataggtata catgttgatg cgggttttac tgatgcatat acagagatgc tttttgttcg  2340
cttggttgtg atgatgtggt gtggttgggc ggtcgttcat tcgttctaga tcggagtaga  2400
atactgtttc aaactacctg gtgtatttat taattttgga actgtatgtg tgtgtcatac  2460
atcttcatag ttacgagttt aagatggatg gaaatatcga tctaggatag gtatacatgt  2520
tgatgtgggt tttactgatg catatacatg atggcatatg cagcatctat tcatatgctc  2580
taaccttgag tacctatcta ttataataaa caagtatgtt ttataattat tttgatcttg  2640
atatacttgg atgatggcat atgcagcagc tatatgtgga ttttttttagc cctgccttca  2700
tacgctattt atttgcttgg tactgtttct tttgtcgatg ctcaccctgt tgtttggtgt  2760
tacttctgca ggtcgactct agaggatcaa ttcgctagcg aagttcctat tccgaagttc  2820
ctattctcta gaaagtatag gaacttcaga tccaccggga tccccgatca tgcaaaaact  2880
cattaactca gtgcaaaact atgcctgggg cagcaaaacg gcgttgactg aactttatgg  2940
tatggaaaat ccgtccagcc agccgatggc cgagctgtgg atgggcgcac atccgaaaag  3000
cagttcacga gtgcagaatg ccgccggaga tatcgtttca ctgcgtgatg tgattgagag  3060
tgataaatcg actctgctcg gagaggccgt tgccaaacgc tttggcgaac tgcctttcct  3120
gttcaaagta ttatgcgcag cacagccact ctccattcag gttcatccaa acaaacacaa  3180
ttctgaaatc ggttttgcca aagaaaatgc cgcaggtatc ccgatggatg ccgccgagcg  3240
taactataaa gatcctaacc acaagccgga gctggttttt gcgctgacgc ctttccttgc  3300
gatgaacgcg tttcgtgaat tttccgagat tgtctcccta ctccagccgg tcgcaggtgc  3360
acatccggcg attgctcact ttttacaaca gcctgatgcc gaacgtttaa gcgaactgtt  3420
cgccagcctg ttgaatatgc agggtgaaga aaaatcccgc gcgctggcga ttttaaaatc  3480
ggccctcgat agccagcagg gtgaaccgtg gcaaacgatt cgtttaattt ctgaatttta  3540
cccggaagac agcggtctgt tctccccgct attgctgaat gtggtgaaat tgaaccctgg  3600
cgaagcgatg ttcctgttcg ctgaaacacc gcacgcttac ctgcaaggcg tggcgctgga  3660
agtgatggca aactccgata acgtgctgcg tgcgggtctg acgcctaaat acattgatat  3720
tccggaactg gttgccaatg tgaaattcga agccaaaccg gctaaccagt tgttgaccca  3780
gccggtgaaa caaggtgcag aactggactt cccgattcca gtggatgatt ttgccttctc  3840
gctgcatgac cttagtgata aagaaaccac cattagccag cagagtgccg ccattttgtt  3900
ctgcgtcgaa ggcgatgcaa cgttgtggaa aggttctcag cagttacagc ttaaaccggg  3960
tgaatcagcg tttattgccg ccaacgaatc accggtgact gtcaaaggcc acggccgttt  4020
agcgcgtgtt tacaacaagc tgtaagagct tactgaaaaa attaacatct cttgctaagc  4080
tgggggtgga acctagactt gtccatcttc tggattggcc aacttaatta atgtatgaaa  4140
taaaaggatg cacacatagt gacatgctaa tcactataat gtgggcatca aagttgtgtg  4200
ttatgtgtaa ttactagtta tctgaataaa agagaaagag atcatccata tttcttatcc  4260
taaatgaatg tcacgtgtct ttataattct ttgatgaacc agatgcattt cattaaccaa  4320
atccatatac atataaatat taatcatata taattaatat caattgggtt agcaaaacaa  4380
atctagtcta ggtgtgtttt gcgaatgcgg ccctagcgta tacgaagttc ctattccgaa  4440
gttcctattc tccagaaagt ataggaactt ctgtacacct gagctgattc cgatgacttc  4500
gtaggttcct agctcaagcc gctcgtgtcc aagcgtcact tacgattagc taatgattac  4560
ggcatctagg accgactagc taactaacta gtaccgaggc cggccccgcg ggagctcggc  4620
gcgcctaagg gccaagtact tgctgtccct gtatctccaa cacgagcctt gattcctgcc  4680
ggccggtgat ggcaatggcc gctagtagtc tccgctagct agggagcggc gatccgacgc  4740
gacgccacca tgtgtctaga aaagaagttt cttgctttgc atgcagactt attagcgcgg  4800
tcgacacctg tggggacccc gtgtcttgag acaatgagac tgcctgtccg cccaagacac  4860
tacttgtagc catgaagcca tcgactcctc tccttgctct ccagtaatcc agtggatgga  4920
tccatcatcg atagtttagt ttatcagtct tcttgaggcc ggtgtccccc atgcataatg  4980
atgacagaaa gcctgggcca ggtaaaagcc aaaaagtttg accctctagg tactggggcc  5040
agccctggcg tttgaacaaa aaaaaaatct gagcgtgtcg ccccggcctg ttttcgaact  5100
cctaaacgac gtcgcaactt tttttataca cacactaccg gtacatggct tt          5152
```

```
SEQ ID NO: 260          moltype = DNA  length = 5146
FEATURE                 Location/Qualifiers
misc_feature            1..5146
                        note = synthesized sequence- TS10Cas-3 donor
source                  1..5146
                        mol_type = other DNA
                        organism = synthetic construct
SEQUENCE: 260
aaatagtaaa cgggagggga ggtcgctagt agtaaacgct aggtagctag gataatccgt  60
ctcgtgttgg acggaaggtt ttggacgcat ctgcgtgcac agcccgctga tacagatctg  120
atcgactagc tagctagatg ccgaggcccc agagcaaggc ccggatactc ctgcacagtc  180
cctgagattt cagcacagca ggtgctgttg catcaatata taaatccctg ctttattaat  240
ttaatctctg tgcatgtatc catacatcgt cagcggctca gcgctatcac actgcagtgc  300
acgcagctag ttgagcgcct gggtcagtat atatatagct agtagggaca aaggggggca  360
ctgtacgttg gtttggtttg gcacgcacgc gatcgagagt ggtggaatgg actgcagatc  420
atcgatcgct gcactgtacg cacgcgcacc ggactgcatt tgcatgcccc tgaaggagga  480
aaggggaagg aaagaaaaga aataggagaa agaagaagaa gcagagaaat acgtcacagt  540
ccaagaagag tgagccgccc tagctagctt caaccctgac gaacccggca gccacacttc  600
cggccatgta tgcatgcatg catggcttag cttcagatgt ccaatcgaat ccatcaagac  660
ctggccggtt ttccatggcc gcctcgcctt cgctagttaa gggccaagta cttgctgtcc  720
ctgtggtacc atttaaatct taagcctagg ataacttcgt atagcataca ttatacgaag  780
ttatggcgcc gctagcctgc agtgcagcgt gacccggtcg tgcccctctc tagagataat  840
```

-continued

```
gagcattgca tgtctaagtt ataaaaaatt accacatatt ttttttgtca cacttgtttg  900
aagtgcagtt tatctatctt tatacatata tttaaacttt actctacgaa taatataatc  960
tatagtacta caataatatc agtgttttag agaatcatat aaatgaacag ttagacatgg  1020
tctaaaggac aattgagtat tttgacaaca ggactctaca gttttatctt tttagtgtgc  1080
atgtgttctc cttttttttt gcaaatagct tcacctatat aatacttcat ccattttatt  1140
agtacatcca tttagggttt agggttaatg gtttttatag actaattttt ttagtacatc  1200
tattttattc tattttagcc tctaaattaa gaaaactaaa actctatttt agttttttta  1260
tttaataatt tagatataaa atagaataaa ataaagtgac taaaaattaa acaaataccc  1320
tttaagaaat taaaaaaact aaggaaacat ttttcttgtt tcgagtagat aatgccagcc  1380
tgttaaacgc cgtcgacgag tctaacggac accaaccagc gaaccagcag cgtcgcgtcg  1440
ggccaagcga agcagacggc acggcatctc tgtcgctgcc tctggacccc tctcgagagt  1500
tccgctccac cgttggactt gctccgctgt cggcatccag aaattgcgtg gcggagcggc  1560
agacgtgagc cggcacggca ggcggcctcc tcctcctctc acggcaccgg cagctacggg  1620
ggattccttt cccaccgctc cttcgctttc ccttcctcgc ccgccgtaat aaatagacac  1680
cccctccaca ccctctttcc ccaacctcgt gttgttcgga gcgcacacac acacaaccag  1740
atctccccca aatccacccg tcggcacctc cgcttcaagg tacgccgctc gtcctccccc  1800
cccccccctct ctaccttctc tagatcggcg ttccggtcca tgcatggtta gggcccggta  1860
gttctacttc tgttcatgtt tgtgttagat ccgtgtttgt gttagatccg tgctgctagc  1920
gttcgtacac ggatgcgacc tgtacgtcag acacgttctg attgctaact tgccagtgtt  1980
tctctttggg gaatcctggg atggctctag ccgttccgca gacgggatcg atttcatgat  2040
ttttttttgtt tcgttgcata gggtttggtt tgcccttttc ctttatttca atatatgccg  2100
tgcacttgtt tgtcgggtca tcttttcatg cttttttttg tcttggttgt gatgatgtgg  2160
tctggttggg cggtcgttct agatcggagt agaattctgt ttcaaactac ctggtggatt  2220
tattaatttt ggatctgtat gtgtgtgcca tacatattca tagttacgaa ttgaagatga  2280
tggatggaaa tatcgatcta ggataggtat acatgttgat gcgggtttta ctgatgcata  2340
tacagagatg ctttttgttc gcttggttgt gatgatgtgg tgtggttggg cggtcgttca  2400
ttcgttctag atcggagtag aatactgttt caaactacct ggtgtattta ttaattttgg  2460
aactgtatgt gtgtgtcata catcttcata gttacgagtt taagatggat ggaaatatcg  2520
atctaggata ggtatacatg ttgatgtggg ttttactgat gcatatacat gatggcatat  2580
gcagcatcta ttcatatgct ctaaccttga gtacctatct attataataa acaagtatgt  2640
tttataatta ttttgatctt gatatacttg gatgatggca tatgcagcag ctatatgtgg  2700
atttttttag ccctgccttc atacgctatt tatttgcttg gtactgtttc ttttgtcgat  2760
gctcaccctg ttgtttggtg ttacttctgc aggtcgactc tagaggatca attcgctagc  2820
gaagttccta ttccgaagtt cctattctct agaaagtata ggaacttcag atccaccggg  2880
atccccgatc atgcaaaaac tcattaactc agtgcaaaac tatgcctggg gcagcaaaac  2940
ggcgttgact gaactttatg gtatggaaaa tccgtccagc cagccgatgg ccgagctgtg  3000
gatgggcgca catccgaaaa gcagttcacg agtgcagaat gccgccggag atatcgtttc  3060
actgcgtgat gtgattgaga gtgataaatc gactctgctc ggagaggccg ttgccaaacg  3120
ctttggcgaa ctgcctttcc tgttcaaagt attatgcgca gcacagccac tctccattca  3180
ggttcatcca aacaaacaca attctgaaat cggttttgcc aaagaaaatg ccgcaggtat  3240
cccgatggat gccgccgagc gtaactataa agatcctaac cacaagccgg agctggtttt  3300
tgcgctgacg cctttccttg cgatgaacgc gtttcgtgaa ttttccgaga ttgtctccct  3360
actccagccg gtcgcaggtg cacatccggc gattgctcac tttttacaac agcctgatgc  3420
cgaacgttta agcgaactgt tcgccagcct gttgaatatg cagggtgaag aaaaatcccg  3480
cgcgctggcg attttaaaat cggccctcga tagccagcag ggtgaaccgt ggcaaacgat  3540
tcgtttaatt tctgaatttt acccggaaga cagcggtctg ttctccccgc tattgctgaa  3600
tgtggtgaaa ttgaaccctg gcgaagcgat gttcctgttc gctgaaacac cgcacgctta  3660
cctgcaaggc gtggcgctgg aagtgatggc aaactccgat aacgtgctgc gtgcgggtct  3720
gacgcctaaa tacattgata ttccggaact ggttgccaat gtgaaattcg aagccaaacc  3780
ggctaaccag ttgttgaccc agccggtgaa acaaggtgca gaactggact tcccgattcc  3840
agtggatgat tttgccttct cgctgcatga ccttagtgat aaagaaacca ccattagcca  3900
gcagagtgcc gccattttgt tctgcgtcga aggcgatgca acgttgtgga aaggttctca  3960
gcagttacag cttaaaccgg gtgaatcagc gtttattgcc gccaacgaat caccggtgac  4020
tgtcaaaggc cacggccgtt tagcgcgtgt ttacaacaag ctgtaagagc ttactgaaaa  4080
aattaacatc tcttgctaag ctgggggtgg aacctagact tgtccatctt ctggattggc  4140
caacttaatt aatgtatgaa ataaaaggat gcacacatag tgacatgcta atcactataa  4200
tgtgggcatc aaagttgtgt gttatgtgta attactagtt atctgaataa aagagaaaga  4260
gatcatccat atttcttatc ctaaatgaat gtcacgtgtc tttataattc tttgatgaac  4320
cagatgcatt tcattaacca aatccatata catataaata ttaatcatat ataattaata  4380
tcaattgggt tagcaaaaca aatctagtct aggtgtgttt tgcgaatgcg gccctagcgt  4440
atacgaagtt cctattccga agttcctatt ctccagaaag tataggaact tctgtacacc  4500
tgagctgatt ccgatgactt cgtaggttcc tagctcaagc cgctcgtgtc caagcgtcac  4560
ttacgattag ctaatgatta cggcatctag gaccgactag ctaactaact agtaccgagg  4620
ccggccccgc gggagctcgg cgcgccatct ccaacacgag ccttgattcc tgccggccgg  4680
tgatggcaat ggccgctagt agtctccgct agctagggag cggcgatccg acgcgacgcc  4740
accatgtgtc tagaaaagaa gtttcttgct ttgcatgcag acttattagc gcggtcgaca  4800
cctgtgggga ccccgtgtct tgagacaatg agactgcctg tccgcccaag acactacttg  4860
tagccatgaa gccatcgact cctctccttg ctctccagta atccagtgga tggatccatc  4920
atcgatagtt tagtttatca gtcttcttga ggccggtgtc ccccatgcat aatgatgaca  4980
gaaagcctgg gccaggtaaa agccaaaaag tttgaccctc taggtactgg ggccagccct  5040
ggcgtttgaa caaaaaaaaa atctgagcgt gtcgccccgg cctgttttcg aactcctaaa  5100
cgacgtcgca actttttttta tacacacact accggtacat ggcttt              5146
```

```
SEQ ID NO: 261         moltype = DNA  length = 32
FEATURE                Location/Qualifiers
misc_feature           1..32
                       note = synthesized sequence- ubir primer from donor
source                 1..32
                       mol_type = other DNA
```

-continued

```
                         organism = synthetic construct
SEQUENCE: 261
ccatgtctaa ctgttcattt atatgattct ct                                32

SEQ ID NO: 262           moltype = DNA  length = 31
FEATURE                  Location/Qualifiers
misc_feature             1..31
                         note = synthesized sequence- psbf primer from dono
source                   1..31
                         mol_type = other DNA
                         organism = synthetic construct
SEQUENCE: 262
gctcgtgtcc aagcgtcact tacgattagc t                                 31

SEQ ID NO: 263           moltype = DNA  length = 27
FEATURE                  Location/Qualifiers
misc_feature             1..27
                         note = synthesized sequence- MHP14 14-1HR1f primer
source                   1..27
                         mol_type = other DNA
                         organism = synthetic construct
SEQUENCE: 263
ctcacatgag gctcttcttt gcttgct                                      27

SEQ ID NO: 264           moltype = DNA  length = 26
FEATURE                  Location/Qualifiers
misc_feature             1..26
                         note = synthesized sequence- MHP14 14-1HR2r primer
source                   1..26
                         mol_type = other DNA
                         organism = synthetic construct
SEQUENCE: 264
aggatcctat tccccaattt gtagat                                       26

SEQ ID NO: 265           moltype = DNA  length = 21
FEATURE                  Location/Qualifiers
misc_feature             1..21
                         note = synthesized sequence- CHR1-8 8HR1f primer
source                   1..21
                         mol_type = other DNA
                         organism = synthetic construct
SEQUENCE: 265
cagtccgtgg attgaagcca t                                            21

SEQ ID NO: 266           moltype = DNA  length = 22
FEATURE                  Location/Qualifiers
misc_feature             1..22
                         note = synthesized sequence- CHR1-8 8HR2r primer
source                   1..22
                         mol_type = other DNA
                         organism = synthetic construct
SEQUENCE: 266
ctctgtctcc gagacgtgct ta                                           22

SEQ ID NO: 267           moltype = DNA  length = 26
FEATURE                  Location/Qualifiers
misc_feature             1..26
                         note = synthesized sequence- CHR1-9 9HR1f primer
source                   1..26
                         mol_type = other DNA
                         organism = synthetic construct
SEQUENCE: 267
ggagcaaatg ttttaggtat gaaatg                                       26

SEQ ID NO: 268           moltype = DNA  length = 28
FEATURE                  Location/Qualifiers
misc_feature             1..28
                         note = synthesized sequence- CHR1-9 9HR2r primer
source                   1..28
                         mol_type = other DNA
                         organism = synthetic construct
SEQUENCE: 268
cggattctaa agatcatacg taaatgaa                                     28

SEQ ID NO: 269           moltype = DNA  length = 21
FEATURE                  Location/Qualifiers
misc_feature             1..21
                         note = synthesized sequence- CHR1-10 10HR1f primer
source                   1..21
```

```
                        mol_type = other DNA
                        organism = synthetic construct
SEQUENCE: 269
tggcttgtct atgcgcatct c                                              21

SEQ ID NO: 270          moltype = DNA  length = 20
FEATURE                 Location/Qualifiers
misc_feature            1..20
                        note = synthesized sequence- CHR1-10 10HR2r primer
source                  1..20
                        mol_type = other DNA
                        organism = synthetic construct
SEQUENCE: 270
ccagacccaa acagcaggtt                                                20

SEQ ID NO: 271          moltype = DNA  length = 18
FEATURE                 Location/Qualifiers
misc_feature            1..18
                        note = synthesized sequence- MHP14Cas-1 probe
source                  1..18
                        mol_type = other DNA
                        organism = synthetic construct
SEQUENCE: 271
cagattcacg tcagattt                                                  18

SEQ ID NO: 272          moltype = DNA  length = 27
FEATURE                 Location/Qualifiers
misc_feature            1..27
                        note = synthesized sequence- MHP14cas-1 forward primer
source                  1..27
                        mol_type = other DNA
                        organism = synthetic construct
SEQUENCE: 272
catagtggtg tatgaaagga agcactt                                        27

SEQ ID NO: 273          moltype = DNA  length = 30
FEATURE                 Location/Qualifiers
misc_feature            1..30
                        note = synthesized sequence- MHP14cas-1 reverse primer
source                  1..30
                        mol_type = other DNA
                        organism = synthetic construct
SEQUENCE: 273
cattttggat tgtaatatgt gtacctcata                                     30

SEQ ID NO: 274          moltype = DNA  length = 17
FEATURE                 Location/Qualifiers
misc_feature            1..17
                        note = synthesized sequence- MHP14Cas-3 probe
source                  1..17
                        mol_type = other DNA
                        organism = synthetic construct
SEQUENCE: 274
caccactatg tcgcttc                                                   17

SEQ ID NO: 275          moltype = DNA  length = 22
FEATURE                 Location/Qualifiers
misc_feature            1..22
                        note = synthesized sequence- MHP14Cas-3 forward primer
source                  1..22
                        mol_type = other DNA
                        organism = synthetic construct
SEQUENCE: 275
cggatgcacg aaaattgtag ga                                             22

SEQ ID NO: 276          moltype = DNA  length = 24
FEATURE                 Location/Qualifiers
misc_feature            1..24
                        note = synthesized sequence- MHP14Cas-3 reverse primer
source                  1..24
                        mol_type = other DNA
                        organism = synthetic construct
SEQUENCE: 276
ctgacgtgaa tctgtttgga attg                                           24

SEQ ID NO: 277          moltype = DNA  length = 18
FEATURE                 Location/Qualifiers
misc_feature            1..18
                        note = synthesized sequence- TS8Cas-1 probe
```

```
source                1..18
                      mol_type = other DNA
                      organism = synthetic construct
SEQUENCE: 277
tacgtaacgt gcagtact                                               18

SEQ ID NO: 278        moltype = DNA  length = 21
FEATURE               Location/Qualifiers
misc_feature          1..21
                      note = synthesized sequence- TS8Cas-1 forward primer
source                1..21
                      mol_type = other DNA
                      organism = synthetic construct
SEQUENCE: 278
acggacggac catacgttat g                                           21

SEQ ID NO: 279        moltype = DNA  length = 26
FEATURE               Location/Qualifiers
misc_feature          1..26
                      note = synthesized sequence- TS8Cas-1 reverse primer
source                1..26
                      mol_type = other DNA
                      organism = synthetic construct
SEQUENCE: 279
tcagctggtg gagtatatta gttcgt                                      26

SEQ ID NO: 280        moltype = DNA  length = 18
FEATURE               Location/Qualifiers
misc_feature          1..18
                      note = synthesized sequence- TS8Cas-2 probe
source                1..18
                      mol_type = other DNA
                      organism = synthetic construct
SEQUENCE: 280
ccagctgatc actgatga                                               18

SEQ ID NO: 281        moltype = DNA  length = 21
FEATURE               Location/Qualifiers
misc_feature          1..21
                      note = synthesized sequence- TS8Cas-2 forward primer
source                1..21
                      mol_type = other DNA
                      organism = synthetic construct
SEQUENCE: 281
acggacggac catacgttat g                                           21

SEQ ID NO: 282        moltype = DNA  length = 26
FEATURE               Location/Qualifiers
misc_feature          1..26
                      note = synthesized sequence- TS8Cas-2 reverse primer
source                1..26
                      mol_type = other DNA
                      organism = synthetic construct
SEQUENCE: 282
cgcacatgtt ataaattaca atgcat                                      26

SEQ ID NO: 283        moltype = DNA  length = 14
FEATURE               Location/Qualifiers
misc_feature          1..14
                      note = synthesized sequence- TS9Cas-2 probe
source                1..14
                      mol_type = other DNA
                      organism = synthetic construct
SEQUENCE: 283
ctgtttgcgg cctc                                                   14

SEQ ID NO: 284        moltype = DNA  length = 19
FEATURE               Location/Qualifiers
misc_feature          1..19
                      note = synthesized sequence- TS9Cas-2 forward primer
source                1..19
                      mol_type = other DNA
                      organism = synthetic construct
SEQUENCE: 284
ctgcggagct gctggcgat                                              19

SEQ ID NO: 285        moltype = DNA  length = 20
FEATURE               Location/Qualifiers
misc_feature          1..20
```

-continued

```
                        note = synthesized sequence- TS9Cas-2 reverse primer
source                  1..20
                        mol_type = other DNA
                        organism = synthetic construct
SEQUENCE: 285
cttgctggct tcgtctgtca                                              20

SEQ ID NO: 286          moltype = DNA  length = 15
FEATURE                 Location/Qualifiers
misc_feature            1..15
                        note = synthesized sequence- TS9Cas-3 probe
source                  1..15
                        mol_type = other DNA
                        organism = synthetic construct
SEQUENCE: 286
ccgacgtgcg tgcaa                                                   15

SEQ ID NO: 287          moltype = DNA  length = 19
FEATURE                 Location/Qualifiers
misc_feature            1..19
                        note = synthesized sequence- TS9Cas-3 forward primer
source                  1..19
                        mol_type = other DNA
                        organism = synthetic construct
SEQUENCE: 287
ctgcggagct gctggcgat                                               19

SEQ ID NO: 288          moltype = DNA  length = 20
FEATURE                 Location/Qualifiers
misc_feature            1..20
                        note = synthesized sequence- TS9Cas-3 reverse primer
source                  1..20
                        mol_type = other DNA
                        organism = synthetic construct
SEQUENCE: 288
cttgctggct tcgtctgtca                                              20

SEQ ID NO: 289          moltype = DNA  length = 17
FEATURE                 Location/Qualifiers
misc_feature            1..17
                        note = synthesized sequence- TS10Cas-1 probe
source                  1..17
                        mol_type = other DNA
                        organism = synthetic construct
SEQUENCE: 289
tcgccttcgc tagttaa                                                 17

SEQ ID NO: 290          moltype = DNA  length = 20
FEATURE                 Location/Qualifiers
misc_feature            1..20
                        note = synthesized sequence- TS10Cas-1 forward primer
source                  1..20
                        mol_type = other DNA
                        organism = synthetic construct
SEQUENCE: 290
aagacctggc cggttttcca                                              20

SEQ ID NO: 291          moltype = DNA  length = 18
FEATURE                 Location/Qualifiers
misc_feature            1..18
                        note = synthesized sequence- TS10Cas-1 reverse primer
source                  1..18
                        mol_type = other DNA
                        organism = synthetic construct
SEQUENCE: 291
tagcggccat tgccatca                                                18

SEQ ID NO: 292          moltype = DNA  length = 19
FEATURE                 Location/Qualifiers
misc_feature            1..19
                        note = synthesized sequence- TS10Cas-3 probe
source                  1..19
                        mol_type = other DNA
                        organism = synthetic construct
SEQUENCE: 292
ctgtatctcc aacacgagc                                               19

SEQ ID NO: 293          moltype = DNA  length = 20
FEATURE                 Location/Qualifiers
```

```
misc_feature          1..20
                      note = synthesized sequence- TS10Cas-3 forward primer
source                1..20
                      mol_type = other DNA
                      organism = synthetic construct
SEQUENCE: 293
aagacctggc cggttttcca                                            20

SEQ ID NO: 294        moltype = DNA  length = 18
FEATURE               Location/Qualifiers
misc_feature          1..18
                      note = synthesized sequence- TS10Cas-3 reverse primer
source                1..18
                      mol_type = other DNA
                      organism = synthetic construct
SEQUENCE: 294
tagcggccat tgccatca                                              18

SEQ ID NO: 295        moltype = DNA  length = 472
FEATURE               Location/Qualifiers
misc_feature          1..472
                      note = GM-U6-9.1 promoter
source                1..472
                      mol_type = genomic DNA
                      organism = Glycine max
SEQUENCE: 295
cccgggttaa gagaattgta agtgtgcttt tatatattta aaattaatat attttgaaat  60
gttaaaatat aaaagaaaat tcaatgtaaa ttaaaaataa ataaatgttt aataaagata  120
aattttaaaa cataaaagaa aatgtctaac aagaggatta agatcctgtg ctcttaaatt  180
tttaggtgtt gaaatcttag ccatacaaaa tatattttat taaaaccaag catgaaaaaa  240
gtcactaaag agctatataa ctcatgcagc tagaaatgaa gtgaagggaa tccagtttgt  300
tctcagtcga aagagtgtct atctttgttc ttttctgcaa ccgagttaag caaaatggga  360
atgcgaggta tcttcctttc gttaggggag caccagatgc atagttagtc ccacattgat  420
gaatataaca agagcttcac agaatatata gcccaggcca cagtaaaagc tt          472

SEQ ID NO: 296        moltype = DNA  length = 5958
FEATURE               Location/Qualifiers
misc_feature          1..5958
                      note = synthesized sequence- EF1A2-CAS9
source                1..5958
                      mol_type = other DNA
                      organism = synthetic construct
SEQUENCE: 296
gggtttactt attttgtggg tatctatact tttattagat ttttaatcag gctcctgatt  60
tctttttatt tcgattgaat tcctgaactt gtattattca gtagatcgaa taaattataa  120
aaagataaaa tcataaaata atattttatc ctatcaatca tattaaagca atgaatatgt  180
aaaattaatc ttatctttat tttaaaaaat catataggtt tagtattttt ttaaaaataa  240
agataggatt agttttacta ttcactgctt attactttta aaaaaatcat aaaggtttag  300
tattttttta aaataaatat aggaatagtt ttactattca ctgctttaat agaaaaatag  360
tttaaaattt aagatagttt taatcccagc atttgccacg tttgaacgtg agccgaaacg  420
atgtcgttac attatcttaa cctagctgaa acgatgtcgt cataatatcg ccaaatgcca  480
actggactac gtcgaaccca caaatcccac aaagcgcgtg aaatcaaatc gctcaaacca  540
caaaaaagaa caacgcgttt gttacacgct caatcccacg cgagtagagc acagtaacct  600
tcaaataagc gaatggggca taatcagaaa tccgaaataa acctaggggc attatcggaa  660
atgaaaagta gctcactcaa tataaaaatc taggaaccct agttttcgtt atcactctgt  720
gctccctcgc tctatttctc agtctctgtg tttgcggctg aggattccga acgagtgacc  780
ttcttcgttt ctcgcaaagg taacagcctc tgctcttgtc tcttcgattc gatctatgcc  840
tgtctcttat ttacgatgat gtttcttcgg ttatgttttt ttatttatgc tttatgctgt  900
tgatgttcgg ttgtttgttt cgctttgttt ttgtggttca gttttttagg attcttttgg  960
tttttgaatc gattaatcgg aagagatttt cgagttattt ggtgtgttgg aggtgaatct  1020
ttttttgag gtcatagatc tgttgtattt gtgttataaa catgcgactt tgtatgattt  1080
tttacgaggt tatgatgttc tggttgtttt attatgaatc tgttgagaca gaaccatgat  1140
ttttgttgat gttcgtttac actattaaag gtttgtttta acaggattaa aagtttttta  1200
agcatgttga aggagtcttg tagatatgta accgtcgata gttttttgt gggtttgttc  1260
acatgttatc aagcttaatc ttttactatg tatgcgacca tatctggatc cagcaaaggc  1320
gattttttaa ttccttgtga aacttttgta atatgaagtt gaaattttgt tattggtaaa  1380
ctataaatgt gtgaagttgg agtatacctt taccttctta tttggctttg tgatagttta  1440
atttatatgt attttgagtt ctgacttgta tttctttgaa ttgattctag tttaagtaat  1500
ccatggacaa aaagtactca atagggctcg acatagggac taactccgtt ggatgggccg  1560
tcatcaccga cgagtacaag gtgccctcca agaagttcaa ggtgttggga aacaccgaca  1620
ggcacagcat aaagaagaat ttgatcggtg ccctcctctt cgactccgga gagaccgctg  1680
aggctaccag gctcaagagg accgctagaa ggcgctacac cagaaggaag aacagaatct  1740
gctacctgca ggagatcttc tccaacgaga tggccaaggt ggacgactcc ttcttccacc  1800
gccttgagga atcattcctg gtggaggagg ataaaaagca cgagagacac ccaatcttcg  1860
ggaacatcgt cgacgaggtg gcctaccatg aaaagtaccc taccatctac cacctgagga  1920
agaagctggt cgactctacc gacaaggctg acttgcgctt gatttacctg gctctcgctc  1980
acatgataaa gttccgcgga cacttcctca ttgagggaga cctgaaccca gacaactccg  2040
acgtggacaa gctcttcatc cagctcgttc agacctacaa ccagcttttc gaggagaacc  2100
caatcaacgc cagtggagtt gacgccaagg ctatcctctc tgctcgtctg tcaaagtcca  2160
```

-continued

```
ggaggcttga gaacttgatt gcccagctgc ctggcgaaaa gaagaacgga ctgttcggaa  2220
acttgatcgc tctctccctg ggattgactc ccaacttcaa gtccaacttc gacctcgccg  2280
aggacgctaa gttgcagttg tctaaagaca cctacgacga tgacctcgac aacttgctgg  2340
cccagatagg cgaccaatac gccgatctct tcctcgccgc taagaacttg tccgacgcaa  2400
tcctgctgtc cgacatcctg agagtcaaca ctgagattac caaagctcct ctgtctgctt  2460
ccatgattaa gcgctacgac gagcaccacc aagatctgac cctgctcaag gccctggtga  2520
gacagcagct gcccgagaag tacaaggaga tctttttcga ccagtccaag aacggctacg  2580
ccggatacat tgacggaggc gcctcccagg aagagttcta caagttcatc aagcccatcc  2640
ttgagaagat ggacggtacc gaggagctgt tggtgaagtt gaacagagag gacctgttga  2700
ggaagcagag aaccttcgac aacggaagca tccctcacca aatccacctg ggagagctcc  2760
acgccatctt gaggaggcag gaggatttct atcccttcct gaaggacaac cgcgagaaga  2820
ttgagaagat cttgaccttc agaattcctt actacgtcgg gccactcgcc agaggaaact  2880
ctaggttcgc ctggatgacc cgcaaatctg aagagaccat tactccctgg aacttcgagg  2940
aagtcgtgga caagggcgct tccgctcagt ctttcatcga gaggatgacc aacttcgata  3000
aaaatctgcc caacgagaag gtgctgccca agcactccct gttgtacgag tatttcacag  3060
tgtacaacga gctcaccaag gtgaagtacg tcacagaggg aatgaggaag cctgccttct  3120
tgtccggaga gcagaagaag gccatcgtcg acctgctctt caagaccaac aggaaggtga  3180
ctgtcaagca gctgaaggag gactacttca agaagatcga gtgcttcgac tccgtcgaga  3240
tctctggtgt cgaggacagg ttcaacgcct cccttgggac ttaccacgat ctgctcaaga  3300
ttattaaaga caaggacttc ctggacaacg aggagaacga ggacatcctt gaggacatcg  3360
tgctcaccct gaccttgttc gaagacaggg aaatgatcga agagaggctc aagacctacg  3420
cccacctctt cgacgacaag gtgatgaaac agctgaagag acgcagatat accggctggg  3480
gaaggctctc ccgcaaattg atcaacggga tcagggacaa gcagtcaggg aagactatac  3540
tcgacttcct gaagtccgac ggattcgcca acaggaactt catgcagctc attcacgacg  3600
actccttgac cttcaaggag gacatccaga aggctcaggt gtctggacag ggtgactcct  3660
tgcatgagca cattgctaac ttggccggct ctcccgctat taagaagggc attttgcaga  3720
ccgtgaaggt cgttgacgag ctcgtgaagg tgatgggacg ccacaagcca gagaacatcg  3780
ttattgagat ggctcgcgag aaccaaacta cccagaaagg gcagaagaat tcccgcgaga  3840
ggatgaagcg cattgaggag ggcataaaag agcttggctc tcagatcctc aaggagcacc  3900
ccgtcgagaa cactcagctg cagaacgaga agctgtacct gtactacctc caaaacggaa  3960
gggacatgta cgtggaccag gagctggaca tcaacaggtt gtccgactac gacgtcgacc  4020
acatcgtgcc tcagtccttc ctgaaggatg actccatcga caataaagtg ctgacacgct  4080
ccgataaaaa tagaggcaag tccgacaacg tcccctccga ggaggtcgtg aagaagatga  4140
aaaactactg gagacagctc ttgaacgcca agctcatcac ccagcgtaag ttcgacaacc  4200
tgactaaggc tgagagagga ggattgtccg agctcgataa ggccggattc atcaagagac  4260
agctcgtcga aacccgccaa attaccaagc acgtggccca aattctggat tcccgcatga  4320
acaccaagta cgatgaaaat gacaagctga tccgcgaggt caaggtgatc accttgaagt  4380
ccaagctggt ctccgacttc cgcaaggact tccagttcta caaggtgagg gagatcaaca  4440
actaccacca cgcacacgac gcctacctca acgctgtcgt tggaaccgcc ctcatcaaaa  4500
aatatcctaa gctggagtct gagttcgtct acggcgacta caaggtgtac gacgtgagga  4560
agatgatcgc taagtctgag caggagatcg gcaaggccac cgccaagtac ttcttctact  4620
ccaacatcat gaacttcttc aagaccgaga tcactctcgc caacggtgag atcaggaagc  4680
gcccactgat cgagaccaac ggtgagactg gagagatcgt gtgggacaaa gggagggatt  4740
tcgctactgt gaggaaggtg ctctccatgc ctcaggtgaa catcgtcaag aagaccgaag  4800
ttcagaccgg aggattctcc aaggagtcca tcctccccaa gagaaactcc gacaagctga  4860
tcgctagaaa gaaagactgg gaccctaaga agtacggagg cttcgattct cctaccgtgg  4920
cctactctgt gctggtcgtg gccaaggtgg agaagggcaa gtccaagaag ctgaaatccg  4980
tcaaggagct cctcgggatt accatcatgg agaggagttc cttcgagaag aaccctatcg  5040
acttcctgga ggccaaggga tataaagagg tgaagaagga cctcatcatc aagctgccca  5100
agtactccct cttcgagttg gagaacggaa ggaagaggat gctggcttct gccggagagt  5160
tgcagaaggg aaatgagctc gcccttccct ccaagtacgt gaacttcctg tacctcgcct  5220
ctcactatga aaagttgaag ggctctcctg aggacaacga gcagaagcag ctcttcgtgg  5280
agcagcacaa gcactacctg gacgaaatta tcgagcagat ctctgagttc tccaagcgcg  5340
tgatattggc cgacgccaac ctcgacaagg tgctgtccgc ctacaacaag cacagggata  5400
agcccattcg cgagcaggct gaaaacatta tccacctgtt taccctcaca aacttgggag  5460
cccctgctgc cttcaagtac ttcgacacca ccattgacag gaagagatac acctccacca  5520
aggaggtgct cgacgcaaca ctcatccacc aatccatcac cggcctctat gaaacaagga  5580
ttgacttgtc ccagctggga ggcgactcta gagccgatcc caagaagaag agaaaggtgt  5640
aggttaacct agacttgtcc atcttctgga ttggccaact taattaatgt atgaaataaa  5700
aggatgcaca catagtgaca tgctaatcac tataatgtgg gcatcaaagt tgtgtgttat  5760
gtgtaattac tagttatctg aataaaagag aaagagatca tccatatttc ttatcctaaa  5820
tgaatgtcac gtgtctttat aattctttga tgaaccagat gcatttcatt aaccaaatcc  5880
atatacatat aaatattaat catatataat taatatcaat tgggttagca aaacaaatct  5940
agtctaggtg tgttttgc                                                5958
```

```
SEQ ID NO: 297          moltype = DNA  length = 573
FEATURE                 Location/Qualifiers
misc_feature            1..573
                        note = synthesized sequence- U6-9.1-DD20CR1
source                  1..573
                        mol_type = other DNA
                        organism = synthetic construct
SEQUENCE: 297
ccgggttaag agaattgtaa gtgtgctttt atatatttaa aattaatata ttttgaaatg  60
ttaaaatata aaagaaaatt caatgtaaat taaaaataaa taaatgttta ataaagataa  120
attttaaaac ataaaagaaa atgtctaaca agaggattaa gatcctgtgc tcttaaattt  180
ttaggtgttg aaatcttagc catacaaaat atattttatt aaaaccaagc atgaaaaaag  240
tcactaaaga gctatataac tcatgcagct agaaatgaag tgaagggaat ccagtttgtt  300
ctcagtcgaa agagtgtcta tctttgttct tttctgcaac cgagttaagc aaaatgggaa  360
```

-continued

```
tgcgaggtat cttcctttcg ttaggggagc accagatgca tagttagtcc cacattgatg  420
aatataacaa gagcttcaca gaatatatag cccaggccac agtaaaagct tggaactgac  480
acacgacatg agttttagag ctagaaatag caagttaaaa taaggctagt ccgttatcaa  540
cttgaaaaag tggcaccgag tcggtgcttt ttt                                573

SEQ ID NO: 298          moltype = DNA  length = 6611
FEATURE                 Location/Qualifiers
misc_feature            1..6611
                        note = synthesized sequence- U6-9.1-DD20CR1+EF1A2-CAS9
source                  1..6611
                        mol_type = other DNA
                        organism = synthetic construct
SEQUENCE: 298
cgcgccggta cccgggttaa gagaattgta agtgtgcttt tatatattta aaattaatat  60
attttgaaat gttaaaatat aaaagaaaat tcaatgtaaa ttaaaaataa ataaatgttt  120
aataaagata aattttaaaa cataaaagaa aatgtctaac aagaggatta agatcctgtg  180
ctcttaaatt tttaggtgtt gaaatcttag ccatacaaaa tatattttat taaaaccaag  240
catgaaaaaa gtcactaaag agctatataa ctcatgcagc tagaaatgaa gtgaagggaa  300
tccagtttgt tctcagtcga aagagtgtct atctttgttc ttttctgcaa ccgagttaag  360
caaaatggga atgcgaggta tcttcctttc gttaggggag caccagatgc atagttagtc  420
ccacattgat gaatataaca agagcttcac agaatatata gcccaggcca cagtaaaagc  480
ttggaactga cacacgacat gagttttaga gctagaaata gcaagttaaa ataaggctag  540
tccgttatca acttgaaaaa gtggcaccga gtcggtgctt tttttgcgg ccgcaattgg  600
atcgggttta cttattttgt gggtatctat actttttatta gatttttaat caggctcctg  660
atttcttttt atttcgattg aattcctgaa cttgtattat tcagtagatc gaataaatta  720
taaaaagata aaatcataaa ataatatttt atcctatcaa tcatattaaa gcaatgaata  780
tgtaaaatta atcttatctt tattttaaaa aatcatatag gtttagtatt tttttaaaaa  840
taaagatagg attagtttta ctattcactg cttattactt ttaaaaaaat cataaaggtt  900
tagtattttt ttaaaataaa tataggaata gttttactat tcactgcttt aatagaaaaa  960
tagtttaaaa tttaagatag ttttaatccc agcatttgcc acgtttgaac gtgagccgaa  1020
acgatgtcgt tacattatct taacctagct gaaacgatgt cgtcataata tcgccaaatg  1080
ccaactggac tacgtcgaac ccacaaatcc cacaaagcgc gtgaaatcaa atcgctcaaa  1140
ccacaaaaaa gaacaacgcg tttgttacac gctcaatccc acgcgagtag agcacagtaa  1200
ccttcaaata agcgaatggg gcataatcag aaatccgaaa taaacctagg ggcattatcg  1260
gaaatgaaaa gtagctcact caatataaaa atctaggaac cctagttttc gttatcactc  1320
tgtgctccct cgctctattt ctcagtctct gtgtttgcgg ctgaggattc cgaacgagtg  1380
accttcttcg tttctcgcaa aggtaacagc ctctgctctt gtctcttcga ttcgatctat  1440
gcctgtctct tatttacgat gatgtttctt cggttatgtt tttttattta tgctttatgc  1500
tgttgatgtt cggttgtttg tttcgctttg tttttgtggt tcagtttttt aggattcttt  1560
tggtttttga atcgattaat cggaagagat tttcgagtta tttggtgtgt tggaggtgaa  1620
tctttttttt gaggtcatag atctgttgta tttgtgttat aaacatgcga ctttgtatga  1680
ttttttacga ggttatgatg ttctggttgt tttattatga atctgttgag acagaaccat  1740
gatttttgtt gatgttcgtt tacactatta aaggtttgtt ttaacaggat taaaagtttt  1800
ttaagcatgt tgaaggagtc ttgtagatat gtaaccgtcg atagtttttt tgtgggtttg  1860
ttcacatgtt atcaagctta atcttttact atgtatgcga ccatatctgg atccagcaaa  1920
ggcgattttt taattccttg tgaaactttt gtaatatgaa gttgaaattt tgttattggt  1980
aaactataaa tgtgtgaagt tggagtatac ctttaccttc ttatttggct ttgtgatagt  2040
ttaatttata tgtattttga gttctgactt gtatttcttt gaattgattc tagtttaagt  2100
aatccatgga caaaaagtac tcaatagggc tcgacatagg gactaactcc gttggatggg  2160
ccgtcatcac cgacgagtac aaggtgccct ccaagaagtt caaggtgttg ggaaacaccg  2220
acaggcacag cataaagaag aatttgatcg gtgccctcct cttcgactcc ggagagaccg  2280
ctgaggctac caggctcaag aggaccgcta gaaggcgcta caccagaagg aagaacagaa  2340
tctgctacct gcaggagatc ttctccaacg agatggccaa ggtggacgac tccttcttcc  2400
accgccttga ggaatcattc ctggtggagg aggataaaaa gcacgagaga cacccaatct  2460
tcgggaacat cgtcgacgag gtggcctacc atgaaaagta ccctaccatc taccacctga  2520
ggaagaagct ggtcgactct accgacaagg ctgacttgcg cttgatttac ctggctctcg  2580
ctcacatgat aaagttccgc ggacacttcc tcattgaggg agacctgaac ccagacaact  2640
ccgacgtgga caagctcttc atccagctcg ttcagaccta caaccagctt ttcgaggaga  2700
acccaatcaa cgccagtgga gttgacgcca aggctatcct ctctgctcgt ctgtcaaagt  2760
ccaggaggct tgagaacttg attgcccagc tgcctggcga aaagaagaac ggactgttcg  2820
gaaacttgat cgctctctcc ctgggattga ctcccaactt caagtccaac ttcgacctcg  2880
ccgaggacgc taagttgcag ttgtctaaag acacctacga cgatgacctc gacaacttgc  2940
tggcccagat aggcgaccaa tacgccgatc tcttcctcgc cgctaagaac ttgtccgacg  3000
caatcctgct gtccgacatc ctgagagtca acactgagat taccaaagct cctctgtctg  3060
cttccatgat taagcgctac gacgagcacc accaagatct gaccctgctc aaggccctgg  3120
tgagacagca gctgcccgag aagtacaagg agatcttttt cgaccagtcc aagaacggct  3180
acgccggata cattgacgga ggcgcctccc aggaagagtt ctacaagttc atcaagccca  3240
tccttgagaa gatggacggt accgaggagc tgttggtgaa gttgaacaga gaggacctgt  3300
tgaggaagca gagaaccttc gacaacggaa gcatccctca ccaaatccac ctgggagagc  3360
tccacgccat cttgaggagg caggaggatt tctatccctt cctgaaggac aaccgcgaga  3420
agattgagaa gatcttgacc ttcagaattc cttactacgt cgggccactc gccagaggaa  3480
actctaggtt cgcctggatg acccgcaaat ctgaagagac cattactccc tggaacttcg  3540
aggaagtcgt ggacaagggc gcttccgctc agtctttcat cgagaggatg accaacttcg  3600
ataaaaatct gcccaacgag aaggtgctgc ccaagcactc cctgttgtac gagtatttca  3660
cagtgtacaa cgagctcacc aaggtgaagt acgtcacaga gggaatgagg aagcctgcct  3720
tcttgtccgg agagcagaag aaggccatcg tcgacctgct cttcaagacc aacaggaagg  3780
tgactgtcaa gcagctgaag gaggactact tcaagaagat cgagtgcttc gactccgtcg  3840
agatctctgg tgtcgaggac aggttcaacg cctcccttgg gacttaccac gatctgctca  3900
agattattaa agacaaggac ttcctggaca acgaggagaa cgaggacatc cttgaggaca  3960
```

```
tcgtgctcac cctgaccttg ttcgaagaca gggaaatgat cgaagagagg ctcaagacct  4020
acgcccacct cttcgacgac aaggtgatga aacagctgaa gagacgcaga tataccggct  4080
ggggaaggct ctcccgcaaa ttgatcaacg ggatcaggga caagcagtca gggaagacta  4140
tactcgactt cctgaagtcc gacggattcg ccaacaggaa cttcatgcag ctcattcacg  4200
acgactcctt gaccttcaag gaggacatcc agaaggctca ggtgtctgga cagggtgact  4260
ccttgcatga gcacattgct aacttggccg gctctcccgc tattaagaag ggcattttgc  4320
agaccgtgaa ggtcgttgac gagctcgtga aggtgatggg acgccacaag ccagagaaca  4380
tcgttattga gatggctcgc gagaaccaaa ctacccagaa agggcagaag aattcccgcg  4440
agaggatgaa gcgcattgag gagggcataa aagagcttgg ctctcagatc ctcaaggagc  4500
accccgtcga gaacactcag ctgcagaacg agaagctgta cctgtactac ctccaaaacg  4560
gaagggacat gtacgtggac caggagctgg acatcaacag gttgtccgac tacgacgtcg  4620
accacatcgt gcctcagtcc ttcctgaagg atgactccat cgacaataaa gtgctgacac  4680
gctccgataa aaatagaggc aagtccgaca acgtcccctc cgaggaggtc gtgaagaaga  4740
tgaaaaacta ctggagacag ctcttgaacg ccaagctcat cacccagcgt aagttcgaca  4800
acctgactaa ggctgagaga ggaggattgt ccgagctcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttggaacc gccctcatca  5100
aaaaatatcc taagctggag tctgagttcg tctacggcga ctacaaggtg tacgacgtga  5160
ggaagatgat cgctaagtct gagcaggaga tcggcaaggc caccgccaag tacttcttct  5220
actccaacat catgaacttc ttcaagaccg agatcactct cgccaacggt gagatcagga  5280
agcgcccact gatcgagacc aacggtgaga ctggagagat cgtgtgggac aaagggaggg  5340
atttcgctac tgtgaggaag gtgctctcca tgcctcaggt gaacatcgtc aagaagaccg  5400
aagttcagac cggaggattc tccaaggagt ccatcctccc caagagaaac tccgacaagc  5460
tgatcgctag aaagaaagac tgggacccta agaagtacgg aggcttcgat tctcctaccg  5520
tggcctactc tgtgctggtc gtggccaagg tggagaaggg caagtccaag aagctgaaat  5580
ccgtcaagga gctcctcggg attaccatca tggagaggag ttccttcgag aagaacccta  5640
tcgacttcct ggaggccaag ggatataaag aggtgaagaa ggacctcatc atcaagctgc  5700
ccaagtactc cctcttcgag ttggagaacg gaaggaagag gatgctggct tctgccggag  5760
agttgcagaa gggaaatgag ctcgcccttc cctccaagta cgtgaacttc ctgtacctcg  5820
cctctcacta tgaaaagttg aagggctctc ctgaggacaa cgagcagaag cagctcttcg  5880
tggagcagca caagcactac ctggacgaaa ttatcgagca gatctctgag ttctccaagc  5940
gcgtgatatt ggccgacgcc aacctcgaca aggtgctgtc cgcctacaac aagcacaggg  6000
ataagcccat tcgcgagcag gctgaaaaca ttatccacct gtttaccctc acaaacttgg  6060
gagcccctgc tgccttcaag tacttcgaca ccaccattga caggaagaga tacacctcca  6120
ccaaggaggt gctcgacgca acactcatcc accaatccat caccggcctc tatgaaacaa  6180
ggattgactt gtcccagctg ggaggcgact ctagagccga tcccaagaag aagagaaagg  6240
tgtaggttaa cctagacttg tccatcttct ggattggcca acttaattaa tgtatgaaat  6300
aaaaggatgc acacatagtg acatgctaat cactataatg tgggcatcaa agttgtgtgt  6360
tatgtgtaat tactagttat ctgaataaaa gagaaagaga tcatccatat ttcttatcct  6420
aaatgaatgt cacgtgtctt tataattctt tgatgaacca gatgcatttc attaaccaaa  6480
tccatataca tataaatatt aatcatatat aattaatatc aattgggtta gcaaaacaaa  6540
tctagtctag gtgtgttttg cgaattcgat atcaagctta tcgataccgt cgaggggggg  6600
cccggtaccg g                                                       6611
```

```
SEQ ID NO: 299          moltype = DNA  length = 5686
FEATURE                 Location/Qualifiers
misc_feature            1..5686
                        note = synthesized sequence- DD20HR1-SAMS:HPT-DD20HR2
source                  1..5686
                        mol_type = other DNA
                        organism = synthetic construct
SEQUENCE: 299
cgcgcctcta gttgaagaca cgttcatgtc ttcatcgtaa gaagacactc agtagtcttc  60
ggccagaatg gccatctgga ttcagcaggc ctagaaggcc atttaaatcc tgaggatctg  120
gtcttcctaa ggacccggga tatcgctatc aactttgtat agaaaagttg ggccgaattc  180
gagctcggta cggccagaat ccggtaagtg actagggtca cgtgacccta gtcacttaaa  240
ttcggccaga atggccatct ggattcagca ggcctagaag gcccggaccg attaaacttt  300
aattcggtcc gggttacctc gagcctagta ataattacac atctaagata tccccttctt  360
tttcaagtaa aataaatatca tatgatctca ttttagtgaa acaatactat ttccctgata  420
actctcttca acattaggga cttcatctaa tcatctactt tcaaggtata actagacgta  480
tttgttcttt taaaaaaaac actagatgta ctcgtcaact caaaattcat cgttcatgca  540
ttttaattaa actttaatta gctaatgagt agaaaaagat catacgagta aaatagaaga  600
atcttcctag attttggaag aatggattgg agtgtaagtg aattgatcca ttagtggaag  660
atgctcttta caatggccaa actgttctaa ttgttagagc acatttgaga tgaaacactt  720
cagtagtgga ggtaacctac aatcctagga tctgtatcct ctatcactaa tggagcaatg  780
ggtttgagat tgacttactc ctttccttgt ctctcgtagt gcatatgcgc actttcaaag  840
gctacacaaa agccgttaac ttttgttta tttaagttac gaaagatagt tgaattagag  900
taaatggtga tattgaatta ggattttaaa taattttaaa agaatttttt taataaaaaa  960
aatattgtgt tgttggatca aaattttttaa ataacatgaa taaggaaatg gattgcaatg  1020
aggttttaaa caattatttt aacatatagg attttagaaa gacttttata atattttgtt  1080
gaagtttaga ttttaatata tttatgtttt aaaattttaa aaaaaacttc atgaatttat  1140
aatatttgaa aaagacacgt gaatatttag aaaacattta aaattacaat aataaatcat  1200
aatgagatag ggtgtattca tgtgtagacg agacaccaag tatatggttc acaagtgaat  1260
catctttttt ttttacagca caagtagatc acttgtactt atcaaaattc ggaactgaca  1320
cacactagtg gtcacctaag tgactagggt cacgtgaccc tagtcactta ttcccaaaca  1380
ctagtaacgg ccgccagtgt gctggaattc gcccttccca agctttgctc tagatcaaac  1440
tcacatccaa acataacatg gatatcttcc ttaccaatca tactaattat tttgggttaa  1500
```

-continued

```
atattaatca ttatttttaa gatattaatt aagaaattaa aagatttttt aaaaaaatgt  1560
ataaaattat attattcatg atttttcata catttgattt tgataataaa tatatttttt  1620
ttaatttctt aaaaaatgtt gcaagacact tattagacat agtcttgttc tgtttacaaa  1680
agcattcatc atttaataca ttaaaaaata tttaatacta acagtagaat cttcttgtga  1740
gtggtgtggg agtaggcaac ctggcattga aacgagagaa agagagtcag aaccagaaga  1800
caaataaaaa gtatgcaaca aacaaatcaa aatcaaaggg caaaggctgg ggttggctca  1860
attggttgct acattcaatt ttcaactcag tcaacggttg agattcactc tgacttcccc  1920
aatctaagcc gcggatgcaa acggttgaat ctaacccaca atccaatctc gttacttagg  1980
ggcttttccg tcattaactc acccctgcca cccggtttcc ctataaattg gaactcaatg  2040
ctcccctcta aactcgtatc gcttcagagt tgagaccaag acacactcgt tcatatatct  2100
ctctgctctt ctcttctctt ctacctctca aggtactttt cttctccctc taccaaatcc  2160
tagattccgt ggttcaattt cggatcttgc acttctggtt tgctttgcct tgctttttcc  2220
tcaactgggt ccatctagga tccatgtgaa actctactct ttctttaata tctgcggaat  2280
acgcgtttga ctttcagatc tagtcgaaat catttcataa ttgcctttct ttcttttagc  2340
ttatgagaaa taaaatcact tttttttat ttcaaaataa accttgggcc ttgtgctgac  2400
tgagatgggg tttggtgatt acagaatttt agcgaatttt gtaattgtac ttgtttgtct  2460
gtagttttgt tttgttttct tgtttctcat acattcctta ggcttcaatt ttattcgagt  2520
ataggtcaca ataggaattc aaactttgag caggggaatt aatcccttcc ttcaaatcca  2580
gtttgtttgt atatatgttt aaaaaatgaa acttttgctt taaattctat tataactttt  2640
tttatggctg aaatttttgc atgtgtcttt gctctctgtt gtaaatttac tgtttaggta  2700
ctaactctag gcttgttgtg cagtttttga agtataacaa cagaagttcc tattccgaag  2760
ttcctattct ctagaaagta taggaacttc cactagtcca tgaaaaagcc tgaactcacc  2820
gcgacgtctg tcgagaagtt tctgatcgaa aagttcgaca gcgtctccga cctgatgcag  2880
ctctcggagg gcgaagaatc tcgtgctttc agcttcgatg taggagggcg tggatatgtc  2940
ctgcgggtaa atagctgcgc cgatggtttc tacaaagatc gttatgttta tcggcacttt  3000
gcatcggccg cgctcccgat tccggaagtg cttgacattg gggaattcag cgagagcctg  3060
acctattgca tctcccgccg tgcacagggt gtcacgttgc aagacctgcc tgaaaccgaa  3120
ctgcccgctg ttctgcagcc ggtcgcggag gccatggatg cgatcgctgc ggccgatctt  3180
agccagacga gcgggttcgg cccattcgga ccgcaaggaa tcggtcaata cactacatgg  3240
cgtgatttca tatgcgcgat tgctgatccc catgtgtatc actggcaaac tgtgatggac  3300
gacaccgtca gtgcgtccgt cgcgcaggct ctcgatgagc tgatgctttg ggccgaggac  3360
tgccccgaag tccggcacct cgtgcacgcg gatttcggct ccaacaatgt cctgacggac  3420
aatggccgca taacagcggt cattgactgg agcgaggcga tgttcgggga ttcccaatac  3480
gaggtcgcca acatcttctt ctggaggccg tggttggctt gtatggagca gcagacgcgc  3540
tacttcgagc ggaggcatcc ggagcttgca ggatcgccgc ggctccgggc gtatatgctc  3600
cgcattggtc ttgaccaact ctatcagagc ttggttgacg gcaatttcga tgatgcagct  3660
tgggcgcagg gtcgatgcga cgcaatcgtc cgatccggag ccgggactgt cgggcgtaca  3720
caaatcgccc gcagaagcgc ggccgtctgg accgatggct gtgtagaagt actcgccgat  3780
agtggaaacc gacgccccag cactcgtccg agggcaaagg aatagtgagg tacctaaaga  3840
aggagtgcgt cgaagcagat cgttcaaaca tttggcaata aagtttctta agattgaatc  3900
ctgttgccgg tcttgcgatg attatcatat aatttctgtt gaattacgtt aagcatgtaa  3960
taattaacat gtaatgcatg acgttattta tgagatgggt ttttatgatt agagtcccgc  4020
aattatacat ttaatacgcg atagaaaaca aaatatagcg cgcaaactag gataaattat  4080
cgcgcgcggt gtcatctatg ttactagatc gatgtcgacc cgggccctag gaggccggcc  4140
cagctgatga tcccggtgaa gttcctattc cgaagttcct attctccaga aagtatagga  4200
acttcactag agcttgcggc cgcgcatgct gacttaatca gctaacgcca ctcgacctgc  4260
aggcatgccc gcggatatcg atgggccccg gccgaagctt caagtttgta caaaaaagca  4320
ggctggcgcc ggaaccaatt cagtcgactg gatccggtac cgaattcgcg gccgcactcg  4380
agatatctag acccagcttt cttgtacaaa gtggccgtta acggatcggc cagaatccgg  4440
taagtgacta gggtcacgtg accctagtca cttaaattcg gccagaatgg ccatctggat  4500
tcagcaggcc tagaaggccc ggaccgatta aactttaatt cggtccgggt tacctctaga  4560
aagcttgtcg acctgcagac acgacatgat ggaacgtgac taaggtgggt ttttgacttt  4620
gcatgtcgaa gtgagagtga ttttattgag agaataatag aagacctaca aaacaaatga  4680
tcccgacgct aaagtaagta cgagagttaa gagaataaat gggaaaatat gcatacatga  4740
ttaggtgtgt gttcgtctca agaaagtacg aatgaatatg gtgtgtttgt agtacatgaa  4800
tgatgtgttt tgagggttca agggaaattg atatttatag agtgaaatgg aaccagaggt  4860
ctttgttgac aagggttgtt atgactcttg caaataatta atagcttata aataatagcc  4920
aataacttat tatagataga gttagagata atatatagct aaatttgaac aaggcataca  4980
aaacaaaaat gctaaatatg aataagacaa tcaaaattgt agtcgatgtt caactctttg  5040
tcgttgaaga acttgtttgc agtggtatag taaatgggtg tgagtgcagt gtctcaccca  5100
tctcacacca cacaaccaac ttcatatcta aagatattgt cgctgaatac aaaattgagt  5160
tatggaatat acaattcata atatagatac gaaaaatcat ttcttacaaa acattcaatc  5220
aaaaattatt caaacataat tctagattaa gtaatccgaa gtacaagtta gtatcctaga  5280
tccgttaatt taaaattatg tttgcataat tttggatttg gtgttctata agggcacaat  5340
tttgttcatt cttacaagtt tgtcaattct aaaatatatg caaatttgaa gaaaaaaaat  5400
ttacgaatgt gtctcaaaca ataacttaat gggaggagaa tgagggatga agaagctcaa  5460
aattaccaac gccttctacc tcaagaagct acttcacaca aaatatgact ggcggaagga  5520
taggggacaa ccgataacga gaaggagata cataaggtaa tgtacgttgt tgtgtgaggg  5580
atccggtcac ctaagtgact agggtcacgt gaccctagtc acttattccc gggcaacttt  5640
attatacaaa gttgatagat ctcgaattca ttccgattaa tcgtgg              5686
```

```
SEQ ID NO: 300          moltype = DNA  length = 6611
FEATURE                 Location/Qualifiers
misc_feature            1..6611
                        note = synthesized sequence- U6-9.1-DD20CR2+EF1A2-CAS9
source                  1..6611
                        mol_type = other DNA
                        organism = synthetic construct
SEQUENCE: 300
```

-continued cgcgccggta cccgggttaa gagaattgta agtgtgcttt tatatattta aaattaatat 60
attttgaaat gttaaaatat aaaagaaaat tcaatgtaaa ttaaaaataa ataaatgttt 120
aataaagata aattttaaaa cataaaagaa aatgtctaac aagaggatta agatcctgtg 180
ctcttaaatt tttaggtgtt gaaatcttag ccatacaaaa tatattttat taaaaccaag 240
catgaaaaaa gtcactaaag agctatataa ctcatgcagc tagaaatgaa gtgaagggaa 300
tccagtttgt tctcagtcga aagagtgtct atctttgttc ttttctgcaa ccgagttaag 360
caaaatggga atgcgaggta tcttcctttc gttaggggag caccagatgc atagttagtc 420
ccacattgat gaatataaca agagcttcac agaatatata gcccaggcca cagtaaaagc 480
ttgacatgat ggaacgtgac tagttttaga gctagaaata gcaagttaaa ataaggctag 540
tccgttatca acttgaaaaa gtggcaccga gtcggtgctt tttttgcgg ccgcaattgg 600
atcgggttta cttattttgt gggtatctat acttttatta gatttttaat caggctcctg 660
atttcttttt atttcgattg aattcctgaa cttgtattat tcagtagatc gaataaatta 720
taaaaagata aaatcataaa ataatatttt atcctatcaa tcatattaaa gcaatgaata 780
tgtaaaatta atcttatctt tattttaaaa aatcatatag gtttagtatt tttttaaaaa 840
taaagatagg attagtttta ctattcactg cttattactt ttaaaaaaat cataaaggtt 900
tagtattttt ttaaaataaa tataggaata gttttactat tcactgcttt aatagaaaaa 960
tagtttaaaa tttaagatag ttttaatccc agcatttgcc acgtttgaac gtgagccgaa 1020
acgatgtcgt tacattatct taacctagct gaaacgatgt cgtcataata tcgccaaatg 1080
ccaactggac tacgtcgaac ccacaaatcc cacaaagcgc gtgaaatcaa atcgctcaaa 1140
ccacaaaaaa gaacaacgcg tttgttacac gctcaatccc acgcgagtag agcacagtaa 1200
ccttcaaata agcgaatggg gcataatcag aaatccgaaa taaacctagg ggcattatcg 1260
gaaatgaaaa gtagctcact caatataaaa atctaggaac cctagttttc gttatcactc 1320
tgtgctccct cgctctattt ctcagtctct gtgtttgcgg ctgaggattc cgaacgagtg 1380
accttcttcg tttctcgcaa aggtaacagc ctctgctctt gtctcttcga ttcgatctat 1440
gcctgtctct tatttacgat gatgtttctt cggttatgtt tttttattta tgctttatgc 1500
tgttgatgtt cggttgtttg tttcgctttg tttttgtggt tcagttttt aggattcttt 1560
tggtttttga atcgattaat cggaagagat tttcgagtta tttggtgtgt tggaggtgaa 1620
tctttttttt gaggtcatag atctgttgta tttgtgttat aaacatgcga ctttgtatga 1680
ttttttacga ggttatgatg ttctggttgt tttattatga atctgttgag acagaaccat 1740
gatttttgtt gatgttcgtt tacactatta aaggtttgtt ttaacaggat taaaagtttt 1800
ttaagcatgt tgaaggagtc ttgtagatat gtaaccgtcg atagtttttt tgtgggtttg 1860
ttcacatgtt atcaagctta atcttttact atgtatgcga ccatatctgg atccagcaaa 1920
ggcgattttt taattccttg tgaaactttt gtaatatgaa gttgaaattt tgttattggt 1980
aaactataaa tgtgtgaagt tggagtatac ctttaccttc ttatttggct ttgtgatagt 2040
ttaatttata tgtattttga gttctgactt gtatttcttt gaattgattc tagtttaagt 2100
aatccatgga caaaaagtac tcaatagggc tcgacatagg gactaactcc gttggatggg 2160
ccgtcatcac cgacgagtac aaggtgccct ccaagaagtt caaggtgttg ggaaacaccg 2220
acaggcacag cataaagaag aatttgatcg gtgccctcct cttcgactcc ggagagaccg 2280
ctgaggctac caggctcaag aggaccgcta gaaggcgcta caccagaagg aagaacagaa 2340
tctgctacct gcaggagatc ttctccaacg agatggccaa ggtggacgac tccttcttcc 2400
accgccttga ggaatcattc ctggtggagg aggataaaaa gcacgagaga cacccaatct 2460
tcgggaacat cgtcgacgag gtggcctacc atgaaaagta ccctaccatc taccacctga 2520
ggaagaagct ggtcgactct accgacaagg ctgacttgcg cttgatttac ctggctctcg 2580
ctcacatgat aaagttccgc ggacacttcc tcattgaggg agacctgaac ccagacaact 2640
ccgacgtgga caagctcttc atccagctcg ttcagaccta caaccagctt ttcgaggaga 2700
acccaatcaa cgccagtgga gttgacgcca aggctatcct ctctgctcgt ctgtcaaagt 2760
ccaggaggct tgagaacttg attgcccagc tgcctggcga aaagaagaac ggactgttcg 2820
gaaacttgat cgctctctcc ctgggattga ctcccaactt caagtccaac ttcgacctcg 2880
ccgaggacgc taagttgcag ttgtctaaag acacctacga cgatgacctc gacaacttgc 2940
tggcccagat aggcgaccaa tacgccgatc tcttcctcgc cgctaagaac ttgtccgacg 3000
caatcctgct gtccgacatc ctgagagtca acactgagat taccaaagct cctctgtctg 3060
cttccatgat taagcgctac gacgagcacc accaagatct gaccctgctc aaggccctgg 3120
tgagacagca gctgcccgag aagtacaagg agatcttttt cgaccagtcc aagaacggct 3180
acgccggata cattgacgga ggcgcctccc aggaagagtt ctacaagttc atcaagccca 3240
tccttgagaa gatggacggt accgaggagc tgttggtgaa gttgaacaga gaggacctgt 3300
tgaggaagca gagaaccttc gacaacggaa gcatccctca ccaaatccac ctgggagagc 3360
tccacgccat cttgaggagg caggaggatt tctatccctt cctgaaggac aaccgcgaga 3420
agattgagaa gatcttgacc ttcagaattc cttactacgt cgggccactc gccagaggaa 3480
actctaggtt cgcctggatg acccgcaaat ctgaagagac cattactccc tggaacttcg 3540
aggaagtcgt ggacaagggc gcttccgctc agtctttcat cgagaggatg accaacttcg 3600
ataaaaatct gcccaacgag aaggtgctgc ccaagcactc cctgttgtac gagtatttca 3660
cagtgtacaa cgagctcacc aaggtgaagt acgtcacaga gggaatgagg aagcctgcct 3720
tcttgtccgg agagcagaag aaggccatcg tcgacctgct cttcaagacc aacaggaagg 3780
tgactgtcaa gcagctgaag gaggactact tcaagaagat cgagtgcttc gactccgtcg 3840
agatctctgg tgtcgaggac aggttcaacg cctcccttgg gacttaccac gatctgctca 3900
agattattaa agacaaggac ttcctggaca acgaggagaa cgaggacatc cttgaggaca 3960
tcgtgctcac cctgaccttg ttcgaagaca gggaaatgat cgaagagagg ctcaagacct 4020
acgcccacct cttcgacgac aaggtgatga aacagctgaa gagacgcaga tataccggct 4080
ggggaaggct ctcccgcaaa ttgatcaacg ggatcaggga caagcagtca gggaagacta 4140
tactcgactt cctgaagtcc gacggattcg ccaacaggaa cttcatgcag ctcattcacg 4200
acgactcctt gaccttcaag gaggacatcc agaaggctca ggtgtctgga cagggtgact 4260
ccttgcatga gcacattgct aacttggccg gctctcccgc tattaagaag ggcattttgc 4320
agaccgtgaa ggtcgttgac gagctcgtga aggtgatggg acgccacaag ccagagaaca 4380
tcgttattga gatggctcgc gagaaccaaa ctacccagaa agggcagaag aattcccgcg 4440
agaggatgaa gcgcattgag gagggcataa aagagcttgg ctctcagatc ctcaaggagc 4500
accccgtcga gaacactcag ctgcagaacg agaagctgta cctgtactac ctccaaaacg 4560
gaagggacat gtacgtggac caggagctgg acatcaacag gttgtccgac tacgacgtcg 4620
accacatcgt gcctcagtcc ttcctgaagg atgactccat cgacaataaa gtgctgacac 4680
gctccgataa aaatagaggc aagtccgaca acgtcccctc cgaggaggtc gtgaagaaga 4740

```
tgaaaaacta ctggagacag ctcttgaacg ccaagctcat cacccagcgt aagttcgaca  4800
acctgactaa ggctgagaga ggaggattgt ccgagctcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttggaacc gccctcatca  5100
aaaaatatcc taagctggag tctgagttcg tctacggcga ctacaaggtg tacgacgtga  5160
ggaagatgat cgctaagtct gagcaggaga tcggcaaggc caccgccaag tacttcttct  5220
actccaacat catgaacttc ttcaagaccg agatcactct cgccaacggt gagatcagga  5280
agcgcccact gatcgagacc aacggtgaga ctggagagat cgtgtgggac aaagggaggg  5340
atttcgctac tgtgaggaag gtgctctcca tgcctcaggt gaacatcgtc aagaagaccg  5400
aagttcagac cggaggattc tccaaggagt ccatcctccc caagagaaac tccgacaagc  5460
tgatcgctag aaagaaagac tgggacccta agaagtacgg aggcttcgat tctcctaccg  5520
tggcctactc tgtgctggtc gtggccaagg tggagaaggg caagtccaag aagctgaaat  5580
ccgtcaagga gctcctcggg attaccatca tggagaggag ttccttcgag aagaacccta  5640
tcgacttcct ggaggccaag ggatataaag aggtgaagaa ggacctcatc atcaagctgc  5700
ccaagtactc cctcttcgag ttggagaacg gaaggaagag gatgctggct tctgccggag  5760
agttgcagaa gggaaatgag ctcgcccttc cctccaagta cgtgaacttc ctgtacctcg  5820
cctctcacta tgaaaagttg aagggctctc ctgaggacaa cgagcagaag cagctcttcg  5880
tggagcagca caagcactac ctggacgaaa ttatcgagca gatctctgag ttctccaagc  5940
gcgtgatatt ggccgacgcc aacctcgaca aggtgctgtc cgcctacaac aagcacaggg  6000
ataagcccat tcgcgagcag gctgaaaaca ttatccacct gtttaccctc acaaacttgg  6060
gagcccctgc tgccttcaag tacttcgaca ccaccattga caggaagaga tacacctcca  6120
ccaaggaggt gctcgacgca acactcatcc accaatccat caccggcctc tatgaaacaa  6180
ggattgactt gtcccagctg ggaggcgact ctagagccga tcccaagaag aagagaaagg  6240
tgtaggttaa cctagacttg tccatcttct ggattggcca acttaattaa tgtatgaaat  6300
aaaaggatgc acacatagtg acatgctaat cactataatg tgggcatcaa agttgtgtgt  6360
tatgtgtaat tactagttat ctgaataaaa gagaaagaga tcatccatat ttcttatcct  6420
aaatgaatgt cacgtgtctt tataattctt tgatgaacca gatgcatttc attaaccaaa  6480
tccatataca tataaatatt aatcatatat aattaatatc aattgggtta gcaaaacaaa  6540
tctagtctag gtgtgttttg cgaattcgat atcaagctta tcgataccgt cgaggggggg  6600
cccggtaccg g                                                        6611
```

```
SEQ ID NO: 301         moltype = DNA  length = 6611
FEATURE                Location/Qualifiers
misc_feature           1..6611
                       note = synthesized sequence- U6-9.1:DD43CR1+EF1A2:CAS9
source                 1..6611
                       mol_type = other DNA
                       organism = synthetic construct
SEQUENCE: 301
cgcgccggta cccgggttaa gagaattgta agtgtgcttt tatatattta aaattaatat  60
attttgaaat gttaaaatat aaaagaaaat tcaatgtaaa ttaaaaaataa ataaatgttt  120
aataaaagata aattttaaaa cataaaagaa aatgtctaac aagaggatta agatcctgtg  180
ctcttaaatt tttaggtgtt gaaatcttag ccatacaaaa tatattttat taaaaccaag  240
catgaaaaaa gtcactaaag agctatataa ctcatgcagc tagaaatgaa gtgaagggaa  300
tccagtttgt tctcagtcga aagagtgtct atctttgttc ttttctgcaa ccgagttaag  360
caaaatggga atgcgaggta tcttcctttc gttaggggag caccagatgc atagttagtc  420
ccacattgat gaatataaca agagcttcac agaatatata gcccaggcca cagtaaaagc  480
ttgtcccttg tacttgtacg tagttttaga gctagaaata gcaagttaaa ataaggctag  540
tccgttatca acttgaaaaa gtggcaccga gtcggtgctt ttttttgcgg ccgcaattgg  600
atcgggttta cttattttgt gggtatctat acttttatta gatttttaat caggctcctg  660
atttcttttt atttcgattg aattcctgaa cttgtattat tcagtagatc gaataaatta  720
taaaaagata aaatcataaa ataatatttt atcctatcaa tcatattaaa gcaatgaata  780
tgtaaaatta atcttatctt tattttaaaa aatcatatag gtttagtatt tttttaaaaa  840
taaagatagg attagtttta ctattcactg cttattactt ttaaaaaaat cataaaggtt  900
tagtattttt ttaaaataaa tataggaata gttttactat tcactgcttt aatagaaaaa  960
tagtttaaaa tttaagatag ttttaatccc agcatttgcc acgtttgaac gtgagccgaa  1020
acgatgtcgt tacattatct taacctagct gaaacgatgt cgtcataata tcgccaaatg  1080
ccaactggac tacgtcgaac ccacaaatcc cacaaagcgc gtgaaatcaa atcgctcaaa  1140
ccacaaaaaa gaacaacgcg tttgttacac gctcaatccc acgcgagtag agcacagtaa  1200
ccttcaaata agcgaatggg gcataatcag aaatccgaaa taaacctagg ggcattatcg  1260
gaaatgaaaa gtagctcact caatataaaa atctaggaac cctagttttc gttatcactc  1320
tgtgctccct cgctctattt ctcagtctct gtgtttgcgg ctgaggattc cgaacgagtg  1380
accttcttcg tttctcgcaa aggtaacagc ctctgctctt gtctcttcga ttcgatctat  1440
gcctgtctct tatttacgat gatgtttctt cggttatgtt tttttattta tgctttatgc  1500
tgttgatgtt cggttgtttg tttcgctttg tttttgtggt tcagtttttt aggattcttt  1560
tggtttttga atcgattaat cggaagagat tttcgagtta tttggtgtgt tggaggtgaa  1620
tcttttttttt gaggtcatag atctgttgta tttgtgttat aaacatgcga ctttgtatga  1680
tttttttacga ggttatgatg ttctggttgt tttattatga atctgttgag acagaaccat  1740
gatttttgtt gatgttcgtt tacactatta aaggtttgtt ttaacaggat taaaagtttt  1800
ttaagcatgt tgaaggagtc ttgtagatat gtaaccgtcg atagtttttt tgtgggtttg  1860
ttcacatgtt atcaagctta atcttttact atgtatgcga ccatatctgg atccagcaaa  1920
ggcgattttt taattccttg tgaaactttt gtaatatgaa gttgaaattt tgttattggt  1980
aaactataaa tgtgtgaagt tggagtatac ctttaccttc ttatttggct ttgtgatagt  2040
ttaatttata tgtattttga gttctgactt gtatttcttt gaattgattc tagtttaagt  2100
aatccatgga caaaaagtac tcaatagggc tcgacatagg gactaactcc gttggatggg  2160
ccgtcatcac cgacgagtac aaggtgccct ccaagaagtt caaggtgttg ggaaacaccg  2220
acaggcacag cataaagaag aatttgatcg gtgccctcct cttcgactcc ggagagaccg  2280
```

-continued

```
ctgaggctac caggctcaag aggaccgcta gaaggcgcta caccagaagg aagaacagaa  2340
tctgctacct gcaggagatc ttctccaacg agatggccaa ggtggacgac tccttcttcc  2400
accgccttga ggaatcattc ctggtggagg aggataaaaa gcacgagaga cacccaatct  2460
tcgggaacat cgtcgacgag gtggcctacc atgaaaagta ccctaccatc taccacctga  2520
ggaagaagct ggtcgactct accgacaagg ctgacttgcg cttgatttac ctggctctcg  2580
ctcacatgat aaagttccgc ggacacttcc tcattgaggg agacctgaac ccagacaact  2640
ccgacgtgga caagctcttc atccagctcg ttcagaccta caaccagctt ttcgaggaga  2700
acccaatcaa cgccagtgga gttgacgcca aggctatcct ctctgctcgt ctgtcaaagt  2760
ccaggaggct tgagaacttg attgcccagc tgcctggcga aaagaagaac ggactgttcg  2820
gaaacttgat cgctctctcc ctgggattga ctcccaactt caagtccaac ttcgacctcg  2880
ccgaggacgc taagttgcag ttgtctaaag acacctacga cgatgacctc gacaacttgc  2940
tggcccagat aggcgaccaa tacgccgatc tcttcctcgc cgctaagaac ttgtccgacg  3000
caatcctgct gtccgacatc ctgagagtca acactgagat taccaaagct cctctgtctg  3060
cttccatgat taagcgctac gacgagcacc accaagatct gaccctgctc aaggccctgg  3120
tgagacagca gctgcccgag aagtacaagg agatcttttt cgaccagtcc aagaacggct  3180
acgccggata cattgacgga ggcgcctccc aggaagagtt ctacaagttc atcaagccca  3240
tccttgagaa gatggacggt accgaggagc tgttggtgaa gttgaacaga gaggacctgt  3300
tgaggaagca gagaaccttc gacaacggaa gcatccctca ccaaatccac ctgggagagc  3360
tccacgccat cttgaggagg caggaggatt tctatccctt cctgaaggac aaccgcgaga  3420
agattgagaa gatcttgacc ttcagaattc cttactacgt cgggccactc gccagaggaa  3480
actctaggtt cgcctggatg acccgcaaat ctgaagagac cattactccc tggaacttcg  3540
aggaagtcgt ggacaagggc gcttccgctc agtctttcat cgagaggatg accaacttcg  3600
ataaaaatct gcccaacgag aaggtgctgc ccaagcactc cctgttgtac gagtatttca  3660
cagtgtacaa cgagctcacc aaggtgaagt acgtcacaga gggaatgagg aagcctgcct  3720
tcttgtccgg agagcagaag aaggccatcg tcgacctgct cttcaagacc aacaggaagg  3780
tgactgtcaa gcagctgaag gaggactact tcaagaagat cgagtgcttc gactccgtcg  3840
agatctctgg tgtcgaggac aggttcaacg cctcccttgg gacttaccac gatctgctca  3900
agattattaa agacaaggac ttcctggaca acgaggagaa cgaggacatc cttgaggaca  3960
tcgtgctcac cctgaccttg ttcgaagaca gggaaatgat cgaagagagg ctcaagacct  4020
acgcccacct cttcgacgac aaggtgatga aacagctgaa gagacgcaga tataccggct  4080
ggggaaggct ctcccgcaaa ttgatcaacg ggatcaggga caagcagtca gggaagacta  4140
tactcgactt cctgaagtcc gacggattcg ccaacaggaa cttcatgcag ctcattcacg  4200
acgactcctt gaccttcaag gaggacatcc agaaggctca ggtgtctgga cagggtgact  4260
ccttgcatga gcacattgct aacttggccg gctctcccgc tattaagaag ggcattttgc  4320
agaccgtgaa ggtcgttgac gagctcgtga aggtgatggg acgccacaag ccagagaaca  4380
tcgttattga gatggctcgc gagaaccaaa ctacccagaa agggcagaag aattcccgcg  4440
agaggatgaa gcgcattgag gagggcataa aagagcttgg ctctcagatc ctcaaggagc  4500
accccgtcga gaacactcag ctgcagaacg agaagctgta cctgtactac ctccaaaacg  4560
gaagggacat gtacgtggac caggagctgg acatcaacag gttgtccgac tacgacgtcg  4620
accacatcgt gcctcagtcc ttcctgaagg atgactccat cgacaataaa gtgctgacac  4680
gctccgataa aaatagaggc aagtccgaca acgtcccctc cgaggaggtc gtgaagaaga  4740
tgaaaaacta ctggagacag ctcttgaacg ccaagctcat cacccagcgt aagttcgaca  4800
acctgactaa ggctgagaga ggaggattgt ccgagctcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttggaacc gccctcatca  5100
aaaaatatcc taagctggag tctgagttcg tctacggcga ctacaaggtg tacgacgtga  5160
ggaagatgat cgctaagtct gagcaggaga tcggcaaggc caccgccaag tacttcttct  5220
actccaacat catgaacttc ttcaagaccg agatcactct cgccaacggt gagatcagga  5280
agcgcccact gatcgagacc aacggtgaga ctggagagat cgtgtgggac aaagggaggg  5340
atttcgctac tgtgaggaag gtgctctcca tgcctcaggt gaacatcgtc aagaagaccg  5400
aagttcagac cggaggattc tccaaggagt ccatcctccc caagagaaac tccgacaagc  5460
tgatcgctag aaagaaagac tggaccccta agaagtacgg aggcttcgat tctcctaccg  5520
tggcctactc tgtgctggtc gtggccaagg tggagaaggg caagtccaag aagctgaaat  5580
ccgtcaagga gctcctcggg attaccatca tggagaggag ttccttcgag aagaacccta  5640
tcgacttcct ggaggccaag ggatataaag aggtgaagaa ggacctcatc atcaagctgc  5700
ccaagtactc cctcttcgag ttggagaacg gaaggaagag gatgctggct tctgccggag  5760
agttgcagaa gggaaatgag ctcgcccttc cctccaagta cgtgaacttc ctgtacctcg  5820
cctctcacta tgaaaagttg aagggctctc ctgaggacaa cgagcagaag cagctcttcg  5880
tggagcagca caagcactac ctggacgaaa ttatcgagca gatctctgag ttctccaagc  5940
gcgtgatatt ggccgacgcc aacctcgaca aggtgctgtc cgcctacaac aagcacaggg  6000
ataagcccat tcgcgagcag gctgaaaaca ttatccacct gtttaccctc acaaacttgg  6060
gagcccctgc tgccttcaag tacttcgaca ccaccattga caggaagaga tacacctcca  6120
ccaaggaggt gctcgacgca acactcatcc accaatccat caccggcctc tatgaaacaa  6180
ggattgactt gtcccagctg ggaggcgact ctagagccga tcccaagaag aagagaaagg  6240
tgtaggttaa cctagacttg tccatcttct ggattggcca acttaattaa tgtatgaaat  6300
aaaaggatgc acacatagtg acatgctaat cactataatg tgggcatcaa agttgtgtgt  6360
tatgtgtaat tactagttat ctgaataaaa gagaaagaga tcatccatat ttcttatcct  6420
aaatgaatgt cacgtgtctt tataattctt tgatgaacca gatgcatttc attaaccaaa  6480
tccatataca tataaatatt aatcatatat aattaatatc aattgggtta gcaaaacaaa  6540
tctagtctag gtgtgttttg cgaattcgat atcaagctta tcgataccgt cgaggggggg  6600
cccggtaccg g                                                        6611
```

SEQ ID NO: 302 moltype = DNA length = 5719
FEATURE Location/Qualifiers
misc_feature 1..5719
note = synthesized sequence- DD43HR1-SAMS:HPT-DD43HR2
source 1..5719

-continued

```
                       mol_type = other DNA
                       organism = synthetic construct
SEQUENCE: 302
cgcgcctcta gttgaagaca cgttcatgtc ttcatcgtaa gaagacactc agtagtcttc  60
ggccagaatg gccatctgga ttcagcaggc ctagaaggcc atttaaatcc tgaggatctg  120
gtcttcctaa ggacccggga tatcgctatc aactttgtat agaaaagttg ggccgaattc  180
gagctcggta cggccagaat ccggtaagtg actagggtca cgtgacccta gtcacttaaa  240
ttcggccaga atggccatct ggattcagca ggcctagaag gcccggaccg attaaacttt  300
aattcggtcc gggttacctc gagatcttgt tcccctcctt ggtttggcat aaattgattt  360
tcatggctct tctcggtcga aactggagct aattcaccct tagtctctct taaaattctg  420
gctgtaagaa acaccacaga acacataaat tataaactaa ttataatttg aagagtaaaa  480
tatgttttta ctcttatgat ttaattagtg tagttttaat tttctccttt ttttaaaaaa  540
ttttggtatt cataaatttc aatttttaa aaataattgt tgttacccgt taatgataac  600
gggatatgtt atgttaccac taaatcggac aaaaaaaatt caaaactttt ataaggatta  660
aaattaacaa aaatatttta aaaaaatcta acctcaataa agttaaattt ataagcacaa  720
aataatactt ttaagcctaa tttggcaaga cacaagcaag ctcacctgta gcattaatag  780
aaaggaagca aagcaagaga aaagcaacca gaaggaagcg tttgcttggt gacacagcca  840
tcttacttga atttatggta ttactgagaa accttgatct tgcttcaaaa tcttctagtt  900
accctctttt tataggcaga aagagaacta gctagttgcc aataggatat gaggacatgt  960
ggtgcaatgc actcactctt caaggacaag aaaaacaatg gctacaattg tggttcaaat  1020
caatgtctcc tgctctgtcc tgcctgaaaa tgacaccctt ttgcttggaa aagaggatca  1080
aagctaagaa caggagtggc ttcattccct tcatgtaacc aaacactttc gcattctgtc  1140
attcgtgaat cagcaaaatc tgcaaccaaa aatatatggt gcctaaataa aagaaataaa  1200
ataatttaga gttgcggact aaaataataa acaaaagaaa tatattataa tctagaatta  1260
atttaggact aaaagaagag gcagactcca attcctcttt tctagaatac cctccgtacg  1320
tacactagtg gtcacctaag tgactagggt cacgtgaccc tagtcactta ttcccaaaca  1380
ctagtaacgg ccgccagtgt gctggaattc gcccttccca agctttgctc tagatcaaac  1440
tcacatccaa acataacatg gatatcttcc ttaccaatca tactaattat tttgggttaa  1500
atattaatca ttatttttaa gatattaatt aagaaattaa aagatttttt aaaaaaatgt  1560
ataaaattat attattcatg atttttcata catttgattt tgataataaa tatatttttt  1620
ttaatttctt aaaaaatgtt gcaagacact tattagacat agtcttgttc tgtttacaaa  1680
agcattcatc atttaataca ttaaaaaata tttaatacta acagtagaat cttcttgtga  1740
gtggtgtggg agtaggcaac ctggcattga aacgagagaa agagagtcag aaccagaaga  1800
caaataaaaa gtatgcaaca aacaaatcaa aatcaaaggg caaaggctgg ggttggctca  1860
attggttgct acattcaatt ttcaactcag tcaacggttg agattcactc tgacttcccc  1920
aatctaagcc gcggatgcaa acggttgaat ctaacccaca atccaatctc gttacttagg  1980
ggcttttccg tcattaactc acccctgcca cccggtttcc ctataaattg gaactcaatg  2040
ctcccctcta aactcgtatc gcttcagagt tgagaccaag acacactcgt tcatatatct  2100
ctctgctctt ctcttctctt ctacctctca aggtactttt cttctccctc taccaaatcc  2160
tagattccgt ggttcaattt cggatcttgc acttctggtt tgctttgcct tgctttttcc  2220
tcaactgggt ccatctagga tccatgtgaa actctactct ttctttaata tctgcggaat  2280
acgcgtttga ctttcagatc tagtcgaaat catttcataa ttgcctttct ttcttttagc  2340
ttatgagaaa taaaatcact tttttttat ttcaaaataa accttgggcc ttgtgctgac  2400
tgagatgggg tttggtgatt acagaatttt agcgaatttt gtaattgtac ttgtttgtct  2460
gtagttttgt tttgttttct tgtttctcat acattcctta ggcttcaatt ttattcgagt  2520
ataggtcaca ataggaattc aaactttgag caggggaatt aatcccttcc ttcaaatcca  2580
gtttgtttgt atatatgttt aaaaaatgaa acttttgctt taaattctat tataactttt  2640
tttatggctg aaatttttgc atgtgtcttt gctctctgtt gtaaatttac tgtttaggta  2700
ctaactctag gcttgttgtg cagtttttga agtataacaa cagaagttcc tattccgaag  2760
ttcctattct ctagaaagta taggaacttc cactagtcca tgaaaaagcc tgaactcacc  2820
gcgacgtctg tcgagaagtt tctgatcgaa aagttcgaca gcgtctccga cctgatgcag  2880
ctctcggagg gcgaagaatc tcgtgctttc agcttcgatg taggagggcg tggatatgtc  2940
ctgcgggtaa atagctgcgc cgatggtttc tacaaagatc gttatgttta tcggcacttt  3000
gcatcggccg cgctcccgat tccggaagtg cttgacattg gggaattcag cgagagcctg  3060
acctattgca tctcccgccg tgcacagggt gtcacgttgc aagacctgcc tgaaaccgaa  3120
ctgcccgctg ttctgcagcc ggtcgcggag gccatggatg cgatcgctgc ggccgatctt  3180
agccagacga gcgggttcgg cccattcgga ccgcaaggaa tcggtcaata cactacatgg  3240
cgtgatttca tatgcgcgat tgctgatccc catgtgtatc actggcaaac tgtgatggac  3300
gacaccgtca gtgcgtccgt cgcgcaggct ctcgatgagc tgatgctttg ggccgaggac  3360
tgccccgaag tccggcacct cgtgcacgcg gatttcggct ccaacaatgt cctgacggac  3420
aatggccgca taacagcggt cattgactgg agcgaggcga tgttcgggga ttcccaatac  3480
gaggtcgcca acatcttctt ctggaggccg tggttggctt gtatggagca gcagacgcgc  3540
tacttcgagc ggaggcatcc ggagcttgca ggatcgccgc ggctccgggc gtatatgctc  3600
cgcattggtc ttgaccaact ctatcagagc ttggttgacg gcaatttcga tgatgcagct  3660
tgggcgcagg gtcgatgcga cgcaatcgtc cgatccggag ccgggactgt cgggcgtaca  3720
caaatcgccc gcagaagcgc ggccgtctgg accgatggct gtgtagaagt actcgccgat  3780
agtggaaacc gacgccccag cactcgtccg agggcaaagg aatagtgagg tacctaaaga  3840
aggagtgcgt cgaagcagat cgttcaaaca tttggcaata aagtttctta agattgaatc  3900
ctgttgccgg tcttgcgatg attatcatat aatttctgtt gaattacgtt aagcatgtaa  3960
taattaacat gtaatgcatg acgttattta tgagatgggt ttttatgatt agagtcccgc  4020
aattatacat ttaatacgcg atagaaaaca aaatatagcg cgcaaactag gataaattat  4080
cgcgcgcggt gtcatctatg ttactagatc gatgtcgacc cgggccctag gaggccggcc  4140
cagctgatga tcccggtgaa gttcctattc cgaagttcct attctccaga aagtatagga  4200
acttcactag agcttgcggc cgcgcatgct gacttaatca gctaacgcca ctcgacctgc  4260
aggcatgccc gcggatatcg atgggccccg gccgaagctt caagtttgta caaaaaagca  4320
ggctggcgcc ggaaccaatt cagtcgactg gatccggtac cgaattcgcg gccgcactcg  4380
agatatctag acccagcttt cttgtacaaa gtggccgtta acggatcggc cagaatccgg  4440
taagtgacta gggtcacgtg accctagtca cttaaattcg gccagaatgg ccatctggat  4500
tcagcaggcc tagaaggccc ggaccgatta aactttaatt cggtccgggt tacctctaga  4560
```

```
aagcttgtcg acctgcaggt acaagtacaa gggacttgtg agttgtaagg ctgtatttac  4620
aatagtgaaa agagaatcat ctgggtgatt gggtttttag tccccagtga cgaattaaag  4680
gtttgaattc ttagtatgtt tgggaatcaa ttaggaattt cgttttggac tttccaaagc  4740
aattattcac tttttcattc attaaatgtg actaaaaaat tgttatttct ccattggcca  4800
ggatgcatcg tttatataaa cataacctta gtgaaagcag tgttttcatg tgacagcggc  4860
agactatatc ttaaacaaaa ttacttgtaa agaaagatac cgttaggaaa aaaatgaaaa  4920
gaaaattgaa gctatcactt gtttactttc ctaatatctt tcaagaatac aatgtggtga  4980
atttcaattt tccctacata tgtataccgt cagcctgacg caacttatga aacttctctt  5040
tctttcattt gatgtatata taaagacaca ttatatataa agaaacttta tatatatctc  5100
catcatattt tagtacttgc tactatgtaa aattagctgt tggaagtatc tcaagaaaca  5160
tttaatttat tgaaccaagc attaaccatt catctacatt tgagttctaa aataaatctt  5220
aaatgatgtg gaggaaggga aattgttaat tatttccctc ttctcctaca tggatatacc  5280
tgaaacatgc aatggatgga ttagatttta acatttgcag cctgagaagt tcactgactt  5340
tcctccagct attttatgtg tgcccgccac catttatagc tcatgattgt agctgaactg  5400
caaaaactgc atcgattgca aactgaaatt gagaatctct tttcaacttt atatgctgat  5460
tgatgcatgc tgagcatgct atactagtac tcgaagttcc tatatgtaga ctttgttact  5520
gcctaatata ctttgtgttt gttctcaagt tcttatttta tttcatattt tttcctataa  5580
aaggttaatg gctctataaa ggttgagtga cggatccggt cacctaagtg actagggtca  5640
cgtgacccta gtcacttatt cccgggcaac tttattatac aaagttgata gatctcgaat  5700
tcattccgat taatcgtgg                                                5719

SEQ ID NO: 303          moltype = DNA  length = 6611
FEATURE                 Location/Qualifiers
misc_feature            1..6611
                        note = synthesized sequence- U6-9.1:DD43CR2+EF1A2:CAS9
source                  1..6611
                        mol_type = other DNA
                        organism = synthetic construct
SEQUENCE: 303
cgcgccggta cccgggttaa gagaattgta agtgtgcttt tatatattta aaattaatat  60
attttgaaat gttaaaatat aaaagaaaat tcaatgtaaa ttaaaaataa ataaatgttt  120
aataaagata aattttaaaa cataaaagaa aatgtctaac aagaggatta agatcctgtg  180
ctcttaaatt tttaggtgtt gaaatcttag ccatacaaaa tatattttat taaaaccaag  240
catgaaaaaa gtcactaaag agctatataa ctcatgcagc tagaaatgaa gtgaagggaa  300
tccagtttgt tctcagtcga aagagtgtct atctttgttc ttttctgcaa ccgagttaag  360
caaaatggga atgcgaggta tcttcctttc gttaggggag caccagatgc atagttagtc  420
ccacattgat gaatataaca agagcttcac agaatatata gcccaggcca cagtaaaagc  480
ttgtattcta gaaaagagga atgttttaga gctagaaata gcaagttaaa ataaggctag  540
tccgttatca acttgaaaaa gtggcaccga gtcggtgctt ttttttgcgg ccgcaattgg  600
atcgggttta cttattttgt gggtatctat actttttatta gatttttaat caggctcctg  660
atttcttttt atttcgattg aattcctgaa cttgtattat tcagtagatc gaataaatta  720
taaaaagata aaatcataaa ataatatttt atcctatcaa tcatattaaa gcaatgaata  780
tgtaaaatta atcttatctt tattttaaaa aatcatatag gtttagtatt tttttaaaaa  840
taaagatagg attagtttta ctattcactg cttattactt ttaaaaaaat cataaaggtt  900
tagtattttt ttaaaataaa tataggaata gttttactat tcactgcttt aatagaaaaa  960
tagtttaaaa tttaagatag ttttaatccc agcatttgcc acgtttgaac gtgagccgaa  1020
acgatgtcgt tacattatct taacctagct gaaacgatgt cgtcataata tcgccaaatg  1080
ccaactggac tacgtcgaac ccacaaatcc cacaaagcgc gtgaaatcaa atcgctcaaa  1140
ccacaaaaaa gaacaacgcg tttgttacac gctcaatccc acgcgagtag agcacagtaa  1200
ccttcaaata agcgaatggg gcataatcag aaatccgaaa taaacctagg ggcattatcg  1260
gaaatgaaaa gtagctcact caatataaaa atctaggaac cctagttttc gttatcactc  1320
tgtgctccct cgctctattt ctcagtctct gtgtttgcgg ctgaggattc cgaacgagtg  1380
accttcttcg tttctcgcaa aggtaacagc ctctgctctt gtctcttcga ttcgatctat  1440
gcctgtctct tatttacgat gatgtttctt cggttatgtt tttttattta tgctttatgc  1500
tgttgatgtt cggttgtttg tttcgctttg tttttgtggt tcagtttttt aggattcttt  1560
tggtttttga atcgattaat cggaagagat tttcgagtta tttggtgtgt tggaggtgaa  1620
tctttttttt gaggtcatag atctgttgta tttgtgttat aaacatgcga ctttgtatga  1680
ttttttacga ggttatgatg ttctggttgt tttattatga atctgttgag acagaaccat  1740
gatttttgtt gatgttcgtt tacactatta aaggtttgtt ttaacaggat taaaagtttt  1800
ttaagcatgt tgaaggagtc ttgtagatat gtaaccgtcg atagtttttt tgtgggtttg  1860
ttcacatgtt atcaagctta atcttttact atgtatgcga ccatatctgg atccagcaaa  1920
ggcgattttt taattccttg tgaaactttt gtaatatgaa gttgaaattt tgttattggt  1980
aaactataaa tgtgtgaagt tggagtatac ctttaccttc ttatttggct ttgtgatagt  2040
ttaatttata tgtattttga gttctgactt gtatttcttt gaattgattc tagtttaagt  2100
aatccatgga caaaaagtac tcaatagggc tcgacatagg gactaactcc gttggatggg  2160
ccgtcatcac cgacgagtac aaggtgccct ccaagaagtt caaggtgttg ggaaacaccg  2220
acaggcacag cataaagaag aatttgatcg gtgccctcct cttcgactcc ggagagaccg  2280
ctgaggctac caggctcaag aggaccgcta gaaggcgcta caccagaagg aagaacagaa  2340
tctgctacct gcaggagatc ttctccaacg agatggccaa ggtggacgac tccttcttcc  2400
accgccttga ggaatcattc ctggtggagg aggataaaaa gcacgagaga cacccaatct  2460
tcgggaacat cgtcgacgag gtggcctacc atgaaaagta ccctaccatc taccacctga  2520
ggaagaagct ggtcgactct accgacaagg ctgacttgcg cttgatttac ctggctctcg  2580
ctcacatgat aaagttccgc ggacacttcc tcattgaggg agacctgaac ccagacaact  2640
ccgacgtgga caagctcttc atccagctcg ttcagaccta caaccagctt ttcgaggaga  2700
acccaatcaa cgccagtgga gttgacgcca aggctatcct ctctgctcgt ctgtcaaagt  2760
ccaggaggct tgagaacttg attgcccagc tgcctggcga aaagaagaac ggactgttcg  2820
gaaacttgat cgctctctcc ctgggattga ctcccaactt caagtccaac ttcgacctcg  2880
ccgaggacgc taagttgcag ttgtctaaag acacctacga cgatgacctc gacaacttgc  2940
tggcccagat aggcgaccaa tacgccgatc tcttcctcgc cgctaagaac ttgtccgacg  3000
```

```
caatcctgct gtccgacatc ctgagagtca acactgagat taccaaagct cctctgtctg  3060
cttccatgat taagcgctac gacgagcacc accaagatct gaccctgctc aaggccctgg  3120
tgagacagca gctgcccgag aagtacaagg agatcttttt cgaccagtcc aagaacggct  3180
acgccggata cattgacgga ggcgcctccc aggaagagtt ctacaagttc atcaagccca  3240
tccttgagaa gatggacggt accgaggagc tgttggtgaa gttgaacaga gaggacctgt  3300
tgaggaagca gagaaccttc gacaacggaa gcatccctca ccaaatccac ctgggagagc  3360
tccacgccat cttgaggagg caggaggatt tctatccctt cctgaaggac aaccgcgaga  3420
agattgagaa gatcttgacc ttcagaattc cttactacgt cgggccactc gccagaggaa  3480
actctaggtt cgcctggatg acccgcaaat ctgaagagac cattactccc tggaacttcg  3540
aggaagtcgt ggacaagggc gcttccgctc agtctttcat cgagaggatg accaacttcg  3600
ataaaaatct gcccaacgag aaggtgctgc ccaagcactc cctgttgtac gagtatttca  3660
cagtgtacaa cgagctcacc aaggtgaagt acgtcacaga gggaatgagg aagcctgcct  3720
tcttgtccgg agagcagaag aaggccatcg tcgacctgct cttcaagacc aacaggaagg  3780
tgactgtcaa gcagctgaag gaggactact tcaagaagat cgagtgcttc gactccgtcg  3840
agatctctgg tgtcgaggac aggttcaacg cctcccttgg gacttaccac gatctgctca  3900
agattattaa agacaaggac ttcctggaca acgaggagaa cgaggacatc cttgaggaca  3960
tcgtgctcac cctgaccttg ttcgaagaca gggaaatgat cgaagagagg ctcaagacct  4020
acgcccacct cttcgacgac aaggtgatga aacagctgaa gagacgcaga tataccggct  4080
ggggaaggct ctcccgcaaa ttgatcaacg ggatcaggga caagcagtca gggaagacta  4140
tactcgactt cctgaagtcc gacggattcg ccaacaggaa cttcatgcag ctcattcacg  4200
acgactcctt gaccttcaag gaggacatcc agaaggctca ggtgtctgga cagggtgact  4260
ccttgcatga gcacattgct aacttggccg gctctcccgc tattaagaag ggcattttgc  4320
agaccgtgaa ggtcgttgac gagctcgtga aggtgatggg acgccacaag ccagagaaca  4380
tcgttattga gatggctcgc gagaaccaaa ctacccagaa agggcagaag aattcccgcg  4440
agaggatgaa gcgcattgag gagggcataa aagagcttgg ctctcagatc ctcaaggagc  4500
accccgtcga gaacactcag ctgcagaacg agaagctgta cctgtactac ctccaaaacg  4560
gaagggacat gtacgtggac caggagctgg acatcaacag gttgtccgac tacgacgtcg  4620
accacatcgt gcctcagtcc ttcctgaagg atgactccat cgacaataaa gtgctgacac  4680
gctccgataa aaatagaggc aagtccgaca acgtcccctc cgaggaggtc gtgaagaaga  4740
tgaaaaacta ctggagacag ctcttgaacg ccaagctcat cacccagcgt aagttcgaca  4800
acctgactaa ggctgagaga ggaggattgt ccgagctcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttggaacc gccctcatca  5100
aaaaatatcc taagctggag tctgagttcg tctacggcga ctacaaggtg tacgacgtga  5160
ggaagatgat cgctaagtct gagcaggaga tcggcaaggc caccgccaag tacttcttct  5220
actccaacat catgaacttc ttcaagaccg agatcactct cgccaacggt gagatcagga  5280
agcgcccact gatcgagacc aacggtgaga ctggagagat cgtgtgggac aaagggaggg  5340
atttcgctac tgtgaggaag gtgctctcca tgcctcaggt gaacatcgtc aagaagaccg  5400
aagttcagac cggaggattc tccaaggagt ccatcctccc caagagaaac tccgacaagc  5460
tgatcgctag aaagaaagac tggaccccta agaagtacgg aggcttcgat tctcctaccg  5520
tggcctactc tgtgctggtc gtggccaagg tggagaaggg caagtccaag aagctgaaat  5580
ccgtcaagga gctcctcggg attaccatca tggagaggag ttccttcgag aagaacccta  5640
tcgacttcct ggaggccaag ggatataaag aggtgaagaa ggacctcatc atcaagctgc  5700
ccaagtactc cctcttcgag ttggagaacg gaaggaagag gatgctggct tctgccggag  5760
agttgcagaa gggaaatgag ctcgcccttc cctccaagta cgtgaacttc ctgtacctcg  5820
cctctcacta tgaaaagttg aagggctctc ctgaggacaa cgagcagaag cagctcttcg  5880
tggagcagca caagcactac ctggacgaaa ttatcgagca gatctctgag ttctccaagc  5940
gcgtgatatt ggccgacgcc aacctcgaca aggtgctgtc cgcctacaac aagcacaggg  6000
ataagcccat tcgcgagcag gctgaaaaca ttatccacct gtttaccctc acaaacttgg  6060
gagcccctgc tgccttcaag tacttcgaca ccaccattga caggaagaga tacacctcca  6120
ccaaggaggt gctcgacgca acactcatcc accaatccat caccggcctc tatgaaacaa  6180
ggattgactt gtcccagctg ggaggcgact ctagagccga tcccaagaag aagagaaagg  6240
tgtaggttaa cctagacttg tccatcttct ggattggcca acttaattaa tgtatgaaat  6300
aaaaggatgc acacatagtg acatgctaat cactataatg tgggcatcaa agttgtgtgt  6360
tatgtgtaat tactagttat ctgaataaaa gagaaagaga tcatccatat ttcttatcct  6420
aaatgaatgt cacgtgtctt tataattctt tgatgaacca gatgcatttc attaaccaaa  6480
tccatataca tataaatatt aatcatatat aattaatatc aattgggtta gcaaaacaaa  6540
tctagtctag gtgtgttttg cgaattcgat atcaagctta tcgataccgt cgaggggggg  6600
cccggtaccg g                                                        6611
```

```
SEQ ID NO: 304         moltype = DNA  length = 64
FEATURE                Location/Qualifiers
misc_feature           1..64
                       note = synthesized sequence- DD20 qPCR amplicon
source                 1..64
                       mol_type = other DNA
                       organism = synthetic construct
SEQUENCE: 304
attcggaact gacacacgac atgatggaac gtgactaagg tgggtttttg actttgcatg  60
tcga                                                                64

SEQ ID NO: 305         moltype = DNA  length = 115
FEATURE                Location/Qualifiers
misc_feature           1..115
                       note = synthesized sequence- DD43 qPCR amplicon
source                 1..115
                       mol_type = other DNA
```

```
                        organism = synthetic construct
SEQUENCE: 305
aaagaagagg cagactccaa ttcctctttt ctagaatacc ctccgtacgt acaagtacaa  60
gggacttgtg agttgtaagg ctgtatttac aatagtgaaa agagaatcat ctggg       115

SEQ ID NO: 306          moltype = DNA  length = 20
FEATURE                 Location/Qualifiers
misc_feature            1..20
                        note = synthesized sequence- primer, DD20-CR1
source                  1..20
                        mol_type = other DNA
                        organism = synthetic construct
SEQUENCE: 306
ggaactgaca cacgacatga                                              20

SEQ ID NO: 307          moltype = DNA  length = 20
FEATURE                 Location/Qualifiers
misc_feature            1..20
                        note = synthesized sequence- primer, DD20-CR2
source                  1..20
                        mol_type = other DNA
                        organism = synthetic construct
SEQUENCE: 307
gacatgatgg aacgtgacta                                              20

SEQ ID NO: 308          moltype = DNA  length = 22
FEATURE                 Location/Qualifiers
misc_feature            1..22
                        note = synthesized sequence- primer, DD20-F
source                  1..22
                        mol_type = other DNA
                        organism = synthetic construct
SEQUENCE: 308
attcggaact gacacacgac at                                           22

SEQ ID NO: 309          moltype = DNA  length = 17
FEATURE                 Location/Qualifiers
misc_feature            1..17
                        note = synthesized sequence- FAM-MGB probe, DD20-T
source                  1..17
                        mol_type = other DNA
                        organism = synthetic construct
SEQUENCE: 309
atggaacgtg actaagg                                                 17

SEQ ID NO: 310          moltype = DNA  length = 22
FEATURE                 Location/Qualifiers
misc_feature            1..22
                        note = synthesized sequence- primer, DD20-R
source                  1..22
                        mol_type = other DNA
                        organism = synthetic construct
SEQUENCE: 310
tcgacatgca aagtcaaaaa cc                                           22

SEQ ID NO: 311          moltype = DNA  length = 20
FEATURE                 Location/Qualifiers
misc_feature            1..20
                        note = synthesized sequence- primer, DD43CR1
source                  1..20
                        mol_type = other DNA
                        organism = synthetic construct
SEQUENCE: 311
gtcccttgta cttgtacgta                                              20

SEQ ID NO: 312          moltype = DNA  length = 20
FEATURE                 Location/Qualifiers
misc_feature            1..20
                        note = synthesized sequence- primer, DD43CR2
source                  1..20
                        mol_type = other DNA
                        organism = synthetic construct
SEQUENCE: 312
gtattctaga aaagaggaat                                              20

SEQ ID NO: 313          moltype = DNA  length = 26
FEATURE                 Location/Qualifiers
misc_feature            1..26
                        note = synthesized sequence- primer, DD43-F
```

```
source                1..26
                      mol_type = other DNA
                      organism = synthetic construct
SEQUENCE: 313
ttctagaata ccctccgtac gtacaa                                       26

SEQ ID NO: 314        moltype = DNA  length = 26
FEATURE               Location/Qualifiers
misc_feature          1..26
                      note = synthesized sequence- primer, DD43-F2
source                1..26
                      mol_type = other DNA
                      organism = synthetic construct
SEQUENCE: 314
aaagaagagg cagactccaa ttcctc                                       26

SEQ ID NO: 315        moltype = DNA  length = 19
FEATURE               Location/Qualifiers
misc_feature          1..19
                      note = synthesized sequence- FAM-MGB probe, DD43-T
source                1..19
                      mol_type = other DNA
                      organism = synthetic construct
SEQUENCE: 315
caagggactt gtgagttgt                                               19

SEQ ID NO: 316        moltype = DNA  length = 26
FEATURE               Location/Qualifiers
misc_feature          1..26
                      note = synthesized sequence- primer, DD43-R
source                1..26
                      mol_type = other DNA
                      organism = synthetic construct
SEQUENCE: 316
cccagatgat tctcttttca ctattg                                       26

SEQ ID NO: 317        moltype = DNA  length = 19
FEATURE               Location/Qualifiers
misc_feature          1..19
                      note = synthesized sequence- primer, Cas9-F
source                1..19
                      mol_type = other DNA
                      organism = synthetic construct
SEQUENCE: 317
ccttcttcca ccgccttga                                               19

SEQ ID NO: 318        moltype = DNA  length = 19
FEATURE               Location/Qualifiers
misc_feature          1..19
                      note = synthesized sequence- FAM-MGB probe, Cas9-T
source                1..19
                      mol_type = other DNA
                      organism = synthetic construct
SEQUENCE: 318
aatcattcct ggtggagga                                               19

SEQ ID NO: 319        moltype = DNA  length = 21
FEATURE               Location/Qualifiers
misc_feature          1..21
                      note = synthesized sequence- primer, Cas9-R
source                1..21
                      mol_type = other DNA
                      organism = synthetic construct
SEQUENCE: 319
tgggtgtctc tcgtgctttt t                                            21

SEQ ID NO: 320        moltype = DNA  length = 22
FEATURE               Location/Qualifiers
misc_feature          1..22
                      note = synthesized sequence- primer, Sams-76F
source                1..22
                      mol_type = other DNA
                      organism = synthetic construct
SEQUENCE: 320
aggcttgttg tgcagttttt ga                                           22

SEQ ID NO: 321        moltype = DNA  length = 22
FEATURE               Location/Qualifiers
misc_feature          1..22
```

```
                        note = synthesized sequence- FAM-MGB probe, FRT1I-63T
source                  1..22
                        mol_type = other DNA
                        organism = synthetic construct
SEQUENCE: 321
tggactagtg gaagttccta ta                                              22

SEQ ID NO: 322          moltype = DNA  length = 21
FEATURE                 Location/Qualifiers
misc_feature            1..21
                        note = synthesized sequence- primer, FRT1I-41F
source                  1..21
                        mol_type = other DNA
                        organism = synthetic construct
SEQUENCE: 322
gcggtgagtt caggcttttt c                                               21

SEQ ID NO: 323          moltype = DNA  length = 31
FEATURE                 Location/Qualifiers
misc_feature            1..31
                        note = synthesized sequence- primer, DD20-LB
source                  1..31
                        mol_type = other DNA
                        organism = synthetic construct
SEQUENCE: 323
ggttatacct tcttcttagt gtggtctatc c                                    31

SEQ ID NO: 324          moltype = DNA  length = 31
FEATURE                 Location/Qualifiers
misc_feature            1..31
                        note = synthesized sequence- primer, Sams-A1
source                  1..31
                        mol_type = other DNA
                        organism = synthetic construct
SEQUENCE: 324
cccaaaataa ttagtatgat tggtaaggaa g                                    31

SEQ ID NO: 325          moltype = DNA  length = 23
FEATURE                 Location/Qualifiers
misc_feature            1..23
                        note = synthesized sequence- primer, QC498A-S1
source                  1..23
                        mol_type = other DNA
                        organism = synthetic construct
SEQUENCE: 325
ggaacttcac tagagcttgc ggc                                             23

SEQ ID NO: 326          moltype = DNA  length = 28
FEATURE                 Location/Qualifiers
misc_feature            1..28
                        note = synthesized sequence- primer, DD20-RB
source                  1..28
                        mol_type = other DNA
                        organism = synthetic construct
SEQUENCE: 326
gccattacat tcttcataag ttcctctc                                        28

SEQ ID NO: 327          moltype = DNA  length = 26
FEATURE                 Location/Qualifiers
misc_feature            1..26
                        note = synthesized sequence- primer, DD43-LB
source                  1..26
                        mol_type = other DNA
                        organism = synthetic construct
SEQUENCE: 327
gtgtagtcca ttgtagccaa gtcacc                                          26

SEQ ID NO: 328          moltype = DNA  length = 24
FEATURE                 Location/Qualifiers
misc_feature            1..24
                        note = synthesized sequence- primer, DD43-RB
source                  1..24
                        mol_type = other DNA
                        organism = synthetic construct
SEQUENCE: 328
caaaccggag agagaggaag aacc                                            24

SEQ ID NO: 329          moltype = DNA  length = 2105
FEATURE                 Location/Qualifiers
```

```
misc_feature           1..2105
                       note = synthesized sequence- DD20 HR1-HR2 PCR amplicon
source                 1..2105
                       mol_type = other DNA
                       organism = synthetic construct
SEQUENCE: 329
ggttatacct tcttcttagt gtggtctatc ccctagtaat aattacacat ctaagatatc  60
cccttctttt tcaagtaaaa taatatcata tgatctcatt ttagtgaaac aatactattt  120
ccctgataac tctcttcaac attagggact tcatctaatc atctactttc aaggtataac  180
tagacgtatt tgttctttta aaaaaaacac tagatgtact cgtcaactca aaattcatcg  240
ttcatgcatt ttaattaaac tttaattagc taatgagtag aaaaagatca tacgagtaaa  300
atagaagaat cttcctagat tttggaagaa tggattggag tgtaagtgaa ttgatccatt  360
agtggaagat gctctttaca atggccaaac tgttctaatt gttagagcac atttgagatg  420
aaacacttca gtagtggagg taacctacaa tcctaggatc tgtatcctct atcactaatg  480
gagcaatggg tttgagattg acttactcct ttccttgtct ctcgtagtgc atatgcgcac  540
tttcaaaggc tacacaaaag ccgttaactt tttgtttatt taagttacga aagatagttg  600
aattagagta aatggtgata ttgaattagg attttaaata attttaaaag aattttttta  660
ataaaaaaaa tattgtgttg ttggatcaaa atttttaaat aacatgaata aggaaatgga  720
ttgcaatgag gttttaaaca attattttaa catataggat tttagaaaga cttttataat  780
attttgttga agtttagatt ttaatatatt tatgttttaa aattttaaaa aaaacttcat  840
gaatttataa tatttgaaaa agacacgtga atatttagaa aacatttaaa attacaataa  900
taaatcataa tgagataggg tgtattcatg tgtagacgag acaccaagta tatggttcac  960
aagtgaatca tctttttttt ttacagcaca agtagatcac ttgtacttat caaaattcgg  1020
aactgacaca cgacatgatg gaacgtgact aaggtgggtt tttgactttg catgtcgaag  1080
tgagagtgat tttattgaga gaataataga agacctacaa aacaaatgat cccgacgcta  1140
aagtaagtac gagagttaag agaataaatg ggaaaatatg catacatgat taggtgtgtg  1200
ttcgtctcaa gaaagtacga atgaatatgg tgtgtttgta gtacatgaat gatgtgtttt  1260
gagggttcaa gggaaattga tatttataga gtgaaatgga accagaggtc tttgttgaca  1320
agggttgtta tgactcttgc aaataattaa tagcttataa ataatagcca ataacttatt  1380
atagatagag ttagagataa tatatagcta aatttgaaca aggcatacaa aacaaaaatg  1440
ctaaatatga ataagacaat caaaattgta gtcgatgttc aactctttgt cgttgaagaa  1500
cttgtttgca gtggtatagt aaatgggtgt gagtgcagtg tctcacccat ctcacaccac  1560
acaaccaact tcatatctaa agatattgtc gctgaataca aaattgagtt atggaatata  1620
caattcataa tatagatacg aaaaatcatt tcttacaaaa cattcaatca aaaattattc  1680
aaacataatt ctagattaag taatccgaag tacaagttag tatcctagat ccgttaattt  1740
aaaattatgt ttgcataatt ttggatttgg tgttctataa gggcacaatt ttgttcattc  1800
ttacaagttt gtcaattcta aaatatatgc aaatttgaag aaaaaaaatt tacgaatgtg  1860
tctcaaacaa taacttaatg ggaggagaat gagggatgaa gaagctcaaa attaccaacg  1920
ccttctacct caagaagcta cttcacacaa aatatgactg gcggaaggat aggggacaac  1980
cgataacgag aaggagatac ataaggtaat gtacgttgtt gtgtgaggta cacaattatg  2040
gggatgaaga agttcaactt tagtcgaaaa aatgtttgag aggaacttat gaagaatgta  2100
atggc                                                              2105

SEQ ID NO: 330         moltype = DNA  length = 1204
FEATURE                Location/Qualifiers
misc_feature           1..1204
                       note = synthesized sequence- DD20 HR1-SAMS PCR amplicon
source                 1..1204
                       mol_type = other DNA
                       organism = synthetic construct
SEQUENCE: 330
ggttatacct tcttcttagt gtggtctatc ccctagtaat aattacacat ctaagatatc  60
cccttctttt tcaagtaaaa taatatcata tgatctcatt ttagtgaaac aatactattt  120
ccctgataac tctcttcaac attagggact tcatctaatc atctactttc aaggtataac  180
tagacgtatt tgttctttta aaaaaaacac tagatgtact cgtcaactca aaattcatcg  240
ttcatgcatt ttaattaaac tttaattagc taatgagtag aaaaagatca tacgagtaaa  300
atagaagaat cttcctagat tttggaagaa tggattggag tgtaagtgaa ttgatccatt  360
agtggaagat gctctttaca atggccaaac tgttctaatt gttagagcac atttgagatg  420
aaacacttca gtagtggagg taacctacaa tcctaggatc tgtatcctct atcactaatg  480
gagcaatggg tttgagattg acttactcct ttccttgtct ctcgtagtgc atatgcgcac  540
tttcaaaggc tacacaaaag ccgttaactt tttgtttatt taagttacga aagatagttg  600
aattagagta aatggtgata ttgaattagg attttaaata attttaaaag aattttttta  660
ataaaaaaaa tattgtgttg ttggatcaaa atttttaaat aacatgaata aggaaatgga  720
ttgcaatgag gttttaaaca attattttaa catataggat tttagaaaga cttttataat  780
attttgttga agtttagatt ttaatatatt tatgttttaa aattttaaaa aaaacttcat  840
gaatttataa tatttgaaaa agacacgtga atatttagaa aacatttaaa attacaataa  900
taaatcataa tgagataggg tgtattcatg tgtagacgag acaccaagta tatggttcac  960
aagtgaatca tctttttttt ttacagcaca agtagatcac ttgtacttat caaaattcgg  1020
aactgacaca cactagtggt cacctaagtg actagggtca cgtgacccta gtcacttatt  1080
cccaaacact agtaacggcc gccagtgtgc tggaattcgc ccttcccaag ctttgctcta  1140
gatcaaactc acatccaaac ataacatgga tatcttcctt accaatcata ctaattattt  1200
tggg                                                               1204

SEQ ID NO: 331         moltype = DNA  length = 1459
FEATURE                Location/Qualifiers
misc_feature           1..1459
                       note = synthesized sequence- DD20 NOS-HR2 PCR amplicon
source                 1..1459
                       mol_type = other DNA
```

```
                         organism = synthetic construct
SEQUENCE: 331
ggaacttcac tagagcttgc ggccgcgcat gctgacttaa tcagctaacg ccactcgacc  60
tgcaggcatg cccgcggata tcgatgggcc ccggccgaag cttcaagttt gtacaaaaaa  120
gcaggctggc gccggaacca attcagtcga ctggatccgg taccgaattc gcggccgcac  180
tcgagatatc tagacccagc tttcttgtac aaagtggccg ttaacggatc ggccagaatc  240
cggtaagtga ctagggtcac gtgaccctag tcacttaaat tcggccagaa tggccatctg  300
gattcagcag gcctagaagg cccggaccga ttaaacttta attcggtccg ggttacctct  360
agaaagcttg tcgacctgca gacacgacat gatggaacgt gactaaggtg ggtttttgac  420
tttgcatgtc gaagtgagag tgattttatt gagagaataa tagaagacct acaaaacaaa  480
tgatcccgac gctaaagtaa gtacgagagt taagagaata aatgggaaaa tatgcataca  540
tgattaggtg tgtgttcgtc tcaagaaagt acgaatgaat atggtgtgtt tgtagtacat  600
gaatgatgtg ttttgagggt tcaagggaaa ttgatattta tagagtgaaa tggaaccaga  660
ggtctttgtt gacaagggtt gttatgactc ttgcaaataa ttaatagctt ataaataata  720
gccaataact tattatagat agagttagag ataatatata gctaaatttg aacaaggcat  780
acaaaacaaa aatgctaaat atgaataaga caatcaaaat tgtagtcgat gttcaactct  840
ttgtcgttga agaacttgtt tgcagtggta tagtaaatgg gtgtgagtgc agtgtctcac  900
ccatctcaca ccacacaacc aacttcatat ctaaagatat tgtcgctgaa tacaaaattg  960
agttatggaa tatacaattc ataatataga tacgaaaaat catttcttac aaaacattca  1020
atcaaaaatt attcaaacat aattctagat taagtaatcc gaagtacaag ttagtatcct  1080
agatccgtta atttaaaatt atgtttgcat aattttggat ttggtgttct ataagggcac  1140
aattttgttc attcttacaa gtttgtcaat tctaaaatat atgcaaattt gaagaaaaaa  1200
aatttacgaa tgtgtctcaa acaataactt aatgggagga gaatgaggga tgaagaagct  1260
caaaattacc aacgccttct acctcaagaa gctacttcac acaaaatatg actggcggaa  1320
ggatagggga caaccgataa cgagaaggag atacataagg taatgtacgt tgttgtgtga  1380
ggtacacaat tatggggatg aagaagttca actttagtcg aaaaaatgtt tgagaggaac  1440
ttatgaagaa tgtaatggc                                               1459

SEQ ID NO: 332           moltype = DNA  length = 2098
FEATURE                  Location/Qualifiers
misc_feature             1..2098
                         note = synthesized sequence- DD43 HR1-HR2 PCR amplicon
source                   1..2098
                         mol_type = other DNA
                         organism = synthetic construct
SEQUENCE: 332
gtgtagtcca ttgtagccaa gtcaccaata tcttgttccc ctccttggtt tggcataaat  60
tgattttcat ggctcttctc ggtcgaaact ggagctaatt caccccttagt ctctcttaaa  120
attctggctg taagaaacac cacagaacac ataaattata aactaattat aatttgaaga  180
gtaaaatatg tttttactct tatgatttaa ttagtgtagt tttaattttc tcctttttt  240
aaaaaatttt ggtattcata aatttcaatt ttttaaaaat aattgttgtt acccgttaat  300
gataacggga tatgttatgt taccactaaa tcggacaaaa aaaattcaaa acttttataa  360
ggattaaaat taacaaaaat attttaaaaa aatctaacct caataaagtt aaatttataa  420
gcacaaaata atacttttaa gcctaatttg gcaagacaca agcaagctca cctgtagcat  480
taatagaaag gaagcaaagc aagagaaaag caaccagaag gaagcgtttg cttggtgaca  540
cagccatctt acttgaattt atggtattac tgagaaacct tgatcttgct tcaaaatctt  600
ctagttaccc tctttttata ggcagaaaga gaactagcta gttgccaata ggatatgagg  660
acatgtggtg caatgcactc actcttcaag gacaagaaaa acaatggcta caattgtggt  720
tcaaatcaat gtctcctgct ctgtcctgcc tgaaaatgac accctttttgc ttggaaaaga  780
ggatcaaagc taagaacagg agtggcttca ttcccttcat gtaaccaaac actttcgcat  840
tctgtcattc gtgaatcagc aaaatctgca accaaaaata tatggtgcct aaataaaaga  900
aataaaataa tttagagttg cggactaaaa taataaacaa aagaaatata ttataatcta  960
gaattaattt aggactaaaa gaagaggcag actccaattc ctcttttcta gaataccctc  1020
cgtacgtaca agtacaaggg acttgtgagt tgtaaggctg tatttacaat agtgaaaaga  1080
gaatcatctg ggtgattggg tttttagtcc ccagtgacga attaaaggtt tgaattctta  1140
gtatgtttgg gaatcaatta ggaatttcgt tttggacttt ccaaagcaat tattcacttt  1200
ttcattcatt aaatgtgact aaaaaattgt tatttctcca ttggccagga tgcatcgttt  1260
atataaacat aaccttagtg aaagcagtgt tttcatgtga cagcggcaga ctatatctta  1320
aacaaaatta cttgtaaaga aagataccgt taggaaaaaa atgaaaagaa aattgaagct  1380
atcacttgtt tactttccta atatctttca agaatacaat gtggtgaatt tcaattttcc  1440
ctacatatgt ataccgtcag cctgacgcaa cttatgaaac ttctctttct ttcatttgat  1500
gtatatataa agacacatta tatataaaga aactttatat atatctccat catattttag  1560
tacttgctac tatgtaaaat tagctgttgg aagtatctca agaaacattt aatttattga  1620
accaagcatt aaccattcat ctacatttga gttctaaaat aaatcttaaa tgatgtggag  1680
gaagggaaat tgttaattat ttccctcttc tcctacatgg atatacctga aacatgcaat  1740
ggatggatta gattttaaca tttgcagcct gagaagttca ctgactttcc tccagctatt  1800
ttatgtgtgc ccgccaccat tttatagctca tgattgtagc tgaactgcaa aaactgcatc  1860
gattgcaaac tgaaattgag aatctctttt caactttata tgctgattga tgcatgctga  1920
gcatgctata ctagtactcg aagttcctat atgtagactt tgttactgcc taatatactt  1980
tgtgtttgtt ctcaagttct tattttattt catatttttt cctataaaag gttaatggct  2040
ctataaaggt tgagtgacat atatatacta taaaggttct tcctctctct ccggtttg    2098

SEQ ID NO: 333           moltype = DNA  length = 1202
FEATURE                  Location/Qualifiers
misc_feature             1..1202
                         note = synthesized sequence- DD43 HR1-SAMS PCR PCR amplicon
source                   1..1202
                         mol_type = other DNA
                         organism = synthetic construct
```

```
SEQUENCE: 333
gtgtagtcca ttgtagccaa gtcaccaata tcttgttccc ctccttggtt tggcataaat  60
tgattttcat ggctcttctc ggtcgaaact ggagctaatt caccccttagt ctctcttaaa  120
attctggctg taagaaacac cacagaacac ataaattata aactaattat aatttgaaga  180
gtaaaatatg tttttactct tatgatttaa ttagtgtagt tttaatttc tcctttttt  240
aaaaaatttt ggtattcata aatttcaatt ttttaaaaat aattgttgtt acccgttaat  300
gataacggga tatgttatgt taccactaaa tcggacaaaa aaaattcaaa acttttataa  360
ggattaaaat taacaaaaat attttaaaaa aatctaacct caataaagtt aaatttataa  420
gcacaaaata atacttttaa gcctaatttg gcaagacaca agcaagctca cctgtagcat  480
taatagaaag gaagcaaagc aagagaaaag caaccagaag gaagcgtttg cttggtgaca  540
cagccatctt acttgaattt atggtattac tgagaaacct tgatcttgct tcaaaatctt  600
ctagttaccc tctttttata ggcagaaaga gaactagcta gttgccaata ggatatgagg  660
acatgtggtg caatgcactc actcttcaag gacaagaaaa acaatggcta caattgtggt  720
tcaaatcaat gtctcctgct ctgtcctgcc tgaaaatgac accctttttgc ttggaaaaga  780
ggatcaaagc taagaacagg agtggcttca ttcccttcat gtaaccaaac actttcgcat  840
tctgtcattc gtgaatcagc aaaatctgca accaaaaata tatggtgcct aaataaaaga  900
aataaaataa tttagagttg cggactaaaa taataaacaa aagaaatata ttataatcta  960
gaattaattt aggactaaaa gaagaggcag actccaattc ctcttttcta gaataccctc  1020
cgtacgtaca ctagtggtca cctaagtgac tagggtcacg tgaccctagt cacttattcc  1080
caaacactag taacggccgc cagtgtgctg gaattcgccc ttcccaagct ttgctctaga  1140
tcaaactcac atccaaacat aacatggata tcttccttac caatcatact aattattttg  1200
gg                                                                 1202

SEQ ID NO: 334         moltype = DNA  length = 1454
FEATURE                Location/Qualifiers
misc_feature           1..1454
                       note = synthesized sequence- DD43 NOS-HR2 PCR PCR amplicon
source                 1..1454
                       mol_type = other DNA
                       organism = synthetic construct
SEQUENCE: 334
ggaacttcac tagagcttgc ggccgcgcat gctgacttaa tcagctaacg ccactcgacc  60
tgcaggcatg cccgcggata tcgatgggcc ccggccgaag cttcaagttt gtacaaaaaa  120
gcaggctggc gccggaacca attcagtcga ctggatccgg taccgaattc gcggccgcac  180
tcgagatatc tagacccagc tttcttgtac aaagtggccg ttaacggatc ggccagaatc  240
cggtaagtga ctagggtcac gtgaccctag tcacttaaat tcggccagaa tggccatctg  300
gattcagcag gcctagaagg cccggaccga ttaaacttta attcggtccg ggttacctct  360
agaaagcttg tcgacctgca ggtacaagta caagggactt gtgagttgta aggctgtatt  420
tacaatagtg aaaagagaat catctgggtg attgggtttt tagtccccag tgacgaatta  480
aaggtttgaa ttcttagtat gtttgggaat caattaggaa tttcgttttg gactttccaa  540
agcaattatt cactttttca ttcattaaat gtgactaaaa aattgttatt tctccattgg  600
ccaggatgca tcgtttatat aaacataacc ttagtgaaag cagtgttttc atgtgacagc  660
ggcagactat atcttaaaca aaattacttg taaagaaaga taccgttagg aaaaaaatga  720
aaagaaaatt gaagctatca cttgtttact ttcctaatat ctttcaagaa tacaatgtgg  780
tgaatttcaa ttttccctac atatgtatac cgtcagcctg acgcaactta tgaaacttct  840
ctttctttca tttgatgtat atataaagac acattatata taaagaaact ttatatatat  900
ctccatcata ttttagtact tgctactatg taaaattagc tgttggaagt atctcaagaa  960
acatttaatt tattgaacca agcattaacc attcatctac atttgagttc taaaataaat  1020
cttaaatgat gtggaggaag ggaaattgtt aattatttcc ctcttctcct acatggatat  1080
acctgaaaca tgcaatggat ggattagatt ttaacatttg cagcctgaga agttcactga  1140
ctttcctcca gctattttat gtgtgcccgc caccatttat agctcatgat tgtagctgaa  1200
ctgcaaaaac tgcatcgatt gcaaactgaa attgagaatc tcttttcaac tttatatgct  1260
gattgatgca tgctgagcat gctatactag tactcgaagt tcctatatgt agactttgtt  1320
actgcctaat atactttgtg tttgttctca agttcttatt ttatttcata tttttcccta  1380
taaaaggtta atggctctat aaaggttgag tgacatatat atactataaa ggttcttcct  1440
ctctctccgg tttg                                                    1454

SEQ ID NO: 335         moltype = DNA  length = 60
FEATURE                Location/Qualifiers
misc_feature           1..60
                       note = soybean genomic DD20CR1 target region
source                 1..60
                       mol_type = genomic DNA
                       organism = Glycine max
SEQUENCE: 335
acttgtactt atcaaaattc ggaactgaca cacgacatga tggaacgtga ctaaggtggg  60

SEQ ID NO: 336         moltype = DNA  length = 59
FEATURE                Location/Qualifiers
source                 1..59
                       mol_type = genomic DNA
                       organism = Glycine max
SEQUENCE: 336
acttgtactt atcaaaattc ggaactgaca cacgactgat ggaacgtgac taaggtggg   59

SEQ ID NO: 337         moltype = DNA  length = 59
FEATURE                Location/Qualifiers
source                 1..59
                       mol_type = genomic DNA
```

```
                         organism = Glycine max
SEQUENCE: 337
acttgtactt atcaaaattc ggaactgaca cacgaatgat ggaacgtgac taaggtggg   59

SEQ ID NO: 338           moltype = DNA  length = 58
FEATURE                  Location/Qualifiers
source                   1..58
                         mol_type = genomic DNA
                         organism = Glycine max
SEQUENCE: 338
acttgtactt atcaaaattc ggaactgaca cacgatgatg gaacgtgact aaggtggg    58

SEQ ID NO: 339           moltype = DNA  length = 58
FEATURE                  Location/Qualifiers
source                   1..58
                         mol_type = genomic DNA
                         organism = Glycine max
SEQUENCE: 339
acttgtactt atcaaaattc ggaactgaca cacgacgatg gaacgtgact aaggtggg    58

SEQ ID NO: 340           moltype = DNA  length = 58
FEATURE                  Location/Qualifiers
source                   1..58
                         mol_type = genomic DNA
                         organism = Glycine max
SEQUENCE: 340
acttgtactt atcaaaattc ggaactgaca cacggtgatg gaacgtgact aaggtggg    58

SEQ ID NO: 341           moltype = DNA  length = 57
FEATURE                  Location/Qualifiers
source                   1..57
                         mol_type = genomic DNA
                         organism = Glycine max
SEQUENCE: 341
acttgtactt atcaaaattc ggaactgaca cacatgatgg aacgtgacta aggtggg     57

SEQ ID NO: 342           moltype = DNA  length = 57
FEATURE                  Location/Qualifiers
source                   1..57
                         mol_type = genomic DNA
                         organism = Glycine max
SEQUENCE: 342
acttgtactt atcaaaattc ggaactgaca cacgtgatgg aacgtgacta aggtggg     57

SEQ ID NO: 343           moltype = DNA  length = 56
FEATURE                  Location/Qualifiers
source                   1..56
                         mol_type = genomic DNA
                         organism = Glycine max
SEQUENCE: 343
acttgtactt atcaaaattc ggaactgaca cactgatgga acgtgactaa ggtggg      56

SEQ ID NO: 344           moltype = DNA  length = 56
FEATURE                  Location/Qualifiers
source                   1..56
                         mol_type = genomic DNA
                         organism = Glycine max
SEQUENCE: 344
acttgtactt atcaaaattc ggaactgaca cacggatgga acgtgactaa ggtggg      56

SEQ ID NO: 345           moltype = DNA  length = 55
FEATURE                  Location/Qualifiers
source                   1..55
                         mol_type = genomic DNA
                         organism = Glycine max
SEQUENCE: 345
acttgtactt atcaaaattc ggaactgaca cacgatggaa cgtgactaag gtggg       55

SEQ ID NO: 346           moltype = DNA  length = 55
FEATURE                  Location/Qualifiers
source                   1..55
                         mol_type = genomic DNA
                         organism = Glycine max
SEQUENCE: 346
acttgtactt atcaaaattc ggaactgaca catgatggaa cgtgactaag gtggg       55

SEQ ID NO: 347           moltype = DNA  length = 54
FEATURE                  Location/Qualifiers
source                   1..54
```

```
                        mol_type = genomic DNA
                        organism = Glycine max
SEQUENCE: 347
acttgtactt atcaaaattc ggaactgaca cacatggaac gtgactaagg tggg        54

SEQ ID NO: 348          moltype = DNA  length = 54
FEATURE                 Location/Qualifiers
source                  1..54
                        mol_type = genomic DNA
                        organism = Glycine max
SEQUENCE: 348
acttgtactt atcaaaattc ggaactgaca ctgatggaac gtgactaagg tggg        54

SEQ ID NO: 349          moltype = DNA  length = 53
FEATURE                 Location/Qualifiers
source                  1..53
                        mol_type = genomic DNA
                        organism = Glycine max
SEQUENCE: 349
acttgtactt atcaaaattc ggaactgaca cgatggaacg tgactaaggt ggg         53

SEQ ID NO: 350          moltype = DNA  length = 51
FEATURE                 Location/Qualifiers
source                  1..51
                        mol_type = genomic DNA
                        organism = Glycine max
SEQUENCE: 350
acttgtactt atcaaaattc ggaactgatg atggaacgtg actaaggtgg g           51

SEQ ID NO: 351          moltype = DNA  length = 50
FEATURE                 Location/Qualifiers
source                  1..50
                        mol_type = genomic DNA
                        organism = Glycine max
SEQUENCE: 351
acttgtactt atcaaaattc ggaactgaca tggaacgtga ctaaggtggg             50

SEQ ID NO: 352          moltype = DNA  length = 50
FEATURE                 Location/Qualifiers
source                  1..50
                        mol_type = genomic DNA
                        organism = Glycine max
SEQUENCE: 352
acttgtactt atcaaaattc ggaactgtga tggaacgtga ctaaggtggg             50

SEQ ID NO: 353          moltype = DNA  length = 51
FEATURE                 Location/Qualifiers
source                  1..51
                        mol_type = genomic DNA
                        organism = Glycine max
SEQUENCE: 353
acttgtactt atcaaaattc ggaactgaca cacgaacgtg actaaggtgg g           51

SEQ ID NO: 354          moltype = DNA  length = 50
FEATURE                 Location/Qualifiers
source                  1..50
                        mol_type = genomic DNA
                        organism = Glycine max
SEQUENCE: 354
acttgtactt atcaaaattc ggaactgaca cggaacgtga ctaaggtggg             50

SEQ ID NO: 355          moltype = DNA  length = 49
FEATURE                 Location/Qualifiers
source                  1..49
                        mol_type = genomic DNA
                        organism = Glycine max
SEQUENCE: 355
acttgtacct atcaaaattc ggaactgaat ggaacgtgac taaggtggg              49

SEQ ID NO: 356          moltype = DNA  length = 48
FEATURE                 Location/Qualifiers
source                  1..48
                        mol_type = genomic DNA
                        organism = Glycine max
SEQUENCE: 356
acttgtactt atcaaaattc ggaactgatg gaacgtgact aaggtggg               48

SEQ ID NO: 357          moltype = DNA  length = 46
FEATURE                 Location/Qualifiers
```

-continued

```
source                 1..46
                       mol_type = genomic DNA
                       organism = Glycine max
SEQUENCE: 357
acttgtactt atcaaaattc ggaactgaga acgtgactaa ggtggg                46

SEQ ID NO: 358         moltype = DNA  length = 38
FEATURE                Location/Qualifiers
source                 1..38
                       mol_type = genomic DNA
                       organism = Glycine max
SEQUENCE: 358
acttgtactt atcaaaattc ggaactgaca cacgacat                         38

SEQ ID NO: 359         moltype = DNA  length = 38
FEATURE                Location/Qualifiers
source                 1..38
                       mol_type = genomic DNA
                       organism = Glycine max
SEQUENCE: 359
acttgtactt atcaaaattc ggaactgaca aaggtggg                         38

SEQ ID NO: 360         moltype = DNA  length = 39
FEATURE                Location/Qualifiers
source                 1..39
                       mol_type = genomic DNA
                       organism = Glycine max
SEQUENCE: 360
acttgtactt atcaaaattc ggaacgtgac taaggtggg                        39

SEQ ID NO: 361         moltype = DNA  length = 24
FEATURE                Location/Qualifiers
source                 1..24
                       mol_type = genomic DNA
                       organism = Glycine max
SEQUENCE: 361
actatggaac gtgactaagg tggg                                        24

SEQ ID NO: 362         moltype = DNA  length = 211
FEATURE                Location/Qualifiers
source                 1..211
                       mol_type = genomic DNA
                       organism = Glycine max
SEQUENCE: 362
acttgtactt atcaaaattc ggaactgaca cacggccggt gatggattgg tggatgagtg  60
ttgcgtcgag cacctccttg gtggaggtgt atctcttcct gtcaatggtg gtgtcgaagt  120
acttgaaggc agcaggggct cccaagtttg tgagggtaaa caggtggata atgttttcag  180
cctgctcgcg atggaacgtg actaaggtgg g                                211

SEQ ID NO: 363         moltype = DNA  length = 90
FEATURE                Location/Qualifiers
source                 1..90
                       mol_type = genomic DNA
                       organism = Glycine max
SEQUENCE: 363
acttgtactt atcaaaaact acttgtgctg taaaaaaaaa gaggaacaat cttcactcat  60
caataagtga tggaacgcga ctaaggtggg                                  90

SEQ ID NO: 364         moltype = DNA  length = 57
FEATURE                Location/Qualifiers
misc_feature           1..57
                       note = soybean genomic DD20CR2 target region
source                 1..57
                       mol_type = genomic DNA
                       organism = Glycine max
SEQUENCE: 364
gacacacgac atgatggaac gtgactaagg tgggtttttg actttgcatg tcgaagt     57

SEQ ID NO: 365         moltype = DNA  length = 61
FEATURE                Location/Qualifiers
source                 1..61
                       mol_type = genomic DNA
                       organism = Glycine max
SEQUENCE: 365
actgacacac gacatgatgg aacgtgaact aaggtgggtt tttgactttg catgtcgaag  60
t                                                                 61

SEQ ID NO: 366         moltype = DNA  length = 59
FEATURE                Location/Qualifiers
```

```
source                   1..59
                         mol_type = genomic DNA
                         organism = Glycine max
SEQUENCE: 366
actgacacac gacatgatgg aacgtactaa ggtgggtttt tgactttgca tgtcgaagt    59

SEQ ID NO: 367           moltype = DNA  length = 58
FEATURE                  Location/Qualifiers
source                   1..58
                         mol_type = genomic DNA
                         organism = Glycine max
SEQUENCE: 367
actgacacac gacatgatgg aacgtctaag gtgggttttt gactttgcat gtcgaagt     58

SEQ ID NO: 368           moltype = DNA  length = 58
FEATURE                  Location/Qualifiers
source                   1..58
                         mol_type = genomic DNA
                         organism = Glycine max
SEQUENCE: 368
actgacacac gacatgatgg aacgtgaaag gtgggttttt gactttgcat gtcgaagt     58

SEQ ID NO: 369           moltype = DNA  length = 57
FEATURE                  Location/Qualifiers
source                   1..57
                         mol_type = genomic DNA
                         organism = Glycine max
SEQUENCE: 369
actgacacac gacatgatgg aacgctaagg tgggtttttg actttgcatg tcgaagt      57

SEQ ID NO: 370           moltype = DNA  length = 57
FEATURE                  Location/Qualifiers
source                   1..57
                         mol_type = genomic DNA
                         organism = Glycine max
SEQUENCE: 370
actgacacac gacatgatgg aacgtgaagg tgggtttttg actttgcatg tcgaagt      57

SEQ ID NO: 371           moltype = DNA  length = 56
FEATURE                  Location/Qualifiers
source                   1..56
                         mol_type = genomic DNA
                         organism = Glycine max
SEQUENCE: 371
actgacacac gacatgatgg aacgtgaggt gggtttttga ctttgcatgt cgaagt       56

SEQ ID NO: 372           moltype = DNA  length = 56
FEATURE                  Location/Qualifiers
source                   1..56
                         mol_type = genomic DNA
                         organism = Glycine max
SEQUENCE: 372
actgacacac gacatgatgg aacgtaaggt gggtttttga ctttgcatgt cgaagt       56

SEQ ID NO: 373           moltype = DNA  length = 56
FEATURE                  Location/Qualifiers
source                   1..56
                         mol_type = genomic DNA
                         organism = Glycine max
SEQUENCE: 373
actgacacac gacatgatgg aacctaaggt gggtttttga ctttgcatgt cgaagt       56

SEQ ID NO: 374           moltype = DNA  length = 56
FEATURE                  Location/Qualifiers
source                   1..56
                         mol_type = genomic DNA
                         organism = Glycine max
SEQUENCE: 374
actgacacac gacatgatgg aacgtgaggt gggtttttga ctttgcatgt cgaagt       56

SEQ ID NO: 375           moltype = DNA  length = 55
FEATURE                  Location/Qualifiers
source                   1..55
                         mol_type = genomic DNA
                         organism = Glycine max
SEQUENCE: 375
actgacacac gacatgatgg aactaaggtg ggtttttgac tttgcatgtc gaagt        55

SEQ ID NO: 376           moltype = DNA  length = 54
```

```
FEATURE               Location/Qualifiers
source                1..54
                      mol_type = genomic DNA
                      organism = Glycine max
SEQUENCE: 376
actgacacac gacatgatgg aataaggtgg gtttttgact ttgcatgtcg aagt        54

SEQ ID NO: 377        moltype = DNA  length = 53
FEATURE               Location/Qualifiers
source                1..53
                      mol_type = genomic DNA
                      organism = Glycine max
SEQUENCE: 377
actgacacac gacatgatgg ctaaggtggg tttttgactt tgcatgtcga agt         53

SEQ ID NO: 378        moltype = DNA  length = 53
FEATURE               Location/Qualifiers
source                1..53
                      mol_type = genomic DNA
                      organism = Glycine max
SEQUENCE: 378
actgacacac gacatgatgg ataaggtggg tttttgactt tgcatgtcga agt         53

SEQ ID NO: 379        moltype = DNA  length = 51
FEATURE               Location/Qualifiers
source                1..51
                      mol_type = genomic DNA
                      organism = Glycine max
SEQUENCE: 379
actgacacac gacatgatgg aaggtgggtt tttgactttg catgtcgaag t           51

SEQ ID NO: 380        moltype = DNA  length = 50
FEATURE               Location/Qualifiers
source                1..50
                      mol_type = genomic DNA
                      organism = Glycine max
SEQUENCE: 380
actgacacac gacatgatgg aggtgggttt ttgactttgc atgtcgaagt             50

SEQ ID NO: 381        moltype = DNA  length = 44
FEATURE               Location/Qualifiers
source                1..44
                      mol_type = genomic DNA
                      organism = Glycine max
SEQUENCE: 381
actgacacac gacatgatgg gtttttgact ttgcatgtcg aagt                   44

SEQ ID NO: 382        moltype = DNA  length = 43
FEATURE               Location/Qualifiers
source                1..43
                      mol_type = genomic DNA
                      organism = Glycine max
SEQUENCE: 382
actgacacac gacaggtggg tttttgactt tgcatgtcga agt                    43

SEQ ID NO: 383        moltype = DNA  length = 40
FEATURE               Location/Qualifiers
source                1..40
                      mol_type = genomic DNA
                      organism = Glycine max
SEQUENCE: 383
actgacacta aggtgggttt ttgactttgc atgtcgaagt                        40

SEQ ID NO: 384        moltype = DNA  length = 25
FEATURE               Location/Qualifiers
source                1..25
                      mol_type = genomic DNA
                      organism = Glycine max
SEQUENCE: 384
actgacacac gacatgatgg aacgt                                        25

SEQ ID NO: 385        moltype = DNA  length = 20
FEATURE               Location/Qualifiers
source                1..20
                      mol_type = genomic DNA
                      organism = Glycine max
SEQUENCE: 385
actgacacac gacatgatgg                                              20
```

-continued

```
SEQ ID NO: 386          moltype = DNA  length = 60
FEATURE                Location/Qualifiers
misc_feature           1..60
                       note = soybean genomic DD43CR1 target region
source                 1..60
                       mol_type = genomic DNA
                       organism = Glycine max
SEQUENCE: 386
agccttacaa ctcacaagtc ccttgtactt gtacgtacgg agggtattct agaaaagagg  60

SEQ ID NO: 387          moltype = DNA  length = 59
FEATURE                Location/Qualifiers
source                 1..59
                       mol_type = genomic DNA
                       organism = Glycine max
SEQUENCE: 387
agccttacaa ctcacaagtc ccttgtactt gtactacgga gggtattcta gaaaagagg   59

SEQ ID NO: 388          moltype = DNA  length = 59
FEATURE                Location/Qualifiers
source                 1..59
                       mol_type = genomic DNA
                       organism = Glycine max
SEQUENCE: 388
agccttacaa ctcacaagtc ccttgtactt gtagtacgga gggtattcta gaaaagagg   59

SEQ ID NO: 389          moltype = DNA  length = 58
FEATURE                Location/Qualifiers
source                 1..58
                       mol_type = genomic DNA
                       organism = Glycine max
SEQUENCE: 389
agccttacaa ctcacaagtc ccttgtactt gtgtacggag ggtattctag aaaagagg    58

SEQ ID NO: 390          moltype = DNA  length = 58
FEATURE                Location/Qualifiers
source                 1..58
                       mol_type = genomic DNA
                       organism = Glycine max
SEQUENCE: 390
agccttacaa ctcacaagtc ccttgtactt gcgtacggag ggtattctag aaaagagg    58

SEQ ID NO: 391          moltype = DNA  length = 57
FEATURE                Location/Qualifiers
source                 1..57
                       mol_type = genomic DNA
                       organism = Glycine max
SEQUENCE: 391
agccttacaa ctcacaagtc ccttgtactt ggtacggagg gtattctaga aaagagg     57

SEQ ID NO: 392          moltype = DNA  length = 57
FEATURE                Location/Qualifiers
source                 1..57
                       mol_type = genomic DNA
                       organism = Glycine max
SEQUENCE: 392
agccttacaa ctcacaagtc ccttgtactt gttacggagg gtattctaga aaagagg     57

SEQ ID NO: 393          moltype = DNA  length = 56
FEATURE                Location/Qualifiers
source                 1..56
                       mol_type = genomic DNA
                       organism = Glycine max
SEQUENCE: 393
agccttacaa ctcacaagtc ccttgtactt gtacggaggg tattctagaa aagagg      56

SEQ ID NO: 394          moltype = DNA  length = 55
FEATURE                Location/Qualifiers
source                 1..55
                       mol_type = genomic DNA
                       organism = Glycine max
SEQUENCE: 394
agccttacaa ctcacaagtc ccttgtactt tacggagggt attctagaaa agagg       55

SEQ ID NO: 395          moltype = DNA  length = 55
FEATURE                Location/Qualifiers
source                 1..55
                       mol_type = genomic DNA
                       organism = Glycine max
```

```
SEQUENCE: 395
agccttacaa ctcacaagtc ccttgtactg tacggagggt attctagaaa agagg       55

SEQ ID NO: 396          moltype = DNA  length = 54
FEATURE                 Location/Qualifiers
source                  1..54
                        mol_type = genomic DNA
                        organism = Glycine max
SEQUENCE: 396
agccttacaa ctcacaagcc ccttgtactt acggagggta ttctagaaaa gagg        54

SEQ ID NO: 397          moltype = DNA  length = 52
FEATURE                 Location/Qualifiers
source                  1..52
                        mol_type = genomic DNA
                        organism = Glycine max
SEQUENCE: 397
agccttacaa ctcacaagtc ccttgtatac ggagggtatt ctagaaaaga gg          52

SEQ ID NO: 398          moltype = DNA  length = 52
FEATURE                 Location/Qualifiers
source                  1..52
                        mol_type = genomic DNA
                        organism = Glycine max
SEQUENCE: 398
agccttacaa ctcacaagtc ccttgtgtac ggagggtatt ctagaaaaga gg          52

SEQ ID NO: 399          moltype = DNA  length = 50
FEATURE                 Location/Qualifiers
source                  1..50
                        mol_type = genomic DNA
                        organism = Glycine max
SEQUENCE: 399
agccttacaa ctcacaagtc ccttgtacgg agggtattct agaaaagagg            50

SEQ ID NO: 400          moltype = DNA  length = 49
FEATURE                 Location/Qualifiers
source                  1..49
                        mol_type = genomic DNA
                        organism = Glycine max
SEQUENCE: 400
agccttacaa ctcacaagtc cctttacgga gggtattcta gaaaagagg             49

SEQ ID NO: 401          moltype = DNA  length = 48
FEATURE                 Location/Qualifiers
source                  1..48
                        mol_type = genomic DNA
                        organism = Glycine max
SEQUENCE: 401
agccttacaa ctcacaagtc ccttacggag ggtattctag aaaagagg              48

SEQ ID NO: 402          moltype = DNA  length = 47
FEATURE                 Location/Qualifiers
source                  1..47
                        mol_type = genomic DNA
                        organism = Glycine max
SEQUENCE: 402
agccttacaa ctcacaagtc cctacggagg gtattctaga aaagagg               47

SEQ ID NO: 403          moltype = DNA  length = 43
FEATURE                 Location/Qualifiers
source                  1..43
                        mol_type = genomic DNA
                        organism = Glycine max
SEQUENCE: 403
agccttacaa ctcacaagtc ccttgtactt gtaagaaaag agg                   43

SEQ ID NO: 404          moltype = DNA  length = 49
FEATURE                 Location/Qualifiers
source                  1..49
                        mol_type = genomic DNA
                        organism = Glycine max
SEQUENCE: 404
agccttacaa ctcacaagtc ctaaattaaa ggttattcta gaaaagagg             49

SEQ ID NO: 405          moltype = DNA  length = 227
FEATURE                 Location/Qualifiers
source                  1..227
                        mol_type = genomic DNA
```

```
                         organism = Glycine max
SEQUENCE: 405
agccttacaa ctcacaagtc ccttgtactt gtagaatcca gttcataaaa caagtgacac  60
acaacagata tgaactggac tacgtcgaac ccacaaatcc cacaaagcgc gtgaaatcaa  120
atcgctcaaa ccacaaaaaa gaacaacgcg tttgttacac gctaatacca aaattatacc  180
caaatcttaa gctatttatg cgtacggagg gtattctaga aaagagg             227

SEQ ID NO: 406           moltype = DNA  length = 97
FEATURE                  Location/Qualifiers
source                   1..97
                         mol_type = genomic DNA
                         organism = Glycine max
SEQUENCE: 406
agccttacaa ctcacaagtc ccttgtactt gtaatgctcc cctctaaact cgtatcgctt  60
cagagttgag agtacggagg gtattctaga aaagagg                         97

SEQ ID NO: 407           moltype = DNA  length = 183
FEATURE                  Location/Qualifiers
source                   1..183
                         mol_type = genomic DNA
                         organism = Glycine max
SEQUENCE: 407
agccttacaa ctcacaagtc ccttgtatat agatacccac aaaataagta aacccgatcc  60
aaaatcttaa atgatgtgga ggaagggaaa ttgttaatta ttcccctctt ctcctacatg  120
gatatacctg aaacatgcaa tggatggatt agattttgta cggagggtat tctagaaaag  180
agg                                                              183

SEQ ID NO: 408           moltype = DNA  length = 234
FEATURE                  Location/Qualifiers
source                   1..234
                         mol_type = genomic DNA
                         organism = Glycine max
SEQUENCE: 408
agccttacaa ctcacaagtc ccttgtactt gtaccagggg atgtttttta tttacattca  60
cgtcttttgg aaagagccgc taaattaagt tctcagttag gcgaaggaag tatgactgct  120
ttaccaatag ttgaaactca atcgggagat gtttcagctt atattcctac taatgtaatt  180
tccattacag atggccaaat attcttacgt acggagggta ttctagaaaa gagg      234

SEQ ID NO: 409           moltype = DNA  length = 280
FEATURE                  Location/Qualifiers
source                   1..280
                         mol_type = genomic DNA
                         organism = Glycine max
SEQUENCE: 409
agccttacaa ctcacaagtc ccttgtactt gtaccgaaaa tttcagccat aaaaaaagtt  60
ataatagaat ttaaagcaaa agtttcattt tttaaacata tatactgaca cgctccgata  120
aaaatagagg caagtccgac aacgtcccct ccgaggaggt cgtgaagaag atgaaaaact  180
actggagaca gctcttgaac gccaagctca tcacccagcg taagctcgac aacctgacta  240
aggctgagag aggtgtacgg agggtattct agaaaagagg                      280

SEQ ID NO: 410           moltype = DNA  length = 250
FEATURE                  Location/Qualifiers
source                   1..250
                         mol_type = genomic DNA
                         organism = Glycine max
SEQUENCE: 410
agccttacaa ctcacaagtc ccttgtactt gtactggatt tggtgaggga tgcttccgtt  60
gtcgaaggtt ctctgcttcc tcaacaggtc ctctctgttc aacttcacca acagctcctc  120
ggtaccgtcc atcttctcaa ggatgaagat cgagtgcttc gactccgtcg agatctctgg  180
tgtcgaggac aggttcaacg cctcccttgg gacttgccac gatcgtacgg agggtattct  240
agaaaagagg                                                       250

SEQ ID NO: 411           moltype = DNA  length = 161
FEATURE                  Location/Qualifiers
source                   1..161
                         mol_type = genomic DNA
                         organism = Glycine max
SEQUENCE: 411
agccttacaa ctcacaagtc ccttatgacc tcaaaaaaaa gattcacctc caacacacca  60
aataactcga aaatctcttt cctattctct agaaagtata ggaacttcca ctagtccatg  120
aaaaagcctg aactcgtacg gagggtattc tagaaaagag g                    161

SEQ ID NO: 412           moltype = DNA  length = 185
FEATURE                  Location/Qualifiers
source                   1..185
                         mol_type = genomic DNA
                         organism = Glycine max
SEQUENCE: 412
agccttacaa ctcacaagtc ccttgtactt gtacacctgg ggcatggaga gcaccttcct  60
```

```
cacagtagcg aaatccctcc ctttgtccca cacgatctct ccagtctcac cgttggtctc  120
gatcagtggg cgcttcctga tctcaccgtt ggcgagagtg tacggagggt attctagaaa  180
agagg                                                              185

SEQ ID NO: 413          moltype = DNA  length = 212
FEATURE                 Location/Qualifiers
source                  1..212
                        mol_type = genomic DNA
                        organism = Glycine max
SEQUENCE: 413
agccttacaa ctcacaagtc ccttgtactt gtgctaggtt agccgaaaga tggttatcgg  60
ttcaaggacg caaggtgccc ctgctttttc agggtaataa ggggtagaga aaatgcctcg  120
agccaaagtt cgagtaccag gcgctacagc gctgaagtaa tccatgccat actcccagga  180
aaagccgtac ggagggtatt ctagaaaaga gg                                212

SEQ ID NO: 414          moltype = DNA  length = 231
FEATURE                 Location/Qualifiers
source                  1..231
                        mol_type = genomic DNA
                        organism = Glycine max
SEQUENCE: 414
agccttacaa ctcacaagtc ccttgtactt gtactcaagt tcttatttta tttcatattt  60
tttcctataa aaggttaatg gctctataaa ggttgagtga cggatccggt cacctaagtg  120
actagggtca cgtgacccta gtcacttatt cccgggcaac tttattatac aaagttgata  180
gatctcgaat tcattccgat taatcgtggc gagggtattc tagaaaagag g           231

SEQ ID NO: 415          moltype = DNA  length = 98
FEATURE                 Location/Qualifiers
source                  1..98
                        mol_type = genomic DNA
                        organism = Zea mays
SEQUENCE: 415
tcctctgtaa cgatttacgc acctgctggg aattgtaccg tacgtgcccc ggtcggagga  60
tatatatacc tcacacgtac gcgtacgcgt atatatac                          98

SEQ ID NO: 416          moltype = DNA  length = 98
FEATURE                 Location/Qualifiers
source                  1..98
                        mol_type = genomic DNA
                        organism = Zea mays
SEQUENCE: 416
tcctctgtaa cgatttacgc acctgctggg aattgtaccg tacgtgcccc ggacggagga  60
tatatatacc tcacacgtac gcgtacgcgt atatatac                          98

SEQ ID NO: 417          moltype = DNA  length = 98
FEATURE                 Location/Qualifiers
source                  1..98
                        mol_type = genomic DNA
                        organism = Zea mays
SEQUENCE: 417
tcctctgtaa cgatttacgc acctgctggg aattgtaccg tacgtgcccc gggcggagga  60
tatatatacc tcacacgtac gcgtacgcgt atatatac                          98

SEQ ID NO: 418          moltype = DNA  length = 98
FEATURE                 Location/Qualifiers
source                  1..98
                        mol_type = genomic DNA
                        organism = Zea mays
SEQUENCE: 418
tcctctgtaa cgatttacgc acctgctggg aattgtaccg tacgtgcccc ggccggagga  60
tatatatacc tcacacgtac gcgtacgcgt atatatac                          98

SEQ ID NO: 419          moltype = DNA  length = 99
FEATURE                 Location/Qualifiers
source                  1..99
                        mol_type = genomic DNA
                        organism = Zea mays
SEQUENCE: 419
tcctctgtaa cgatttacgc acctgctggg aattgtaccg tacgtgcccc ggatcggagg  60
atatatatac ctcacacgta cgcgtacgcg tatatatac                         99

SEQ ID NO: 420          moltype = DNA  length = 94
FEATURE                 Location/Qualifiers
source                  1..94
                        mol_type = genomic DNA
                        organism = Zea mays
SEQUENCE: 420
tcctctgtaa cgatttacgc acctgctggg aattgtaccg tacgtgcccc ggaggatata  60
tatacctcac acgtacgcgt acgcgtatat atac                              94
```

```
SEQ ID NO: 421          moltype = DNA  length = 81
FEATURE                 Location/Qualifiers
source                  1..81
                        mol_type = genomic DNA
                        organism = Zea mays
SEQUENCE: 421
tcctctgtaa cgatttacgc acctgctggg aattgtaccg tacgtgcccc ggttcacacg  60
tacgcgtacg cgtatatata c                                            81

SEQ ID NO: 422          moltype = DNA  length = 65
FEATURE                 Location/Qualifiers
source                  1..65
                        mol_type = genomic DNA
                        organism = Zea mays
SEQUENCE: 422
tcctctgtaa cgatttacgc acctgctggg aattgtaccg tacgtacgcg tacgcgtata  60
tatac                                                              65

SEQ ID NO: 423          moltype = DNA  length = 99
FEATURE                 Location/Qualifiers
source                  1..99
                        mol_type = genomic DNA
                        organism = Zea mays
SEQUENCE: 423
tcctctgtaa cgatttacgc acctgctggg aattgtaccg tacgtgcccc ggttcggagg  60
atatatatac ctcacacgta cgcgtacgcg tatatatac                         99

SEQ ID NO: 424          moltype = DNA  length = 95
FEATURE                 Location/Qualifiers
source                  1..95
                        mol_type = genomic DNA
                        organism = Zea mays
SEQUENCE: 424
tcctctgtaa cgatttacgc acctgctggg aattgtaccg tacgtgcccc cggaggatat  60
atatacctca cacgtacgcg tacgcgtata tatac                             95

SEQ ID NO: 425          moltype = DNA  length = 98
FEATURE                 Location/Qualifiers
source                  1..98
                        mol_type = genomic DNA
                        organism = Zea mays
SEQUENCE: 425
gaagctgtaa cgatttacgc acctgctggg aattgtaccg tacgtgaccc cggcggagga  60
tatatatacc tcacacgtac gcgtacgcgt atatatac                          98

SEQ ID NO: 426          moltype = DNA  length = 98
FEATURE                 Location/Qualifiers
source                  1..98
                        mol_type = genomic DNA
                        organism = Zea mays
SEQUENCE: 426
gaagctgtaa cgatttacgc acctgctggg aattgtaccg tacgtgtccc cggcggagga  60
tatatatacc tcacacgtac gcgtacgcgt atatatac                          98

SEQ ID NO: 427          moltype = DNA  length = 96
FEATURE                 Location/Qualifiers
source                  1..96
                        mol_type = genomic DNA
                        organism = Zea mays
SEQUENCE: 427
gaagctgtaa cgatttacgc acctgctggg aattgtaccg tacgtccccg gcggaggata  60
tatatacctc acacgtacgc gtacgcgtat atatac                            96

SEQ ID NO: 428          moltype = DNA  length = 98
FEATURE                 Location/Qualifiers
source                  1..98
                        mol_type = genomic DNA
                        organism = Zea mays
SEQUENCE: 428
gaagctgtaa cgatttacgc acctgctggg aattgtaccg tacgtggccc cggcggagga  60
tatatatacc tcacacgtac gcgtacgcgt atatatac                          98

SEQ ID NO: 429          moltype = DNA  length = 99
FEATURE                 Location/Qualifiers
source                  1..99
                        mol_type = genomic DNA
                        organism = Zea mays
SEQUENCE: 429
```

```
gaagctgtaa cgatttacgc acctgctggg aattgtaccg tacgtgcacc ccggcggagg  60
atatatatac ctcacacgta cgcgtacgcg tatatatac                          99

SEQ ID NO: 430          moltype = DNA  length = 87
FEATURE                 Location/Qualifiers
source                  1..87
                        mol_type = genomic DNA
                        organism = Zea mays
SEQUENCE: 430
gaagctgtaa cgatttacgc acctgctggg aattgtaccc ggcggaggat atatatacct  60
cacacgtacg cgtacgcgta tatatac                                       87

SEQ ID NO: 431          moltype = DNA  length = 92
FEATURE                 Location/Qualifiers
source                  1..92
                        mol_type = genomic DNA
                        organism = Zea mays
SEQUENCE: 431
gaagctgtaa cgatttacgc acctgctggg aattgtaccg tccccggcgg aggatatata  60
tacctcacac gtacgcgtac gcgtatatat ac                                 92

SEQ ID NO: 432          moltype = DNA  length = 94
FEATURE                 Location/Qualifiers
source                  1..94
                        mol_type = genomic DNA
                        organism = Zea mays
SEQUENCE: 432
gaagctgtaa cgatttacgc acctgctggg aattgtaccg tacccccggc ggaggatata  60
tatacctcac acgtacgcgt acgcgtatat atac                               94

SEQ ID NO: 433          moltype = DNA  length = 95
FEATURE                 Location/Qualifiers
source                  1..95
                        mol_type = genomic DNA
                        organism = Zea mays
SEQUENCE: 433
gaagctgtaa cgatttacgc acctgctggg aattgtaccg tacgccccgg cggaggatat  60
atatacctca cacgtacgcg tacgcgtata tatac                              95

SEQ ID NO: 434          moltype = DNA  length = 88
FEATURE                 Location/Qualifiers
source                  1..88
                        mol_type = genomic DNA
                        organism = Zea mays
SEQUENCE: 434
gaagctgtaa cgatttacgc acctgctggg aattgtaccc cggcggagga tatatatacc  60
tcacacgtac gcgtacgcgt atatatac                                      88

SEQ ID NO: 435          moltype = DNA  length = 98
FEATURE                 Location/Qualifiers
source                  1..98
                        mol_type = genomic DNA
                        organism = Zea mays
SEQUENCE: 435
aaggcgcaaa tgagtagcag cgcacgtata tatacgcgta cgcgtacgtt gtgaggtata  60
tatatcctcc gccggggcac gtacggtaca attcccag                           98

SEQ ID NO: 436          moltype = DNA  length = 96
FEATURE                 Location/Qualifiers
source                  1..96
                        mol_type = genomic DNA
                        organism = Zea mays
SEQUENCE: 436
aaggcgcaaa tgagtagcag cgcacgtata tatacgcgta cgcgtacggt gaggtatata  60
tatcctccgc cggggcacgt acggtacaat tcccag                             96

SEQ ID NO: 437          moltype = DNA  length = 95
FEATURE                 Location/Qualifiers
source                  1..95
                        mol_type = genomic DNA
                        organism = Zea mays
SEQUENCE: 437
aaggcgcaaa tgagtagcag cgcacgtata tatacgcgta cgcgtacgtg aggtatatat  60
atcctccgcc ggggcacgta cggtacaatt cccag                              95

SEQ ID NO: 438          moltype = DNA  length = 96
FEATURE                 Location/Qualifiers
source                  1..96
                        mol_type = genomic DNA
```

```
                         organism = Zea mays
SEQUENCE: 438
aaggcgcaaa tgagtagcag cgcacgtata tatacgcgta cgcgtactgt gaggtatata  60
tatcctccgc cggggcacgt acggtacaat tcccag                            96

SEQ ID NO: 439           moltype = DNA  length = 68
FEATURE                  Location/Qualifiers
source                   1..68
                         mol_type = genomic DNA
                         organism = Zea mays
SEQUENCE: 439
aaggcgcaaa tgagtagcag cgcacgtata tatatcctcc gccggggcac gtacggtaca  60
attcccag                                                           68

SEQ ID NO: 440           moltype = DNA  length = 93
FEATURE                  Location/Qualifiers
source                   1..93
                         mol_type = genomic DNA
                         organism = Zea mays
SEQUENCE: 440
aaggcgcaaa tgagtagcag cgcacgtata tatacgcgta cgcgtgtgag gtatatatat  60
cctccgccgg ggcacgtacg gtacaattcc cag                               93

SEQ ID NO: 441           moltype = DNA  length = 89
FEATURE                  Location/Qualifiers
source                   1..89
                         mol_type = genomic DNA
                         organism = Zea mays
SEQUENCE: 441
aaggcgcaaa tgagtagcag cgcacgtata tatacgcgta cgtgaggtat atatatcctc  60
cgccggggca cgtacggtac aattcccag                                    89

SEQ ID NO: 442           moltype = DNA  length = 89
FEATURE                  Location/Qualifiers
source                   1..89
                         mol_type = genomic DNA
                         organism = Zea mays
SEQUENCE: 442
aaggcgcaaa tgagtagcag cgcacgtata tatacgcgta cgcgtactat atatatcctc  60
cgccggggca cgtacggtac aattcccag                                    89

SEQ ID NO: 443           moltype = DNA  length = 94
FEATURE                  Location/Qualifiers
source                   1..94
                         mol_type = genomic DNA
                         organism = Zea mays
SEQUENCE: 443
aaggcgcaaa tgagtagcag cgcacgtata tatacgcgta cgcgtacgga ggtatatata  60
tcctccgccg gggcacgtac ggtacaattc ccag                              94

SEQ ID NO: 444           moltype = DNA  length = 96
FEATURE                  Location/Qualifiers
source                   1..96
                         mol_type = genomic DNA
                         organism = Zea mays
SEQUENCE: 444
aaggcgcaaa tgagtagcag cgcacgtata tatacgcgta cgcgtacgat gaggtatata  60
tatcctccgc cggggcacgt acggtacaat tcccag                            96

SEQ ID NO: 445           moltype = DNA  length = 1051
FEATURE                  Location/Qualifiers
misc_feature             1..1051
                         note = synthesized sequence-
                          LIGCas-1_crRNA_Expression_Cassette
source                   1..1051
                         mol_type = other DNA
                         organism = synthetic construct
SEQUENCE: 445
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
```

```
attcgaattt ctactagcag taagtcgtgt ttagaaatta ttttttttata taccttttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gtaccgtacg tgccccggcg  1020
ggttttagag ctatgctgtt ttgttttttt t                                1051

SEQ ID NO: 446          moltype = DNA  length = 1051
FEATURE                 Location/Qualifiers
misc_feature            1..1051
                        note = synthesized sequence-
                         LIGCas-2_crRNA_Expression_Cassette
source                  1..1051
                        mol_type = other DNA
                        organism = synthetic construct
SEQUENCE: 446
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta ttttttttata taccttttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt ggaattgtac cgtacgtgcc  1020
cgttttagag ctatgctgtt ttgttttttt t                                1051

SEQ ID NO: 447          moltype = DNA  length = 1047
FEATURE                 Location/Qualifiers
misc_feature            1..1047
                        note = synthesized sequence-
                         LIGCas-3_crRNA_Expression_Cassette
source                  1..1047
                        mol_type = other DNA
                        organism = synthetic construct
SEQUENCE: 447
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta ttttttttata taccttttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt gcgtacgcgt acgtgtggtt  1020
ttagagctat gctgttttgt ttttttt                                     1047

SEQ ID NO: 448          moltype = DNA  length = 1087
FEATURE                 Location/Qualifiers
misc_feature            1..1087
                        note = synthesized sequence- tracrRNA_Expression_Cassette
source                  1..1087
                        mol_type = other DNA
                        organism = synthetic construct
SEQUENCE: 448
tgagagtaca atgatgaacc tagattaatc aatgccaaag tctgaaaaat gcaccctcag  60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
```

-continued

```
gatttcttct gtttgttagc gcatgtacaa ggaatgcaag ttttgagcga gggggcatca  480
aagatctggc tgtgtttcca gctgtttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta ttttttata tacctttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt ggaaccattc aaaacagcat  1020
agcaagttaa aataaggcta gtccgttatc aacttgaaaa agtggcaccg agtcggtgct  1080
ttttttt                                                            1087

SEQ ID NO: 449          moltype = DNA  length = 63
FEATURE                 Location/Qualifiers
misc_feature            1..63
                        note = synthesized sequence- LIGCas-2 forward primer for
                         primary
source                  1..63
                        mol_type = other DNA
                        organism = synthetic construct
SEQUENCE: 449
ctacactctt tccctacacg acgctcttcc gatctgaagc tgtaacgatt tacgcacctg  60
ctg                                                                63

SEQ ID NO: 450          moltype = DNA  length = 60
FEATURE                 Location/Qualifiers
misc_feature            1..60
                        note = synthesized sequence- LIGCas-3 forward primer for
                         primary PCR
source                  1..60
                        mol_type = other DNA
                        organism = synthetic construct
SEQUENCE: 450
ctacactctt tccctacacg acgctcttcc gatctttccc gcaaatgagt agcagcgcac  60

SEQ ID NO: 451          moltype = DNA  length = 19
FEATURE                 Location/Qualifiers
source                  1..19
                        mol_type = genomic DNA
                        organism = Zea mays
SEQUENCE: 451
gcgtgcatcg atccatcgc                                               19

SEQ ID NO: 452          moltype = DNA  length = 21
FEATURE                 Location/Qualifiers
source                  1..21
                        mol_type = genomic DNA
                        organism = Zea mays
SEQUENCE: 452
ggctacggat agatatgatg c                                            21

SEQ ID NO: 453          moltype = DNA  length = 20
FEATURE                 Location/Qualifiers
source                  1..20
                        mol_type = genomic DNA
                        organism = Zea mays
SEQUENCE: 453
gttacttctc taagcacggc                                              20

SEQ ID NO: 454          moltype = DNA  length = 21
FEATURE                 Location/Qualifiers
misc_feature            1..21
                        note = synthesized sequence- P1, Forward_primer
source                  1..21
                        mol_type = other DNA
                        organism = synthetic construct
SEQUENCE: 454
gcgccattcc ctaaaggtaa c                                            21

SEQ ID NO: 455          moltype = DNA  length = 23
FEATURE                 Location/Qualifiers
misc_feature            1..23
                        note = synthesized sequence- P2, Reverse_primer
source                  1..23
                        mol_type = other DNA
                        organism = synthetic construct
SEQUENCE: 455
gctaatcgta agtgacgctt gga                                          23
```

```
SEQ ID NO: 456          moltype = DNA  length = 31
FEATURE                 Location/Qualifiers
misc_feature            1..31
                        note = synthesized sequence- P3, Forward_primer
source                  1..31
                        mol_type = other DNA
                        organism = synthetic construct
SEQUENCE: 456
gctcgtgtcc aagcgtcact tacgattagc t                                31

SEQ ID NO: 457          moltype = DNA  length = 20
FEATURE                 Location/Qualifiers
misc_feature            1..20
                        note = synthesized sequence- P4, Reverse_primer
source                  1..20
                        mol_type = other DNA
                        organism = synthetic construct
SEQUENCE: 457
ctgcgaactg cttgattccg                                             20

SEQ ID NO: 458          moltype = DNA  length = 24
FEATURE                 Location/Qualifiers
misc_feature            1..24
                        note = synthesized sequence- P5, Forward_primer
source                  1..24
                        mol_type = other DNA
                        organism = synthetic construct
SEQUENCE: 458
accgtcctta tctctgcatc atct                                        24

SEQ ID NO: 459          moltype = DNA  length = 31
FEATURE                 Location/Qualifiers
misc_feature            1..31
                        note = synthesized sequence- PBS, Primer Binding Site
source                  1..31
                        mol_type = other DNA
                        organism = synthetic construct
SEQUENCE: 459
gctcgtgtcc aagcgtcact tacgattagc t                                31

SEQ ID NO: 460          moltype = DNA  length = 1823
FEATURE                 Location/Qualifiers
misc_feature            1..1823
                        note = Zm-GOS2 PRO-GOS2 INTRON, maize GOS2 promoter and
                         GOS2 intron1 including the promoter, 5'-UTR1, INTRON1 and
                         5'-UTR2 sequence
source                  1..1823
                        mol_type = genomic DNA
                        organism = Zea mays
SEQUENCE: 460
taattattgg ctgtaggatt ctaaacagag cctaaatagc tggaatagct ctagccctca  60
atccaaacta atgatatcta tacttatgca actctaaatt tttattctaa aagtaatatt  120
tcatttttgt caacgagatt ctctactcta ttccacaatc ttttgaagct atatttacct  180
taaatctgta ctctatacca ataatcatat attctattat ttatttttat ctctctccta  240
aggagcatcc ctctatgtct gcatggcccc cgcctcgggt cccaatctct tgctctgcta  300
gtagcacaga agaaaacact agaaatgact tgcttgactt agagtatcag ataaacatca  360
tgtttactta actttaattt gtatcggttt ctactatttt tataatattt ttgtctctat  420
agatactacg tgcaacagta taatcaacct agtttaatcc agagcgaagg attttttact  480
aagtacgtga ctccatatgc acagcgttcc ttttatggtt cctcactggg cacagcataa  540
acgaaccctg tccaatgttt tcagcgcgaa caaacagaaa ttccatcagc gaacaaacaa  600
catacatgcg agatgaaaat aaataataaa aaaagctccg tctcgatagg ccggcacgaa  660
tcgagagcct ccatagccag tttttttccat cggaacggcg gttcgcgcac ctaattatat  720
gcaccacacg cctataaagc caaccaaccc gtcggagggg cgcaagccag acagaagaca  780
gcccgtcagc ccctctcgtt tttcatccgc cttcgcctcc aaccgcgtgc gctccacgcc  840
tcctccagga aagcgagagg tgagcgcagt cccctttccc ctccttccaa ttcaattcgt  900
cttctcgttc gcagccctag gatttggggg tctggagggg tttgatcgtt tctcgccgtg  960
aatctgcttt ggtgtaaacc aacggatctc ggatcgtagt cttcagaaga tcccggattt  1020
tgcggtttgg cccctcctgg attcaattcg tcgtatcgtt cgcagcccta ggatttgggg  1080
atctggaggg gtttgatcgt ttctcgccgc gaatctgctc tggtgtaaac caacggatct  1140
cgggtcgtag tcttcagaag gtcccggatt ttgcggtttg gcccctcctg gattcaattc  1200
gtcgtatcgt tcgcagccct aggatttggg gatctggagg ggtttgatcc tttctcgccg  1260
cgaatctgct ctggtataac caacggatct cgggtcgtag tcttcagaag gtcccggatt  1320
ttgcggtttg gtggttcttg ctctatgaat cagagggatg gttcttcccg gatttatgcc  1380
ttgcggccac tctgtcgaat catggggttt cgacccgatt cgtaggcgtg ctccctgttt  1440
tggatgggaa gtaggcgtgt ttgtagtatt cgtgcttcga ttcgtcaacg gagattagaa  1500
gacctgggat gggatttgag gaaatctagg tatctgtcta gcacgtttct agatctattc  1560
ttcagctgtt atatgagagt aattttggaa ccctggtggg gtatgtttga ccgagtattc  1620
tgtagattat tgtccgtgac ttgctggctg ttaccgtcct tatctctgca tcatctatct  1680
```

-continued

```
gtgctagttt ctgcgtgctt ctcaaatatt tccggcctgt gtagcatgtg actgataata  1740
tgattttggc agcttctgca taagaacaac aaatcaaaag cttgatcagc tcggtgccta  1800
caaaacctca acaaccaagt ttc                                          1823

SEQ ID NO: 461         moltype = DNA  length = 556
FEATURE                Location/Qualifiers
misc_feature           1..556
                       note = Zm-ARGOS8 promoter
source                 1..556
                       mol_type = genomic DNA
                       organism = Zea mays
SEQUENCE: 461
gttacttctc taagcacggc tggatttcag gcctctagtc ctctactagt actagctaca  60
cgacgtgcac gcatgcatca cagcatcaac aactagacac gcacacgctg cacgcggccg  120
gggaacccac tgattccccc cttccccgcg cgcggtttga tttcctttcc tggtacggat  180
ccatatctga gggcttgttc ggttattccc aacacacatg tattggatgg gattgaaaaa  240
aaaatgagaa gaagtttgac ttgtttggga ttcaaaccca tccaatccca ctcaatccac  300
atggattgag agctaaccga acaagccctc atagtacata cctggtacgg atccatatca  360
tagtacatag atccagtaga atagaaggtg atccgaccgc cggcgcttgc gttgttttcc  420
ccggtccatt gaacctgcca accctcctaa ccacaggcac gccaaaccgc gggctccggc  480
caccaccgcc accgccacct gccctgccgc acctctccaa ccccaaatcc aggggggggg  540
gggggcacca tgcgtg                                                  556

SEQ ID NO: 462         moltype = DNA  length = 155
FEATURE                Location/Qualifiers
misc_feature           1..155
                       note = Zm-ARGOS8 5'-UTR
source                 1..155
                       mol_type = genomic DNA
                       organism = Zea mays
SEQUENCE: 462
catcgatcca tcgctggcgc gcgggtccgg cggggcggtc tgtgagggca aatttatata  60
ggtctagtgg gtacccggct acggatagat atgatgctgc actgcacatt ggctatatct  120
gaggctcctg cgcgcgcctt ggccaggtgt ctgtc                             155

SEQ ID NO: 463         moltype = DNA  length = 285
FEATURE                Location/Qualifiers
source                 1..285
                       mol_type = genomic DNA
                       organism = Zea mays
SEQUENCE: 463
atgcgggcga tgccgcagga agaggaagcc gcggtggcga cgacgaccat ggccgggggc  60
aaggtggcgg cgctgctggc cacggcggcc gcgctgctgc tgctgctccc gctggcgctg  120
ccgccgctgc cgccgccgcc cacgcagctg ttgttcgtcc ccgtggtctt gctgctcctc  180
gtggcgtccc tcgcgttctg ccccgccgcg accccctcgc cgtcgccgat gcatgccgcc  240
gaccacgggt cgttcgggac cactggatca ccgcacctat gttga                  285

SEQ ID NO: 464         moltype = DNA  length = 2843
FEATURE                Location/Qualifiers
misc_feature           1..2843
                       note = Zm-GOS2 gene, including promoter, 5'-UTR, CDS,
                        3'-UTR and introns sequence
source                 1..2843
                       mol_type = genomic DNA
                       organism = Zea mays
SEQUENCE: 464
taattattgg ctgtaggatt ctaaacagag cctaaatagc tggaatagct ctagccctca  60
atccaaacta atgatatcta tacttatgca actctaaatt tttattctaa aagtaatatt  120
tcatttttgt caacgagatt ctctactcta ttccacaatc ttttgaagct atatttacct  180
taaatctgta ctctatacca ataatcatat attctattat ttatttttat ctctctccta  240
aggagcatcc ctctatgtct gcatggcccc cgcctcgggt cccaatctct tgctctgcta  300
gtagcacaga agaaaacact agaaatgact tgcttgactt agagtatcag ataaacatca  360
tgtttactta actttaattt gtatcggttt ctactatttt tataatattt ttgtctctat  420
agatactacg tgcaacagta taatcaacct agtttaatcc agagcgaagg attttttact  480
aagtacgtga ctccatatgc acagcgttcc ttttatggtt cctcactggg cacagcataa  540
acgaaccctg tccaatgttt tcagcgcgaa caaacagaaa ttccatcagc gaacaaacaa  600
catacatgcg agatgaaaat aaataataaa aaaagctccg tctcgatagg ccggcacgaa  660
tcgagagcct ccatagccag ttttttccat cggaacggcg gttcgcgcac ctaattatat  720
gcaccacacg cctataaagc caaccaaccc gtcggagggg cgcaagccag acagaagaca  780
gcccgtcagc ccctctcgtt tttcatccgc cttcgcctcc aaccgcgtgc gctccacgcc  840
tcctccagga aagcgagagg tgagcgcagt cccctttccc ctccttccaa ttcaattcgt  900
cttctcgttc gcagccctag gatttggggg tctggagggg tttgatcgtt tctcgccgtg  960
aatctgcttt ggtgtaaacc aacggatctc ggatcgtagt cttcagaaga tcccggattt  1020
tgcggtttgg cccctcctgg attcaattcg tcgtatcgtt cgcagcccta ggatttgggg  1080
atctggaggg gtttgatcgt ttctcgccgc gaatctgctc tggtgtaaac caacggatct  1140
cgggtcgtag tcttcagaag gtcccggatt ttgcggtttg gcccctcctg gattcaattc  1200
gtcgtatcgt tcgcagccct aggatttggg gatctggagg ggtttgatcc tttctcgccg  1260
cgaatctgct ctggtataac caacggatct cgggtcgtag tcttcagaag gtcccggatt  1320
ttgcggtttg gtggttcttg ctctatgaat cagagggatg gttcttcccg gatttatgcc  1380
```

```
ttgcggccac tctgtcgaat catggggttt cgacccgatt cgtaggcgtg ctccctgttt  1440
tggatgggaa gtaggcgtgt ttgtagtatt cgtgcttcga ttcgtcaacg gagattagaa  1500
gacctgggat gggatttgag gaaatctagg tatctgtcta gcacgtttct agatctattc  1560
ttcagctgtt atatgagagt aattttggaa ccctggtggg gtatgtttga ccgagtattc  1620
tgtagattat tgtccgtgac ttgctggctg ttaccgtcct tatctctgca tcatctatct  1680
gtgctagttt ctgcgtgctt ctcaaatatt tccggcctgt gtagcatgtg actgataata  1740
tgattttggc agcttctgca taagaacaac aaatcaaaag cttgatcagc tcggtgccta  1800
caaaacctca acaaccaagt ttcatgtctg atctcgacgt ccagcttcca tctgcctttg  1860
gtatggctac ttctcaattc atgatgccat gttttttttt atattgtggt tttacataat  1920
acatagcatc ttccagcttc ctgaagagta ttactgaata gattgataac atcatacaca  1980
cgaagttcat cttgaacatg cttattagtg ttctgtttgc atctgatggt atggcatcat  2040
ctttgataga tccgtttgct gaggcaaatg ctgaggactc tggtgctggt cctggaacga  2100
aggattatgt gcatgtgcgc atccagcagc gcaacggcag aaagagtctg actacagtcc  2160
agggtctgaa gaaagagttc agctataaca agatcctcaa ggatctgaag aaggaattct  2220
gctgcaatgg tactgtagtt caggacccag agctaggcca ggtaagatac gagaacaatg  2280
catttcaagc ttgtaaaaat ggtatctgcc ggttggtgga tatactgatc tgtttgtccg  2340
ctgcaggtca ttcagctcca aggtgaccag cgcaagaatg ttgctacttt cctagttcag  2400
gtattcagaa tcttcagacc tggccagctg aatactgttt taccataccg atagatgttc  2460
aatctgttaa tactgatcgt gcaattatta cttgtcttgg taggctggga ttgcgaagaa  2520
agagaacatc aagattcacg ggttctaagg gacctgtaaa tgcttgtgcc ctatattgtg  2580
tgcctccaca tattggggag cttgaagcat cgacagttac tagtcattgc ttacttatat  2640
aagaacataa gtagtatttg ctattgtcaa gtgtgccttg cttgatgcaa gttgtgtttt  2700
cgtatcatta ttattatgca cggccatcgt acgtgtatgg cttgtatggg ttattgccaa  2760
cttaataaaa gcacactctg tttgcctata agcactgatg tttgcctcgt catgcacatg  2820
ttgagtcggg ttttatttgt att                                          2843

SEQ ID NO: 465         moltype = DNA  length = 800
FEATURE                Location/Qualifiers
misc_feature           1..800
                       note = Zm-GOS2 PRO, maize GOS2 promoter
source                 1..800
                       mol_type = genomic DNA
                       organism = Zea mays
SEQUENCE: 465
taattattgg ctgtaggatt ctaaacagag cctaaatagc tggaatagct ctagccctca  60
atccaaacta atgatatcta tacttatgca actctaaatt tttattctaa aagtaatatt  120
tcatttttgt caacgagatt ctctactcta ttccacaatc ttttgaagct atatttacct  180
taaatctgta ctctatacca ataatcatat attctattat ttatttttat ctctctccta  240
aggagcatcc ctctatgtct gcatggcccc cgcctcgggt cccaatctct tgctctgcta  300
gtagcacaga agaaaacact agaaatgact tgcttgactt agagtatcag ataaacatca  360
tgtttactta actttaattt gtatcggttt ctactatttt tataatattt ttgtctctat  420
agatactacg tgcaacagta taatcaacct agtttaatcc agagcgaagg atttttttact  480
aagtacgtga ctccatatgc acagcgttcc ttttatggtt cctcactggg cacagcataa  540
acgaaccctg tccaatgttt tcagcgcgaa caaacagaaa ttccatcagc gaacaaacaa  600
catacatgcg agatgaaaat aaataataaa aaaagctccg tctcgatagg ccggcacgaa  660
tcgagagcct ccatagccag ttttttccat cggaacggcg gttcgcgcac ctaattatat  720
gcaccacacg cctataaagc caaccaaccc gtcggagggg cgcaagccag acagaagaca  780
gcccgtcagc ccctctcgtt                                              800

SEQ ID NO: 466         moltype = DNA  length = 1023
FEATURE                Location/Qualifiers
misc_feature           1..1023
                       note = GOS2 INTRON, maize GOS2 5'-UTR1 and intron1 and
                        5'-UTR2 sequence
source                 1..1023
                       mol_type = genomic DNA
                       organism = Zea mays
SEQUENCE: 466
tttcatccgc cttcgcctcc aaccgcgtgc gctccacgcc tcctccagga aagcgagagg  60
tgagcgcagt cccctttccc ctccttccaa ttcaattcgt cttctcgttc gcagccctag  120
gatttggggg tctggagggg tttgatcgtt tctcgccgtg aatctgcttt ggtgtaaacc  180
aacggatctc ggatcgtagt cttcagaaga tcccggattt tgcggtttgg cccctcctgg  240
attcaattcg tcgtatcgtt cgcagcccta ggatttgggg atctggaggg gtttgatcgt  300
ttctcgccgc gaatctgctc tggtgtaaac caacggatct cgggtcgtag tcttcagaag  360
gtcccggatt ttgcggtttg gcccctcctg gattcaattc gtcgtatcgt tcgcagccct  420
aggatttggg gatctggagg ggtttgatcc tttctcgccg cgaatctgct ctggtataac  480
caacggatct cgggtcgtag tcttcagaag gtcccggatt ttgcggtttg gtggttcttg  540
ctctatgaat cagagggatg gttcttcccg gatttatgcc ttgcggccac tctgtcgaat  600
catggggttt cgacccgatt cgtaggcgtg ctccctgttt tggatgggaa gtaggcgtgt  660
ttgtagtatt cgtgcttcga ttcgtcaacg gagattagaa gacctgggat gggatttgag  720
gaaatctagg tatctgtcta gcacgtttct agatctattc ttcagctgtt atatgagagt  780
aattttggaa ccctggtggg gtatgtttga ccgagtattc tgtagattat tgtccgtgac  840
ttgctggctg ttaccgtcct tatctctgca tcatctatct gtgctagttt ctgcgtgctt  900
ctcaaatatt tccggcctgt gtagcatgtg actgataata tgattttggc agcttctgca  960
taagaacaac aaatcaaaag cttgatcagc tcggtgccta caaaacctca acaaccaagt  1020
ttc                                                                1023

SEQ ID NO: 467         moltype = DNA  length = 23
FEATURE                Location/Qualifiers
```

```
source                  1..23
                        mol_type = genomic DNA
                        organism = Glycine max
SEQUENCE: 467
gcgtcctttg acagcagctg tgg                                          23

SEQ ID NO: 468          moltype = DNA  length = 23
FEATURE                 Location/Qualifiers
source                  1..23
                        mol_type = genomic DNA
                        organism = Glycine max
SEQUENCE: 468
gcaaccacag ctgctgtcaa agg                                          23

SEQ ID NO: 469          moltype = DNA  length = 434
FEATURE                 Location/Qualifiers
source                  1..434
                        mol_type = genomic DNA
                        organism = Glycine max
SEQUENCE: 469
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaa                                                    434

SEQ ID NO: 470          moltype = DNA  length = 9093
FEATURE                 Location/Qualifiers
misc_feature            1..9093
                        note = synthesized sequence- QC878
source                  1..9093
                        mol_type = other DNA
                        organism = synthetic construct
SEQUENCE: 470
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg cgtcctttga cagcagctgg ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attcttttgg tttttgaatc gattaatcgg aagagatttt cgagttattt  1560
ggtgtgttgg aggtgaatct tttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttttgt gggtttgttc acatgttatc aagcttaatc ttttactatg tatgcgacca  1860
tatctggatc cagcaaaggc gatttttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggacaa aaagtactca atagggctcg acatagggac  2100
taactccgtt ggatgggccg tcatcaccga cgagtacaag gtgccctcca agaagttcaa  2160
ggtgttggga aacaccgaca ggcacagcat aaagaagaat ttgatcggtg ccctcctctt  2220
cgactccgga gagaccgctg aggctaccag gctcaagagg accgctagaa ggcgctacac  2280
cagaaggaag aacagaatct gctacctgca ggagatcttc tccaacgaga tggccaaggt  2340
ggacgactcc ttcttccacc gccttgagga atcattcctg gtggaggagg ataaaaagca  2400
cgagagacac ccaatcttcg ggaacatcgt cgacgaggtg gcctaccatg aaaagtaccc  2460
taccatctac cacctgagga agaagctggt cgactctacc gacaaggctg acttgcgctt  2520
```

-continued

```
gatttacctg gctctcgctc acatgataaa gttccgcgga cacttcctca ttgagggaga  2580
cctgaaccca gacaactccg acgtggacaa gctcttcatc cagctcgttc agacctacaa  2640
ccagcttttc gaggagaacc caatcaacgc cagtggagtt gacgccaagg ctatcctctc  2700
tgctcgtctg tcaaagtcca ggaggcttga gaacttgatt gcccagctgc ctggcgaaaa  2760
gaagaacgga ctgttcggaa acttgatcgc tctctccctg ggattgactc ccaacttcaa  2820
gtccaacttc gacctcgccg aggacgctaa gttgcagttg tctaaagaca cctacgacga  2880
tgacctcgac aacttgctgg cccagatagg cgaccaatac gccgatctct tcctcgccgc  2940
taagaacttg tccgacgcaa tcctgctgtc cgacatcctg agagtcaaca ctgagattac  3000
caaagctcct ctgtctgctt ccatgattaa gcgctacgac gagcaccacc aagatctgac  3060
cctgctcaag gccctggtga gacagcagct gcccgagaag tacaaggaga tctttttcga  3120
ccagtccaag aacggctacg ccggatacat tgacggaggc gcctcccagg aagagttcta  3180
caagttcatc aagcccatcc ttgagaagat ggacggtacc gaggagctgt tggtgaagtt  3240
gaacagagag gacctgttga ggaagcagag aaccttcgac aacggaagca tccctcacca  3300
aatccacctg ggagagctcc acgccatctt gaggaggcag gaggatttct atcccttcct  3360
gaaggacaac cgcgagaaga ttgagaagat cttgaccttc agaattcctt actacgtcgg  3420
gccactcgcc agaggaaact ctaggttcgc ctggatgacc cgcaaatctg aagagaccat  3480
tactccctgg aacttcgagg aagtcgtgga caagggcgct tccgctcagt ctttcatcga  3540
gaggatgacc aacttcgata aaaatctgcc caacgagaag gtgctgccca agcactccct  3600
gttgtacgag tatttcacag tgtacaacga gctcaccaag gtgaagtacg tcacagaggg  3660
aatgaggaag cctgccttct tgtccggaga gcagaagaag gccatcgtcg acctgctctt  3720
caagaccaac aggaaggtga ctgtcaagca gctgaaggag gactacttca agaagatcga  3780
gtgcttcgac tccgtcgaga tctctggtgt cgaggacagg ttcaacgcct cccttgggac  3840
ttaccacgat ctgctcaaga ttattaaaga caaggacttc ctggacaacg aggagaacga  3900
ggacatcctt gaggacatcg tgctcaccct gaccttgttc gaagacaggg aaatgatcga  3960
agagaggctc aagacctacg cccacctctt cgacgacaag gtgatgaaac agctgaagag  4020
acgcagatat accggctggg gaaggctctc ccgcaaattg atcaacggga tcagggacaa  4080
gcagtcaggg aagactatac tcgacttcct gaagtccgac ggattcgcca acaggaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaagggc attttgcaga ccgtgaaggt cgttgacgag ctcgtgaagg tgatgggacg  4320
ccacaagcca gagaacatcg ttattgagat ggctcgcgag aaccaaacta cccagaaagg  4380
gcagaagaat tcccgcgaga ggatgaagcg cattgaggag ggcataaaag agcttggctc  4440
tcagatcctc aaggagcacc ccgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tcccctccga  4680
ggaggtcgtg aagaagatga aaaactactg gagacagctc ttgaacgcca agctcatcac  4740
ccagcgtaag ttcgacaacc tgactaaggc tgagagagga ggattgtccg agctcgataa  4800
ggccggattc atcaagagac agctcgtcga aacccgccaa attaccaagc acgtggccca  4860
aattctggat tcccgcatga acaccaagta cgatgaaaat gacaagctga tccgcgaggt  4920
caaggtgatc accttgaagt ccaagctggt ctccgacttc cgcaaggact tccagttcta  4980
caaggtgagg gagatcaaca actaccacca cgcacacgac gcctacctca acgctgtcgt  5040
tggaaccgcc ctcatcaaaa aatatcctaa gctggagtct gagttcgtct acggcgacta  5100
caaggtgtac gacgtgagga agatgatcgc taagtctgag caggagatcg gcaaggccac  5160
cgccaagtac ttcttctact ccaacatcat gaacttcttc aagaccgaga tcactctcgc  5220
caacggtgag atcaggaagc gcccactgat cgagaccaac ggtgagactg gagagatcgt  5280
gtgggacaaa gggagggatt tcgctactgt gaggaaggtg ctctccatgc ctcaggtgaa  5340
catcgtcaag aagaccgaag ttcagaccgg aggattctcc aaggagtcca tcctccccaa  5400
gagaaactcc gacaagctga tcgctagaaa gaaagactgg gaccctaaga agtacggagg  5460
cttcgattct cctaccgtgg cctactctgt gctggtcgtg gccaaggtgg agaagggcaa  5520
gtccaagaag ctgaaatccg tcaaggagct cctcgggatt accatcatgg agaggagttc  5580
cttcgagaag aaccctatcg acttcctgga ggccaaggga tataaagagg tgaagaagga  5640
cctcatcatc aagctgccca agtactccct cttcgagttg gagaacggaa ggaagaggat  5700
gctggcttct gccggagagt tgcagaaggg aaatgagctc gcccttccct ccaagtacgt  5760
gaacttcctg tacctcgcct ctcactatga aaagttgaag ggctctcctg aggacaacga  5820
gcagaagcag ctcttcgtgg agcagcacaa gcactacctg gacgaaatta tcgagcagat  5880
ctctgagttc tccaagcgcg tgatattggc cgacgccaac ctcgacaagg tgctgtccgc  5940
ctacaacaag cacagggata agcccattcg cgagcaggct gaaaacatta tccacctgtt  6000
taccctcaca aacttgggag cccctgctgc cttcaagtac ttcgacacca ccattgacag  6060
gaagagatac acctccacca aggaggtgct cgacgcaaca ctcatccacc aatccatcac  6120
cggcctctat gaaacaagga ttgacttgtc ccagctggga ggcgactcta gagccgatcc  6180
caagaagaag agaaaggtgt aggttaacct agacttgtcc atcttctgga ttggccaact  6240
taattaatgt atgaaataaa aggatgcaca catagtgaca tgctaatcac tataatgtgg  6300
gcatcaaagt tgtgtgttat gtgtaattac tagttatctg aataaaagag aaagagatca  6360
tccatatttc ttatcctaaa tgaatgtcac gtgtctttat aattctttga tgaaccagat  6420
gcatttcatt aaccaaatcc atatacatat aaatattaat catatataat taatatcaat  6480
tgggttagca aaacaaatct agtctaggtg tgttttgcga attcgatatc aagcttatcg  6540
ataccgtcga ggggggggccc ggtaccggcg cgccgttcta tagtgtcacc taaatcgtat  6600
gtgtatgata cataaggtta tgtattaatt gtagccgcgt tctaacgaca atatgtccat  6660
atggtgcact ctcagtacaa tctgctctga tgccgcatag ttaagccagc cccgacaccc  6720
gccaacaccc gctgacgcgc cctgacgggc ttgtctgctc ccggcatccg cttacagaca  6780
agctgtgacc gtctccggga gctgcatgtg tcagaggttt tcaccgtcat caccgaaacg  6840
cgcgagacga aagggcctcg tgatacgcct atttttatag gttaatgtca tgaccaaaat  6900
cccttaacgt gagttttcgt tccactgagc gtcagacccc gtagaaaaga tcaaaggatc  6960
ttcttgagat cctttttttc tgcgcgtaat ctgctgcttg caaacaaaaa aaccaccgct  7020
accagcggtg gtttgtttgc cggatcaaga gctaccaact ctttttccga aggtaactgg  7080
cttcagcaga gcgcagatac caaatactgt ccttctagtg tagccgtagt taggccacca  7140
cttcaagaac tctgtagcac cgcctacata cctcgctctg ctaatcctgt taccagtggc  7200
tgctgccagt ggcgataagt cgtgtcttac cgggttggac tcaagacgat agttaccgga  7260
```

-continued

```
taaggcgcag cggtcgggct gaacgggggg ttcgtgcaca cagcccagct tggagcgaac  7320
gacctacacc gaactgagat acctacagcg tgagcattga gaaagcgcca cgcttcccga  7380
agggagaaag gcggacaggt atccggtaag cggcagggtc ggaacaggag agcgcacgag  7440
ggagcttcca gggggaaacg cctggtatct ttatagtcct gtcgggtttc gccacctctg  7500
acttgagcgt cgatttttgt gatgctcgtc aggggggcgg agcctatgga aaaacgccag  7560
caacgcggcc tttttacggt tcctggcctt ttgctggcct tttgctcaca tgttctttcc  7620
tgcgttatcc cctgattctg tggataaccg tattaccgcc tttgagtgag ctgataccgc  7680
tcgccgcagc cgaacgaccg agcgcagcga gtcagtgagc gaggaagcgg aagagcgccc  7740
aatacgcaaa ccgcctctcc ccgcgcgttg gccgattcat taatgcaggt tgatcagatc  7800
tcgatcccgc gaaattaata cgactcacta tagggagacc acaacggttt ccctctagaa  7860
ataattttgt ttaactttaa gaaggagata tacccatgga aaagcctgaa ctcaccgcga  7920
cgtctgtcga gaagtttctg atcgaaaagt tcgacagcgt ctccgacctg atgcagctct  7980
cggagggcga agaatctcgt gctttcagct tcgatgtagg agggcgtgga tatgtcctgc  8040
gggtaaatag ctgcgccgat ggtttctaca aagatcgtta tgtttatcgg cactttgcat  8100
cggccgcgct cccgattccg gaagtgcttg acattgggga attcagcgag agcctgacct  8160
attgcatctc ccgccgtgca cagggtgtca cgttgcaaga cctgcctgaa accgaactgc  8220
ccgctgttct gcagccggtc gcggaggcta tggatgcgat cgctgcggcc gatcttagcc  8280
agacgagcgg gttcggccca ttcggaccgc aaggaatcgg tcaatacact acatggcgtg  8340
atttcatatg cgcgattgct gatccccatg tgtatcactg gcaaactgtg atggacgaca  8400
ccgtcagtgc gtccgtcgcg caggctctcg atgagctgat gctttgggcc gaggactgcc  8460
ccgaagtccg gcacctcgtg cacgcggatt tcggctccaa caatgtcctg acggacaatg  8520
gccgcataac agcggtcatt gactggagcg aggcgatgtt cggggattcc caatacgagg  8580
tcgccaacat cttcttctgg aggccgtggt tggcttgtat ggagcagcag acgcgctact  8640
tcgagcggag gcatccggag cttgcaggat cgccgcggct ccgggcgtat atgctccgca  8700
ttggtcttga ccaactctat cagagcttgg ttgacggcaa tttcgatgat gcagcttggg  8760
cgcagggtcg atgcgacgca atcgtccgat ccggagccgg gactgtcggg cgtacacaaa  8820
tcgcccgcag aagcgcggcc gtctggaccg atggctgtgt agaagtactc gccgatagtg  8880
gaaaccgacg ccccagcact cgtccgaggg caaaggaata gtgaggtaca gcttggatcg  8940
atccggctgc taacaaagcc cgaaaggaag ctgagttggc tgctgccacc gctgagcaat  9000
aactagcata accccttggg gcctctaaac gggtcttgag gggttttttg ctgaaaggag  9060
gaactatatc cggatgatcg ggcgcgccgg tac                              9093

SEQ ID NO: 471         moltype = DNA  length = 9093
FEATURE                Location/Qualifiers
misc_feature           1..9093
                       note = synthesized sequence- QC879
source                 1..9093
                       mol_type = other DNA
                       organism = synthetic construct
SEQUENCE: 471
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg caaccacagc tgctgtcaag ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gtttttttagg attcttttgg tttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttttgt gggtttgttc acatgttatc aagcttaatc ttttactatg tatgcgacca  1860
tatctggatc cagcaaaggc gatttttttaa ttccttgtga aactttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggacaa aaagtactca atagggctcg acatagggac  2100
taactccgtt ggatgggccg tcatcaccga cgagtacaag gtgccctcca agaagttcaa  2160
ggtgttggga aacaccgaca ggcacagcat aaagaagaat ttgatcggtg ccctcctctt  2220
cgactccgga gagaccgctg aggctaccag gctcaagagg accgctagaa ggcgctacac  2280
cagaaggaag aacagaatct gctacctgca ggagatcttc tccaacgaga tggccaaggt  2340
```

-continued

```
ggacgactcc ttcttccacc gccttgagga atcattcctg gtggaggagg ataaaaagca  2400
cgagagacac ccaatcttcg ggaacatcgt cgacgaggtg gcctaccatg aaaagtaccc  2460
taccatctac cacctgagga agaagctggt cgactctacc gacaaggctg acttgcgctt  2520
gatttacctg gctctcgctc acatgataaa gttccgcgga cacttcctca ttgagggaga  2580
cctgaaccca gacaactccg acgtggacaa gctcttcatc cagctcgttc agacctacaa  2640
ccagcttttc gaggagaacc caatcaacgc cagtggagtt gacgccaagg ctatcctctc  2700
tgctcgtctg tcaaagtcca ggaggcttga gaacttgatt gcccagctgc ctggcgaaaa  2760
gaagaacgga ctgttcggaa acttgatcgc tctctccctg ggattgactc ccaacttcaa  2820
gtccaacttc gacctcgccg aggacgctaa gttgcagttg tctaaagaca cctacgacga  2880
tgacctcgac aacttgctgg cccagatagg cgaccaatac gccgatctct tcctcgccgc  2940
taagaacttg tccgacgcaa tcctgctgtc cgacatcctg agagtcaaca ctgagattac  3000
caaagctcct ctgtctgctt ccatgattaa gcgctacgac gagcaccacc aagatctgac  3060
cctgctcaag gccctggtga gacagcagct gcccgagaag tacaaggaga tctttttcga  3120
ccagtccaag aacggctacg ccggatacat tgacggaggc gcctcccagg aagagttcta  3180
caagttcatc aagcccatcc ttgagaagat ggacggtacc gaggagctgt tggtgaagtt  3240
gaacagagag gacctgttga ggaagcagag aaccttcgac aacggaagca tccctcacca  3300
aatccacctg ggagagctcc acgccatctt gaggaggcag gaggatttct atcccttcct  3360
gaaggacaac cgcgagaaga ttgagaagat cttgaccttc agaattcctt actacgtcgg  3420
gccactcgcc agaggaaact ctaggttcgc ctggatgacc cgcaaatctg aagagaccat  3480
tactccctgg aacttcgagg aagtcgtgga caagggcgct tccgctcagt ctttcatcga  3540
gaggatgacc aacttcgata aaaatctgcc caacgagaag gtgctgccca agcactccct  3600
gttgtacgag tatttcacag tgtacaacga gctcaccaag gtgaagtacg tcacagaggg  3660
aatgaggaag cctgccttct tgtccggaga gcagaagaag gccatcgtcg acctgctctt  3720
caagaccaac aggaaggtga ctgtcaagca gctgaaggag gactacttca agaagatcga  3780
gtgcttcgac tccgtcgaga tctctggtgt cgaggacagg ttcaacgcct cccttgggac  3840
ttaccacgat ctgctcaaga ttattaaaga caaggacttc ctggacaacg aggagaacga  3900
ggacatcctt gaggacatcg tgctcaccct gaccttgttc gaagacaggg aaatgatcga  3960
agagaggctc aagacctacg cccacctctt cgacgacaag gtgatgaaac agctgaagag  4020
acgcagatat accggctggg gaaggctctc ccgcaaattg atcaacggga tcagggacaa  4080
gcagtcaggg aagactatac tcgacttcct gaagtccgac ggattcgcca acaggaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaagggc attttgcaga ccgtgaaggt cgttgacgag ctcgtgaagg tgatgggacg  4320
ccacaagcca gagaacatcg ttattgagat ggctcgcgag aaccaaacta cccagaaagg  4380
gcagaagaat tcccgcgaga ggatgaagcg cattgaggag ggcataaaag agcttggctc  4440
tcagatcctc aaggagcacc ccgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tcccctccga  4680
ggaggtcgtg aagaagatga aaaactactg gagacagctc ttgaacgcca agctcatcac  4740
ccagcgtaag ttcgacaacc tgactaaggc tgagagagga ggattgtccg agctcgataa  4800
ggccggattc atcaagagac agctcgtcga aacccgccaa attaccaagc acgtggccca  4860
aattctggat tcccgcatga acaccaagta cgatgaaaat gacaagctga tccgcgaggt  4920
caaggtgatc accttgaagt ccaagctggt ctccgacttc cgcaaggact tccagttcta  4980
caaggtgagg gagatcaaca actaccacca cgcacacgac gcctacctca acgctgtcgt  5040
tggaaccgcc ctcatcaaaa aatatcctaa gctggagtct gagttcgtct acggcgacta  5100
caaggtgtac gacgtgagga agatgatcgc taagtctgag caggagatcg gcaaggccac  5160
cgccaagtac ttcttctact ccaacatcat gaacttcttc aagaccgaga tcactctcgc  5220
caacggtgag atcaggaagc gcccactgat cgagaccaac ggtgagactg gagagatcgt  5280
gtgggacaaa gggagggatt tcgctactgt gaggaaggtg ctctccatgc ctcaggtgaa  5340
catcgtcaag aagaccgaag ttcagaccgg aggattctcc aaggagtcca tcctccccaa  5400
gagaaactcc gacaagctga tcgctagaaa gaaagactgg gaccctaaga agtacggagg  5460
cttcgattct cctaccgtgg cctactctgt gctggtcgtg gccaaggtgg agaagggcaa  5520
gtccaagaag ctgaaatccg tcaaggagct cctcgggatt accatcatgg agaggagttc  5580
cttcgagaag aaccctatcg acttcctgga ggccaaggga tataaagagg tgaagaagga  5640
cctcatcatc aagctgccca agtactccct cttcgagttg gagaacggaa ggaagaggat  5700
gctggcttct gccggagagt tgcagaaggg aaatgagctc gcccttccct ccaagtacgt  5760
gaacttcctg tacctcgcct ctcactatga aaagttgaag ggctctcctg aggacaacga  5820
gcagaagcag ctcttcgtgg agcagcacaa gcactacctg gacgaaatta tcgagcagat  5880
ctctgagttc tccaagcgcg tgatattggc cgacgccaac ctcgacaagg tgctgtccgc  5940
ctacaacaag cacagggata agcccattcg cgagcaggct gaaaacatta tccacctgtt  6000
taccctcaca aacttgggag cccctgctgc cttcaagtac ttcgacacca ccattgacag  6060
gaagagatac acctccacca aggaggtgct cgacgcaaca ctcatccacc aatccatcac  6120
cggcctctat gaaacaagga ttgacttgtc ccagctggga ggcgactcta gagccgatcc  6180
caagaagaag agaaaggtgt aggttaacct agacttgtcc atcttctgga ttggccaact  6240
taattaatgt atgaaataaa aggatgcaca catagtgaca tgctaatcac tataatgtgg  6300
gcatcaaagt tgtgtgttat gtgtaattac tagttatctg aataaaagag aaagagatca  6360
tccatatttc ttatcctaaa tgaatgtcac gtgtctttat aattctttga tgaaccagat  6420
gcatttcatt aaccaaatcc atatacatat aaatattaat catatataat taatatcaat  6480
tgggttagca aaacaaatct agtctaggtg tgttttgcga attcgatatc aagcttatcg  6540
ataccgtcga ggggggcccc ggtaccggcg cgccgttcta tagtgtcacc taaatcgtat  6600
gtgtatgata cataaggtta tgtattaatt gtagccgcgt tctaacgaca atatgtccat  6660
atggtgcact ctcagtacaa tctgctctga tgccgcatag ttaagccagc cccgacaccc  6720
gccaacaccc gctgacgcgc cctgacgggc ttgtctgctc ccggcatccg cttacagaca  6780
agctgtgacc gtctccggga gctgcatgtg tcagaggttt tcaccgtcat caccgaaacg  6840
cgcgagacga aagggcctcg tgatacgcct atttttatag gttaatgtca tgaccaaaat  6900
cccttaacgt gagttttcgt tccactgagc gtcagacccc gtagaaaaga tcaaaggatc  6960
ttcttgagat cctttttttc tgcgcgtaat ctgctgcttg caaacaaaaa aaccaccgct  7020
accagcggtg gtttgtttgc cggatcaaga gctaccaact ctttttccga aggtaactgg  7080
```

```
cttcagcaga gcgcagatac caaatactgt ccttctagtg tagccgtagt taggccacca  7140
cttcaagaac tctgtagcac cgcctacata cctcgctctg ctaatcctgt taccagtggc  7200
tgctgccagt ggcgataagt cgtgtcttac cgggttggac tcaagacgat agttaccgga  7260
taaggcgcag cggtcgggct gaacgggggg ttcgtgcaca cagcccagct tggagcgaac  7320
gacctacacc gaactgagat acctacagcg tgagcattga gaaagcgcca cgcttcccga  7380
agggagaaag gcggacaggt atccggtaag cggcagggtc ggaacaggag agcgcacgag  7440
ggagcttcca gggggaaacg cctggtatct ttatagtcct gtcgggtttc gccacctctg  7500
acttgagcgt cgatttttgt gatgctcgtc aggggggcgg agcctatgga aaaacgccag  7560
caacgcggcc tttttacggt tcctggcctt ttgctggcct tttgctcaca tgttctttcc  7620
tgcgttatcc cctgattctg tggataaccg tattaccgcc tttgagtgag ctgataccgc  7680
tcgccgcagc cgaacgaccg agcgcagcga gtcagtgagc gaggaagcgg aagagcgccc  7740
aatacgcaaa ccgcctctcc ccgcgcgttg gccgattcat taatgcaggt tgatcagatc  7800
tcgatcccgc gaaattaata cgactcacta tagggagacc acaacggttt ccctctagaa  7860
ataattttgt ttaactttaa gaaggagata tacccatgga aaagcctgaa ctcaccgcga  7920
cgtctgtcga gaagtttctg atcgaaaagt tcgacagcgt ctccgacctg atgcagctct  7980
cggagggcga agaatctcgt gctttcagct tcgatgtagg agggcgtgga tatgtcctgc  8040
gggtaaatag ctgcgccgat ggtttctaca aagatcgtta tgtttatcgg cactttgcat  8100
cggccgcgct cccgattccg gaagtgcttg acattgggga attcagcgag agcctgacct  8160
attgcatctc ccgccgtgca cagggtgtca cgttgcaaga cctgcctgaa accgaactgc  8220
ccgctgttct gcagccggtc gcggaggcta tggatgcgat cgctgcggcc gatcttagcc  8280
agacgagcgg gttcggccca ttcggaccgc aaggaatcgg tcaatacact acatggcgtg  8340
atttcatatg cgcgattgct gatccccatg tgtatcactg gcaaactgtg atggacgaca  8400
ccgtcagtgc gtccgtcgcg caggctctcg atgagctgat gctttgggcc gaggactgcc  8460
ccgaagtccg gcacctcgtg cacgcggatt tcggctccaa caatgtcctg acggacaatg  8520
gccgcataac agcggtcatt gactggagcg aggcgatgtt cggggattcc caatacgagg  8580
tcgccaacat cttcttctgg aggccgtggt tggcttgtat ggagcagcag acgcgctact  8640
tcgagcggag gcatccggag cttgcaggat cgccgcggct ccgggcgtat atgctccgca  8700
ttggtcttga ccaactctat cagagcttgg ttgacggcaa tttcgatgat gcagcttggg  8760
cgcagggtcg atgcgacgca atcgtccgat ccggagccgg gactgtcggg cgtacacaaa  8820
tcgcccgcag aagcgcggcc gtctggaccg atggctgtgt agaagtactc gccgatagtg  8880
gaaaccgacg ccccagcact cgtccgaggg caaaggaata gtgaggtaca gcttggatcg  8940
atccggctgc taacaaagcc cgaaaggaag ctgagttggc tgctgccacc gctgagcaat  9000
aactagcata accccttggg gcctctaaac gggtcttgag gggttttttg ctgaaaggag  9060
gaactatatc cggatgatcg ggcgcgccgg tac                               9093
```

```
SEQ ID NO: 472         moltype = DNA  length = 1357
FEATURE                Location/Qualifiers
misc_feature           1..1357
                       note = synthesized sequence- RTW1013A
source                 1..1357
                       mol_type = other DNA
                       organism = synthetic construct
SEQUENCE: 472
ctagaagata aaccctcccc caaaacacaa attagaatga catttcaagt tccatgtatg  60
tcactttcat tctattattt ttacaacttt tagttactta acagatgtct tgttcagcat  120
aaattataat ttattctgtt tttttttagg gaacaactgt tgtagacaac ttgttgtata  180
gtgaggatat tcattacatg cttggtgcat taaggaccct tggactgcgt gtggaagatg  240
acaaaaacaac caaacaagca attgttgaag gctgtgggggg attgtttccc actagtaagg  300
aatctaaaga tgaaatcaat ttattccttg gaaatgctgg tattgcaatg agatctttga  360
cagcagctgt tgttgctgca ggtggaaatg caaggtctgt ttttttttt tttgttcagc  420
ataatctttg aattgttcct cgtataacta atcacaacag agtacgtgtt cttcttcctg  480
ttataatcta aaaatctcat ccagattagt catcctttct tcttaaaagg aacctttaat  540
tatcaatgta tttatttaat atttaaatta gcttgtcaaa gtctagcata tacatatttt  600
gattatattc tgagaaatgc acctgagggt gttcctcatg atctacttca acctctgtta  660
ttattagatt ttctatcatg attactggtt tgagtctcta agtagaccat cttgatgttc  720
aaaatatttc agctacgtac ttgatggggt gccccgaatg agagagaggc caattgggga  780
tttggttgct ggtcttaagc aacttggtgc agatgttgat tgctttcttg gcacaaactg  840
tccacctgtt cgtgtaaatg ggaagggagg acttcctggc ggaaaggtat ggtttggatt  900
tcatttagaa taaggtggag taactttcct ggatcaaaat tctaatttaa gaagcctccc  960
tgttttcctc tctttagaat aagactaagg gtaggtttag gagttgggtt ttggagagaa  1020
atggaaggga gagcaatttt tttcttcttc taataaatat tctttaattt gatacatttt  1080
ttaagtaaaa gaatataaag atagattagc ataacttaat gttttaatct tttatttatt  1140
tttataaata ttatatacct gtctatttaa aaatcaaata tttgtcctcc attccctttc  1200
ccttcaaaac ctcagttcca aatataccgt agttgaatta tattttggaa ggcctattgg  1260
ttggagactt ttccttttca gagattatcc ctcaccttta ttatagcctt tctattttta  1320
aacttcatat agacgccatt cttggggcgg ccgcgat                            1357
```

```
SEQ ID NO: 473         moltype = DNA  length = 1357
FEATURE                Location/Qualifiers
misc_feature           1..1357
                       note = synthesized sequence- RTW1012A
source                 1..1357
                       mol_type = other DNA
                       organism = synthetic construct
SEQUENCE: 473
ctagaagata aaccctcccc caaaacacaa attagaatga catttcaagt tccatgtatg  60
tcactttcat tctattattt ttacaacttt tagttactta acagatgtct tgttcagcat  120
aaattataat ttattctgtt tttttttagg gaacaactgt tgtagacaac ttgttgtata  180
gtgaggatat tcattacatg cttggtgcat taaggaccct tggactgcgt gtggaagatg  240
```

```
acaaaacaac caaacaagca attgttgaag gctgtggggg attgtttccc actagtaagg  300
aatctaaaga tgaaatcaat ttattccttg gaaatgctgg tattgcaatg agatctttga  360
cagcagctgt ggttgctgca ggtggaaatg caaggtctgt tttttttttt tttgttcagc  420
ataatctttg aattgttcct cgtataacta atcacaacag agtacgtgtt cttcttcctg  480
ttataatcta aaaatctcat ccagattagt catcctttct tcttaaaagg aacctttaat  540
tatcaatgta tttatttaat atttaaatta gcttgtcaaa gtctagcata tacatatttt  600
gattatattc tgagaaatgc acctgagggt gttcctcatg atctacttca acctctgtta  660
ttattagatt ttctatcatg attactggtt tgagtctcta agtagaccat cttgatgttc  720
aaaatatttc agctacgtac ttgatggggt gccccgaatg agagagaggc caattgggga  780
tttggttgct ggtcttaagc aacttggtgc agatgttgat tgctttcttg gcacaaactg  840
tccacctgtt cgtgtaaatg ggaagggagg acttcctggc ggaaaggtat ggtttggatt  900
tcatttagaa taaggtggag taactttcct ggatcaaaat tctaatttaa gaagcctccc  960
tgttttcctc tctttagaat aagactaagg gtaggtttag gagttgggtt ttggagagaa  1020
atggaaggga gagcaatttt tttcttcttc taataaatat tctttaattt gatacatttt  1080
ttaagtaaaa gaatataaag atagattagc ataacttaat gttttaatct tttatttatt  1140
tttataaata ttatatacct gtctatttaa aaatcaaata tttgtcctcc attccctttc  1200
ccttcaaaac ctcagttcca aatataccgt agttgaatta tattttggaa ggcctattgg  1260
ttggagactt ttcctttca gagattatcc ctcaccttta ttatagcctt tctattttta  1320
aacttcatat agacgccatt cttggggcgg ccgcgat                          1357

SEQ ID NO: 474         moltype = DNA  length = 30
FEATURE                Location/Qualifiers
misc_feature           1..30
                       note = synthesized sequence- primer, soy1-F1
source                 1..30
                       mol_type = other DNA
                       organism = synthetic construct
SEQUENCE: 474
ccactagtaa ggaatctaaa gatgaaatca                                  30

SEQ ID NO: 475         moltype = DNA  length = 24
FEATURE                Location/Qualifiers
misc_feature           1..24
                       note = synthesized sequence- primer, soy1-R2
source                 1..24
                       mol_type = other DNA
                       organism = synthetic construct
SEQUENCE: 475
cctgcagcaa ccacagctgc tgtc                                        24

SEQ ID NO: 476         moltype = DNA  length = 15
FEATURE                Location/Qualifiers
misc_feature           1..15
                       note = synthesized sequence- probe, soy1-T1(FAM-MGB
source                 1..15
                       mol_type = other DNA
                       organism = synthetic construct
SEQUENCE: 476
ctgcaatgcg tcctt                                                  15

SEQ ID NO: 477         moltype = DNA  length = 19
FEATURE                Location/Qualifiers
misc_feature           1..19
                       note = synthesized sequence- primer, cas9-F
source                 1..19
                       mol_type = other DNA
                       organism = synthetic construct
SEQUENCE: 477
ccttcttcca ccgccttga                                              19

SEQ ID NO: 478         moltype = DNA  length = 21
FEATURE                Location/Qualifiers
misc_feature           1..21
                       note = synthesized sequence- primer, Cas9-R
source                 1..21
                       mol_type = other DNA
                       organism = synthetic construct
SEQUENCE: 478
tgggtgtctc tcgtgctttt t                                           21

SEQ ID NO: 479         moltype = DNA  length = 19
FEATURE                Location/Qualifiers
misc_feature           1..19
                       note = synthesized sequence- probe, Cas9-T(FAM-MGB)
source                 1..19
                       mol_type = other DNA
                       organism = synthetic construct
SEQUENCE: 479
aatcattcct ggtggagga                                              19
```

-continued

```
SEQ ID NO: 480         moltype = DNA  length = 25
FEATURE                Location/Qualifiers
misc_feature           1..25
                       note = synthesized sequence- primer, pINII-99F
source                 1..25
                       mol_type = other DNA
                       organism = synthetic construct
SEQUENCE: 480
tgatgcccac attatagtga ttagc                                        25

SEQ ID NO: 481         moltype = DNA  length = 22
FEATURE                Location/Qualifiers
misc_feature           1..22
                       note = synthesized sequence- primer, pINII-13R
source                 1..22
                       mol_type = other DNA
                       organism = synthetic construct
SEQUENCE: 481
catcttctgg attggccaac tt                                           22

SEQ ID NO: 482         moltype = DNA  length = 17
FEATURE                Location/Qualifiers
misc_feature           1..17
                       note = synthesized sequence- probe, pINII-69T(FAM-MGB)
source                 1..17
                       mol_type = other DNA
                       organism = synthetic construct
SEQUENCE: 482
actatgtgtg catcctt                                                 17

SEQ ID NO: 483         moltype = DNA  length = 23
FEATURE                Location/Qualifiers
misc_feature           1..23
                       note = synthesized sequence- primer, SIP-130F
source                 1..23
                       mol_type = other DNA
                       organism = synthetic construct
SEQUENCE: 483
ttcaagttgg gctttttcag aag                                          23

SEQ ID NO: 484         moltype = DNA  length = 22
FEATURE                Location/Qualifiers
misc_feature           1..22
                       note = synthesized sequence- primer, SIP-198R
source                 1..22
                       mol_type = other DNA
                       organism = synthetic construct
SEQUENCE: 484
tctccttggt gctctcatca ca                                           22

SEQ ID NO: 485         moltype = DNA  length = 15
FEATURE                Location/Qualifiers
misc_feature           1..15
                       note = synthesized sequence- probe, SIP-170T(VIC-MGB)
source                 1..15
                       mol_type = other DNA
                       organism = synthetic construct
SEQUENCE: 485
ctgcagcaga accaa                                                   15

SEQ ID NO: 486         moltype = DNA  length = 24
FEATURE                Location/Qualifiers
misc_feature           1..24
                       note = synthesized sequence- WOL569, Forward_primer
source                 1..24
                       mol_type = other DNA
                       organism = synthetic construct
SEQUENCE: 486
ggacccatta ggtgagagcg tggg                                         24

SEQ ID NO: 487         moltype = DNA  length = 19
FEATURE                Location/Qualifiers
misc_feature           1..19
                       note = synthesized sequence- WOL876, Reverse_primer
source                 1..19
                       mol_type = other DNA
                       organism = synthetic construct
SEQUENCE: 487
```

```
cagctgctgt caaagatct                                        19

SEQ ID NO: 488         moltype = DNA  length = 29
FEATURE                Location/Qualifiers
misc_feature           1..29
                       note = synthesized sequence- WOL570, Reverse_primer
source                 1..29
                       mol_type = other DNA
                       organism = synthetic construct
SEQUENCE: 488
tctaataata acagaggttg aagtagatc                             29

SEQ ID NO: 489         moltype = DNA  length = 4104
FEATURE                Location/Qualifiers
source                 1..4104
                       mol_type = genomic DNA
                       organism = Glycine max
SEQUENCE: 489
atggacaaaa agtactcaat agggctcgac atagggacta actccgttgg atgggccgtc  60
atcaccgacg agtacaaggt gccctccaag aagttcaagg tgttgggaaa caccgacagg  120
cacagcataa agaagaattt gatcggtgcc ctcctcttcg actccggaga gaccgctgag  180
gctaccaggc tcaagaggac cgctagaagg cgctacacca gaaggaagaa cagaatctgc  240
tacctgcagg agatcttctc caacgagatg gccaaggtgg acgactcctt cttccaccgc  300
cttgaggaat cattcctggt ggaggaggat aaaaagcacg agagacaccc aatcttcggg  360
aacatcgtcg acgaggtggc ctaccatgaa aagtacccta ccatctacca cctgaggaag  420
aagctggtcg actctaccga caaggctgac ttgcgcttga tttacctggc tctcgctcac  480
atgataaagt tccgcggaca cttcctcatt gagggagacc tgaacccaga caactccgac  540
gtggacaagc tcttcatcca gctcgttcag acctacaacc agcttttcga ggagaaccca  600
atcaacgcca gtggagttga cgccaaggct atcctctctg ctcgtctgtc aaagtccagg  660
aggcttgaga acttgattgc ccagctgcct ggcgaaaaga agaacggact gttcggaaac  720
ttgatcgctc tctccctggg attgactccc aacttcaagt ccaacttcga cctcgccgag  780
gacgctaagt tgcagttgtc taaagacacc tacgacgatg acctcgacaa cttgctggcc  840
cagataggcg accaatacgc cgatctcttc ctcgccgcta agaacttgtc cgacgcaatc  900
ctgctgtccg acatcctgag agtcaacact gagattacca aagctcctct gtctgcttcc  960
atgattaagc gctacgacga gcaccaccaa gatctgaccc tgctcaaggc cctggtgaga  1020
cagcagctgc ccgagaagta caaggagatc tttttcgacc agtccaagaa cggctacgcc  1080
ggatacattg acggaggcgc ctcccaggaa gagttctaca agttcatcaa gcccatcctt  1140
gagaagatgg acggtaccga ggagctgttg gtgaagttga acagagagga cctgttgagg  1200
aagcagagaa ccttcgacaa cggaagcatc cctcaccaaa tccacctggg agagctccac  1260
gccatcttga ggaggcagga ggatttctat cccttcctga aggacaaccg cgagaagatt  1320
gagaagatct tgaccttcag aattccttac tacgtcgggc cactcgccag aggaaactct  1380
aggttcgcct ggatgacccg caaatctgaa gagaccatta ctccctggaa cttcgaggaa  1440
gtcgtggaca agggcgcttc cgctcagtct ttcatcgaga ggatgaccaa cttcgataaa  1500
aatctgccca acgagaaggt gctgcccaag cactccctgt tgtacgagta tttcacagtg  1560
tacaacgagc tcaccaaggt gaagtacgtc acagagggaa tgaggaagcc tgccttcttg  1620
tccggagagc agaagaaggc catcgtcgac ctgctcttca agaccaacag gaaggtgact  1680
gtcaagcagc tgaaggagga ctacttcaag aagatcgagt gcttcgactc cgtcgagatc  1740
tctggtgtcg aggacaggtt caacgcctcc cttgggactt accacgatct gctcaagatt  1800
attaaagaca aggacttcct ggacaacgag gagaacgagg acatccttga ggacatcgtg  1860
ctcaccctga ccttgttcga agacagggaa atgatcgaag agaggctcaa gacctacgcc  1920
cacctcttcg acgacaaggt gatgaaacag ctgaagagac gcagatatac cggctgggga  1980
aggctctccc gcaaattgat caacgggatc agggacaagc agtcagggaa gactatactc  2040
gacttcctga agtccgacgg attcgccaac aggaacttca tgcagctcat tcacgacgac  2100
tccttgacct tcaaggagga catccagaag gctcaggtgt ctggacaggg tgactccttg  2160
catgagcaca ttgctaactt ggccggctct cccgctatta agaagggcat tttgcagacc  2220
gtgaaggtcg ttgacgagct cgtgaaggtg atggacgcc acaagccaga gaacatcgtt  2280
attgagatgg ctcgcgagaa ccaaactacc cagaaagggc agaagaattc ccgcgagagg  2340
atgaagcgca ttgaggaggg cataaaagag cttggctctc agatcctcaa ggagcacccc  2400
gtcgagaaca ctcagctgca gaacgagaag ctgtacctgt actacctcca aaacggaagg  2460
gacatgtacg tggaccagga gctggacatc aacaggttgt ccgactacga cgtcgaccac  2520
atcgtgcctc agtccttcct gaaggatgac tccatcgaca ataaagtgct gacacgctcc  2580
gataaaaata gaggcaagtc cgacaacgtc ccctccgagg aggtcgtgaa gaagatgaaa  2640
aactactgga gacagctctt gaacgccaag ctcatcaccc agcgtaagtt cgacaacctg  2700
actaaggctg agagaggagg attgtccgag ctcgataagg ccggattcat caagagacag  2760
ctcgtcgaaa cccgccaaat taccaagcac gtggcccaaa ttctggattc ccgcatgaac  2820
accaagtacg atgaaaatga caagctgatc cgcgaggtca aggtgatcac cttgaagtcc  2880
aagctggtct ccgacttccg caaggacttc cagttctaca aggtgaggga gatcaacaac  2940
taccaccacg cacacgacgc ctacctcaac gctgtcgttg gaaccgccct catcaaaaaa  3000
tatcctaagc tggagtctga gttcgtctac ggcgactaca aggtgtacga cgtgaggaag  3060
atgatcgcta agtctgagca ggagatcggc aaggccaccg ccaagtactt cttctactcc  3120
aacatcatga acttcttcaa gaccgagatc actctcgcca acggtgagat caggaagcgc  3180
ccactgatcg agaccaacgg tgagactgga gagatcgtgt gggacaaagg gagggatttc  3240
gctactgtga ggaaggtgct ctccatgcct caggtgaaca tcgtcaagaa gaccgaagtt  3300
cagaccggag gattctccaa ggagtccatc ctccccaaga gaaactccga caagctgatc  3360
gctagaaaga aagactggga ccctaagaag tacggaggct tcgattctcc taccgtggcc  3420
tactctgtgc tggtcgtggc caaggtggag aagggcaagt ccaagaagct gaaatccgtc  3480
aaggagctcc tcgggattac catcatggag aggagttcct tcgagaagaa ccctatcgac  3540
ttcctggagg ccaagggata taaagaggtg aagaaggacc tcatcatcaa gctgcccaag  3600
tactccctct tcgagttgga gaacggaagg aagaggatgc tggcttctgc cggagagttg  3660
```

-continued

```
cagaagggaa atgagctcgc ccttccctcc aagtacgtga acttcctgta cctcgcctct  3720
cactatgaaa agttgaaggg ctctcctgag gacaacgagc agaagcagct cttcgtggag  3780
cagcacaagc actacctgga cgaaattatc gagcagatct ctgagttctc caagcgcgtg  3840
atattggccg acgccaacct cgacaaggtg ctgtccgcct acaacaagca cagggataag  3900
cccattcgcg agcaggctga aaacattatc cacctgttta ccctcacaaa cttgggagcc  3960
cctgctgcct tcaagtactt cgacaccacc attgacagga agagatacac ctccaccaag  4020
gaggtgctcg acgcaacact catccaccaa tccatcaccg gcctctatga aacaaggatt  4080
gacttgtccc agctgggagg cgac                                         4104

SEQ ID NO: 490         moltype = DNA  length = 23
FEATURE                Location/Qualifiers
source                 1..23
                       mol_type = genomic DNA
                       organism = Glycine max
SEQUENCE: 490
gtttgtttgt tgttgggtgt ggg                                          23

SEQ ID NO: 491         moltype = DNA  length = 22
FEATURE                Location/Qualifiers
source                 1..22
                       mol_type = genomic DNA
                       organism = Glycine max
SEQUENCE: 491
tgttgttggg tgtgggaata gg                                           22

SEQ ID NO: 492         moltype = DNA  length = 9174
FEATURE                Location/Qualifiers
misc_feature           1..9174
                       note = synthesized sequence- RTW1199
source                 1..9174
                       mol_type = other DNA
                       organism = synthetic construct
SEQUENCE: 492
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg tttgtttgtt gttgggtgtg ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attcttttgg tttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttgt gggtttgttc acatgttatc aagcttaatc ttttactatg tatgcgacca  1860
tatctggatc cagcaaaggc gatttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggcacc gaagaagaag cgcaaggtga tggacaaaaa  2100
gtactcaata gggctcgaca tagggactaa ctccgttgga tgggccgtca tcaccgacga  2160
gtacaaggtg ccctccaaga agttcaaggt gttgggaaac accgacaggc acagcataaa  2220
gaagaatttg atcggtgccc tcctcttcga ctccggagag accgctgagg ctaccaggct  2280
caagaggacc gctagaaggc gctacaccag aaggaagaac agaatctgct acctgcagga  2340
gatcttctcc aacgagatgg ccaaggtgga cgactccttc ttccaccgcc ttgaggaatc  2400
attcctggtg gaggaggata aaaagcacga gagacaccca atcttcggga acatcgtcga  2460
cgaggtggcc taccatgaaa agtaccctac catctaccac ctgaggaaga agctggtcga  2520
ctctaccgac aaggctgact tgcgcttgat ttacctggct ctcgctcaca tgataaagtt  2580
ccgcggacac ttcctcattg agggagacct gaacccagac aactccgacg tggacaagct  2640
cttcatccag ctcgttcaga cctacaacca gcttttcgag gagaacccaa tcaacgccag  2700
tggagttgac gccaaggcta tcctctctgc tcgtctgtca aagtccagga ggcttgagaa  2760
```

```
cttgattgcc cagctgcctg gcgaaaagaa gaacggactg ttcggaaact tgatcgctct  2820
ctccctggga ttgactccca acttcaagtc caacttcgac ctcgccgagg acgctaagtt  2880
gcagttgtct aaagacacct acgacgatga cctcgacaac ttgctggccc agataggcga  2940
ccaatacgcc gatctcttcc tcgccgctaa gaacttgtcc gacgcaatcc tgctgtccga  3000
catcctgaga gtcaacactg agattaccaa agctcctctg tctgcttcca tgattaagcg  3060
ctacgacgag caccaccaag atctgaccct gctcaaggcc ctggtgagac agcagctgcc  3120
cgagaagtac aaggagatct tttcgacca gtccaagaac ggctacgccg gatacattga  3180
cggaggcgcc tcccaggaag agttctacaa gttcatcaag cccatccttg agaagatgga  3240
cggtaccgag gagctgttgg tgaagttgaa cagagaggac ctgttgagga agcagagaac  3300
cttcgacaac ggaagcatcc ctcaccaaat ccacctggga gagctccacg ccatcttgag  3360
gaggcaggag gatttctatc ccttcctgaa ggacaaccgc gagaagattg agaagatctt  3420
gaccttcaga attccttact acgtcgggcc actcgccaga ggaaactcta ggttcgcctg  3480
gatgacccgc aaatctgaag agaccattac tccctggaac ttcgaggaag tcgtggacaa  3540
gggcgcttcc gctcagtctt tcatcgagag gatgaccaac ttcgataaaa atctgcccaa  3600
cgagaaggtg ctgcccaagc actccctgtt gtacgagtat ttcacagtgt acaacgagct  3660
caccaaggtg aagtacgtca cagagggaat gaggaagcct gccttcttgt ccggagagca  3720
gaagaaggcc atcgtcgacc tgctcttcaa gaccaacagg aaggtgactg tcaagcagct  3780
gaaggaggac tacttcaaga agatcgagtg cttcgactcc gtcgagatct ctggtgtcga  3840
ggacaggttc aacgcctccc ttgggactta ccacgatctg ctcaagatta ttaaagacaa  3900
ggacttcctg gacaacgagg agaacgagga catccttgag gacatcgtgc tcaccctgac  3960
cttgttcgaa gacagggaaa tgatcgaaga gaggctcaag acctacgccc acctcttcga  4020
cgacaaggtg atgaaacagc tgaagagacg cagatatacc ggctggggaa ggctctcccg  4080
caaattgatc aacgggatca gggacaagca gtcagggaag actatactcg acttcctgaa  4140
gtccgacgga ttcgccaaca ggaacttcat gcagctcatt cacgacgact ccttgacctt  4200
caaggaggac atccagaagg ctcaggtgtc tggacagggt gactccttgc atgagcacat  4260
tgctaacttg gccggctctc ccgctattaa gaagggcatt ttgcagaccg tgaaggtcgt  4320
tgacgagctc gtgaaggtga tgggacgcca caagccagag aacatcgtta ttgagatggc  4380
tcgcgagaac caaactaccc agaaagggca gaagaattcc cgcgagagga tgaagcgcat  4440
tgaggagggc ataaaagagc ttggctctca gatcctcaag gagcaccccg tcgagaacac  4500
tcagctgcag aacgagaagc tgtacctgta ctacctccaa aacggaaggg acatgtacgt  4560
ggaccaggag ctggacatca acaggttgtc cgactacgac gtcgaccaca tcgtgcctca  4620
gtccttcctg aaggatgact ccatcgacaa taaagtgctg acacgctccg ataaaaatag  4680
aggcaagtcc gacaacgtcc cctccgagga ggtcgtgaag aagatgaaaa actactggag  4740
acagctcttg aacgccaagc tcatcaccca gcgtaagttc gacaacctga ctaaggctga  4800
gagaggagga ttgtccgagc tcgataaggc cggattcatc aagagacagc tcgtcgaaac  4860
ccgccaaatt accaagcacg tggcccaaat tctggattcc cgcatgaaca ccaagtacga  4920
tgaaaatgac aagctgatcc gcgaggtcaa ggtgatcacc ttgaagtcca agctggtctc  4980
cgacttccgc aaggacttcc agttctacaa ggtgagggag atcaacaact accaccacgc  5040
acacgacgcc tacctcaacg ctgtcgttgg aaccgccctc atcaaaaaat atcctaagct  5100
ggagtctgag ttcgtctacg gcgactacaa ggtgtacgac gtgaggaaga tgatcgctaa  5160
gtctgagcag gagatcggca aggccaccgc caagtacttc ttctactcca acatcatgaa  5220
cttcttcaag accgagatca ctctcgccaa cggtgagatc aggaagcgcc cactgatcga  5280
gaccaacggt gagactggag agatcgtgtg ggacaaaggg agggatttcg ctactgtgag  5340
gaaggtgctc tccatgcctc aggtgaacat cgtcaagaag accgaagttc agaccggagg  5400
attctccaag gagtccatcc tccccaagag aaactccgac aagctgatcg ctagaaagaa  5460
agactgggac cctaagaagt acggaggctt cgattctcct accgtggcct actctgtgct  5520
ggtcgtggcc aaggtggaga agggcaagtc caagaagctg aaatccgtca aggagctcct  5580
cgggattacc atcatggaga ggagttcctt cgagaagaac cctatcgact tcctggaggc  5640
caagggatat aaagaggtga agaaggacct catcatcaag ctgcccaagt actccctctt  5700
cgagttggag aacggaagga agaggatgct ggcttctgcc ggagagttgc agaagggaaa  5760
tgagctcgcc cttccctcca agtacgtgaa cttcctgtac ctcgcctctc actatgaaaa  5820
gttgaagggc tctcctgagg acaacgagca gaagcagctc ttcgtggagc agcacaagca  5880
ctacctggac gaaattatcg agcagatctc tgagttctcc aagcgcgtga tattggccga  5940
cgccaacctc gacaaggtgc tgtccgccta caacaagcac agggataagc ccattcgcga  6000
gcaggctgaa aacattatcc acctgtttac cctcacaaac ttgggagccc ctgctgcctt  6060
caagtacttc gacaccacca ttgacaggaa gagatacacc tccaccaagg aggtgctcga  6120
cgcaacactc atccaccaat ccatcaccgg cctctatgaa acaaggattg acttgtccca  6180
gctgggaggc gactctagag ccgatcccaa gaagaagaga aaggtgaaga gaccacggga  6240
ccgccacgat ggcgagctgg gaggccgcaa gcgggcaagg taggttaacc tagacttgtc  6300
catcttctgg attggccaac ttaattaatg tatgaaataa aaggatgcac acatagtgac  6360
atgctaatca ctataatgtg ggcatcaaag ttgtgtgtta tgtgtaatta ctagttatct  6420
gaataaaaga gaaagagatc atccatattt cttatcctaa atgaatgtca cgtgtcttta  6480
taattctttg atgaaccaga tgcatttcat taaccaaatc catatacata taaatattaa  6540
tcatatataa ttaatatcaa ttgggttagc aaaacaaatc tagtctaggt gtgttttgcg  6600
aattcgatat caagcttatc gataccgtcg aggggggccc cggtaccggc gcgccgttct  6660
atagtgtcac ctaaatcgta tgtgtatgat acataaggtt atgtattaat tgtagccgcg  6720
ttctaacgac aatatgtcca tatggtgcac tctcagtaca atctgctctg atgccgcata  6780
gttaagccag ccccgacacc cgccaacacc cgctgacgcg ccctgacggg cttgtctgct  6840
cccggcatcc gcttacagac aagctgtgac cgtctccggg agctgcatgt gtcagaggtt  6900
ttcaccgtca tcaccgaaac gcgcgagacg aaagggcctc gtgatacgcc tatttttata  6960
ggttaatgtc atgaccaaaa tcccttaacg tgagttttcg ttccactgag cgtcagaccc  7020
cgtagaaaag atcaaaggat cttcttgaga tccttttttt ctgcgcgtaa tctgctgctt  7080
gcaaacaaaa aaaccaccgc taccagcggt ggtttgtttg ccggatcaag agctaccaac  7140
tctttttccg aaggtaactg gcttcagcag agcgcagata ccaaatactg ttcttctagt  7200
gtagccgtag ttaggccacc acttcaagaa ctctgtagca ccgcctacat acctcgctct  7260
gctaatcctg ttaccagtgg ctgctgccag tggcgataag tcgtgtctta ccgggttgga  7320
ctcaagacga tagttaccgg ataaggcgca gcggtcgggc tgaacggggg gttcgtgcac  7380
acagcccagc ttggagcgaa cgacctacac cgaactgaga tacctacagc gtgagctatg  7440
agaaagcgcc acgcttcccg aagggagaaa ggcggacagg tatccggtaa gcggcagggt  7500
```

```
cggaacagga gagcgcacga gggagcttcc agggggaaac gcctggtatc tttatagtcc  7560
tgtcgggttt cgccacctct gacttgagcg tcgatttttg tgatgctcgt caggggggcg  7620
gagcctatgg aaaaacgcca gcaacgcggc ctttttacgg ttcctggcct tttgctggcc  7680
ttttgctcac atgttctttc ctgcgttatc ccctgattct gtggataacc gtattaccgc  7740
ctttgagtga gctgataccg ctcgccgcag ccgaacgacc gagcgcagcg agtcagtgag  7800
cgaggaagcg gaagagcgcc caatacgcaa accgcctctc cccgcgcgtt ggccgattca  7860
ttaatgcagg ttgatcagat ctcgatcccg cgaaattaat acgactcact atagggagac  7920
cacaacggtt tccctctaga aataattttg tttaacttta agaaggagat atacccatgg  7980
aaaagcctga actcaccgcg acgtctgtcg agaagtttct gatcgaaaag ttcgacagcg  8040
tctccgacct gatgcagctc tcggagggcg aagaatctcg tgctttcagc ttcgatgtag  8100
gagggcgtgg atatgtcctg cgggtaaata gctgcgccga tggtttctac aaagatcgtt  8160
atgtttatcg gcactttgca tcggccgcgc tcccgattcc ggaagtgctt gacattgggg  8220
aattcagcga gagcctgacc tattgcatct cccgccgtgc acagggtgtc acgttgcaag  8280
acctgcctga aaccgaactg cccgctgttc tgcagccggt cgcggaggct atggatgcga  8340
tcgctgcggc cgatcttagc cagacgagcg ggttcggccc attcggaccg caaggaatcg  8400
gtcaatacac tacatggcgt gatttcatat gcgcgattgc tgatccccat gtgtatcact  8460
ggcaaactgt gatggacgac accgtcagtg cgtccgtcgc gcaggctctc gatgagctga  8520
tgctttgggc cgaggactgc cccgaagtcc ggcacctcgt gcacgcggat ttcggctcca  8580
acaatgtcct gacggacaat ggccgcataa cagcggtcat tgactggagc gaggcgatgt  8640
tcggggattc ccaatacgag gtcgccaaca tcttcttctg gaggccgtgg ttggcttgta  8700
tggagcagca gacgcgctac ttcgagcgga ggcatccgga gcttgcagga tcgccgcggc  8760
tccgggcgta tatgctccgc attggtcttg accaactcta tcagagcttg gttgacggca  8820
atttcgatga tgcagcttgg gcgcagggtc gatgcgacgc aatcgtccga tccggagccg  8880
ggactgtcgg gcgtacacaa atcgcccgca gaagcgcggc cgtctggacc gatggctgtg  8940
tagaagtact cgccgatagt ggaaaccgac gccccagcac tcgtccgagg gcaaaggaat  9000
agtgaggtac agcttggatc gatccggctg ctaacaaagc ccgaaaggaa gctgagttgg  9060
ctgctgccac cgctgagcaa taactagcat aaccccttgg ggcctctaaa cgggtcttga  9120
ggggtttttt gctgaaagga ggaactatat ccggatgctc gggcgcgccg gtac        9174
```

```
SEQ ID NO: 493          moltype = DNA  length = 9174
FEATURE                 Location/Qualifiers
misc_feature            1..9174
                        note = synthesized sequence- RTW1200
source                  1..9174
                        mol_type = other DNA
                        organism = synthetic construct
SEQUENCE: 493
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg tgttgttggg tgtgggaatg ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attcttttgg tttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttttgt gggtttgttc acatgttatc aagcttaatc ttttactatg tatgcgacca  1860
tatctggatc cagcaaaggc gattttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggcacc gaagaagaag cgcaaggtga tggacaaaaa  2100
gtactcaata gggctcgaca tagggactaa ctccgttgga tgggccgtca tcaccgacga  2160
gtacaaggtg ccctccaaga agttcaaggt gttgggaaac accgacaggc acagcataaa  2220
gaagaatttg atcggtgccc tcctcttcga ctccggagag accgctgagg ctaccaggct  2280
caagaggacc gctagaaggc gctacaccag aaggaagaac agaatctgct acctgcagga  2340
gatcttctcc aacgagatgg ccaaggtgga cgactccttc ttccaccgcc ttgaggaatc  2400
attcctggtg gaggaggata aaaagcacga gagacaccca atcttcggga acatcgtcga  2460
cgaggtggcc taccatgaaa agtaccctac catctaccac ctgaggaaga agctggtcga  2520
```

-continued

```
ctctaccgac aaggctgact tgcgcttgat ttacctggct ctcgctcaca tgataaagtt  2580
ccgcggacac ttcctcattg agggagacct gaacccagac aactccgacg tggacaagct  2640
cttcatccag ctcgttcaga cctacaacca gcttttcgag gagaacccaa tcaacgccag  2700
tggagttgac gccaaggcta tcctctctgc tcgtctgtca aagtccagga ggcttgagaa  2760
cttgattgcc cagctgcctg gcgaaaagaa gaacggactg ttcggaaact tgatcgctct  2820
ctccctggga ttgactccca acttcaagtc caacttcgac ctcgccgagg acgctaagtt  2880
gcagttgtct aaagacacct acgacgatga cctcgacaac ttgctggccc agataggcga  2940
ccaatacgcc gatctcttcc tcgccgctaa gaacttgtcc gacgcaatcc tgctgtccga  3000
catcctgaga gtcaacactg agattaccaa agctcctctg tctgcttcca tgattaagcg  3060
ctacgacgag caccaccaag atctgaccct gctcaaggcc ctggtgagac agcagctgcc  3120
cgagaagtac aaggagatct tttcgacca gtccaagaac ggctacgccg gatacattga  3180
cggaggcgcc tcccaggaag agttctacaa gttcatcaag cccatccttg agaagatgga  3240
cggtaccgag gagctgttgg tgaagttgaa cagagaggac ctgttgagga agcagagaac  3300
cttcgacaac ggaagcatcc ctcaccaaat ccacctggga gagctccacg ccatcttgag  3360
gaggcaggag gatttctatc ccttcctgaa ggacaaccgc gagaagattg agaagatctt  3420
gaccttcaga attccttact acgtcgggcc actcgccaga ggaaactcta ggttcgcctg  3480
gatgacccgc aaatctgaag agaccattac tccctggaac ttcgaggaag tcgtggacaa  3540
gggcgcttcc gctcagtctt tcatcgagag gatgaccaac ttcgataaaa atctgcccaa  3600
cgagaaggtg ctgcccaagc actccctgtt gtacgagtat ttcacagtgt acaacgagct  3660
caccaaggtg aagtacgtca cagagggaat gaggaagcct gccttcttgt ccggagagca  3720
gaagaaggcc atcgtcgacc tgctcttcaa gaccaacagg aaggtgactg tcaagcagct  3780
gaaggaggac tacttcaaga agatcgagtg cttcgactcc gtcgagatct ctggtgtcga  3840
ggacaggttc aacgcctccc ttgggactta ccacgatctg ctcaagatta ttaaagacaa  3900
ggacttcctg gacaacgagg agaacgagga catccttgag gacatcgtgc tcaccctgac  3960
cttgttcgaa gacagggaaa tgatcgaaga gaggctcaag acctacgccc acctcttcga  4020
cgacaaggtg atgaaacagc tgaagagacg cagatatacc ggctggggaa ggctctcccg  4080
caaattgatc aacgggatca gggacaagca gtcagggaag actatactcg acttcctgaa  4140
gtccgacgga ttcgccaaca ggaacttcat gcagctcatt cacgacgact ccttgacctt  4200
caaggaggac atccagaagg ctcaggtgtc tggacagggt gactccttgc atgagcacat  4260
tgctaacttg gccggctctc ccgctattaa gaagggcatt ttgcagaccg tgaaggtcgt  4320
tgacgagctc gtgaaggtga tgggacgcca caagccagag aacatcgtta ttgagatggc  4380
tcgcgagaac caaactaccc agaaagggca gaagaattcc cgcgagagga tgaagcgcat  4440
tgaggagggc ataaaagagc ttggctctca gatcctcaag gagcaccccg tcgagaacac  4500
tcagctgcag aacgagaagc tgtacctgta ctacctccaa aacggaaggg acatgtacgt  4560
ggaccaggag ctggacatca acaggttgtc cgactacgac gtcgaccaca tcgtgcctca  4620
gtccttcctg aaggatgact ccatcgacaa taaagtgctg acacgctccg ataaaaatag  4680
aggcaagtcc gacaacgtcc cctccgagga ggtcgtgaag aagatgaaaa actactggag  4740
acagctcttg aacgccaagc tcatcaccca gcgtaagttc gacaacctga ctaaggctga  4800
gagaggagga ttgtccgagc tcgataaggc cggattcatc aagagacagc tcgtcgaaac  4860
ccgccaaatt accaagcacg tggcccaaat tctggattcc cgcatgaaca ccaagtacga  4920
tgaaaatgac aagctgatcc gcgaggtcaa ggtgatcacc ttgaagtcca agctggtctc  4980
cgacttccgc aaggacttcc agttctacaa ggtgagggag atcaacaact accaccacgc  5040
acacgacgcc tacctcaacg ctgtcgttgg aaccgccctc atcaaaaaat atcctaagct  5100
ggagtctgag ttcgtctacg gcgactacaa ggtgtacgac gtgaggaaga tgatcgctaa  5160
gtctgagcag gagatcggca aggccaccgc caagtacttc ttctactcca acatcatgaa  5220
cttcttcaag accgagatca ctctcgccaa cggtgagatc aggaagcgcc cactgatcga  5280
gaccaacggt gagactggag agatcgtgtg ggacaaaggg agggatttcg ctactgtgag  5340
gaaggtgctc tccatgcctc aggtgaacat cgtcaagaag accgaagttc agaccggagg  5400
attctccaag gagtccatcc tccccaagag aaactccgac aagctgatcg ctagaaagaa  5460
agactgggac cctaagaagt acggaggctt cgattctcct accgtggcct actctgtgct  5520
ggtcgtggcc aaggtggaga agggcaagtc caagaagctg aaatccgtca aggagctcct  5580
cgggattacc atcatggaga ggagttcctt cgagaagaac cctatcgact tcctggaggc  5640
caagggatat aaagaggtga agaaggacct catcatcaag ctgcccaagt actccctctt  5700
cgagttggag aacggaagga agaggatgct ggcttctgcc ggagagttgc agaagggaaa  5760
tgagctcgcc cttccctcca agtacgtgaa cttcctgtac ctcgcctctc actatgaaaa  5820
gttgaagggc tctcctgagg acaacgagca gaagcagctc ttcgtggagc agcacaagca  5880
ctacctggac gaaattatcg agcagatctc tgagttctcc aagcgcgtga tattggccga  5940
cgccaacctc gacaaggtgc tgtccgccta caacaagcac agggataagc ccattcgcga  6000
gcaggctgaa aacattatcc acctgtttac cctcacaaac ttgggagccc ctgctgcctt  6060
caagtacttc gacaccacca ttgacaggaa gagatacacc tccaccaagg aggtgctcga  6120
cgcaacactc atccaccaat ccatcaccgg cctctatgaa acaaggattg acttgtccca  6180
gctgggaggc gactctagag ccgatcccaa gaagaagaga aaggtgaaga gaccacggga  6240
ccgccacgat ggcgagctgg gaggccgcaa gcgggcaagg taggttaacc tagacttgtc  6300
catcttctgg attggccaac ttaattaatg tatgaaataa aaggatgcac acatagtgac  6360
atgctaatca ctataatgtg ggcatcaaag ttgtgtgtta tgtgtaatta ctagttatct  6420
gaataaaaga gaaagagatc atccatattt cttatcctaa atgaatgtca cgtgtcttta  6480
taattctttg atgaaccaga tgcatttcat taaccaaatc catatacata taaatattaa  6540
tcatatataa ttaatatcaa ttgggttagc aaaacaaatc tagtctaggt gtgttttgcg  6600
aattcgatat caagcttatc gataccgtcg agggggggcc cggtaccggc gcgccgttct  6660
atagtgtcac ctaaatcgta tgtgtatgat acataaggtt atgtattaat tgtagccgcg  6720
ttctaacgac aatatgtcca tatggtgcac tctcagtaca atctgctctg atgccgcata  6780
gttaagccag ccccgacacc cgccaacacc cgctgacgcg ccctgacggg cttgtctgct  6840
cccggcatcc gcttacagac aagctgtgac cgtctccggg agctgcatgt gtcagaggtt  6900
ttcaccgtca tcaccgaaac gcgcgagacg aaagggcctc gtgatacgcc tatttttata  6960
ggttaatgtc atgaccaaaa tcccttaacg tgagttttcg ttccactgag cgtcagaccc  7020
cgtagaaaag atcaaaggat cttcttgaga tcctttttt ctgcgcgtaa tctgctgctt  7080
gcaaacaaaa aaaccaccgc taccagcggt ggtttgtttg ccggatcaag agctaccaac  7140
tctttttccg aaggtaactg gcttcagcag agcgcagata ccaaatactg ttcttctagt  7200
gtagccgtag ttaggccacc acttcaagaa ctctgtagca ccgcctacat acctcgctct  7260
```

```
gctaatcctg ttaccagtgg ctgctgccag tggcgataag tcgtgtctta ccgggttgga  7320
ctcaagacga tagttaccgg ataaggcgca gcggtcgggc tgaacggggg gttcgtgcac  7380
acagcccagc ttggagcgaa cgacctacac cgaactgaga tacctacagc gtgagctatg  7440
agaaagcgcc acgcttcccg aagggagaaa ggcggacagg tatccggtaa gcggcagggt  7500
cggaacagga gagcgcacga gggagcttcc agggggaaac gcctggtatc tttatagtcc  7560
tgtcgggttt cgccacctct gacttgagcg tcgatttttg tgatgctcgt caggggggcg  7620
gagcctatgg aaaaacgcca gcaacgcggc ctttttacgg ttcctggcct tttgctggcc  7680
ttttgctcac atgttctttc ctgcgttatc ccctgattct gtggataacc gtattaccgc  7740
ctttgagtga gctgataccg ctcgccgcag ccgaacgacc gagcgcagcg agtcagtgag  7800
cgaggaagcg gaagagcgcc caatacgcaa accgcctctc cccgcgcgtt ggccgattca  7860
ttaatgcagg ttgatcagat ctcgatcccg cgaaattaat acgactcact atagggagac  7920
cacaacggtt tccctctaga aataattttg tttaacttta agaaggagat atacccatgg  7980
aaaagcctga actcaccgcg acgtctgtcg agaagtttct gatcgaaaag ttcgacagcg  8040
tctccgacct gatgcagctc tcggagggcg aagaatctcg tgctttcagc ttcgatgtag  8100
gagggcgtgg atatgtcctg cgggtaaata gctgcgccga tggtttctac aaagatcgtt  8160
atgtttatcg gcactttgca tcggccgcgc tcccgattcc ggaagtgctt gacattgggg  8220
aattcagcga gagcctgacc tattgcatct cccgccgtgc acagggtgtc acgttgcaag  8280
acctgcctga aaccgaactg cccgctgttc tgcagccggt cgcggaggct atggatgcga  8340
tcgctgcggc cgatcttagc cagacgagcg ggttcggccc attcggaccg caaggaatcg  8400
gtcaatacac tacatggcgt gatttcatat gcgcgattgc tgatccccat gtgtatcact  8460
ggcaaactgt gatggacgac accgtcagtg cgtccgtcgc gcaggctctc gatgagctga  8520
tgctttgggc cgaggactgc cccgaagtcc ggcacctcgt gcacgcggat ttcggctcca  8580
acaatgtcct gacggacaat ggccgcataa cagcggtcat tgactggagc gaggcgatgt  8640
tcggggattc ccaatacgag gtcgccaaca tcttcttctg gaggccgtgg ttggcttgta  8700
tggagcagca gacgcgctac ttcgagcgga ggcatccgga gcttgcagga tcgccgcggc  8760
tccgggcgta tatgctccgc attggtcttg accaactcta tcagagcttg gttgacggca  8820
atttcgatga tgcagcttgg gcgcagggtc gatgcgacgc aatcgtccga tccggagccg  8880
ggactgtcgg gcgtacacaa atcgcccgca gaagcgcggc cgtctggacc gatggctgtg  8940
tagaagtact cgccgatagt ggaaaccgac gccccagcac tcgtccgagg gcaaaggaat  9000
agtgaggtac agcttggatc gatccggctg ctaacaaagc ccgaaaggaa gctgagttgg  9060
ctgctgccac cgctgagcaa taactagcat aaccccttgg ggcctctaaa cgggtcttga  9120
ggggtttttt gctgaaagga ggaactatat ccggatgctc gggcgcgccg gtac        9174
```

```
SEQ ID NO: 494         moltype = DNA  length = 3175
FEATURE                Location/Qualifiers
misc_feature           1..3175
                       note = synthesized sequence- RTW1190A
source                 1..3175
                       mol_type = other DNA
                       organism = synthetic construct
SEQUENCE: 494
cgaattctac aggtcactaa taccatctaa gtagttggtt catagtgact gcatatgtaa  60
aaattatcct tattttaagg aaattaaaaa ttatcatata tatataagtt ttaaattaat  120
tatcttatat atgtaccaaa aagttttaaa gcaattatta taaaaattaa taaatttatc  180
atataaaata atttataatt aaattttaaa ttatcaattc attaaattaa attatttaaa  240
atttttgaat gataatataa taattttatc ctctactaag tcccaacgtt tcctatttta  300
ttccactttt agcaataaat tttgtcataa acacttataa caaaaaaagt aagtaaaaaa  360
taaaaaaaag tttttcaata aagtataaac taatttgtat aaacttttag aaaaaataaa  420
gttatacatt gataatataa attttttaca taattatccg atcaactcat tatatatgat  480
aaatttattg atttttaaa ataattatct taaaataatt taaacaatga tttgcaatta  540
gatgataata taaaattatt ttacacacta catgtattaa actcaaactt ttatatatta  600
gtttttctaa aaactaattt ttaactcaaa aaaaatgtta cttataattt tcttatcttc  660
ttttttata agtatttttt aagaaattta ttgaaacatg accatgcttg ggtcaataat  720
actactctct tagacaccaa acaacccttc ccaaactata atctaatcca aaagccatca  780
ttcattttcc ttggtaggta aagttccaag accttcacca actttttcac tcaattgttt  840
tggtgtaagc aattcgacat gtgttagtgt tagttggcaa ccaaaaaatcc ctttatgtga  900
ctcaatccaa caaccactca caccaccaac ccccataacc atttctcaca atacccttca  960
tttacacatt atcatcacca aaaataaata aaaaaaacct ctcatttcag agagagagag  1020
agagacttca cagaccaaag tgcagagaac aacaaagttc acaactttaa ggaaaattga  1080
aatggcccaa gtgagcagag tgcacaatct tgctcaaagc actcaaattt ttggccattc  1140
ttccaactcc aacaaactca aatcggtgaa ttcggtttca ttgaggccac gcctttgggg  1200
ggcctcaaaa tctcgcatcc cgatgcataa aaatggaagc tttatgggaa attttaatgt  1260
ggggaaggga aattccggcg tgtttaaggt ttctgcatcg gtcgccgccg cagagaagcc  1320
gtcaacgtcg ccggagatcg tgttggaacc catcaaagac ttctcgggta ccatcacatt  1380
gccagggtcc aagtctctgt ccaatcgaat tttgcttctt gctgctctct ctgaggttcg  1440
tagatttctt ccgttttttt ttcttcttct ttattgtttg ttctacatca gcatgatgtt  1500
gatttgattg tgttttctat cgtttcatcg attataaatt ttcataatca gaagattcag  1560
cttttattaa tgcaagaacg tccttaattg atgattttat aaccgtaaat taggtctaat  1620
tagagttttt ttcataaaga ttttcagatc cgtttacaac aagccttaat tgttgattct  1680
gtagtcgtag attaaggttt ttttcatgaa ctacttcaga tccgttaaac aacagcctta  1740
tttgttgata cttcagtcgt ttttcaagaa attgttcaga tccgttgata aaagccttat  1800
tcgttgattc tgtatggtat ttcaagagat attgctcagg tcctttagca actaccttat  1860
ttgttgattc tgtggccata gattaggatt ttttttcacg aaattgcttc ttgaaattac  1920
gtgatggatt ttgattctga tttatcttgt gattgttgac tctacaggga acaactgttg  1980
tagacaactt gttgtatagt gaggatattc attacatgct tggtgcatta aggacccttg  2040
gactgcgtgt ggaagatgac aaaacaacca aacaagcaat tgttgaaggc tgtgggggat  2100
tgtttcccac tagtaaggaa tctaaagatg aaatcaattt attccttgga aatgctggta  2160
ttgcaatgag atctttgaca gcagctgttg ttgctgcagg tggaaatgca aggtctgttt  2220
ttttttttt tgttcagcat aatctttgaa ttgttcctcg tataactaat cacaacagag  2280
```

```
tacgtgttct tcttcctgtt ataatctaaa aatctcatcc agattagtca tcctttcttc  2340
ttaaaaggaa cctttaatta tcaatgtatt tatttaatat ttaaattagc ttgtcaaagt  2400
ctagcatata catattttga ttatattctg agaaatgcac ctgagggtgt tcctcatgat  2460
ctacttcaac ctctgttatt attagatttt ctatcatgat tactggtttg agtctctaag  2520
tagaccatct tgatgttcaa aatatttcag ctacgtactt gatggggtgc cccgaatgag  2580
agagaggcca attggggatt tggttgctgg tcttaagcaa cttggtgcag atgttgattg  2640
ctttcttggc acaaactgtc cacctgttcg tgtaaatggg aagggaggac ttcctggcgg  2700
aaaggtatgg tttggatttc atttagaata aggtggagta actttcctgg atcaaaattc  2760
taatttaaga agcctccctg ttttcctctc tttagaataa gactaagggt aggtttagga  2820
gttgggtttt ggagagaaat ggaagggaga gcaatttttt tcttcttcta ataaatattc  2880
tttaatttga tacatttttt aagtaaaaga atataaagat agattagcat aacttaatgt  2940
tttaatcttt tatttatttt tataaatatt atatacctgt ctatttaaaa atcaaatatt  3000
tgtcctccat tccctttccc ttcaaaacct cagttccaaa tataccgtag ttgaattata  3060
ttttggaagg cctattggtt ggagactttt ccttttcaga gattatccct cacctttatt  3120
atagcctttc tatttttaaa cttcatatag acgccattct tggggcggcc gcgat       3175

SEQ ID NO: 495         moltype = DNA  length = 23
FEATURE                Location/Qualifiers
misc_feature           1..23
                       note = synthesized sequence- primer, soy1-F3
source                 1..23
                       mol_type = other DNA
                       organism = synthetic construct
SEQUENCE: 495
gtttgtttgt tgttgggtgt ggg                                          23

SEQ ID NO: 496         moltype = DNA  length = 25
FEATURE                Location/Qualifiers
misc_feature           1..25
                       note = synthesized sequence- primer, soy1-R3
source                 1..25
                       mol_type = other DNA
                       organism = synthetic construct
SEQUENCE: 496
gacatgatgc ttcattttca cagaa                                        25

SEQ ID NO: 497         moltype = DNA  length = 18
FEATURE                Location/Qualifiers
misc_feature           1..18
                       note = synthesized sequence- probe, soy1-T2(FAM-MGB)
source                 1..18
                       mol_type = other DNA
                       organism = synthetic construct
SEQUENCE: 497
tgtgtagagt ggattttg                                                18

SEQ ID NO: 498         moltype = DNA  length = 22
FEATURE                Location/Qualifiers
misc_feature           1..22
                       note = synthesized sequence- primer, soy1-F2
source                 1..22
                       mol_type = other DNA
                       organism = synthetic construct
SEQUENCE: 498
tgttgttggg tgtgggaata gg                                           22

SEQ ID NO: 499         moltype = DNA  length = 31
FEATURE                Location/Qualifiers
misc_feature           1..31
                       note = synthesized sequence- WOL1001, Forward_primer
source                 1..31
                       mol_type = other DNA
                       organism = synthetic construct
SEQUENCE: 499
aggtttaatt ttatataatg ttagcataca g                                 31

SEQ ID NO: 500         moltype = DNA  length = 28
FEATURE                Location/Qualifiers
misc_feature           1..28
                       note = synthesized sequence- 500 WOL1002, Reverse_primer
source                 1..28
                       mol_type = other DNA
                       organism = synthetic construct
SEQUENCE: 500
atcaacatca tgctgatgta gaacaaac                                     28

SEQ ID NO: 501         moltype = DNA  length = 29
FEATURE                Location/Qualifiers
misc_feature           1..29
```

```
                        note = synthesized sequence- 501 WOL1003, Forward_primer
source                  1..29
                        mol_type = other DNA
                        organism = synthetic construct
SEQUENCE: 501
attctgattt atcttgtgat tgttgactc                                         29

SEQ ID NO: 502          moltype = DNA  length = 27
FEATURE                 Location/Qualifiers
misc_feature            1..27
                        note = synthesized sequence- WOL1004, Reverse_primer
source                  1..27
                        mol_type = other DNA
                        organism = synthetic construct
SEQUENCE: 502
atttactttg gagagaataa ggagggg                                           27

SEQ ID NO: 503          moltype = DNA  length = 23
FEATURE                 Location/Qualifiers
source                  1..23
                        mol_type = genomic DNA
                        organism = Glycine max
SEQUENCE: 503
gaaacgttgg gacttagtag agg                                               23

SEQ ID NO: 504          moltype = DNA  length = 23
FEATURE                 Location/Qualifiers
source                  1..23
                        mol_type = genomic DNA
                        organism = Glycine max
SEQUENCE: 504
ggaataaaat aggaaacgtt ggg                                               23

SEQ ID NO: 505          moltype = DNA  length = 9174
FEATURE                 Location/Qualifiers
misc_feature            1..9174
                        note = synthesized sequence- RTW1201
source                  1..9174
                        mol_type = other DNA
                        organism = synthetic construct
SEQUENCE: 505
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg aaacgttggg acttagtagg ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attcttttgg tttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttgt gggtttgttc acatgttatc aagcttaatc ttttactatg tatgcgacca  1860
tatctggatc cagcaaaggc gatttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggcacc gaagaagaag cgcaaggtga tggacaaaaa  2100
gtactcaata gggctcgaca tagggactaa ctccgttgga tgggccgtca tcaccgacga  2160
gtacaaggtg ccctccaaga agttcaaggt gttgggaaac accgacaggc acagcataaa  2220
gaagaatttg atcggtgccc tcctcttcga ctccggagag accgctgagg ctaccaggct  2280
```

-continued

```
caagaggacc gctagaaggc gctacaccag aaggaagaac agaatctgct acctgcagga  2340
gatcttctcc aacgagatgg ccaaggtgga cgactccttc ttccaccgcc ttgaggaatc  2400
attcctggtg gaggaggata aaaagcacga gagacaccca atcttcggga acatcgtcga  2460
cgaggtggcc taccatgaaa agtaccctac catctaccac ctgaggaaga agctggtcga  2520
ctctaccgac aaggctgact tgcgcttgat ttacctggct ctcgctcaca tgataaagtt  2580
ccgcggacac ttcctcattg agggagacct gaacccagac aactccgacg tggacaagct  2640
cttcatccag ctcgttcaga cctacaacca gcttttcgag gagaacccaa tcaacgccag  2700
tggagttgac gccaaggcta tcctctctgc tcgtctgtca aagtccagga ggcttgagaa  2760
cttgattgcc cagctgcctg gcgaaaagaa gaacggactg ttcggaaact tgatcgctct  2820
ctccctggga ttgactccca acttcaagtc caacttcgac ctcgccgagg acgctaagtt  2880
gcagttgtct aaagacacct acgacgatga cctcgacaac ttgctggccc agataggcga  2940
ccaatacgcc gatctcttcc tcgccgctaa gaacttgtcc gacgcaatcc tgctgtccga  3000
catcctgaga gtcaacactg agattaccaa agctcctctg tctgcttcca tgattaagcg  3060
ctacgacgag caccaccaag atctgaccct gctcaaggcc ctggtgagac agcagctgcc  3120
cgagaagtac aaggagatct tttcgacca gtccaagaac ggctacgccg gatacattga  3180
cggaggcgcc tcccaggaag agttctacaa gttcatcaag cccatccttg agaagatgga  3240
cggtaccgag gagctgttgg tgaagttgaa cagagaggac ctgttgagga agcagagaac  3300
cttcgacaac ggaagcatcc ctcaccaaat ccacctggga gagctccacg ccatcttgag  3360
gaggcaggag gatttctatc ccttcctgaa ggacaaccgc gagaagattg agaagatctt  3420
gaccttcaga attccttact acgtcgggcc actcgccaga ggaaactcta ggttcgcctg  3480
gatgacccgc aaatctgaag agaccattac tccctggaac ttcgaggaag tcgtggacaa  3540
gggcgcttcc gctcagtctt tcatcgagag gatgaccaac ttcgataaaa atctgcccaa  3600
cgagaaggtg ctgcccaagc actccctgtt gtacgagtat ttcacagtgt acaacgagct  3660
caccaaggtg aagtacgtca cagagggaat gaggaagcct gccttcttgt ccggagagca  3720
gaagaaggcc atcgtcgacc tgctcttcaa gaccaacagg aaggtgactg tcaagcagct  3780
gaaggaggac tacttcaaga agatcgagtg cttcgactcc gtcgagatct ctggtgtcga  3840
ggacaggttc aacgcctccc ttgggactta ccacgatctg ctcaagatta ttaaagacaa  3900
ggacttcctg gacaacgagg agaacgagga catccttgag gacatcgtgc tcaccctgac  3960
cttgttcgaa gacagggaaa tgatcgaaga gaggctcaag acctacgccc acctcttcga  4020
cgacaaggtg atgaaacagc tgaagagacg cagatatacc ggctggggaa ggctctcccg  4080
caaattgatc aacgggatca gggacaagca gtcagggaag actatactcg acttcctgaa  4140
gtccgacgga ttcgccaaca ggaacttcat gcagctcatt cacgacgact ccttgacctt  4200
caaggaggac atccagaagg ctcaggtgtc tggacagggt gactccttgc atgagcacat  4260
tgctaacttg gccggctctc ccgctattaa gaagggcatt ttgcagaccg tgaaggtcgt  4320
tgacgagctc gtgaaggtga tgggacgcca caagccagag aacatcgtta ttgagatggc  4380
tcgcgagaac caaactaccc agaaagggca gaagaattcc cgcgagagga tgaagcgcat  4440
tgaggagggc ataaaagagc ttggctctca gatcctcaag gagcaccccg tcgagaacac  4500
tcagctgcag aacgagaagc tgtacctgta ctacctccaa aacggaaggg acatgtacgt  4560
ggaccaggag ctggacatca acaggttgtc cgactacgac gtcgaccaca tcgtgcctca  4620
gtccttcctg aaggatgact ccatcgacaa taaagtgctg acacgctccg ataaaaatag  4680
aggcaagtcc gacaacgtcc cctccgagga ggtcgtgaag aagatgaaaa actactggag  4740
acagctcttg aacgccaagc tcatcaccca gcgtaagttc gacaacctga ctaaggctga  4800
gagaggagga ttgtccgagc tcgataaggc cggattcatc aagagacagc tcgtcgaaac  4860
ccgccaaatt accaagcacg tggcccaaat tctggattcc cgcatgaaca ccaagtacga  4920
tgaaaatgac aagctgatcc gcgaggtcaa ggtgatcacc ttgaagtcca agctggtctc  4980
cgacttccgc aaggacttcc agttctacaa ggtgagggag atcaacaact accaccacgc  5040
acacgacgcc tacctcaacg ctgtcgttgg aaccgccctc atcaaaaaat atcctaagct  5100
ggagtctgag ttcgtctacg gcgactacaa ggtgtacgac gtgaggaaga tgatcgctaa  5160
gtctgagcag gagatcggca aggccaccgc caagtacttc ttctactcca acatcatgaa  5220
cttcttcaag accgagatca ctctcgccaa cggtgagatc aggaagcgcc cactgatcga  5280
gaccaacggt gagactggag agatcgtgtg ggacaaaggg agggatttcg ctactgtgag  5340
gaaggtgctc tccatgcctc aggtgaacat cgtcaagaag accgaagttc agaccggagg  5400
attctccaag gagtccatcc tccccaagag aaactccgac aagctgatcg ctagaaagaa  5460
agactgggac cctaagaagt acggaggctt cgattctcct accgtggcct actctgtgct  5520
ggtcgtggcc aaggtggaga agggcaagtc caagaagctg aaatccgtca aggagctcct  5580
cgggattacc atcatggaga ggagttcctt cgagaagaac cctatcgact tcctggaggc  5640
caagggatat aaagaggtga agaaggacct catcatcaag ctgcccaagt actccctctt  5700
cgagttggag aacggaagga agaggatgct ggcttctgcc ggagagttgc agaagggaaa  5760
tgagctcgcc cttccctcca agtacgtgaa cttcctgtac ctcgcctctc actatgaaaa  5820
gttgaagggc tctcctgagg acaacgagca gaagcagctc ttcgtggagc agcacaagca  5880
ctacctggac gaaattatcg agcagatctc tgagttctcc aagcgcgtga tattggccga  5940
cgccaacctc gacaaggtgc tgtccgccta caacaagcac agggataagc ccattcgcga  6000
gcaggctgaa aacattatcc acctgtttac cctcacaaac ttgggagccc ctgctgcctt  6060
caagtacttc gacaccacca ttgacaggaa gagatacacc tccaccaagg aggtgctcga  6120
cgcaacactc atccaccaat ccatcaccgg cctctatgaa acaaggattg acttgtccca  6180
gctgggaggc gactctagag ccgatcccaa gaagaagaga aaggtgaaga gaccacggga  6240
ccgccacgat ggcgagctgg gaggccgcaa gcgggcaagg taggttaacc tagacttgtc  6300
catcttctgg attggccaac ttaattaatg tatgaaataa aaggatgcac acatagtgac  6360
atgctaatca ctataatgtg ggcatcaaag ttgtgtgtta tgtgtaatta ctagttatct  6420
gaataaaaga gaaagagatc atccatattt cttatcctaa atgaatgtca cgtgtcttta  6480
taattctttg atgaaccaga tgcatttcat taaccaaatc catatacata taaatattaa  6540
tcatatataa ttaatatcaa ttgggttagc aaaacaaatc tagtctaggt gtgttttgcg  6600
aattcgatat caagcttatc gataccgtcg aggggggggcc cggtaccggc gcgccgttct  6660
atagtgtcac ctaaatcgta tgtgtatgat acataaggtt atgtattaat tgtagccgcg  6720
ttctaacgac aatatgtcca tatggtgcac tctcagtaca atctgctctg atgccgcata  6780
gttaagccag ccccgacacc cgccaacacc cgctgacgcg ccctgacggg cttgtctgct  6840
cccggcatcc gcttacagac aagctgtgac cgtctccggg agctgcatgt gtcagaggtt  6900
ttcaccgtca tcaccgaaac gcgcgagacg aaagggcctc gtgatacgcc tatttttata  6960
ggttaatgtc atgaccaaaa tcccttaacg tgagttttcg ttccactgag cgtcagaccc  7020
```

-continued

```
cgtagaaaag atcaaaggat cttcttgaga tcctttttt ctgcgcgtaa tctgctgctt  7080
gcaaacaaaa aaaccaccgc taccagcggt ggtttgtttg ccggatcaag agctaccaac  7140
tctttttccg aaggtaactg gcttcagcag agcgcagata ccaaatactg ttcttctagt  7200
gtagccgtag ttaggccacc acttcaagaa ctctgtagca ccgcctacat acctcgctct  7260
gctaatcctg ttaccagtgg ctgctgccag tggcgataag tcgtgtctta ccgggttgga  7320
ctcaagacga tagttaccgg ataaggcgca gcggtcgggc tgaacggggg gttcgtgcac  7380
acagcccagc ttggagcgaa cgacctacac cgaactgaga tacctacagc gtgagctatg  7440
agaaagcgcc acgcttcccg aagggagaaa ggcggacagg tatccggtaa gcggcagggt  7500
cggaacagga gagcgcacga gggagcttcc agggggaaac gcctggtatc tttatagtcc  7560
tgtcgggttt cgccacctct gacttgagcg tcgatttttg tgatgctcgt caggggggcg  7620
gagcctatgg aaaaacgcca gcaacgcggc ctttttacgg ttcctggcct tttgctggcc  7680
ttttgctcac atgttctttc ctgcgttatc ccctgattct gtggataacc gtattaccgc  7740
ctttgagtga gctgataccg ctcgccgcag ccgaacgacc gagcgcagcg agtcagtgag  7800
cgaggaagcg gaagagcgcc caatacgcaa accgcctctc cccgcgcgtt ggccgattca  7860
ttaatgcagg ttgatcagat ctcgatcccg cgaaattaat acgactcact atagggagac  7920
cacaacggtt tccctctaga aataattttg tttaacttta agaaggagat atacccatgg  7980
aaaagcctga actcaccgcg acgtctgtcg agaagtttct gatcgaaaag ttcgacagcg  8040
tctccgacct gatgcagctc tcggagggcg aagaatctcg tgctttcagc ttcgatgtag  8100
gagggcgtgg atatgtcctg cgggtaaata gctgcgccga tggtttctac aaagatcgtt  8160
atgtttatcg gcactttgca tcggccgcgc tcccgattcc ggaagtgctt gacattgggg  8220
aattcagcga gagcctgacc tattgcatct cccgccgtgc acagggtgtc acgttgcaag  8280
acctgcctga aaccgaactg cccgctgttc tgcagccggt cgcggaggct atggatgcga  8340
tcgctgcggc cgatcttagc cagacgagcg ggttcggccc attcggaccg caaggaatcg  8400
gtcaatacac tacatggcgt gatttcatat gcgcgattgc tgatccccat gtgtatcact  8460
ggcaaactgt gatggacgac accgtcagtg cgtccgtcgc gcaggctctc gatgagctga  8520
tgctttgggc cgaggactgc cccgaagtcc ggcacctcgt gcacgcggat ttcggctcca  8580
acaatgtcct gacggacaat ggccgcataa cagcggtcat tgactggagc gaggcgatgt  8640
tcggggattc ccaatacgag gtcgccaaca tcttcttctg gaggccgtgg ttggcttgta  8700
tggagcagca gacgcgctac ttcgagcgga ggcatccgga gcttgcagga tcgccgcggc  8760
tccgggcgta tatgctccgc attggtcttg accaactcta tcagagcttg gttgacggca  8820
atttcgatga tgcagcttgg gcgcagggtc gatgcgacgc aatcgtccga tccggagccg  8880
ggactgtcgg gcgtacacaa atcgcccgca gaagcgcggc cgtctggacc gatggctgtg  8940
tagaagtact cgccgatagt ggaaaccgac gccccagcac tcgtccgagg gcaaaggaat  9000
agtgaggtac agcttggatc gatccggctg ctaacaaagc ccgaaaggaa gctgagttgg  9060
ctgctgccac cgctgagcaa taactagcat aaccccttgg ggcctctaaa cgggtcttga  9120
ggggtttttt gctgaaagga ggaactatat ccggatgctc gggcgcgccg gtac        9174

SEQ ID NO: 506          moltype = DNA  length = 9174
FEATURE                 Location/Qualifiers
misc_feature            1..9174
                        note = synthesized sequence- RTW1202
source                  1..9174
                        mol_type = other DNA
                        organism = synthetic construct
SEQUENCE: 506
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg gaataaaata ggaaacgttg ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gtttttttagg attcttttgg tttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttttgt gggtttgttc acatgttatc aagcttaatc ttttactatg tatgcgacca  1860
tatctggatc cagcaaaggc gatttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
```

-continued

```
ttgattctag tttaagtaat ccatggcacc gaagaagaag cgcaaggtga tggacaaaaa  2100
gtactcaata gggctcgaca tagggactaa ctccgttgga tgggccgtca tcaccgacga  2160
gtacaaggtg ccctccaaga agttcaaggt gttgggaaac accgacaggc acagcataaa  2220
gaagaatttg atcggtgccc tcctcttcga ctccggagag accgctgagg ctaccaggct  2280
caagaggacc gctagaaggc gctacaccag aaggaagaac agaatctgct acctgcagga  2340
gatcttctcc aacgagatgg ccaaggtgga cgactccttc ttccaccgcc ttgaggaatc  2400
attcctggtg gaggaggata aaaagcacga gagacaccca atcttcggga acatcgtcga  2460
cgaggtggcc taccatgaaa agtaccctac catctaccac ctgaggaaga agctggtcga  2520
ctctaccgac aaggctgact tgcgcttgat ttacctggct ctcgctcaca tgataaagtt  2580
ccgcggacac ttcctcattg agggagacct gaacccagac aactccgacg tggacaagct  2640
cttcatccag ctcgttcaga cctacaacca gcttttcgag gagaacccaa tcaacgccag  2700
tggagttgac gccaaggcta tcctctctgc tcgtctgtca aagtccagga ggcttgagaa  2760
cttgattgcc cagctgcctg gcgaaaagaa gaacggactg ttcggaaact tgatcgctct  2820
ctccctggga ttgactccca acttcaagtc caacttcgac ctcgccgagg acgctaagtt  2880
gcagttgtct aaagacacct acgacgatga cctcgacaac ttgctggccc agataggcga  2940
ccaatacgcc gatctcttcc tcgccgctaa gaacttgtcc gacgcaatcc tgctgtccga  3000
catcctgaga gtcaacactg agattaccaa agctcctctg tctgcttcca tgattaagcg  3060
ctacgacgag caccaccaag atctgaccct gctcaaggcc ctggtgagac agcagctgcc  3120
cgagaagtac aaggagatct tttcgacca gtccaagaac ggctacgccg gatacattga  3180
cggaggcgcc tcccaggaag agttctacaa gttcatcaag cccatccttg agaagatgga  3240
cggtaccgag gagctgttgg tgaagttgaa cagagaggac ctgttgagga agcagagaac  3300
cttcgacaac ggaagcatcc ctcaccaaat ccacctggga gagctccacg ccatcttgag  3360
gaggcaggag gatttctatc ccttcctgaa ggacaaccgc gagaagattg agaagatctt  3420
gaccttcaga attccttact acgtcgggcc actcgccaga ggaaactcta ggttcgcctg  3480
gatgacccgc aaatctgaag agaccattac tccctggaac ttcgaggaag tcgtggacaa  3540
gggcgcttcc gctcagtctt tcatcgagag gatgaccaac ttcgataaaa atctgcccaa  3600
cgagaaggtg ctgcccaagc actccctgtt gtacgagtat ttcacagtgt acaacgagct  3660
caccaaggtg aagtacgtca cagagggaat gaggaagcct gccttcttgt ccggagagca  3720
gaagaaggcc atcgtcgacc tgctcttcaa gaccaacagg aaggtgactg tcaagcagct  3780
gaaggaggac tacttcaaga agatcgagtg cttcgactcc gtcgagatct ctggtgtcga  3840
ggacaggttc aacgcctccc ttgggactta ccacgatctg ctcaagatta ttaaagacaa  3900
ggacttcctg gacaacgagg agaacgagga catccttgag gacatcgtgc tcaccctgac  3960
cttgttcgaa gacagggaaa tgatcgaaga gaggctcaag acctacgccc acctcttcga  4020
cgacaaggtg atgaaacagc tgaagagacg cagatatacc ggctggggaa ggctctcccg  4080
caaattgatc aacgggatca gggacaagca gtcagggaag actatactcg acttcctgaa  4140
gtccgacgga ttcgccaaca ggaacttcat gcagctcatt cacgacgact ccttgacctt  4200
caaggaggac atccagaagg ctcaggtgtc tggacagggt gactccttgc atgagcacat  4260
tgctaacttg gccggctctc ccgctattaa gaagggcatt ttgcagaccg tgaaggtcgt  4320
tgacgagctc gtgaaggtga tgggacgcca caagccagag aacatcgtta ttgagatggc  4380
tcgcgagaac caaactaccc agaaagggca gaagaattcc cgcgagagga tgaagcgcat  4440
tgaggagggc ataaaagagc ttggctctca gatcctcaag gagcaccccg tcgagaacac  4500
tcagctgcag aacgagaagc tgtacctgta ctacctccaa aacggaaggg acatgtacgt  4560
ggaccaggag ctggacatca acaggttgtc cgactacgac gtcgaccaca tcgtgcctca  4620
gtccttcctg aaggatgact ccatcgacaa taaagtgctg acacgctccg ataaaaatag  4680
aggcaagtcc gacaacgtcc cctccgagga ggtcgtgaag aagatgaaaa actactggag  4740
acagctcttg aacgccaagc tcatcaccca gcgtaagttc gacaacctga ctaaggctga  4800
gagaggagga ttgtccgagc tcgataaggc cggattcatc aagagacagc tcgtcgaaac  4860
ccgccaaatt accaagcacg tggcccaaat tctggattcc cgcatgaaca ccaagtacga  4920
tgaaaatgac aagctgatcc gcgaggtcaa ggtgatcacc ttgaagtcca agctggtctc  4980
cgacttccgc aaggacttcc agttctacaa ggtgagggag atcaacaact accaccacgc  5040
acacgacgcc tacctcaacg ctgtcgttgg aaccgccctc atcaaaaaat atcctaagct  5100
ggagtctgag ttcgtctacg gcgactacaa ggtgtacgac gtgaggaaga tgatcgctaa  5160
gtctgagcag gagatcggca aggccaccgc caagtacttc ttctactcca acatcatgaa  5220
cttcttcaag accgagatca ctctcgccaa cggtgagatc aggaagcgcc cactgatcga  5280
gaccaacggt gagactggag agatcgtgtg ggacaaaggg agggatttcg ctactgtgag  5340
gaaggtgctc tccatgcctc aggtgaacat cgtcaagaag accgaagttc agaccggagg  5400
attctccaag gagtccatcc tccccaagag aaactccgac aagctgatcg ctagaaagaa  5460
agactgggac cctaagaagt acggaggctt cgattctcct accgtggcct actctgtgct  5520
ggtcgtggcc aaggtggaga agggcaagtc caagaagctg aaatccgtca aggagctcct  5580
cgggattacc atcatggaga ggagttcctt cgagaagaac cctatcgact tcctggaggc  5640
caagggatat aaagaggtga agaaggacct catcatcaag ctgcccaagt actccctctt  5700
cgagttggag aacggaagga agaggatgct ggcttctgcc ggagagttgc agaagggaaa  5760
tgagctcgcc cttccctcca agtacgtgaa cttcctgtac ctcgcctctc actatgaaaa  5820
gttgaagggc tctcctgagg acaacgagca gaagcagctc ttcgtggagc agcacaagca  5880
ctacctggac gaaattatcg agcagatctc tgagttctcc aagcgcgtga tattggccga  5940
cgccaacctc gacaaggtgc tgtccgccta caacaagcac agggataagc ccattcgcga  6000
gcaggctgaa aacattatcc acctgtttac cctcacaaac ttgggagccc ctgctgcctt  6060
caagtacttc gacaccacca ttgacaggaa gagatacacc tccaccaagg aggtgctcga  6120
cgcaacactc atccaccaat ccatcaccgg cctctatgaa acaaggattg acttgtccca  6180
gctgggaggc gactctagag ccgatcccaa gaagaagaga aaggtgaaga gaccacggga  6240
ccgccacgat ggcgagctgg gaggccgcaa gcgggcaagg taggttaacc tagacttgtc  6300
catcttctgg attggccaac ttaattaatg tatgaaataa aaggatgcac acatagtgac  6360
atgctaatca ctataatgtg ggcatcaaag ttgtgtgtta tgtgtaatta ctagttatct  6420
gaataaaaga gaaagagatc atccatattt cttatcctaa atgaatgtca cgtgtcttta  6480
taattctttg atgaaccaga tgcatttcat taaccaaatc catatacata taaatattaa  6540
tcatatataa ttaatatcaa ttgggttagc aaaacaaatc tagtctaggt gtgttttgcg  6600
aattcgatat caagcttatc gataccgtcg aggggggggcc cggtaccggc gcgccgttct  6660
atagtgtcac ctaaatcgta tgtgtatgat acataaggtt atgtattaat tgtagccgcg  6720
ttctaacgac aatatgtcca tatggtgcac tctcagtaca atctgctctg atgccgcata  6780
```

```
gttaagccag ccccgacacc cgccaacacc cgctgacgcg ccctgacggg cttgtctgct  6840
cccggcatcc gcttacagac aagctgtgac cgtctccggg agctgcatgt gtcagaggtt  6900
ttcaccgtca tcaccgaaac gcgcgagacg aaagggcctc gtgatacgcc tatttttata  6960
ggttaatgtc atgaccaaaa tcccttaacg tgagttttcg ttccactgag cgtcagaccc  7020
cgtagaaaag atcaaaggat cttcttgaga tcctttttt ctgcgcgtaa tctgctgctt  7080
gcaaacaaaa aaaccaccgc taccagcggt ggtttgtttg ccggatcaag agctaccaac  7140
tctttttccg aaggtaactg gcttcagcag agcgcagata ccaaatactg ttcttctagt  7200
gtagccgtag ttaggccacc acttcaagaa ctctgtagca ccgcctacat acctcgctct  7260
gctaatcctg ttaccagtgg ctgctgccag tggcgataag tcgtgtctta ccgggttgga  7320
ctcaagacga tagttaccgg ataaggcgca gcggtcgggc tgaacggggg gttcgtgcac  7380
acagcccagc ttggagcgaa cgacctacac cgaactgaga tacctacagc gtgagctatg  7440
agaaagcgcc acgcttcccg aagggagaaa ggcggacagg tatccggtaa gcggcagggt  7500
cggaacagga gagcgcacga gggagcttcc agggggaaac gcctggtatc tttatagtcc  7560
tgtcgggttt cgccacctct gacttgagcg tcgatttttg tgatgctcgt caggggggcg  7620
gagcctatgg aaaaacgcca gcaacgcggc ctttttacgg ttcctggcct tttgctggcc  7680
ttttgctcac atgttctttc ctgcgttatc ccctgattct gtggataacc gtattaccgc  7740
ctttgagtga gctgataccg ctcgccgcag ccgaacgacc gagcgcagcg agtcagtgag  7800
cgaggaagcg gaagagcgcc caatacgcaa accgcctctc cccgcgcgtt ggccgattca  7860
ttaatgcagg ttgatcagat ctcgatcccg cgaaattaat acgactcact atagggagac  7920
cacaacggtt tccctctaga aataattttg tttaacttta agaaggagat atacccatgg  7980
aaaagcctga actcaccgcg acgtctgtcg agaagtttct gatcgaaaag ttcgacagcg  8040
tctccgacct gatgcagctc tcggagggcg aagaatctcg tgctttcagc ttcgatgtag  8100
gagggcgtgg atatgtcctg cgggtaaata gctgcgccga tggtttctac aaagatcgtt  8160
atgtttatcg gcactttgca tcggccgcgc tcccgattcc ggaagtgctt gacattgggg  8220
aattcagcga gagcctgacc tattgcatct cccgccgtgc acagggtgtc acgttgcaag  8280
acctgcctga aaccgaactg cccgctgttc tgcagccggt cgcggaggct atggatgcga  8340
tcgctgcggc cgatcttagc cagacgagcg ggttcggccc attcggaccg caaggaatcg  8400
gtcaatacac tacatggcgt gatttcatat gcgcgattgc tgatccccat gtgtatcact  8460
ggcaaactgt gatggacgac accgtcagtg cgtccgtcgc gcaggctctc gatgagctga  8520
tgctttgggc cgaggactgc cccgaagtcc ggcacctcgt gcacgcggat ttcggctcca  8580
acaatgtcct gacggacaat ggccgcataa cagcggtcat tgactggagc gaggcgatgt  8640
tcggggattc ccaatacgag gtcgccaaca tcttcttctg gaggccgtgg ttggcttgta  8700
tggagcagca gacgcgctac ttcgagcgga ggcatccgga gcttgcagga tcgccgcggc  8760
tccgggcgta tatgctccgc attggtcttg accaactcta tcagagcttg gttgacggca  8820
atttcgatga tgcagcttgg gcgcagggtc gatgcgacgc aatcgtccga tccggagccg  8880
ggactgtcgg gcgtacacaa atcgcccgca gaagcgcggc cgtctggacc gatggctgtg  8940
tagaagtact cgccgatagt ggaaaccgac gccccagcac tcgtccgagg gcaaaggaat  9000
agtgaggtac agcttggatc gatccggctg ctaacaaagc ccgaaaggaa gctgagttgg  9060
ctgctgccac cgctgagcaa taactagcat aaccccttgg ggcctctaaa cgggtcttga  9120
ggggtttttt gctgaaagga ggaactatat ccggatgctc gggcgcgccg gtac        9174
```

```
SEQ ID NO: 507          moltype = DNA  length = 6113
FEATURE                 Location/Qualifiers
misc_feature            1..6113
                        note = synthesized sequence- RTW1192A
source                  1..6113
                        mol_type = other DNA
                        organism = synthetic construct
SEQUENCE: 507
caagtagttc tagtcttaat acaaatgtca aatggcacaa gtgagatttt gaatttctga  60
tgttgtaaaa atctcaggac atgaatacta ttgggaagca attattcata cttcaccaat  120
ccaaactgac ccaaaattct caaatcacat gaaagcaaaa atgcatataa cacgaagaat  180
aagaagaaga ggaactaacc tggggtttcg atgattaaag cgttgttgtt gatgatgaaa  240
acgatgatta tggagagaaa ttgttgttga atggtgaaat tgttatagaa agagaacgaa  300
gatagagaaa aagatatata gatttttcaa ggctcaaacc ctaaaatcac catgagagag  360
aacaaagatt gagaaaccta caaccactat gagagagaat gagcagaaca gaagcgtgag  420
atagagaacg agagttaagg tgcgagagga cacgaagaac aaaaggtgtg agagaaagaa  480
caaaggagcc tacggtgtga gatgagagaa tttgaaattc ttaccattta ggtggaattt  540
caattctaca attttattct attaaaatta ttttaaaaaa tgatgtcatt ttaaattctt  600
taaaatctca tatccaacaa ctgaattatg atagaggtat ttcaaattca cttaaaaaaa  660
ttatcttatt taaataccc atccaaacat agcgaaatgt tcatgagaag gatcaagtgg  720
tttggaaaca tagtactaat ggtgtttata cagttcatgg aatccttgat agataattta  780
aaggttgctg gaaattggat gaaggtgtgg agattaaata ttcttccaaa aataaagcgt  840
tttatttgga gagtgttgtg tggttgtctc ccctgtaggc aaaagcttcg atgtaaagga  900
gttcaatgtc caataaccta tgctttctat ccctcgatta ttgaaaatga atgacacatt  960
ttatttggtt gaaatcaaga aataagcatg tggcaagcaa cgggtatttg acaattcata  1020
gaacaaaagg tgaatgcagc aaaagaatta atgaactcct tttcgatcta cttggatcac  1080
tacatggaga tattatcaac aaatttgatg ttactttatg gagcagttgg aattcttgga  1140
atgacaagat atgaaatgaa cataccaacc ctcctcttgt ttctgtttcg gtttctatgc  1200
agtattttgt tgaatggcaa agtgcaaggt aatatgctcc tcaacatcaa ttaacaaatg  1260
ttcatgacat ctcttaccag ctccaacttg gggacgtttg acaaacacca ccgtcaagtt  1320
tccttaaatg caacattaat gttgctcatt tcaaggagga gaatagtttt ggtgtcggca  1380
tgatactcca tcaaggaaga ttcgtcaaag ctcactcacg ttttcgacat gggtcgacat  1440
gggttacctg acccaaaggc tgaggcttag gcttgggttt gcttcaagta ttgatctggg  1500
cccagactat tggtttacat aatatcattt ttgaaaacct aacatctaaa actcaaggtt  1560
gtttagaggt gcgccattcc aaaataagat tatcctattt gtgcatgaat gcgaccaact  1620
atctcctgtt tcagcattat aaagtataaa caacaaactt ctttaatcaa gggactaaaa  1680
gatattggac atacaagcta aaagtgatag aatttgagaa aacaaatatt gacaacaata  1740
ttcaagagga cactaaaaca taattctcaa attttttttg tttatttaaa ataaagtggt  1800
```

-continued

```
tcattaggta gctccgggtg attgcggtta catcatgtac ggaaaaaataa ttctaatcct  1860
tgatttaaat ttgaacttga ctatttattt attctttatt tcattttgta aatcatttta  1920
tgtatctcct ggcaagcaat tttatccacc ttgcaccaac accttcgggt tccataatca  1980
aaccacctta acttcacacc atgctgtaac tcacaccgcc cagcatctcc aatgtgaaag  2040
aagctaaaat ttaataaaca atcatacgaa gcagtgacaa aataccagat ggtattaatg  2100
cttcgataaa attaattgga aagtataaaa tggtagaaaa taataaatta taattaattt  2160
aagtaagata aaaaataatt aaaaactaaa atgttaaaat tttaaaaaaa ttattttaaa  2220
taatatttaa aaacattaaa aatcatttta aaaaatttat ttatagaaca attaaataaa  2280
tatttcagct aataaaaaac aaaagcttac ctagccttag aagacaactt gtccaacaat  2340
tagatgatac ccattgccct tacgttttct ttaacatcaa ttattgtttt tgtcaacaag  2400
ctatctttta gttttatttt attggtaaaa aatatgtcgc cttcaagttg catcatttaa  2460
cacatctcgt cattagaaaa ataaaactct tccctaaacg attagtagaa aaaatcattc  2520
gataataaat aagaaagaaa aattagaaaa aaataacttc attttaaaaa aatcattaag  2580
gctatatttt ttaaatgact aattttatat agactgtaac taaaagtata caatttatta  2640
tgctatgtat cttaaagaat tacttataaa aatctacgga agaatatctt acaaagtgaa  2700
aaacaaatga gaaagaattt agtgggatga ttatgatttt atttgaaaat tgaaaaaata  2760
attattaaag actttagtgg agtaagaaag ctttcctatt agtcttttct tatccataaa  2820
aaaaaaaaaa aaaatctagc gtgacagctt ttccatagat tttaataatg taaaatactg  2880
gtagcagccg accgttcagg taatggacac tgtggtccta acttgcaacg ggtgcgggcc  2940
caatttaata acgccgtggt aacggataaa gccaagcgtg aagcggtgaa ggtacatctc  3000
tgactccgtc aagattacga aaccgtcaac tacgaaggac tccccgaaat atcatctgtg  3060
tcataaacac caagtcacac catacatggg cacgcgtcac aatatgattg gagaacggtt  3120
ccaccgcata tgctataaaa tgccccccaca cccctcgacc ctaatcgcac ttcaattgca  3180
atcaaattag ttcattctct ttgcgcagtt ccctacctct cctttcaagg ttcgtagatt  3240
tcttccgttt ttttttcttc ttctttattg tttgttctac atcagcatga tgttgatttg  3300
attgtgtttt ctatcgtttc atcgattata aattttcata atcagaagat tcagctttta  3360
ttaatgcaag aacgtcctta attgatgatt ttataaccgt aaattaggtc taattagagt  3420
tttttcata aagattttca gatccgttta caacaagcct taattgttga ttctgtagtc  3480
gtagattaag gttttttca tgaactactt cagatccgtt aaacaacagc cttatttgtt  3540
gatacttcag tcgtttttca agaaattgtt cagatccgtt gataaaagcc ttattcgttg  3600
attctgtatg gtatttcaag agatattgct caggtccttt agcaactacc ttatttgttg  3660
attctgtggc catagattag gatttttttt cacgaaattg cttcttgaaa ttacgtgatg  3720
gattttgatt ctgatttatc ttgtgattgt tgactctaca gatggcccaa gtgagcagag  3780
tgcacaatct tgctcaaagc actcaaattt ttggccattc ttccaactcc aacaaactca  3840
aatcggtgaa ttcggtttca ttgaggccac gcctttgggg ggcctcaaaa tctcgcatcc  3900
cgatgcataa aaatggaagc tttatgggaa attttaatgt ggggaaggga aattccggcg  3960
tgtttaaggt ttctgcatcg gtcgccgccg cagagaagcc gtcaacgtcg ccggagatcg  4020
tgttggaacc catcaaagac ttctcgggta ccatcacatt gccagggtcc aagtctctgt  4080
ccaatcgaat tttgcttctt gctgctctct ctgaggtgaa gtttatttat ttatttattt  4140
gtttgtttgt tgttgggtgt gggaatagga gtttgatgtg tagagtggat tttgaatatt  4200
tgattttttt ttgtattatt ctgtgaaaat gaagcatcat gtcccatgaa agaaatggac  4260
acgaaattaa gtggcttatg atgtgaaatg aggatagaaa tgtgtgtagg gttttttaat  4320
gggtagcaat aagcatattc aatatctgga ttgatttgga cgtttctgta taaaggagta  4380
tgctagcaat gtgttaatgt atggcttgct aaaatactcc taaaaatcaa gtgggagtag  4440
tatacatatc tacagcaaat gtattaggtg aggcatttgg cttctctatt gtaaggaaca  4500
aataatatca gttaatgtga aaatcaatgg ttgatattcc aatacattca tgatgtgtta  4560
tttatatgta cctaatattg actgttgttt ttctccgcaa tgaccaagat tatttatttt  4620
atcctctaaa gtgactaatt gagttgctta ctttagagaa gttggaccca ttaggtgaga  4680
gcgtgggggg aactaatctt gaatatacaa tctgagtctt gattatccaa gtatggttgt  4740
atgaacaatg ttagctctag aagataaacc ctcccccaaa acacaaatta gaatgacatt  4800
tcaagttcca tgtatgtcac tttcattcta ttatttttac aacttttagt tacttaacag  4860
atgtcttgtt cagcataaat tataatttat tctgtttttt tttagggaac aactgttgta  4920
gacaacttgt tgtatagtga ggatattcat tacatgcttg gtgcattaag gacccttgga  4980
ctgcgtgtgg aagatgacaa aacaaccaaa caagcaattg ttgaaggctg tgggggattg  5040
tttcccacta gtaaggaatc taaagatgaa atcaatttat tccttggaaa tgctggtatt  5100
gcaatgagat ctttgacagc agctgttgtt gctgcaggtg gaaatgcaag gtctgttttt  5160
tttttttttg ttcagcataa tctttgaatt gttcctcgta taactaatca caacagagta  5220
cgtgttcttc ttcctgttat aatctaaaaa tctcatccag attagtcatc ctttcttctt  5280
aaaaggaacc tttaattatc aatgtattta tttaatattt aaattagctt gtcaaagtct  5340
agcatataca tattttgatt atattctgag aaatgcacct gagggtgttc ctcatgatct  5400
acttcaacct ctgttattat tagattttct atcatgatta ctggtttgag tctctaagta  5460
gaccatcttg atgttcaaaa tatttcagct acgtacttga tggggtgccc cgaatgagag  5520
agaggccaat tggggatttg gttgctggtc ttaagcaact tggtgcagat gttgattgct  5580
ttcttggcac aaactgtcca cctgttcgtg taaatgggaa gggaggactt cctggcggaa  5640
aggtatggtt tggatttcat ttagaataag gtggagtaac tttcctggat caaaattcta  5700
atttaagaag cctccctgtt ttcctctctt tagaataaga ctaagggtag gtttaggagt  5760
tgggttttgg agagaaatgg aagggagagc aattttttc ttcttctaat aaatattctt  5820
taatttgata catttttaa gtaaaagaat ataaagatag attagcataa cttaatgttt  5880
taatctttta tttattttta taaatattat atacctgtct atttaaaaat caaatatttg  5940
tcctccattc cctttccctt caaaacctca gttccaaata taccgtagtt gaattatatt  6000
ttggaaggcc tattggttgg agacttttcc ttttcagaga ttatccctca cctttattat  6060
agcctttcta tttttaaact tcatatagac gccattcttg gggcggccgc gat         6113
```

```
SEQ ID NO: 508          moltype = DNA  length = 32
FEATURE                 Location/Qualifiers
misc_feature            1..32
                        note = synthesized sequence- primer, soy1-F4
source                  1..32
                        mol_type = other DNA
```

```
                         organism = synthetic construct
SEQUENCE: 508
tcaataatac tactctctta gacaccaaac aa                                32

SEQ ID NO: 509           moltype = DNA  length = 23
FEATURE                  Location/Qualifiers
misc_feature             1..23
                         note = synthesized sequence- primer, soy1-R4
source                   1..23
                         mol_type = other DNA
                         organism = synthetic construct
SEQUENCE: 509
caaggaaaat gaatgatggc ttt                                          23

SEQ ID NO: 510           moltype = DNA  length = 18
FEATURE                  Location/Qualifiers
misc_feature             1..18
                         note = synthesized sequence- probe, soy1-T3(FAM-MGB)
source                   1..18
                         mol_type = other DNA
                         organism = synthetic construct
SEQUENCE: 510
ccttcccaaa ctataatc                                                18

SEQ ID NO: 511           moltype = DNA  length = 27
FEATURE                  Location/Qualifiers
misc_feature             1..27
                         note = synthesized sequence- WOL1005, Forward_primer
source                   1..27
                         mol_type = other DNA
                         organism = synthetic construct
SEQUENCE: 511
aaatgttatc agaggaacat gagctgc                                      27

SEQ ID NO: 512           moltype = DNA  length = 28
FEATURE                  Location/Qualifiers
misc_feature             1..28
                         note = synthesized sequence- WOL1006, Reverse_primer
source                   1..28
                         mol_type = other DNA
                         organism = synthetic construct
SEQUENCE: 512
attatttttc cgtacatgat gtaaccgc                                     28

SEQ ID NO: 513           moltype = DNA  length = 438
FEATURE                  Location/Qualifiers
source                   1..438
                         mol_type = genomic DNA
                         organism = Cauliflower mosaic virus
SEQUENCE: 513
cccatggagt caaagattca aatagaggac ctaacagaac tcgccgtaaa gactggcgaa  60
cagttcatac agagtctctt acgactcaat gacaagaaga aaatcttcgt caacatggtg  120
gagcacgaca cgcttgtcta ctccaaaaat atcaaagata cagtctcaga agaccaaagg  180
gcaattgaga cttttcaaca aagggtaata tccggaaacc tcctcggatt ccattgccca  240
gctatctgtc actttattgt gaagatagtg gaaaaggaag gtggctccta caaatgccat  300
cattgcgata aaggaaaggc catcgttgaa gatgcctctg ccgacagtgg tcccaaagat  360
ggacccccac ccacgaggag catcgtggaa aaagaagacg ttccaaccac gtcttcaaag  420
caagtggatt gatgtgat                                                438

SEQ ID NO: 514           moltype = DNA  length = 19
FEATURE                  Location/Qualifiers
source                   1..19
                         mol_type = genomic DNA
                         organism = Cauliflower mosaic virus
SEQUENCE: 514
gtctcagaag accaaaggg                                               19

SEQ ID NO: 515           moltype = DNA  length = 25
FEATURE                  Location/Qualifiers
source                   1..25
                         mol_type = genomic DNA
                         organism = Cauliflower mosaic virus
SEQUENCE: 515
tgccatcatt gcgataaagg aaagg                                        25

SEQ ID NO: 516           moltype = DNA  length = 20
FEATURE                  Location/Qualifiers
source                   1..20
                         mol_type = genomic DNA
```

```
                        organism = Cauliflower mosaic virus
SEQUENCE: 516
gatgcctctg ccgacagtgg                                             20

SEQ ID NO: 517          moltype = DNA  length = 3708
FEATURE                 Location/Qualifiers
source                  1..3708
                        mol_type = genomic DNA
                        organism = Zea mays
SEQUENCE: 517
ctgcagccca tcaaggagat ctccggcacc gtcaagctgc cggggtccaa gtcgctttcc  60
aacaggatcc tcctgctcgc cgccctgtcc gaggtgagcg attttggtgc ttgctgcgct  120
gccctgtctc actgctacct aaatgttttg cctgtcgaat accatggatt ctcggtgtaa  180
tccatctcac gatcagatgc accgcatgtc gcatgcctag ctctctctaa tttgtctagt  240
agtttgtata cggattaaga ttgataaatc ggtaccgcaa aagctaggtg taaataaaca  300
ctacaaaatt ggatgttccc ctatcggcct gtactcggct actcgttctt gtgatggcat  360
gttatttctt cttggtgttt ggtgaactcc cttatgaaat ttgggcgcaa agaaatcgcc  420
ctcaagggtt gatcttatgc catcgtcatg ataaacagtg aagcacggat gatcctttac  480
gttgttttta acaaactttg tcagaaaact agcaatgtta acttcttaat gatgatttca  540
caacaaaaaa ggtaaccttg ctactaacat aacaaaagac ttgttgctta ttaattatat  600
gtttttttaa tctttgatca ggggacaaca gtggttgata acctgttgaa cagtgaggat  660
gtccactaca tgctcggggc cttgaggact cttggtctct ctgtcgaagc ggacaaagct  720
gccaaaagag ctgtagttgt tggctgtggt ggaaagttcc cagttgagga tgctagagag  780
gaagtgcagc tcttcttggg gaatgctgga atcgcaatgc ggtcattgac agcagctgtt  840
actgctgctg gtggaaatgc aacgtatgtt tcctctctct ctctacaata cttgttggag  900
ttagtatgaa acccatgtgt atgtctagtg gcttatggtg tattggtttt tgaacttcag  960
ttacgtgctt gatggagtac caagaatgag ggagagaccc attggcgact tggttgtcgg  1020
attgaagcag cttggtgcag atgttgattg tttccttggc actgactgcc cacctgttcg  1080
tgtcaatgga atcggagggc tacctggtgg caaggttagt tactaagggc cacatgttac  1140
attcttctgt aaatggtaca actattgtcg agcttttgca tttgtaagga aaacattgat  1200
tgatctgaat ttgatgctac accacaaaat atctacaaat ggtcatccct aactagcaaa  1260
ccatgtctcc attaagctca atgaagtaat acttggcatg tgtttatcaa cttaatttcc  1320
atcttctggg gtattgcctg ttttctagtc taatagcatt tgtttttaga attagctctt  1380
acaactgtta tgttctacag gtcaagctgt ctggctccat cagcagtcag tacttgagtg  1440
ccttgctgat ggctgctcct ttggctcttg gggatgtgga gattgaaatc attgataaat  1500
taatctccat tccctacgtc gaaatgacat tgagattgat ggagcgtttt ggtgtgaaag  1560
cagagcattc tgatagctgg gacagattct acattaaggg aggtcaaaaa tacaagtaag  1620
ctctgtaatg tatttcacta ctttgatgcc aatgtttcag ttttcagttt tccaaacagt  1680
cgcatcaata tttgaataga tgcactgtag aaaaaaatca ttgcagggaa aaactagtac  1740
tgagtatttt gactgtaaat tatttaacca gtcggaatat agtcagtcta ttggagtcaa  1800
gagcgtgaac cgaaatagcc agttaattat cccattatac agaggacaac catgtatact  1860
attgaaactt ggtttaagag aatctaggta gctggactcg tagctgcttg gcatggatac  1920
cttcttatct ttaggaaaag acacttgatt ttttttctgt ggccctctat gatgtgtgaa  1980
cctgcttctc tattgcttta gaaggatata tctatgtcgt tatgcaacat gcttccctta  2040
gtcatttgta ctgaaatcag tttcataagt tcgttagtgg ttccctaaac gaaaccttgt  2100
ttttctttgc aatcaacagg tcccctaaaa atgcctatgt tgaaggtgat gcctcaagcg  2160
caagctattt cttggctggt gctgcaatta ctggagggac tgtgactgtg gaaggttgtg  2220
gcaccaccag tttgcaggta aagatttctt ggctggtgct acgataactg cttttgtctt  2280
tttggtttca gcattgttct cagagtcact aaataacatt atcatctgca aacgtcaaat  2340
agacatactt aggtgaatgg atattcatgt aaccgtttcc ttacaaattt gctgaaacct  2400
cagggtgatg tgaagtttgc tgaggtactg gagatgatgg gagcgaaggt tacatggacc  2460
gagactagcg taactgttac tggcccaccg cgggagccat ttgggaggaa acacctcaag  2520
gcgattgatg tcaacatgaa caagatgcct gatgtcgcca tgactcttgc tgtggttgcc  2580
ctctttgccg atggcccgac agccatcaga gacggtaaaa cattctcagc cctacaacca  2640
tgcctcttct acatcactac ttgacaagac taaaaactat tggctcgttg gcagtggctt  2700
cctggagagt aaaggagacc gagaggatgg ttgcgatccg gacggagcta accaaggtaa  2760
ggctacatac ttcacatgtc tcacgtcgtc tttccatagc tcgctgcctc ttagcggctt  2820
gcctgcggtc gctccatcct cggttgctgt ctgtgttttc cacagctggg agcatctgtt  2880
gaggaagggc cggactactg catcatcacg ccgccggaga agctgaacgt gacggcgatc  2940
gacacgtacg acgaccacag gatggccatg gccttctccc ttgccgcctg tgccgaggtc  3000
cccgtgacca tccgggaccc tgggtgcacc cggaagacct tccccgacta cttcgatgtg  3060
ctgagcactt tcgtcaagaa ttaataaagc gtgcgatact accacgcagc ttgattgaag  3120
tgataggctt gtgctgagga aatacatttc ttttgttctg ttttttctct ttcacgggat  3180
taagttttga gtctgtaacg ttagttgttt gtagcaagtt tctatttcgg atcttaagtt  3240
tgtgcactgt aagccaaatt tcatttcaag agtggttcgt tggaataata agaataataa  3300
attacgtttc agtggctgtc aagcctgctg ctacgtttta ggagatggca ttagacattc  3360
atcatcaaca acaataaaac cttttagcct caaacaataa tagtgaagtt atttttagt  3420
cctaaacaag ttgcattagg atatagttaa aacacaaaag aagctaaagt tagggtttag  3480
acatgtggat attgttttcc atgtatagta tgttctttct ttgagtctca tttaactacc  3540
tctacacata ccaactttag ttttttttct acctcttcat gttactatgg tgccttctta  3600
tcccactgag cattggtata tttagaggtt tttgttgaac atgcctaaat catctcaatc  3660
aacgatggac aatcttttct tcgattgagc tgaggtacgt catctaga              3708

SEQ ID NO: 518          moltype = DNA  length = 3714
FEATURE                 Location/Qualifiers
source                  1..3714
                        mol_type = genomic DNA
                        organism = Zea mays
SEQUENCE: 518
```

```
ctgcagccca tcaaggagat ctccggcacc gtcaagctgc cggggtccaa gtcgctttcc  60
aacaggatcc tcctgctcgc cgccctgtcc gaggtgagcg attttggtgc ttgctgcgct  120
gccctgtctc actgctacct aaatgttttg cctgtcgaat accatggatt ctcggtgtaa  180
tccatatctg cacgatcaga tatgcaccgc atgtcgcata tctgagctct ctctaatttg  240
tctagtagtt tgtatacgga ttaagattga taaatcggta ccgcaaaagc taggtgtaaa  300
taaacactac aaaattggat gttcccctat cggcctgtac tcggctactc gttcttgtga  360
tggcatgtta tttcttcttg gtgtttggtg aactccctta tgaaatttgg gcgcaaagaa  420
atcgccctca agggttgatc ttatgccatc gtcatgataa acagtgaagc acggatgatc  480
ctttacgttg tttttaacaa actttgtcag aaaactagca atgttaactt cttaatgatg  540
atttcacaac aaaaaaggta accttgctac taacataaca aaagacttgt tgcttattaa  600
ttatatgttt ttttaatctt tgatcagggg acaacagtgg ttgataacct gttgaacagt  660
gaggatgtcc actacatgct cggggccttg aggactcttg gtctctctgt cgaagcggac  720
aaagctgcca aaagagctgt agttgttggc tgtggtggaa agttcccagt tgaggatgct  780
aaagaggaag tgcagctctt cttggggaat gctggaatcg caatgcggtc attgacagca  840
gctgttactg ctgctggtgg aaatgcaacg tatgtttcct ctctctctct acaatacttg  900
ttggagttag tatgaaaccc atgtgtatgt ctagtggctt atggtgtatt ggtttttgaa  960
cttcagttac gtgcttgatg gagtaccaag aatgagggag agacccattg gcgacttggt  1020
tgtcggattg aagcagcttg gtgcagatgt tgattgtttc cttggcactg actgccccacc  1080
tgttcgtgtc aatggaatcg gagggctacc tggtggcaag gttagttact aagggccaca  1140
tgttacattc ttctgtaaat ggtacaacta ttgtcgagct tttgcatttg taaggaaaac  1200
attgattgat ctgaatttga tgctacacca caaaatatct acaaatggtc atccctaact  1260
agcaaaccat gtctccatta agctcaatga agtaatactt ggcatgtgtt tatcaactta  1320
atttccatct tctggggtat tgcctgtttt ctagtctaat agcatttgtt tttagaatta  1380
gctcttacaa ctgttatgtt ctacaggtca agctgtctgg ctccatcagc agtcagtact  1440
tgagtgcctt gctgatggct gctcctttgg ctcttgggga tgtggagatt gaaatcattg  1500
ataaattaat ctccattccc tacgtcgaaa tgacattgag attgatggag cgttttggtg  1560
tgaaagcaga gcattctgat agctgggaca gattctacat taagggaggt caaaaataca  1620
agtaagctct gtaatgtatt tcactacttt gatgccaatg tttcagtttt cagttttcca  1680
aacagtcgca tcaatatttg aatagatgca ctgtagaaaa aaatcattgc agggaaaaac  1740
tagtactgag tattttgact gtaaattatt taaccagtcg gaatatagtc agtctattgg  1800
agtcaagagc gtgaaccgaa atagccagtt aattatccca ttatacagag gacaaccatg  1860
tatactattg aaacttggtt taagagaatc taggtagctg gactcgtagc tgcttggcat  1920
ggataccttc ttatctttag gaaaagacac ttgatttttt ttctgtggcc ctctatgatg  1980
tgtgaacctg cttctctatt gctttagaag gatatatcta tgtcgttatg caacatgctt  2040
cccttagtca tttgtactga aatcagtttc ataagttcgt tagtggttcc ctaaacgaaa  2100
ccttgttttt ctttgcaatc aacaggtccc ctaaaaatgc ctatgttgaa ggtgatgcct  2160
caagcgcaag ctatttcttg gctggtgctg caattactgg agggactgtg actgtggaag  2220
gttgtggcac caccagtttg caggtaaaga tttcttggct ggtgctacga taactgcttt  2280
tgtctttttg gtttcagcat tgttctcaga gtcactaaat aacattatca tctgcaaacg  2340
tcaaatagac atacttaggt gaatggatat tcatgtaacc gtttccttac aaatttgctg  2400
aaacctcagg gtgatgtgaa gtttgctgag gtactggaga tgatgggagc gaaggttaca  2460
tggaccgaga ctagcgtaac tgttactggc ccaccgcggg agccatttgg gaggaaacac  2520
ctcaaggcga ttgatgtcaa catgaacaag atgcctgatg tcgccatgac tcttgctgtg  2580
gttgccctct ttgccgatgg cccgacagcc atcagagacg gtaaaacatt ctcagcccta  2640
caaccatgcc tcttctacat cactacttga caagactaaa aactattggc tcgttggcag  2700
tggcttcctg gagagtaaag gagaccgaga ggatggttgc gatccggacg gagctaacca  2760
aggtaaggct acatacttca catgtctcac gtcgtctttc catagctcgc tgcctcttag  2820
cggcttgcct gcggtcgctc catcctcggt tgctgtctgt gttttccaca gctgggagca  2880
tctgttgagg aagggccgga ctactgcatc atcacgccgc cggagaagct gaacgtgacg  2940
gcgatcgaca cgtacgacga ccacaggatg gccatggcct tctcccttgc cgcctgtgcc  3000
gaggtccccg tgaccatccg ggaccctggg tgcacccgga agaccttccc cgactacttc  3060
gatgtgctga gcactttcgt caagaattaa taaagcgtgc gatactacca cgcagcttga  3120
ttgaagtgat aggcttgtgc tgaggaaata catttctttt gttctgtttt ttctctttca  3180
cgggattaag ttttgagtct gtaacgttag ttgtttgtag caagtttcta tttcggatct  3240
taagtttgtg cactgtaagc caaatttcat ttcaagagtg gttcgttgga ataataagaa  3300
taataaatta cgtttcagtg gctgtcaagc ctgctgctac gttttaggag atggcattag  3360
acattcatca tcaacaacaa taaaaccttt tagcctcaaa caataatagt gaagttattt  3420
tttagtccta aacaagttgc attaggatat agttaaaaca caaaagaagc taaagttagg  3480
gtttagacat gtggatattg ttttccatgt atagtatgtt ctttctttga gtctcattta  3540
actacctcta cacataccaa ctttagtttt ttttctacct cttcatgtta ctatggtgcc  3600
ttcttatccc actgagcatt ggtatattta gaggttttttg ttgaacatgc ctaaatcatc  3660
tcaatcaacg atggacaatc ttttcttcga ttgagctgag gtacgtcatc taga        3714
```

```
SEQ ID NO: 519          moltype = DNA  length = 3708
FEATURE                 Location/Qualifiers
source                  1..3708
                        mol_type = genomic DNA
                        organism = Zea mays
SEQUENCE: 519
ctgcagccca tcaaggagat ctccggcacc gtcaagctgc cggggtccaa gtcgctttcc  60
aacaggatcc tcctgctcgc cgccctgtcc gaggtgagcg attttggtgc ttgctgcgct  120
gccctgtctc actgctacct aaatgttttg cctgtcgaat accatggatt ctcggtgtaa  180
tccatctcac gatcagatgc accgcatgtc gcatgcctag ctctctctaa tttgtctagt  240
agtttgtata cggattaaga ttgataaatc ggtaccgcaa aagctaggtg taaataaaca  300
ctacaaaatt ggatgttccc ctatcggcct gtactcggct actcgttctt gtgatggcat  360
gttatttctt cttggtgttt ggtgaactcc cttatgaaat ttgggcgcaa agaaatcgcc  420
ctcaagggtt gatcttatgc catcgtcatg ataaacagtg aagcacggat gatcctttac  480
gttgttttta acaaactttg tcagaaaact agcaatgtta acttcttaat gatgatttca  540
caacaaaaaa ggtaaccttg ctactaacat aacaaaagac ttgttgctta ttaattatat  600
```

```
gtttttttaa tctttgatca ggggacaaca gtggttgata acctgttgaa cagtgaggat  660
gtccactaca tgctcggggc cttgaggact cttggtctct ctgtcgaagc ggacaaagct  720
gccaaaagag ctgtagttgt tggctgtggt ggaaagttcc cagttgagga tgctagaaag  780
gaagtgcagc tcttcttggg gaatgctgga atcgcaatgc ggtcattgac agcagctgtt  840
actgctgctg gtggaaatgc aacgtatgtt tcctctctct ctctacaata cttgttggag  900
ttagtatgaa acccatgtgt atgtctagtg gcttatggtg tattggtttt tgaacttcag  960
gtacgtgctt gatggagtac caagaatgag ggagagaccc attggcgact tggttgtcgg  1020
attgaagcag cttggtgcag atgttgattg tttccttggc actgactgcc cacctgttcg  1080
tgtcaatgga atcggagggc tacctggtgg caaggttagt tactaagggc cacatgttac  1140
attcttctgt aaatggtaca actattgtcg agcttttgca tttgtaagga aaacattgat  1200
tgatctgaat ttgatgctac accacaaaat atctacaaat ggtcatccct aactagcaaa  1260
ccatgtctcc attaagctca atgaagtaat acttggcatg tgtttatcaa cttaatttcc  1320
atcttctggg gtattgcctg ttttctagtc taatagcatt tgtttttaga attagctctt  1380
acaactgtta tgttctacag gtcaagctgt ctggctccat cagcagtcag tacttgagtg  1440
ccttgctgat ggctgctcct ttggctcttg gggatgtgga gattgaaatc attgataaat  1500
taatctccat tccctacgtc gaaatgacat tgagattgat ggagcgtttt ggtgtgaaag  1560
cagagcattc tgatagctgg gacagattct acattaaggg aggtcaaaaa tacaagtaag  1620
ctctgtaatg tatttcacta ctttgatgcc aatgtttcag ttttcagttt tccaaacagt  1680
cgcatcaata tttgaataga tgcactgtag aaaaaaatca ttgcagggaa aaactagtac  1740
tgagtatttt gactgtaaat tatttaacca gtcggaatat agtcagtcta ttggagtcaa  1800
gagcgtgaac cgaaatagcc agttaattat cccattatac agaggacaac catgtatact  1860
attgaaactt ggtttaagag aatctaggta gctggactcg tagctgcttg gcatggatac  1920
cttcttatct ttaggaaaag acacttgatt ttttttctgt ggccctctat gatgtgtgaa  1980
cctgcttctc tattgcttta gaaggatata tctatgtcgt tatgcaacat gcttccctta  2040
gtcatttgta ctgaaatcag tttcataagt tcgttagtgg ttccctaaac gaaaccttgt  2100
ttttctttgc aatcaacagg tcccctaaaa atgcctatgt tgaaggtgat gcctcaagcg  2160
caagctattt cttggctggt gctgcaatta ctggagggac tgtgactgtg gaaggttgtg  2220
gcaccaccag tttgcaggta aagatttctt ggctggtgct acgataactg cttttgtctt  2280
tttggtttca gcattgttct cagagtcact aaataacatt atcatctgca aacgtcaaat  2340
agacatactt aggtgaatgg atattcatgt aaccgtttcc ttacaaattt gctgaaacct  2400
cagggtgatg tgaagtttgc tgaggtactg gagatgatgg gagcgaaggt tacatggacc  2460
gagactagcg taactgttac tggcccaccg cgggagccat ttgggaggaa acacctcaag  2520
gcgattgatg tcaacatgaa caagatgcct gatgtcgcca tgactcttgc tgtggttgcc  2580
ctctttgccg atggcccgac agccatcaga gacggtaaaa cattctcagc cctacaacca  2640
tgcctcttct acatcactac ttgacaagac taaaaactat tggctcgttg gcagtggctt  2700
cctggagagt aaaggagacc gagaggatgg ttgcgatccg gacggagcta accaaggtaa  2760
ggctacatac ttcacatgtc tcacgtcgtc tttccatagc tcgctgcctc ttagcggctt  2820
gcctgcggtc gctccatcct cggttgctgt ctgtgttttc cacagctggg agcatctgtt  2880
gaggaagggc cggactactg catcatcacg ccgccggaga agctgaacgt gacggcgatc  2940
gacacgtacg acgaccacag gatggccatg gccttctccc ttgccgcctg tgccgaggtc  3000
cccgtgacca tccgggaccc tgggtgcacc cggaagacct tccccgacta cttcgatgtg  3060
ctgagcactt tcgtcaagaa ttaataaagc gtgcgatact accacgcagc ttgattgaag  3120
tgataggctt gtgctgagga aatacatttc ttttgttctg ttttttctct ttcacgggat  3180
taagttttga gtctgtaacg ttagttgttt gtagcaagtt tctatttcgg atcttaagtt  3240
tgtgcactgt aagccaaatt tcatttcaag agtggttcgt tggaataata agaataataa  3300
attacgtttc agtggctgtc aagcctgctg ctacgtttta ggagatggca ttagacattc  3360
atcatcaaca acaataaaac cttttagcct caaacaataa tagtgaagtt attttttagt  3420
cctaaacaag ttgcattagg atatagttaa aacacaaaag aagctaaagt tagggtttag  3480
acatgtggat attgttttcc atgtatagta tgttctttct ttgagtctca tttaactacc  3540
tctacacata ccaactttag ttttttttct acctcttcat gttactatgg tgccttctta  3600
tcccactgag cattggtata tttagaggtt tttgttgaac atgcctaaat catctcaatc  3660
aacgatggac aatcttttct tcgattgagc tgaggtacgt catctaga            3708

SEQ ID NO: 520          moltype = AA  length = 464
FEATURE                 Location/Qualifiers
source                  1..464
                        mol_type = protein
                        organism = Zea mays
SEQUENCE: 520
MQLDLNVAEA PPPVEMEASD SGSSVLNASE AASAGGAPAP AEEGSSSTPA VLEFSILIRS  60
DSDAAGADED EDATPSPPPR HRHQHQQQLV TRELFPAGAG PPAPTPRHWA ELGFFRADLQ  120
QQQAPGPRIV PHPHAAPPPA KKSRRGPRSR SSQYRGVTFY RRTGRWESHI WDCGKQVYLG  180
GFDTAHAAAR AYDRAAIKFR GVDADINFNL SDYEDDMKQM GSLSKEEFVH VLRRQSTGFS  240
RGSSRYRGVT LHKCGRWEAR MGQFLGKKYI YLGLFDSEVE AARAYDKAAI KCNGREAVTN  300
FEPSTYHGEL PTEVADVDLN LSISQPSPQR DKNSCLGLQL HHGPFEGSEL KKTKIDDAPS  360
ELPGRPRQLS PLVAEHPPAW PAQPPHPFFV FTNHEMSASG DLHRRPAGAV PSWAWQVAAA  420
APPPAALPSS AAASSGFSNT ATTAATTAPS ASSLRYCPPP PPPS                  464

SEQ ID NO: 521          moltype = DNA  length = 1413
FEATURE                 Location/Qualifiers
source                  1..1413
                        mol_type = genomic DNA
                        organism = Zea mays
SEQUENCE: 521
atgcagttgg atctgaacgt ggccgaggcg ccgccgccgg tggagatgga ggcgagcgac  60
tcggggtcgt cggtgctgaa cgcgtcggaa gcggcgtcgg cgggcggcgc gcccgcgccg  120
gcggaggagg gatctagctc aacgccggcc gtgctggagt tcagcatcct catccggagc  180
gatagcgacg cggccggcgc ggacgaggac gaggacgcca cgccatcgcc tcctcctcgc  240
caccgccacc agcaccagca gcagctcgtg acccgcgagc tgttcccggc cggcgccggt  300
```

```
ccgccggccc cgacgccgcg gcattgggcc gagctcggct tcttccgcgc cgacctgcag  360
cagcaacagg cgccgggccc caggatcgtg ccgcacccac acgccgcgcc gccgccggcc  420
aagaagagcc gccgcggccc gcgctcccgc agctcgcagt accgcggcgt caccttctac  480
cgccgcacag gccgctggga gtcccacatc tgggattgcg gcaagcaggt gtacctaggt  540
ggattcgaca ccgctcacgc cgctgcaagg gcgtacgacc gggcggcgat caagttccgc  600
ggcgtcgacg ccgacatcaa cttcaacctc agcgactacg aggacgacat gaagcagatg  660
gggagcctgt ccaaggagga gttcgtgcac gtcctgcgcc gtcagagcac cggcttctcg  720
agaggcagct ccaggtacag aggcgtcacc ctgcacaagt gcggccgctg ggaggcgcgc  780
atggggcagt tcctcggcaa gaagtacata taccttgggc tattcgacag cgaagtagag  840
gctgcaagag cctacgacaa ggccgccatc aaatgcaatg gcagagaggc cgtgacgaac  900
ttcgagccga gcacgtatca cggggagctg ccgactgaag ttgctgatgt cgatctgaac  960
ctgagcatat ctcagccgag cccccaaaga gacaagaaca gctgcctagg tctgcagctc  1020
caccacggac cattcgaggg ctccgaactg aagaaaacca agatcgacga tgctccctct  1080
gagctaccgg gccgccctcg tcagctgtct cctctcgtgg ctgagcatcc gccggcctgg  1140
cctgcgcagc cgcctcaccc cttcttcgtc ttcacaaacc atgagatgag tgcatcagga  1200
gatctccaca ggaggcctgc aggggctgtt cccagctggg catggcaggt ggcagcagca  1260
gctcctcctc ctgccgccct gccgtcgtcc gctgcagcat catcaggatt ctccaacacc  1320
gccacgacag ctgccaccac cgccccatcg gcctcctccc tccggtactg cccgccgccg  1380
ccgccgccgt cgagccatca ccatccccgc tga                               1413
```

```
SEQ ID NO: 522          moltype = AA  length = 514
FEATURE                 Location/Qualifiers
source                  1..514
                        mol_type = protein
                        organism = Zea mays
SEQUENCE: 522
MTTSTTAKQL RRVRTLGRGA SGAVVWLASD EASGELVAVK SARAAGAAAQ LQREGRVLRG  60
LSSPHIVPCL GSRAAAGGEY QLLLEFAPGG SLADEAARSG GGRLAERAIG AYAGDVARGL  120
AYLHGRSLVH GDVKARNVVI GGDGRARLTD FGCARPAGGS TRPVGGTPAF MAPEVARGQE  180
QGPAADVWAL GCMVVELATG RAPWSDVEGD DLLAALHRIG YTDDVPEVPA WLSPEAKDFL  240
AGCFERRAAA RPTAAQPAAH PFVVASASAA AAIRGPAKQE VVPSPKSTLH DAFWDSDAED  300
EADEMSTGAA AERIGALACA ASALPDWDTE EGWIDLQDDH SAGTADAPPA PVADYFISWA  360
EPSDAELEPF VAVAAAAGLP HVAGVALAGA TAVNLQGSYY YYPPMHLGVR GNEIPRPLLD  420
HHGDGLEKGQ GSHRVCNRET EKVTMKRISL KRRAAFLLDQ HHVRSLDKLE YRPRHDRMLR  480
RRQSIYRSNS VLGYDVSKGR QVRWRRAVCI AVAA                              514
```

```
SEQ ID NO: 523          moltype = DNA  length = 1545
FEATURE                 Location/Qualifiers
source                  1..1545
                        mol_type = genomic DNA
                        organism = Zea mays
SEQUENCE: 523
atgacgacgt cgaccacggc gaagcagctc cggcgcgtgc gcacgctcgg ccgcggcgcg  60
tcgggcgccg tggtgtggct ggcctccgac gaggcctcgg gcgagctggt ggcggtcaag  120
tcggcgcgcg ccgccggggc cgcggcgcag ctgcagcgcg agggccgcgt cctccggggc  180
ctctcgtcgc cgcacatcgt gccctgcctc ggctcccgcg ccgcggcggg cggcgagtac  240
cagctcctgc tggagttcgc gccgggcggg tcgctggccg acgaggccgc caggagcggc  300
gggggccgcc tcgcggagcg cgccatcggc gcctacgccg gggacgtggc gcgcgggctg  360
gcgtacctcc acggccggtc gctcgtgcac ggggacgtca aggcccggaa cgtggtcatc  420
ggcggcgacg ggcgcgccag gctgaccgac ttcgggtgcg cgaggccggc cggcgggtcg  480
acgcgccccg tcgggggcac cccggcgttc atggcgcccg aggtggcgcg cggccaggag  540
cagggccccg ccgccgacgt ctgggcgctc gggtgcatgg tcgtcgagct ggccacgggc  600
cgcgcgccct ggagcgacgt ggagggcgac gacctcctcg ccgcgctcca ccggatcggg  660
tacacggacg acgtgccgga ggtgcccgcg tggctgtcgc ccgaggccaa ggacttcctg  720
gccggctgct tcgagcgccg cgccgccgcc cggcccacgg ccgcgcagcc cgcggcgcac  780
ccgttcgtcg tcgcctccgc ctccgccgcc gccgccatcc gcggcccggc gaagcaggag  840
gtggtcccgt cacccaagag cacgctgcac gacgcgttct gggactcgga cgccgaggac  900
gaagcggacg agatgtcgac gggcgcggcg gccgagagga tcggggcatt ggcgtgcgcc  960
gcctccgcgc tgcctgactg ggacaccgag gaaggctgga tcgacctcca ggacgaccac  1020
tcggccggaa ctgccgacgc accgccggcg cccgtcgcgg actacttcat cagctgggcg  1080
gagccgtcag acgcagagct ggaaccattc gtcgccgtcg ccgccgccgc aggtctcccg  1140
cacgttgcag gagttgcatt agcaggcgcc accgccgtta acctgcaggg cagttattat  1200
tattacccgc ctatgcatct aggcgtccgc ggaaacgaga ttccacgccc gttgttggat  1260
catcatggcg acgggttaga aaaggggcag ggatcccacc gcgtttgtaa cagagaaaca  1320
gaaaaggtaa caatgaaacg aatttcgtta aaaagaagag ctgctttcct tctcgaccag  1380
catcacgtgc gatcgctgga caaactggaa tatcgtccac gtcacgaccg aatgctgcgt  1440
cgacggcaat ctatatatcg gagcaatagc gtccttggtt acgacgttag caaaggtagg  1500
caggtccgtt ggcgccgtgc ggtttgcatt gccgttgctg cctga                  1545
```

```
SEQ ID NO: 524          moltype = DNA  length = 671
FEATURE                 Location/Qualifiers
source                  1..671
                        mol_type = genomic DNA
                        organism = Zea mays
SEQUENCE: 524
cggatccact agtaacggcc gccagtgtgc tggaattcgc ccttgacggc ccgggctggt  60
atttcaaaac tatagtattt taaaattgca ttaacaaaca tgtcctaatt ggtactcctg  120
agatactata ccctcctgtt ttaaaatagt tggcattatc gaattatcat tttacttttt  180
aatgttttct cttcttttaa tatattttat gaattttaat gtattttaaa atgttatgca  240
```

```
gttcgctctg gacttttctg ctgcgcctac acttgggtgt actgggccta aattcagcct  300
gaccgaccgc ctgcattgaa taatggatga gcaccggtaa aatccgcgta cccaactttc  360
gagaagaacc gagacgtggc gggccgggcc accgacgcac ggcaccagcg actgcacacg  420
tcccgccggc gtacgtgtac gtgctgttcc ctcactggcc gcccaatcca ctcatgcatg  480
cccacgtaca cccctgccgt ggcgcgccca gatcctaatc ctttcgccgt tctgcacttc  540
tgctgcctat aaatggcggc atcgaccgtc acctgcttca ccaccggcga gccacatcga  600
gaacacgatc gagcacacaa gcacgaagac tcgtttagga gaaaccacaa accaccaagc  660
cgtgcaagca c                                                       671

SEQ ID NO: 525         moltype = AA  length = 245
FEATURE                Location/Qualifiers
source                 1..245
                       mol_type = protein
                       organism = Zea mays
SEQUENCE: 525
MGRGKVQLKR IENKINRQVT FSKRRSGLLK KAHEISVLCD AEVALIIFST KGKLYEYSTD  60
SCMDKILERY ERYSYAEKVL ISAEYETQGN WCHEYRKLKA KVETIQKCQK HLMGEDLETL  120
NLKELQQLEQ QLESSLKHIR TRKSQLMVES ISALQRKEKS LQEENKVLQK ELAEKQKDQR  180
QQVQRDQTQQ QTSSSSTSFM LREAAPTTNV SIFPVAAGGR VVEGAAAQPQ ARVGLPPWML  240
SHLSC                                                              245

SEQ ID NO: 526         moltype = DNA  length = 738
FEATURE                Location/Qualifiers
source                 1..738
                       mol_type = genomic DNA
                       organism = Zea mays
SEQUENCE: 526
atggggcgcg ggaaggtgca gctgaagcgg atcgagaaca agatcaaccg ccaggtgaca  60
ttctccaagc gccgctcggg gctactcaag aaggcgcacg agatctccgt gctctgcgac  120
gccgaggtcg cgctcatcat cttctccacc aagggcaagc tctacgagta ctctaccgat  180
tcatgtatgg acaaaattct tgaacggtat gagcgctact cctatgcaga aaaggttctc  240
atttccgcag aatatgaaac tcagggcaat tggtgccatg aatatagaaa actaaaggcg  300
aaggtcgaga caatacagaa atgtcaaaag cacctcatgg gagaggatct tgaaactttg  360
aatctcaaag agcttcagca actagagcag cagctggaga gttcactgaa acatatcaga  420
acaaggaaga gccagcttat ggtcgagtca atttcagcgc tccaacggaa ggagaagtca  480
ctgcaggagg agaacaaggt tctgcagaag gagctcgcgg agaagcagaa agaccagcgg  540
cagcaagtgc aacgggacca aactcaacag cagaccagtt cgtcttccac gtccttcatg  600
ttaagggaag ctgccccaac aacaaatgtc agcatcttcc ctgtggcagc aggcgggagg  660
gtggtggaag ggcagcagc gcagccgcag gctcgcgttg gactgccacc atggatgctt  720
agccatctga gctgctga                                                738

SEQ ID NO: 527         moltype = DNA  length = 80
FEATURE                Location/Qualifiers
misc_feature           1..80
                       note = sequence of Figure 34B
source                 1..80
                       mol_type = genomic DNA
                       organism = Zea mays
SEQUENCE: 527
gctaaagagg aagtgcagct cttcttgggg aatgctggaa ctgcaatgcg gccattgaca  60
gcagctgtta ctgctgctgg                                              80

SEQ ID NO: 528         moltype = DNA  length = 80
FEATURE                Location/Qualifiers
misc_feature           1..80
                       note = sequence of Figure 34c
source                 1..80
                       mol_type = genomic DNA
                       organism = Zea mays
SEQUENCE: 528
gctagagagg aagtgcagct cttcttgggg aatgctggaa tcgcaatgcg gtcattgaca  60
gcagctgtta ctgctgctgg                                              80

SEQ ID NO: 529         moltype = DNA  length = 37
FEATURE                Location/Qualifiers
misc_feature           1..37
                       note = sequence of Figure 35b
source                 1..37
                       mol_type = genomic DNA
                       organism = Zea mays
SEQUENCE: 529
catctcacga tcagatgcac cgcatgtcgc atgccta                           37

SEQ ID NO: 530         moltype = DNA  length = 42
FEATURE                Location/Qualifiers
misc_feature           1..42
                       note = sequence of Figure 35c
source                 1..42
                       mol_type = genomic DNA
```

```
                         organism = Zea mays
SEQUENCE: 530
catatctgca cgatcagata tgcaccgcat gtcgcatatc tg                   42

SEQ ID NO: 531         moltype = DNA  length = 31
FEATURE                Location/Qualifiers
misc_feature           1..31
                       note = sequence of Figure 37
source                 1..31
                       mol_type = genomic DNA
                       organism = Zea mays
SEQUENCE: 531
gtttttgaac ttcagttacg tgcttgatgg a                               31

SEQ ID NO: 532         moltype = DNA  length = 31
FEATURE                Location/Qualifiers
misc_feature           1..31
                       note = sequence of Figure 37
source                 1..31
                       mol_type = genomic DNA
                       organism = Zea mays
SEQUENCE: 532
gtttttgaac ttcaggtacg tgcttgatgg a                               31

SEQ ID NO: 533         moltype = DNA  length = 459
FEATURE                Location/Qualifiers
misc_feature           1..459
                       note = synthesized sequence- Southern genomic probe
source                 1..459
                       mol_type = other DNA
                       organism = synthetic construct
SEQUENCE: 533
agctttatcc atccatccat cgcgctagct ggctgcaggc acgggttatc ttatcttgtc  60
gtccagagga cgacacacgg ccggccggtg aagtaaaagg gagtaatctt attttgccag  120
gacgaggggc ggtacatgat attacacacg taccatgcat gcatatatgc atggacaagg  180
tacgtcgtcg tcgatcgacg tcgatgcata tgtgtgtatg tatgtacgtg cataatgcat  240
ggtaccagct gctggcttat atatatttgt caccgatcga tgcatgctgc tgctctacac  300
ggtttgacac tttaatttga ctcatcgatg accttgctag atagtagcgg ctcgtcaatt  360
aatgagccat caagttaaca agagggcacg ggcttgcgcg actgattcca ccttattaac  420
atacgccctg cgcccgcgcg tgctgtacgt acgagaatt                       459

SEQ ID NO: 534         moltype = DNA  length = 446
FEATURE                Location/Qualifiers
misc_feature           1..446
                       note = synthesized sequence- Southern MoPAT probe
source                 1..446
                       mol_type = other DNA
                       organism = synthetic construct
SEQUENCE: 534
tcgaagtcgc gctgccagaa gccgacgtcg tgccagccgc cgtgcttgta gccggcggcg  60
cggagggtgc cgcgggcggt gtagccgagg gcctcgtgga ggcgcacgga cgggtcgttc  120
gggaggccga tcacggccac cacggacttg aagccctggg cctccatgct cttgaggagg  180
tgggtgtaga gggtggagcc gaggccgagg cgctggtggc ggtgggacac gtacacggtg  240
gactccacgg tccagtcgta ggcgttgcgg gccttccacg ggccggcgta ggcgatgccg  300
gccaccacgc cctccacctc ggccacgagc cacgggtagc ggtcctggag gcgctccagg  360
tcgtcgatcc actcctgcgg ggtctgcggc tcggtgcgga agttcacggt ggaggtctcg  420
atgtagtggt tcacgatgtc gcacac                                     446

SEQ ID NO: 535         moltype = DNA  length = 20
FEATURE                Location/Qualifiers
misc_feature           1..20
                       note = synthesized sequence- RF-FPCas-1
source                 1..20
                       mol_type = other DNA
                       organism = synthetic construct
SEQUENCE: 535
gcaggtctca cgacggttgg                                            20

SEQ ID NO: 536         moltype = DNA  length = 23
FEATURE                Location/Qualifiers
misc_feature           1..23
                       note = synthesized sequence- RF-FPCas-2
source                 1..23
                       mol_type = other DNA
                       organism = synthetic construct
SEQUENCE: 536
gtaaagtacg cgtacgtgtg agg                                        23

SEQ ID NO: 537         moltype = DNA  length = 23
```

```
FEATURE                Location/Qualifiers
misc_feature           1..23
                       note = synthesized sequence- ALSCas-4
source                 1..23
                       mol_type = other DNA
                       organism = synthetic construct
SEQUENCE: 537
gctgctcgat tccgtcccca tgg                                          23

SEQ ID NO: 538         moltype = DNA  length = 804
FEATURE                Location/Qualifiers
misc_feature           1..804
                       note = synthesized sequence- ALS modification repair
                        template 804
source                 1..804
                       mol_type = other DNA
                       organism = synthetic construct
SEQUENCE: 538
agcttacagc cgccgcaacc atggccaccg ccgccgccgc gtctaccgcg ctcactggcg  60
ccactaccgc tgcgcccaag gcgaggcgcc gggcgcacct cctggccacc cgccgcgccc  120
tcgccgcgcc catcaggtgc tcagcggcgt cacccgccat gccgatggct cccccggcca  180
ccccgctccg gccgtggggc cccaccgatc cccgcaaggg cgccgacatc ctcgtcgagt  240
ccctcgagcg ctgcggcgtc cgcgacgtct tcgcctaccc cggcggcgcg tccatggaga  300
tccaccaggc actcacccgc tcccccgtca tcgccaacca cctcttccgc cacgagcaag  360
gggaggcctt tgcggcctcc ggctacgcgc gctcctcggg ccgcgtcggc gtctgcatcg  420
ccacctccgg ccccggcgcc accaaccttg tctccgcgct cgccgacgcg ttgctcgact  480
ccgtccccat tgtcgccatc acgggacagg tgtcgcgacg catgattggc accgacgcct  540
tccaggagac gcccatcgtc gaggtcaccc gctccatcac caagcacaac tacctggtcc  600
tcgacgtcga cgacatcccc cgcgtcgtgc aggaggcttt cttcctcgcc tcctctggtc  660
gaccagggcc ggtgcttgtc gacatcccca aggacatcca gcagcagatg gcggtgcctg  720
tctgggacaa gcccatgagt ctgcctgggt acattgcgcg ccttcccaag ccccctgcga  780
ctgagttgct tgagcagaag ggcg                                         804

SEQ ID NO: 539         moltype = DNA  length = 127
FEATURE                Location/Qualifiers
misc_feature           1..127
                       note = synthesized sequence- ALS modification repair
                        template 127
source                 1..127
                       mol_type = other DNA
                       organism = synthetic construct
SEQUENCE: 539
aaccttgtct ccgcgctcgc cgacgcgttg ctcgactccg tccccattgt cgccatcacg  60
ggacaggtgt cgcgacgcat gattggcacc gacgccttcc aggagacgcc catcgtcgag  120
gtcaccc                                                            127

SEQ ID NO: 540         moltype = DNA  length = 25
FEATURE                Location/Qualifiers
misc_feature           1..25
                       note = synthesized sequence- ALS Forward_primer;
source                 1..25
                       mol_type = other DNA
                       organism = synthetic construct
SEQUENCE: 540
ctacgcacat ccccctttct cccac                                        25

SEQ ID NO: 541         moltype = DNA  length = 36
FEATURE                Location/Qualifiers
misc_feature           1..36
                       note = synthesized sequence- ALS Reverse_primer
source                 1..36
                       mol_type = other DNA
                       organism = synthetic construct
SEQUENCE: 541
atgcatacct agcatgcgca gagacagtgg gtcgtc                            36

SEQ ID NO: 542         moltype = DNA  length = 22
FEATURE                Location/Qualifiers
source                 1..22
                       mol_type = genomic DNA
                       organism = Glycine max
SEQUENCE: 542
caccggccag gtcccccgcc gg                                           22

SEQ ID NO: 543         moltype = DNA  length = 22
FEATURE                Location/Qualifiers
source                 1..22
                       mol_type = genomic DNA
                       organism = Glycine max
```

SEQUENCE: 543
ggcgtcggtg ccgatcatcc gg 22

SEQ ID NO: 544 moltype = DNA length = 9093
FEATURE Location/Qualifiers
misc_feature 1..9093
note = synthesized sequence- QC880
source 1..9093
mol_type = other DNA
organism = synthetic construct
SEQUENCE: 544
ccgggtgtga tttagtataa agtgaagtaa tggtcaaaag aaaaagtgta aaacgaagta 60
cctagtaata agtaatattg aacaaaataa atggtaaagt gtcagatata taaaataggc 120
tttaataaaa ggaagaaaaa aaacaaacaa aaaataggtt gcaatggggc agagcagagt 180
catcatgaag ctagaaaggc taccgataga taaactatag ttaattaaat acattaaaaa 240
atacttggat ctttctctta ccctgtttat attgagacct gaaacttgag agagatacac 300
taatcttgcc ttgttgtttc attccctaac ttacaggact cagcgcatgt catgtggtct 360
cgttccccat ttaagtccca caccgtctaa acttattaaa ttattaatgt ttataactag 420
atgcacaaca acaaagcttg caccggccag gtcccccgcg ttttagagct agaaatagca 480
agttaaaata aggctagtcc gttatcaact tgaaaaagtg gcaccgagtc ggtgcttttt 540
tttgcggccg caattggatc gggtttactt attttgtggg tatctatact tttattagat 600
ttttaatcag gctcctgatt tctttttatt tcgattgaat tcctgaactt gtattattca 660
gtagatcgaa taaattataa aaagataaaa tcataaaata atattttatc ctatcaatca 720
tattaaagca atgaatatgt aaaattaatc ttatctttat tttaaaaaat catataggtt 780
tagtattttt ttaaaaataa agataggatt agttttacta ttcactgctt attactttta 840
aaaaaatcat aaaggtttag tattttttta aaataaatat aggaatagtt ttactattca 900
ctgctttaat agaaaaatag tttaaaattt aagatagttt taatcccagc atttgccacg 960
tttgaacgtg agccgaaacg atgtcgttac attatcttaa cctagctgaa acgatgtcgt 1020
cataatatcg ccaaatgcca actggactac gtcgaaccca caaatcccac aaagcgcgtg 1080
aaatcaaatc gctcaaacca caaaaaagaa caacgcgttt gttacacgct caatcccacg 1140
cgagtagagc acagtaacct tcaaataagc gaatggggca taatcagaaa tccgaaataa 1200
acctaggggc attatcggaa atgaaaagta gctcactcaa tataaaaatc taggaaccct 1260
agttttcgtt atcactctgt gctccctcgc tctatttctc agtctctgtg tttgcggctg 1320
aggattccga acgagtgacc ttcttcgttt ctcgcaaagg taacagcctc tgctcttgtc 1380
tcttcgattc gatctatgcc tgtctcttat ttacgatgat gtttcttcgg ttatgttttt 1440
ttatttatgc tttatgctgt tgatgttcgg ttgtttgttt cgctttgttt ttgtggttca 1500
gttttttagg attcttttgg tttttgaatc gattaatcgg aagagatttt cgagttattt 1560
ggtgtgttgg aggtgaatct ttttttgag gtcatagatc tgttgtattt gtgttataaa 1620
catgcgactt tgtatgattt tttacgaggt tatgatgttc tggttgtttt attatgaatc 1680
tgttgagaca gaaccatgat ttttgttgat gttcgtttac actattaaag gtttgtttta 1740
acaggattaa aagtttttta agcatgttga aggagtcttg tagatatgta accgtcgata 1800
gtttttttgt gggtttgttc acatgttatc aagcttaatc ttttactatg tatgcgacca 1860
tatctggatc cagcaaaggc gatttttaa ttccttgtga aacttttgta atatgaagtt 1920
gaaattttgt tattggtaaa ctataaatgt gtgaagttgg agtatacctt taccttctta 1980
tttggctttg tgatagttta atttatatgt attttgagtt ctgacttgta tttctttgaa 2040
ttgattctag tttaagtaat ccatggacaa aaagtactca atagggctcg acatagggac 2100
taactccgtt ggatgggccg tcatcaccga cgagtacaag gtgccctcca agaagttcaa 2160
ggtgttggga aacaccgaca ggcacagcat aaagaagaat ttgatcggtg ccctcctctt 2220
cgactccgga gagaccgctg aggctaccag gctcaagagg accgctagaa ggcgctacac 2280
cagaaggaag aacagaatct gctacctgca ggagatcttc tccaacgaga tggccaaggt 2340
ggacgactcc ttcttccacc gccttgagga atcattcctg gtggaggagg ataaaaagca 2400
cgagagacac ccaatcttcg ggaacatcgt cgacgaggtg gcctaccatg aaaagtaccc 2460
taccatctac cacctgagga agaagctggt cgactctacc gacaaggctg acttgcgctt 2520
gatttacctg gctctcgctc acatgataaa gttccgcgga cacttcctca ttgagggaga 2580
cctgaaccca gacaactccg acgtggacaa gctcttcatc cagctcgttc agacctacaa 2640
ccagcttttc gaggagaacc caatcaacgc cagtggagtt gacgccaagg ctatcctctc 2700
tgctcgtctg tcaaagtcca ggaggcttga gaacttgatt gcccagctgc ctggcgaaaa 2760
gaagaacgga ctgttcggaa acttgatcgc tctctccctg ggattgactc ccaacttcaa 2820
gtccaacttc gacctcgccg aggacgctaa gttgcagttg tctaaagaca cctacgacga 2880
tgacctcgac aacttgctgg cccagatagg cgaccaatac gccgatctct tcctcgccgc 2940
taagaacttg tccgacgcaa tcctgctgtc cgacatcctg agagtcaaca ctgagattac 3000
caaagctcct ctgtctgctt ccatgattaa gcgctacgac gagcaccacc aagatctgac 3060
cctgctcaag gccctggtga gacagcagct gcccgagaag tacaaggaga tctttttcga 3120
ccagtccaag aacggctacg ccggatacat tgacggaggc gcctcccagg aagagttcta 3180
caagttcatc aagcccatcc ttgagaagat ggacggtacc gaggagctgt tggtgaagtt 3240
gaacagagag gacctgttga ggaagcagag aaccttcgac aacggaagca tccctcacca 3300
aatccacctg ggagagctcc acgccatctt gaggaggcag gaggatttct atcccttcct 3360
gaaggacaac cgcgagaaga ttgagaagat cttgaccttc agaattcctt actacgtcgg 3420
gccactcgcc agaggaaact ctaggttcgc ctggatgacc cgcaaatctg aagagaccat 3480
tactccctgg aacttcgagg aagtcgtgga caagggcgct tccgctcagt ctttcatcga 3540
gaggatgacc aacttcgata aaaatctgcc caacgagaag gtgctgccca agcactccct 3600
gttgtacgag tatttcacag tgtacaacga gctcaccaag gtgaagtacg tcacagaggg 3660
aatgaggaag cctgccttct tgtccggaga gcagaagaag gccatcgtcg acctgctctt 3720
caagaccaac aggaaggtga ctgtcaagca gctgaaggag gactacttca agaagatcga 3780
gtgcttcgac tccgtcgaga tctctggtgt cgaggacagg ttcaacgcct cccttgggac 3840
ttaccacgat ctgctcaaga ttattaaaga caaggacttc ctggacaacg aggagaacga 3900
ggacatcctt gaggacatcg tgctcaccct gaccttgttc gaagacaggg aaatgatcga 3960
agagaggctc aagacctacg cccacctctt cgacgacaag gtgatgaaac agctgaagag 4020
acgcagatat accggctggg gaaggctctc ccgcaaattg atcaacggga tcagggacaa 4080

-continued

```
gcagtcaggg aagactatac tcgacttcct gaagtccgac ggattcgcca acaggaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaagggc attttgcaga ccgtgaaggt cgttgacgag ctcgtgaagg tgatgggacg  4320
ccacaagcca gagaacatcg ttattgagat ggctcgcgag aaccaaacta cccagaaagg  4380
gcagaagaat tcccgcgaga ggatgaagcg cattgaggag ggcataaaag agcttggctc  4440
tcagatcctc aaggagcacc ccgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tcccctccga  4680
ggaggtcgtg aagaagatga aaaactactg gagacagctc ttgaacgcca agctcatcac  4740
ccagcgtaag ttcgacaacc tgactaaggc tgagagagga ggattgtccg agctcgataa  4800
ggccggattc atcaagagac agctcgtcga aacccgccaa attaccaagc acgtggccca  4860
aattctggat tcccgcatga acaccaagta cgatgaaaat gacaagctga tccgcgaggt  4920
caaggtgatc accttgaagt ccaagctggt ctccgacttc cgcaaggact tccagttcta  4980
caaggtgagg gagatcaaca actaccacca cgcacacgac gcctacctca acgctgtcgt  5040
tggaaccgcc ctcatcaaaa aatatcctaa gctggagtct gagttcgtct acggcgacta  5100
caaggtgtac gacgtgagga agatgatcgc taagtctgag caggagatcg gcaaggccac  5160
cgccaagtac ttcttctact ccaacatcat gaacttcttc aagaccgaga tcactctcgc  5220
caacggtgag atcaggaagc gcccactgat cgagaccaac ggtgagactg gagagatcgt  5280
gtgggacaaa gggagggatt tcgctactgt gaggaaggtg ctctccatgc ctcaggtgaa  5340
catcgtcaag aagaccgaag ttcagaccgg aggattctcc aaggagtcca tcctccccaa  5400
gagaaactcc gacaagctga tcgctagaaa gaaagactgg gaccctaaga agtacggagg  5460
cttcgattct cctaccgtgg cctactctgt gctggtcgtg gccaaggtgg agaagggcaa  5520
gtccaagaag ctgaaatccg tcaaggagct cctcgggatt accatcatgg agaggagttc  5580
cttcgagaag aaccctatcg acttcctgga ggccaaggga tataaagagg tgaagaagga  5640
cctcatcatc aagctgccca agtactccct cttcgagttg gagaacggaa ggaagaggat  5700
gctggcttct gccggagagt tgcagaaggg aaatgagctc gcccttccct ccaagtacgt  5760
gaacttcctg tacctcgcct ctcactatga aaagttgaag ggctctcctg aggacaacga  5820
gcagaagcag ctcttcgtgg agcagcacaa gcactacctg gacgaaatta tcgagcagat  5880
ctctgagttc tccaagcgcg tgatattggc cgacgccaac ctcgacaagg tgctgtccgc  5940
ctacaacaag cacagggata agcccattcg cgagcaggct gaaaacatta tccacctgtt  6000
taccctcaca aacttgggag cccctgctgc cttcaagtac ttcgacacca ccattgacag  6060
gaagagatac acctccacca aggaggtgct cgacgcaaca ctcatccacc aatccatcac  6120
cggcctctat gaaacaagga ttgacttgtc ccagctggga ggcgactcta gagccgatcc  6180
caagaagaag agaaaggtgt aggttaacct agacttgtcc atcttctgga ttggccaact  6240
taattaatgt atgaaataaa aggatgcaca catagtgaca tgctaatcac tataatgtgg  6300
gcatcaaagt tgtgtgttat gtgtaattac tagttatctg aataaaagag aaagagatca  6360
tccatatttc ttatcctaaa tgaatgtcac gtgtctttat aattctttga tgaaccagat  6420
gcatttcatt aaccaaatcc atatacatat aaatattaat catatataat taatatcaat  6480
tgggttagca aaacaaatct agtctaggtg tgttttgcga attcgatatc aagcttatcg  6540
ataccgtcga ggggggcccc ggtaccggcg cgccgttcta tagtgtcacc taaatcgtat  6600
gtgtatgata cataaggtta tgtattaatt gtagccgcgt tctaacgaca atatgtccat  6660
atggtgcact ctcagtacaa tctgctctga tgccgcatag ttaagccagc cccgacaccc  6720
gccaacaccc gctgacgcgc cctgacgggc ttgtctgctc ccggcatccg cttacagaca  6780
agctgtgacc gtctccggga gctgcatgtg tcagaggttt tcaccgtcat caccgaaacg  6840
cgcgagacga aagggcctcg tgatacgcct atttttatag gttaatgtca tgaccaaaat  6900
cccttaacgt gagttttcgt tccactgagc gtcagacccc gtagaaaaga tcaaaggatc  6960
ttcttgagat cctttttttc tgcgcgtaat ctgctgcttg caaacaaaaa aaccaccgct  7020
accagcggtg gtttgtttgc cggatcaaga gctaccaact ctttttccga aggtaactgg  7080
cttcagcaga gcgcagatac caaatactgt ccttctagtg tagccgtagt taggccacca  7140
cttcaagaac tctgtagcac cgcctacata cctcgctctg ctaatcctgt taccagtggc  7200
tgctgccagt ggcgataagt cgtgtcttac cgggttggac tcaagacgat agttaccgga  7260
taaggcgcag cggtcgggct gaacgggggg ttcgtgcaca cagcccagct tggagcgaac  7320
gacctacacc gaactgagat acctacagcg tgagcattga gaaagcgcca cgcttcccga  7380
agggagaaag gcggacaggt atccggtaag cggcagggtc ggaacaggag agcgcacgag  7440
ggagcttcca gggggaaacg cctggtatct ttatagtcct gtcgggtttc gccacctctg  7500
acttgagcgt cgatttttgt gatgctcgtc aggggggcgg agcctatgga aaaacgccag  7560
caacgcggcc tttttacggt tcctggcctt ttgctggcct tttgctcaca tgttctttcc  7620
tgcgttatcc cctgattctg tggataaccg tattaccgcc tttgagtgag ctgataccgc  7680
tcgccgcagc cgaacgaccg agcgcagcga gtcagtgagc gaggaagcgg aagagcgccc  7740
aatacgcaaa ccgcctctcc ccgcgcgttg gccgattcat taatgcaggt tgatcagatc  7800
tcgatcccgc gaaattaata cgactcacta tagggagacc acaacggttt ccctctagaa  7860
ataattttgt ttaactttaa gaaggagata tacccatgga aaagcctgaa ctcaccgcga  7920
cgtctgtcga gaagtttctg atcgaaaagt tcgacagcgt ctccgacctg atgcagctct  7980
cggagggcga agaatctcgt gctttcagct tcgatgtagg agggcgtgga tatgtcctgc  8040
gggtaaatag ctgcgccgat ggtttctaca aagatcgtta tgtttatcgg cactttgcat  8100
cggccgcgct cccgattccg gaagtgcttg acattgggga attcagcgag agcctgacct  8160
attgcatctc ccgccgtgca cagggtgtca cgttgcaaga cctgcctgaa accgaactgc  8220
ccgctgttct gcagccggtc gcggaggcta tggatgcgat cgctgcggcc gatcttagcc  8280
agacgagcgg gttcggccca ttcggaccgc aaggaatcgg tcaatacact acatggcgtg  8340
atttcatatg cgcgattgct gatccccatg tgtatcactg gcaaactgtg atggacgaca  8400
ccgtcagtgc gtccgtcgcg caggctctcg atgagctgat gctttgggcc gaggactgcc  8460
ccgaagtccg gcacctcgtg cacgcggatt tcggctccaa caatgtcctg acggacaatg  8520
gccgcataac agcggtcatt gactggagcg aggcgatgtt cggggattcc caatacgagg  8580
tcgccaacat cttcttctgg aggccgtggt tggcttgtat ggagcagcag acgcgctact  8640
tcgagcggag gcatccggag cttgcaggat cgccgcggct ccgggcgtat atgctccgca  8700
ttggtcttga ccaactctat cagagcttgg ttgacggcaa tttcgatgat gcagcttggg  8760
cgcagggtcg atgcgacgca atcgtccgat ccggagccgg gactgtcggg cgtacacaaa  8820
```

-continued

```
tcgcccgcag aagcgcggcc gtctggaccg atggctgtgt agaagtactc gccgatagtg  8880
gaaaccgacg ccccagcact cgtccgaggg caaaggaata gtgaggtaca gcttggatcg  8940
atccggctgc taacaaagcc cgaaaggaag ctgagttggc tgctgccacc gctgagcaat  9000
aactagcata accccttggg gcctctaaac gggtcttgag gggttttttg ctgaaaggag  9060
gaactatatc cggatgatcg ggcgcgccgg tac                               9093

SEQ ID NO: 545          moltype = DNA  length = 9093
FEATURE                 Location/Qualifiers
misc_feature            1..9093
                        note = synthesized sequence- QC881
source                  1..9093
                        mol_type = other DNA
                        organism = synthetic construct
SEQUENCE: 545
ccgggtgtga tttagtataa agtgaagtaa tggtcaaaag aaaaagtgta aaacgaagta  60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg ggcgtcggtg ccgatcatcg ttttagagct agaaatagca  480
agttaaaata aggctagtcc gttatcaact tgaaaaagtg gcaccgagtc ggtgcttttt  540
tttgcggccg caattggatc gggtttactt attttgtggg tatctatact tttattagat  600
ttttaatcag gctcctgatt tctttttatt tcgattgaat tcctgaactt gtattattca  660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agttttacta ttcactgctt attactttta  840
aaaaaatcat aaaggtttag tattttttta aaataaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt  1020
cataatatcg ccaaatgcca actggactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attcttttgg tttttgaatc gattaatcgg aagagatttt cgagttattt  1560
ggtgtgttgg aggtgaatct ttttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagtttttta agcatgttga aggagtcttg tagatatgta accgtcgata  1800
gttttttttgt gggtttgttc acatgttatc aagcttaatc ttttactatg tatgcgacca  1860
tatctggatc cagcaaaggc gatttttttaa ttccttgtga aacttttgta atatgaagtt  1920
gaaattttgt tattggtaaa ctataaatgt gtgaagttgg agtatacctt taccttctta  1980
tttggctttg tgatagttta atttatatgt attttgagtt ctgacttgta tttctttgaa  2040
ttgattctag tttaagtaat ccatggacaa aaagtactca atagggctcg acatagggac  2100
taactccgtt ggatgggccg tcatcaccga cgagtacaag gtgccctcca agaagttcaa  2160
ggtgttggga aacaccgaca ggcacagcat aaagaagaat ttgatcggtg ccctcctctt  2220
cgactccgga gagaccgctg aggctaccag gctcaagagg accgctagaa ggcgctacac  2280
cagaaggaag aacagaatct gctacctgca ggagatcttc tccaacgaga tggccaaggt  2340
ggacgactcc ttcttccacc gccttgagga atcattcctg gtggaggagg ataaaaagca  2400
cgagagacac ccaatcttcg ggaacatcgt cgacgaggtg gcctaccatg aaaagtaccc  2460
taccatctac cacctgagga agaagctggt cgactctacc gacaaggctg acttgcgctt  2520
gatttacctg gctctcgctc acatgataaa gttccgcgga cacttcctca ttgagggaga  2580
cctgaaccca gacaactccg acgtggacaa gctcttcatc cagctcgttc agacctacaa  2640
ccagcttttc gaggagaacc caatcaacgc cagtggagtt gacgccaagg ctatcctctc  2700
tgctcgtctg tcaaagtcca ggaggcttga gaacttgatt gcccagctgc ctggcgaaaa  2760
gaagaacgga ctgttcggaa acttgatcgc tctctccctg ggattgactc ccaacttcaa  2820
gtccaacttc gacctcgccg aggacgctaa gttgcagttg tctaaagaca cctacgacga  2880
tgacctcgac aacttgctgg cccagatagg cgaccaatac gccgatctct tcctcgccgc  2940
taagaacttg tccgacgcaa tcctgctgtc cgacatcctg agagtcaaca ctgagattac  3000
caaagctcct ctgtctgctt ccatgattaa gcgctacgac gagcaccacc aagatctgac  3060
cctgctcaag gccctggtga gacagcagct gcccgagaag tacaaggaga tcttttttcga  3120
ccagtccaag aacggctacg ccggatacat tgacggaggc gcctcccagg aagagttcta  3180
caagttcatc aagcccatcc ttgagaagat ggacggtacc gaggagctgt tggtgaagtt  3240
gaacagagag gacctgttga ggaagcagag aaccttcgac aacggaagca tccctcacca  3300
aatccacctg ggagagctcc acgccatctt gaggaggcag gaggatttct atcccttcct  3360
gaaggacaac cgcgagaaga ttgagaagat cttgaccttc agaattcctt actacgtcgg  3420
gccactcgcc agaggaaact ctaggttcgc ctggatgacc cgcaaatctg aagagaccat  3480
tactccctgg aacttcgagg aagtcgtgga caagggcgct tccgctcagt ctttcatcga  3540
gaggatgacc aacttcgata aaaatctgcc caacgagaag gtgctgccca agcactccct  3600
gttgtacgag tatttcacag tgtacaacga gctcaccaag gtgaagtacg tcacagaggg  3660
aatgaggaag cctgccttct tgtccggaga gcagaagaag gccatcgtcg acctgctctt  3720
caagaccaac aggaaggtga ctgtcaagca gctgaaggag gactacttca agaagatcga  3780
gtgcttcgac tccgtcgaga tctctggtgt cgaggacagg ttcaacgcct cccttgggac  3840
ttaccacgat ctgctcaaga ttattaaaga caaggacttc ctggacaacg aggagaacga  3900
```

-continued

```
ggacatcctt gaggacatcg tgctcaccct gaccttgttc gaagacaggg aaatgatcga  3960
agagaggctc aagacctacg cccacctctt cgacgacaag gtgatgaaac agctgaagag  4020
acgcagatat accggctggg gaaggctctc ccgcaaattg atcaacggga tcagggacaa  4080
gcagtcaggg aagactatac tcgacttcct gaagtccgac ggattcgcca acaggaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaagggc attttgcaga ccgtgaaggt cgttgacgag ctcgtgaagg tgatgggacg  4320
ccacaagcca gagaacatcg ttattgagat ggctcgcgag aaccaaacta cccagaaagg  4380
gcagaagaat tcccgcgaga ggatgaagcg cattgaggag ggcataaaag agcttggctc  4440
tcagatcctc aaggagcacc ccgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tcccctccga  4680
ggaggtcgtg aagaagatga aaaactactg gagacagctc ttgaacgcca agctcatcac  4740
ccagcgtaag ttcgacaacc tgactaaggc tgagagagga ggattgtccg agctcgataa  4800
ggccggattc atcaagagac agctcgtcga aacccgccaa attaccaagc acgtggccca  4860
aattctggat tcccgcatga acaccaagta cgatgaaaat gacaagctga tccgcgaggt  4920
caaggtgatc accttgaagt ccaagctggt ctccgacttc cgcaaggact tccagttcta  4980
caaggtgagg gagatcaaca actaccacca cgcacacgac gcctacctca acgctgtcgt  5040
tggaaccgcc ctcatcaaaa aatatcctaa gctggagtct gagttcgtct acggcgacta  5100
caaggtgtac gacgtgagga agatgatcgc taagtctgag caggagatcg gcaaggccac  5160
cgccaagtac ttcttctact ccaacatcat gaacttcttc aagaccgaga tcactctcgc  5220
caacggtgag atcaggaagc gcccactgat cgagaccaac ggtgagactg gagagatcgt  5280
gtgggacaaa gggagggatt tcgctactgt gaggaaggtg ctctccatgc ctcaggtgaa  5340
catcgtcaag aagaccgaag ttcagaccgg aggattctcc aaggagtcca tcctccccaa  5400
gagaaactcc gacaagctga tcgctagaaa gaaagactgg gaccctaaga agtacggagg  5460
cttcgattct cctaccgtgg cctactctgt gctggtcgtg gccaaggtgg agaagggcaa  5520
gtccaagaag ctgaaatccg tcaaggagct cctcgggatt accatcatgg agaggagttc  5580
cttcgagaag aaccctatcg acttcctgga ggccaaggga tataaagagg tgaagaagga  5640
cctcatcatc aagctgccca agtactccct cttcgagttg gagaacggaa ggaagaggat  5700
gctggcttct gccggagagt tgcagaaggg aaatgagctc gcccttccct ccaagtacgt  5760
gaacttcctg tacctcgcct ctcactatga aaagttgaag ggctctcctg aggacaacga  5820
gcagaagcag ctcttcgtgg agcagcacaa gcactacctg gacgaaatta tcgagcagat  5880
ctctgagttc tccaagcgcg tgatattggc cgacgccaac ctcgacaagg tgctgtccgc  5940
ctacaacaag cacagggata agcccattcg cgagcaggct gaaaacatta tccacctgtt  6000
taccctcaca aacttgggag cccctgctgc cttcaagtac ttcgacacca ccattgacag  6060
gaagagatac acctccacca aggaggtgct cgacgcaaca ctcatccacc aatccatcac  6120
cggcctctat gaaacaagga ttgacttgtc ccagctggga ggcgactcta gagccgatcc  6180
caagaagaag agaaaggtgt aggttaacct agacttgtcc atcttctgga ttggccaact  6240
taattaatgt atgaaataaa aggatgcaca catagtgaca tgctaatcac tataatgtgg  6300
gcatcaaagt tgtgtgttat gtgtaattac tagttatctg aataaaagag aaagagatca  6360
tccatatttc ttatcctaaa tgaatgtcac gtgtctttat aattctttga tgaaccagat  6420
gcatttcatt aaccaaatcc atatacatat aaatattaat catatataat taatatcaat  6480
tgggttagca aaacaaatct agtctaggtg tgttttgcga attcgatatc aagcttatcg  6540
ataccgtcga ggggggggcc ggtaccggcg cgccgttcta tagtgtcacc taaatcgtat  6600
gtgtatgata cataaggtta tgtattaatt gtagccgcgt tctaacgaca atatgtccat  6660
atggtgcact ctcagtacaa tctgctctga tgccgcatag ttaagccagc cccgacaccc  6720
gccaacaccc gctgacgcgc cctgacgggc ttgtctgctc ccggcatccg cttacagaca  6780
agctgtgacc gtctccggga gctgcatgtg tcagaggttt tcaccgtcat caccgaaacg  6840
cgcgagacga aagggcctcg tgatacgcct atttttatag gttaatgtca tgaccaaaat  6900
cccttaacgt gagttttcgt tccactgagc gtcagacccc gtagaaaaga tcaaaggatc  6960
ttcttgagat cctttttttc tgcgcgtaat ctgctgcttg caaacaaaaa aaccaccgct  7020
accagcggtg gtttgtttgc cggatcaaga gctaccaact ctttttccga aggtaactgg  7080
cttcagcaga gcgcagatac caaatactgt ccttctagtg tagccgtagt taggccacca  7140
cttcaagaac tctgtagcac cgcctacata cctcgctctg ctaatcctgt taccagtggc  7200
tgctgccagt ggcgataagt cgtgtcttac cgggttggac tcaagacgat agttaccgga  7260
taaggcgcag cggtcgggct gaacgggggg ttcgtgcaca cagcccagct tggagcgaac  7320
gacctacacc gaactgagat acctacagcg tgagcattga gaaagcgcca cgcttcccga  7380
agggagaaag gcggacaggt atccggtaag cggcagggtc ggaacaggag agcgcacgag  7440
ggagcttcca gggggaaacg cctggtatct ttatagtcct gtcgggtttc gccacctctg  7500
acttgagcgt cgatttttgt gatgctcgtc aggggggcgg agcctatgga aaaacgccag  7560
caacgcggcc tttttacggt tcctggcctt ttgctggcct tttgctcaca tgttctttcc  7620
tgcgttatcc cctgattctg tggataaccg tattaccgcc tttgagtgag ctgataccgc  7680
tcgccgcagc cgaacgaccg agcgcagcga gtcagtgagc gaggaagcgg aagagcgccc  7740
aatacgcaaa ccgcctctcc ccgcgcgttg gccgattcat taatgcaggt tgatcagatc  7800
tcgatcccgc gaaattaata cgactcacta tagggagacc acaacggttt ccctctagaa  7860
ataattttgt ttaactttaa gaaggagata tacccatgga aaagcctgaa ctcaccgcga  7920
cgtctgtcga gaagtttctg atcgaaaagt tcgacagcgt ctccgacctg atgcagctct  7980
cggagggcga agaatctcgt gctttcagct tcgatgtagg agggcgtgga tatgtcctgc  8040
gggtaaatag ctgcgccgat ggtttctaca aagatcgtta tgtttatcgg cactttgcat  8100
cggccgcgct cccgattccg gaagtgcttg acattgggga attcagcgag agcctgacct  8160
attgcatctc ccgccgtgca cagggtgtca cgttgcaaga cctgcctgaa accgaactgc  8220
ccgctgttct gcagccggtc gcggaggcta tggatgcgat cgctgcggcc gatcttagcc  8280
agacgagcgg gttcggccca ttcggaccgc aaggaatcgg tcaatacact acatggcgtg  8340
atttcatatg cgcgattgct gatccccatg tgtatcactg gcaaactgtg atggacgaca  8400
ccgtcagtgc gtccgtcgcg caggctctcg atgagctgat gctttgggcc gaggactgcc  8460
ccgaagtccg gcacctcgtg cacgcggatt tcggctccaa caatgtcctg acggacaatg  8520
gccgcataac agcggtcatt gactggagcg aggcgatgtt cggggattcc caatacgagg  8580
tcgccaacat cttcttctgg aggccgtggt tggcttgtat ggagcagcag acgcgctact  8640
```

-continued

```
tcgagcggag gcatccggag cttgcaggat cgccgcggct ccgggcgtat atgctccgca  8700
ttggtcttga ccaactctat cagagcttgg ttgacggcaa tttcgatgat gcagcttggg  8760
cgcagggtcg atgcgacgca atcgtccgat ccggagccgg gactgtcggg cgtacacaaa  8820
tcgcccgcag aagcgcggcc gtctggaccg atggctgtgt agaagtactc gccgatagtg  8880
gaaaccgacg ccccagcact cgtccgaggg caaaggaata gtgaggtaca gcttggatcg  8940
atccggctgc taacaaagcc cgaaaggaag ctgagttggc tgctgccacc gctgagcaat  9000
aactagcata accccttggg gcctctaaac gggtcttgag gggttttttg ctgaaaggag  9060
gaactatatc cggatgatcg ggcgcgccgg tac                               9093

SEQ ID NO: 546         moltype = DNA  length = 1113
FEATURE                Location/Qualifiers
misc_feature           1..1113
                       note = synthesized sequence- RTW1026A
source                 1..1113
                       mol_type = other DNA
                       organism = synthetic construct
SEQUENCE: 546
agcttggtac cgagctcgga tccactagta tggcggccac cgcttccaga accacccgat  60
tctcttcttc ctcttcacac cccaccttcc ccaaacgcat tactagatcc accctccctc  120
tctctcatca aaccctcacc aaacccaacc acgctctcaa aatcaaatgt tccatctcca  180
aaccccccac ggcggcgccc ttcaccaagg aagcgccgac cacggagccc ttcgtgtcac  240
ggttcgcctc cggcgaacct cgcaagggcg cggacatcct tgtggaggcg ctggagaggc  300
agggcgtgac gacggtgttc gcgtaccccg gcggtgcgtc gatggagatc caccaggcgc  360
tcacgcgctc cgccgccatc cgcaacgtgc tcccgcgcca cgagcagggc ggcgtcttcg  420
ccgccgaagg ctacgcgcgt tcctccggcc tccccggcgt ctgcattgcc acctccggcc  480
ccggcgccac caacctcgtg agcggcctcg ccgacgcttt aatggacagc gtcccagtcg  540
tcgccatcac cggccaggtc agccgtcgca tgatcggtac cgacgccttc caagaaaccc  600
cgatcgtgga ggtgagcaga tccatcacga agcacaacta cctcatcctc gacgtcgacg  660
acatcccccg cgtcgtcgcc gaggctttct tcgtcgccac ctccggccgc cccggtccgg  720
tcctcatcga cattcccaaa gacgttcagc agcaactcgc cgtgcctaat tgggacgagc  780
ccgttaacct ccccggttac ctcgccaggc tgcccaggcc ccccgccgag gcccaattgg  840
aacacattgt cagactcatc atggaggccc aaaagcccgt tctctacgtc ggcggtggca  900
gtttgaattc cagtgctgaa ttgaggcgct ttgttgaact cactggtatt cccgttgcta  960
gcactttaat gggtcttgga acttttccta ttggtgatga atattccctt cagatgctgg  1020
gtatgcatgg tactgtttat gctaactatg ctgttgacaa tagtgatttg ttgcttgcct  1080
ttggggtaag gtttgatgac cgtgttactg gga                               1113

SEQ ID NO: 547         moltype = DNA  length = 17
FEATURE                Location/Qualifiers
misc_feature           1..17
                       note = synthesized sequence- WOL900, Forward_primer
source                 1..17
                       mol_type = other DNA
                       organism = synthetic construct
SEQUENCE: 547
atcaccggcc aggtcag                                                 17

SEQ ID NO: 548         moltype = DNA  length = 25
FEATURE                Location/Qualifiers
misc_feature           1..25
                       note = synthesized sequence- WOL578, Reverse_primer
source                 1..25
                       mol_type = other DNA
                       organism = synthetic construct
SEQUENCE: 548
acttaccctc cactcctttc tcctc                                        25

SEQ ID NO: 549         moltype = DNA  length = 29
FEATURE                Location/Qualifiers
misc_feature           1..29
                       note = synthesized sequence- WOL573, Forward_primer
source                 1..29
                       mol_type = other DNA
                       organism = synthetic construct
SEQUENCE: 549
atggcggcca ccgcttccag aaccacccg                                    29

SEQ ID NO: 550         moltype = AA  length = 638
FEATURE                Location/Qualifiers
source                 1..638
                       mol_type = protein
                       organism = Zea mays
SEQUENCE: 550
MATAAAASTA LTGATTAAPK ARRRAHLLAT RRALAAPIRC SAASPAMPMA PPATPLRPWG  60
PTEPRKGADI LVESLERCGV RDVFAYPGGA SMEIHQALTR SPVIANHLFR HEQGEAFAAS  120
GYARSSGRVG VCIATSGPGA TNLVSALADA LLDSVPMVAI TGQVPRRMIG TDAFQETPIV  180
EVTRSITKHN YLVLDVDDIP RVVQEAFFLA SSGRPGPVLV DIPKDIQQQM AVPVWDKPMS  240
LPGYIARLPK PPATELLEQV LRLVGESRRP VLYVGGGCAA SGEELRRFVE LTGIPVTTTL  300
MGLGNFPSDD PLSLRMLGMH GTVYANYAVD KADLLLALGV RFDDRVTGKI EAFASRAKIV  360
```

```
HVDIDPAEIG KNKQPHVSIC ADVKLALQGM NALLEGSTSK KSFDFGSWND ELDQQKREFP  420
LGYKTSNEEI QPQYAIQVLD ELTKGEAIIG TGVGQHQMWA AQYYTYKRPR QWLSSAGLGA  480
MGFGLPAAAG ASVANPGVTV VDIDGDGSFL MNVQELAMIR IENLPVKVFV LNNQHLGMVV  540
QWEDRFYKAN RAHTYLGNPE NESEIYPDFV TIAKGFNIPA VRVTKKNEVR AAIKKMLETP  600
GPYLLDIIVP HQEHVLPMIP SGGAFKDMIL DGDGRTVY                          638

SEQ ID NO: 551          moltype = DNA  length = 43
FEATURE                 Location/Qualifiers
misc_feature            1..43
                        note = sense genome sequence Figure 2A and 2B
source                  1..43
                        mol_type = genomic DNA
                        organism = Zea mays
SEQUENCE: 551
gatatatata cctcacacgt acgcgtacgc gtatatatac gtg                    43

SEQ ID NO: 552          moltype = DNA  length = 43
FEATURE                 Location/Qualifiers
misc_feature            1..43
                        note = complementary genome sequence Figure 2A and 2B
source                  1..43
                        mol_type = genomic DNA
                        organism = Zea mays
SEQUENCE: 552
cacgtatata tacgcgtacg cgtacgtgtg aggtatatat atc                    43

SEQ ID NO: 553          moltype = DNA  length = 104
FEATURE                 Location/Qualifiers
misc_feature            1..104
                        note = synthesized sequence- sequence of Figure 8B
source                  1..104
                        mol_type = other DNA
                        organism = synthetic construct
SEQUENCE: 553
gtcccttgta cttgtacgta gttttagagc tagaaatagc aagttaaaat aaggctagtc  60
cgttatcaac ttgaaaaagt ggcaccgagt cggtgctttt tttt                   104

SEQ ID NO: 554          moltype = DNA  length = 70
FEATURE                 Location/Qualifiers
source                  1..70
                        mol_type = genomic DNA
                        organism = Glycine max
SEQUENCE: 554
atcaaaattc ggaactgaca cacgacatga tggaacgtga ctaaggtggg tttttgactt  60
tgcatgtcga                                                         70

SEQ ID NO: 555          moltype = DNA  length = 70
FEATURE                 Location/Qualifiers
source                  1..70
                        mol_type = genomic DNA
                        organism = Glycine max
SEQUENCE: 555
tcgacatgca aagtcaaaaa cccaccttag tcacgttcca tcatgtcgtg tgtcagttcc  60
gaattttgat                                                         70

SEQ ID NO: 556          moltype = DNA  length = 70
FEATURE                 Location/Qualifiers
source                  1..70
                        mol_type = genomic DNA
                        organism = Glycine max
SEQUENCE: 556
ggcagactcc aattcctctt ttctagaata ccctccgtac gtacaagtac aagggacttg  60
tgagttgtaa                                                         70

SEQ ID NO: 557          moltype = DNA  length = 70
FEATURE                 Location/Qualifiers
source                  1..70
                        mol_type = genomic DNA
                        organism = Glycine max
SEQUENCE: 557
ttacaactca caagtccctt gtacttgtac gtacggaggg tattctagaa aagaggaatt  60
ggagtctgcc                                                         70

SEQ ID NO: 558          moltype = AA  length = 8
FEATURE                 Location/Qualifiers
REGION                  1..8
                        note = MISC_FEATURE - Maize EPSPS polyubiquitination site
REGION                  1..8
                        note = MISC_FEATURE - Maize EPSPS polyubiquitination site
```

```
source                  1..8
                        mol_type = protein
                        organism = Zea mays
SEQUENCE: 558
VEDAKEEV                                                                  8

SEQ ID NO: 559          moltype = AA  length = 8
FEATURE                 Location/Qualifiers
REGION                  1..8
                        note = MISC_FEATURE - Petunia EPSPS polyubiquitination site
source                  1..8
                        mol_type = protein
                        organism = Petunia hybrida
SEQUENCE: 559
GKESKEEI                                                                  8

SEQ ID NO: 560          moltype = AA  length = 8
FEATURE                 Location/Qualifiers
REGION                  1..8
                        note = MISC_FEATURE - Tomato EPSPS polyubiquitination site
source                  1..8
                        mol_type = protein
                        organism = Solanum lycopersicum
SEQUENCE: 560
GKKSEEEI                                                                  8

SEQ ID NO: 561          moltype = AA  length = 8
FEATURE                 Location/Qualifiers
REGION                  1..8
                        note = MISC_FEATURE - Sorghum EPSPS polyubiquitination site
source                  1..8
                        mol_type = protein
                        organism = Sorghum bicolor
SEQUENCE: 561
EKDAKEEV                                                                  8

SEQ ID NO: 562          moltype = AA  length = 8
FEATURE                 Location/Qualifiers
REGION                  1..8
                        note = MISC_FEATURE - Rice EPSPS polyubiquitination site
source                  1..8
                        mol_type = protein
                        organism = Oryza sativa
SEQUENCE: 562
VEDSKEEV                                                                  8

SEQ ID NO: 563          moltype = AA  length = 8
FEATURE                 Location/Qualifiers
REGION                  1..8
                        note = MISC_FEATURE - Amaranthus EPSPS polyubiquitination
                         site
source                  1..8
                        mol_type = protein
                        organism = Amaranthus floridanus
SEQUENCE: 563
GKDGKEEI                                                                  8

SEQ ID NO: 564          moltype = DNA  length = 80
FEATURE                 Location/Qualifiers
source                  1..80
                        mol_type = genomic DNA
                        organism = Zea mays
SEQUENCE: 564
gctaaagagg aagtgcagct cttcttgggg aatgctggaa ctgcaatgcg gccattgaca  60
gcagctgtta ctgctgctgg                                              80

SEQ ID NO: 565          moltype = DNA  length = 80
FEATURE                 Location/Qualifiers
source                  1..80
                        mol_type = genomic DNA
                        organism = Zea mays
SEQUENCE: 565
gctagagagg aagtgcagct cttcttgggg aatgctggaa tcgcaatgcg gtcattgaca  60
gcagctgtta ctgctgctgg                                              80

SEQ ID NO: 566          moltype = DNA  length = 37
FEATURE                 Location/Qualifiers
source                  1..37
                        mol_type = genomic DNA
```

-continued

```
                        organism = Zea mays
SEQUENCE: 566
catctcacga tcagatgcac cgcatgtcgc atgccta                          37

SEQ ID NO: 567          moltype = DNA  length = 42
FEATURE                 Location/Qualifiers
source                  1..42
                        mol_type = genomic DNA
                        organism = Zea mays
SEQUENCE: 567
catatctgca cgatcagata tgcaccgcat gtcgcatatc tg                    42
```